US007943742B2

(12) United States Patent
Violette et al.

(10) Patent No.: US 7,943,742 B2

(45) Date of Patent: May 17, 2011

(54) ANTI-$\alpha_v\beta_6$ ANTIBODIES AND USES THEREOF

(75) Inventors: Shelia M. Violette, Lexington, MA (US); Louise A. Koopman, Brookline, MA (US); Kenneth J. Simon, Cambridge, MA (US); Paul H. Weinreb, Andover, MA (US); Herman W. T. van Vlijmen, Mechelen (BE); Jose W. Saldanha, Endfield (GB); Alexey A. Lugovskoy, Woburn, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 389 days.

(21) Appl. No.: 11/483,190

(22) Filed: Jul. 10, 2006

(65) Prior Publication Data

US 2008/0286269 A1 Nov. 20, 2008

Related U.S. Application Data

(60) Provisional application No. 60/697,442, filed on Jul. 8, 2005, provisional application No. 60/773,310, filed on Feb. 15, 2006.

(51) Int. Cl.

| | |
|---|---|
| ***C12P 21/08*** | (2006.01) |
| ***C07K 16/00*** | (2006.01) |
| *A61K 39/395* | (2006.01) |
| *C12P 21/04* | (2006.01) |

(52) U.S. Cl. ............ 530/387.3; 530/388.1; 530/388.22; 530/388.8; 424/133.1; 424/141.1; 424/143.1; 424/155.1; 435/69.6; 435/70.21

(58) Field of Classification Search ........................ None
See application file for complete search history.

(56) References Cited

U.S. PATENT DOCUMENTS

| | | | |
|---|---|---|---|
| 5,530,101 | A * | 6/1996 | Queen et al. |
| 7,465,449 | B2 * | 12/2008 | Violette et al. |
| 2005/0255102 | A1 * | 11/2005 | Violette et al. |

OTHER PUBLICATIONS

Fundamental Immunology, William E. Paul, M.D. ed., 3rd ed., pp. 242, 292-295, 1993.*
Rudikoff et al. Proc. Natl. Acad. Sci. USA, 79(6):1979-1983, Mar. 1982.*
Colman P. M. Research in Immunology, 145:33-36, 1994.*
Bendig M. M. Methods: a Companion to Methods in Enzymology, 8:83-93, 1995.*
Weinreb et al. The Journal of Biological Chemistry, 279(17):17875-17887, Apr. 23, 2004.*

* cited by examiner

*Primary Examiner* — David J. Blanchard
(74) *Attorney, Agent, or Firm* — McAndrews Held & Malloy Ltd.

(57) ABSTRACT

The present invention is in the fields of cell biology, immunology and oncology. The invention provides humanized antibodies that recognize $\alpha_v\beta_6$ integrins, which antibodies comprise a variable region of nonhuman origin and at least a portion of an immunoglobulin of human origin. The invention also provides methods for preparation of such antibodies, pharmaceutical compositions comprising them, and methods of treating, diagnosing and/or preventing various diseases and disorders by administering the humanized anti-$\alpha_v\beta_6$ antibodies of the invention. The invention also relates to the identification of differential expression of the integrin $\alpha_v\beta_6$ on the surfaces of tumor cells and tissues, the use of this differential expression in determining the metastatic potential of tumor cells, and methods of diagnosis and treatment/prevention of tumor metastasis and for elimination of residual metastatic tumor cells using ligands, particularly antibodies, that bind to integrin $\alpha_v\beta_6$.

14 Claims, 79 Drawing Sheets

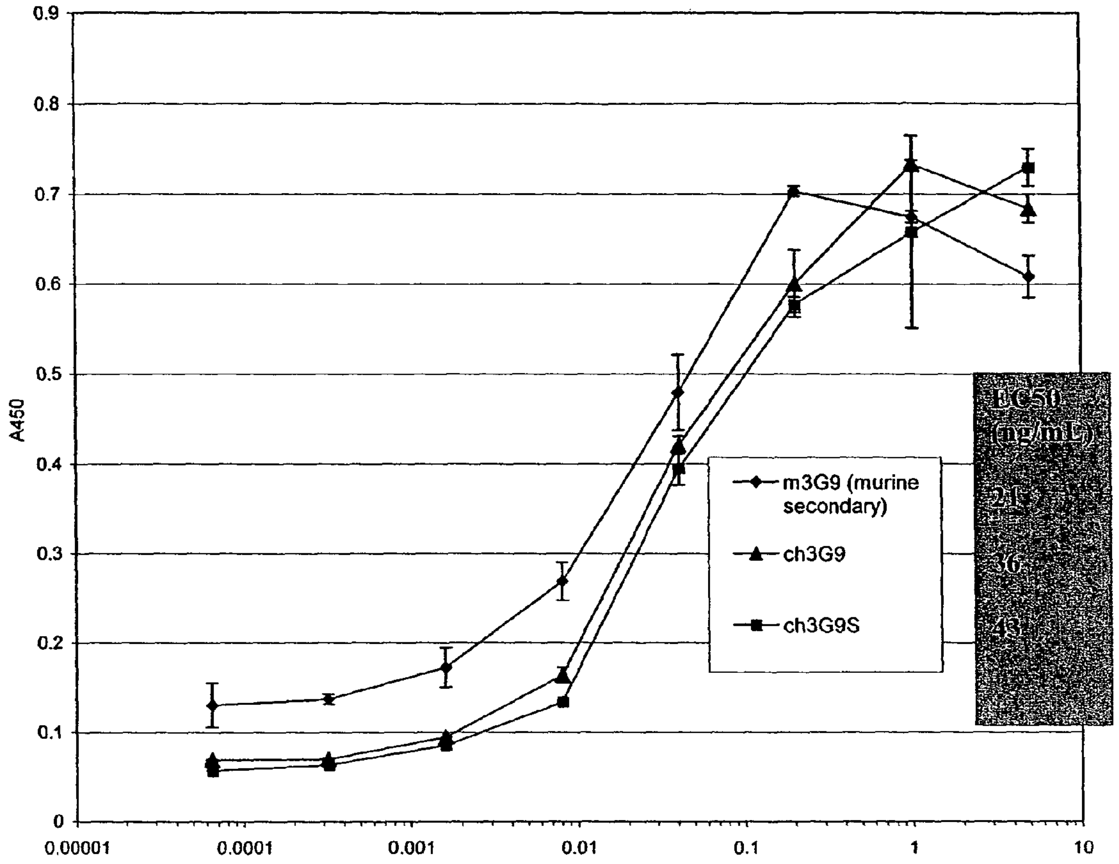
Figure 1. Binding ELISA of purified and chimerized 3G9 antibody variants to $\alpha_v\beta_6$.

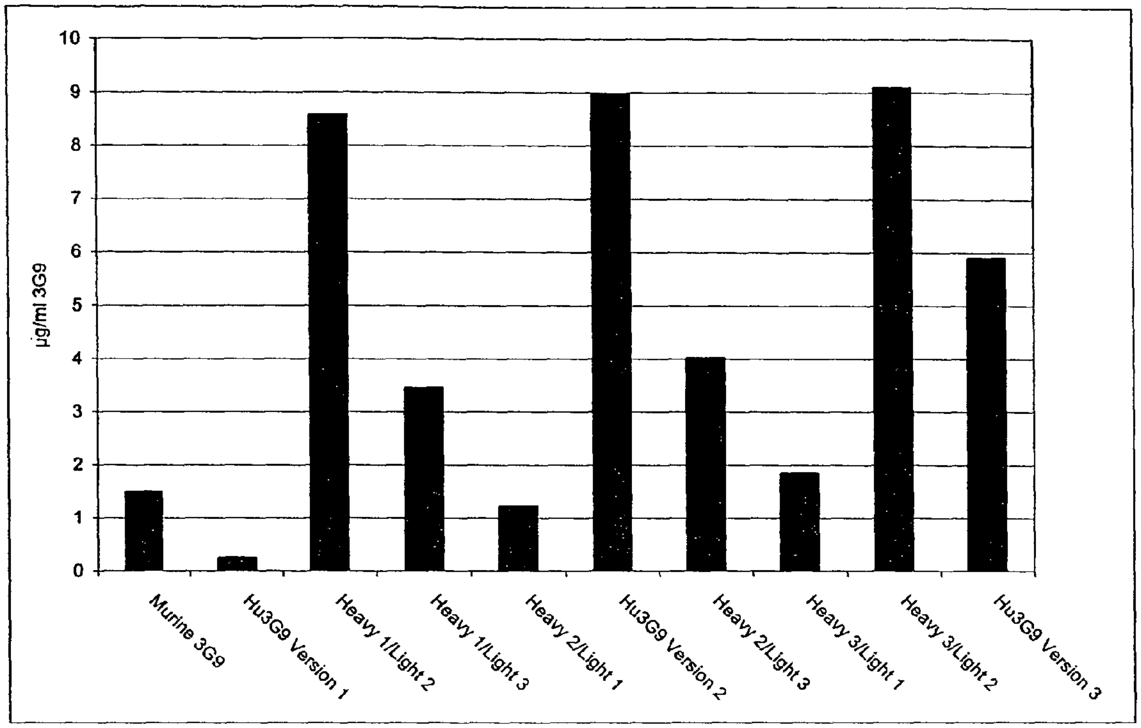
Figure 2. Easy Titer expression analysis of 3G9 humanization variants from transfected 293E cells.

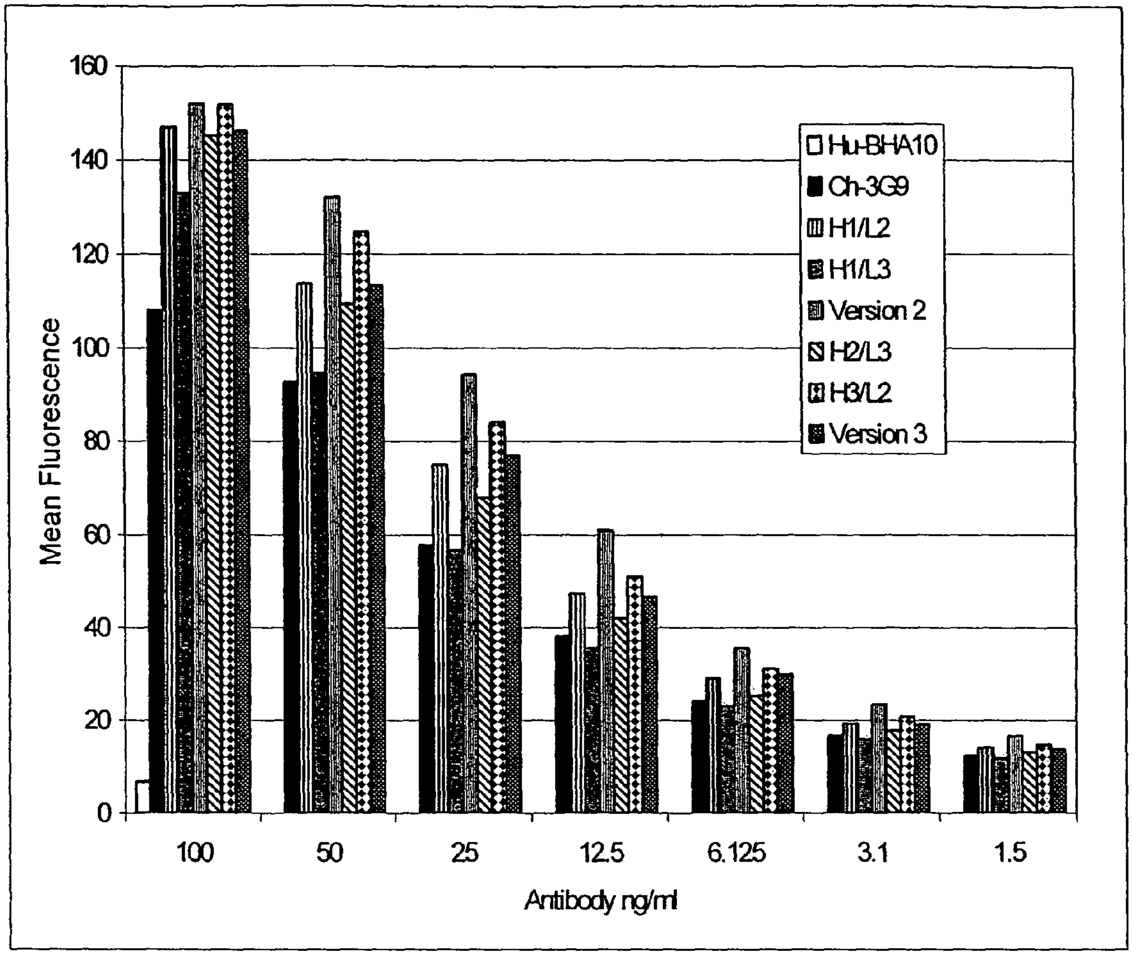
Figure 3. FACS analysis of hu-3G9 antibody variants binding to $\alpha_v\beta_6$ integrin expressing SW480 cells.

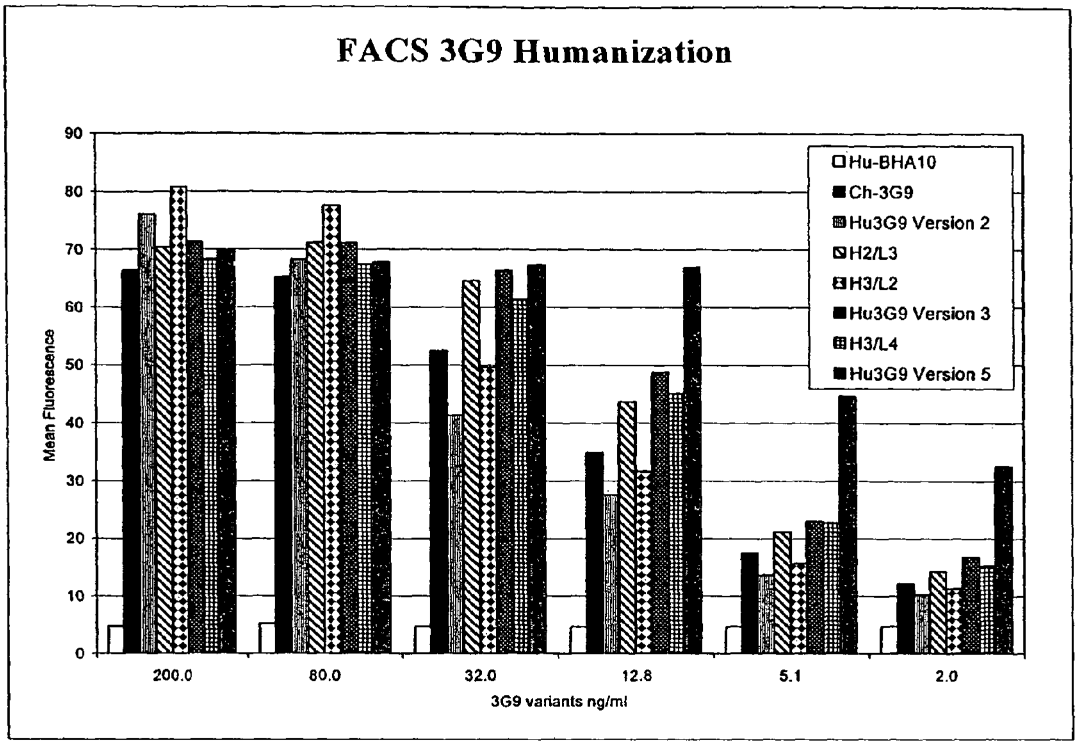
Figure 4. FACS analysis of hu-3G9 antibody versions 2-5 binding to FDCP1-β6 cells.

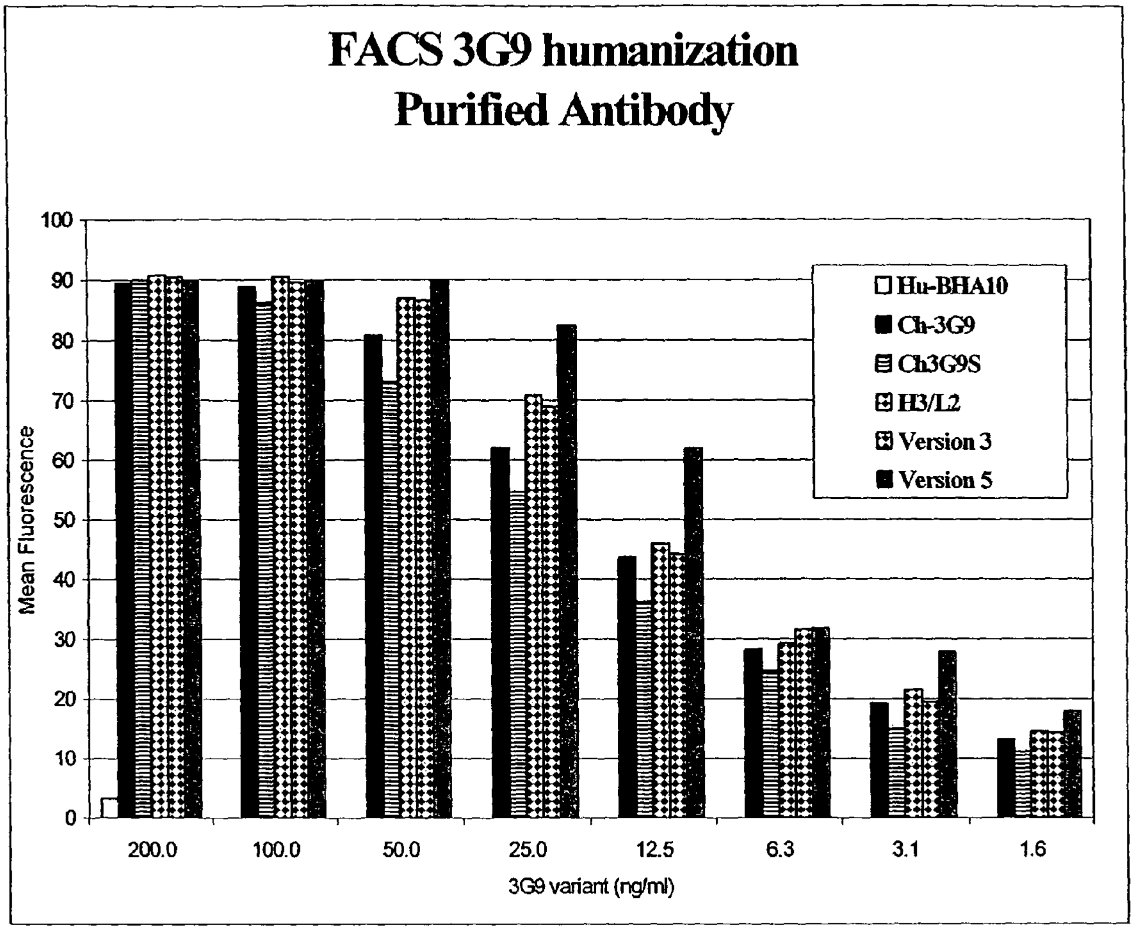
Figure 5. FACS analysis of purified hu-3G9 antibody versions 2-5 binding to FDCP1-β6 cells.

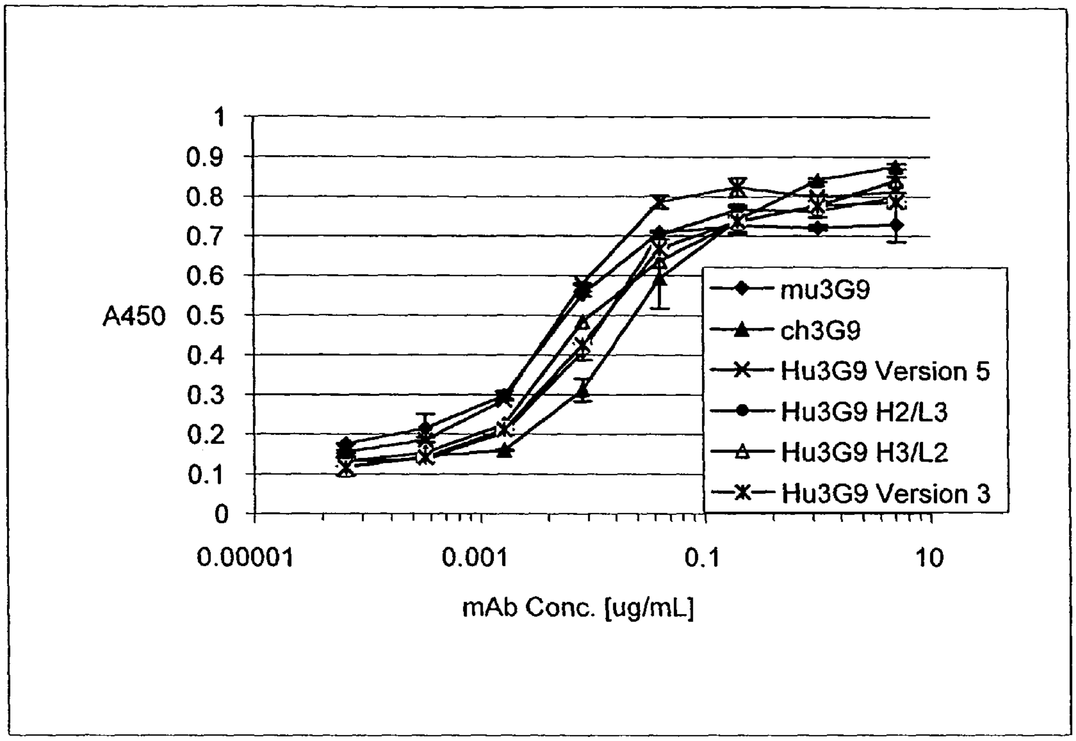
Figure 6. Binding ELISA of purified hu-3G9 antibody versions 2-5 binding to $\alpha_V\beta_6$.

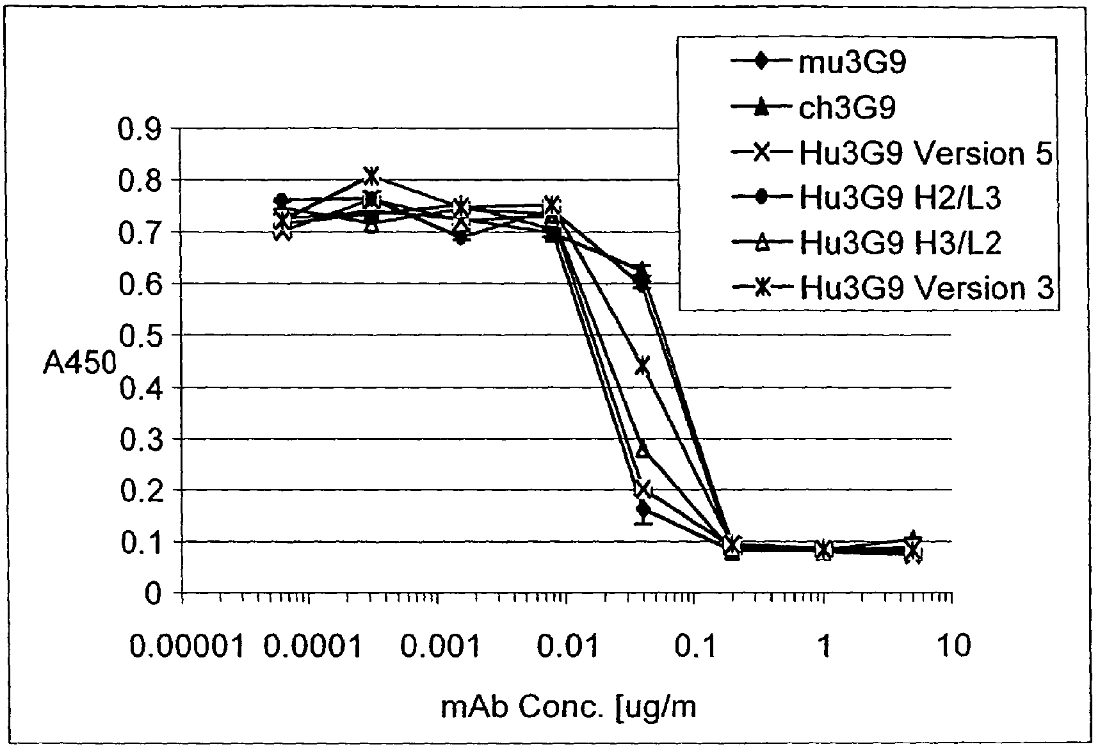
Figure 7. Blocking ELISA of purified hu-3G9 antibody versions 2-5 binding to $\alpha_V\beta_6$.

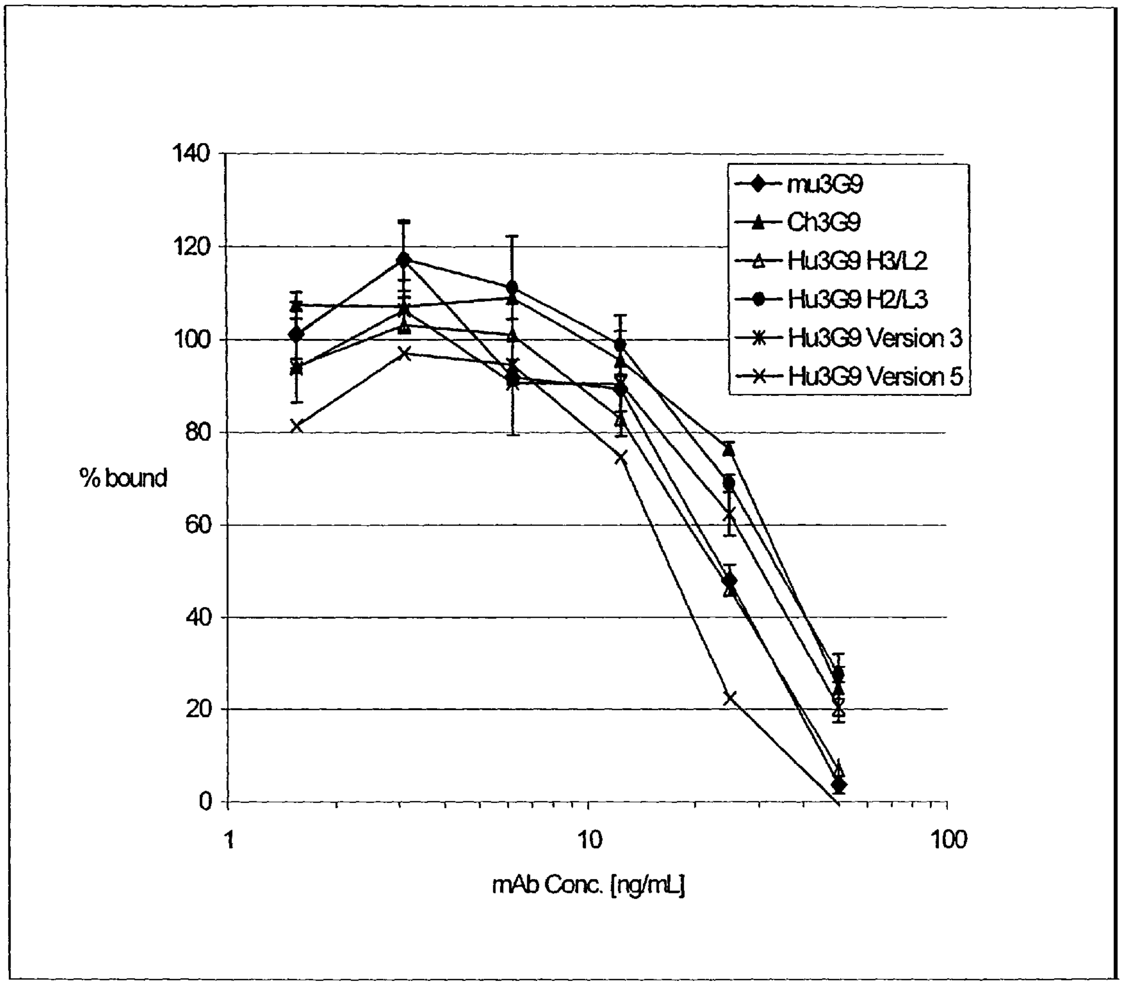
Figure 8. Cell-adhesion assay of purified hu-3G9 antibody versions 2-5.

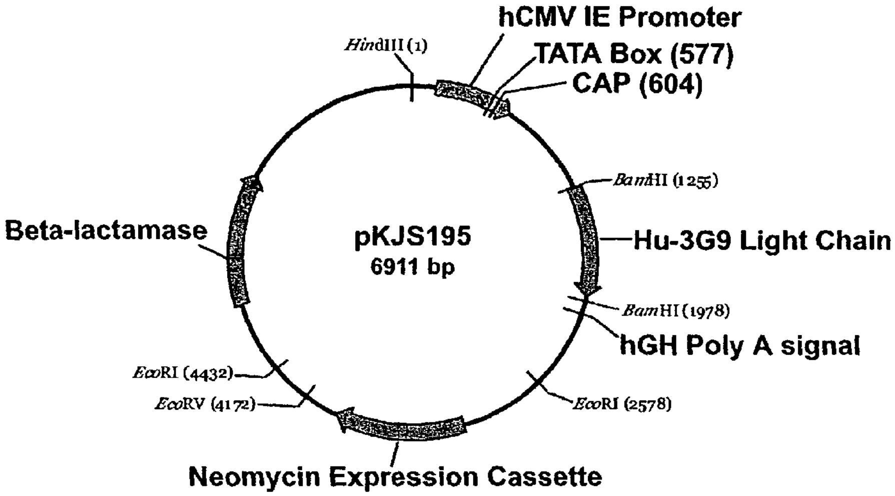

1263 ATG GAC TTC CAG GTG CAG ATC TTC AGC TTC CTG CTG ATC AGC GTG AGC GTG ATC ATG AGC CGC GGC GAG ATC GTG CTG ACC CAG
1 Met Asp Phe Gln Val Gln Ile Phe Ser Phe Leu Leu Ile Ser Val Ser Val Ile Met Ser Arg Gly Glu Ile Val Leu Thr Gln

1347 AGC CCC GCC ACC CTG AGC CTG AGC CCC GGC GAG AGG GCC ACC CTG AGC TGC AGC GCC AGC AGC AGC GTG AGC AGC AGC TAC CTG
29 Ser Pro Ala Thr Leu Ser Leu Ser Pro Gly Glu Arg Ala Thr Leu Ser Cys Ser Ala Ser Ser Ser Val Ser Ser Ser Tyr Leu

1431 TAC TGG TAC CAG CAG AAG CCC GGC CAG GCC CCC AGG CTG CTG ATC TAC AGC ACC AGC AAC CTG GCC AGC GGC ATC CCC GCC CGC
56 Tyr Trp Tyr Gln Gln Lys Pro Gly Gln Ala Pro Arg Leu Leu Ile Tyr Ser Thr Ser Asn Leu Ala Ser Gly Ile Pro Ala Arg

1515 TTC AGC GGC AGC GGC AGC GGC ACC GAC TTC ACC CTG ACC ATC AGC AGC CTG GAG CCC GAG GAC TTC GCC GTG TAC TAC TGC CAC
83 Phe Ser Gly Ser Gly Ser Gly Thr Asp Phe Thr Leu Thr Ile Ser Ser Leu Glu Pro Glu Asp Phe Ala Val Tyr Tyr Cys His

1599 CAG TGG AGC ACC TAC CCC CCC ACC TTC GGC GGC GGC ACC AAG GTG GAG ATC AAG CGT ACG GTG GCT GCA CCA TCT GTC TTC ATC
110 Gln Trp Ser Thr Tyr Pro Pro Thr Phe Gly Gly Gly Thr Lys Val Glu Ile Lys Arg Thr Val Ala Ala Pro Ser Val Phe Ile

1683 TTC CCG CCA TCT GAT GAG CAG TTG AAA TCT GGA ACT GCC TCT GTT GTG TGC CTG CTG AAT AAC TTC TAT CCC AGA GAG GCC AAA
137 Phe Pro Pro Ser Asp Glu Gln Leu Lys Ser Gly Thr Ala Ser Val Val Cys Leu Leu Asn Asn Phe Tyr Pro Arg Glu Ala Lys

1767 GTA CAG TGG AAG GTG GAT AAC GCC CTC CAA TCG GGT AAC TCC CAG GAG AGT GTC ACA GAG CAG GAC AGC AAG GAC AGC ACC TAC
164 Val Gln Trp Lys Val Asp Asn Ala Leu Gln Ser Gly Asn Ser Gln Glu Ser Val Thr Glu Gln Asp Ser Lys Asp Ser Thr Tyr

1851 AGC CTC AGC AGC ACC CTG ACG CTG AGC AAA GCA GAC TAC GAG AAA CAC AAA GTC TAC GCC TGC GAA GTC ACC CAT CAG GGC CTG
191 Ser Leu Ser Ser Thr Leu Thr Leu Ser Lys Ala Asp Tyr Glu Lys His Lys Val Tyr Ala Cys Glu Val Thr His Gln Gly Leu

1935 AGC TCG CCC GTC ACA AAG AGC TTC AAC AGG GGA GAG TGT
218 Ser Ser Pro Val Thr Lys Ser Phe Asn Arg Gly Glu Cys

Figure 9. Plasmid map of pKJS195 and 3G9 version 5 Light Chain Sequence.

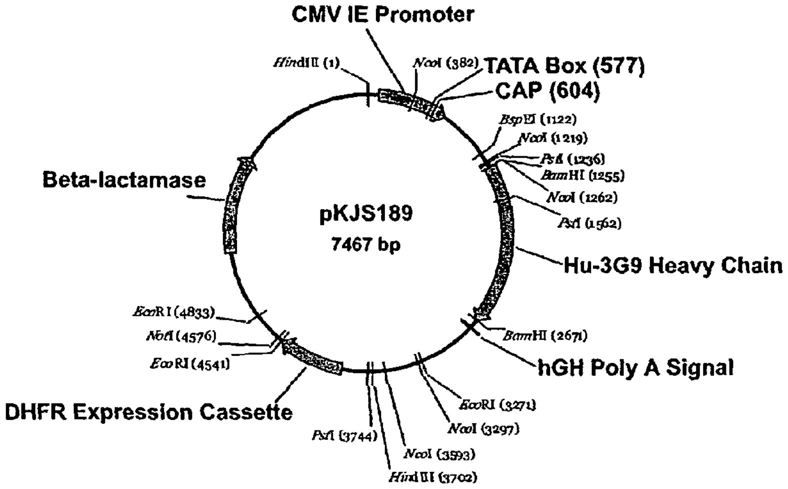

1263 ATG GAC TTC GGC CTG AGC TGG GTG TTC CTG GTG CTG GTG CTG AAG GGC GTG CAG TGC GAG GTG CAG CTG GTG GAG AGC GGC GGC
1 Met Asp Phe Gly Leu Ser Trp Val Phe Leu Val Leu Val Leu Lys Gly Val Gln Cys Glu Val Gln Leu Val Glu Ser Gly Gly

1347 GGC CTG GTG CAG CCC GGC GGC AGC CTG AGG CTG AGC TGC GCC GCC AGC GGC TTC ACC TTC AGC CGC TAC GTG ATG AGC TGG GTG
29 Gly Leu Val Gln Pro Gly Gly Ser Leu Arg Leu Ser Cys Ala Ala Ser Gly Phe Thr Phe Ser Arg Tyr Val Met Ser Trp Val

1431 CGC CAG GCC CCC GGC AAG GGC CTG GAG TGG GTG GCC AGC ATC AGC AGC GGA GGC CGC ATG TAC TAC CCC GAC ACC GTG AAG GGC
57 Arg Gln Ala Pro Gly Lys Gly Leu Glu Trp Val Ala Ser Ile Ser Ser Gly Gly Arg Met Tyr Tyr Pro Asp Thr Val Lys Gly

1515 CGC TTC ACC ATC AGC CGC GAC AAC GCC AAG AAC AGC CTG TAC CTG CAG ATG AAC AGC CTG CGC GCC GAG GAC ACC GCC GTG TAC
85 Arg Phe Thr Ile Ser Arg Asp Asn Ala Lys Asn Ser Leu Tyr Leu Gln Met Asn Ser Leu Arg Ala Glu Asp Thr Ala Val Tyr

1599 TAC TGC GCC CGC GGC AGC ATC TAC GAC GGC TAC TAC GTG TTC CCC TAC TGG GGC CAG GGC ACC CTG GTG ACC GTG AGC TCC GCC
113 Tyr Cys Ala Arg Gly Ser Ile Tyr Asp Gly Tyr Tyr Val Phe Pro Tyr Trp Gly Gln Gly Thr Leu Val Thr Val Ser Ser Ala

1683 AGC ACC AAG GGC CCC AGC GTG TTC CCC CTG GCC CCC AGC AGC AAG AGC ACC AGC GGC GGC ACC GCC GCC CTG GGC TGC CTG GTG
141 Ser Thr Lys Gly Pro Ser Val Phe Pro Leu Ala Pro Ser Ser Lys Ser Thr Ser Gly Gly Thr Ala Ala Leu Gly Cys Leu Val

1767 AAG GAC TAC TTC CCC GAA CCG GTG ACG GTG TCG TGG AAC TCA GGC GCC CTG ACC AGC GGC GTG CAC ACC TTC CCG GCT GTC CTA
169 Lys Asp Tyr Phe Pro Glu Pro Val Thr Val Ser Trp Asn Ser Gly Ala Leu Thr Ser Gly Val His Thr Phe Pro Ala Val Leu

1851 CAG TCC TCA GGA CTC TAC TCC CTC AGC AGC GTG GTG ACC GTG CCC TCC AGC AGC TTG GGC ACC CAG ACC TAC ATC TGC AAC GTG
197 Gln Ser Ser Gly Leu Tyr Ser Leu Ser Ser Val Val Thr Val Pro Ser Ser Ser Leu Gly Thr Gln Thr Tyr Ile Cys Asn Val

1935 AAT CAC AAG CCC AGC AAC ACC AAG GTG GAC AAG AAA GTT GAG CCC AAA TCT TGT GAC AAG ACT CAC ACA TGC CCA CCG TGC CCA
225 Asn His Lys Pro Ser Asn Thr Lys Val Asp Lys Lys Val Glu Pro Lys Ser Cys Asp Lys Thr His Thr Cys Pro Pro Cys Pro

2019 GCA CCT GAA CTC CTG GGG GGA CCG TCA GTC TTC CTC TTC CCC CCA AAA CCC AAG GAC ACC CTC ATG ATC TCC CGG ACC CCT GAG
253 Ala Pro Glu Leu Leu Gly Gly Pro Ser Val Phe Leu Phe Pro Pro Lys Pro Lys Asp Thr Leu Met Ile Ser Arg Thr Pro Glu

2103 GTC ACA TGC GTG GTG GTG GAC GTG AGC CAC GAA GAC CCT GAG GTC AAG TTC AAC TGG TAC GTG GAC GGC GTG GAG GTG CAT AAT
281 Val Thr Cys Val Val Val Asp Val Ser His Glu Asp Pro Glu Val Lys Phe Asn Trp Tyr Val Asp Gly Val Glu Val His Asn

2187 GCC AAG ACA AAG CCG CGG GAG GAG CAG TAC AAC AGC ACG TAC CGT GTG GTC AGC GTC CTC ACC GTC CTG CAC CAG GAC TGG CTG
309 Ala Lys Thr Lys Pro Arg Glu Glu Gln Tyr Asn Ser Thr Tyr Arg Val Val Ser Val Leu Thr Val Leu His Gln Asp Trp Leu

2271 AAT GGC AAG GAG TAC AAG TGC AAG GTC TCC AAC AAA GCC CTC CCA GCC CCC ATC GAG AAA ACC ATC TCC AAA GCC AAA GGG CAG
337 Asn Gly Lys Glu Tyr Lys Cys Lys Val Ser Asn Lys Ala Leu Pro Ala Pro Ile Glu Lys Thr Ile Ser Lys Ala Lys Gly Gln

2355 CCC CGA GAA CCA CAG GTG TAC ACC CTG CCC CCA TCC CGG GAT GAG CTG ACC AAG AAC CAG GTC AGC CTG ACC TGC CTG GTC AAA
365 Pro Arg Glu Pro Gln Val Tyr Thr Leu Pro Pro Ser Arg Asp Glu Leu Thr Lys Asn Gln Val Ser Leu Thr Cys Leu Val Lys

2439 GGC TTC TAT CCC AGC GAC ATC GCC GTG GAG TGG GAG AGC AAT GGG CAG CCG GAG AAC AAC TAC AAG ACC ACG CCT CCC GTG TTG
393 Gly Phe Tyr Pro Ser Asp Ile Ala Val Glu Trp Glu Ser Asn Gly Gln Pro Glu Asn Asn Tyr Lys Thr Thr Pro Pro Val Leu

2523 GAC TCC GAC GGC TCC TTC TTC CTC TAC AGC AAG CTC ACC GTG GAC AAG AGC AGG TGG CAG CAG GGG AAC GTC TTC TCA TGC TCC
421 Asp Ser Asp Gly Ser Phe Phe Leu Tyr Ser Lys Leu Thr Val Asp Lys Ser Arg Trp Gln Gln Gly Asn Val Phe Ser Cys Ser

2607 GTG ATG CAT GAG GCT CTG CAC AAC CAC TAC ACG CAG AAG AGC CTC TCC CTG TCT CCC GGT
449 Val Met His Glu Ala Leu His Asn His Tyr Thr Gln Lys Ser Leu Ser Leu Ser Pro Gly

Figure 10. Plasmid map of pKJS189 and 3G9 version 3 Heavy Chain Sequence.

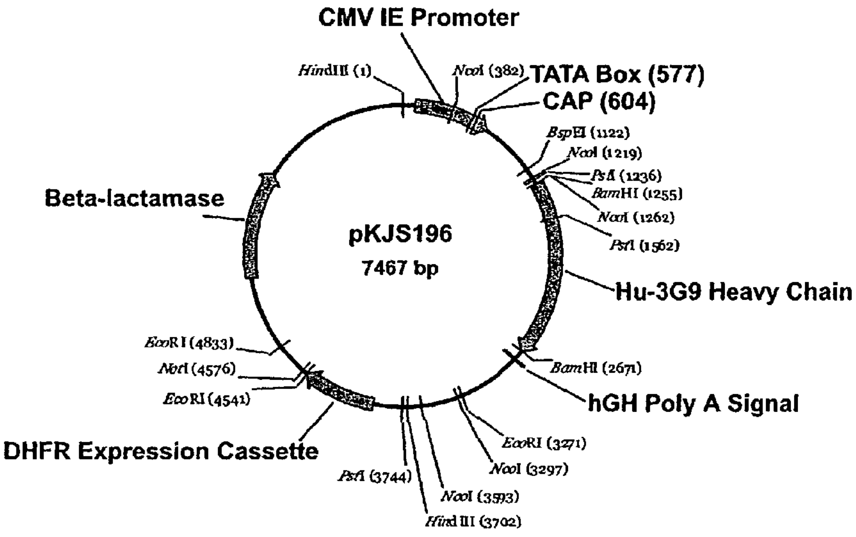

```
1263  ATG GAC TTC GGC CTG AGC TGG GTG TTC CTG GTG CTG GTG CTG AAG GGC GTG CAG TGC GAG GTG CAG CTG GTG GAG AGC GGC GGC
1     Met Asp Phe Gly Leu Ser Trp Val Phe Leu Val Leu Val Leu Lys Gly Val Gln Cys Glu Val Gln Leu Val Glu Ser Gly Gly
1347  GGC CTG GTG CAG CCC GGC GGC AGC CTG AGG CTG AGC TGC GCC GCC AGC GGC TTC ACC TTC AGC CGC TAC GTG ATG AGC TGG GTG
29    Gly Leu Val Gln Pro Gly Gly Ser Leu Arg Leu Ser Cys Ala Ala Ser Gly Phe Thr Phe Ser Arg Tyr Val Met Ser Trp Val
1431  CGC CAG GCC CCC GGC AAG GGC CTG GAG TGG GTG GCC AGC ATC AGC AGC GGA GGC CGC ATG TAC TAC CCC GAC ACC GTG AAG GGC
57    Arg Gln Ala Pro Gly Lys Gly Leu Glu Trp Val Ala Ser Ile Ser Ser Gly Gly Arg Met Tyr Tyr Pro Asp Thr Val Lys Gly
1515  CGC TTC ACC ATC AGC CGC GAC AAC GCC AAG AAC AGC CTG TAC CTG CAG ATG AAC AGC CTG CGC GCC GAG GAC ACC GCC GTG TAC
85    Arg Phe Thr Ile Ser Arg Asp Asn Ala Lys Asn Ser Leu Tyr Leu Gln Met Asn Ser Leu Arg Ala Glu Asp Thr Ala Val Tyr
1599  TAC TGC GCC CGC GGC AGC ATC TAC GAC GGC TAC TAC GTG TTC CCC TAC TGG GGC CAG GGC ACC CTG GTG ACC GTG AGC TCC GCC
113   Tyr Cys Ala Arg Gly Ser Ile Tyr Asp Gly Tyr Tyr Val Phe Pro Tyr Trp Gly Gln Gly Thr Leu Val Thr Val Ser Ser Ala
1683  AGC ACC AAG GGC CCC AGC GTG TTC CCC CTG GCC CCC AGC AGC AAG AGC ACC AGC GGC GGC ACC GCC GCC CTG GGC TGC CTG GTG
141   Ser Thr Lys Gly Pro Ser Val Phe Pro Leu Ala Pro Ser Ser Lys Ser Thr Ser Gly Gly Thr Ala Ala Leu Gly Cys Leu Val
1767  AAG GAC TAC TTC CCC GAA CCG GTG ACG GTG TCG TGG AAC TCA GGC GCC CTG ACC AGC GGC GTG CAC ACC TTC CCG GCT GTC CTA
169   Lys Asp Tyr Phe Pro Glu Pro Val Thr Val Ser Trp Asn Ser Gly Ala Leu Thr Ser Gly Val His Thr Phe Pro Ala Val Leu
1851  CAG TCC TCA GGA CTC TAC TCC CTC AGC AGC GTG GTG ACC GTG CCC TCC AGC AGC TTG GGC ACC CAG ACC TAC ATC TGC AAC GTG
197   Gln Ser Ser Gly Leu Tyr Ser Leu Ser Ser Val Val Thr Val Pro Ser Ser Ser Leu Gly Thr Gln Thr Tyr Ile Cys Asn Val
1935  AAT CAC AAG CCC AGC AAC ACC AAG GTG GAC AAG AAA GTT GAG CCC AAA TCT TGT GAC AAG ACT CAC ACA TGC CCA CCG TGC CCA
225   Asn His Lys Pro Ser Asn Thr Lys Val Asp Lys Lys Val Glu Pro Lys Ser Cys Asp Lys Thr His Thr Cys Pro Pro Cys Pro
2019  GCA CCT GAA CTC CTG GGG GGA CCG TCA GTC TTC CTC TTC CCC CCA AAA CCC AAG GAC ACC CTC ATG ATC TCC CGG ACC CCT GAG
253   Ala Pro Glu Leu Leu Gly Gly Pro Ser Val Phe Leu Phe Pro Pro Lys Pro Lys Asp Thr Leu Met Ile Ser Arg Thr Pro Glu
2103  GTC ACA TGC GTG GTG GTG GAC GTG AGC CAC GAA GAC CCT GAG GTC AAG TTC AAC TGG TAC GTG GAC GGC GTG GAG GTG CAT AAT
281   Val Thr Cys Val Val Val Asp Val Ser His Glu Asp Pro Glu Val Lys Phe Asn Trp Tyr Val Asp Gly Val Glu Val His Asn
2187  GCC AAG ACA AAG CCG CGG GAG GAG CAG TAC CAG AGC ACG TAC CGT GTG GTC AGC GTC CTC ACC GTC CTG CAC CAG GAC TGG CTG
309   Ala Lys Thr Lys Pro Arg Glu Glu Gln Tyr Gln Ser Thr Tyr Arg Val Val Ser Val Leu Thr Val Leu His Gln Asp Trp Leu
2271  AAT GGC AAG GAG TAC AAG TGC AAG GTC TCC AAC AAA GCC CTC CCA GCC CCC ATC GAG AAA ACC ATC TCC AAA GCC AAA GGG CAG
337   Asn Gly Lys Glu Tyr Lys Cys Lys Val Ser Asn Lys Ala Leu Pro Ala Pro Ile Glu Lys Thr Ile Ser Lys Ala Lys Gly Gln
2355  CCC CGA GAA CCA CAG GTG TAC ACC CTG CCC CCA TCC CGG GAT GAG CTG ACC AAG AAC CAG GTC AGC CTG ACC TGC CTG GTC AAA
365   Pro Arg Glu Pro Gln Val Tyr Thr Leu Pro Pro Ser Arg Asp Glu Leu Thr Lys Asn Gln Val Ser Leu Thr Cys Leu Val Lys
2439  GGC TTC TAT CCC AGC GAC ATC GCC GTG GAG TGG GAG AGC AAT GGG CAG CCG GAG AAC AAC TAC AAG ACC ACG CCT CCC GTG TTG
393   Gly Phe Tyr Pro Ser Asp Ile Ala Val Glu Trp Glu Ser Asn Gly Gln Pro Glu Asn Asn Tyr Lys Thr Thr Pro Pro Val Leu
2523  GAC TCC GAC GGC TCC TTC TTC CTC TAC AGC AAG CTC ACC GTG GAC AAG AGC AGG TGG CAG CAG GGG AAC GTC TTC TCA TGC TCC
421   Asp Ser Asp Gly Ser Phe Phe Leu Tyr Ser Lys Leu Thr Val Asp Lys Ser Arg Trp Gln Gln Gly Asn Val Phe Ser Cys Ser
2607  GTG ATG CAT GAG GCT CTG CAC AAC CAC TAC ACG CAG AAG AGC CTC TCC CTG TCT CCC GGT
449   Val Met His Glu Ala Leu His Asn His Tyr Thr Gln Lys Ser Leu Ser Leu Ser Pro Gly
```

Figure 11. Plasmid map of pKJS196 and Aglycosyl 3G9 version 3 Heavy Chain Sequence.

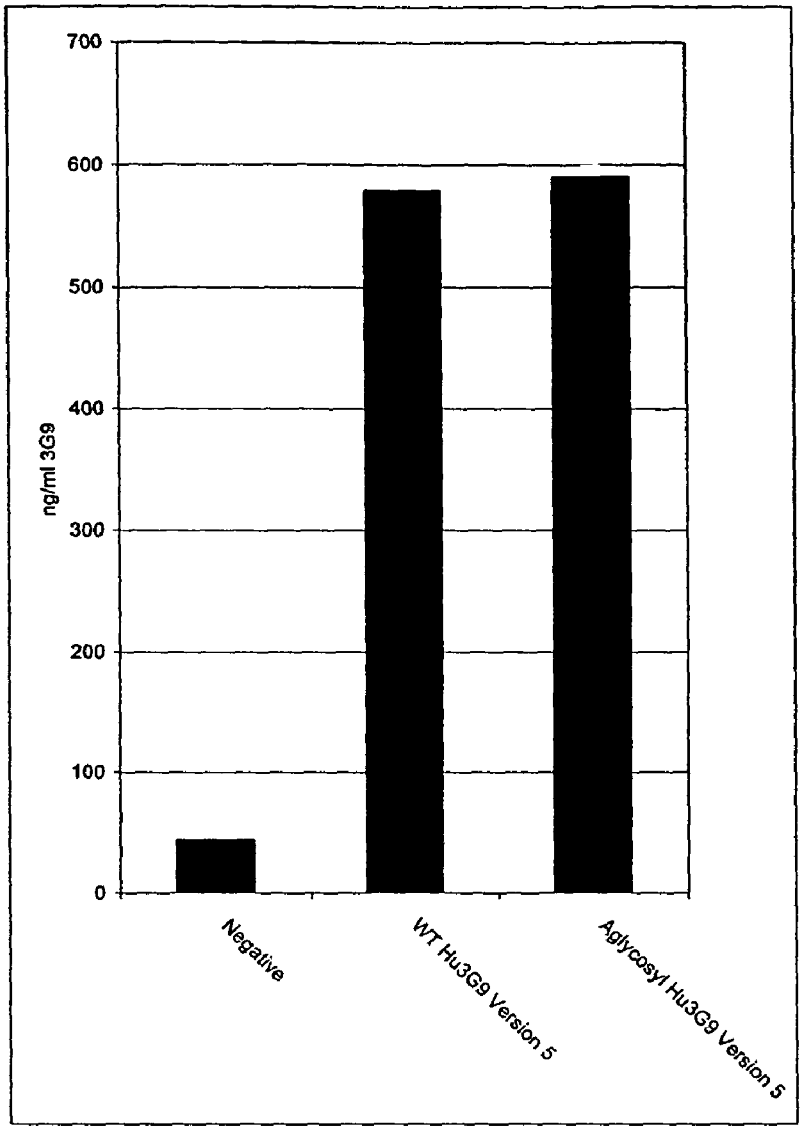
Figure 12. Easy Titer assay of CHO cells transiently transfected with hu-3G9 CHO expression vectors.

Matched cases
Pancreatic Adenocarcinoma, *Ductal*

Matched cases
Pancreatic Carcinoma

Figure 26
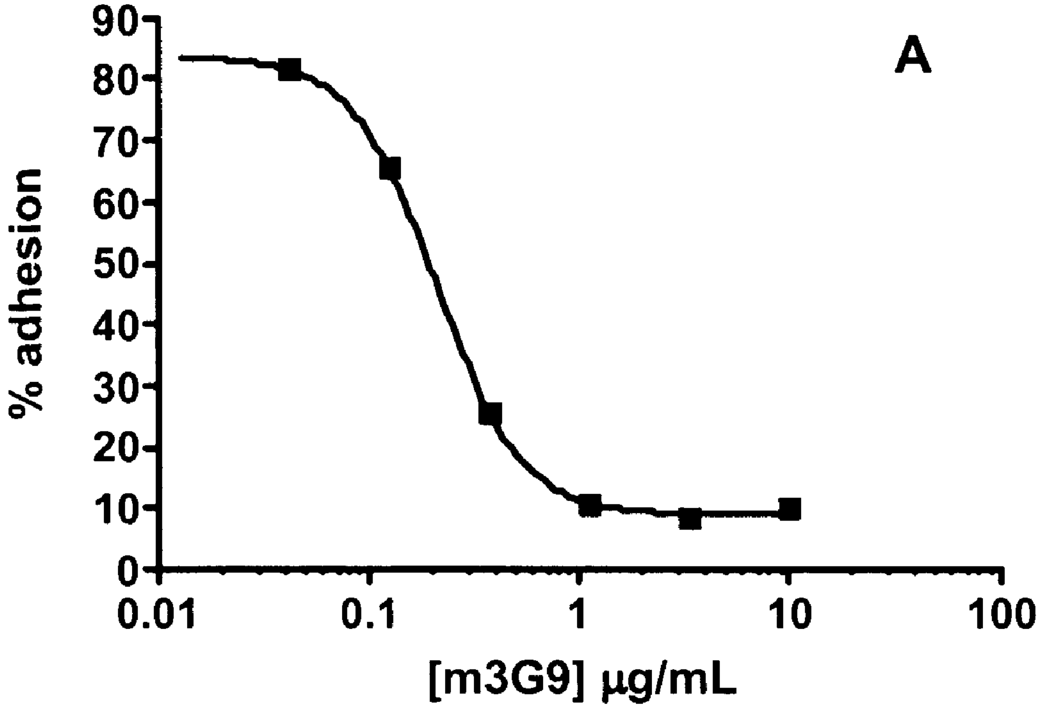
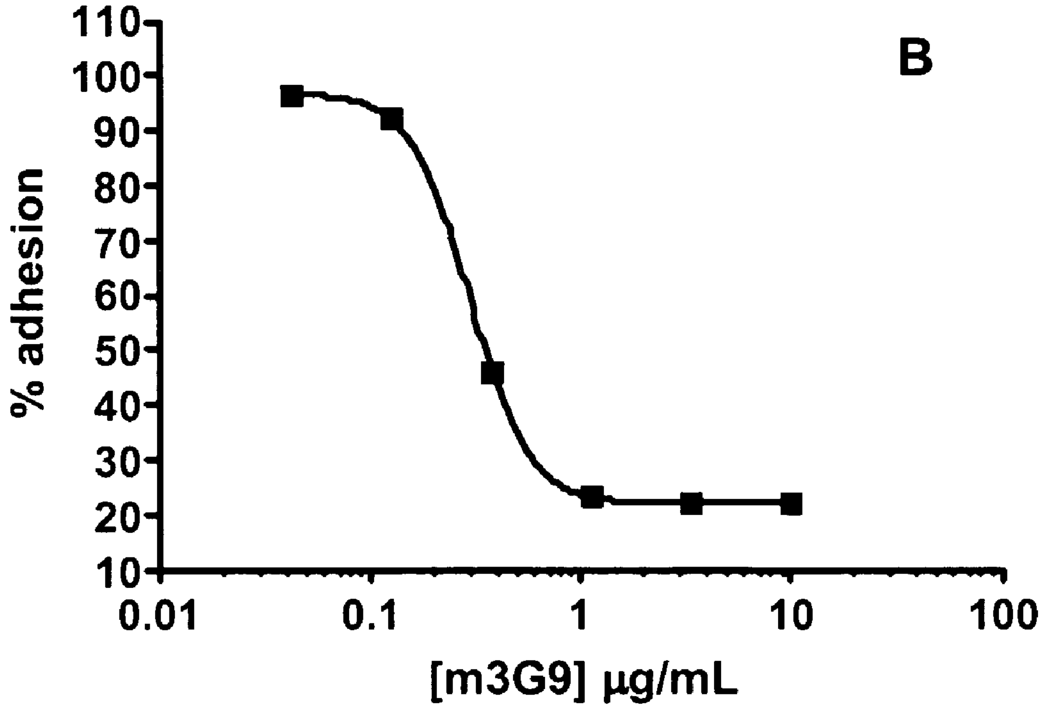

A

B

Medulla

C

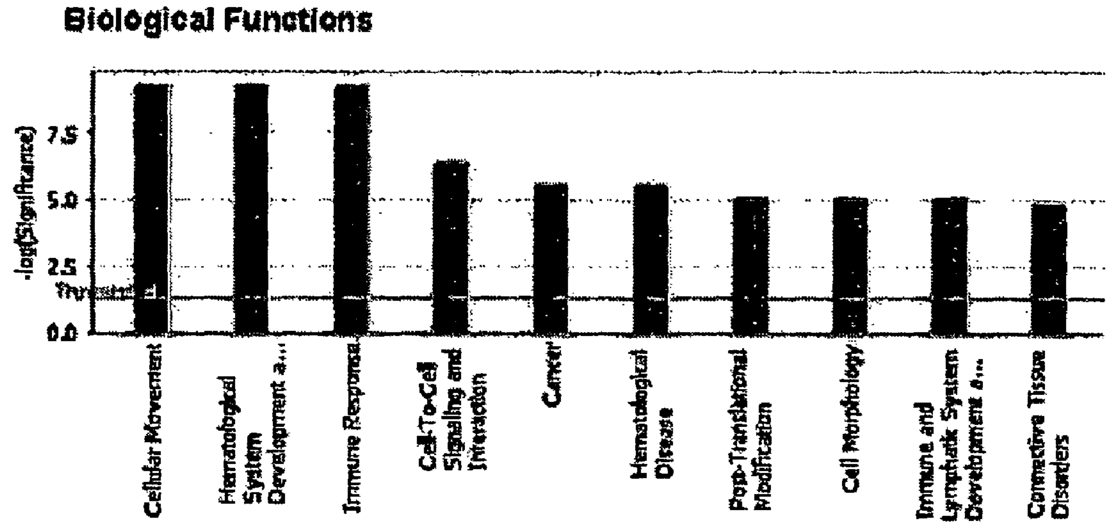
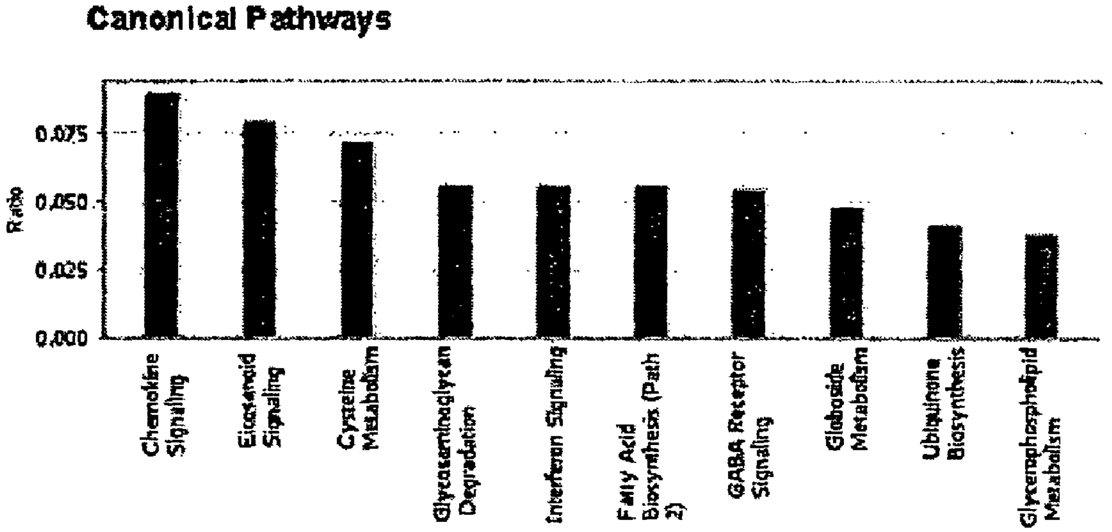
FIGURE 68

SEQUENCE LISTING

```
<160> NUMBER OF SEQ ID NOS: 152

<210> SEQ ID NO 1
<211> LENGTH: 120
<212> TYPE: PRT
<213> ORGANISM: Artificial Sequence
<220> FEATURE:
<223> OTHER INFORMATION: Humanized 3G9 Heavy Chain

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Ser Trp Val Arg Gln Ala Pro Gly Lys Gly Leu Glu Trp Val
        35                  40                  45

Ala Ser Ile Ser Ser Gly Gly Arg Met Tyr Tyr Pro Asp Thr Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Ile Tyr Asp Gly Tyr Tyr Val Phe Pro Tyr Trp Gly Gln
            100                 105                 110

Gly Thr Leu Val Thr Val Ser Ser
        115                 120


<210> SEQ ID NO 2
<211> LENGTH: 108
<212> TYPE: PRT
<213> ORGANISM: Artificial Sequence
<220> FEATURE:
<223> OTHER INFORMATION: Humanized 3G9 Light Chain

<400> SEQUENCE: 2

Glu Ile Val Leu Thr Gln Ser Pro Ala Thr Leu Ser Leu Ser Pro Gly
1               5                   10                  15
```

```
Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Thr Tyr Pro
                85                  90                  95

Pro Thr Phe Gly Gly Gly Thr Lys Val Glu Ile Lys
            100                 105


<210> SEQ ID NO 3
<211> LENGTH: 126
<212> TYPE: PRT
<213> ORGANISM: Artificial Sequence
<220> FEATURE:
<223> OTHER INFORMATION: Humanized 8G6 Heavy Chain

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Met
        35                  40                  45

Gly Val Ile Ser Thr Tyr Tyr Gly Asn Thr Asn Tyr Asn Gln Lys Phe
    50                  55                  60

Lys Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Leu Arg Arg Gly Asp Arg Pro Ser Leu Arg Tyr Ala
            100                 105                 110

Met Asp Tyr Trp Gly Gln Gly Thr Leu Val Thr Val Ser Ser
        115                 120                 125


<210> SEQ ID NO 4
<211> LENGTH: 111
<212> TYPE: PRT
<213> ORGANISM: Artificial Sequence
<220> FEATURE:
<223> OTHER INFORMATION: Humanized 8G6 Light Chain

<400> SEQUENCE: 4

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Ser Tyr Ser Tyr Met Tyr Trp Tyr Gln Gln Lys Pro Gly Gln Ala Pro
        35                  40                  45

Arg Leu Leu Ile Tyr Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Asn Trp
                85                  90                  95
```

```
Glu Ile Pro Phe Thr Phe Gly Gly Gly Thr Lys Val Glu Ile Lys
            100                 105                 110


<210> SEQ ID NO 5
<211> LENGTH: 711
<212> TYPE: DNA
<213> ORGANISM: Artificial Sequence
<220> FEATURE:
<223> OTHER INFORMATION: pKJS195 vector - 3G9 version 5 light chain
<220> FEATURE:
<221> NAME/KEY: CDS
<222> LOCATION: (1)..(711)

<400> SEQUENCE: 5

atg gac ttc cag gtg cag atc ttc agc ttc ctg ctg atc agc gtg agc       48
Met Asp Phe Gln Val Gln Ile Phe Ser Phe Leu Leu Ile Ser Val Ser
1               5                   10                  15

gtg atc atg agc cgc ggc gag atc gtg ctg acc cag agc ccc gcc acc       96
Val Ile Met Ser Arg Gly Glu Ile Val Leu Thr Gln Ser Pro Ala Thr
            20                  25                  30

ctg agc ctg agc ccc ggc gag agg gcc acc ctg agc tgc agc gcc agc      144
Leu Ser Leu Ser Pro Gly Glu Arg Ala Thr Leu Ser Cys Ser Ala Ser
        35                  40                  45

agc agc gtg agc agc agc tac ctg tac tgg tac cag cag aag ccc ggc      192
Ser Ser Val Ser Ser Ser Tyr Leu Tyr Trp Tyr Gln Gln Lys Pro Gly
    50                  55                  60

cag gcc ccc agg ctg ctg atc tac agc acc agc aac ctg gcc agc ggc      240
Gln Ala Pro Arg Leu Leu Ile Tyr Ser Thr Ser Asn Leu Ala Ser Gly
65                  70                  75                  80

atc ccc gcc cgc ttc agc ggc agc ggc agc ggc acc gac ttc acc ctg      288
Ile Pro Ala Arg Phe Ser Gly Ser Gly Ser Gly Thr Asp Phe Thr Leu
                85                  90                  95

acc atc agc agc ctg gag ccc gag gac ttc gcc gtg tac tac tgc cac      336
Thr Ile Ser Ser Leu Glu Pro Glu Asp Phe Ala Val Tyr Tyr Cys His
            100                 105                 110

cag tgg agc acc tac ccc ccc acc ttc ggc ggc ggc acc aag gtg gag      384
Gln Trp Ser Thr Tyr Pro Pro Thr Phe Gly Gly Gly Thr Lys Val Glu
        115                 120                 125

atc aag cgt acg gtg gct gca cca tct gtc ttc atc ttc ccg cca tct      432
Ile Lys Arg Thr Val Ala Ala Pro Ser Val Phe Ile Phe Pro Pro Ser
    130                 135                 140

gat gag cag ttg aaa tct gga act gcc tct gtt gtg tgc ctg ctg aat      480
Asp Glu Gln Leu Lys Ser Gly Thr Ala Ser Val Val Cys Leu Leu Asn
145                 150                 155                 160

aac ttc tat ccc aga gag gcc aaa gta cag tgg aag gtg gat aac gcc      528
Asn Phe Tyr Pro Arg Glu Ala Lys Val Gln Trp Lys Val Asp Asn Ala
                165                 170                 175

ctc caa tcg ggt aac tcc cag gag agt gtc aca gag cag gac agc aag      576
Leu Gln Ser Gly Asn Ser Gln Glu Ser Val Thr Glu Gln Asp Ser Lys
            180                 185                 190

gac agc acc tac agc ctc agc agc acc ctg acg ctg agc aaa gca gac      624
Asp Ser Thr Tyr Ser Leu Ser Ser Thr Leu Thr Leu Ser Lys Ala Asp
        195                 200                 205

tac gag aaa cac aaa gtc tac gcc tgc gaa gtc acc cat cag ggc ctg      672
Tyr Glu Lys His Lys Val Tyr Ala Cys Glu Val Thr His Gln Gly Leu
    210                 215                 220

agc tcg ccc gtc aca aag agc ttc aac agg gga gag tgt                  711
Ser Ser Pro Val Thr Lys Ser Phe Asn Arg Gly Glu Cys
225                 230                 235


<210> SEQ ID NO 6
<211> LENGTH: 1404
```

```
<212> TYPE: DNA
<213> ORGANISM: Artificial sequence
<220> FEATURE:
<223> OTHER INFORMATION: pKJS189 vector - 3G9 vector 3 heavy chain
<220> FEATURE:
<221> NAME/KEY: CDS
<222> LOCATION: (1)..(1404)

<400> SEQUENCE: 6

atg gac ttc ggc ctg agc tgg gtg ttc ctg gtg ctg gtg ctg aag ggc       48
Met Asp Phe Gly Leu Ser Trp Val Phe Leu Val Leu Val Leu Lys Gly
1               5                   10                  15

gtg cag tgc gag gtg cag ctg gtg gag agc ggc ggc ggc ctg gtg cag       96
Val Gln Cys Glu Val Gln Leu Val Glu Ser Gly Gly Gly Leu Val Gln
            20                  25                  30

ccc ggc ggc agc ctg agg ctg agc tgc gcc gcc agc ggc ttc acc ttc      144
Pro Gly Gly Ser Leu Arg Leu Ser Cys Ala Ala Ser Gly Phe Thr Phe
        35                  40                  45

agc cgc tac gtg atg agc tgg gtg cgc cag gcc ccc ggc aag ggc ctg      192
Ser Arg Tyr Val Met Ser Trp Val Arg Gln Ala Pro Gly Lys Gly Leu
    50                  55                  60

gag tgg gtg gcc agc atc agc agc gga ggc cgc atg tac tac ccc gac      240
Glu Trp Val Ala Ser Ile Ser Ser Gly Gly Arg Met Tyr Tyr Pro Asp
65                  70                  75                  80

acc gtg aag ggc cgc ttc acc atc agc cgc gac aac gcc aag aac agc      288
Thr Val Lys Gly Arg Phe Thr Ile Ser Arg Asp Asn Ala Lys Asn Ser
                85                  90                  95

ctg tac ctg cag atg aac agc ctg cgc gcc gag gac acc gcc gtg tac      336
Leu Tyr Leu Gln Met Asn Ser Leu Arg Ala Glu Asp Thr Ala Val Tyr
            100                 105                 110

tac tgc gcc cgc ggc agc atc tac gac ggc tac tac gtg ttc ccc tac      384
Tyr Cys Ala Arg Gly Ser Ile Tyr Asp Gly Tyr Tyr Val Phe Pro Tyr
        115                 120                 125

tgg ggc cag ggc acc ctg gtg acc gtg agc tcc gcc agc acc aag ggc      432
Trp Gly Gln Gly Thr Leu Val Thr Val Ser Ser Ala Ser Thr Lys Gly
    130                 135                 140

ccc agc gtg ttc ccc ctg gcc ccc agc agc aag agc acc agc ggc ggc      480
Pro Ser Val Phe Pro Leu Ala Pro Ser Ser Lys Ser Thr Ser Gly Gly
145                 150                 155                 160

acc gcc gcc ctg ggc tgc ctg gtg aag gac tac ttc ccc gaa ccg gtg      528
Thr Ala Ala Leu Gly Cys Leu Val Lys Asp Tyr Phe Pro Glu Pro Val
                165                 170                 175

acg gtg tcg tgg aac tca ggc gcc ctg acc agc ggc gtg cac acc ttc      576
Thr Val Ser Trp Asn Ser Gly Ala Leu Thr Ser Gly Val His Thr Phe
            180                 185                 190

ccg gct gtc cta cag tcc tca gga ctc tac tcc ctc agc agc gtg gtg      624
Pro Ala Val Leu Gln Ser Ser Gly Leu Tyr Ser Leu Ser Ser Val Val
        195                 200                 205

acc gtg ccc tcc agc agc ttg ggc acc cag acc tac atc tgc aac gtg      672
Thr Val Pro Ser Ser Ser Leu Gly Thr Gln Thr Tyr Ile Cys Asn Val
    210                 215                 220

aat cac aag ccc agc aac acc aag gtg gac aag aaa gtt gag ccc aaa      720
Asn His Lys Pro Ser Asn Thr Lys Val Asp Lys Lys Val Glu Pro Lys
225                 230                 235                 240

tct tgt gac aag act cac aca tgc cca ccg tgc cca gca cct gaa ctc      768
Ser Cys Asp Lys Thr His Thr Cys Pro Pro Cys Pro Ala Pro Glu Leu
                245                 250                 255

ctg ggg gga ccg tca gtc ttc ctc ttc ccc cca aaa ccc aag gac acc      816
Leu Gly Gly Pro Ser Val Phe Leu Phe Pro Pro Lys Pro Lys Asp Thr
            260                 265                 270

ctc atg atc tcc cgg acc cct gag gtc aca tgc gtg gtg gtg gac gtg      864
Leu Met Ile Ser Arg Thr Pro Glu Val Thr Cys Val Val Val Asp Val
```

```
        275                 280                 285

agc cac gaa gac cct gag gtc aag ttc aac tgg tac gtg gac ggc gtg      912
Ser His Glu Asp Pro Glu Val Lys Phe Asn Trp Tyr Val Asp Gly Val
    290                 295                 300

gag gtg cat aat gcc aag aca aag ccg cgg gag gag cag tac aac agc      960
Glu Val His Asn Ala Lys Thr Lys Pro Arg Glu Glu Gln Tyr Asn Ser
305                 310                 315                 320

acg tac cgt gtg gtc agc gtc ctc acc gtc ctg cac cag gac tgg ctg     1008
Thr Tyr Arg Val Val Ser Val Leu Thr Val Leu His Gln Asp Trp Leu
                325                 330                 335

aat ggc aag gag tac aag tgc aag gtc tcc aac aaa gcc ctc cca gcc     1056
Asn Gly Lys Glu Tyr Lys Cys Lys Val Ser Asn Lys Ala Leu Pro Ala
            340                 345                 350

ccc atc gag aaa acc atc tcc aaa gcc aaa ggg cag ccc cga gaa cca     1104
Pro Ile Glu Lys Thr Ile Ser Lys Ala Lys Gly Gln Pro Arg Glu Pro
        355                 360                 365

cag gtg tac acc ctg ccc cca tcc cgg gat gag ctg acc aag aac cag     1152
Gln Val Tyr Thr Leu Pro Pro Ser Arg Asp Glu Leu Thr Lys Asn Gln
    370                 375                 380

gtc agc ctg acc tgc ctg gtc aaa ggc ttc tat ccc agc gac atc gcc     1200
Val Ser Leu Thr Cys Leu Val Lys Gly Phe Tyr Pro Ser Asp Ile Ala
385                 390                 395                 400

gtg gag tgg gag agc aat ggg cag ccg gag aac aac tac aag acc acg     1248
Val Glu Trp Glu Ser Asn Gly Gln Pro Glu Asn Asn Tyr Lys Thr Thr
                405                 410                 415

cct ccc gtg ttg gac tcc gac ggc tcc ttc ttc ctc tac agc aag ctc     1296
Pro Pro Val Leu Asp Ser Asp Gly Ser Phe Phe Leu Tyr Ser Lys Leu
            420                 425                 430

acc gtg gac aag agc agg tgg cag cag ggg aac gtc ttc tca tgc tcc     1344
Thr Val Asp Lys Ser Arg Trp Gln Gln Gly Asn Val Phe Ser Cys Ser
        435                 440                 445

gtg atg cat gag gct ctg cac aac cac tac acg cag aag agc ctc tcc     1392
Val Met His Glu Ala Leu His Asn His Tyr Thr Gln Lys Ser Leu Ser
    450                 455                 460

ctg tct ccc ggt                                                     1404
Leu Ser Pro Gly
465


<210> SEQ ID NO 7
<211> LENGTH: 1404
<212> TYPE: DNA
<213> ORGANISM: Artificial sequence
<220> FEATURE:
<223> OTHER INFORMATION: pKJS196 vector - aglycosyl-3G9 version 3 heavy
      chain
<220> FEATURE:
<221> NAME/KEY: CDS
<222> LOCATION: (1)..(1404)

<400> SEQUENCE: 7

atg gac ttc ggc ctg agc tgg gtg ttc ctg gtg ctg gtg ctg aag ggc       48
Met Asp Phe Gly Leu Ser Trp Val Phe Leu Val Leu Val Leu Lys Gly
1               5                   10                  15

gtg cag tgc gag gtg cag ctg gtg gag agc ggc ggc ggc ctg gtg cag       96
Val Gln Cys Glu Val Gln Leu Val Glu Ser Gly Gly Gly Leu Val Gln
            20                  25                  30

ccc ggc ggc agc ctg agg ctg agc tgc gcc gcc agc ggc ttc acc ttc      144
Pro Gly Gly Ser Leu Arg Leu Ser Cys Ala Ala Ser Gly Phe Thr Phe
        35                  40                  45

agc cgc tac gtg atg agc tgg gtg cgc cag gcc ccc ggc aag ggc ctg      192
Ser Arg Tyr Val Met Ser Trp Val Arg Gln Ala Pro Gly Lys Gly Leu
    50                  55                  60
```

-continued

```
gag tgg gtg gcc agc atc agc agc gga ggc cgc atg tac tac ccc gac      240
Glu Trp Val Ala Ser Ile Ser Ser Gly Gly Arg Met Tyr Tyr Pro Asp
65                  70                  75                  80

acc gtg aag ggc cgc ttc acc atc agc cgc gac aac gcc aag aac agc      288
Thr Val Lys Gly Arg Phe Thr Ile Ser Arg Asp Asn Ala Lys Asn Ser
                85                  90                  95

ctg tac ctg cag atg aac agc ctg cgc gcc gag gac acc gcc gtg tac      336
Leu Tyr Leu Gln Met Asn Ser Leu Arg Ala Glu Asp Thr Ala Val Tyr
            100                 105                 110

tac tgc gcc cgc ggc agc atc tac gac ggc tac tac gtg ttc ccc tac      384
Tyr Cys Ala Arg Gly Ser Ile Tyr Asp Gly Tyr Tyr Val Phe Pro Tyr
        115                 120                 125

tgg ggc cag ggc acc ctg gtg acc gtg agc tcc gcc agc acc aag ggc      432
Trp Gly Gln Gly Thr Leu Val Thr Val Ser Ser Ala Ser Thr Lys Gly
    130                 135                 140

ccc agc gtg ttc ccc ctg gcc ccc agc agc aag agc acc agc ggc ggc      480
Pro Ser Val Phe Pro Leu Ala Pro Ser Ser Lys Ser Thr Ser Gly Gly
145                 150                 155                 160

acc gcc gcc ctg ggc tgc ctg gtg aag gac tac ttc ccc gaa ccg gtg      528
Thr Ala Ala Leu Gly Cys Leu Val Lys Asp Tyr Phe Pro Glu Pro Val
                165                 170                 175

acg gtg tcg tgg aac tca ggc gcc ctg acc agc ggc gtg cac acc ttc      576
Thr Val Ser Trp Asn Ser Gly Ala Leu Thr Ser Gly Val His Thr Phe
            180                 185                 190

ccg gct gtc cta cag tcc tca gga ctc tac tcc ctc agc agc gtg gtg      624
Pro Ala Val Leu Gln Ser Ser Gly Leu Tyr Ser Leu Ser Ser Val Val
        195                 200                 205

acc gtg ccc tcc agc agc ttg ggc acc cag acc tac atc tgc aac gtg      672
Thr Val Pro Ser Ser Ser Leu Gly Thr Gln Thr Tyr Ile Cys Asn Val
    210                 215                 220

aat cac aag ccc agc aac acc aag gtg gac aag aaa gtt gag ccc aaa      720
Asn His Lys Pro Ser Asn Thr Lys Val Asp Lys Lys Val Glu Pro Lys
225                 230                 235                 240

tct tgt gac aag act cac aca tgc cca ccg tgc cca gca cct gaa ctc      768
Ser Cys Asp Lys Thr His Thr Cys Pro Pro Cys Pro Ala Pro Glu Leu
                245                 250                 255

ctg ggg gga ccg tca gtc ttc ctc ttc ccc cca aaa ccc aag gac acc      816
Leu Gly Gly Pro Ser Val Phe Leu Phe Pro Pro Lys Pro Lys Asp Thr
            260                 265                 270

ctc atg atc tcc cgg acc cct gag gtc aca tgc gtg gtg gtg gac gtg      864
Leu Met Ile Ser Arg Thr Pro Glu Val Thr Cys Val Val Val Asp Val
        275                 280                 285

agc cac gaa gac cct gag gtc aag ttc aac tgg tac gtg gac ggc gtg      912
Ser His Glu Asp Pro Glu Val Lys Phe Asn Trp Tyr Val Asp Gly Val
    290                 295                 300

gag gtg cat aat gcc aag aca aag ccg cgg gag gag cag tac cag agc      960
Glu Val His Asn Ala Lys Thr Lys Pro Arg Glu Glu Gln Tyr Gln Ser
305                 310                 315                 320

acg tac cgt gtg gtc agc gtc ctc acc gtc ctg cac cag gac tgg ctg     1008
Thr Tyr Arg Val Val Ser Val Leu Thr Val Leu His Gln Asp Trp Leu
                325                 330                 335

aat ggc aag gag tac aag tgc aag gtc tcc aac aaa gcc ctc cca gcc     1056
Asn Gly Lys Glu Tyr Lys Cys Lys Val Ser Asn Lys Ala Leu Pro Ala
            340                 345                 350

ccc atc gag aaa acc atc tcc aaa gcc aaa ggg cag ccc cga gaa cca     1104
Pro Ile Glu Lys Thr Ile Ser Lys Ala Lys Gly Gln Pro Arg Glu Pro
        355                 360                 365

cag gtg tac acc ctg ccc cca tcc cgg gat gag ctg acc aag aac cag     1152
Gln Val Tyr Thr Leu Pro Pro Ser Arg Asp Glu Leu Thr Lys Asn Gln
    370                 375                 380
```

```
gtc agc ctg acc tgc ctg gtc aaa ggc ttc tat ccc agc gac atc gcc     1200
Val Ser Leu Thr Cys Leu Val Lys Gly Phe Tyr Pro Ser Asp Ile Ala
385                 390                 395                 400

gtg gag tgg gag agc aat ggg cag ccg gag aac aac tac aag acc acg     1248
Val Glu Trp Glu Ser Asn Gly Gln Pro Glu Asn Asn Tyr Lys Thr Thr
                405                 410                 415

cct ccc gtg ttg gac tcc gac ggc tcc ttc ttc ctc tac agc aag ctc     1296
Pro Pro Val Leu Asp Ser Asp Gly Ser Phe Phe Leu Tyr Ser Lys Leu
            420                 425                 430

acc gtg gac aag agc agg tgg cag cag ggg aac gtc ttc tca tgc tcc     1344
Thr Val Asp Lys Ser Arg Trp Gln Gln Gly Asn Val Phe Ser Cys Ser
        435                 440                 445

gtg atg cat gag gct ctg cac aac cac tac acg cag aag agc ctc tcc     1392
Val Met His Glu Ala Leu His Asn His Tyr Thr Gln Lys Ser Leu Ser
    450                 455                 460

ctg tct ccc ggt                                                     1404
Leu Ser Pro Gly
465
```

<210> SEQ ID NO 8
<211> LENGTH: 39
<212> TYPE: DNA
<213> ORGANISM: Artificial sequence
<220> FEATURE:
<223> OTHER INFORMATION: PCR primer for murine 3G9 heavy chain variable domain

<400> SEQUENCE: 8
aggtctagaa yctccacaca caggrrccag tggatagac 39

<210> SEQ ID NO 9
<211> LENGTH: 39
<212> TYPE: DNA
<213> ORGANISM: Artificial sequence
<220> FEATURE:
<223> OTHER INFORMATION: PCR primer for murine 3G9 heavy chain variable domain

<400> SEQUENCE: 9
ggggatatcc accatgract tcgggytgag ctkggtttt 39

<210> SEQ ID NO 10
<211> LENGTH: 29
<212> TYPE: DNA
<213> ORGANISM: Artificial sequence
<220> FEATURE:
<223> OTHER INFORMATION: PCR primer for murine 3G9 light chain variable domain

<400> SEQUENCE: 10
gcgtctagaa ctggatggtg ggagatgga 29

<210> SEQ ID NO 11
<211> LENGTH: 39
<212> TYPE: DNA
<213> ORGANISM: Artificial sequence
<220> FEATURE:
<223> OTHER INFORMATION: PCR primer for murine 3G9 light chain variable domain

<400> SEQUENCE: 11
ggggatatcc accatggatt ttcaggtgca gattttcag 39

<210> SEQ ID NO 12
<211> LENGTH: 33
<212> TYPE: DNA

-continued

<213> ORGANISM: Artificial sequence
<220> FEATURE:
<223> OTHER INFORMATION: PCR primer for construction of heavy chain chimeric 3G9

<400> SEQUENCE: 12
ctgtctctgc aggtaagctt acacccccat ctg 33

<210> SEQ ID NO 13
<211> LENGTH: 33
<212> TYPE: DNA
<213> ORGANISM: Artificial sequence
<220> FEATURE:
<223> OTHER INFORMATION: PCR primer for construction of heavy chain chimeric 3G9

<400> SEQUENCE: 13
cagatggggg tgtaagctta cctgcagaga cag 33

<210> SEQ ID NO 14
<211> LENGTH: 35
<212> TYPE: DNA
<213> ORGANISM: Artificial sequence
<220> FEATURE:
<223> OTHER INFORMATION: PCR primer for construction of light chain chimeric 3G9

<400> SEQUENCE: 14
ggcaccaagc tggagatcta acgggctgat gctgc 35

<210> SEQ ID NO 15
<211> LENGTH: 35
<212> TYPE: DNA
<213> ORGANISM: Artificial sequence
<220> FEATURE:
<223> OTHER INFORMATION: PCR primer for construction of light chain chimeric 3G9

<400> SEQUENCE: 15
gcagcatcag cccgttagat ctccagcttg gtgcc 35

<210> SEQ ID NO 16
<211> LENGTH: 35
<212> TYPE: DNA
<213> ORGANISM: Artificial sequence
<220> FEATURE:
<223> OTHER INFORMATION: PCR primer for construction of light chain chimeric 3G9

<400> SEQUENCE: 16
ggaacttaca cttgagctgg cactgcatgt caagg 35

<210> SEQ ID NO 17
<211> LENGTH: 35
<212> TYPE: DNA
<213> ORGANISM: Artificial sequence
<220> FEATURE:
<223> OTHER INFORMATION: PCR primer for construction of light chain chimeric 3G9

<400> SEQUENCE: 17
ccttgacatg cagtgccagc tcaagtgtaa gttcc 35

<210> SEQ ID NO 18
<211> LENGTH: 24
<212> TYPE: DNA
<213> ORGANISM: Artificial sequence
<220> FEATURE:

-continued

<223> OTHER INFORMATION: PCR primer for construction of heavy chain
      hu3G9 versions 1 & 2

<400> SEQUENCE: 18
gctgacagcg gccgcgggat ccac 24

<210> SEQ ID NO 19
<211> LENGTH: 22
<212> TYPE: DNA
<213> ORGANISM: Artificial sequence
<220> FEATURE:
<223> OTHER INFORMATION: PCR primer for construction of heavy chain
      hu3G9 versions 1 & 2

<400> SEQUENCE: 19
gctcacggtc accggttcgg gg 22

<210> SEQ ID NO 20
<211> LENGTH: 24
<212> TYPE: DNA
<213> ORGANISM: Artificial sequence
<220> FEATURE:
<223> OTHER INFORMATION: PCR primer for construction of light chain
      hu3G9 versions 1, 2 & 3

<400> SEQUENCE: 20
gctgacagcg gccgcgggat ccac 24

<210> SEQ ID NO 21
<211> LENGTH: 24
<212> TYPE: DNA
<213> ORGANISM: Artificial sequence
<220> FEATURE:
<223> OTHER INFORMATION: PCR primer for construction of light chain
      hu3G9 versions 1, 2 & 3

<400> SEQUENCE: 21
ggaagatgaa cacactgggt gcgg 24

<210> SEQ ID NO 22
<211> LENGTH: 109
<212> TYPE: DNA
<213> ORGANISM: Artificial sequence
<220> FEATURE:
<223> OTHER INFORMATION: Top strand 5' phosphorylated oligonucleotide
      for 3G9 heavy chain

<400> SEQUENCE: 22
gctgacagcg gccgcgggat ccaccatgga cttcggcctg agctgggtgt tcctggtgct 60
ggtgctgaag ggcgtgcagt gcgaggtgat gctggtggag agcggcggc 109

<210> SEQ ID NO 23
<211> LENGTH: 122
<212> TYPE: DNA
<213> ORGANISM: Artificial sequence
<220> FEATURE:
<223> OTHER INFORMATION: Top strand 5' phosphorylated oligonucleotide
      for 3G9 heavy chain

<400> SEQUENCE: 23
ggcctggtgc agcccggcgg cagcctgagg ctgagctgcg ccgccagcgg cttcaccttc 60
agccgctacg tgatgagctg ggtgcgccag gcccccggca agggcctgga gtgggtggcc 120
ag 122

<210> SEQ ID NO 24

-continued

<211> LENGTH: 118
<212> TYPE: DNA
<213> ORGANISM: Artificial sequence
<220> FEATURE:
<223> OTHER INFORMATION: Top strand 5' phosphorylated oligonucleotide
      for 3G9 heavy chain

<400> SEQUENCE: 24
catcagcagc ggaggccgca tgtactaccc cgacaccgtg aagggccgct tcaccatcag     60
ccgcgacagc gccaagaaca gcctgtacct gcagatgaac agcctgcgcg ccgaggac      118

<210> SEQ ID NO 25
<211> LENGTH: 102
<212> TYPE: DNA
<213> ORGANISM: artificial sequence
<220> FEATURE:
<223> OTHER INFORMATION: Top strand 5' phosphorylated oligonucleotide
      for 3G9 heavy chain

<400> SEQUENCE: 25
accgccgtgt actactgcgc ccgcggcagc atctacgacg gctactacgt gttcccctac     60
tggggccagg gcaccctggt gaccgtgagc tccgccagca cc                       102

<210> SEQ ID NO 26
<211> LENGTH: 111
<212> TYPE: DNA
<213> ORGANISM: Artificial sequence
<220> FEATURE:
<223> OTHER INFORMATION: Top strand 5' phosphorylated oligonucleotide
      for 3G9 heavy chain

<400> SEQUENCE: 26
aagggcccca gcgtgttccc cctggccccc agcagcaaga gcaccagcgg cggcaccgcc     60
gccctgggct gcctggtgaa ggactacttc cccgaaccgg tgaccgtgag c             111

<210> SEQ ID NO 27
<211> LENGTH: 26
<212> TYPE: DNA
<213> ORGANISM: Artificial sequence
<220> FEATURE:
<223> OTHER INFORMATION: Bottom strand oligonucleotide for 3G9 heavy
      chain

<400> SEQUENCE: 27
gctgcaccag gccgccgccg ctctcc                                          26

<210> SEQ ID NO 28
<211> LENGTH: 24
<212> TYPE: DNA
<213> ORGANISM: Artificial sequence
<220> FEATURE:
<223> OTHER INFORMATION: Bottom strand oligonucleotide for 3G9 heavy
      chain

<400> SEQUENCE: 28
ccgctgctga tgctggccac ccac                                            24

<210> SEQ ID NO 29
<211> LENGTH: 30
<212> TYPE: DNA
<213> ORGANISM: artificial sequence
<220> FEATURE:
<223> OTHER INFORMATION: Bottom strand oligonucleotide for 3G9 heavy
      chain

<400> SEQUENCE: 29
gcagtagtac acggcggtgt cctcggcgcg 30

<210> SEQ ID NO 30
<211> LENGTH: 23
<212> TYPE: DNA
<213> ORGANISM: Artificial sequence
<220> FEATURE:
<223> OTHER INFORMATION: Bottom strand oligonucleotide for 3G9 heavy chain

<400> SEQUENCE: 30
gctggggccc ttggtgctgg cgg 23

<210> SEQ ID NO 31
<211> LENGTH: 109
<212> TYPE: DNA
<213> ORGANISM: Artificial sequence
<220> FEATURE:
<223> OTHER INFORMATION: Top strand 5' phosphorylated oligonucleotide for 3G9 heavy chain

<400> SEQUENCE: 31
gctgacagcg gccgcgggat ccaccatgga cttcggcctg agctgggtgt tcctggtgct 60
ggtgctgaag ggcgtgcagt gcgaggtgca gctggtggag agcggcggc 109

<210> SEQ ID NO 32
<211> LENGTH: 122
<212> TYPE: DNA
<213> ORGANISM: Artificial sequence
<220> FEATURE:
<223> OTHER INFORMATION: Top strand 5' phosphorylated oligonucleotide for 3G9 heavy chain

<400> SEQUENCE: 32
ggcctggtgc agcccggcgg cagcctgagg ctgagctgcg ccgccagcgg cttcaccttc 60
agccgctacg tgatgagctg ggtgcgccag gcccccggca agggcctgga gtgggtggcc 120
ag 122

<210> SEQ ID NO 33
<211> LENGTH: 118
<212> TYPE: DNA
<213> ORGANISM: Artificial sequence
<220> FEATURE:
<223> OTHER INFORMATION: Top strand 5' phosphorylated oligonucleotide for 3G9 heavy chain

<400> SEQUENCE: 33
catcagcagc ggaggccgca tgtactaccc cgacaccgtg aagggccgct tcaccatcag 60
ccgcgacagc gccaagaaca gcctgtacct gcagatgaac agcctgcgcg ccgaggac 118

<210> SEQ ID NO 34
<211> LENGTH: 102
<212> TYPE: DNA
<213> ORGANISM: Artificial sequence
<220> FEATURE:
<223> OTHER INFORMATION: Top strand 5' phosphorylated oligonucleotide for 3G9 heavy chain

<400> SEQUENCE: 34
accgccgtgt actactgcgc ccgcggcagc atctacgacg gctactacgt gttcccctac 60
tggggccagg gcaccctggt gaccgtgagc tccgccagca cc 102

<210> SEQ ID NO 35
<211> LENGTH: 111

<212> TYPE: DNA
<213> ORGANISM: Artificial sequence
<220> FEATURE:
<223> OTHER INFORMATION: Top strand 5' phosphorylated oligonucleotide
for 3G9 heavy chain

<400> SEQUENCE: 35
aagggcccca gcgtgttccc cctggccccc agcagcaaga gcaccagcgg cggcaccgcc 60
gccctgggct gcctggtgaa ggactacttc cccgaaccgg tgaccgtgag c 111

<210> SEQ ID NO 36
<211> LENGTH: 26
<212> TYPE: DNA
<213> ORGANISM: Artificial sequence
<220> FEATURE:
<223> OTHER INFORMATION: Bottom strand oligonucleotide for 3G9 heavy
chain

<400> SEQUENCE: 36
gctgcaccag gccgccgccg ctctcc 26

<210> SEQ ID NO 37
<211> LENGTH: 24
<212> TYPE: DNA
<213> ORGANISM: Artificial sequence
<220> FEATURE:
<223> OTHER INFORMATION: Bottom strand oligonucleotide for 3G9 heavy
chain

<400> SEQUENCE: 37
ccgctgctga tgctggccac ccac 24

<210> SEQ ID NO 38
<211> LENGTH: 30
<212> TYPE: DNA
<213> ORGANISM: Artificial sequence
<220> FEATURE:
<223> OTHER INFORMATION: Bottom strand oligonucleotide for 3G9 heavy
chain

<400> SEQUENCE: 38
gcagtagtac acggcggtgt cctcggcgcg 30

<210> SEQ ID NO 39
<211> LENGTH: 23
<212> TYPE: DNA
<213> ORGANISM: Artificial sequence
<220> FEATURE:
<223> OTHER INFORMATION: Bottom strand oligonucleotide for 3G9 heavy
chain

<400> SEQUENCE: 39
gctggggccc ttggtgctgg cgg 23

<210> SEQ ID NO 40
<211> LENGTH: 32
<212> TYPE: DNA
<213> ORGANISM: Artificial sequence
<220> FEATURE:
<223> OTHER INFORMATION: PCR primer for 3G9 heavy chain

<400> SEQUENCE: 40
ccatcagccg cgacaacgcc aagaacagcc tg 32

<210> SEQ ID NO 41
<211> LENGTH: 32
<212> TYPE: DNA

<213> ORGANISM: Artificial sequence
<220> FEATURE:
<223> OTHER INFORMATION: PCR primer for 3G9 heavy chain

<400> SEQUENCE: 41
caggctgttc ttggcgttgt cgcggctgat gg 32

<210> SEQ ID NO 42
<211> LENGTH: 106
<212> TYPE: DNA
<213> ORGANISM: Artificial sequence
<220> FEATURE:
<223> OTHER INFORMATION: Top strand 5' phosphorylated oligonucleotide
for 3G9 light chain

<400> SEQUENCE: 42
gctgacagcg gccgcgggat ccaccatgga cttccaggtg cagatcttca gcttcctgct 60
gatcagcgtg agcgtgatca tgagccgcgg cgagatcgtg ctgacc 106

<210> SEQ ID NO 43
<211> LENGTH: 117
<212> TYPE: DNA
<213> ORGANISM: Artificial sequence
<220> FEATURE:
<223> OTHER INFORMATION: Top strand 5' phosphorylated oligonucleotide
for 3G9 light chain

<400> SEQUENCE: 43
cagagccccg ccaccctgag cctgagcccc ggcgagaggg ccaccctgag ctgcagcgcc 60
agcagcagcg tgagcagcag ctacctgtac tggtaccagc agaagcccgg ccaggcc 117

<210> SEQ ID NO 44
<211> LENGTH: 117
<212> TYPE: DNA
<213> ORGANISM: Artificial sequence
<220> FEATURE:
<223> OTHER INFORMATION: Top strand 5' phosphorylated oligonucleotide
for 3G9 light chain

<400> SEQUENCE: 44
cccaggctgt ggatctacag caccagcaac ctggccagcg gcgtgcccgt gcgcttcagc 60
ggcagcggca gcggcaccga cttcaccctg accatcagca gcctggagcc cgaggac 117

<210> SEQ ID NO 45
<211> LENGTH: 109
<212> TYPE: DNA
<213> ORGANISM: Artificial sequence
<220> FEATURE:
<223> OTHER INFORMATION: Top strand 5' phosphorylated oligonucleotide
for 3G9 light chain

<400> SEQUENCE: 45
ttcgccgtgt acttctgcca ccagtggagc acctaccccc ccaccttcgg cggcggcacc 60
aaggtggaga tcaagcgtac ggtggccgca cccagtgtgt tcatcttcc 109

<210> SEQ ID NO 46
<211> LENGTH: 24
<212> TYPE: DNA
<213> ORGANISM: Artificial sequence
<220> FEATURE:
<223> OTHER INFORMATION: Bottom strand oligonucleotide for 3G9 light
chain

<400> SEQUENCE: 46
gcggggctct gggtcagcac gatc 24

<210> SEQ ID NO 47
<211> LENGTH: 22
<212> TYPE: DNA
<213> ORGANISM: Artificial sequence
<220> FEATURE:
<223> OTHER INFORMATION: Bottom strand oligonucleotide for 3G9 light chain

<400> SEQUENCE: 47
ccacagcctg ggggcctggc cg 22

<210> SEQ ID NO 48
<211> LENGTH: 24
<212> TYPE: DNA
<213> ORGANISM: Artificial sequence
<220> FEATURE:
<223> OTHER INFORMATION: Bottom strand oligonucleotide for 3G9 light chain

<400> SEQUENCE: 48
gtacacggcg aagtcctcgg gctc 24

<210> SEQ ID NO 49
<211> LENGTH: 106
<212> TYPE: DNA
<213> ORGANISM: Artificial sequence
<220> FEATURE:
<223> OTHER INFORMATION: Top strand 5' phosphorylated oligonucleotide for 3G9 light chain

<400> SEQUENCE: 49
gctgacagcg gccgcgggat ccaccatgga cttccaggtg cagatcttca gcttcctgct 60
gatcagcgtg agcgtgatca tgagccgcgg cgagatcgtg ctgacc 106

<210> SEQ ID NO 50
<211> LENGTH: 117
<212> TYPE: DNA
<213> ORGANISM: Artificial sequence
<220> FEATURE:
<223> OTHER INFORMATION: Top strand 5' phosphorylated oligonucleotide for 3G9 light chain

<400> SEQUENCE: 50
cagagccccg ccaccctgag cctgagcccc ggcgagaggg ccaccctgag ctgcagcgcc 60
agcagcagcg tgagcagcag ctacctgtac tggtaccagc agaagcccgg ccaggcc 117

<210> SEQ ID NO 51
<211> LENGTH: 117
<212> TYPE: DNA
<213> ORGANISM: Artificial sequence
<220> FEATURE:
<223> OTHER INFORMATION: Top strand 5' phosphorylated oligonucleotide for 3G9 light chain

<400> SEQUENCE: 51
cccaggctgt ggatctacag caccagcaac ctggccagcg gcgtgcccgc ccgcttcagc 60
ggcagcggca gcggcaccga cttcaccctg accatcagca gcctggagcc cgaggac 117

<210> SEQ ID NO 52
<211> LENGTH: 109
<212> TYPE: DNA
<213> ORGANISM: Artificial sequence
<220> FEATURE:
<223> OTHER INFORMATION: Top strand 5' phosphorylated oligonucleotide for 3G9 light chain

<400> SEQUENCE: 52
ttcgccgtgt actactgcca ccagtggagc acctaccccc ccaccttcgg cggcggcacc 60
aaggtggaga tcaagcgtac ggtggccgca cccagtgtgt tcatcttcc 109

<210> SEQ ID NO 53
<211> LENGTH: 24
<212> TYPE: DNA
<213> ORGANISM: Artificial sequence
<220> FEATURE:
<223> OTHER INFORMATION: Bottom strand oligonucleotide for 3G9 light chain

<400> SEQUENCE: 53
gcggggctct gggtcagcac gatc 24

<210> SEQ ID NO 54
<211> LENGTH: 22
<212> TYPE: DNA
<213> ORGANISM: Artificial sequence
<220> FEATURE:
<223> OTHER INFORMATION: Bottom strand oligonucleotide for 3G9 light chain

<400> SEQUENCE: 54
ccacagcctg ggggcctggc cg 22

<210> SEQ ID NO 55
<211> LENGTH: 24
<212> TYPE: DNA
<213> ORGANISM: Artificial sequence
<220> FEATURE:
<223> OTHER INFORMATION: Bottom strand oligonucleotide for 3G9 light chain

<400> SEQUENCE: 55
gtacacggcg aagtcctcgg gctc 24

<210> SEQ ID NO 56
<211> LENGTH: 106
<212> TYPE: DNA
<213> ORGANISM: Artificial sequence
<220> FEATURE:
<223> OTHER INFORMATION: Top strand 5' phosphorylated oligonucleotide for 3G9 light chain

<400> SEQUENCE: 56
gctgacagcg gccgcgggat ccaccatgga cttccaggtg cagatcttca gcttcctgct 60
gatcagcgtg agcgtgatca tgagccgcgg cgagatcgtg ctgacc 106

<210> SEQ ID NO 57
<211> LENGTH: 117
<212> TYPE: DNA
<213> ORGANISM: Artificial sequence
<220> FEATURE:
<223> OTHER INFORMATION: Top strand 5' phosphorylated oligonucleotide for 3G9 light chain

<400> SEQUENCE: 57
cagagccccg ccaccctgag cctgagcccc ggcgagaggg ccaccctgag ctgcagcgcc 60
agcagcagcg tgagcagcag ctacctgtac tggtaccagc agaagcccgg ccaggcc 117

<210> SEQ ID NO 58
<211> LENGTH: 117
<212> TYPE: DNA

<213> ORGANISM: Artificial sequence
<220> FEATURE:
<223> OTHER INFORMATION: Top strand 5' phosphorylated oligonucleotide
for 3G9 light chain

<400> SEQUENCE: 58
cccaggctgt ggatctacag caccagcaac ctggccagcg gcatccccgc ccgcttcagc 60
ggcagcggca gcggcaccga cttcaccctg accatcagca gcctggagcc cgaggac 117

<210> SEQ ID NO 59
<211> LENGTH: 109
<212> TYPE: DNA
<213> ORGANISM: Artificial sequence
<220> FEATURE:
<223> OTHER INFORMATION: Top strand 5' phosphorylated oligonucleotide
for 3G9 light chain

<400> SEQUENCE: 59
ttcgccgtgt actactgcca ccagtggagc acctaccccc ccaccttcgg cggcggcacc 60
aaggtggaga tcaagcgtac ggtggccgca cccagtgtgt tcatcttcc 109

<210> SEQ ID NO 60
<211> LENGTH: 24
<212> TYPE: DNA
<213> ORGANISM: Artificial sequence
<220> FEATURE:
<223> OTHER INFORMATION: Bottom strand oligonucleotide for 3G9 light
chain

<400> SEQUENCE: 60
gcggggctct gggtcagcac gatc 24

<210> SEQ ID NO 61
<211> LENGTH: 22
<212> TYPE: DNA
<213> ORGANISM: Artificial sequence
<220> FEATURE:
<223> OTHER INFORMATION: Bottom strand oligonucleotide for 3G9 light
chain

<400> SEQUENCE: 61
ccacagcctg ggggcctggc cg 22

<210> SEQ ID NO 62
<211> LENGTH: 24
<212> TYPE: DNA
<213> ORGANISM: Artificial sequence
<220> FEATURE:
<223> OTHER INFORMATION: Bottom strand oligonucleotide for 3G9 light
chain

<400> SEQUENCE: 62
gtacacggcg aagtcctcgg gctc 24

<210> SEQ ID NO 63
<211> LENGTH: 30
<212> TYPE: DNA
<213> ORGANISM: Artificial sequence
<220> FEATURE:
<223> OTHER INFORMATION: PCR primer for generation of 3G9 light chain

<400> SEQUENCE: 63
gtcagcacga tctggccgcg gctcatgatc 30

<210> SEQ ID NO 64
<211> LENGTH: 30

<212> TYPE: DNA
<213> ORGANISM: Artificial sequence
<220> FEATURE:
<223> OTHER INFORMATION: PCR primer for generation of 3G9 light chain

<400> SEQUENCE: 64
gatcatgagc cgcggccaga tcgtgctgac 30

<210> SEQ ID NO 65
<211> LENGTH: 24
<212> TYPE: DNA
<213> ORGANISM: Artificial sequence
<220> FEATURE:
<223> OTHER INFORMATION: PCR primer for generation of 3G9 light chain

<400> SEQUENCE: 65
cccaggctgc tgatctacag cacc 24

<210> SEQ ID NO 66
<211> LENGTH: 24
<212> TYPE: DNA
<213> ORGANISM: Artificial sequence
<220> FEATURE:
<223> OTHER INFORMATION: PCR primer for generation of 3G9 light chain

<400> SEQUENCE: 66
ggtgctgtag atcagcagcc tggg 24

<210> SEQ ID NO 67
<211> LENGTH: 324
<212> TYPE: DNA
<213> ORGANISM: Artificial sequence
<220> FEATURE:
<223> OTHER INFORMATION: hu3G9 version 1 light chain
<220> FEATURE:
<221> NAME/KEY: CDS
<222> LOCATION: (1)..(324)

<400> SEQUENCE: 67

```
gag atc gtg ctg acc cag agc ccc gcc acc ctg agc ctg agc ccc ggc       48
Glu Ile Val Leu Thr Gln Ser Pro Ala Thr Leu Ser Leu Ser Pro Gly
1               5                   10                  15

gag agg gcc acc ctg agc tgc agc gcc agc agc agc gtg agc agc agc       96
Glu Arg Ala Thr Leu Ser Cys Ser Ala Ser Ser Ser Val Ser Ser Ser
            20                  25                  30

tac ctg tac tgg tac cag cag aag ccc ggc cag gcc ccc agg ctg tgg      144
Tyr Leu Tyr Trp Tyr Gln Gln Lys Pro Gly Gln Ala Pro Arg Leu Trp
        35                  40                  45

atc tac agc acc agc aac ctg gcc agc ggc gtg ccc gtg cgc ttc agc      192
Ile Tyr Ser Thr Ser Asn Leu Ala Ser Gly Val Pro Val Arg Phe Ser
    50                  55                  60

ggc agc ggc agc ggc acc gac ttc acc ctg acc atc agc agc ctg gag      240
Gly Ser Gly Ser Gly Thr Asp Phe Thr Leu Thr Ile Ser Ser Leu Glu
65                  70                  75                  80

ccc gag gac ttc gcc gtg tac ttc tgc cac cag tgg agc acc tac ccc      288
Pro Glu Asp Phe Ala Val Tyr Phe Cys His Gln Trp Ser Thr Tyr Pro
                85                  90                  95

ccc acc ttc ggc ggc ggc acc aag gtg gag atc aag                      324
Pro Thr Phe Gly Gly Gly Thr Lys Val Glu Ile Lys
            100                 105
```

<210> SEQ ID NO 68
<211> LENGTH: 324
<212> TYPE: DNA
<213> ORGANISM: Artificial sequence
<220> FEATURE:

```
<223> OTHER INFORMATION: hu3G9 version 2 light chain
<220> FEATURE:
<221> NAME/KEY: CDS
<222> LOCATION: (1)..(324)

<400> SEQUENCE: 68

gag atc gtg ctg acc cag agc ccc gcc acc ctg agc ctg agc ccc ggc       48
Glu Ile Val Leu Thr Gln Ser Pro Ala Thr Leu Ser Leu Ser Pro Gly
1               5                   10                  15

gag agg gcc acc ctg agc tgc agc gcc agc agc agc gtg agc agc agc       96
Glu Arg Ala Thr Leu Ser Cys Ser Ala Ser Ser Ser Val Ser Ser Ser
            20                  25                  30

tac ctg tac tgg tac cag cag aag ccc ggc cag gcc ccc agg ctg tgg      144
Tyr Leu Tyr Trp Tyr Gln Gln Lys Pro Gly Gln Ala Pro Arg Leu Trp
        35                  40                  45

atc tac agc acc agc aac ctg gcc agc ggc gtg ccc gcc cgc ttc agc      192
Ile Tyr Ser Thr Ser Asn Leu Ala Ser Gly Val Pro Ala Arg Phe Ser
    50                  55                  60

ggc agc ggc agc ggc acc gac ttc acc ctg acc atc agc agc ctg gag      240
Gly Ser Gly Ser Gly Thr Asp Phe Thr Leu Thr Ile Ser Ser Leu Glu
65                  70                  75                  80

ccc gag gac ttc gcc gtg tac tac tgc cac cag tgg agc acc tac ccc      288
Pro Glu Asp Phe Ala Val Tyr Tyr Cys His Gln Trp Ser Thr Tyr Pro
            85                  90                  95

ccc acc ttc ggc ggc ggc acc aag gtg gag atc aag                      324
Pro Thr Phe Gly Gly Gly Thr Lys Val Glu Ile Lys
            100                 105


<210> SEQ ID NO 69
<211> LENGTH: 324
<212> TYPE: DNA
<213> ORGANISM: Artificial sequence
<220> FEATURE:
<223> OTHER INFORMATION: hu3G9 version 3 light chain
<220> FEATURE:
<221> NAME/KEY: CDS
<222> LOCATION: (1)..(324)

<400> SEQUENCE: 69

gag atc gtg ctg acc cag agc ccc gcc acc ctg agc ctg agc ccc ggc       48
Glu Ile Val Leu Thr Gln Ser Pro Ala Thr Leu Ser Leu Ser Pro Gly
1               5                   10                  15

gag agg gcc acc ctg agc tgc agc gcc agc agc agc gtg agc agc agc       96
Glu Arg Ala Thr Leu Ser Cys Ser Ala Ser Ser Ser Val Ser Ser Ser
            20                  25                  30

tac ctg tac tgg tac cag cag aag ccc ggc cag gcc ccc agg ctg tgg      144
Tyr Leu Tyr Trp Tyr Gln Gln Lys Pro Gly Gln Ala Pro Arg Leu Trp
        35                  40                  45

atc tac agc acc agc aac ctg gcc agc ggc atc ccc gcc cgc ttc agc      192
Ile Tyr Ser Thr Ser Asn Leu Ala Ser Gly Ile Pro Ala Arg Phe Ser
    50                  55                  60

ggc agc ggc agc ggc acc gac ttc acc ctg acc atc agc agc ctg gag      240
Gly Ser Gly Ser Gly Thr Asp Phe Thr Leu Thr Ile Ser Ser Leu Glu
65                  70                  75                  80

ccc gag gac ttc gcc gtg tac tac tgc cac cag tgg agc acc tac ccc      288
Pro Glu Asp Phe Ala Val Tyr Tyr Cys His Gln Trp Ser Thr Tyr Pro
            85                  90                  95

ccc acc ttc ggc ggc ggc acc aag gtg gag atc aag                      324
Pro Thr Phe Gly Gly Gly Thr Lys Val Glu Ile Lys
            100                 105


<210> SEQ ID NO 70
<211> LENGTH: 324
<212> TYPE: DNA
```

```
<213> ORGANISM: Artificial sequence
<220> FEATURE:
<223> OTHER INFORMATION: hu3G9 version 4 light chain
<220> FEATURE:
<221> NAME/KEY: CDS
<222> LOCATION: (1)..(324)

<400> SEQUENCE: 70

cag atc gtg ctg acc cag agc ccc gcc acc ctg agc ctg agc ccc ggc       48
Gln Ile Val Leu Thr Gln Ser Pro Ala Thr Leu Ser Leu Ser Pro Gly
1               5                   10                  15

gag agg gcc acc ctg agc tgc agc gcc agc agc agc gtg agc agc agc       96
Glu Arg Ala Thr Leu Ser Cys Ser Ala Ser Ser Ser Val Ser Ser Ser
            20                  25                  30

tac ctg tac tgg tac cag cag aag ccc ggc cag gcc ccc agg ctg tgg      144
Tyr Leu Tyr Trp Tyr Gln Gln Lys Pro Gly Gln Ala Pro Arg Leu Trp
        35                  40                  45

atc tac agc acc agc aac ctg gcc agc ggc atc ccc gcc cgc ttc agc      192
Ile Tyr Ser Thr Ser Asn Leu Ala Ser Gly Ile Pro Ala Arg Phe Ser
    50                  55                  60

ggc agc ggc agc ggc acc gac ttc acc ctg acc atc agc agc ctg gag      240
Gly Ser Gly Ser Gly Thr Asp Phe Thr Leu Thr Ile Ser Ser Leu Glu
65                  70                  75                  80

ccc gag gac ttc gcc gtg tac tac tgc cac cag tgg agc acc tac ccc      288
Pro Glu Asp Phe Ala Val Tyr Tyr Cys His Gln Trp Ser Thr Tyr Pro
                85                  90                  95

ccc acc ttc ggc ggc ggc acc aag gtg gag atc aag                      324
Pro Thr Phe Gly Gly Gly Thr Lys Val Glu Ile Lys
            100                 105


<210> SEQ ID NO 71
<211> LENGTH: 324
<212> TYPE: DNA
<213> ORGANISM: Artificial sequence
<220> FEATURE:
<223> OTHER INFORMATION: hu3G9 version 5 light chain
<220> FEATURE:
<221> NAME/KEY: CDS
<222> LOCATION: (1)..(324)

<400> SEQUENCE: 71

gag atc gtg ctg acc cag agc ccc gcc acc ctg agc ctg agc ccc ggc       48
Glu Ile Val Leu Thr Gln Ser Pro Ala Thr Leu Ser Leu Ser Pro Gly
1               5                   10                  15

gag agg gcc acc ctg agc tgc agc gcc agc agc agc gtg agc agc agc       96
Glu Arg Ala Thr Leu Ser Cys Ser Ala Ser Ser Ser Val Ser Ser Ser
            20                  25                  30

tac ctg tac tgg tac cag cag aag ccc ggc cag gcc ccc agg ctg ctg      144
Tyr Leu Tyr Trp Tyr Gln Gln Lys Pro Gly Gln Ala Pro Arg Leu Leu
        35                  40                  45

atc tac agc acc agc aac ctg gcc agc ggc atc ccc gcc cgc ttc agc      192
Ile Tyr Ser Thr Ser Asn Leu Ala Ser Gly Ile Pro Ala Arg Phe Ser
    50                  55                  60

ggc agc ggc agc ggc acc gac ttc acc ctg acc atc agc agc ctg gag      240
Gly Ser Gly Ser Gly Thr Asp Phe Thr Leu Thr Ile Ser Ser Leu Glu
65                  70                  75                  80

ccc gag gac ttc gcc gtg tac tac tgc cac cag tgg agc acc tac ccc      288
Pro Glu Asp Phe Ala Val Tyr Tyr Cys His Gln Trp Ser Thr Tyr Pro
                85                  90                  95

ccc acc ttc ggc ggc ggc acc aag gtg gag atc aag                      324
Pro Thr Phe Gly Gly Gly Thr Lys Val Glu Ile Lys
            100                 105


<210> SEQ ID NO 72
```

-continued

<211> LENGTH: 360
<212> TYPE: DNA
<213> ORGANISM: Artificial sequence
<220> FEATURE:
<223> OTHER INFORMATION: hu3G9 version 1 heavy chain
<220> FEATURE:
<221> NAME/KEY: CDS
<222> LOCATION: (1)..(360)

<400> SEQUENCE: 72 gag gtg atg ctg gtg gag agc ggc ggc ggc ctg gtg cag ccc ggc ggc 48
Glu Val Met Leu Val Glu Ser Gly Gly Gly Leu Val Gln Pro Gly Gly
1 5 10 15 agc ctg agg ctg agc tgc gcc gcc agc ggc ttc acc ttc agc cgc tac 96
Ser Leu Arg Leu Ser Cys Ala Ala Ser Gly Phe Thr Phe Ser Arg Tyr
20 25 30 gtg atg agc tgg gtg cgc cag gcc ccc ggc aag ggc ctg gag tgg gtg 144
Val Met Ser Trp Val Arg Gln Ala Pro Gly Lys Gly Leu Glu Trp Val
35 40 45 gcc agc atc agc agc gga ggc cgc atg tac tac ccc gac acc gtg aag 192
Ala Ser Ile Ser Ser Gly Gly Arg Met Tyr Tyr Pro Asp Thr Val Lys
50 55 60 ggc cgc ttc acc atc agc cgc gac agc gcc aag aac agc ctg tac ctg 240
Gly Arg Phe Thr Ile Ser Arg Asp Ser Ala Lys Asn Ser Leu Tyr Leu
65 70 75 80 cag atg aac agc ctg cgc gcc gag gac acc gcc gtg tac tac tgc gcc 288
Gln Met Asn Ser Leu Arg Ala Glu Asp Thr Ala Val Tyr Tyr Cys Ala
85 90 95 cgc ggc agc atc tac gac ggc tac tac gtg ttc ccc tac tgg ggc cag 336
Arg Gly Ser Ile Tyr Asp Gly Tyr Tyr Val Phe Pro Tyr Trp Gly Gln
100 105 110 ggc acc ctg gtg acc gtg agc tcc 360
Gly Thr Leu Val Thr Val Ser Ser
115 120

<210> SEQ ID NO 73
<211> LENGTH: 360
<212> TYPE: DNA
<213> ORGANISM: Artificial sequence
<220> FEATURE:
<223> OTHER INFORMATION: hu3G9 version 2 heavy chain
<220> FEATURE:
<221> NAME/KEY: CDS
<222> LOCATION: (1)..(360)

<400> SEQUENCE: 73 gag gtg cag ctg gtg gag agc ggc ggc ggc ctg gtg cag ccc ggc ggc 48
Glu Val Gln Leu Val Glu Ser Gly Gly Gly Leu Val Gln Pro Gly Gly
1 5 10 15 agc ctg agg ctg agc tgc gcc gcc agc ggc ttc acc ttc agc cgc tac 96
Ser Leu Arg Leu Ser Cys Ala Ala Ser Gly Phe Thr Phe Ser Arg Tyr
20 25 30 gtg atg agc tgg gtg cgc cag gcc ccc ggc aag ggc ctg gag tgg gtg 144
Val Met Ser Trp Val Arg Gln Ala Pro Gly Lys Gly Leu Glu Trp Val
35 40 45 gcc agc atc agc agc gga ggc cgc atg tac tac ccc gac acc gtg aag 192
Ala Ser Ile Ser Ser Gly Gly Arg Met Tyr Tyr Pro Asp Thr Val Lys
50 55 60 ggc cgc ttc acc atc agc cgc gac agc gcc aag aac agc ctg tac ctg 240
Gly Arg Phe Thr Ile Ser Arg Asp Ser Ala Lys Asn Ser Leu Tyr Leu
65 70 75 80 cag atg aac agc ctg cgc gcc gag gac acc gcc gtg tac tac tgc gcc 288
Gln Met Asn Ser Leu Arg Ala Glu Asp Thr Ala Val Tyr Tyr Cys Ala
85 90 95

```
cgc ggc agc atc tac gac ggc tac tac gtg ttc ccc tac tgg ggc cag      336
Arg Gly Ser Ile Tyr Asp Gly Tyr Tyr Val Phe Pro Tyr Trp Gly Gln
            100                 105                 110

ggc acc ctg gtg acc gtg agc tcc                                      360
Gly Thr Leu Val Thr Val Ser Ser
        115                 120


<210> SEQ ID NO 74
<211> LENGTH: 360
<212> TYPE: DNA
<213> ORGANISM: Artificial sequence
<220> FEATURE:
<223> OTHER INFORMATION: hu3G9 versions 3 and 5 heavy chain
<220> FEATURE:
<221> NAME/KEY: CDS
<222> LOCATION: (1)..(360)

<400> SEQUENCE: 74

gag gtg cag ctg gtg gag agc ggc ggc ggc ctg gtg cag ccc ggc ggc       48
Glu Val Gln Leu Val Glu Ser Gly Gly Gly Leu Val Gln Pro Gly Gly
1               5                   10                  15

agc ctg agg ctg agc tgc gcc gcc agc ggc ttc acc ttc agc cgc tac       96
Ser Leu Arg Leu Ser Cys Ala Ala Ser Gly Phe Thr Phe Ser Arg Tyr
            20                  25                  30

gtg atg agc tgg gtg cgc cag gcc ccc ggc aag ggc ctg gag tgg gtg      144
Val Met Ser Trp Val Arg Gln Ala Pro Gly Lys Gly Leu Glu Trp Val
        35                  40                  45

gcc agc atc agc agc gga ggc cgc atg tac tac ccc gac acc gtg aag      192
Ala Ser Ile Ser Ser Gly Gly Arg Met Tyr Tyr Pro Asp Thr Val Lys
    50                  55                  60

ggc cgc ttc acc atc agc cgc gac aac gcc aag aac agc ctg tac ctg      240
Gly Arg Phe Thr Ile Ser Arg Asp Asn Ala Lys Asn Ser Leu Tyr Leu
65                  70                  75                  80

cag atg aac agc ctg cgc gcc gag gac acc gcc gtg tac tac tgc gcc      288
Gln Met Asn Ser Leu Arg Ala Glu Asp Thr Ala Val Tyr Tyr Cys Ala
                85                  90                  95

cgc ggc agc atc tac gac ggc tac tac gtg ttc ccc tac tgg ggc cag      336
Arg Gly Ser Ile Tyr Asp Gly Tyr Tyr Val Phe Pro Tyr Trp Gly Gln
            100                 105                 110

ggc acc ctg gtg acc gtg agc tcc                                      360
Gly Thr Leu Val Thr Val Ser Ser
        115                 120


<210> SEQ ID NO 75
<211> LENGTH: 111
<212> TYPE: PRT
<213> ORGANISM: Artificial sequence
<220> FEATURE:
<223> OTHER INFORMATION: hu8G6 version 1 light chain

<400> SEQUENCE: 75

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Ser Tyr Ser Tyr Met Tyr Trp Tyr Gln Gln Lys Pro Gly Gln Ala Pro
        35                  40                  45

Arg Phe Leu Ile Lys Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Asn Trp
                85                  90                  95
```

```
Glu Ile Pro Phe Thr Phe Gly Gly Gly Thr Lys Val Glu Ile Lys
            100                 105                 110


<210> SEQ ID NO 76
<211> LENGTH: 111
<212> TYPE: PRT
<213> ORGANISM: Artificial sequence
<220> FEATURE:
<223> OTHER INFORMATION: hu8G6 version 2 light chain

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Ser Tyr Ser Tyr Met Tyr Trp Tyr Gln Gln Lys Pro Gly Gln Ala Pro
        35                  40                  45

Arg Phe Leu Ile Lys Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Asn Trp
                85                  90                  95

Glu Ile Pro Phe Thr Phe Gly Gly Gly Thr Lys Val Glu Ile Lys
            100                 105                 110


<210> SEQ ID NO 77
<211> LENGTH: 111
<212> TYPE: PRT
<213> ORGANISM: Artificial sequence
<220> FEATURE:
<223> OTHER INFORMATION: hu8G6 version 3 light chain

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Ser Tyr Ser Tyr Met Tyr Trp Tyr Gln Gln Lys Pro Gly Gln Ala Pro
        35                  40                  45

Arg Leu Leu Ile Lys Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Asn Trp
                85                  90                  95

Glu Ile Pro Phe Thr Phe Gly Gly Gly Thr Lys Val Glu Ile Lys
            100                 105                 110


<210> SEQ ID NO 78
<211> LENGTH: 126
<212> TYPE: PRT
<213> ORGANISM: Artificial sequence
<220> FEATURE:
<223> OTHER INFORMATION: hu8G6 version 1 heavy chain

<400> SEQUENCE: 78

Gln Val Gln Leu Val Gln Ser Gly Ala Glu Val Lys Lys Pro Gly Ala
1               5                   10                  15

Ser Val Lys Val Ser Cys Lys Gly Ser Ser Tyr Thr Phe Thr Asp Tyr
```

-continued

```
            20                  25                  30

Ala Met His Trp Val Arg Leu Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Leu Arg Arg Gly Asp Arg Pro Ser Leu Arg Tyr Ala
            100                 105                 110

Met Asp Tyr Trp Gly Gln Gly Thr Leu Val Thr Val Ser Ser
        115                 120                 125


<210> SEQ ID NO 79
<211> LENGTH: 126
<212> TYPE: PRT
<213> ORGANISM: Artificial sequence
<220> FEATURE:
<223> OTHER INFORMATION: hu8G6 version 2 heavy chain

<400> SEQUENCE: 79

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Leu Arg Arg Gly Asp Arg Pro Ser Leu Arg Tyr Ala
            100                 105                 110

Met Asp Tyr Trp Gly Gln Gly Thr Leu Val Thr Val Ser Ser
        115                 120                 125


<210> SEQ ID NO 80
<211> LENGTH: 126
<212> TYPE: PRT
<213> ORGANISM: Artificial sequence
<220> FEATURE:
<223> OTHER INFORMATION: hu8G6 version 3 heavy chain

<400> SEQUENCE: 80

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Met
        35                  40                  45

Gly Val Ile Ser Thr Tyr Tyr Gly Asn Thr Asn Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
```

```
                85                  90                  95

Ala Arg Gly Gly Leu Arg Arg Gly Asp Arg Pro Ser Leu Arg Tyr Ala
            100                 105                 110

Met Asp Tyr Trp Gly Gln Gly Thr Leu Val Thr Val Ser Ser
        115                 120                 125


<210> SEQ ID NO 81
<211> LENGTH: 97
<212> TYPE: PRT
<213> ORGANISM: Artificial sequence
<220> FEATURE:
<223> OTHER INFORMATION: murine heavy chain sequence for hu3G9

<400> SEQUENCE: 81

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Arg Tyr
            20                  25                  30

Val Met Ser Trp Val Arg Gln Thr Pro Glu Lys Arg Leu Glu Trp Val
        35                  40                  45

Ala Ser Ile Ser Ser Gly Gly Arg Met Tyr Tyr Pro Asp Thr Val Lys
    50                  55                  60

Gly Arg Phe Thr Ile Ser Arg Asp Ser Ala Arg Asn Ile Leu Tyr Leu
65                  70                  75                  80

Gln Met Ser Ser Leu Arg Ser Glu Asp Thr Ala Met Tyr Tyr Cys Ala
                85                  90                  95

Arg


<210> SEQ ID NO 82
<211> LENGTH: 97
<212> TYPE: PRT
<213> ORGANISM: Artificial sequence
<220> FEATURE:
<223> OTHER INFORMATION: 3G9HV1 heavy chain sequence for hu3G9

<400> SEQUENCE: 82

Glu Val Met Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Ser Trp Val Arg Gln Ala Pro Gly Lys Gly Leu Glu Trp Val
        35                  40                  45

Ala Ser Ile Ser Ser Gly Gly Arg Met Tyr Tyr Pro Asp Thr Val Lys
    50                  55                  60

Gly Arg Phe Thr Ile Ser Arg Asp Ser Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg


<210> SEQ ID NO 83
<211> LENGTH: 97
<212> TYPE: PRT
<213> ORGANISM: Artificial sequence
<220> FEATURE:
<223> OTHER INFORMATION: 3G9HV2 heavy chain sequence for hu3G9

<400> SEQUENCE: 83

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Arg Tyr
            20                  25                  30

Val Met Ser Trp Val Arg Gln Ala Pro Gly Lys Gly Leu Glu Trp Val
        35                  40                  45

Ala Ser Ile Ser Ser Gly Gly Arg Met Tyr Tyr Pro Asp Thr Val Lys
    50                  55                  60

Gly Arg Phe Thr Ile Ser Arg Asp Ser Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg


<210> SEQ ID NO 84
<211> LENGTH: 97
<212> TYPE: PRT
<213> ORGANISM: Artificial sequence
<220> FEATURE:
<223> OTHER INFORMATION: 3G9HV3 heavy chain sequence for hu3G9

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Ser Trp Val Arg Gln Ala Pro Gly Lys Gly Leu Glu Trp Val
        35                  40                  45

Ala Ser Ile Ser Ser Gly Gly Arg Met Tyr Tyr Pro Asp Thr Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg


<210> SEQ ID NO 85
<211> LENGTH: 76
<212> TYPE: PRT
<213> ORGANISM: Artificial sequence
<220> FEATURE:
<223> OTHER INFORMATION: VH3-7 heavy chain sequence for hu3G9

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Trp Val
            20                  25                  30

Arg Gln Ala Pro Gly Lys Gly Leu Glu Trp Val Ala Arg Phe Thr Ile
        35                  40                  45

Ser Arg Asp Asn Ala Lys Asn Ser Leu Tyr Leu Gln Met Asn Ser Leu
    50                  55                  60

Arg Ala Glu Asp Thr Ala Val Tyr Tyr Cys Ala Arg
65                  70                  75


<210> SEQ ID NO 86
<211> LENGTH: 98
<212> TYPE: PRT
<213> ORGANISM: Artificial sequence
<220> FEATURE:
<223> OTHER INFORMATION: murine for light chain sequence for hu3G9
```

<400> SEQUENCE: 86

```
Gln Ile Val Leu Thr Gln Ser Pro Ala Ile Met Ser Ala Ser Pro Gly
1               5                   10                  15

Glu Lys Val Thr Leu Thr Cys Ser Ala Asn Ser Ser Val Ser Ser Ser
            20                  25                  30

Tyr Leu Tyr Trp Tyr Gln Gln Lys Ser Gly Ser Ser Pro Lys Leu Trp
        35                  40                  45

Ile Tyr Ser Thr Ser Asn Leu Ala Ser Gly Val Pro Val Arg Phe Ser
    50                  55                  60

Gly Ser Gly Ser Gly Thr Ser Phe Ser Leu Thr Ile Ser Ser Met Glu
65                  70                  75                  80

Ala Glu Asp Ala Ala Ser Tyr Phe Cys His Gln Trp Ser Thr Tyr Pro
                85                  90                  95

Pro Thr
```

<210> SEQ ID NO 87
<211> LENGTH: 98
<212> TYPE: PRT
<213> ORGANISM: Artificial sequence
<220> FEATURE:
<223> OTHER INFORMATION: 3G9LV1 light chain sequence for hu3G9

<400> SEQUENCE: 87

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Tyr Ser Thr Ser Asn Leu Ala Ser Gly Val Pro Val Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Phe Cys His Gln Trp Ser Thr Tyr Pro
                85                  90                  95

Pro Thr
```

<210> SEQ ID NO 88
<211> LENGTH: 98
<212> TYPE: PRT
<213> ORGANISM: Artificial sequence
<220> FEATURE:
<223> OTHER INFORMATION: 3G9LV2 light chain sequence for hu3G9

<400> SEQUENCE: 88

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Thr Tyr Pro
                85                  90                  95
```

Pro Thr

<210> SEQ ID NO 89
<211> LENGTH: 98
<212> TYPE: PRT
<213> ORGANISM: artificial sequence
<220> FEATURE:
<223> OTHER INFORMATION: 3G9LV3 light chain sequence for hu3G9

<400> SEQUENCE: 89

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Thr Tyr Pro
                85                  90                  95

Pro Thr
```

<210> SEQ ID NO 90
<211> LENGTH: 98
<212> TYPE: PRT
<213> ORGANISM: Artificial sequence
<220> FEATURE:
<223> OTHER INFORMATION: 3G9LV4 light chain sequence for hu3G9

<400> SEQUENCE: 90

```
Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Thr Tyr Pro
                85                  90                  95

Pro Thr
```

<210> SEQ ID NO 91
<211> LENGTH: 98
<212> TYPE: PRT
<213> ORGANISM: Artificial sequence
<220> FEATURE:
<223> OTHER INFORMATION: 3G9LV5 light chain sequence for hu3G9

<400> SEQUENCE: 91

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Leu
```

35 40 45

Ile Tyr Ser Thr Ser Asn Leu Ala Ser Gly Ile Pro Ala Arg Phe Ser
50 55 60

Gly Ser Gly Ser Gly Thr Asp Phe Thr Leu Thr Ile Ser Ser Leu Glu
65 70 75 80

Pro Glu Asp Phe Ala Val Tyr Tyr Cys His Gln Trp Ser Thr Tyr Pro
85 90 95

Pro Thr

<210> SEQ ID NO 92
<211> LENGTH: 71
<212> TYPE: PRT
<213> ORGANISM: Artificial sequence
<220> FEATURE:
<223> OTHER INFORMATION: L6 light chain sequence for hu3G9

<400> SEQUENCE: 92

Glu Ile Val Leu Thr Gln Ser Pro Ala Thr Leu Ser Leu Ser Pro Gly
1 5 10 15

Glu Arg Ala Thr Leu Ser Cys Ser Trp Tyr Gln Gln Lys Pro Gly Gln
20 25 30

Ala Pro Arg Leu Leu Ile Tyr Gly Ile Pro Ala Arg Phe Ser Gly Ser
35 40 45

Gly Ser Gly Thr Asp Phe Thr Leu Thr Ile Ser Ser Leu Glu Pro Glu
50 55 60

Asp Phe Ala Val Tyr Tyr Cys
65 70

<210> SEQ ID NO 93
<211> LENGTH: 98
<212> TYPE: PRT
<213> ORGANISM: Artificial sequence
<220> FEATURE:
<223> OTHER INFORMATION: murine heavy chain sequence for hu8G6

<400> SEQUENCE: 93

Gln Val Gln Leu Gln Gln Ser Gly Pro Glu Leu Val Arg Pro Gly Val
1 5 10 15

Ser Val Lys Ile Ser Cys Lys Gly Ser Ser Tyr Thr Phe Thr Asp Tyr
20 25 30

Ala Met His Trp Val Lys Leu Ser His Ala Lys Ser Leu Glu Trp Ile
35 40 45

Gly Val Ile Ser Thr Tyr Tyr Gly Asn Thr Asn Tyr Asn Gln Lys Phe
50 55 60

Lys Gly Lys Ala Thr Met Thr Val Asp Lys Ser Ser Ser Thr Ala Tyr
65 70 75 80

Met Glu Leu Ala Arg Leu Thr Ser Glu Asp Ser Ala Val Tyr Tyr Cys
85 90 95

Ala Arg

<210> SEQ ID NO 94
<211> LENGTH: 98
<212> TYPE: PRT
<213> ORGANISM: Artificial sequence
<220> FEATURE:
<223> OTHER INFORMATION: 8G6HV1 heavy chain sequence for hu8G6

<400> SEQUENCE: 94

Gln Val Gln Leu Val Gln Ser Gly Ala Glu Val Lys Lys Pro Gly Ala
1 5 10 15

```
Ser Val Lys Val Ser Cys Lys Gly Ser Ser Tyr Thr Phe Thr Asp Tyr
            20                  25                  30

Ala Met His Trp Val Arg Leu Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg


<210> SEQ ID NO 95
<211> LENGTH: 98
<212> TYPE: PRT
<213> ORGANISM: Artificial sequence
<220> FEATURE:
<223> OTHER INFORMATION: 8G6HV2 heavy chain sequences for hu8G6

<400> SEQUENCE: 95

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Ile
        35                  40                  45

Gly Val Ile Ser Thr Tyr Tyr Gly Asn Thr Asn Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg


<210> SEQ ID NO 96
<211> LENGTH: 98
<212> TYPE: PRT
<213> ORGANISM: Artificial sequence
<220> FEATURE:
<223> OTHER INFORMATION: 8G6VH3 heavy chain sequence for hu8G6

<400> SEQUENCE: 96

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Ala Met His Trp Val Arg Gln Ala Pro Gly Gln Gly Leu Glu Trp Met
        35                  40                  45

Gly Val Ile Ser Thr Tyr Tyr Gly Asn Thr Asn Tyr Asn Gln Lys Phe
    50                  55                  60

Lys Gly Arg Ala Thr Met Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg


<210> SEQ ID NO 97
```

```
<211> LENGTH: 76
<212> TYPE: PRT
<213> ORGANISM: Artificial sequence
<220> FEATURE:
<223> OTHER INFORMATION: VH1-2 heavy chain sequence for hu8G6

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Trp Val
            20                  25                  30

Arg Gln Ala Pro Gly Gln Gly Leu Glu Trp Met Gly Arg Val Thr Met
        35                  40                  45

Thr Arg Asp Thr Ser Ile Ser Thr Ala Tyr Met Glu Leu Ser Arg Leu
    50                  55                  60

Arg Ser Asp Asp Thr Ala Val Tyr Tyr Cys Ala Arg
65                  70                  75


<210> SEQ ID NO 98
<211> LENGTH: 99
<212> TYPE: PRT
<213> ORGANISM: Artificial sequence
<220> FEATURE:
<223> OTHER INFORMATION: murine light chain sequence for hu8G6

<400> SEQUENCE: 98

Asp Ile Val Leu Thr Gln Ser Pro Ala Ser Leu Ala Val Ser Leu Gly
1               5                   10                  15

Gln Arg Ala Ile Ile Ser Cys Arg Ala Ser Gln Ser Val Ser Thr Ser
            20                  25                  30

Ser Tyr Ser Tyr Met Tyr Trp Tyr Gln Gln Lys Pro Gly Gln Ser Pro
        35                  40                  45

Lys Phe Leu Ile Lys Tyr Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Asn Trp
                85                  90                  95

Glu Ile Pro


<210> SEQ ID NO 99
<211> LENGTH: 99
<212> TYPE: PRT
<213> ORGANISM: Artificial sequence
<220> FEATURE:
<223> OTHER INFORMATION: 8G6LV1 light chain sequence for hu8G6

<400> SEQUENCE: 99

Asp Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Ser Tyr Ser Tyr Met Tyr Trp Tyr Gln Gln Lys Pro Gly Gln Ala Pro
        35                  40                  45

Arg Phe Leu Ile Lys Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Asn Trp
                85                  90                  95
```

Glu Ile Pro

<210> SEQ ID NO 100
<211> LENGTH: 99
<212> TYPE: PRT
<213> ORGANISM: Artificial sequence
<220> FEATURE:
<223> OTHER INFORMATION: 8G6LV2 light chain sequence for hu8G6

<400> SEQUENCE: 100

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Ser Tyr Ser Tyr Met Tyr Trp Tyr Gln Gln Lys Pro Gly Gln Ala Pro
        35                  40                  45

Arg Phe Leu Ile Lys Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Asn Trp
                85                  90                  95

Glu Ile Pro
```

<210> SEQ ID NO 101
<211> LENGTH: 10
<212> TYPE: PRT
<213> ORGANISM: Artificial Sequence
<220> FEATURE:
<223> OTHER INFORMATION: Heavy chain CDR1 sequence for 8G6 antibody

<400> SEQUENCE: 101

```
Ser Tyr Thr Phe Thr Asp Tyr Ala Met His
1               5                   10
```

<210> SEQ ID NO 102
<211> LENGTH: 10
<212> TYPE: PRT
<213> ORGANISM: Artificial sequence
<220> FEATURE:
<223> OTHER INFORMATION: Heavy chain CDR1 sequence for 1A8 antibody

<400> SEQUENCE: 102

```
Ser Tyr Thr Phe Thr Asp Tyr Thr Met His
1               5                   10
```

<210> SEQ ID NO 103
<211> LENGTH: 10
<212> TYPE: PRT
<213> ORGANISM: Artificial sequence
<220> FEATURE:
<223> OTHER INFORMATION: Heavy chain CDR1 sequence for 2B1 and 3G9
      antibodies

<400> SEQUENCE: 103

```
Gly Phe Thr Phe Ser Arg Tyr Val Met Ser
1               5                   10
```

<210> SEQ ID NO 104
<211> LENGTH: 10
<212> TYPE: PRT
<213> ORGANISM: Artificial sequence
<220> FEATURE:
<223> OTHER INFORMATION: Heavy chain CDR1 sequence for 2A1 antibody

<400> SEQUENCE: 104

Gly Tyr Asp Phe Asn Asn Asp Leu Ile Glu
1 5 10

<210> SEQ ID NO 105
<211> LENGTH: 10
<212> TYPE: PRT
<213> ORGANISM: Artificial sequence
<220> FEATURE:
<223> OTHER INFORMATION: Heavy chain CDR1 sequence for 2G2 antibody

<400> SEQUENCE: 105

Gly Tyr Ala Phe Thr Asn Tyr Leu Ile Glu
1 5 10

<210> SEQ ID NO 106
<211> LENGTH: 17
<212> TYPE: PRT
<213> ORGANISM: Artificial sequence
<220> FEATURE:
<223> OTHER INFORMATION: Heavy chain CDR2 sequence for 8G6 antibody

<400> SEQUENCE: 106

Val Ile Ser Thr Tyr Tyr Gly Asn Thr Asn Tyr Asn Gln Lys Phe Lys
1 5 10 15

Gly

<210> SEQ ID NO 107
<211> LENGTH: 17
<212> TYPE: PRT
<213> ORGANISM: Artificial sequence
<220> FEATURE:
<223> OTHER INFORMATION: Heavy chain CDR2 sequence for 1A8 antibody

<400> SEQUENCE: 107

Val Ile Asp Thr Tyr Tyr Gly Lys Thr Asn Tyr Asn Gln Lys Phe Glu
1 5 10 15

Gly

<210> SEQ ID NO 108
<211> LENGTH: 16
<212> TYPE: PRT
<213> ORGANISM: Artificial sequence
<220> FEATURE:
<223> OTHER INFORMATION: Heavy chain CDR2 sequence for 2B1 antibody

<400> SEQUENCE: 108

Ser Ile Ser Ser Gly Gly Ser Thr Tyr Tyr Pro Asp Ser Val Lys Gly
1 5 10 15

<210> SEQ ID NO 109
<211> LENGTH: 16
<212> TYPE: PRT
<213> ORGANISM: Artificial sequence
<220> FEATURE:
<223> OTHER INFORMATION: Heavy chain CDR2 sequence for 3G9 antibody

<400> SEQUENCE: 109

Ser Ile Ser Ser Gly Gly Arg Met Tyr Tyr Pro Asp Thr Val Lys Gly
1 5 10 15

<210> SEQ ID NO 110
<211> LENGTH: 17
<212> TYPE: PRT
<213> ORGANISM: Artificial sequence
<220> FEATURE:
<223> OTHER INFORMATION: Heavy chain CDR2 sequence for 2A1 antibody

<400> SEQUENCE: 110

Val Ile Asn Pro Gly Ser Gly Arg Thr Asn Tyr Asn Glu Lys Phe Lys
1 5 10 15

Gly

<210> SEQ ID NO 111
<211> LENGTH: 17
<212> TYPE: PRT
<213> ORGANISM: Artificial sequence
<220> FEATURE:
<223> OTHER INFORMATION: Heavy chain CDR2 sequence for 2G2 antibody

<400> SEQUENCE: 111

Val Ile Ser Pro Gly Ser Gly Ile Ile Asn Tyr Asn Glu Lys Phe Lys
1 5 10 15

Gly

<210> SEQ ID NO 112
<211> LENGTH: 17
<212> TYPE: PRT
<213> ORGANISM: Artificial sequence
<220> FEATURE:
<223> OTHER INFORMATION: Heavy chain CDR3 sequence for 8G6 antibody

<400> SEQUENCE: 112

Gly Gly Leu Arg Arg Gly Asp Arg Pro Ser Leu Arg Tyr Ala Met Asp
1 5 10 15

Tyr

<210> SEQ ID NO 113
<211> LENGTH: 17
<212> TYPE: PRT
<213> ORGANISM: Artificial Sequence
<220> FEATURE:
<223> OTHER INFORMATION: Heavy chain CDR3 sequence for 1A8 antibody

<400> SEQUENCE: 113

Gly Gly Phe Arg Arg Gly Asp Arg Pro Ser Leu Arg Tyr Ala Met Asp
1 5 10 15

Ser

<210> SEQ ID NO 114
<211> LENGTH: 12
<212> TYPE: PRT
<213> ORGANISM: Artificial sequence
<220> FEATURE:
<223> OTHER INFORMATION: Heavy chain CDR3 sequence for 2B1 antibody

<400> SEQUENCE: 114

Gly Ala Ile Tyr Asp Gly Tyr Tyr Val Phe Ala Tyr
1 5 10

<210> SEQ ID NO 115
<211> LENGTH: 12
<212> TYPE: PRT
<213> ORGANISM: Artificial sequence
<220> FEATURE:
<223> OTHER INFORMATION: Heavy chain CDR3 sequence for 3G9 antibody

<400> SEQUENCE: 115

Gly Ser Ile Tyr Asp Gly Tyr Tyr Val Phe Pro Tyr
1 5 10

<210> SEQ ID NO 116
<211> LENGTH: 12
<212> TYPE: PRT
<213> ORGANISM: Artificial sequence
<220> FEATURE:
<223> OTHER INFORMATION: Heavy chain CDR3 sequence for 2A1 antibody

<400> SEQUENCE: 116

Ile Tyr Tyr Gly Pro His Ser Tyr Ala Met Asp Tyr
1 5 10

<210> SEQ ID NO 117
<211> LENGTH: 11
<212> TYPE: PRT
<213> ORGANISM: Artificial sequence
<220> FEATURE:
<223> OTHER INFORMATION: Heavy chain CDR3 sequence for 2G2 antibody

<400> SEQUENCE: 117

Ile Asp Tyr Ser Gly Pro Tyr Ala Val Asp Asp
1 5 10

<210> SEQ ID NO 118
<211> LENGTH: 15
<212> TYPE: PRT
<213> ORGANISM: Artificial sequence
<220> FEATURE:
<223> OTHER INFORMATION: Light chain CDR1 sequence for 8G6 antibody

<400> SEQUENCE: 118

Arg Ala Ser Gln Ser Val Ser Thr Ser Ser Tyr Ser Tyr Met Tyr
1 5 10 15

<210> SEQ ID NO 119
<211> LENGTH: 15
<212> TYPE: PRT
<213> ORGANISM: Artificial sequence
<220> FEATURE:
<223> OTHER INFORMATION: Light chain CDR1 sequence for 1A8 antibody

<400> SEQUENCE: 119

Arg Ala Ser Gln Ser Val Ser Ile Ser Thr Tyr Ser Tyr Ile His
1 5 10 15

<210> SEQ ID NO 120
<211> LENGTH: 12
<212> TYPE: PRT
<213> ORGANISM: Artificial sequence
<220> FEATURE:
<223> OTHER INFORMATION: Light chain CDR1 sequence for 2B1 antibody

<400> SEQUENCE: 120

Ser Ala Ser Ser Ser Val Ser Ser Ser Tyr Leu Tyr
1 5 10

<210> SEQ ID NO 121
<211> LENGTH: 12
<212> TYPE: PRT
<213> ORGANISM: Artificial sequence
<220> FEATURE:
<223> OTHER INFORMATION: Light chain CDR1 sequence for 3G9 antibody

<400> SEQUENCE: 121

Ser Ala Asn Ser Ser Val Ser Ser Ser Tyr Leu Tyr
1 5 10

-continued

<210> SEQ ID NO 122
<211> LENGTH: 11
<212> TYPE: PRT
<213> ORGANISM: Artificial sequence
<220> FEATURE:
<223> OTHER INFORMATION: Light chain CDR1 sequence for 2A1 antibody

<400> SEQUENCE: 122

Lys Ala Ser Leu Asp Val Arg Thr Ala Val Ala
1 5 10

<210> SEQ ID NO 123
<211> LENGTH: 11
<212> TYPE: PRT
<213> ORGANISM: Artificial sequence
<220> FEATURE:
<223> OTHER INFORMATION: Light chain CDR1 sequence for 2G2 antibody

<400> SEQUENCE: 123

Lys Ala Ser Gln Ala Val Asn Thr Ala Val Ala
1 5 10

<210> SEQ ID NO 124
<211> LENGTH: 7
<212> TYPE: PRT
<213> ORGANISM: Artificial sequence
<220> FEATURE:
<223> OTHER INFORMATION: Light chain CDR2 sequence for 8G6 and 1A8 antibodies

<400> SEQUENCE: 124

Tyr Ala Ser Asn Leu Glu Ser
1 5

<210> SEQ ID NO 125
<211> LENGTH: 7
<212> TYPE: PRT
<213> ORGANISM: Artificial sequence
<220> FEATURE:
<223> OTHER INFORMATION: Light chain CDR1 sequence for 2B1 and 3G9 antibodies

<400> SEQUENCE: 125

Ser Thr Ser Asn Leu Ala Ser
1 5

<210> SEQ ID NO 126
<211> LENGTH: 7
<212> TYPE: PRT
<213> ORGANISM: Artificial sequence
<220> FEATURE:
<223> OTHER INFORMATION: Light chain CDR2 sequence for 2A1 antibody

<400> SEQUENCE: 126

Ser Ala Ser Tyr Arg Tyr Thr
1 5

<210> SEQ ID NO 127
<211> LENGTH: 7
<212> TYPE: PRT
<213> ORGANISM: Artificial sequence
<220> FEATURE:
<223> OTHER INFORMATION: Light chain CDR2 sequence for 2G2 antibody

<400> SEQUENCE: 127

Ser Ala Ser Tyr Gln Tyr Thr
1 5

<210> SEQ ID NO 128
<211> LENGTH: 9
<212> TYPE: PRT
<213> ORGANISM: Artificial sequence
<220> FEATURE:
<223> OTHER INFORMATION: Light chain CDR3 sequence for 8G6 antibody

<400> SEQUENCE: 128

Gln His Asn Trp Glu Ile Pro Phe Thr
1               5

<210> SEQ ID NO 129
<211> LENGTH: 9
<212> TYPE: PRT
<213> ORGANISM: Artificial sequence
<220> FEATURE:
<223> OTHER INFORMATION: Light chain CDR3 sequence for 1A8 antibody

<400> SEQUENCE: 129

Gln His Ser Trp Glu Ile Pro Tyr Thr
1               5

<210> SEQ ID NO 130
<211> LENGTH: 9
<212> TYPE: PRT
<213> ORGANISM: Artificial sequence
<220> FEATURE:
<223> OTHER INFORMATION: Light chain CDR3 sequence for 2B1 antibody

<400> SEQUENCE: 130

His Gln Trp Ser Ser Tyr Pro Pro Thr
1               5

<210> SEQ ID NO 131
<211> LENGTH: 9
<212> TYPE: PRT
<213> ORGANISM: Artificial sequence
<220> FEATURE:
<223> OTHER INFORMATION: Light Chain CDR3 sequence for 3G9 antibody

<400> SEQUENCE: 131

His Gln Trp Ser Thr Tyr Pro Pro Thr
1               5

<210> SEQ ID NO 132
<211> LENGTH: 9
<212> TYPE: PRT
<213> ORGANISM: Artificial sequence
<220> FEATURE:
<223> OTHER INFORMATION: Light chain CDR3 sequence for 2A1 antibody

<400> SEQUENCE: 132

Gln Gln His Tyr Gly Ile Pro Trp Thr
1               5

<210> SEQ ID NO 133
<211> LENGTH: 9
<212> TYPE: PRT
<213> ORGANISM: Artificial sequence
<220> FEATURE:
<223> OTHER INFORMATION: Light chain CDR3 sequence for 2G2 antibody

<400> SEQUENCE: 133

Gln His His Tyr Gly Val Pro Trp Thr
1               5

<210> SEQ ID NO 134
<211> LENGTH: 99

<212> TYPE: PRT
<213> ORGANISM: Artificial sequence
<220> FEATURE:
<223> OTHER INFORMATION: 8G6LV3 light chain sequence for hu8G6

<400> SEQUENCE: 134

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Thr Ser
            20                  25                  30

Ser Tyr Ser Tyr Met Tyr Trp Tyr Gln Gln Lys Pro Gly Gln Ala Pro
        35                  40                  45

Arg Leu Leu Ile Lys Tyr Ala Ser Asn Leu Glu Ser Gly Ile Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Asn Trp
                85                  90                  95

Glu Ile Pro
```

<210> SEQ ID NO 135
<211> LENGTH: 70
<212> TYPE: PRT
<213> ORGANISM: Artificial sequence
<220> FEATURE:
<223> OTHER INFORMATION: L6 light chain sequence for hu8G6

<400> SEQUENCE: 135

```
Glu Ile Val Leu Thr Gln Ser Pro Ala Thr Leu Ser Leu Ser Pro Gly
1               5                   10                  15

Glu Arg Ala Thr Leu Ser Cys Trp Tyr Gln Gln Lys Pro Gly Gln Ala
            20                  25                  30

Pro Arg Leu Leu Ile Tyr Gly Ile Pro Ala Arg Phe Ser Gly Ser Gly
        35                  40                  45

Ser Gly Thr Asp Phe Thr Leu Thr Ile Ser Ser Leu Glu Pro Glu Asp
    50                  55                  60

Phe Ala Val Tyr Tyr Cys
65                  70
```

<210> SEQ ID NO 136
<211> LENGTH: 237
<212> TYPE: PRT
<213> ORGANISM: Artificial Sequence
<220> FEATURE:
<223> OTHER INFORMATION: pKJS195 vector - 3G9 version 5 light chain

<400> SEQUENCE: 136

```
Met Asp Phe Gln Val Gln Ile Phe Ser Phe Leu Leu Ile Ser Val Ser
1               5                   10                  15

Val Ile Met Ser Arg Gly Glu Ile Val Leu Thr Gln Ser Pro Ala Thr
            20                  25                  30

Leu Ser Leu Ser Pro Gly Glu Arg Ala Thr Leu Ser Cys Ser Ala Ser
        35                  40                  45

Ser Ser Val Ser Ser Ser Tyr Leu Tyr Trp Tyr Gln Gln Lys Pro Gly
    50                  55                  60

Gln Ala Pro Arg Leu Leu Ile Tyr Ser Thr Ser Asn Leu Ala Ser Gly
65                  70                  75                  80

Ile Pro Ala Arg Phe Ser Gly Ser Gly Ser Gly Thr Asp Phe Thr Leu
                85                  90                  95
```

```
Thr Ile Ser Ser Leu Glu Pro Glu Asp Phe Ala Val Tyr Tyr Cys His
            100                 105                 110

Gln Trp Ser Thr Tyr Pro Pro Thr Phe Gly Gly Gly Thr Lys Val Glu
        115                 120                 125

Ile Lys Arg Thr Val Ala Ala Pro Ser Val Phe Ile Phe Pro Pro Ser
    130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235


<210> SEQ ID NO 137
<211> LENGTH: 468
<212> TYPE: PRT
<213> ORGANISM: Artificial sequence
<220> FEATURE:
<223> OTHER INFORMATION: pKJS189 vector - 3G9 vector 3 heavy chain

<400> SEQUENCE: 137

Met Asp Phe Gly Leu Ser Trp Val Phe Leu Val Leu Val Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg Tyr Val Met Ser Trp Val Arg Gln Ala Pro Gly Lys Gly Leu
    50                  55                  60

Glu Trp Val Ala Ser Ile Ser Ser Gly Gly Arg Met Tyr Tyr Pro Asp
65                  70                  75                  80

Thr Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Gly Ser Ile Tyr Asp Gly Tyr Tyr Val Phe Pro Tyr
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
```

```
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465


<210> SEQ ID NO 138
<211> LENGTH: 468
<212> TYPE: PRT
<213> ORGANISM: Artificial sequence
<220> FEATURE:
<223> OTHER INFORMATION: pKJS196 vector - aglycosyl-3G9 version 3 heavy
      chain

<400> SEQUENCE: 138

Met Asp Phe Gly Leu Ser Trp Val Phe Leu Val Leu Val Leu Lys Gly
1               5                   10                  15

Val Gln Cys Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Phe
        35                  40                  45

Ser Arg Tyr Val Met Ser Trp Val Arg Gln Ala Pro Gly Lys Gly Leu
    50                  55                  60

Glu Trp Val Ala Ser Ile Ser Ser Gly Gly Arg Met Tyr Tyr Pro Asp
65                  70                  75                  80

Thr Val Lys Gly Arg Phe Thr Ile Ser Arg Asp Asn Ala Lys Asn Ser
                85                  90                  95

Leu Tyr Leu Gln Met Asn Ser Leu Arg Ala Glu Asp Thr Ala Val Tyr
            100                 105                 110

Tyr Cys Ala Arg Gly Ser Ile Tyr Asp Gly Tyr Tyr Val Phe Pro Tyr
```

```
        115                 120                 125

Trp Gly Gln Gly Thr Leu Val Thr Val Ser Ser Ala Ser Thr Lys Gly
    130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
        195                 200                 205

Thr Val Pro Ser Ser Ser Leu Gly Thr Gln Thr Tyr Ile Cys Asn Val
    210                 215                 220

Asn His Lys Pro Ser Asn Thr Lys Val Asp Lys Lys Val Glu Pro Lys
225                 230                 235                 240

Ser Cys Asp Lys Thr His Thr Cys Pro Pro Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Gln Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365

Gln Val Tyr Thr Leu Pro Pro Ser Arg Asp Glu Leu Thr Lys Asn Gln
    370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
                405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
        435                 440                 445

Val Met His Glu Ala Leu His Asn His Tyr Thr Gln Lys Ser Leu Ser
    450                 455                 460

Leu Ser Pro Gly
465
```

<210> SEQ ID NO 139
<211> LENGTH: 108
<212> TYPE: PRT
<213> ORGANISM: Artificial sequence
<220> FEATURE:
<223> OTHER INFORMATION: hu3G9 version 1 light chain

<400> SEQUENCE: 139

```
Glu Ile Val Leu Thr Gln Ser Pro Ala Thr Leu Ser Leu Ser Pro Gly
1               5                   10                  15
```

-continued

```
Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Tyr Ser Thr Ser Asn Leu Ala Ser Gly Val Pro Val Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Phe Cys His Gln Trp Ser Thr Tyr Pro
                85                  90                  95

Pro Thr Phe Gly Gly Gly Thr Lys Val Glu Ile Lys
            100                 105


<210> SEQ ID NO 140
<211> LENGTH: 108
<212> TYPE: PRT
<213> ORGANISM: Artificial sequence
<220> FEATURE:
<223> OTHER INFORMATION: hu3G9 version 2 light chain

<400> SEQUENCE: 140

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Tyr Ser Thr Ser Asn Leu Ala Ser Gly Val Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Thr Tyr Pro
                85                  90                  95

Pro Thr Phe Gly Gly Gly Thr Lys Val Glu Ile Lys
            100                 105


<210> SEQ ID NO 141
<211> LENGTH: 108
<212> TYPE: PRT
<213> ORGANISM: Artificial sequence
<220> FEATURE:
<223> OTHER INFORMATION: hu3G9 version 3 light chain

<400> SEQUENCE: 141

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Thr Tyr Pro
                85                  90                  95

Pro Thr Phe Gly Gly Gly Thr Lys Val Glu Ile Lys
            100                 105
```

<210> SEQ ID NO 142
<211> LENGTH: 108
<212> TYPE: PRT
<213> ORGANISM: Artificial sequence
<220> FEATURE:
<223> OTHER INFORMATION: hu3G9 version 4 light chain

<400> SEQUENCE: 142

```
Gln Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Trp
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Thr Tyr Pro
                85                  90                  95

Pro Thr Phe Gly Gly Gly Thr Lys Val Glu Ile Lys
            100                 105
```

<210> SEQ ID NO 143
<211> LENGTH: 108
<212> TYPE: PRT
<213> ORGANISM: Artificial sequence
<220> FEATURE:
<223> OTHER INFORMATION: hu3G9 version 5 light chain

<400> SEQUENCE: 143

```
Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Ser Ser
            20                  25                  30

Tyr Leu Tyr Trp Tyr Gln Gln Lys Pro Gly Gln Ala Pro Arg Leu Leu
        35                  40                  45

Ile Tyr Ser Thr Ser Asn Leu Ala Ser Gly Ile Pro Ala Arg Phe Ser
    50                  55                  60

Gly Ser Gly Ser Gly Thr Asp Phe Thr Leu Thr Ile Ser Ser Leu Glu
65                  70                  75                  80

Pro Glu Asp Phe Ala Val Tyr Tyr Cys His Gln Trp Ser Thr Tyr Pro
                85                  90                  95

Pro Thr Phe Gly Gly Gly Thr Lys Val Glu Ile Lys
            100                 105
```

<210> SEQ ID NO 144
<211> LENGTH: 120
<212> TYPE: PRT
<213> ORGANISM: Artificial sequence
<220> FEATURE:
<223> OTHER INFORMATION: hu3G9 version 1 heavy chain

<400> SEQUENCE: 144

```
Glu Val Met Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Ser Trp Val Arg Gln Ala Pro Gly Lys Gly Leu Glu Trp Val
```

```
        35                  40                  45

Ala Ser Ile Ser Ser Gly Gly Arg Met Tyr Tyr Pro Asp Thr Val Lys
    50                  55                  60

Gly Arg Phe Thr Ile Ser Arg Asp Ser Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Ile Tyr Asp Gly Tyr Tyr Val Phe Pro Tyr Trp Gly Gln
            100                 105                 110

Gly Thr Leu Val Thr Val Ser Ser
        115                 120


<210> SEQ ID NO 145
<211> LENGTH: 120
<212> TYPE: PRT
<213> ORGANISM: Artificial sequence
<220> FEATURE:
<223> OTHER INFORMATION: hu3G9 version 2 heavy chain

<400> SEQUENCE: 145

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Ser Trp Val Arg Gln Ala Pro Gly Lys Gly Leu Glu Trp Val
        35                  40                  45

Ala Ser Ile Ser Ser Gly Gly Arg Met Tyr Tyr Pro Asp Thr Val Lys
    50                  55                  60

Gly Arg Phe Thr Ile Ser Arg Asp Ser Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Ile Tyr Asp Gly Tyr Tyr Val Phe Pro Tyr Trp Gly Gln
            100                 105                 110

Gly Thr Leu Val Thr Val Ser Ser
        115                 120


<210> SEQ ID NO 146
<211> LENGTH: 120
<212> TYPE: PRT
<213> ORGANISM: Artificial sequence
<220> FEATURE:
<223> OTHER INFORMATION: hu3G9 versions 3 and 5 heavy chain

<400> SEQUENCE: 146

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Val Met Ser Trp Val Arg Gln Ala Pro Gly Lys Gly Leu Glu Trp Val
        35                  40                  45

Ala Ser Ile Ser Ser Gly Gly Arg Met Tyr Tyr Pro Asp Thr Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Ile Tyr Asp Gly Tyr Tyr Val Phe Pro Tyr Trp Gly Gln
```

-continued 100 105 110

Gly Thr Leu Val Thr Val Ser Ser
115 120

<210> SEQ ID NO 147
<211> LENGTH: 20
<212> TYPE: DNA
<213> ORGANISM: Artificial sequence
<220> FEATURE:
<223> OTHER INFORMATION: oligonucleotide primer used to amplify oligonucleotide standard templates

<400> SEQUENCE: 147
catggccttc cgtgttccta 20

<210> SEQ ID NO 148
<211> LENGTH: 16
<212> TYPE: DNA
<213> ORGANISM: Artificial sequence
<220> FEATURE:
<223> OTHER INFORMATION: oligonucleotide primer used to amplify oligonucleotide standard templates

<400> SEQUENCE: 148
gcggcacgtc agatcc 16

<210> SEQ ID NO 149
<211> LENGTH: 16
<212> TYPE: DNA
<213> ORGANISM: Artificial sequence
<220> FEATURE:
<223> OTHER INFORMATION: Probe to recognize GADPH

<400> SEQUENCE: 149
ccccaatgtg tccgtc 16

<210> SEQ ID NO 150
<211> LENGTH: 63
<212> TYPE: DNA
<213> ORGANISM: Artificial sequence
<220> FEATURE:
<223> OTHER INFORMATION: PCR primer used to amplify the RNA first strand

<400> SEQUENCE: 150
ggccagtgaa ttgtaatacg actcactata gggaggcggt tttttttttt tttttttttt ttt 63

<210> SEQ ID NO 151
<211> LENGTH: 11
<212> TYPE: PRT
<213> ORGANISM: Artificial sequence
<220> FEATURE:
<223> OTHER INFORMATION: human FR4 derived from a consensus framework sequence

<400> SEQUENCE: 151

Trp Gly Gln Gly Thr Leu Val Thr Val Ser Ser
1 5 10

<210> SEQ ID NO 152
<211> LENGTH: 10
<212> TYPE: PRT
<213> ORGANISM: Artificial sequence
<220> FEATURE:
<223> OTHER INFORMATION: human FR4 derived from a consensus framework sequence

<400> SEQUENCE: 152

-continued

```
Phe Gly Gly Gly Thr Lys Val Glu Ile Lys
1               5                   10
```

ANTI-$\alpha_v\beta_6$ ANTIBODIES AND USES THEREOF

CROSS REFERENCE TO RELATED APPLICATIONS

The present application claims the benefit of the filing dates of U.S. Provisional Appl. Nos. 60/697,442, filed Jul. 8, 2005, and 60/773,310, filed Feb. 15, 2006, the disclosures of which are incorporated herein by reference in their entireties.

BACKGROUND OF THE INVENTION

1. Field of the Invention

The present invention is in the fields of cell biology, immunology and oncology. Specifically, the invention relates to humanized antibodies that recognizes $\alpha_v\beta_6$ integrins which comprises a variable region of nonhuman origin and at least—a portion of an immunoglobulin of human origin. The invention also relates to processes for their preparation, to pharmaceutical compositions comprising them and to methods of treating various diseases by administering humanized anti-$\alpha_v\beta_6$ antibodies. The invention also relates to the identification of differential expression of the integrin $\alpha_v\beta_6$ on the surfaces of tumor cells and tissues, the use of this differential expression in determining the metastatic potential of tumor cells, and methods of diagnosis and treatment/prevention of tumor metastasis and for elimination of residual metastatic tumor cells using ligands, particularly antibodies, that bind to integrin $\alpha_v\beta_6$.

2. Related Art

Integrins are cell surface glycoprotein receptors which bind extracellular matrix proteins and mediate cell-cell and cell-extracellular matrix interactions (generally referred to as cell adhesion events) (Ruoslahti, E., *J. Clin. Invest.* 87:1-5 (1991); Hynes, R. O., *Cell* 69:11-25 (1992)). These receptors are composed of noncovalently associated alpha ($\alpha$) and beta ($\beta$) chains which combine to give a variety of heterodimeric proteins with distinct cellular and adhesive specificities (Albeda, S. M., *Lab. Invest.* 68:4-14 (1993)). Recent studies have implicated certain integrins in the regulation of a variety of cellular processes including cellular adhesion, migration, invasion, differentiation, proliferation, apoptosis and gene expression (Albeda, S. M., *Lab. Invest.* 68:4-14 (1993); Juliano, R., *Cancer Met. Rev.* 13:25-30 (1994); Ruoslahti, E. and Reed, J. C., *Cell* 77:477-478 (1994); and Ruoslahti, E. and Giancotti, F. G., *Cancer Cells* 1:119-126 (1989); Plow, Haas et al. 2000; van der Flier and Sonnenberg 2001).

The $\alpha_v\beta_6$ receptor is one member of a family of integrins that are expressed as cell surface heterodimeric proteins (Busk, M. et al., *J. Biol. Chem.* 267(9):5790-5796 (1992)). While the $\alpha_v$ subunit can form a heterodimer with a variety of $\beta$ subunits ($\beta_1$, $\beta_3$, $\beta_5$, $\beta_6$ and $\beta_8$), the $\beta_6$ subunit can only be expressed as a heterodimer with the $\alpha_v$ subunit. The $\alpha_v\beta_6$ integrin is known to be a fibronectin-, latency associated peptide (LAP)- and tenascin C-binding cell surface receptor, interacting with the extracellular matrix through the RGD tripeptide binding sites thereon (Busk, M. et al., *J. Biol. Chem.* 267:5790-5796 (1992); Weinacker, A. et al., *J. Biol. Chem.* 269:6940-6948 (1994); Prieto, A. L. et al., *Proc. Natl. Acad. Sci. USA* 90:10154-10158 (1993)). Although the $\alpha_v\beta_6$ integrin was first identified and sequenced more than 10 years ago, the biological significance of $\alpha_v\beta_6$, especially in disease, is still under investigation. The expression of $\alpha_v\beta_6$ is restricted to epithelial cells where it is expressed at relatively low levels in healthy tissue and significantly upregulated during development, injury, and wound healing (Breuss, J. M. et al., *J. Histochem. Cytochem.* 41:1521-1527 (1993); Breuss, J. M. et al., *J Cell Sci.* 108:2241-2251 (1995); Koivisto, L. et al., *Cell Adhes. Communic.* 7:245-257 (1999); Zambruno, G. et al., *J. Cell Biol.* 129(3):853-865 (1995); Hakkinen, L. et al., *J. Histochem. Cytochem.* 48(6):985-998 (2000)). An increasing number of recent reports demonstrate that $\alpha_v\beta_6$ is upregulated on cancers of epithelial origin, including colon carcinoma (Niu, J. et al, *Int. J. Cancer* 92:40-48 (2001); Bates, R. C. et al., *J. Clin. Invest.* 115:339-347 (2005)), ovarian cancer (Ahmed, N. et al., *J. Cell. Biochem.* 84:675-686 (2002); Ahmed, N. et al., *J. Histochem. Cytochem.* 50:1371-1379 (2002); Ahmed, N. et al., *Carcinogen.* 23:237-244 (2002)), squamous cell carcinoma (Koivisto, L. et al., *Exp. Cell Res.* 255:10-17 (2000); Xue, H. et al., *Biochem. Biophys. Res. Comm.* 288:610-618 (2001); Thomas, G. J. et al., *J. Invest. Dermatol.* 117:67-73 (2001); Thomas, G. J. et al., *Int. J. Cancer* 92:641-650 (2001); Ramos, D. M. et al., *Matrix Biol.* 21:297-307 (2002); (Agrez, M. et al., *Br. J. Cancer* 81:90-97 (1999); Hamidi, S. et al., *Br. J. Cancer* 82(8):1433-1440 (2000); Kawashima, A. et al., *Pathol. Res. Pract.* 99(2):57-64 (2003)), and breast cancer (Arihiro, K. et al., *Breast Cancer* 7:19-26 (2000)). It has also been reported that the $\alpha_v$ subunit may be involved in tumor metastasis, and that blocking this subunit consequently may prevent metastasis (for review, see Imhof, B. A. et al., in: "Attempts to Understand Metastasis Formation I," U. Günthert and W. Birchmeier, eds., Berlin: Springer-Verlag, pp. 195-203 (1996)).

The $\alpha_v\beta_6$ integrin may have multiple regulatory functions in tumor cell biology. Recent studies have demonstrated that the extracellular and cytoplasmic domains of the $\beta_6$ subunit mediate different cellular activities. The extracellular and transmembrane domains have been shown to mediate TGF-$\beta$ activation and adhesion (Sheppard, D., *Cancer and Metastasis Rev.* 24:395-402 (2005); Munger, J. S. et al., *Cell* 96:319-328 (1999)). The cytoplasmic domain of the $\beta_6$ subunit contains a unique 11-amino acid sequence that is important in mediating $\alpha_v\beta_6$ regulated cell proliferation, MMP production, migration, and pro-survival (Li, X. et al., *J. Biol. Chem.* 278(43):41646-41653 (2003); Thomas, G. J. et al., *J. Invest. Derm.* 117(1):67-73 (2001); Thomas, G. J. et al., *Br. J. Cancer* 87(8):859-867 (2002); Janes, S. M. and Watt, F. M., *J. Cell Biol* 166(3):419-431 (2004)). The $\beta_6$ subunit has been cloned, expressed and purified (Sheppard et al., U.S. Pat. No. 6,787,322 B2, the disclosure of which is incorporated herein by reference in its entirety), and function-blocking antibodies that selectively bind to the $\alpha_v\beta_6$ integrin have been reported (Weinreb et al., *J. Biol. Chem.* 279:17875-17877 (2004), the disclosure of which is incorporated herein by reference in its entirety). Antagonists of $\alpha_v\beta_6$ (including certain monoclonal antibodies) have also been suggested as possible treatments for certain forms of acute lung injury and fibrosis (see U.S. Pat. No. 6,692,741 B2 and WO 99/07405, the disclosures of which are incorporated herein by reference in their entireties).

$\alpha_v\beta_6$ can bind to several ligands including fibronectin, tenascin, and the latency associated peptide-1 and -3 (LAP1 and LAP3), the N-terminal 278 amino acids of the latent precursor form of TGF-$\beta$1 through a direct interaction with an arginine-glycine-aspartate ("RGD") motif (Busk, M. et al., *J. Biol. Chem.* 267(9):5790-5796 (1992); Yokosaki, Y. et al., *J. Biol. Chem.* 271(39):24144-24150 (1996); Huang, X. Z. et al., *J. Cell. Sci.* 111:2189-2195 (1998); Munger, J. S. et al., *Cell* 96:319-328 (1999)). The TGF-$\beta$ cytokine is synthesized as a latent complex which has the N-terminal LAP non-covalently associated with the mature active C-terminal TGF-$\beta$ cytokine. The latent TGF-$\beta$ complex cannot bind to its cognate receptor and thus is not biologically active until converted to an active form (Barcellos-Hoff, M. H., *J. Mamm.*

*Gland Biol.* 1(4):353-363 (1996); Gleizes, P. E. et al., *Stem Cells* 15(3):190-197 (1997); Munger, J. S. et al., *Kid. Int.* 51:1376-1382 (1997); Khalil, N., *Microbes Infect.* 1(15): 1255-1263 (1999)). $\alpha_v\beta_6$ binding to LAP1 or LAP3 leads to activation of the latent precursor form of TGF-β1 and TGF-β3 (Munger, J. S. et al., *Cell* 96:319-328 (1999)), proposed as a result of a conformational change in the latent complex allowing TGF-β to bind to its receptor. Thus, upregulated expression of $\alpha_v\beta_6$ can lead to local activation of TGF-β which in turn can activate a cascade of events downstream events.

The TGF-β1 cytokine is a pleiotropic growth factor that regulates cell proliferation, differentiation, and immune responses (Wahl, S. M., *J. Exp. Med.* 180:1587-1590 (1994); Massague, J., *Annu. Rev. Biochem.* 67:753-791 (1998); Chen, W. and Wahl, S. M., *TGF-β: Receptors, Signaling Pathways and Autoimmunity*, Basel: Karger, pp. 62-91 (2002); Thomas, D. A. and Massague, J., *Cancer Cell* 8:369-380 (2005)). The role that TGF-β1 plays in cancer is two-sided. TGF-β is recognized to tumor suppressor and growth inhibitory activity yet, many tumors evolve a resistance to growth suppressive activities of TGF-β1 (Yingling, J. M. et al., *Nature Rev. Drug Discov.* 3(12):1011-1022 (2004); Akhurst, R. J. et al., Trends Cell Biol. 11(11):S44-S51 (2001); Balmain, A. and Akhurst, R. J., *Nature* 428(6980):271-272 (2004)). In established tumors, TGF-β1 expression and activity has been implicated in promoting tumor survival, progression, and metastases (Akhurst, R. J. et al., Trends Cell Biol. 11(11): S44-S51 (2001); Muraoka, R. S. et al., *J. Clin. Invest.* 109 (12):1551 (2002); Yang, Y. A. et al., *J. Clin. Invest.* 109(12): 1607-1615 (2002)). This is postulated to be mediated by both autocrine and paracrine effects in the local tumor-stromal environment including the effects of TGF-β on immune surveillance, angiogenesis, and increased tumor interstitial pressure. Several studies have now shown the anti-tumor and anti-metastatic effects of inhibiting TGF-β1 (Akhurst, R. J., *J. Clin. Invest.* 109(12):1533-1536 (2002); Muraoka, R. S. et al., *J. Clin. Invest.* 109(12):1551 (2002); Yingling, J. M. et al., *Nat. Rev. Drug Discov.* 3(12):1011-1022 (2004); Yang, Y. A. et al., *J. Clin. Invest.* 109(12):1607-1615 (2002); Halder, S. K. et al., *Neoplasia* 7(5):509-521 (2005); Iyer, S. et al., *Cancer Biol. Ther.* 4(3):261-266 (2005)).

Increased expression of $\alpha_v\beta_6$ on tumors, particularly at the tumor-stromal interface, may reflect a unique mechanism for local activation of TGF-β1 and the ability to promote tumor survival, invasion, and metastasis. The high level of expression in human metastases infers a potential role for $\alpha_v\beta_6$ in establishing metastases which is consistent with previous reports that $\alpha_v\beta_6$ can mediate epithelial to mesenchymal transition, tumor cell invasion in vitro, and expression correlated with metastases in a mouse model (Bates, R. C. et al., *J. Clin. Invest.* 115(2):339-347 (2005); Thomas, G. J. et al., *Br. J. Cancer* 87(8):859-867 (2002); Morgan, M. R. et al., *J. Biol. Chem.* 279(25):26533-26539 (2004)).

We have previously described the generation of potent and selective anti-$\alpha_v\beta_6$ monoclonal antibodies (mAbs) that bind to both the human and murine forms of $\alpha_v\beta_6$ and block the binding of $\alpha_v\beta_6$ to its ligands and $\alpha_v\beta_6$ mediated activation of TGF-β1 (Weinreb, P. H. et al., *J. Biol. Chem.* 279(17):17875-17887 (2004)). As also described in PCT Publication WO 03/100033, herein incorporated in its entirety by reference, high affinity antibodies against $\alpha_v\beta_6$, including the identification and analysis of key amino acid residues in the complementary determining regions (CDRs) of such antibodies, were discovered and characterized. In particular, these high affinity antibodies (a) specifically bind to $\alpha_v\beta_6$; (b) inhibit the binding of $\alpha_v\beta_6$ to its ligand such as LAP, fibronectin, vitronectin, and tenascin with an $IC_{50}$ value lower than that of 10D5 (International Patent Application Publication WO 99/07405); (c) block activation of TGF-β; (d) contain certain amino acid sequences in the CDRs that provide binding specificity to $\alpha_v\beta_6$; (e) specifically bind to the $\beta_6$ subunit; and/or (f) recognize $\alpha_v\beta_6$ in immunostaining procedures, such as immunostaining of paraffin-embedded tissues.

WO 03/100033 also describes the discovery that antibodies that bind to $\alpha_v\beta_6$ can be grouped into biophysically distinct classes and subclasses. One class of antibodies exhibits the ability to block binding of a ligand (e.g., LAP) to $\alpha_v\beta_6$ (blockers). This class of antibodies can be further divided into subclasses of cation-dependent blockers and cation-independent blockers. Some of the cation-dependent blockers contain an arginine-glycine-aspartate (RGD) peptide sequence, whereas the cation-independent blockers do not contain an RGD sequence. Another class of antibodies exhibits the ability to bind to $\alpha_v\beta_6$ and yet does not block binding of $\alpha_v\beta_6$ to a ligand (nonblockers).

Furthermore, WO 03/100033 discloses antibodies comprising heavy chains and light chains whose complementarity determining regions (CDR) 1, 2 and 3 consist of certain amino acid sequences that provide binding specificity to $\alpha_v\beta_6$. WO 03/100033 also provides for antibodies that specifically bind to $\alpha_v\beta_6$ but do not inhibit the binding of $\alpha_v\beta_6$ to latency associated peptide (LAP) as well as antibodies that bind to the same epitope.

WO 03/100033 further discloses cells of hybridomas 6.1A8, 6.2B10, 6.3G9, 6.8G6, 6.2B1, 6.2A1, 6.2E5, 7.1G10, 7.7G5, and 7.1C5, isolated nucleic acids comprising a coding sequences and isolated polypeptides comprising amino acid sequences of the anti-$\alpha_v\beta_6$ antibodies. In particular, WO 03/100033 discloses anti-$\alpha_v\beta_6$ antibodies comprising heavy and light chain polypeptide sequences as antibodies produced by hybridomas 6.1A8, 6.3G9, 6.8G6, 6.2B1, 6.2B10, 6.2A1, 6.2E5, 7.1G10, 7.7G5, or 7.1C5. Several of the hybridomas were deposited at the American Type Culture Collection ("ATCC"; P.O. Box 1549, Manassas, Va. 20108, USA) under the Budapest Treaty. In particular, hybridoma clones 6.3G9 and 6.8G6 were deposited on Aug. 16, 2001, and have accession numbers ATCC PTA-3649 and PTA-3645, respectively. The murine antibodies produced by hybridomas 6.3G9 and 6.8G6 are being further explored in the present application for their potential development as humanized antibodies.

The murine monoclonal antibody 3G9 is a murine IgG1, kappa antibody isolated from the $\beta_6$ integrin −/− mouse (Huang et al., *J. Cell Biol.* 133:921-928 (1996)) immunized with human soluble $\alpha_v\beta_6$. The 3G9 antibody specifically recognizes the $\alpha_v\beta_6$ integrin epitope which is expressed at upregulated levels during injury, fibrosis and cancer (see, e.g., Thomas et al., *J. Invest. Dermatology* 117:67-73 (2001); Brunton et al., *Neoplasia* 3: 215-226 (2001); Agrez et al., *Int. J. Cancer* 81:90-97 (1999); Breuss, *J. Cell Science* 108:2241-2251 (1995)). It does not bind to other $\alpha_v$ integrins and is cross-reactive to both human and murine molecules. The murine monoclonal antibody 3G9 has been described to block the binding of $\alpha_v\beta_6$ to LAP as determined by blocking of ligand binding either to purified human soluble $\alpha_v\beta_6$ or to $\beta_6$-expressing cells, thereby inhibiting the pro-fibrotic activity of TGF-β receptor activation (see WO 03/100033). It has also been shown to inhibit $\alpha_v\beta_6$-mediated activation of TGF-β with an $IC_{50}$ value lower than one of the known $\alpha_v\beta_6$ antibodies, 10D5 (Huang et al., *J. Cell Sci.* 111:2189-2195 (1998)).

The murine monoclonal antibody 8G6 is a murine IgG1, kappa antibody which also recognizes the $\alpha_v\beta_6$ integrin epitope, as described in WO 03/100033. The murine monoclonal antibody 8G6 is a cation-dependent, high affinity blocker of $\alpha_v\beta_6$ displaying the ability to inhibit $\alpha_v\beta_6$-mediated activation of TGF-β with an $IC_{50}$ value lower than 10D5 (see WO 03/100033).

Both the 3G9 and 8G6 murine antibodies were effective in preventing fibrosis of the kidney and lung, as described in WO 03/100033. Furthermore, the murine antibody 3G9 was able to effectively inhibit tumor growth in a human tumor xenograft model, suggesting the potential role of $\alpha_v\beta_6$ in cancer pathology and the effectiveness of such blockade using antibodies directed at $\alpha_v\beta_6$.

Accordingly, there is a need to develop $\alpha_v\beta_6$ antibodies that are less antigenic in humans and that may be useful in the treatment of diseases involved in the $\alpha_v\beta_6$ pathway. With the advent of recombinant DNA methodology, it has become possible to structurally engineer antibody genes and produce modified antibody molecules with properties not obtainable by hybridoma technology. In the therapeutic arena, one aim of this methodology has been to reduce the immunogenicity in humans of rodent monoclonal antibodies by modifying their primary amino acid structure. Reduction of the immunogenicity of therapeutic antibodies is desirable because induction of an immune response can cause a spectrum of adverse effects in a patient, ranging from accelerated elimination of the therapeutic antibody, with consequent loss of efficacy, to fatal anaphylaxis at the most extreme.

One strategy to reduce immunogenicity of foreign monoclonal antibodies has been to replace the light and heavy chain constant domains of the monoclonal antibody with analogous domains of human origin, leaving the variable region domains of the foreign antibody intact. The variable region domains of the light and heavy chains are responsible for the interaction between the antibody and the antigen. Chimeric antibody molecules having mouse variable domains joined to human constant domains usually bind antigen with the same affinity constant as the mouse antibody from which the chimeric was derived. Such chimeric antibodies are less immunogenic in humans than their fully murine counterparts. Nevertheless, antibodies that preserve entire murine variable domains tend to provoke immune responses in a substantial fraction of patients.

That humans would mount an immune response to whole murine variable domains was predictable, thus, efforts to obtain variable domains with more human character had begun even before clinical trials of such standard chimeric antibodies had been reported. One category of methods frequently referred to as "humanizing," aims to convert the variable domains of murine monoclonal antibodies to a more human form by recombinantly constructing an antibody variable domain having both mouse and human character. Humanizing strategies are based on several consensual understandings of antibody structure data. First, variable domains contain contiguous tracts of peptide sequence that are conserved within a species, but which differ between evolutionarily remote species, such as mice and humans. Second, other contiguous tracts are not conserved within a species, but even differ even between antibody producing cells within the same individual. Third, contacts between antibody and antigen occur principally through the non-conserved regions of the variable domain. Fourth, the molecular architecture of antibody variable domains is sufficiently similar across species that correspondent amino acid residue positions between species may be identified based on position alone, without experimental data.

Humanized strategies share the premise that replacement of amino acid residues that are characteristic of murine sequences with residues found in the correspondent positions of human antibodies will reduce the immunogenicity in humans of the resulting antibody. However, replacement of sequences between species usually results in reduction of antibody binding to its antigen. The art of humanization therefore lies in balancing replacement of the original murine sequence to reduce immunogenicity with the need for the humanized molecule to retain sufficient antigen binding to be therapeutically useful. This balance has been struck using two approaches.

In one approach, exemplified by U.S. Pat. No. 5,869,619, characteristically human residues are substituted for murine variable domain residues that are determined or predicted (i) to play no significant chemical role in the interaction with antigens and (ii) to be positioned with side chains projecting into the solvent. Thus, exterior residues remote from the antigen binding site are humanized, while interior residues, antigen binding residues, and residues forming the interface between variable domains remain murine. One disadvantage of this approach is that rather extensive experimental data is required to determine whether a residue plays no significant chemical role in antigen binding or will be positioned in the solvent in a particular three dimensional antibody structure.

In another more general approach, exemplified by U.S. Pat. No. 5,225,539, contiguous tracts of murine variable domain peptide sequence considered conserved are replaced with the correspondent tracts from a human antibody. In this more general approach, all variable domain residues are humanized except for the non-conserved regions implicated in antigen binding. To determine appropriate contiguous tracks for replacement, U.S. Pat. No. 5,225,539 utilized a classification of antibody variable domain sequences that had been developed previously by Wu and Kabat, *J Exp Med.* 132(2):211-250 (1970).

Wu and Kabat pioneered the alignment of antibody peptide sequences, and their contributions in this regard were severalfold: First, through study of sequence similarities between variable domains, they identified correspondent residues that to a greater or lesser extent were homologous across all antibodies in all vertebrate species, inasmuch as they adopted similar three-dimensional structure, played similar functional roles, interacted similarly with neighboring residues, and existed in similar chemical environments. Second, they devised a peptide sequence numbering system in which homologous immunoglobulin residues were assigned the same position number. One skilled in the art can unambiguously assign what is now commonly called Kabat numbering, to any variable domain sequence, without reliance on any experimental data beyond the sequence itself. Third, for each Kabat-numbered sequence position, Kabat and Wu calculated variability, by which is meant the finding of few or many possible amino acids when variable domain sequences are aligned. They identified three contiguous regions of high variability embedded within four less variable contiguous regions. Other workers had previously noted variability approximately in these regions (hypervariable regions) and posited that the highly variable regions represented amino acid residues used for antigen binding. Kabat and Wu formally demarcated residues constituting these variable tracts, and designated these "complementarity determining regions" (CDRs), referring to chemical complementarity between antibody and antigen. A role in three-dimensional folding of the variable domain, but not in antigen recognition, was ascribed to the remaining less-variable regions, which are now termed "framework regions". Fourth, Kabat and Wu established a public database of antibody peptide and nucleic acid sequences, which continues to be maintained and is well known to those skilled in the art.

The humanization method disclosed by U.S. Pat. No. 5,225,539 in using the Kabat classification results in a chimeric antibody comprising CDRs from one antibody and framework regions from another antibody that differs in species origin, specificity, subclass, or other characteristics. However, no particular sequences or properties were ascribed to the framework regions, indeed, U.S. Pat. No. 5,225,539 taught that any set of frameworks could be combined with any set of CDRs. Framework sequences have since been recognized as being important for conferring the three dimensional structure of an antibody variable region necessary to retain good antigen binding. Subsequent developments in the field have been refinements within the scope of U.S. Pat. No. 5,225,539 to deal with loss of avidity for antigen observed with some humanized antibodies relative to the avidity of the corresponding mouse antibodies.

U.S. Pat. No. 5,693,761 discloses one refinement on U.S. Pat. No. 5,225,539 for humanizing antibodies, and is based on the premise that ascribes avidity loss to problems in the structural motifs in the humanized framework which, because of steric or other chemical incompatibility, interfere with the folding of the CDRs into the binding-capable conformation found in the mouse antibody. To address this problem, U.S. Pat. No. 5,693,761 teaches using human framework sequences closely homologous in linear peptide sequence to framework sequences of the mouse antibody to be humanized. Accordingly, the methods of U.S. Pat. No. 5,693,761 focus on comparing framework sequences between species. Typically, all available human variable domain sequences are compared to a particular mouse sequence and the percentage identity between correspondent framework residues is calculated. The human variable domain with the highest percentage is selected to provide the framework sequences for the humanizing project. U.S. Pat. No. 5,693,761 also teaches that it is important to retain in the humanized framework, certain amino acid residues from the mouse framework critical for supporting the CDRs in a binding-capable conformation.

In other approaches, criticality of particular framework amino acid residues is determined experimentally once a low-avidity humanized construct is obtained, by reversion of single residues to the mouse sequence and assaying antigen binding as described by Riechmann et al., *Nature* 332(6162): 323-327 (1988). Another example approach for identifying criticality of amino acids in framework sequences is disclosed by U.S. Pat. No. 5,821,337 and U.S. Pat. No. 5,859,205. These references disclose specific Kabat residue positions in the framework, which, in a humanized antibody may require substitution with the correspondent mouse amino acid to preserve avidity. Accordingly, the resulting frameworks constructed, which are part human and part mouse, still frequently exhibit human immunogenicity or lowered antigen binding, thereby requiring numerous iterations in framework construction to obtain a suitable framework for therapeutic uses.

There is therefore, a need in the art to develop $\alpha_v\beta_6$ antibodies that are less antigenic in humans. The present invention provides for the generation of humanized antibodies that are specifically reactive with $\alpha_v\beta_6$. The present invention also provides methods for making such humanized antibodies by providing humanized antibodies that reliably identify suitable human framework sequences to support non-human CDR regions and further to provide humanized antibodies that retain high antigen binding with low immunogenicity in humans. The present invention also provides for uses of such humanized antibodies reactive with $\alpha_v\beta_6$ in the treatment, diagnosis and/or prevention of various diseases and disorders.

BRIEF SUMMARY OF THE INVENTION

The present invention is based at least in part upon the discovery and characterization of high affinity humanized antibodies against $\alpha_v\beta_6$, including the identification and analysis of key amino acid residues in the complementary determining regions (CDRs) of such antibodies as well as identification and analysis of critical amino acid residues in the framework sequences.

In one embodiment, the present invention relates to humanized monoclonal antibodies having binding specificity for $\alpha_v\beta_6$ integrins, wherein the antibody comprises heavy and light chain variable domains of SEQ ID NO: 1 and SEQ ID NO: 2, respectively. Such humanized antibodies are derived from the humanization of the murine 3G9 antibody. In certain embodiments, the humanized antibodies comprise a heavy chain whose complementarity determining regions (CDR) 1, 2 and 3 are defined by amino acid residues 31-35, 50-65 and 98-109, respectively, of SEQ ID NO: 1. In certain embodiments, the humanized antibodies comprise a light chain whose CDRs 1, 2 and 3 are defined by amino acid residues 24-35, 51-57 and 90-98, respectively, of SEQ ID NO: 2. In certain embodiments, the humanized antibodies comprise a heavy chain whose framework regions (FR) 1, 2, 3 and 4 are defined by amino acid residues 1-30, 36-49, 66-97 and 110-120, respectively, of SEQ ID NO: 1. In certain embodiments, the humanized antibodies comprise a light chain whose framework regions (FR) 1, 2, 3 and 4 are defined by amino acid residues 1-23, 36-50, 58-89 and 99-108, respectively, of SEQ ID NO: 2.

In certain embodiments, the humanized antibodies comprise at least one of the following amino acid substitutions in the heavy chain consisting of Q3M and N74S of SEQ ID NO: 1. In certain embodiments, the humanized antibodies comprise at least one of the following amino acid substitutions in the light chain consisting of E1Q, L47W, I58V, A60V and Y87F of SEQ ID NO: 2.

In certain embodiments, the humanized antibody comprises a heavy chain version 1 ("HV1") wherein the heavy chain consists of amino acid substitutions Q3M and N74S of SEQ ID NO: 1. In certain embodiments, the humanized antibody comprises a heavy chain version 2 ("HV2") wherein the heavy chain consists of amino acid substitution N74S of SEQ ID NO: 1. In certain embodiments, the humanized antibody comprises a heavy chain version 3 ("HV3") wherein the heavy chain consists of SEQ ID NO: 1.

In certain embodiments, the humanized antibody comprises a light chain version 1 ("LV1") wherein the light chain consists of amino acid substitutions L47W, I58V, A60V and Y87F of SEQ ID NO: 2. In certain embodiments, the humanized antibody comprises a light chain version 2 ("LV2") wherein the light chain consists of amino acid substitutions L47W and I58V of SEQ ID NO: 2. In certain embodiments, the humanized antibody comprises a light chain version 3 ("LV3") wherein the light chain consists of amino acid substitution L47W of SEQ ID NO: 2. In certain embodiments, the humanized antibody comprises a light chain version 4 ("LV4") wherein the light chain consists of amino acid substitutions E1Q and L47W of SEQ ID NO: 2. In certain embodiments, the humanized antibody comprises a light chain version 5 ("LV5") wherein the light chain consists of SEQ ID NO: 2.

In certain embodiments, the humanized antibody comprises a heavy and light chain variable domain comprising HV3 wherein the heavy chain consists of SEQ ID NO: 1 and LV5 wherein the light chain consists of SEQ ID NO: 2.

In certain embodiments, the humanized antibodies have CDRs derived from the murine 6.3G9 antibody (ATCC Accession No. PTA-3649).

In related embodiments, the present invention also relates to humanized monoclonal antibodies having binding specificity for $\alpha_v\beta_6$ integrins, wherein the antibodies comprises a heavy and light chain variable domains of SEQ ID NO: 3 and SEQ ID NO: 4. Such humanized antibodies are derived from the humanization of the murine 8G6 antibody. In certain embodiments, the humanized antibodies comprise a heavy chain whose complementarity determining regions (CDR) 1, 2 and 3 are defined by amino acid residues (i.e., with the exception of some conservative variations) 31-35, 50-66 and 99-115, respectively, of SEQ ID NO: 3. In certain embodiments, the humanized antibodies comprise a light chain whose CDRs 1, 2 and 3 are defined by amino acid residues 24-38, 54-60 and 93-101, respectively, of SEQ ID NO: 4. In certain embodiments, the humanized antibodies comprise a heavy chain whose framework regions (FR) 1, 2, 3 and 4 are defined by amino acid residues 1-30, 36-49, 67-98 and 116-126, respectively, of SEQ ID NO: 3. In certain embodiments, the humanized antibodies comprise a light chain whose FR 1, 2, 3 and 4 are defined by amino acid residues 1-23, 39-53, 61-92 and 102-111, respectively, of SEQ ID NO: 4.

In certain embodiments, the humanized antibodies comprise at least one of the following amino acid substitutions in the heavy chain consisting of A24G, G26S, Q39L, M48I, V68A, R72V and T74K of SEQ ID NO: 3. In certain embodiments, the humanized antibodies comprise at least one of the following amino acid substitutions in the light chain consisting of E1D, L46F and Y49K of SEQ ID NO: 4.

In certain embodiments, the humanized antibody comprises a heavy chain version 1 ("HV1") wherein the heavy chain consists of amino acid substitutions A24G, G26S, Q39L, M48I, V68A, R72V and T74K of SEQ ID NO: 3. In certain embodiments, the humanized antibody comprises a heavy chain version 2 ("HV2") wherein the heavy chain consists of amino acid substitutions M48I, V68A, R72V and T74K of SEQ ID NO: 3. In certain embodiments, the humanized antibody comprises a heavy chain version 3 ("HV3") wherein the heavy chain consists of amino acid substitutions V68A, R72V and T74K of SEQ ID NO: 3.

In certain embodiments, the humanized antibody comprises a light chain version 1 ("LV1") wherein the light chain consists of amino acid substitutions E1D, L46F and Y49K of SEQ ID NO: 4. In certain embodiments, the humanized antibody comprises a light chain version 2 ("LV2") wherein the light chain consists of amino acid substitution L46F and Y49K of SEQ ID NO: 4. In certain embodiments, the humanized antibody comprises a light chain version 3 ("LV3") wherein the light chain consists of amino acid substitution Y49K of SEQ ID NO: 4.

In certain embodiments, the humanized antibodies have CDRs derived from the murine 6.8G6 antibody. In certain embodiments, the humanized antibodies can compete for binding to $\alpha_v\beta_6$ with murine 8G6 antibody.

The present invention also embraces humanized antibodies that bind to the same epitope as any of the above-described antibodies.

The present invention also embraces humanized antibodies produced by a recombinant vector comprising a nucleic acid encoding said antibodies. In certain embodiments, the recombinant vector may be a plasmid selected from the group consisting of pKJS195 (SEQ ID NO: 5), pKJS189 (SEQ ID NO: 6) and pKJS196 (SEQ ID NO: 7).

The present invention also embraces isolated nucleic acids comprising a coding sequence for any one of SEQ ID NOs: 1-7 and isolated polypeptides comprising an amino acid sequence of any one of SEQ ID NOs: 1-7.

The present invention also embraces recombinant vectors comprising the nucleic acids of any of the above-described humanized antibodies.

The invention also embraces host cells comprising the recombinant vectors comprising the nucleic acids of any of the above-described humanized antibodies.

This invention also embraces compositions comprising one or more humanized antibodies of this invention, and a pharmaceutically acceptable carrier. In some of these compositions, the humanized antibodies are conjugated to a cytotoxic agent (i.e., an agent that impairs the viability and/or the functions of a cell) such as a toxin or a radionuclide. The compositions can be administered to a subject (e.g., a mammal such as a human) having or at risk of having a disease mediated by $\alpha_v\beta_6$, so as to treat (e.g., alleviating, mitigating, reducing, preventing, postponing the onset of) the disease. Examples of such diseases include, but are not limited to: fibrosis (e.g., scleroderma, scarring, liver fibrosis, lung fibrosis, and kidney fibrosis); psoriasis; cancer (as described elsewhere herein, e.g., epithelial cancer; oral, skin, cervical, ovarian, pharyngeal, laryngeal, esophageal, lung, breast, kidney, pancreatic, prostatic or colorectal cancer); Alport's Syndrome; acute and chronic injuries of the lung, liver, kidney and other internal organs; and sclerosis of the lung, liver, kidney and other internal organs. Risks of having such diseases may result from genetic predisposition; certain lifestyles such as smoking and alcoholism; exposure to environmental pollutants such as asbestos; physiological conditions such as diabetes, hepatitis viral infection (e.g., hepatitis C viral infection), autoimmune diseases; and medical treatments such as radiation therapy.

The present invention also embraces methods of preparing any of the above-described humanized antibodies by culturing any of the above-described host cells under conditions appropriate for expression of the humanized antibody, wherein humanized antibody chains are expressed and humanized antibodies are produced. In certain embodiments, the methods further comprising the steps of isolating the humanized antibodies. In certain embodiments, the host cell is a CHO cell.

Hybridoma clones 6.3G9 and 6.8G6 were deposited on Aug. 16, 2001 at the American Type Culture Collection ("ATCC"; P.O. Box 1549, Manassas, Va. 20108, USA) under the Budapest Treaty, and have accession numbers ATCC PTA-3649 and -3645, respectively.

A humanized antibody of the present invention refers to a full antibody, e.g., an antibody comprising two heavy chains and two light chains, or to an antigen-binding fragment of a full antibody such as a Fab fragment, a Fab' fragment, a $F(ab')_2$ fragment or a F(v) fragment. A humanized antibody of this invention can be of any isotype and subtype, for example, IgA (e.g., IgA1 and IgA2), IgG (e.g., IgG1, IgG2, IgG3 and IgG4), IgE, IgD, IgM, wherein the light chains of the immunoglobulin may be of type kappa or lambda.

In some embodiments, the humanized antibody of the present invention may comprise a mutation (e.g., deletion, substitution or addition) at one or more (e.g., 2, 3, 4, 5, or 6) of certain positions in the heavy chain such that the effector function of the antibody (e.g., the ability of the antibody to bind to a Fc receptor or a complement factor) is altered without affecting the antibody's antigen-binding ability.

In other embodiments, the humanized antibody of this invention may contain a mutation at an amino acid residue that is a site for glycosylation such that the glycosylation site is eliminated. Such a humanized antibody may have clinically beneficial, reduced effector functions or other undesired functions while retaining its antigen-binding affinity. Mutation of a glycosylation site can also be beneficial for process development (e.g., protein expression and purification).

In certain embodiments of this invention, the humanized antibody comprises an aglycosyl light chain whose CDRs are derived from the murine 3G9 antibody. In certain embodiments, the humanized 3G9 antibody contains a light chain variable domain wherein the CDR1 region contains an asparagine (N) to serine (S) substitution at amino acid residue 26 of SEQ ID NO: 2. The murine 3G9 CDR1 region contains an asparagine at this amino acid position. However, in the humanized version of the 3G9 antibody, all five versions of the light chain (LV1, LV2, LV3, LV4 and LV5) contains a serine within the 3G9 CDR1 region at this position. Aglycosylation of this site in all light chain versions of the humanized 3G9 antibody has been shown to be beneficial for both protein expression and purification of the light chains. In certain other embodiments, the humanized 3G9 antibody contains a mutation at a glycosylation site that is normally required for normal Fc receptor binding. In certain embodiments, the humanized 3G9 antibody contains an asparagine (N) to glutamine (Q) amino acid substitution. In certain embodiments, the humanized 3G9 antibody contains the N to Q amino acid substitution in the heavy chain version 3 (HV3) produced by a recombinant vector comprising the plasmid pKJS196 (SEQ ID NO: 7). In certain embodiments, the N to Q amino acid substitution occurs at amino acid residue 319 of SEQ ID NO: 7. Aglycosylation of this site in heavy chain version 3 (HV3) of the humanized 3G9 antibody has been shown to remove a glycosylation signal required for normal Fc receptor binding without affecting the antigen-binding affinity of the humanized antibody. In certain embodiments, the humanized 3G9 antibody comprises the heavy chain version 3 (HV3) produced by a recombinant vector comprising plasmid pKJS189 (SEQ ID NO: 6) and the light chain version 5 (LV5) produced by a recombinant vector comprising plasmid pKJS195 (SEQ ID NO: 5). In certain embodiments, the humanized 3G9 antibody comprises the aglycosyl heavy chain version 3 (a-HV3) produced by a recombinant vector comprising plasmid pKJS196 (SEQ ID NO: 7) and the light chain version 5 (LV5) produced by a recombinant vector comprising plasmid pKJS195 (SEQ ID NO: 5).

In still other embodiments, the heavy or light chains can contain mutations that increase affinity or potency.

The humanized antibodies of the invention are useful for treating any clinically undesirable condition or disease (as discussed herein) that is mediated by binding of $\alpha_v\beta_6$ to its ligand, such as LAP and fibronectin. These humanized antibodies can be more potent, via higher affinity or avidity, and cation dependency or independency of binding to ligand, than previously known $\alpha_v\beta_6$ antibodies. In contrast to murine monoclonal antibodies, the humanized antibodies of this invention will not cause anti-mouse immunoglobulin antibody production in the subject's, especially a human body, but instead show a prolonged blood half-life, with a reduced frequency of adverse effects, so that it can be expected to be superior to be mouse monoclonal antibodies in the efficacy in the treatment of diseases mediated by $\alpha_v\beta_6$.

In additional aspects, the present invention relates to methods of cancer diagnosis, treatment and prevention using $\alpha_v\beta_6$-binding ligands, such as $\alpha_v\beta_6$-binding antibodies. In one embodiment, the present invention provides methods for reducing or preventing the metastasis of a primary tumor to a secondary location in a patient, comprising administering to the patient a therapeutically effective amount of one or more ligands that binds to one or more subunits of integrin $\alpha_v\beta_6$ on one or more cells in the primary tumor, wherein the binding of the ligand to the integrin results in the death, chemosensitivity or decreased invasiveness of the tumor cell. In related embodiments, the invention provides methods of reducing or preventing the progression of a pre-metastatic tumor to a metastatic tumor in a patient, comprising administering to the patient a therapeutically effective amount of one or more ligands that binds to one or more subunits of integrin $\alpha_v\beta_6$ on one or more cells in the pre-metastatic tumor, wherein the binding of the ligand to the integrin results in the reduction or prevention of invasion of cells of the pre-metastatic cancer into tissue areas surrounding the primary tumor. In certain such embodiments of the invention, the tumor cell is a carcinoma, such as an adenocarcinoma. In more particular embodiments, the carcinoma is a breast carcinoma, an endometrial carcinoma, a pancreatic carcinoma, a colorectal carcinoma, a lung carcinoma, an ovarian carcinoma, a cervical carcinoma, a prostatic carcinoma, a liver carcinoma, an esophageal carcinoma, a head and neck carcinoma, a stomach carcinoma or a splenic carcinoma. More particularly, the carcinoma is a breast carcinoma (including but not limited to an in situ breast carcinoma, such as ductal carcinoma in situ (DCIS) or lobular carcinoma in situ (LCIS)), an endometrial carcinoma, a pancreatic carcinoma, a colorectal carcinoma, a cervical carcinoma, or a lung carcinoma.

Suitable embodiments according to this aspect of the invention use $\alpha_v\beta_6$ integrin-binding ligands which are $\alpha_v\beta_6$-binding antibodies or $\alpha_v\beta_6$ epitope-binding fragments thereof. According to certain such embodiments, the antibodies are monoclonal antibodies (which may be chimeric, primatized or humanized), including those disclosed in U.S. patent application publication no. US 2005/0255102 A1, the disclosure of which is incorporated herein in its entirety. Suitable such antibodies include, but are not limited to, the $\alpha_v\beta_6$-binding monoclonal antibodies designated 1A8, 3G9, 8G6, 2B1, 2B10, 2A1, 2E5, 1G10, 7G5, 1C5, 10D5 (ATCC deposit no. HB12382) and CSβ6, as well as fragments, chimeras and hybrids thereof. Particularly suitable for use in such embodiments of the invention are monoclonal antibodies 3G9 and 8G6. Also particularly suitable for use in such embodiments of the invention are humanized monoclonal antibodies, such as the humanized 3G9 antibody designated hu3G9 (BG00011) and the humanized 8G6 antibody designated hu8G6.

In certain such therapeutic embodiments of the invention, the $\alpha_v\beta_6$-binding ligands (e.g., $\alpha_v\beta_6$-binding antibodies) are conjugated with or bound to one or more cytotoxic compounds or agents which lead to or cause the death of the cell or tissue upon binding of the $\alpha_v\beta_6$-binding ligand-toxic compound conjugate to one or more $\alpha_v\beta_6$ integrins on the cell or tissue. In additional therapeutic embodiments of the invention, the $\alpha_v\beta_6$-binding ligands (e.g., $\alpha_v\beta_6$-binding antibodies) are administered to a patient in conjunction with one or more such cytotoxic compounds or agents. Cytotoxic compounds or agents which can be suitably used according to these aspects of the invention include, but are not limited to, cytotoxic agents (e.g., cisplatin, carboplatin, oxaliplatin, paclitaxel, melphalan, doxorubicin, methotrexate, 5-fluorouracil, etoposide, mechlorethamine, cyclophosphamide, bleomycin, a calicheamicin, a maytansine, a trichothene, CC1065, diphtheria A chain, *Pseudomonas aeruginosa* exotoxin A chain, ricin A chain, abrin A chain, modeccin A chain, alpha-sarcin, *Aleuritesfordii* proteins, dianthin proteins, *Phytolaca americana* proteins, *momordica charantia* inhibitors, curcin, crotin, sapaonaria officinalis inhibitors, gelonin, mitogellin, restrictocin, phenomycin, enomycin, tricothecenes, ribonucleases and deoxyribonucleases), radioisotopes (such as $^{211}$At, $^{131}$I, $^{125}$I, $^{90}$Y, $^{186}$Re, $^{188}$Re, $^{153}$Sm, $^{212}$Bi, $^{32}$P, and radioactive isotopes of Lu) and prodrug-activating enzymes (such as alkaline phosphatase, arylsulfatase, cytosine deaminase, proteases, D-alanylcarboxy-peptidases, carbohydrate-cleaving enzymes, P-lactamase and penicillin amidase. In certain embodiments, the one or more $\alpha_v\beta_6$ integrin-binding ligands are administered to the patient in the form of a pharmaceutical composition comprising an effective amount of one or more of the $\alpha_v\beta_6$ integrin-binding ligands and one or more pharmaceutically acceptable carriers or excipients. The one or more $\alpha_v\beta_6$ integrin-binding ligands and/or one or more pharmaceutical compositions comprising the one or more $\alpha_v\beta_6$ integrin-binding ligands can be administered to the patient by any suitable mode of administering pharmaceutical compositions, including but not limited to oral administration, parenteral administration (including, for example, injection via an intramuscular, intravenous, intraarterial, intraperitoneal, or subcutaneous route), intracranial administration, transdermal administration, intrapulmonary administration and intranasal administration.

In additional embodiments, the present invention provides methods of diagnosing or identifying a carcinoma, such as an adenocarcinoma, that is more likely to progress to an invasive carcinoma, and/or that is more likely to respond to treatment with a ligand that binds to one or more subunits of integrin $\alpha_v\beta_6$. Suitable such methods may comprise, for example, (a) obtaining from a patient a cancerous epithelial tissue sample comprising a tumor or a portion thereof, and a noncancerous epithelial tissue sample; (b) contacting the tissue samples with one or more ligands that binds to one or more subunits of integrin $\alpha_v\beta_6$; and (c) determining the level of expression of integrin $\alpha_v\beta_6$ in the tissue samples, wherein an increase in the level of expression of integrin $\alpha_v\beta_6$ in the cancerous tissue sample relative to the level of expression of integrin $\alpha_v\beta_6$ in the noncancerous tissue sample indicates the presence in the patient of a carcinoma that: (a) has an increased likelihood of progressing from an in situ or noninvasive form, to an invasive, metastatic form; and/or (b) is more likely to respond to treatment with one or more of the above-referenced treatment methods that relies upon the binding of an $\alpha_v\beta_6$-binding ligand, particularly an $\alpha_v\beta_6$-binding ligand that is conjugated to or that is administered in conjunction with one or more cytotoxic compounds or agents such as those described above. Such methods are suitable for diagnosing or identifying a variety of carcinomas, including but not limited to those involving the epithelial tissues noted above. In certain such embodiments, the ligand that binds to one or more subunits of integrin $\alpha_v\beta_6$ is an $\alpha_v\beta_6$ integrin-binding antibody (which may be a monoclonal antibody such as those described above) or an $\alpha_v\beta_6$ epitope-binding fragment thereof. Particularly suitable for use in such diagnostic methods of the invention are $\alpha_v\beta_6$-binding ligands (e.g., antibodies) that are detectably labeled, i.e., that comprise, are conjugated to, or are bound with at least one detectable label such as a chromogenic label (e.g., diaminobenzidine or 4-hydroxyazobenzene-2-carboxylic acid), an enzyme label (e.g., malate dehydrogenase, staphylococcal nuclease, delta-5-steroid isomerase, yeast-alcohol dehydrogenase, alpha-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase or acetylcholine esterase), a radioisotopic label (e.g., $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc or $^{109}$Pd), a non-radioactive isotopic label (e.g., $^{157}$Gd, $^{55}$Mn, $^{162}$Dy, $^{52}$Tr, $^{56}$Fe, $^{99m}$Tc or $^{112}$In), a fluorescent label (e.g., a $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label or a fluorescamine label), a toxic label (e.g., a diphtheria toxin label, a ricin label or a cholera toxin label), a chemiluminescent label (e.g., a luminol label, an isoluminol label, an aromatic acridinium ester label, an imidazole label, an acridinium salt label, an oxalate ester label, a luciferin label, a luciferase label or an aequorin label), an X-radiographic label (e.g., barium or cesium), a spin label (e.g., deuterium) and a nuclear magnetic resonance contrast agent label (e.g., Gd, Mn and iron).

In additional embodiments, the invention provides methods of eliminating $\alpha_v\beta_6$-positive metastatic tumor cells in a patient, comprising administering to the patient a therapeutically effective amount of one or more ligands that binds to one or more subunits of integrin $\alpha_v\beta_6$ on one or more $\alpha_v\beta_6$-positive metastatic tumor cells, wherein the binding of the ligand to the integrin results in the death, chemosensitization or decreased invasiveness of the metastatic tumor cell. Such methods are suitable for eliminating a variety of metastatic tumor cells in a patient, such as those arising from metastatic carcinomas, including but not limited to those involving the epithelial tissues noted above. Suitable embodiments according to this aspect of the invention use $\alpha_v\beta_6$ integrin-binding ligands which are $\alpha_v\beta_6$-binding antibodies or $\alpha_v\beta_6$ epitope-binding fragments thereof, particularly the monoclonal antibodies, or variants or fragments thereof, described above. In certain such therapeutic embodiments of the invention, the $\alpha_v\beta_6$-binding ligands (e.g., $\alpha_v\beta_6$-binding antibodies) are conjugated with or bound to one or more cytotoxic compounds or agents which lead to or cause the death of the cell or tissue upon binding of the $\alpha_v\beta_6$-binding ligand-toxic compound conjugate to one or more $\alpha_v\beta_6$ integrins on the cell or tissue. In additional therapeutic embodiments of the invention, the $\alpha_v\beta_6$-binding ligands (e.g., $\alpha_v\beta_6$-binding antibodies) are administered to a patient in conjunction with one or more such cytotoxic compounds or agents. Cytotoxic compounds or agents which can be suitably used according to these aspects of the invention include, but are not limited to, the cytotoxic agents, radioisotopes and prodrug-activating enzymes described above. According to this aspect of the invention, the $\alpha_v\beta_6$ integrin-binding ligand, or a pharmaceutical composition comprising the ligand and one or more pharmaceutical carriers or excipients, can be administered to the patient according to the modes of administration described above.

In additional embodiments, the invention provides methods of eliminating residual $\alpha_v\beta_6$-positive tumor cells from a patient following surgical excision of a tumor from a tissue or organ of the patient, comprising administering to the patient a therapeutically effective amount of one or more ligands that binds to one or more subunits of integrin $\alpha_v\beta_6$ on one or more residual tumor cells in the tissue or organ, wherein the binding of the ligand to said integrin results in the death, chemosensitivity or decreased invasiveness of the tumor cell. Such methods are suitable for eliminating a variety of metastatic tumor cells in a variety of patient tissues, such as those arising from carcinomas, including but not limited to those involving the epithelial tissues noted above. Suitable embodiments according to this aspect of the invention use $\alpha_v\beta_6$ integrin-binding ligands which are $\alpha_v\beta_6$-binding antibodies or $\alpha_v\beta_6$ epitope-binding fragments thereof, particularly the monoclonal antibodies, or variants or fragments thereof, described above. In certain such therapeutic embodiments of the invention, the $\alpha_v\beta_6$-binding ligands (e.g., $\alpha_v\beta_6$-binding antibodies) are conjugated with or bound to one or more cytotoxic compounds or agents which lead to or cause the death of the cell or tissue upon binding of the $\alpha_v\beta_6$-binding ligand-toxic compound conjugate to one or more $\alpha_v\beta_6$ integrins on the cell or tissue. Cytotoxic compounds or agents which can be suitably used according to this aspect of the invention include, but are not limited to, the cytotoxic agents, radioisotopes and pro-drug-activating enzymes described above.

Other preferred embodiments of the present invention will be apparent to one of ordinary skill in light of the following drawings and description of the invention, and of the claims.

BRIEF DESCRIPTION OF THE DRAWINGS

FIG. 1 is a binding ELISA assay of purified, chimerized 3G9 variants to $\alpha_v\beta_6$. Plates coated with soluble $\alpha_v\beta_6$ were incubated with either purified hybridoma derived murine 3G9 antibody, (m3G9) purified chimeric 3G9 antibody (ch3G9), or purified chimeric 3G9 antibody containing a N to S substitution within the N-linked glycosylation site in the first CDR of the light chain (ch3G9S). After washing with wash buffer, the plates were incubated with peroxide-conjugated anti-mouse IgG (for the hybridoma derived material) or anti-human IgG (for the chimeric antibodies) followed by washing with wash buffer. The plates were developed with TMB solution, reactions stopped with sulphuric acid and assayed with a plate reader at $A_{450}$. There was no detectable significant difference between the 2 forms of chimeric 3G9 antibody.

FIG. 2 displays results showing the expression of 3G9 humanized variants from transfected 293E cells using the Easy Titer Assay (Pierce). Supernatants from transiently transfected 293E cells were assayed for antibody titer by the Easy Titer method following the manufacturer's protocol (Pierce). The expression of different variants of humanized 3G9 antibody were analyzed. Variants of 3G9 containing version 1 of the light chain are poorly expressed while variants containing version 2 of the light chain are expressed at higher levels. There is a trend towards higher expression with increasing humanization.

FIG. 3 shows the results of FACS analysis of hu-3G9 antibody variants binding to $\alpha_v\beta_6$ integrin expressing SW480 cells as determined by the flow cytometry assay. SW480 cells were harvested by trypsinization, washed and resuspended in FACS buffer. $2\times10^5$ cells were then incubated on ice for 1 hour in FACS buffer containing the indicated transfectant supernatant, the titers of which were determined by the Easy Titer method according to the manufacturer's protocol (Pierce). After incubation, cells were washed with FACS buffer and resuspended in FACS buffer containing phycoerythrin conjugated anti-human IgG (Jackson ImmunoResearch) and incubated on ice for 30 min. Cells were then washed and resuspended in 200 μL of FACS buffer. Binding of the labeled secondary antibody was monitored by flow cytometry. All humanization versions tested bound to SW480 cells at least as well as chimeric 3G9. Variants containing light chain version 2 significantly exceeded the activity of chimeric 3G9. The anti-lymphotoxin-beta receptor antibody Hu-BHA10 served as a negative control.

FIG. 4 displays the FACS analysis of hu-3G9 antibody versions 2-5 binding to FDCP1-β6 cells. FACS analysis was carried out as described in FIG. 3 except that FDCP1-β6 cells were used in place of the SW480 cells. The fully humanized variant version 5 (H3/L5) bound to FDCP1-β6 significantly better than all other humanization versions.

FIG. 5 displays the FACS analysis of purified hu-3G9 antibody versions 2-5 binding to FDCP1-β6 cells. FACS analysis was carried out as described in FIG. 4 using purified 3G9 humanization variants. The fully humanized variant version 5 (H3/L5) bound to FDCP1-β6 significantly better than all other humanization versions.

FIG. 6 is a binding ELISA assay of purified hu-3G9 antibody versions 2-5 binding to $\alpha_v\beta_6$. The binding ELISA was carried out as described in FIG. 1. Humanized 3G9 version 5 (H3/L5) appears to bind to $\alpha_v\beta_6$ slightly better than other derivatives of the antibody.

FIG. 7 is a blocking ELISA of purified hu-3G9 antibody versions 2-5 binding to $\alpha_v\beta_6$. Plates were coated with either 0.3 μg/ml of LAP or 2.5 μg/ml of LAP-Fc fusion protein and incubated at 4° C. overnight. The coating solution was removed and the plates were blocked, washed, and incubated with a mixture of biotinylated $\alpha_v\beta_6$ and the 3G9 derivatives as indicated in the figure legend in the presence of calcium and magnesium. The plate was again washed and incubated with extravidin-horseradish peroxidase conjugate (Sigma). Bound protein was detected using TMB substrate followed by detection in a plate reader at $A_{450}$. Humanized 3G9 version 5 (H3/L5) appears to block $\alpha_v\beta_6$ binding to LAP slightly better than other derivatives of the antibody.

FIG. 8 displays the results from a cell-adhesion assay of purified hu-3G9 antibody versions 2-5. Microtiter plates were coated with 50 μl/well of 0.5 μg/ml LAP at 4° C. overnight. The plates were then washed and blocked. FDCP1-β6 cells ($5\times10^6$ cells/ml) were detached from culture flasks, labeled with fluorescent dye (Calcein-AM, Molecular Probes, Eugene, Oreg.) and resuspended in assay buffer. The plates were incubated with the purified antibodies indicated above, and the labeled FDCP1-β6 cells in the presence of calcium and magnesium. The plate was washed and the fluorescence due to captured cells on the plate was recorded. Percent binding was determined by comparing the fluorescence of total cells to that of bound cells. Humanized 3G9 version 5 (H3/L5) appears to block the binding of $\alpha_v\beta_6$ expressing cells to LAP slightly better than other derivatives of the antibody.

FIG. 9 is a schematic representation of the plasmid map of pKJS195 and 3G9 version 5 light chain sequence (SEQ ID NO: 5). This plasmid contains the 3G9 version 5 light chain (LV5) and neomycin resistance genes. The light chain expression cassette contains the human CMV immediate early promoter and first intron (containing a small deletion) as well as the human growth hormone polyadenylation sequence.

FIG. 10 is a schematic representation of the plasmid map of pKJS189 and 3G9 version 3 heavy chain sequence. This plasmid contains the 3G9 version 3 heavy chain (HV3) and dehydrofolate reductase (dhfr) genes. The heavy chain expression cassette contains the human CMV immediate early promoter and first intron (containing a small deletion) as well as the human growth hormone polyadenylation sequence. The dhfr expression cassette contains the SV40 early promoter and SV40 polyadenylation sequence.

FIG. 11 is a schematic representation of the plasmid map of pKJS196 and aglycosyl 3G9 version 3 heavy chain sequence (SEQ ID NO: 7). This plasmid contains the aglycosyl-3G9 version 3 heavy chain (a-HV3) and dhfr genes. This construct is identical to pKJS189 except for a N319Q substitution that abolishes a N-linked glycosylation site in the heavy chain constant region.

FIG. 12 displays the results of assembly and expression of hu-3G9 CHO expression vectors transiently transfected into CHO cells using the Easy Titer Assay (Pierce). The Easy Titer assay was carried out as described in FIG. 2 according to the manufacturer's protocol (Pierce). Wild-type (H3/L5) and aglycosyl (a-H3/L5) humanized 3G9 version 5 vectors were transiently transfected into CHO cells to demonstrate efficient assembly and secretion of humanized 3G9 from these cells. Both forms of hu3G9 antibodies are equally assembled and expressed in CHO cells.

FIG. 14A: tonque to lymph node; FIG. 14B: tonque to lymph node; FIG. 14C: Esophagus to lymph node; FIG. 14D skin to lymph node; FIG. 14E skin to neck; FIG. 14F: larynx to lung; FIG. 14G: cervix to lymph node; FIG. 14H anus to liver; and FIG. 14I: neck to lung.

FIG. 16A: expression in primary tumor sample from patient with ductal carcinoma in situ (DCIS). FIG. 16B: expression in primary tumor sample from patient with invasive breast carcinoma.

FIGS. 17A-17C: expression in primary tumor samples from three different patients. FIGS. 17D-17F: expression in matched lymph node metastases from these same three patients. FIGS. 17G-17H: expression in normal pancreatic tissue obtained from two of the three patients.

FIGS. 18A-18E: expression in primary tumor samples from five different patients, three with tumors characterized as adenosquamous (FIGS. 18A-18C), and two with tumors characterized as poorly differentiated (FIGS. 18D-18E). FIGS. 18F-18J: expression in matched lymph node metastases from these same five patients. FIGS. 18K-18L: expression in normal pancreatic tissue obtained from two of the five patients.

FIG. 19A: photomicrograph of a section of xenograft tumor stained via immunohistochemistry with an anti-$\alpha_v\beta_6$ monoclonal antibody (3G9). FIG. 19B: BxPC-3 xenograft tumor growth curves during treatment with $\alpha_v\beta_6$ mAb 3G9 (▲), soluble TGFbRII-Fc-Ig fusion protein (▼), or vehicle PBS (■). FIG. 19C: scatter plot of individual tumor sizes at the end of the study (day 66).

FIGS. 20A and 20B: migration (FIG. 20A) or invasion (FIG. 20B) of cells across extracellular matrix. "Unt": untreated cells; "3G9": cells treated with 10 μg/ml 3G9 anti-$\alpha_v\beta_6$ monoclonal antibody; "sTGFbR-Fc": cells treated with 10 μg/ml soluble TGF-βRII-Fc conjugate. Open bars: cells transfected with and expressing $\beta_6$ integrin (VB6 cells); closed bars: mock-transfected cells not expressing $\beta_6$ integrin (C1 cells). FIG. 20C: production of MMP9 (ng/ml) by C1 or VB6 cells that were untreated (open bars), treated with 10 μg/ml 3G9 (hatched bars) or treated with 10 μg/ml sTGF-βRII-Fc conjugate (closed bars).

FIG. 22A: LIM1863 xenograft tumor growth curves during treatment with $\alpha_v\beta_6$ mAb 3G9 (▲), soluble TGFbRII-Fc-Ig fusion protein (▼), or vehicle PBS (■). FIG. 22B: scatter plot of individual tumor sizes at the end of the study (day 52). FIG. 22C: quantitation of $\alpha_v\beta_6$ positive areas across whole tumor sections. FIG. 22D-22F: photomicrographs depicting representative $\alpha_v\beta_6$ staining in tumors harvested from each indicated treatment group.

FIGS. 26A-26B are titration curves demonstrating the inhibition by m3G9 of adhesion of NHP $\alpha_v\beta_6$-expressing cell lines to LAP (A, 12 MBr6; B, 4 MBr5).

FIG. 30 demonstrates $\alpha_v\beta_6$ immunostaining in Col4A3 +/− and Col4A3 −/− mouse kidneys.

FIG. 31 demonstrates the specificity of $\alpha_v\beta_6$ mAb binding.

FIG. 32 demonstrates SMA immunostaining in Col4A3 −/− kidneys with various treatments.

FIG. 37A: Venn diagram of the probeset lists. The areas of the Venn circles, their unions, and intersections are proportional to the numbers probesets in the corresponding lists. FIGS. 37B, 37C: Highest scoring regulatory networks inferred from the lists of probesets significantly (>2-fold variation between treated and naive Alport kidneys, p<0.05) affected by the $\alpha_v\beta_6$-blocking mAbs 3G9 (FIG. 37B) and 8G6 (FIG. 37C). Edges of the networks show directions of interactions among the genes depicted as the nodes and arranged according to their cellular localization.

FIG. 38A: Kidney sections from Col4A3+/− and Col4A3−/− mice treated with indicated agents immunostained for TGF-β1 expression. Staining shown for a representative section from each treatment group. FIG. 38B: Taqman analysis of TGF-β1 mRNA levels in treatment groups.

FIG. 41A: Normal uninjured kidney; FIG. 41B: 7 days after UUO; FIG. 41C: 10 days after UUO; FIG. 41D: 14 days after UUO.

Sham mice were instilled with intratracheal saline and treated with PBS. Lung luciferase content assayed at day 14. Error bars represent standard errors. Group means and standard deviations are provided in Appendix C of Example 16. *=significantly different from the PBS-treated group by ANOVA

FIG. 68 is a pair of bar graphs depicting the IPA annotation of genes significantly affected by mu3G9.

DETAILED DESCRIPTION OF THE INVENTION

Figure 13:
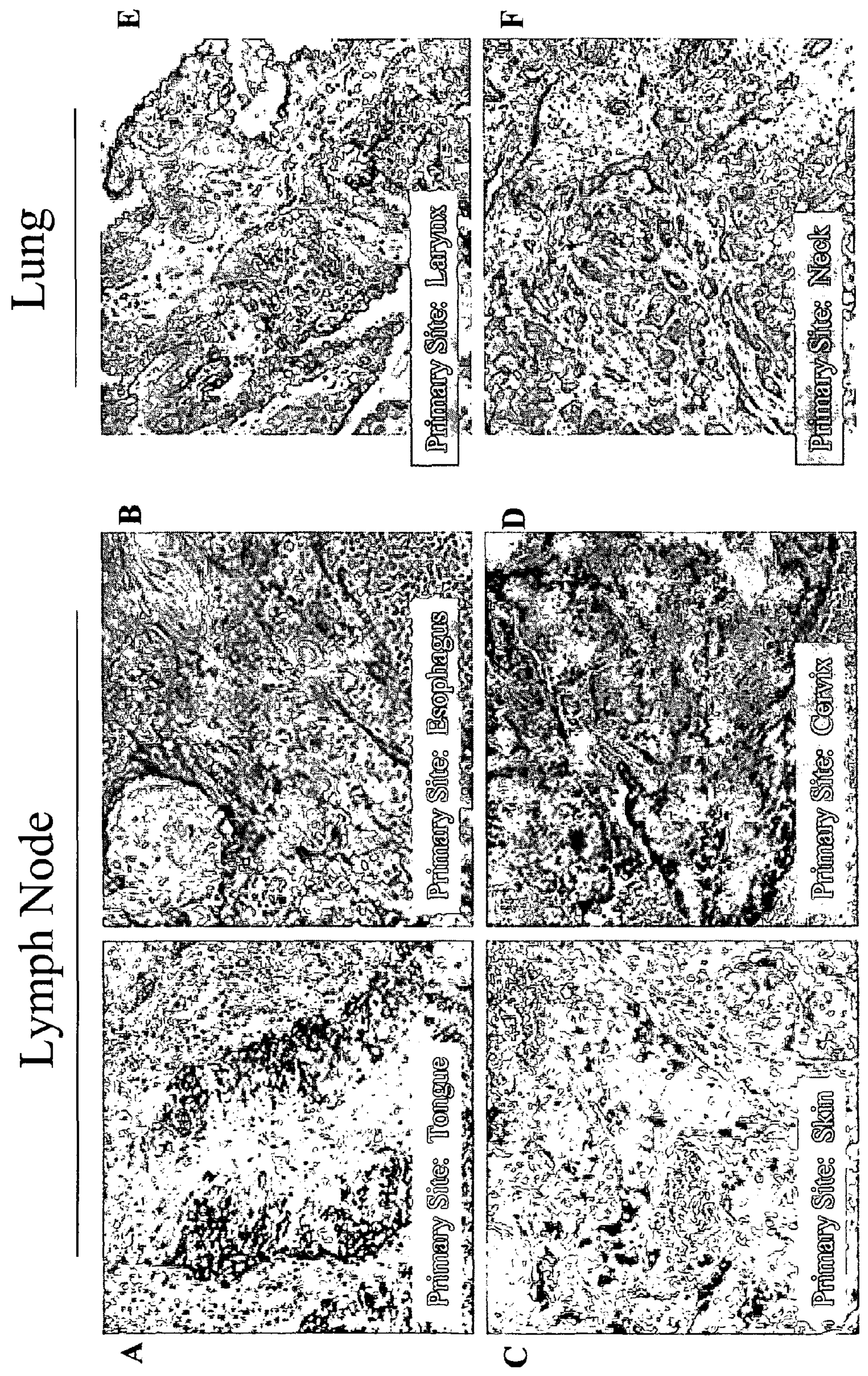
FIG. 13 is a composite of photomicrographs depicting the levels of $\alpha_v\beta_6$ expression (dark areas) in certain human carcinomas that have metastasized to either lymph node (FIGS. 13A-13D) or lung (FIGS. 13E-13F), from the indicated primary tumor sites.
Figure 14:
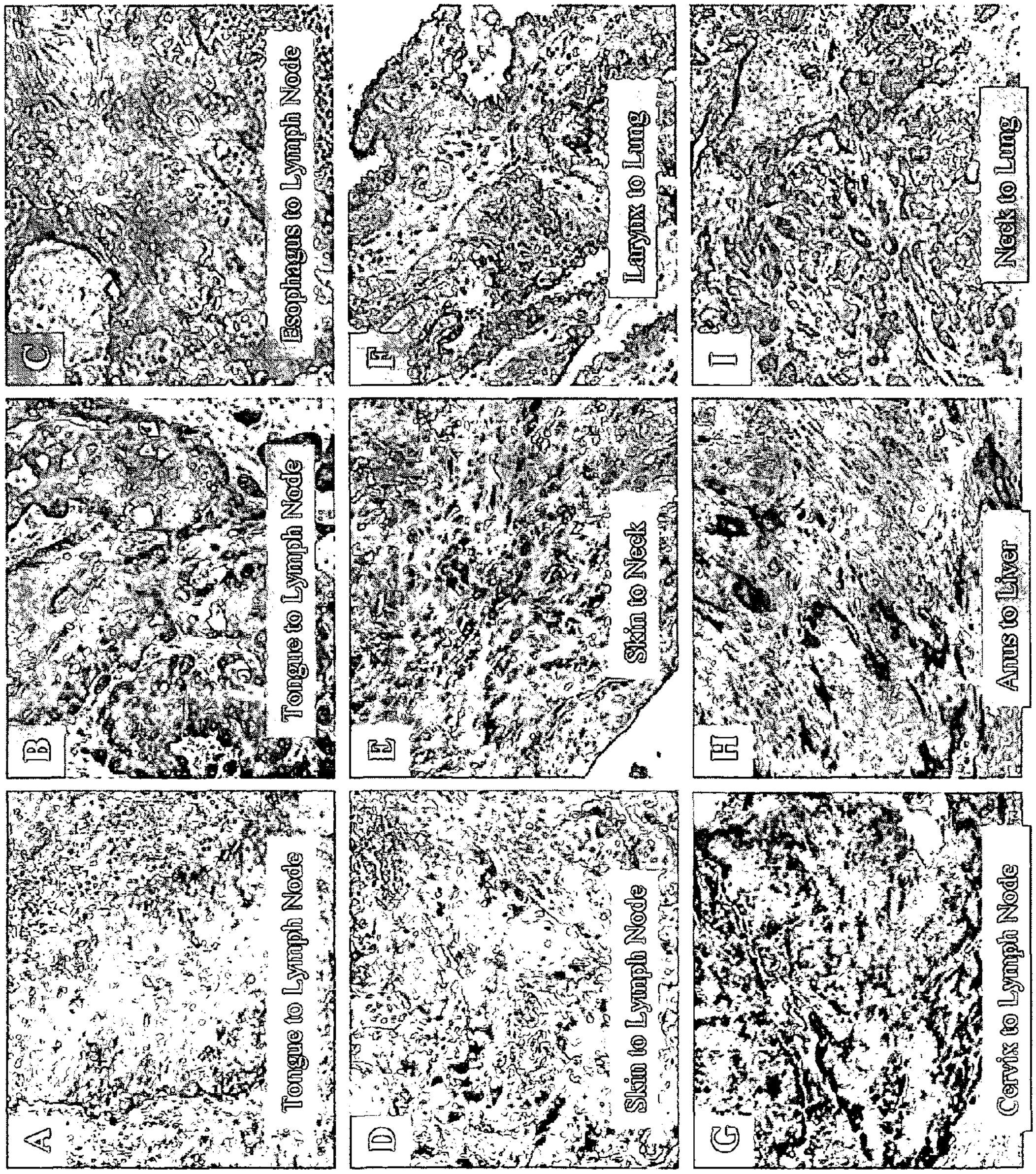
FIG. 14 is a composite of photomicrographs depicting the levels of $\alpha_v\beta_6$ expression (dark areas) in certain human carcinomas that have metastasized from the indicated primary tumor site to the indicated metastatic tumor site.
Figure 15:
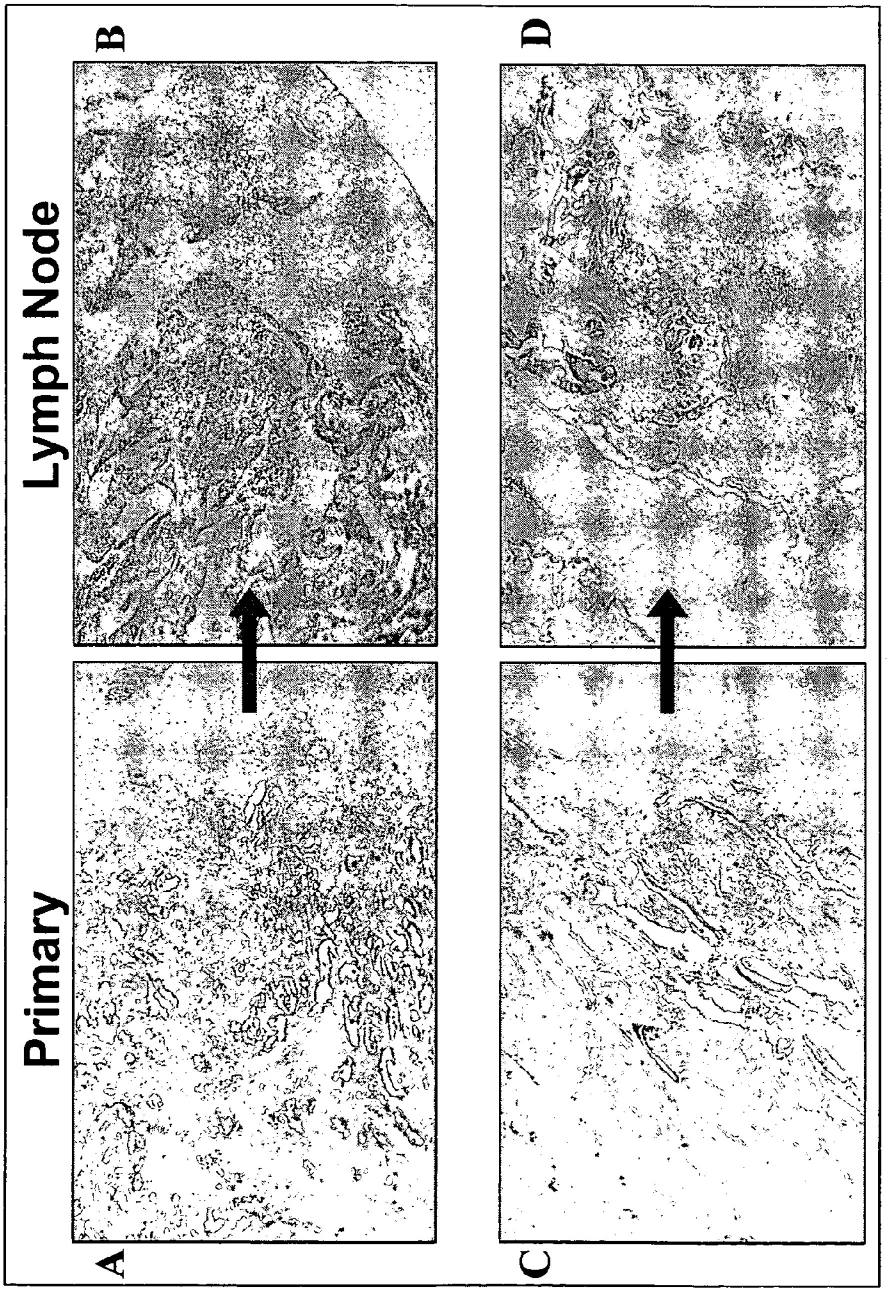
FIG. 15 is a composite of photomicrographs depicting the levels of $\alpha_v\beta_6$ expression (dark areas) observed in primary endometrial carcinoma tumors (FIG. 15A, 15C), and in matched lymph node metastases (FIG. 15B, 15D).

Unless defined otherwise herein, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described hereinafter. Exemplary methods and materials are described below, although methods and materials similar or equivalent to those described herein can also be used in the practice of the present invention. All publications and other references mentioned herein are incorporated by reference in their entirety. In case of conflict, the present specification, including definitions, will control. The materials, methods, and examples are illustrative only and not intended to be limiting. Throughout this specification, the word "comprise," or variations such as "comprises" or "comprising" will be understood to imply the inclusion of a stated integer or group of integers but not the exclusion of any other integer or group of integers.

Definitions

About: As used herein when referring to any numerical value, the term "about" means a value of ±10% of the stated value (e.g., "about 50° C." encompasses a range of temperatures from 45° C. to 55° C., inclusive; similarly, "about 100 mM" encompasses a range of concentrations from 90 mM to 110 mM, inclusive).

Antagonist: As used herein, the term "antagonist" refers to a compound, molecule, moiety or complex that reduces, substantially reduces or completely inhibits the biological and/or physiological effects of the $\alpha_v\beta_6$ integrin in a cell, tissue or organism. Antagonists, which may be ligands for $\alpha_v\beta_6$, may carry out such effects in a variety of ways, including but not limited to competing with another ligand for binding to $\alpha_v\beta_6$ on the cell surface; interacting with $\alpha_v\beta_6$ in such a way as to reduce, substantially reduce or inhibit the ability of the integrin to bind other ligands; binding to and inducing a conformational change in cell surface $\alpha_v\beta_6$ such that the integrin assumes a structure to which other ligands can no longer bind (or can bind only with reduced or substantially reduced affinity and/or efficiency); inducing a physiological change (e.g., increase in intracellular signaling complexes; increase in transcriptional inhibitors; reduction in cell surface $\alpha_v\beta_6$ expression; etc.) in cells, tissues or organisms such that the binding of other ligands, or the physiological signal induced by such ligands upon binding to the $\alpha_v\beta_6$ on the cell, is reduced, substantially reduced or completely inhibited; and other mechanisms by which antagonists may carry out their activities, that will be familiar to the ordinarily skilled artisan. As the ordinarily skilled artisan will understand, an antagonist may have a similar structure to another $\alpha_v\beta_6$-binding moiety (e.g., an $\alpha_v\beta_6$-binding ligand) that it antagonizes (e.g., the antagonist may be a mutein, variant, fragment or derivative of the agonist), or may have a wholly unrelated structure.

Bound: As used herein, the term "bound" refers to binding or attachment that may be covalent, e.g., by chemically coupling, or non-covalent, e.g., ionic interactions, hydrophobic interactions, hydrogen bonds, etc. Covalent bonds can be, for example, ester, ether, phosphoester, thioester, thioether, urethane, amide, amine, peptide, imide, hydrazone, hydrazide, carbon-sulfur bonds, carbon-phosphorus bonds, and the like. The term "bound" is broader than and includes terms such as "coupled," "conjugated" and "attached."

Conjugate/conjugation: As used herein, "conjugate" refers to the product of covalent attachment of a moiety, e.g., a chemical or radioisotope, to a ligand that binds to $\alpha_v\beta_6$ e.g., an $\alpha_v\beta_6$-binding antibody or fragment thereof. "Conjugation" refers to the formation of a conjugate as defined in the previous sentence. Any method normally used by those skilled in the art of conjugation of chemicals or radioisotopes to biologically active materials, such as proteins or polypeptides (including antibodies) can be used in the present invention.

Disease, disorder, condition: As used herein, the terms "disease" or "disorder" refer to any adverse condition of a human or animal including tumors, cancer, allergies, addiction, autoimmunity, infection, poisoning or impairment of optimal mental or bodily function. "Conditions" as used herein includes diseases and disorders but also refers to physiologic states. For example, fertility is a physiologic state but not a disease or disorder. Compositions of the invention suitable for preventing pregnancy by decreasing fertility would therefore be described as a treatment of a condition (fertility), but not a treatment of a disorder or disease. Other conditions are understood by those of ordinary skill in the art.

Effective Amount: As used herein, the term "effective amount" refers to an amount of a given compound, conjugate or composition that is necessary or sufficient to realize a desired biologic effect. An effective amount of a given compound, conjugate or composition in accordance with the methods of the present invention would be the amount that achieves this selected result, and such an amount can be determined as a matter of routine by a person skilled in the art, using assays that are known in the art and/or that are described herein, without the need for undue experimentation. For example, an effective amount for treating or preventing cancer metastasis could be that amount necessary to prevent migration and invasion of a tumor cell across the basement membrane or across an endothelial layer in vivo. The term is also synonymous with "sufficient amount." The effective amount for any particular application can vary depending on such factors as the disease, disorder or condition being treated, the particular composition being administered, the route of administration, the size of the subject, and/or the severity of the disease or condition. One of ordinary skill in the art can determine empirically the effective amount of a particular compound, conjugate or composition of the present invention, in accordance with the guidance provided herein, without necessitating undue experimentation.

One, a, or an: When the terms "one," "a," or "an" are used in this disclosure, they mean "at least one" or "one or more," unless otherwise indicated. As such, the terms "a" (or "an"), "one or more," and "at least one" can be used interchangeably herein.

Peptide, polypeptide, protein: As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis. In accordance with this definition, polypeptides used in the present invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue. Preferred polypeptides used in accordance with the invention include polypeptides that are ligands or that bind to an $\alpha_v\beta_6$ integrin on the surface of a cell, including but not limited to antibodies (especially monoclonal antibodies) that recognize and bind to one or more epitopes on $\alpha_v\beta_6$.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to anti-$\alpha_v\beta_6$ antibodies or antibody polypeptides include any polypeptides which retain at least some of the antigen-binding properties of the corresponding native antibody or polypeptide, i.e., those polypeptides that retain the ability to bind to one or more epitopes on an $\alpha_v\beta_6$ integrin. Fragments of polypeptides of the present invention include proteolytic fragments, as well as deletion fragments, in addition to specific antibody fragments discussed elsewhere herein. Variants of anti-$\alpha_v\beta_6$ antibodies and antibody polypeptides useful in accordance with the present invention include fragments as described above, and also polypeptides with altered amino acid sequences due to amino acid substitutions, deletions, or insertions. Variants may occur naturally or be non-naturally occurring Non-naturally occurring variants may be produced using art-known mutagenesis techniques. Variant polypeptides may comprise conservative or non-conservative amino acid substitutions, deletions or additions. Derivatives of anti-$\alpha_v\beta_6$ antibodies and antibody polypeptides useful in accordance with the present invention are polypeptides which have been altered so as to exhibit additional features not found on the native polypeptide. Examples include fusion proteins. Variant polypeptides may also be referred to herein as "polypeptide analogs." As used herein a "derivative" of an anti-$\alpha_v\beta_6$ antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Substantially, substantial: As used herein, conjugation of a protein is said not to interfere "substantially" with the ability of the protein to bind to its receptor(s) if the rate and/or amount of binding of a conjugated protein to a receptor is not less than about 40%, about 50%, about 60%, about 65%, about 70%, about 75%, about 80%, about 85%, about 90%, about 91%, about 92%, about 93%, about 94%, about 95%, about 96%, about 97%, about 98%, about 99% or about 100% or more, of the binding rate and/or amount of the corresponding cytokine, chemokine, growth factor or polypeptide hormone that has not been conjugated.

Treatment: As used herein, the terms "treatment," "treat," "treated" or "treating" refer to prophylaxis and/or therapy, particularly wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. By "subject" or "individual" or "animal" or "patient" or "mammal," is meant any subject, particularly a mammalian subject, for whom diagnosis, prognosis, or therapy is desired. Mammalian subjects include humans and other primates, domestic animals, farm animals, and zoo, sports, or pet animals such as dogs, cats, guinea pigs, rabbits, rats, mice, horses, cattle, cows, and the like.

Overview

This invention features humanized antibodies that are specific for the integrin $\alpha_v\beta_6$. Described herein are various methods of making the antibodies of this invention. Methods that are known in the art but not specifically described herein are also within the scope of this invention.

The present invention is also based at least in part upon the findings that the integrin $\alpha_v\beta_6$ is differentially expressed on the surfaces of tumor cells, in that it is expressed in increased amounts on tumor cells that are metastatic or have a higher metastatic potential relative to the expression levels observed on tumor cells that are non-metastatic or that have a lower metastatic potential. To analyze this differential expression, the invention uses using ligands, particularly antibodies (and more particularly the humanized antibodies provided by the present invention), that bind to integrin $\alpha_v\beta_6$. In other embodiments, the invention also provides methods using identification of this differential expression in determining the invasive and/or metastatic potential of tumor cells and in identifying those carcinomas, such as certain adenocarcinomas and in situ carcinomas (including DCIS and LCIS), that may be more likely to progress to invasive or metastatic carcinomas. The invention also provides methods of identifying those tumors in which the cells making up the tumor may be more likely to respond to treatment with one or more ligands that bind to integrin $\alpha_v\beta_6$. The invention also provides methods of diagnosis and treatment/prevention of tumor metastasis, and for elimination of residual metastatic tumor cells following surgical excision of tumors.

Humanized Antibodies

In one embodiment, the antibodies provided by the present invention are monoclonal antibodies, which in a preferred embodiment are humanized versions of cognate anti-$\alpha_v\beta_6$ antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer non-human components.

Suitable methods for making the humanized antibodies of the present invention are described in, e.g., Winter EP 0 239 400; Jones et al., *Nature* 321:522-525 (1986); Riechmann et al., *Nature* 332:323-327 (1988); Verhoeyen et al., *Science* 239: 1534-1536 (1988); Queen et al., *Proc. Nat. Acad. Sci. USA* 86:10029 (1989); U.S. Pat. No. 6,180,370; and Orlandi et al., *Proc. Natl. Acad. Sci. USA* 86:3833 (1989); the disclosures of all of which are incorporated by reference herein in their entireties. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs encoding the CDRs are transferred to the corresponding regions of a human antibody heavy or light chain variable domain coding sequence by site directed mutagenesis. Then human constant region gene segments of a desired isotype (e.g., $\gamma1$ for $C_H$ and $\kappa$ for $C_L$) are added. The humanized heavy and light chain genes are co-expressed in mammalian host cells (e.g., CHO or NSO cells) to produce soluble humanized antibody. To facilitate large scale production of antibodies, it is often desirable to produce such humanized antibodies in bioreactors containing the antibody-expressing cells, or to produce transgenic mammals (e.g., goats, cows, or sheep) that express the antibody in milk (see, e.g., U.S. Pat. No. 5,827,690).

At times, direct transfer of CDRs to a human framework leads to a loss of antigen-binding affinity of the resultant antibody. This is because in some cognate antibodies, certain amino acids within the framework regions interact with the CDRs and thus influence the overall antigen binding affinity of the antibody. In such cases, it would be critical to introduce "back mutations" (supra) in the framework regions of the acceptor antibody in order to retain the antigen-binding activity of the cognate antibody.

The general approach of making back mutations is known in the art. For instance, Queen et al. (supra), Co et al., *Proc. Nat. Acad. Sci. USA* 88:2869-2873 (1991), and WO 90/07861 (Protein Design Labs Inc.) describe an approach that involves two key steps. First, the human variable framework regions are chosen by computer analysis for optimal protein sequence homology to the variable region framework of the cognate murine antibody. Then, the tertiary structure of the murine variable region is modeled by computer in order to visualize framework amino acid residues that are likely to interact with the murine CDRs, and these murine amino acid residues are then superimposed on the homologous human framework.

Under this two-step approach, there are several criteria for designing humanized antibodies. The first criterion is to use as the human acceptor the framework from a particular human immunoglobulin that is usually homologous to the non-human donor immunoglobulin, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs.

One may also use a different approach as described in, e.g., Tempest, *Biotechnology* 9: 266-271 (1991). Under this approach, the variable region frameworks derived from NEWM and REI heavy and light chains, respectively, are used for CDR-grafting without radical introduction of mouse residues. An advantage of using this approach is that the three-dimensional structures of NEWM and REI variable regions are known from X-ray crystallography and thus specific interactions between CDRs and variable region framework residues can be readily modeled.

The present inventors prepared the antibody heavy chain variable region cDNA and light chain variable region cDNAs from mRNAs isolated from the hybridomas 6.3G9 and 6.8G6, as described in WO 03/100033. These hybridomas produce IgG1 class mouse monoclonal antibodies that bind to the $\alpha_v\beta_6$ integrin. Chimeric human antibody expression vectors were constructed by inserting the cDNA into an expression vector containing human antibody heavy chain constant region or human antibody light chain constant region encoding sequences. Such vectors were then introduced into animal cells to effect the production of anti-$\alpha_v\beta_6$ chimeric human antibodies. Among the chimeric antibodies produced, the anti-$\alpha_v\beta_6$ chimeric human antibody, 3G9 and 8G6, were found to react with the $\alpha_v\beta_6$ integrin and display blocking activity.

Using the above-described approaches, humanized versions of the chimeric antibodies 3G9 and 8G6, were generated. For the 3G9 antibody, this involved the cloning of the murine 3G9 variable heavy and light chain regions as described in the Examples herein. The cDNAs encoding the murine 3G9 variable regions of the light and heavy chains were then used to construct vectors for expression of murine-human chimeras in which the murine 3G9 variable regions were linked to human IgG1 (for heavy chain) and human kappa (for light chain) constant regions, as described in the Examples herein. Expression of the light chain and heavy chain 3G9 expression vectors following transfection into 293-EBNA cells indicated that chimeric 3G9 transfected cells synthesized and efficiently assembled the heavy and light chains and secreted antibody (see Example 2). In addition, an aglycosyl mutant form of the chimeric 3G9 antibody was also created. An amino acid substitution of an asparagine (N) to a serine (S) within an N-linked glycosylation site in the first CDR of the light chain of 3G9 was shown to greatly improve protein expression and purification without altering binding affinity (FIG. 1).

In order to produce humanized 3G9 antibodies, the human acceptor framework domains were chosen by homology matching to human germline sequences. For the light chain, the human L6 acceptor frameworks were found to be most homologous and for the heavy chain, the human 3-7 acceptor frameworks were found to most homologous, as described in Example 3. Using these chosen human acceptor frameworks, the light and heavy chain variable domains were designed and a number of variants/versions of each were generated and expressed (Example 4).

The present invention describes the humanized 3G9 antibodies as comprising a heavy chain variable domain of SEQ ID NO: 1 and light chain variable domain of SEQ ID NO: 2.

```
        SEQ ID NO: 1
EVQLVESGGGLVQPGGSLRLSCAASGFTFSRYVMSWVRQAPGKGLE
WVASISSGGRMYYPDTVKGRFTISRDNAKNSLYLQMNSLRAEDTAV
YYCARGSIYDGYYVFPYWGQGTLVTVSS

        SEQ ID NO: 2
EIVLTQSPATLSLSPGERATLSCSASSSCSSSYLYWYQQKPGQAPRLLIY
STSNLASGIPARFSGSGSGTDFTLTISSLEPEDFAVYYCHQWSTYPPTFG
GGTKVEIK
```

Different variants/versions of the 3G9 heavy and light chains were generated with different degrees of back mutations to determine which combination produced the best humanized antibody with superior binding affinity and blocking activity to $\alpha_v\beta_6$. Of the five different versions of light chains and the three different versions of heavy chains generated, the pairing of 3G9 heavy chain version 3 (HV3) with 3G9 light chain version 5 (LV5) generated the best humanized antibody (Example 4). This humanized 3G9 version 5 (H3/L5) antibody is produced by expression of the recombinant vector for heavy chain version 3 (H3) comprising the plasmid pKJS189 (SEQ ID NO: 6) in combination with the recombinant vector for light chain version 5 (LV5) comprising the plasmid pKJS195 (SEQ ID NO: 5).

SEQ ID NOS: 6 and 137

```
1263   ATG GAC TTC GGC CTG AGC TGG GTG TTC CTG GTG CTG GTG CTG AAG GGC GTG CAG TGC GAG GTG CAG CTG GTG GAG AGC GGC GGC
   1   Met Asp Phe Gly Leu Ser Trp Val Phe Leu Val Leu Val Leu Lys Cly Val Gln Cys Glu Val Gln Leu Val Glu Ser Gly Gly

1347   GGC CTG GTG CAG CCC GGC GGC AGC CTG AGG CTG AGC TGC GCC GCC AGC GGC TTC ACC TTC AGC CGC TAC GTG ATG AGC TGG GTG
  29   Gly Leu Val Gln Pro Gly Gly Ser Leu Arg Leu Ser Cys Ala Ala Ser Gly Phe Thr Phe Ser Arg Tyr Val Met Ser Trp Val

1431   CGC CAG GCC CCC GGC AAG GGC CTG GAG TGG GTG GCC AGC ATC AGC AGC GGA GGC CGC ATG TAC TAC CCC GAC ACC GTG AAG GGC
  57   Arg Gln Ala Pro Gly Lys Gly Leu Glu Trp Val Ala Ser Ile Ser Ser Gly Gly Arg Met Tyr Tyr Pro Asp Thr Val Lys Gly

1515   CGC TTC ACC ATC AGC CGC GAC AAC GCC AAG AAC AGC CTG TAC CTG CAG ATG AAC AGC CTG CGC GCC GAG GAC ACC GCC GTG TAC
  85   Arg Phe Thr Ile Ser Arg Asp Aen Ala Lys Asn Ser Leu Tyr Leu Gln Met Aen Ser Leu Arg Ala Glu Asp Thr Ala Val Tyr

1599   TAC TGC GCC CGC GGC AGC ATC TAC GAC GGC TAC TAC GTG TTC CCC TAC TGG GGC CAG GGC ACC CTG GTG ACC GTG AGC TCC GCC
 113   Tyr Cys Ala Arg Gly Ser Ile Tyr Asp Gly Tyr Tyr Val Phe Pro Tyr Trp Gly Gln Gly Thr Leu Val Thr Val Ser Ser Ala

1683   AGC ACC AAG GGC CCC AGC GTG TTC CCC CTG GCC CCC AGC AGC AAG AGC ACC AGC GGC GGC ACC GCC GCC CTG GGC TGC CTG GTG
 141   Ser Thr Lys Gly Pro Ser Val Phe Pro Leu Ala Pro Ser Ser Lys Ser Thr Ser Gly Gly Thr Ala Ala Leu Gly Cys Leu Val

1767   AAG GAC TAC TTC CCC GAA CCG GTG ACG GTG TCG TGG AAC TCA GGC GCC CTG ACC AGC GGC GTG CAC ACC TTC CCG GCT GTC CTA
 169   Lys Asp Tyr Phe Pro Glu Pro Val Thr Val Ser Trp Asn Ser Gly Ala Leu Thr Ser Gly Val His Thr Phe Pro Ala Val Leu

1851   CAG TCC TCA GGA CTC TAC TCC CTC AGC AGC GTG GTG ACC GTG CCC TCC AGC AGC TTG GGC ACC CAG ACC TAC ATC TGC AAC GTG
 197   Gln Ser Ser Gly Leu Tyr Ser Leu Ser Ser Val Val Thr Val Pro Ser Ser Ser Leu Gly Thr Gln Thr Tyr Ile Cys Asn Val

1935   AAT CAC AAG CCC AGC AAC ACC AAG GTG GAC AAG AAA GTT GAG CCC AAA TCT TGT GAC AAG ACT CAC ACA TGC CCA CCG TGC CCA
 225   Asn His Lys Pro Ser Asn Thr Lys Val Asp Lys Lys Val Glu Pro Lys Ser Cys Asp Lys Thr His Thr cys Pro Pro Cys Pro

2019   GCA CCT GAA CTC CTG GGG GGA CCG TCA GTC TTC CTC TTC CCC CCA AAA CCC AAG GAC ACC CTC ATG ATC TCC CGG ACC CCT GAG
 253   Ala Pro Glu Leu Leu Gly Gly Pro Ser Val Phe Leu Phe Pro Pro Lys Pro Lys Asp Thr Leu Met Ile Ser Ary Thr Pro Glu

2103   GTC ACA TGC GTG GTG GTG GAC GTG AGC CAC GAA GAC CCT GAG GTC AAG TTC AAC TGG TAC GTG GAC GGC GTG GAG GTG CAT AAT
 281   Val Thr Cys Val Val Val Asp Val Ser His Glu Asp Pro Glu Val Lys Phe Asn Trp Tyr Val Asp Gly Val Glu Val His Asn

2187   GCC AAG ACA AAG CCG CGG GAG GAG CAG TAC AAC AGC ACG TAC CGT GTG GTC AGC GTC CTC ACC GTC CTG CAC CAG GAC TGG CTG
 309   Ala Lys Thr Lys Pro Arg Glu Glu Gln Tyr Asn Ser Thr Tyr Arg Val Val Ser Val Leu Thr Val Leu His Gln Asp Trp Leu

2271   AAT GGC AAG GAG TAC AAG TGC AAG GTC TCC AAC AAA GCC CTC CCA GCC CCC ATC GAG AAA ACC ATC TCC AAA GCC AAA GGG CAG
 337   Asn Gly Lys Glu Tyr Lys Cys Lys Val Ser Asn Lys Ala Leu Pro Ala Pro Ile Glu Lys Thr Ile Ser Lys Ala Lys Gly Gln

2355   CCC CGA GAA CCA CAG GTG TAC ACC CTG CCC CCA TCC CGG GAT GAG CTG ACC AAG AAC CAG GTC AGC CTG ACC TGC CTG GTC AAA
 365   Pro Arg Glu Pro Gln Val Tyr Thr Leu Pro Pro Ser Arg Asp Glu Leu Thr Lys Asn Gln Val Ser Leu Thr Cys Leu Val Lys

2439   GGC TTC TAT CCC AGC GAC ATC GCC GTG GAG TGG GAG AGC AAT GGG GAG CCG GAG AAC AAC TAC AAG ACC ACG CCT CCC GTG TTG
 393   Gly Phe Tyr Pro Ser Asp Ile Ala Val Glu Trp Glu Ser Asn Gly Gln Pro Glu Asn Asn Tyr Lys Thr Thr Pro Pro Val Leu

2523   GAC TCC GAC GGC TCC TTC TTC CTC TAC AGC AAG CTC ACC GTG GAC AAG AGC AGG TGG CAG CAG GGG AAC GTC TTC TCA TGC TCC
 421   Asp Ser Asp Gly Ser Phe Phe Leu Tyr Ser Lys Leu Thr Val Asp Lys Ser Ary Trp Gln Gln Gly Asn Val Phe Ser Cys Ser

2607   GTG ATG CAT GAG GCT CTG CAC AAC CAC TAC ACG CAG AAG AGC CTC TCC CTG TCT CCC GGT
 449   Val Met His Glu Ala Leu His Asn His Tyr Thr Gln Lys Ser Leu Ser Leu Ser Pro Gly
```

-continued

SEQ ID NOS: 5 and 136

```
1263   ATG GAC TTC CAG GTG CAG ATC CTC AGC TTC CTG CTG ATC AGC GTG AGC GTG ATC ATG AGC CGC GGC GAG ATC GTG CTG ACC CAG
   1   Met Asp Phe Gln Val Gln Ile Phe Ser Phe Leu Leu Ile Ser Val Ser Val Ile Met Ser Arg Gly Glu Ile Val Leu Thr Gln

1347   AGC CCC GCC ACC CTG AGC CTG AGC CCC GGC GAG AGG GCC ACC CTG AGC TGC AGC GCC AGC AGC AGC GTG AGC AGC AGC TAC CTG
  29   Ser Pro Ala Thr Leu Ser Leu Ser Pro Gly Glu Arg Ala Thr Leu Ser Cys Ser Ala Ser Ser Ser Val Ser Ser Ser Tyr Leu

1431   TAC TGG TAC CAG CAG AAG CCC GGC CAG GCC CCC AGG CTG CTG ATC TAC AGC ACC AGC AAC CTG GCC AGC GGC ATC CCC GCC CGC
  56   Tyr Trp Tyr Gln Gln Lys Pro Gly Gln Ala Pro Arg Leu Leu Ile Tyr Ser Thr Ser Asn Leu Ala Ser Gly Ile Pro Ala Arg

1515   TTC AGC GGC AGC GGC AGC GGC ACC GAC TTC ACC CTG ACC ATC AGC AGC CTG GAG CCC GAG GAC TTC GCC GTG TAC TAC TGC CAC
  83   Phe Ser Gly Ser Gly Ser Gly Thr Asp Phe Thr Leu Thr Ile Ser Ser Leu Glu Pro Glu Asp Phe Ala Val Tyr Tyr Cys His

1599   CAG TGG AGC ACC TAC CCC CCC ACC TTC GGC GGC GGC ACC AAG GTG GAG ATC AAG CGT ACG GTG GCT GCA CGA TCT GTC TTC ATC
 110   Gln Trp Ser Thr Tyr Pro Pro Thr Phe Gly Gly Gly Thr Lys Val Glu Ile Lys Arg Thr Val Ala Ala Pro Ser Val Phe Ile

1683   TTC CCG CCA TCT GAT GAG CAG TTG AAA TCT GGA ACT GCC TCT GTT GTG TGC CTG CTG AAT AAC TTC TAT CCC AGA GAG GCC AAA
 137   Phe Pro Pro Ser Asp Glu Gln Leu Lys Ser Gly Thr Ala Ser Val Val Cys Leu Leu Asn Asn Phe Tyr Pro Arg Glu Ala Lys

1767   GTA CAG TGG AAG GTG GAT AAC GCC CTC CAA TCG GGT AAC TCC CAG GAG AGT GTC ACA GAG CAG GAC AGC AAG GAC AGC ACC TAC
 164   Val Gln Trp Lys Val Asp Asn Ala Leu Gln Ser Gly Asn Ser Gln Glu Ser Val Thr Glu Gln Asp Ser Lys Asp Ser Thr Tyr

1851   AGC CTC AGC AGC ACC CTG ACG CTG AGC AAA GCA GAC TAC GAG AAA CAC AAA GTC TAC GCC TGC GAA GTC ACC CAT CAG GGC CTG
 191   Ser Leu Ser Ser Thr Leu Thr Leu Ser Lys Ala Asp Tyr Glu Lys His Lys Val Tyr Ala Cys Glu Val Thr His Gln Gly Leu

1935   AGC TCG CCC GTC ACA AAG AGC TTC AAC AGG GGA GAG TGT
 218   Ser Ser Pro Val Thr Lys Ser Phe Asn Arg Gly Glu Cys
```

Another version of the humanized 3G9 version 5 (H3/L5) antibody was also generated in which the heavy chain was mutated to remove a glycosylation site in the constant region, which has been shown to be required for normal Fc receptor binding (Example 5). This aglycosyl form of humanized 3G9 antibody (a-H3/L5) is produced by substituting an amino acid residue asparagine (N) with a glutamine (Q) in the constant region of heavy chain version 3 (H3). The aglycosyl humanized 3G9 (a-H3/L5) antibody is produced by expression of the recombinant vector for aglycosyl heavy chain version 3 (a-H3) comprising the plasmid pKJS196 (SEQ ID NO: 7) in combination with the recombinant vector for light chain version 5 (L5) comprising the plasmid pKJS195 (SEQ ID NO: 5; see above).

SEQ ID NOS: 7 and 138

```
1263  ATG GAC TTC GGC CTG AGC TGG GTG TTC CTG GTG CTG GTG CTG AAG GGC GTG CAG TGC GAG GTG CAG CTG GTG GAG AGC GGC GGC
   1  Met Asp Phe Gly Leu Ser Trp Val Phe Leu Val Leu Val Leu Lys Gly Val Gln Cys Glu Val Gln Leu Val Glu Ser Gly Gly

1347  GGC CTG GTG CAG CCC GGC GGC AGC CTG AGG CTG AGC TGC GCC GCC AGC GGC TTC ACC TTC AGC CGC TAC GTG ATG AGC TGG GTG
  29  Gly Leu Val Gln Pro Gly Gly Ser Leu Ar9 Leu Ser Cys Ala Ala Ser Gly Phe Thr Phe Ser Arg Tyr Val Met Ser Trp Val

1431  CGC CAG GCC CCC GGC AAG GGC CTG GAG TGG GTG GCC AGC ATC AGC AGC GGA GGC CGC ATG TAC TAC CCC GAC ACC GTG AAG GGC
  57  Arg Gln Ala Pro Gly Lys Gly Leu Glu Trp Val Ala Ser Ile Ser Ser Gly Gly Arg Met Tyr Tyr Pro Asp Thr Val Lys Gly

1515  CGC TTC ACC ATC AGC CGC GAC AAC GCC AAG AAC AGC CTG TAC CTG CAG ATG AAC AGC CTG CGC GCC GAG GAC ACC GCC GTG TAC
  85  Arg Phe Thr Ile Ser Arg Asp Asn Ala Lys Asn Ser Leu Tyr Leu Gln Met Asn Ser Leu Arg Ala Glu Asp Thr Ala Val Tyr

1599  TAC TGC GCC CGC GGC AGC ATC TAC GAC GGC TAC TAC GTG TTC CCC TAC TGG GGC CAG GGC ACC CTG GTG ACC GTG AGC TCC GCC
 113  Tyr Cys Ala Ary Gly Ser Ile Tyr Asp Gly Tyr Tyr Val Phe Pro Tyr Trp Gly Gln Gly Thr Leu Val Thr Val Ser Ser Ala

1683  AGC ACC AAG GGC CCC AGC GTG TTC CCC CTG GCC CCC AGC AGC AAG AGC ACC AGC GGC GGC ACC GCC GCC CTG GGC TGC CTG GTG
 141  Ser Thr Lys Gly Pro Ser Val Phe Pro Leu Ala Pro Ser Ser Lys Ser Thr Ser Gly Gly Thr Ala Ala Leu Gly Cys Leu Val

1767  AAG GAC TAC TTC CCC GAA CCG GTG ACG GTG TCG TGG AAC TCA GGC GCC CTG ACC AGC GGC GTG CAC ACC TTC CCG GCT GTC CTA
 169  Lys Asp Tyr Phe Pro Glu Pro Val Thr Val Ser Trp Asn Ser Gly Ala Leu Thr Ser Gly Val His Thr Phe Pro Ala Val Leu

1851  CAG TCC TCA GGA CTC TAC TCC CTC AGC AGC GTG GTG ACC GTG CCC TCC AGC AGC TTG GGC ACC CAG ACC TAC ATC TGC AAC GTG
 197  Gln Ser Ser Gly Leu Tyr Ser Leu Ser Ser Val Val Thr Val Pro Ser Ser Ser Leu Gly Thr Gln Thr Tyr Ile Cys Asn Val

1935  AAT CAC AAG CCC AGC AAC ACC AAG GTG GAC AAG AAA GTT GAG CCC AAA TCT TGT GAC AAG ACT CAC ACA TGC CCA CCG TGC CCA
 225  Asn His Lys Pro Ser Asn Thr Lys Val Asp Lys Lys Val Glu Pro Lys Ser Cys Asp Lys Thr His Thr Cys Pro Pro Cys Pro

2019  GCA CCT GAA CTC CTG GGG GGA CCG TGA GTC TTC CTC TTC CCC CCA AAA CCC AAG GAC ACC CTC ATG ATC TCC CGG ACC CCT GAG
 253  Ala Pro Glu Leu Leu Gly Gly Pro Ser Val Phe Leu Phe Pro Pro Lys Pro Lys Asp Thr Leu Met Ile Ser Arg Thr Pro Glu

2102  GTC ACA TGC GTG GTG GTG GAC GTG AGC CAC GAA GAC CCT GAG GTC AAG TTC AAC TGG TAC GTG GAC GGC GTG GAG GTG CAT AAT
 281  Val Thr Cys Val Val Val Asp Val Ser His Glu Asp Pro Glu Val Lys Phe Asn Trp Tyr Val Asp Gly Val Glu Val His Asn

2187  GCC AAG ACA AAG CCG CGG GAG GAG CAG TAC CAG AGC ACG TAC CGT GTG GTC AGC GTC CTC ACC GTC CTG CAC CAG GAC TGG CTG
 309  Ala Lys Thr Lys Pro Ary Glu Glu Gln Tyr Gln Ser Thr Tyr Arg Val Val Ser Val Leu Thr Val Leu His Gln Asp Trp Leu

2271  AAT GGC AAG GAG TAC AAG TGC AAG GTC TCC AAC AAA GCC CTC CGA GCC CCC ATC GAG AAA ACC ATC TCC AAA GCC AAA GGG CAG
 337  Asn Gly Lys Glu Tyr Lys Cys Lys Val Ser Asn Lys Ala Leu Pro Ala Pro Ile Glu Lys Thr Ile Ser Lys Ala Lys Gly Gln

2355  CCC CGA GAA CGA CAG GTG TAC ACC CTG CCC CCA TCC CGG GAT GAG CTG ACC AAG AAC CAG GTC AGC CTG ACC TGC CTG GTC AAA
 385  Pro Arg Glu Pro Gln Val Tyr Thr Leu Pro Pro Ser Arg Asp Glu Lou Thr Lys Asn Gln Val Ser Leu Thr Cys Leu Val Lys

2439  GGC TTC TAT CCC AGC GAC ATC GCC GTG GAG TGG GAG AGC AAT GGG CAG CCG GAG AAC AAC TAC AAG ACC ACG CCT CCC GTG TTG
 393  Gly Phe Tyr Pro Ser Asp Ile Ala Val Glu Trp Glu Ser Asn Gly Gln Pro Glu Asn Asn Tyr Lys Thr Thr Pro Pro Val Leu

2523  GAC TCC GAC GGC TCC TTC TTC CTC TAC AGC AAG CTC ACC GTG GAC AAG AGC AGG TGG CAG CAG GGG AAC GTC TTC TCA TGC TCC
 421  Asp Ser Asp Gly Ser Phe Phe Leu Tyr Ser Lys Leu Thr Val Asp Lys Ser Arg Trp Gln Gln Gly Asn Val Phe Ser Cys Ser

2607  GTG ATG CAT GAG GCT CTG CAC AAC CAC TAC ACG CAG AAG AGC CTC TCC CTG TCT CCC GGT
 449  Val Met His Glu Ala Leu His Asn His Tyr Thr Gln Lys Ser Leu Ser Leu Ser Pro Gly
```

Similar approaches were used in the design of the humanized 8G6 antibody (Example 7). Three versions of the 8G6 variable light chain and variable heavy chain were designed, with the first version containing the most back mutations and the third version containing the fewest (the most "humanized") (Example 5).

```
(hu8G6 version 1 light chain)          SEQ ID NO: 75
DIVLTQSPATLSLSPGERATLSCRASQSVSTSSYSYMYWYQQKPGQAP
RFLIKYASNLESGIPARFSGSGSGTDFTLTISSLEPEDFAVYYCQHNWEI
PFTFGGGTKVEIK

(hu8G6 version 2 light chain)          SEQ ID NO: 76
EIVLTQSPATLSLSPGERATLSCRASQSVSTSSYSYMYWYQQKPGQAP
RFLIKYASNLESGIPARFSGSGSGTDFTLTISSLEPEDFAVYYCQHNWEI
PFTFGGGTKVEIK

(hu8G6 version 3 light chain)          SEQ ID NO: 77
EIVLTQSPATLSLSPGERATLSCRASQSVSTSSYSYMYWYQQKPGQAP
RLLIKYASNLESGIPARFSGSGSGTDFTLTISSLEPEDFAVYYCQHNWEI
PFTFGGGTKVEIK

(hu8G6 version 1 heavy chain)          SEQ ID NO: 78
QVQLVQSGAEVKKPGASVKVSCKGSSYTFTDYAMHWVRLAPGQGLEWIG
VISTYYGNTNYNQKFKGRATMTVDKSISTAYMELSRLRSDDTAVYYCAR
GGLRRGDRPSLRYAMDYWGQGTLVTVSS

(hu8G6 version 2 heavy chain)          SEQ ID NO: 79
QVQLVQSGAEVKKPGASVKVSCKASGYTFTDYAMHWVRQAPGQGLEWIG
VISTYYGNTNYNQKFKGRATMTVDKSISTAYMELSRLRSDDTAVYYCAR
GGLRRGDRPSLRYAMDYWGQGTLVTVSS

(hu8G6 version 3 heavy chain)          SEQ ID NO: 80
QVQLVQSGAEVKKPGASVKVSCKASGYTFTDYAMHWVRQAPGQGLEWMG
VISTYYGNTNYNQKFKGRATMTVDKSISTAYMELSRLRSDDTAVYYCAR
GGLRRGDRPSLRYAMDYWGQGTLVTVSS
```

Other Moieties

As described in further detail hereinbelow, the humanized monoclonal antibodies of this invention may further comprise other moieties to effect the desired functions. For instance, the humanized antibodies may include a toxin moiety (e.g., tetanus toxoid or ricin) or a radionuclide (e.g., $^{111}$In or $^{90}$Y) for killing of cells targeted by the antibodies (see, e.g., U.S. Pat. No. 6,307,026). The humanized antibodies may comprise a moiety (e.g., biotin, fluorescent moieties, radioactive moieties, histidine tag or other peptide tags) for easy isolation or detection. The humanized antibodies may also comprise a moiety that can prolong their serum half life, for example, a polyethylene glycol (PEG) moiety.

A variety of chemotherapeutic agents can be coupled to the targeting humanized antibody. Preferably, a humanized antibody that internalizes upon binding would be best, however, the use of non-internalizing humanized antibodies is not precluded. For example, use of antibody-drug conjugates that bind to a tumor cell surface, release the drug within the tumor or tumor cell vicinity and diffusion or transport into the cell may afford anti-tumor activity depending upon the drug used. The list of drugs one could use for preparing conjugates is extensive and one of skill in the art would know how to make chemical modifications to the desired compound in order to make reactions of that compound more convenient for purposes of preparing conjugates of the invention. For example, the drug would be coupled via "releasable linkers that are differentially more stable in serum yet release the active drug inside the tumor cell. Several release mechanisms could be used, depending on the specific drug. Examples of these release mechanism include the use of acid-sensitive hydrazones, redox sensitive linkers, e.g., disulfide, and proteolytically-cleaved peptide linkers. The following are some representative drugs from several different classes:

(A) alkylating agents. Some specific examples of theses drugs are, cyclophosphamide, chlorambucil, busulfan, melphalan, and nitrosourea.

(B) antimetabolites and anti-proliferative agents such as the anthracyclines, vinca drugs, mitomycins, bleomycins, nucleosides, pteridines, endiynes. Examples are adriamycin, daunorubicin, doxorubicin, aminopterin, methotrexate, mitomycin C, actinomycin-D, 5-fluorouracil, 6-mercaptopurine, cytosine arabinoside, taxol, taxane, cytochalasin B, colchicin, and puromycin etoposide, melphalan, vinblastine, vincristine, calicheamicin, maytanasines derivatives, and dolistatin derivatives.

(C) hormones and hormone antagonists such as corticosteroids, progestins, and estrogens.

Prodrugs are defined as drugs that exist in a "less potent" chemical form when attached to the antibody, yet upon internalization are cleaved enzymatically to yield the more potent drug form. This same application can be made to antibody conjugates that do not internalize, e.g., enzymatic cleavage occurs on the tumor cell surface and the drug is released into the immediate tumor environment and assimilated by the tumor cell. Some examples of this are drugs containing phosphates, sulfates, and peptides.

Attachment of biologically active protein toxins such as ricin A chain, diptheria toxin, shigatoxin, tetanus, or a toxic enzyme is another form of antibody-conjugate contemplated by this invention. Such conjugates can be prepared using chemical conjugation methods or using genetic engineering techniques that allow for direct expression of the antibody-toxin construct, which are readily known to one of skill in the art.

The humanized monoclonal antibodies of this invention may also comprise other moieties such as radionuclides. For the purposes of radioimmunotherapy, the use of the humanized $\alpha_v\beta_6$ antibodies to specifically target therapeutic radioisotopes for treating cancer is contemplated by this invention. The list of relevant isotopes, may include, but is not limited to, $^{90}$Y, $^{125}$I, $^{131}$I, $^{123}$I, $^{111}$I, $^{105}$Rh, $^{153}$Sm, $^{67}$Cu, $^{67}$Ga, $^{166}$Ho, $^{177}$Lu, $^{186}$Re and $^{188}$Re. Also contemplated are alpha emitter isotopes such as $^{211}$At, $^{212}$Bi. The methods of isotope attachment are varied and dependent upon the specific isotope used. One of skill in the art would be familiar with and be able to determine the conjugation chemistry method for any specific isotope attachment.

For the purposes of radioimmunodiagnostics, the humanized $\alpha_v\beta_6$ antibodies may afford the opportunity to image and perform dosimetry for the targeted cancer and/or diseased organ/tissue of any particular disease. This would be useful for confirming localization to the known tumor sites as well as enabling optimized dosing of the therapeutic administration. In particular, positron radioisotopes (e.g., $^{86}$Y) in addition to the pure gamma isotope $^{99M}$Tc, could be given during therapeutic administration.

The above radioimmunotherapy/radioimmunodiagnostic applications are not limited to the use of non-internalizing antibodies. There are examples of the effective use of internalizing antibodies for targeting radioisotopes, particularly with isotopes that are retained in the cell as a chelate after catabolism. For example, $^{90}$Y-labeled antibodies prepared using high-affinity chelators such as MX-DTPA or CHX-DTPA.

Any of the above antibody conjugates also includes the use of fragments Fab, F(ab')2, scFvs, minibodies, CH2 domain-deleted antibody constructs, and FcRn-mutants. These Ab fragments or generically-modified constructs have different pharmacokinetic, tumor penetration, and tumor localization properties from intact IgG that may afford advantages in particular applications. For example, the faster-clearing Fab may be useful for diagnostics applications for radioimmunodiagnostic applications. On the other hand, for radioimmunotherapy or drug targeting, selecting a targeting vehicle with a longer serum $t_{1/2}$ may be more effective.

Diseased Conditions and Animal Models

The humanized antibodies of the invention are useful in the diagnosis and treatment, including prevention, of $\alpha_v\beta_6$-mediated diseases. For example, these humanized antibodies can be used to treat fibrosis (e.g., lung fibrosis, acute lung injury, kidney fibrosis, liver fibrosis, Alport's Syndrome, and scleroderma), and other diseases and disorders described elsewhere herein, by blocking the activation of TGF-β or blocking the binding of $\alpha_v\beta_6$ to any other ligands, such as fibronectin, vitronectin, and tenascin. In particular, the humanized antibodies of this invention can be used to treat lung diseases associated with injury/fibrosis such as, but not limited to, idiopathic pulmonary fibrosis, radiation induced fibrosis, chronic obstructive pulmonary disease (COPD), scleroderma, bleomycin induced fibrosis, chronic asthma, silicosis, asbestos induced fibrosis, acute lung injury and acute respiratory distress, (including bacterial pneumonia induced, trauma induced, viral pneumonia induced, ventilator induced, non-pulmonary sepsis induced and aspiration induced). The humanized antibodies of this invention can also be used to treat chronic nephropathies associated with injury/fibrosis such as, but not limited to, lupus, diabetes, scleroderma, glomerular nephritis, focal segmental glomerular sclerosis, IgA nephropathy, hypertension, allograft and Alport's disease. The humanized antibodies may also be useful to treat gut fibrosis, scleroderma, radiation-induced fibrosis. The humanized antibodies of this invention can also be used to treat liver fibrosis such as, but not limited to, biliary duct injury induced fibrosis. Other indications which the humanized antibodies of this invention can be useful to treat also include head and neck fibrosis, radiation induced fibrosis, corneal scarring, LASIX, corneal transplant, trabeculectomy, hypertrophic scarring, burn induced fibrosis, surgical fibrosis, sarcoidosis, psoriasis and spinal cord injury/fibrosis.

As described in detail hereinbelow, other than fibrotic diseases or conditions, the humanized antibodies of the invention are useful in treating cancer or cancer metastasis (including tumor growth and invasion), particularly epithelial cancers. A subset of epithelial cancers is squamous cell carcinoma, e.g., head and neck (including oral, laryngeal, pharyngeal, esophageal), breast, lung, prostate, cervical, colon, pancreatic, skin (basal cell carcinomas) and ovarian cancers. Our studies using the new $\alpha_v\beta_6$ monoclonal antibodies demonstrated that $\alpha_v\beta_6$ is highly expressed in many epithelial cancers, especially on the leading edge of the tumors. The new antibodies can also be used to any other diseases mediated by $\alpha_v\beta_6$, including psoriasis.

The efficacy of the antibodies of the invention can be tested in various animal models, some of which are described in the non-limiting examples hereinbelow. Mouse models for lung fibrosis include bleomycin- (Pittet et al., *J. Clin. Invest.* 107 (12):1537-1544 (2001); and Munger et al., supra) and irradiation-inducible lung fibrosis (Franko et al., *Rad. Res.* 140: 347-355 (1994)). In bleomycin-treated mice, the expression of $\alpha_v\beta_6$ increases in the epithelial alveolar cells of the lungs. But $\beta_6$ knockout mice are protected from bleomycin-induced injury and fibrosis.

Mouse models for kidney fibrosis include COL4A3 −/− mice (see, e.g., Cosgrove et al., *Amer. J. Path.* 157:1649-1659 (2000), mice with adriamycin-induced injury (Wang et al., *Kidney International* 58: 1797-1804 (2000); Deman et al., *Nephrol Dial Transplant* 16: 147-150 (2001)), db/db mice (Ziyadeh et al., *PNAS USA* 97:8015-8020 (2000)), and mice with unilateral ureteral obstruction (Fogo et al., *Lab Investigation* 81: 189A (2001); and Fogo et al., *Journal of the American Society of Nephrology* 12:819 A (2001)). In all of these models, the mice develop kidney injury and fibrosis that can progress to renal failure. $\alpha_v\beta_6$ is upregulated in the epithelial lining of the ascending and descending tubules of the kidneys of the COL4A3 −/− mice, adriamycin-treated mice, and mice that undergo unilateral ureteral obstruction. It is likely that $\alpha_v\beta_6$ expression also increases in a variety of kidney injury models.

As is also described in detail hereinbelow, anti-$\alpha_v\beta_6$ monoclonal antibodies can also be tested for their ability to inhibit tumor growth, progression, and metastasis in such animal models as the standard in vivo tumor growth and metastasis models. See, e.g., Rockwell et al., *J. Natl. Cancer Inst.* 49:735 (1972); Guy et al., *Mol. Cell Biol.* 12:954 (1992); Wyckoff et al., *Cancer Res.* 60:2504 (2000); and Oft et al., *Curr. Biol.* 8:1243 (1998). Important $\alpha_v\beta_6$ ligands in cancer may include TGF-β, which is involved in metastasis (for review see Akhurst et al., *Trends in Cell Biology* 11:S44-S51 (2001)), fibronectin and vitronectin.

The efficacy of the treatments of this invention may be measured by a number of available diagnostic tools, including physical examination, blood tests, proteinuria measurements, creatinine levels and creatinine clearance, pulmonary function tests, plasma blood urea nitrogen (BUN) levels, observation and scoring of scarring or fibrotic lesions, deposition of extracellular matrix such as collagen, smooth muscle actin and fibronectin, kidney function tests, ultrasound, magnetic resonance imaging (MRI), and CT scan.

Pharmaceutical Compositions

The present invention also provides pharmaceutical compositions which comprise one or more humanized antibodies of the present invention, or pharmaceutically acceptable derivatives thereof, optionally with any pharmaceutically acceptable carrier. The term "carrier" as used herein includes known acceptable adjuvants and vehicles.

According to this invention, the pharmaceutical compositions may be in the form of a sterile injectable preparation, for example a sterile injectable aqueous or oleaginous suspension. This suspension may be formulated according to techniques known in the art using suitable dispersing, wetting, and suspending agents.

The pharmaceutical compositions of this invention may be given orally, topically, intravenously, subcutaneously, intraperitoneally, intramuscularly, intramedullarily, intra-articularly, intra-synovially, intrasternally, intrathecally, intrahepatically, or intracranially as desired, or just locally at sites of inflammation or tumor growth. The pharmaceutical compositions of this invention may also be administered by inhalation through the use of, e.g., a nebulizer, a dry powder inhaler or a metered dose inhaler.

The dosage and dose rate of the antibodies of this invention effective to produce the desired effects will depend on a variety of factors, such as the nature of the disease to be treated, the size of the subject, the goal of the treatment, the specific pharmaceutical composition used, and the judgment of the treating physician. Dosage levels of between about 0.001 and about 100 mg/kg body weight per day, for example between about 0.1 and about 50 mg/kg body weight per day, of the active ingredient compound are useful. For instance, an antibody of the invention will be administered at a dose ranging between about 0.01 mg/kg body weight/day and about 20 mg/kg body weight/day, e.g., ranging between about 0.1 mg/kg body weight/day and about 10 mg/kg body weight/day, and at intervals of every one to fourteen days. In another embodiment, the antibody is administered at a dose of about 0.3 to 1 mg/kg body weight when administered intraperitoneally. In yet another embodiment, the antibody is administered at a dose of about 5 to 12.5 mg/kg body weight when administered intravenously. In one embodiment, an antibody composition is administered in an amount effective to provide a plasma level of antibody of at least 1 mg/ml.

Other suitable dosages and administration regimens and modes will be familiar to those of orginary skill; still others are described in additional detail hereinbelow.

Ligands Binding to Integrin $\alpha_v\beta_6$

In an additional embodiment, the present invention is also directed to methods for identifying metastatic cancer cells, or for predicting the metastatic potential of cells in a tumor (i.e., the likelihood that cells in the tumor will metastasize from the primary tumor site to a secondary, or metastatic, site in vivo), by determining the level of expression of integrin $\alpha_v\beta_6$ by the cells, wherein an increase in the cell surface expression of $\alpha_v\beta_6$ indicates that the cancer cell is more likely to be metastatic. In related embodiments, the invention is directed to methods for eliminating residual tumor cells that express $\alpha_v\beta_6$, particularly metastatic tumor cells, following medical intervention to remove a tumor (e.g., surgical excision of the tumor, or chemotherapeutic or radiotherapeutic reduction or ablation of the tumor). In additional related embodiments, the invention provides methods of identifying noninvasive forms of carcinoma, particularly of adenocarcinomas or in situ carcinomas (such as ductal carcinoma in situ (DCIS) or lobular carcinoma in situ (LCIS) of the breast), which are more likely to progress to an invasive or metastatic form. Certain such embodiments comprise determining the level of expression of integrin $\alpha_v\beta_6$ in cells of the carcinoma, or in the myoepithelium surrounding the carcinoma, in tissue sections obtained from a patient suffering from such a carcinoma, wherein an increased level of expression of integrin $\alpha_v\beta_6$ relative to non-tumor tissue samples (ideally, from the same organ in the same patient) indicates that the carcinoma is more likely to progress to an invasive or metastatic form of cancer at some time in the near future. In each such embodiment, the invention relies upon identification or exploitation of the increased expression of $\alpha_v\beta_6$ in tumor cells, which identification is accomplished by contacting the tissue, tumor or tumor cells with one or more ligands that binds to integrin $\alpha_v\beta_6$ in the tissue, tumor or tumor cells. In certain embodiments, the tissue, tumor or tumor cells are carcinoma tissues, tumors or tumor cells, including those from carcinomas such as adenocarcinomas. In more particular embodiments, the carcinoma is a breast carcinoma, an endometrial carcinoma, a pancreatic carcinoma, a colorectal carcinoma, a lung carcinoma, an ovarian carcinoma, a cervical carcinoma, a prostatic carcinoma, a liver carcinoma, an esophageal carcinoma, a head and neck carcinoma, a stomach carcinoma or a splenic carcinoma. More particularly, the carcinoma is a breast carcinoma (including but not limited to an in situ breast carcinoma, such as ductal carcinoma in situ (DCIS) or lobular carcinoma in situ (LCIS)), an endometrial carcinoma, a pancreatic carcinoma, a colorectal carcinoma, a cervical carcinoma, or a lung carcinoma.

In certain embodiments of the invention, the ligands that bind to $\alpha_v\beta_6$ are antagonists of $\alpha_v\beta_6$. Such antagonists include but are not limited to antibodies which specifically bind to $\alpha_v\beta_6$; antibodies which specifically bind to $\beta_6$; antibodies that bind to $\alpha_v$; antibodies that bind to ligands for $\alpha_v\beta_6$; ligands for $\alpha_v\beta_6$; antisense nucleic acids; and peptide, non-peptide, and peptidomimetic analogs of such ligands.

In certain such embodiments of the present invention, the ligand that binds to integrin $\alpha_v\beta_6$ is an antibody that binds to integrin $\alpha_v\beta_6$ or integrin $\alpha_v\beta_6$-binding fragments, variants, or derivatives thereof. Such antibodies may bind to one subunit of the integrin (e.g., antibodies that bind to an epitope located on the $\alpha_v$ subunit or to an epitope that is located on the $\beta_6$ subunit), or to both subunits (e.g., antibodies that bind to an epitope that is located in a region of the integrin heterodimer that bridges both the $\alpha_v$ and $\beta_6$ subunits). Unless specifically referring to full-sized antibodies such as naturally occurring antibodies, the term "$\alpha_v\beta_6$ antibodies" encompasses full-sized antibodies as well as $\alpha_v\beta_6$-binding fragments, variants, analogs, or derivatives of such antibodies, e.g., naturally occurring antibody or immunoglobulin molecules or engineered antibody molecules or fragments that bind antigen in a manner similar to antibody molecules. Antibodies can be synthetic, monoclonal, or polyclonal and can be made by techniques well known in the art. For therapeutic applications, "human" monoclonal antibodies having human constant and variable regions are often preferred so as to minimize the immune response of a patient against the antibody. Such antibodies can be generated by immunizing transgenic animals which contain human immunoglobulin genes (see, e.g., Jakobovits et al., *Ann. N.Y. Acad. Sci.* 764:525-535 (1995)). In connection with synthetic and semi-synthetic antibodies, such terms are intended to cover but are not limited to antibody fragments, isotype switched antibodies, humanized antibodies (e.g., mouse-human, human-mouse, and the like), hybrids, antibodies having plural specificities, fully synthetic antibody-like molecules, and the like.

The terms "antibody" and "immunoglobulin" are used interchangeably herein. An antibody or immunoglobulin comprises at least the variable domain of a heavy chain, and normally comprises at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988). As will be understood by those of ordinary skill, the terms "antibody" and "immunoglobulin" comprise various broad classes of polypeptides that can be distinguished biochemically. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernable to the skilled artisan in view of the instant disclosure and, accordingly, are within the scope of the instant invention.

Antibodies that bind to $\alpha_v\beta_6$, or $\alpha_v\beta_6$-binding fragments, variants, or derivatives thereof, that are suitable for use in the present invention include but are not limited to polyclonal, monoclonal, multispecific, human, humanized, primatized, or chimeric antibodies, single chain antibodies, epitope-binding fragments, e.g., Fab, Fab' and $F(ab')_2$, Fd, Fvs, single-chain Fvs (scFv), single-chain antibodies, disulfide-linked Fvs (sdFv), fragments comprising either a $V_L$ or $V_H$ domain, fragments produced by a Fab expression library, and anti-idiotypic (anti-Id) antibodies (including, e.g., anti-Id antibodies to anti-$\alpha_v\beta_6$ antibodies disclosed herein). ScFv molecules are known in the art and are described, e.g., in U.S. Pat. No. 5,892,019. Immunoglobulin or antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule.

Antibody fragments, including single-chain antibodies, may comprise the variable region(s) alone or in combination with the entirety or a portion of the following: hinge region, $C_H1$, $C_H2$, and $C_H3$ domains. Also included in the invention are antigen-binding fragments also comprising any combination of variable region(s) with a hinge region, $C_H1$, $C_H2$, and $C_H3$ domains. Antibodies or immunospecific fragments thereof for use in the diagnostic and therapeutic methods disclosed herein may be from any animal origin including birds and mammals. Preferably, the antibodies are human, murine, rat, donkey, rabbit, goat, guinea pig, camel, llama, horse, bovine or chicken antibodies. Most preferably, the antibodies are human, humanized or primatized antibodies, or chimeric antibodies, particularly monoclonal antibodies. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al. As used herein, the term "chimeric antibody" will be held to mean any antibody wherein the immunoreactive region or site is obtained or derived from a first species and the constant region (which may be intact, partial or modified in accordance with the instant invention) is obtained from a second species. In preferred embodiments the target binding region or site will be from a non-human source (e.g. mouse or primate) and the constant region is human.

Particularly preferred antibodies for use in accordance with the present invention are anti-$\alpha_v\beta_6$ monoclonal antibodies such as those disclosed in Weinreb et al., *J. Biol. Chem.* 279(17):17875-17877 (2004) (the disclosure of which is incorporated herein by reference in its entirety), including monoclonal antibodies 6.8G6 ("8G6") and 6.3G9 ("3G9") disclosed therein. Additional antibodies that bind to $\alpha_v\beta_6$ and that therefore are suitable for use in accordance with the present invention include antibodies (or fragments, variants or derivatives thereof) that bind to the $\beta_6$ subunit of integrin $\alpha_v\beta_6$ (and that are therefore considered "anti-$\beta_6$ antibodies"), such as those disclosed in Weinacker et al., *J. Cell Biol.* 269:1-9 (1994), which is incorporated herein by reference in its entirety; and in U.S. Pat. No. 6,692,741 B2, which is incorporated herein by reference in its entirety, particularly at columns 2-3 and 7-8 thereof, including the monoclonal antibody designated 10D5 (ATCC deposit no. HB12382, deposited Aug. 6, 1997, American type Culture Collection, P.O. Box 1549, Manassas, Va. 20108) (see U.S. Pat. No. 6,692,741 at col. 3, lines 7-13, and at cols. 7-8) and CS$\beta$6 (see U.S. Pat. No. 6,692,741 at cols. 7-8). Suitable embodiments according to this aspect of the invention use $\alpha_v\beta_6$ integrin-binding ligands which are $\alpha_v\beta_6$-binding antibodies or $\alpha_v\beta_6$ epitope-binding fragments thereof. Additional antibodies suitable for use in accordance with this aspect of the invention include, but are not limited to, the $\alpha_v\beta_6$-binding monoclonal antibodies disclosed in U.S. patent application publication no. US 2005/0255102 A1, the disclosure of which is incorporated herein in its entirety, including those designated therein as 3G9, 8G6, 1A8, 2B1, 2B10, 2A1, 2E5, 1G10, 7G5, 1C5, as well as fragments, chimeras and hybrids thereof. Particularly suitable antibodies for use in accordance with the present invention are monoclonal antibodies 2B1, 3G9 and 8G6.

In some embodiments, the antibodies comprise the same heavy and light chain polypeptide sequences as an antibody produced by hybridoma 6.1A8, 6.3G9, 6.8G6, 6.2B1, 6.2B10, 6.2A1, 6.2E5, 7.1G10, 7.7G5, or 7.1C5. Particularly suitable antibodies for use in accordance with the present invention are monoclonal antibodies that comprise the same heavy and light chain polypeptide sequences as 2B1 antibodies produced by hybridoma 6.2B1 (ATCC deposit no. PTA-3646, deposited Aug. 16, 2001, American Type Culture Collection, P.O. Box 1549, Manassas, Va. 20108), 8G6 antibodies produced by hybridoma 6.8G6 (ATCC deposit no. PTA-3645, deposited Aug. 16, 2001, American Type Culture Collection, P.O. Box 1549, Manassas, Va. 20108) and 3G9 antibodies produced by hybridoma 6.3G9 (ATCC deposit no. PTA-3649, deposited Aug. 16, 2001, American Type Culture Collection, P.O. Box 1549, Manassas, Va. 20108) (see published. U.S. Appl. No. US 2005/0255102 A1, the disclosure of which is incorporated herein by reference in its entirety, particularly at page 1, paragraph 0008; at page 2, paragraphs 0032 and 0036; and in the Examples at pages 6-14), and the antibody designated as 10D5 (the hybridoma secreting which antibody was deposited on Aug. 6, 1997, as ATCC deposit no. HB12382, American Type Culture Collection, P.O. Box 1549, Manassas, Va. 20108) (see U.S. Pat. No. 6,692,741, the disclosure of which is incorporated herein by reference in its entirety, particularly at col. 3, lines 7-13, and at cols. 7-8).

In some embodiments, the antibodies comprise a heavy chain whose complementarity determining regions (CDR) 1, 2 and 3 consist essentially (i.e., with the exception of some conservative variations) of the sequences shown in Table 1 below. In certain such embodiments, the antibodies comprise a heavy chain whose CDR1 consists essentially of any one of SEQ ID NOs:101-105; whose CDR2 consists essentially of any one of SEQ ID NOs: 106-111; and whose CDR3 consists essentially of any one of SEQ ID NOs:112-117; and/or a light chain whose CDRs 1, 2 and 3 consist essentially of any one of the sequences of SEQ ID NOs:118-123, 124-127, and 128-133, respectively.

TABLE 1

| Antibody | Amino Acid Sequence | SEQ ID NO: |
|---|---|---|
| | Heavy Chain CDR1 Sequences | |
| 8G6 | SYTFTDYAMH | 101 |
| 1A8 | SYTFTDYTMH | 102 |
| 2B1 | GFTFSRYVMS | 103 |
| 3G9 | GFTFSRYVMS | 103 |
| 2A1 | GYDFNNDLIE | 104 |
| 2G2 | GYAFTNYLIE | 105 |
| | Heavy Chain CDR2 Sequences | |
| 8G6 | VISTYYGNTNYNQKFKG | 106 |
| 1A8 | VIDTYYGKTNYNQKFEG | 107 |
| 2B1 | SISSG-GSTYYPDSVKG | 108 |
| 3G9 | SISSG-GRMYYPDTVKG | 109 |
| 2A1 | VINPGSGRTNYNEKFKG | 110 |
| 2G2 | VISPGSGIINYNEKFKG | 111 |
| | Heavy Chain CDR3 Sequences | |
| 8G6 | GGLRRGDRPSLRYAMDY | 112 |
| 1A8 | GGFRRGDRPSLRYAMDS | 113 |
| 2B1 | GAIYDG-----YYVFAY | 114 |
| 3G9 | GSIYDG-----YYVFPY | 115 |
| 2A1 | IYYGPH-----SYAMDY | 116 |
| 2G2 | ID-YSG-----PYAVDD | 117 |
| | Light Chain CDR1 Sequences | |
| 8G6 | RASQSVSTSS-YSYMY | 118 |
| 1A8 | RASQSVSIST-YSYIH | 119 |
| 2B1 | SASSSVSSS----YLY | 120 |
| 3G9 | SANSSVSSS----YLY | 121 |
| 2A1 | KASLDVRTAVA | 122 |
| 2G2 | KASQAVNTAVA | 123 |

TABLE 1-continued

| Antibody | Amino Acid Sequence | SEQ ID NO: |
|---|---|---|
| | Light Chain CDR2 Sequences | |
| 8G6 | YASNLES | 124 |
| 1A8 | YASNLES | 124 |
| 2B1 | STSNLAS | 125 |
| 3G9 | STSNLAS | 125 |
| 2A1 | SASYRYT | 126 |
| 2G2 | SASYQYT | 127 |
| | Light Chain CDR3 Sequences | |
| 8G6 | QHNWEIPFT | 128 |
| 1A8 | QHSWEIPYT | 129 |
| 2B1 | HQWSSYPPT | 130 |
| 3G9 | HQWSTYPPT | 131 |
| 2A1 | QQHYGIPWT | 132 |
| 2G2 | QHHYGVPWT | 133 |

In other related embodiments, the monoclonal in accordance with the present invention are chimeric those in which a cognate antibody from one species (e.g., bit) is altered by recombinant DNA technology such that part or all of the hinge and/or constant regions of the heavy and/or light chains are replaced with the corresponding components of an antibody from another species (e.g., human). Generally, the variable domains of the engineered antibody remain identical or substantially so to the variable domains of the cognate antibody. Such an engineered antibody is called a chimeric antibody and is less antigenic than the cognate antibody when administered to an individual of the species from which the hinge and/or constant region is derived (e.g., a human). Methods of making chimeric antibodies are well known in the art.

In other related embodiments, the monoclonal antibodies used in accordance with the present invention are fully human antibodies. Methods for producing such fully human monoclonal antibodies are well known in the art (see, e.g., US 2005/0255102 A1 at page 4, paragraphs 0069-0070, which are incorporated herein by reference).

In other related embodiments, the monoclonal antibodies used in accordance with the present invention are humanized versions of cognate anti-$\alpha_v\beta_6$ antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has, on both of its heavy and light chain: (a) constant regions of a human antibody; (b) framework regions from the variable domains of a human antibody; and (c) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Humanized antibodies generally are less likely to elicit an immune response in humans as compared to chimeric human antibodies because the former contain considerably fewer non-human components. Methods for producing such humanized monoclonal antibodies are well known in the art (see, e.g., US 2005/0255102 A1 at pages 4-5, paragraphs 0072-0077, which are incorporated herein by reference).

In additional such embodiments, the humanized antibodies comprise one or more CDRs in the heavy and/or light chain that are derived from the corresponding CDRs in the heavy and/or light chain of a different antibody. One suitable non-limiting example of such an antibody is a humanized 3G9 antibody comprising a light chain CDR1 that has the sequence of the light chain CDR1 derived from the 2B1 antibody (SEQ ID NO:120) instead of the sequence of the light chain CDR1 for the deposited 3G9 antibody (SEQ ID NO:121). Such a humanized 3G9 antibody having a light chain CDR1 sequence set forth in SEQ ID NO:120 is designated herein as hu3G9 (or BG00011). Another suitable non-limiting example of such an antibody is a humanized 8G6 antibody comprising a light chain CDR1 that has the sequence of the light chain CDR1 derived from the 2B1 antibody (SEQ ID NO:120) instead of the sequence of the light chain CDR1 for the deposited 8G6 antibody (SEQ ID NO:118). Such a humanized 8G6 antibody having a light chain CDR1 sequence set forth in SEQ ID NO:120 is designated herein as hu8G9. Additional examples of such derivative antibodies, in which one or more heavy chain and/or light chain CDRs has been replaced with one or more corresponding heavy chain and/or light chain CDRs from another antibody, and which are suitable for use in accordance with the present invention, will be readily apparent to those of ordinary skill in view of the sequences depicted in Table 1 and the guidance provided herein. Suitable methods for preparing such humanized antibodies, including such derivative humanized antibodies, are familiar to those of ordinary skill and are set forth, for example, in US published application no. 2005/0255102 A1, the disclosure of which is incorporated herein by reference in its entirety.

Conjugates and Other Modifications of $\alpha_v\beta_6$-Binding Ligands

In certain embodiments, the ligands, e.g., the antibodies, that bind to $\alpha_v\beta_6$ can be used in unconjugated form. In other embodiments, the ligands, e.g., the antibodies, that bind to $\alpha_v\beta_6$ can be conjugated, e.g., to a detectable label, a drug, a prodrug or an isotope.

In certain methods of the invention described in more detail below, such as methods of detecting $\alpha_v\beta_6$ expression in cells or tissues as a measure of the metastatic potential of tumor cells, or as a way of identifying in situ carcinomas (e.g., DCIS or LCIS) in tissues, the $\alpha_v\beta_6$-binding ligands (e.g., antibodies) are conjugated to one or more detectable labels. For such uses, the $\alpha_v\beta_6$-binding ligands, e.g., $\alpha_v\beta_6$-binding antibodies, may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid.

Examples of suitable enzyme labels include malate dehydrogenase, staphylococcal nuclease, Δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^3H$, $^{111}In$, $^{125}I$, $^{131}I$, $^{32}P$, $^{35}S$, $^{14}C$, $^{51}Cr$, $^{57}To$, $^{58}Co$, $^{59}Fe$, $^{75}Se$, $^{152}Eu$, $^{90}Y$, $^{67}Cu$, $^{217}Ci$, $^{211}At$, $^{212}Pb$, $^{47}Sc$, $^{109}Pd$, etc. $^{111}In$ is a preferred isotope where in vivo imaging is used since its avoids the problem of dehalogenation of the $^{125}I$ or $^{131}I$-labeled $\alpha_v\beta_6$-binding ligands by the liver. In addition, this radionucleotide has a more favorable gamma emission energy for imaging (Perkins et al., *Eur. J. Nucl. Med.* 10:296-301 (1985); Carasquillo et al., *J. Nucl. Med.* 28:281-287 (1987)). For example, $^{111}In$ coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861-870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label.

Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to $\alpha_v\beta_6$-binding ligands, e.g., $\alpha_v\beta_6$-binding antibodies, are provided by Kennedy et al., *Clin. Chim. Acta* 70:1-31 (1976), and Schurs et al., *Clin. Chim. Acta* 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

For use in certain therapeutic approaches of the invention such as ablation of residual tumor cells following surgery, or prevention of metastasis, the $\alpha_v\beta_6$-binding ligands can be conjugated to one or more drugs, prodrugs or isotopes. Preferred such conjugates comprise one or more ligands, e.g., one or more antibodies or fragments, derivatives or variants thereof, that bind to $\alpha_v\beta_6$, conjugated to one or more cytotoxic agents; such conjugates are useful in the methods of treatment and prevention of tumor metastasis provided by the invention. According to certain such embodiments of the invention, the $\alpha_v\beta_6$-binding ligand, e.g., antibody, is conjugated to a cytotoxic agent. Cytotoxic, e.g., chemotherapeutic, agents useful in the generation of $\alpha_v\beta_6$-binding ligand-cytotoxic agent conjugates are well known in the art, and include but are not limited to cisplatin, carboplatin, oxaliplatin, paclitaxel, melphalan, doxorubicin, methotrexate, 5-fluorouracil, etoposide, mechlorethamine, cyclophosphamide and bleomycin. Other chemotherapeutic agents suitable for use in accordance with this aspect of the invention are well-known and will be familiar to the ordinarily skilled artisan.

The use of conjugates of one or more $\alpha_v\beta_6$-binding ligand, e.g., one or more $\alpha_v\beta_6$-binding antibodies, and one or more small molecule toxins, such as a calicheamicin, a maytansine (U.S. Pat. No. 5,208,020), a trichothene, and CC1065, are also contemplated herein. In one embodiment of the invention, the $\alpha_v\beta_6$-binding ligand is conjugated to one or more maytansine molecules (e.g. about 1 to about 10 maytansine molecules per $\alpha_v\beta_6$-binding ligand). Maytansine may, for example, be converted to May-SS-Me which may be reduced to May-SH3 and reacted with modified $\alpha_v\beta_6$-binding ligands (Chari et al. *Cancer Research* 52: 127-131 (1992)) to generate a maytansinoid-$\alpha_v\beta_6$-binding ligand conjugate.

Alternatively, the $\alpha_v\beta_6$-binding ligand can be conjugated to one or more calicheamicin molecules. The calicheamicin family of antibiotics are capable of producing double-stranded DNA breaks at sub-picomolar concentrations. Structural analogues of calicheamicin which may be used include, but are not limited to, $\gamma_1^1$, $\alpha_2^1$, $\alpha_3^1$, N-acetyl-$\gamma_1^1$, PSAG and $\Phi_1^1$ (Hinman et al. *Cancer Research* 53: 3336-3342 (1993) and Lode et al. *Cancer Research* 58: 2925-2928 (1998)).

Enzymatically active toxins and fragments thereof which can be used to produce conjugates with one or more $\alpha_v\beta_6$-binding ligands, e.g., one or more $\alpha_v\beta_6$-binding antibodies, include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleuritesfordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published in the English language on Oct. 28, 1993, the disclosure of which is incorporated herein by reference in its entirety. Mytansinoids may also be conjugated to one or more $\alpha_v\beta_6$-binding ligands, e.g., one or more $\alpha_v\beta_6$-binding antibodies.

The present invention further contemplates $\alpha_v\beta_6$-binding ligands conjugated with a compound with nucleolytic activity (e.g., a ribonuclease or a DNA endonuclease such as a deoxyribonuclease; DNase).

A variety of radioactive isotopes are also available for the production of radioconjugated $\alpha_v\beta_6$-binding ligands for use in therapeutic methods of the invention. Examples include $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

Conjugates of the $\alpha_v\beta_6$-binding ligands and cytotoxic agents may be made using a variety of bifunctional protein coupling agents such as N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), his-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). $^{14}$-Carbon-labeled 1-isothiocyanatobenzyl-3-methyldiethylene triaminepentaacetic acid (MX-DTPA) is an exemplary chelating agent for conjugation of radionucleotide to the $\alpha_v\beta_6$-binding ligand. See WO 94/11026. The linker may be a "cleavable linker" facilitating release of the cytotoxic drug in the cell. For example, an acid-labile linker, peptidase-sensitive linker, dimethyl linker or disulfide-containing linker (Chari et al. *Cancer Research* 52:127-131 (1992)) may be used.

Alternatively, a fusion protein comprising the $\alpha_v\beta_6$-binding ligand and cytotoxic agent may be made, e.g. by recombinant techniques or peptide synthesis.

In yet another embodiment, the $\alpha_v\beta_6$-binding ligand may be conjugated to a "receptor" (such streptavidin) for utilization in "pretargeting" wherein the $\alpha_v\beta_6$-binding ligand-receptor conjugate is administered to the patient, followed by removal of unbound conjugate from the circulation using a clearing agent and then administration of a "ligand" (e.g. avidin) which is conjugated to a cytotoxic agent (e.g., a radionucleotide).

The $\alpha_v\beta_6$-binding ligands of the present invention may also be conjugated with a prodrug-activating enzyme which converts a prodrug (e.g. a peptidyl chemotherapeutic agent, see WO 81/01145) to an active drug. See, for example, WO 88/07378 and U.S. Pat. No. 4,975,278. The enzyme component of such conjugates includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *Serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as O-galactosidase and neuraminidase useful for converting glycosylated prodrugs into free drugs; P-lactamase useful for converting drugs derivatized with P-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs.

Enzymes can be covalently bound to the $\alpha_v\beta_6$-binding ligand by techniques well known in the art such as the use of the heterobifunctional crosslinking reagents. Alternatively, fusion proteins comprising at least the antigen binding region of a $\alpha_v\beta_6$-binding ligand of the invention linked to at least a functionally active portion of an enzyme can be constructed using recombinant DNA techniques well known in the art (see, e.g., Neuberger et al., *Nature* 312: 604-608 (1984)).

Disease Diagnosis and Prognosis

It has now been found that cells from certain tumors that are metastatic express significantly enhanced levels of integrin $\alpha_v\beta_6$ when compared to cells that are less metastatic or non-metastatic. In addition, the present inventors have discovered that in certain forms of in situ carcinoma, e.g., ductal carcinoma in situ (DCIS) or lobular carcinoma in situ (LCIS) of the breast, the myoepithelium surrounding the tumor expresses significantly enhanced levels of integrin $\alpha_v\beta_6$ relative to the tumor cells of the carcinoma and relative to normal breast tissue. Thus, the invention provides a method useful in diagnosing the metastatic potential of a tumor cell, including tumors from carcinomas such as an adenocarcinoma. In more particular embodiments, the carcinoma is a breast carcinoma, an endometrial carcinoma, a pancreatic carcinoma, a colorectal carcinoma, a lung carcinoma, an ovarian carcinoma, a cervical carcinoma, a prostatic carcinoma, a liver carcinoma, an esophageal carcinoma, a head and neck carcinoma, a stomach carcinoma or a splenic carcinoma. More particularly, the carcinoma is a breast carcinoma (including but not limited to an in situ breast carcinoma, such as ductal carcinoma in situ (DCIS) or lobular carcinoma in situ (LCIS)), an endometrial carcinoma, a pancreatic carcinoma, a colorectal carcinoma, a cervical carcinoma, or a lung carcinoma.

Methods according to this aspect of the invention involve assaying the level of expression of $\alpha_v\beta_6$ in the tumor cells or in the myoepithelium in a tissue sample, and comparing these expression levels with a standard $\alpha_v\beta_6$ expression level (e.g., in normal cells, non-metastatic cells, or normal tissue, preferably obtained from the same animal, such as a human patient), wherein an increase in the expression of $\alpha_v\beta_6$ in a tumor or in the cells thereof is indicative of a higher invasive and/or metastatic potential of that tumor or cells thereof, or wherein an increase in the expression of $\alpha_v\beta_6$ in the myoepithelium surrounding a tumor or epithelial cell cluster in a tissue section is indicative of the presence of an in situ carcinoma, e.g., DCIS or LCIS, that is more likely to become invasive and potentially form metastases.

Where a diagnosis of a cancer has already been made according to conventional methods, the present invention is useful as a prognostic indicator, whereby tumor cells exhibiting increased levels of expression of $\alpha_v\beta_6$ will be predicted to be more likely to become invasive and to metastasize from the primary tumor site to a distal, metastatic site. Similarly, where a suspected diagnosis of an in situ carcinoma has been made according to conventional methods (e.g., mammographic detection of calcified nodules in the breast), the present invention is useful as a confirmatory indicator, whereby biopsied tissue from the area of calcification exhibiting increased levels of expression of $\alpha_v\beta_6$ in the myoepithelium indicates the presence of an in situ carcinoma, e.g., DCIS or LCIS that will become invasive and may respond to $\alpha_v\beta_6$ mAb treatment. Based on such prognostic and diagnostic outcomes, the treating physician can then adjust the treatment regimen accordingly, thereby providing for earlier detection of a pre-metastatic or pre-cancerous condition and thus a more favorable clinical outcome for the patient.

By "assaying the levels of expression of $\alpha_v\beta_6$" is intended qualitatively or quantitatively measuring or estimating the levels of $\alpha_v\beta_6$ in a first biological sample (e.g., a tumor sample, a tissue biopsy or aspirate, etc.) either directly (e.g., by determining or estimating absolute amount of $\alpha_v\beta_6$ in the sample) or relatively (e.g., by comparing the level of expression of $\alpha_v\beta_6$ in a first biological sample to that in a second biological sample). Preferably, the level of $\alpha_v\beta_6$ in the first biological sample is measured or estimated and compared to that in a standard taken from a second biological sample obtained from an individual not having a cancer or pre-cancerous lesion. As will be appreciated by one of ordinary skill in the art, once a standard $\alpha_v\beta_6$ expression level is known for a given non-cancerous tissue, it can be used repeatedly as a standard for comparison.

By "biological sample" is intended any biological sample obtained from an individual (such as a patient), cell line, tissue culture, or other source which may contain cells or cellular products such as extracellular matrix. Such biological samples include mammalian body tissues and cells, including leukocyte, ovary, prostate, heart, placenta, pancreas, liver, spleen, lung, breast, head and neck tissues (e.g., oral, pharyngeal, lingual and laryngeal tissues), endometrium, colon (or colorectal), cervix, stomach and umbilical tissues which may express $\alpha_v\beta_6$. Methods for obtaining tissue biopsies and body fluids from mammals are well known in the art. Preferred mammals include monkeys, apes, cats, dogs, cows, pigs, horses, rabbits and humans. Particularly preferred are humans.

Assaying $\alpha_v\beta_6$ expression levels in a biological sample can occur using any art-known method. Preferred for assaying $\alpha_v\beta_6$ expression levels in a biological sample are immunological techniques. For example, $\alpha_v\beta_6$ expression in tissues can be studied with classical immunohistological methods. In these, the specific recognition is provided by a primary ligand, e.g., an antibody (polyclonal or monoclonal), that binds to $\alpha_v\beta_6$. This primary ligand can be labeled, e.g., with a fluorescent, chemiluminescent, phosphorescent, enzymatic or radioisotopic label. Alternatively, these methods of the invention can use a secondary detection system in which a second ligand that recognizes and binds to the $\alpha_v\beta_6$-binding ligand, e.g., a so-called "secondary" antibody which recognizes and binds to a first $\alpha_v\beta_6$-binding antibody, is detectably labeled as described above. As a result, an immunohistological staining of tissue section for pathological examination is obtained. Alternatively, tissues and cell samples can also be extracted, e.g., with urea and neutral detergent, for the liberation of $\alpha_v\beta_6$ protein for Western-blot or dot/slot assay (Jalkanen, M., et al., *J. Cell. Biol.* 101:976-985 (1985); Jalkanen, M., et al., *J. Cell. Biol.* 105:3087-3096 (1987)) for direct quantitation, relative to a standard tissue or cell sample known to have lower levels of expression of $\alpha_v\beta_6$.

As noted above, the methods of the present invention are useful for detecting metastatic cancers in mammals, for determining the metastatic potential of a tumor cell (i.e., predicting the likelihood that a given tumor cell will metastasize from the primary tumor site to a distal metastatic site), and for determining the likelihood that a noninvasive or in situ carcinoma will progress to an invasive or metastatic carcinoma. In particular the methods of the invention are useful in detecting invasive and/or metastatic cancers of epithelial tissues (i.e., invasive and/or metastatic carcinomas), including of the breast, ovary, prostate, liver, lung, pancreas, colon (or colorectal), head and neck tissues (e.g., oral, pharyngeal, lingual and laryngeal tissues), endometrium, cervix, stomach and spleen. Particularly suitable to detection by the methods of the present invention are invasive and/or metastatic adenocarcinomas, including but not limited to breast carcinomas, pancreatic carcinomas, colorectal carcinomas, cervical carcinomas, lung carcinomas, and in situ carcinomas, such as certain ductal carcinoma in situ (DCIS) or lobular carcinoma in situ (LCIS) of the breast, that are of increased likelihood to progress to an invasive and/or metastatic phenotype. Early identification and treatment of such carcinomas is associated with a better long-term prognosis for patients. For example, it has been reported that if left untreated, a significant proportion of DCIS tumors become invasive and can lead to metastatic cancers which have a much poorer prognosis (see Sakorafas, G. H., and Tsiotou, A. G. H., *Cancer Treatment Rev.* 26:103-125 (2000)).

Accordingly, the present invention contemplates methods of treating or preventing metastatic cancers by identifying pre-invasive lesions or carcinomas in patients, and treating the patient to eliminate the pre-invasive lesion before it has the opportunity to evolve into an invasive form. Such methods comprise, for example, (a) obtaining a tissue sample that is suspected of containing a cancer or a pre-invasive lesion, and a tissue sample that does not contain a cancer or pre-invasive lesion (preferably from the same tissue or organ as that suspected of containing a cancer or pre-invasive lesion); (b) contacting the tissue samples with one or more $\alpha_v\beta_6$-binding ligands, such as one or more $\alpha_v\beta_6$-binding antibodies or fragments thereof, under conditions favoring the binding of the one or more $\alpha_v\beta_6$-binding ligands to $\alpha_v\beta_6$ integrins in the tissue wherever present; and (c) detecting the level or pattern of binding of the $\alpha_v\beta_6$-binding ligand(s) to the tissue, wherein an increase in the localized binding of the $\alpha_v\beta_6$-binding ligand in the myoepithelium surrounding a hyperplasia (e.g., a tumor) relative to the binding in the hyperplasia itself (or cells thereof), or an increase in the level of binding of the $\alpha_v\beta_6$-binding ligand in the tissue sample containing the cancerous or pre-invasive lesion relative to the binding in the non-cancerous tissue sample (or cells thereof), is indicative of carcinoma that is more likely to become invasive and potentially metastasize. In other related embodiments, the invention contemplates methods of reducing or preventing the progression of a pre-metastatic or pre-invasive tumor to a metastatic or invasive tumor in a patient, comprising administering to the patient a therapeutically effective amount of one or more ligands that binds to one or more subunits of integrin $\alpha_v\beta_6$ on one or more cells in the pre-metastatic or pre-invasive tumor, wherein the binding of the ligand to the integrin results in the reduction or prevention of invasion of cells of the pre-metastatic or pre-invasive cancer into tissue areas surrounding the primary tumor.

Suitable tissues and organs from which samples can be obtained for use in accordance with these methods of the invention include, but are not limited to, the epithelial tissues described elsewhere herein. Cancers and tumors that may be advantageously treated or prevented according to such methods of the invention include, but are not necessarily limited to, carcinomas, particularly adenocarcinomas, including the carcinomas and adenocarcinomas described in detail elsewhere herein. Once such a carcinoma has been detected according to the methods of the invention, it can then be eliminated from the patient via surgical, chemotherapeutic, radiological or other methods of cancer therapy that are well-known in the art and that therefore will be familiar to those of ordinary skill. Alternatively, such a carcinoma can be eliminated using the methods of treatment of the present invention, by administering to the patient, or to the organs or tissues of the patient, one or more $\alpha_v\beta_6$-binding ligands, such as one or more $\alpha_v\beta_6$-binding antibodies or fragments thereof. In certain non-limiting examples of such embodiments, the one or more $\alpha_v\beta_6$-binding ligands have been conjugated with one or more cytotoxic compounds or agents as described in detail hereinabove. In additional non-limiting examples of such embodiments, the one or more $\alpha_v\beta_6$-binding ligands, such as one or more $\alpha_v\beta_6$-binding antibodies or fragments thereof, are administered to a subject, such as a patient, in conjunction with one or more cytotoxic compounds or agents as described in detail hereinabove.

In related embodiments, the invention contemplates determining the metastatic potential of a tumor or cancer cell by measuring the expression of $\alpha_v\beta_6$ by the tumor or cancer cell. In such embodiments, tumor or cell samples are obtained from a patient as described above and are assayed according to the methods described herein for the level of expression of $\alpha_v\beta_6$ on the tumor or cancer cell. Preferred such methods include immunohistochemistry, using $\alpha_v\beta_6$-binding antibodies (or fragments, variants or derivatives thereof such as those described herein. According to these methods of the invention, there is a direct correlation between the level of expression of $\alpha_v\beta_6$ by the tumor or cancer cell and the metastatic potential of the tumor or cancer cell: an increase in the expression of $\alpha_v\beta_6$ by a tumor or cancer cell indicates that that tumor or cancer cell is more likely to metastasize to a secondary locus from the primary tumor site. Hence, the level of expression of $\alpha_v\beta_6$ by a tumor or cancer cell can be used as a prognostic indicator of the metastatic potential of a tumor or cancer cell, which can assist cancer patients and their physicians in making appropriate treatment decisions based on the present or predicted future aggressiveness or invasiveness of the cancer.

In addition to assaying $\alpha_v\beta_6$ expression levels in a biological sample obtained from an individual, such as a tissue or tumor cell sample, the level and pattern of expression of $\alpha_v\beta_6$ can also be detected in vivo by imaging. In such methods of the invention, one or more $\alpha_v\beta_6$-binding ligands, e.g., one or more $\alpha_v\beta_6$-binding antibodies, are detectably labeled with one or more labels suitable for in vivo imaging. Suitable labels or markers for in vivo imaging include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium.

A ligand binding to $\alpha_v\beta_6$, e.g., an $\alpha_v\beta_6$-binding antibody or antibody fragment, which has been labeled with an appropriate detectable imaging moiety, such as a radioisotope (for example, $^{131}I$, $^{112}In$, $^{99m}Tc$), a radio-opaque substance, or a material detectable by nuclear magnetic resonance, is introduced (for example, parenterally, subcutaneously or intraperitoneally) into the mammal to be examined for cancer or carcinoma in situ. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}Tc$. The labeled $\alpha_v\beta_6$ ligand, e.g., $\alpha_v\beta_6$-binding antibody or antibody fragment, will then preferentially accumulate at the location of cells or tissues which contain or express $\alpha_v\beta_6$ integrin. In vivo tumor imaging is then accomplished as described in S. W. Burchiel et al., "Immunopharmacokinetics of Radiolabelled Antibodies and Their Fragments" (Chapter 13 in *Tumor Imaging: The Radiochemical Detection of Cancer*, S. W. Burchiel and B. A. Rhodes, eds., Masson Publishing Inc. (1982)).

Therapeutic Uses of $\alpha_v\beta_6$-Binding Ligands

In additional embodiments of the invention, $\alpha_v\beta_6$-binding ligands, such as $\alpha_v\beta_6$-binding antibodies or fragments thereof, may be used in therapeutic regimens for treating mammals afflicted with certain diseases, particularly with certain carcinomas such as those described elsewhere herein. Such methods of the invention are useful in treating cancer and associated events, including tumor growth, metastasis and angiogenesis. Particularly amenable to such an approach are those diseases or cancers that are characterized by increased levels of $\alpha_v\beta_6$ expression in the tissues or cells of a mammal suffering from the disease, and which are responsive to treatments which target the tissues or cells expressing increased levels of $\alpha_v\beta_6$ and eliminate those tissues or cells. Diseases that are particularly treatable by these methods include metastatic cancers of epithelial tissues (i.e., metastatic carcinomas and/or adenocarcinomas), including of the breast, ovary, prostate, liver, lung, pancreas, colon, head and neck tissues (e.g., oral, pharyngeal, lingual and laryngeal tissues), endometrium, cervix, stomach and spleen. Particularly suitable for treatment by these methods of the present invention are carcinomas of the endometrium, pancreas, colon (e.g., colorectal carcinomas), cervix, lung and breast (including ductal carcinoma in situ (DCIS) and lobular carcinoma in situ (LCIS) of the breast). Preferred mammals for treatment include monkeys, apes, cats, dogs, cows, pigs, horses, rabbits and humans. Particularly preferred are humans.

In certain such therapeutic regimens, the methods of the invention are suitable for eliminating residual tumor cells, e.g., of residual metastatic cells, following removal, treatment or eradication of a tumor by a different approach. For example, such methods of the invention can be used to eliminate residual tumor cells or metastatic cells that may remain in the patient following surgical excision of a tumor, or tumor eradication by methods such as irradiation, chemotherapy and the like. In such therapeutic regimens, the methods of the invention may comprise administering the $\alpha_v\beta_6$-binding ligands, e.g., the $\alpha_v\beta_6$-binding antibodies or fragments thereof, to a patient prior to, during, and/or following surgical, radiological and/or chemotherapeutic ablation of the tumor.

In related embodiments, as described above, the invention provides methods of reducing or preventing the progression of a pre-metastatic tumor to a metastatic tumor in a patient, comprising administering to the patient a therapeutically effective amount of one or more ligands that binds to one or more subunits of integrin $\alpha_v\beta_6$ on one or more cells in the pre-metastatic tumor, wherein the binding of the ligand to the integrin results in the reduction or prevention of invasion of cells of the pre-metastatic cancer into tissue areas surrounding the primary tumor.

In carrying out these therapeutic methods of the invention, $\alpha_v\beta_6$-binding ligands, such as $\alpha_v\beta_6$-binding antibodies or fragments thereof, may be administered to patients in the form of therapeutic formulations (which are also referred to herein interchangeably and equivalently as pharmaceutical compositions). Therapeutic formulations of the $\alpha_v\beta_6$-binding ligands used in accordance with the present invention are prepared for storage by mixing a $\alpha_v\beta_6$-binding ligand having the desired degree of purity with optional pharmaceutically acceptable carriers, excipients or stabilizers (Remington's Pharmaceutical Sciences 16th edition, Osol, A. Ed. (1980)), for example in the form of lyophilized formulations or aqueous solutions. In addition to the pharmacologically active compounds such as the $\alpha_v\beta_6$-binding ligands, the compositions used in the therapeutic methods of the invention can contain one or more suitable pharmaceutically acceptable carriers comprising excipients and auxiliaries that facilitate processing of the active compounds into preparations that can be used pharmaceutically. The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as starch paste, using, for example, maize starch, wheat starch, rice starch, potato starch, gelatin, tragacanth, methyl cellulose, hydroxypropylmethylcellulose, sodium carboxy-methylcellulose, and/or polyvinyl pyrrolidone. If desired, disintegrating agents can be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example silica, talc, stearic acid or salts thereof, such as magnesium stearate or calcium stearate, and/or polyethylene glycol. Dragee cores are provided with suitable coatings, that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Dye stuffs or pigments can be added to the tablets or dragee coatings, for example, for identification or in order to characterize combinations of active compound doses.

Other pharmaceutical preparations that can be used orally include push-fit capsules made of gelatin, as well as soft, sealed capsules made of gelatin and a plasticizer such as glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids such as fatty oils or liquid paraffin. In addition, stabilizers may be added.

Suitable formulations for parenteral administration include aqueous solutions of the active compounds in water-soluble form, for example water-soluble salts and alkaline solutions. Alkaline salts can include ammonium salts prepared, for example, with Tris, choline hydroxide, bis-Tris propane, N-methylglucamine, or arginine. In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example sodium carboxymethyl cellulose, sorbitol, and/or dextran. Optionally, the suspension may also contain stabilizers.

The compounds of the present invention may be administered to the eye in animals and humans as a drop, or within ointments, gels, liposomes, or biocompatible polymer discs, pellets or carried within contact lenses. The intraocular composition may also contain a physiologically compatible ophthalmic vehicle as those skilled in the art can select using conventional criteria. The vehicles may be selected from the known ophthalmic vehicles which include but are not limited to water, polyethers such as polyethylene glycol 400, polyvinyls such as polyvinyl alcohol, povidone, cellulose derivatives such as carboxymethylcellulose, methylcellulose and hydroxypropyl methylcellulose, petroleum derivatives such as mineral oil and white petrolatum, animal fats such as lanolin, vegetable fats such as peanut oil, polymers of acrylic acid such as carboxylpolymethylene gel, polysaccharides such as dextrans and glycosaminoglycans such as sodium chloride and potassium, chloride, zinc chloride and buffer such as sodium bicarbonate or sodium lactate. High molecular weight molecules can also be used. Physiologically compatible preservatives which do not inactivate the compounds of the present invention in the composition include alcohols such as chlorobutanol, benzalkonium chloride and EDTA, or any other appropriate preservative known to those skilled in the art.

Lyophilized formulations of antibodies adapted for subcutaneous administration are described in U.S. Pat. No. 6,267,958, the disclosure of which is incorporated herein by reference in its entirety. Such lyophilized formulations may be reconstituted with a suitable diluent to a high protein concentration and the reconstituted formulation may be administered subcutaneously to the patient to be treated herein.

The $\alpha_v\beta_6$-binding ligands may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of $\alpha_v\beta_6$-binding ligands may be prepared. Suitable examples of sustained-release preparations include semipermeable matrices of solid hydrophobic polymers containing the $\alpha_v\beta_6$-binding ligand, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile. This is readily accomplished by filtration through sterile filtration membranes.

The $\alpha_v\beta_6$-binding ligand may be administered to the subject or patient by any suitable means, including parenteral, intrapulmonary, intracranial, transdermal and intranasal. Parenteral infusions include intramuscular, intravenous, intraarterial, intraperitoneal, or subcutaneous administration. In addition, the $\alpha_v\beta_6$-binding ligand may suitably be administered by pulse infusion, e.g., with declining doses of the $\alpha_v\beta_6$-binding ligand. Preferably the dosing is given by injections, most preferably intravenous or subcutaneous injections, depending in part on whether the administration is brief or chronic.

In certain exemplary embodiments of the invention, the $\alpha_v\beta_6$-binding ligands are administered to the patient (e.g., intravenously) in a dosage of between about 1 mg/m$^2$ and about 500 mg/m$^2$. For instance, the $\alpha_v\beta_6$-binding ligand may be administered in a dosage of about 1 mg/m$^2$, 2 mg/m$^2$, 3 mg/m$^2$, 4 mg/m$^2$, 5 mg/m$^2$, 10 mg/m$^2$, 15 mg/m$^2$, 20 mg/m$^2$, 25 mg/m$^2$, 30 mg/m$^2$, 35 mg/m$^2$, 40 mg/m$^2$, 45 mg/m$^2$, 50 mg/m$^2$, 55 mg/m$^2$, 60 mg/m$^2$, 65 mg/m$^2$, 70 mg/m$^2$, 75 mg/m$^2$, 80 mg/m$^2$, 85 mg/m$^2$, 90 mg/m$^2$, 95 mg/m$^2$, 100 mg/m$^2$, 105 mg/m$^2$, 110 mg/m$^2$, 115 mg/m$^2$, 120 mg/m$^2$, 125 mg/m$^2$, 130 mg/m$^2$, 135 mg/m$^2$, 140 mg/m$^2$, 145 mg/m$^2$, 150 mg/m$^2$, 155 mg/m$^2$, 160 mg/m$^2$, 165 mg/m$^2$, 170 mg/m$^2$, 175 mg/m$^2$, 180 mg/m$^2$, 185 mg/m$^2$, 190 mg/m$^2$, 195 mg/m$^2$, 200 mg/m$^2$, 205 mg/m$^2$, 210 mg/m$^2$, 215 mg/m$^2$, 220 mg/m$^2$, 225 mg/m$^2$, 230 mg/m$^2$, 235 mg/m$^2$, 240 mg/m$^2$, 245 mg/m$^2$, 250 mg/m$^2$, 255 mg/m$^2$, 260 mg/m$^2$, 265 mg/m$^2$, 270 mg/m$^2$, 275 mg/m$^2$, 280 mg/m$^2$, 285 mg/m$^2$, 290 mg/m$^2$, 295 mg/m$^2$, 300 mg/m$^2$, 305 mg/m$^2$, 310 mg/m$^2$, 315 mg/m$^2$, 320 mg/m$^2$, 325 mg/m$^2$, 330 mg/m$^2$, 335 mg/m$^2$, 340 mg/m$^2$, 345 mg/m$^2$, 350 mg/m$^2$, 355 mg/m$^2$, 360 mg/m$^2$, 365 mg/m$^2$, 370 mg/m$^2$, 375 mg/m$^2$, 380 mg/m$^2$, 385 mg/m$^2$, 390 mg/m$^2$, 395 mg/m$^2$ or 400 mg/m$^2$.

The $\alpha_v\beta_6$-binding ligand can be administered according to a wide variety of dosing schedules. For example, the $\alpha_v\beta_6$-binding ligand can be administered once daily for a predetermined amount of time (e.g., four to eight weeks, or more), or according to a weekly schedule (e.g., one day per week, two days per week, three days per week, four days per week, five days per week, six days per week or seven days per week) for a predetermined amount of time (e.g., four to eight weeks, or more). A specific example of a "once weekly" dosing schedule is administration of the $\alpha_v\beta_6$-binding ligand on days 1, 8, 15 and 22 of the treatment period. In alternative embodiments the $\alpha_v\beta_6$-binding ligand may be administered intermittently over a period of months. For example, the $\alpha_v\beta_6$-binding ligand may be administered weekly for three consecutive weeks biannually (i.e., repeat the weekly dosing schedule every six months). It will be appreciated that such administration regimens may be continued for extended periods (on the order of years) to maintain beneficial therapeutic effects provided by initial treatments. In yet other embodiments such maintenance therapy may be effected following an acute dosing regimen designed to reduce the immediate symptoms of the cancerous, metastatic or in situ carcinoma condition.

The amount of $\alpha_v\beta_6$-binding ligand administered each time throughout the treatment period can be the same; alternatively, the amount administered each time during the treatment period can vary (e.g., the amount administered at a given time can be more or less than the amount administered previously). For example, doses given during maintenance therapy may be lower than those administered during the acute phase of treatment. Appropriate dosing schedules depending on the specific circumstances will be apparent to persons of ordinary skill in the art.

In certain embodiments of the invention, multiple types or species of $\alpha_v\beta_6$-binding ligands are combined with one another and administered to a patient to treat one or more cancerous, metastatic or in situ carcinoma conditions. For example, the invention contemplates the administration of two or more different $\alpha_v\beta_6$-binding antibodies to a patient, such as those disclosed herein. When multiple $\alpha_v\beta_6$-binding ligands are administered to a patient, the different $\alpha_v\beta_6$-binding ligands can be administered together in a single pharmaceutical composition, or, more preferably, can be administered sequentially in separate dosages. The effective amount of such other agents depends on the amount of $\alpha_v\beta_6$-binding ligand present in the formulation, the type of disease or disorder or treatment, and other factors.

The present invention also includes methods for treating cancerous, metastatic or in situ carcinoma conditions that comprise administering to a patient a first agent in conjunction with a second agent, wherein the first agent is a $\alpha_v\beta_6$-binding ligand and the second agent is an agent that is useful for treating one or more cancerous, metastatic or in situ carcinoma conditions but that is not necessarily a $\alpha_v\beta_6$-binding ligand. By administering a first agent "in conjunction with" a second agent is meant that the first agent can be administered to the patient prior to, simultaneously with, or after, administering the second agent to the patient, such that both agents are administered to the patient during the therapeutic regimen. For example, according to certain such embodiments of the invention, a $\alpha_v\beta_6$-binding ligand is administered to a patient in conjunction (i.e., before, simultaneously with, or after) administration of an antagonist of one or more other integrin receptors (e.g., $\alpha_1\beta_1$, $\alpha_4\beta_1$, $\alpha_v\beta_8$, $\alpha_v\beta_5$, $\alpha_5\beta_1$, etc.) to the patient, including antibodies, polypeptide antagonists and/or small molecule antagonists specific for one or more integrin receptors (e.g., $\alpha_1\beta_1$, $\alpha_4\beta_1$, $\alpha_v\beta_8$, $\alpha_v\beta_5$, $\alpha_5\beta_1$, etc.) which are known in the art.

In certain embodiments of this aspect of the invention, the second agent that is administered in conjunction with an $\alpha_v\beta_6$-binding ligand is, e.g., a steroid, a cytotoxic compound (including those described elsewhere herein), a radioisotope (including those described elsewhere herein), a prodrug-activating enzyme (including those described elsewhere herein), colchicine, oxygen, an antioxidant (e.g., N-acetylcysteine), a metal chelator (e.g., terathiomolybdate), IFN-β, IFN-γ, alpha-antitrypsin and the like. Additional second agents or compounds that can be administered to a patient in conjunction with one or more first agents, such as one or more $\alpha_v\beta_6$-binding ligands, for therapeutic purposes according to this aspect of the invention, will be familiar to those of ordinary skill in the art; the use of such additional second agents or compounds is therefore considered to be encompassed by the present invention.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Cloning of the mu3G9 Variable Regions

Total cellular RNA from 3G9 murine hybridoma cells was prepared using the Qiagen RNeasy mini kit following the manufacturer's recommended protocol. Complementary DNA encoding the variable regions of the heavy and light chains were cloned by RT-PCR from total cellular RNA using the Amersham/Pharmacia First Strand cDNA Synthesis kit following the manufacturer's recommended protocol using random hexamers for priming.

The primers used for PCR amplification of the murine 3G9 immunoglobulin heavy chain variable domain were:

```
                                    (SEQ ID NO: 8)
5' AGGTCTAGAAYCTCCACACACAGGRRCCAGTGGATAGAC 3';

                                    (SEQ ID NO: 9)
5' GGGGATATCCACCATGRACTTCGGGYTGAGCTKGGTTTT 3';

(S = C/G, M = A/C, R = A/G, K = G/T, W = A/T,

and Y = C/T).
```

The reaction consisted of an initial melt at 95° C. for 2.5 minutes followed by 10 cycles of melting at 94° C. for 30 seconds, annealing at 60° C. minus 1° C. per cycle for 45 seconds, and elongation at 68° C. for 1 minute using Clontech's Advantage Taq DNA polymerase. The reaction continued for an additional 10 cycles of melting at 94° C. for 30 seconds, annealing at 55° C. for 45 seconds, elongation at 68° C. for 1 minute and a final 9 minute elongation at 68° C. The reactions were purified using the Qiagen Qiaquick PCR purification kit following the manufacturer's protocol. The ends of the Advantage Taq amplified DNA were polished to generate blunt ends with T7 DNA polymerase in the presence of excess dNTP's. Purified and blunted 3G9 heavy chain variable region gene PCR products were subcloned into Invitrogen's pCR4Blunt-TOPO cloning vector using their TOPO cloning kit following the manufacturer's recommended protocol. The heavy chain RT-PCR subclones were designated pKJS062.

The 3G9 light chain variable domain gene was amplified with primers:

```
                                    (SEQ ID NO: 10)
5' GCGTCTAGAACTGGATGGTGGGAGATGGA 3';

                                    (SEQ ID NO: 11)
5' GGGGATATCCACCATGGATTTTCAGGTGCAGATTTTCAG 3'.
```

The reaction consisted of an initial melt at 95° C. for 2.5 minutes followed by 6 cycles of melting at 94° C. for 30 seconds, annealing at 60° C. minus 1° C. per cycle for 45 seconds, and elongation at 68° C. for 2 minutes using Clontech's Advantage Taq DNA polymerase. The reaction continued for an additional 24 cycles of melting at 94° C. for 30 seconds, annealing at 54° C. for 45 seconds, elongation at 68° C. for 2 minutes and a final 10 minute elongation at 68° C. One tenth of the reaction was the used as a template for a second round of amplification with Pfu DNA polymerase (Stratagene). That reaction consisted of an initial melt at 95°

C. for 2.5 minutes followed by 20 cycles of melting at 94° C. for 30 seconds, annealing at 55° C. for 45 seconds, and elongation at 72° C. for 1 minute. The reaction products were gel purified using the Qiagen Qiaquick gel extraction kit following the manufacturer's recommended protocol. Purified 3G9 light chain variable region gene PCR products were subcloned into Invitrogen's pCR4Blunt-TOPO cloning vector using their TOPO cloning kit. The light chain RT-PCR subclones were designated pKJS054.

Inserts from multiple independent subclones of both pKJS054 and pKJS062 were sequenced. In both cases, the insert sequences of multiple independent subclones were identical. Blast analyses of the variable domain sequences confirmed their immunoglobulin identity. The 3G9 heavy chain variable domain is a member of murine subgroup IIID. The 3G9 light chain variable region is a member of murine kappa subgroup IV.

Example 2

Construction and Expression of ch3G9 cDNAs encoding the murine 3G9 variable regions of the heavy and light chains were used to construct vectors for expression of murine-human chimeras (ch3G9) in which the mu3G9 variable regions were linked to human IgG1 and kappa constant regions.

For construction of the heavy chain chimera, the 508 bp EcoRI fragment from the 3G9 heavy chain variable domain plasmid pKJ062 was subcloned into the EcoRI site of the linearized dephosphorylated pUC-derived cloning vector pNN09. This step added flanking NotI sites in the resulting plasmid, pKJS093. The heavy chain sequence in plasmid pKJS093 was confirmed by DNA sequencing. A splice donor site followed immediately by a HindIII restriction site was added to plasmid pKJS093 just downstream of the variable region coding sequence by site directed mutagenesis with mutagenic oligonucleotides:

```
                                 (SEQ ID NO: 12)
5' CTGTCTCTGCAGGTAAGCTTACACCCCCATCTG 3',

                                 (SEQ ID NO: 13)
5' CAGATGGGGGTGTAAGCTTACCTGCAGAGACAG 3'
```

using Stratagene's Quickchange mutagenesis kit following the manufacturer's recommended protocol. This step generated plasmid pKJS116. The 0.48 kb NotI-HindIII heavy chain variable domain fragment from pKJS116 and the 1.22 kb HindIII-NotI fragment from the plasmid pEAG964, containing a human IgG1 constant region, were subcloned into the NotI site of the pCEP4 (Invitrogen) EBV expression vector-derived plasmid pCH269, producing plasmid pKJS136.

For construction of the light chain chimera, the 474 base pair EcoRI fragment from the 3G9 light chain variable domain plasmid pKJS054 was subcloned into the EcoRI site of the linearized dephosphorylated cloning vector pNN09 adding flanking NotI sites in the resulting plasmid, pKJS112. The light chain sequence in plasmid pKJS112 was confirmed by DNA sequencing. A BglII restriction site was added to plasmid pKJS112 immediately downstream of the variable region coding sequence by site directed mutagenesis with mutagenic oligonucleotides:

```
                                    (SEQ ID NO: 14)
5' GGCACCAAGCTGGAGATCTAACGGGCTGATGCTGC 3',

                                    (SEQ ID NO: 15)
5' GCAGCATCAGCCCGTTAGATCTCCAGCTTGGTGCC 3'
```

using Stratagene's Quickchange mutagenesis kit generating plasmid pKJS132. The 453 bp NotI-BglII light chain variable domain fragment from pKJS132 and the 678 bp BclI-NotI fragment from the plasmid pEAG963 containing a human kappa light chain constant domain, were subcloned into the NotI site of the pCEP4 (Invitrogen) EBV expression vector-derived plasmid pCH269, producing plasmid pKJS141. It was noted during the cloning of mu3G9 that the first CDR of the light chain contained a glycosylation signal sequence (NXT/S). A single round of Quickchange site directed mutagenesis with oligonucleotides:

```
                                    (SEQ ID NO: 16)
5' GGAACTTACACTTGAGCTGGCACTGCATGTCAAGG 3',

                                    (SEQ ID NO: 17)
5' CCTTGACATGCAGTGCCAGCTCAAGTGTAAGTTCC 3',
```

converting the NSS motif to SSS and creating the expression vector pKJS157, removed this glycosylation signal sequence. The light chain variable region sequence of pKJS157 was confirmed by DNA sequencing.

Expression vectors (light chain pKJS141 or pKJS157 and heavy chain pKJS136) were co-transfected into 293-EBNA cells and transfected cells were tested for antibody secretion and specificity. Empty vector transfected cells and cells co-transfected with EBV expression vectors for chM92 (a molecularly cloned CD154-specific mAb) served as controls. Antibody titer analysis, using the Pierce Easy Titer kit, following the manufacturer's recommended protocol, and Western blot analysis (developed with anti-human heavy and light chain antibodies) from conditioned medium indicated that ch3G9-transfected cells synthesized and efficiently assembled heavy and light chains and secreted antibody. An ELISA assay against $\alpha_v\beta_6$ demonstrated that ch3G9 bound to $\alpha_v\beta_6$ similarly to mu3G9 while chM92 did not.

As shown in FIG. 1, chimeric 3G9 (ch3G9; indicated by the triangular symbol) and an aglycosyl mutant form of the chimeric 3G9 containing a N to S substitution within an N-linked glycosylation site in the first CDR of the light chain (ch3G9S; indicated by the square symbol) produced from a large-scale transient transfections were purified and demonstrated similar binding to $\alpha_v\beta_6$ in an ELISA assay. The removal of the glycosylation site within the CDR1 of the light chain variable domain has been shown to improve protein expression and purification without altering or affecting the binding affinity of the antibody.

Example 3

Construction of the hu3G9 Versions 1, 2 & 3

Design of the reshaped variable domains to produce humanized 3G9 (hu3G9) was done as follows. The 3G9 light chain variable domain corresponds to human kappa 3, and the heavy chain variable domain to human heavy subgroup 3. The choice of the human acceptor frameworks was by homology matching to human germline sequences using the program IgBLAST: human L6 (with the J region derived from human JK4) for the light chain, and human 3-7 (with the J region derived from human JH4) for the heavy chain. Three versions of each of the variable light and heavy reshaped chains were designed, as shown in Table 1. The first version contains the most backmutations to the murine donor sequences, while the third version contains the fewest (i.e., the most "humanized").

The CDR regions of the heavy and light chain variable domains as shown in Table 1 below are being defined by the conventional Kabat numbering classification system. However, the numbering of the sequences are represented below based on the relative linear positioning of the different sequences with respect to each other.

TABLE 1

Heavy and Light Chain Sequences for hu3G9

Table 1a - Heavy Chain Sequences

| | | FR1 | CDR1 | FR2 | |
|---|---|---|---|---|---|
| Murine | (1) | EVMLVESGGGLVKPGGSLKLSCAASGFTFS | RYVMS | WVRQTPEKRLEWVA | |
| 3G9HV1 | (1) | EVMLVESGGGLVQPGGSLRLSCAASGFTFS | RYVMS | WVRQAPGKGLEWVA | |
| 3G9HV2 | (1) | EVQLVESGGGLVQPGGSLRLSCAASGFTFS | RYVMS | WVRQAPGKGLEWVA | |
| 3G9HV3 | (1) | EVQLVESGGGLVQPGGSLRLSCAASGFTFS | RYVMS | WVRQAPGKGLEWVA | |
| VH3-7 | (1) | EVQLVESGGGLVQPGGSLRLSCAASGFTFS | ----- | WVRQAPGKGLEWVA | |

| | | CDR2 | FR3 | |
|---|---|---|---|---|
| Murine | (50) | SISS-GGRMYYPDTVKG | RFTISRDSARNILYLQMSSLRSEDTAMYYCAR | (SEQ ID NO: 81) |
| 3G9HV1 | (50) | SISS-GGRMYYPDTVKG | RFTISRDSAKNSLYLQMNSLRAEDTAVYYCAR | (SEQ ID NO: 82) |
| 3G9HV2 | (50) | SISS-GGRMYYPDTVKG | RFTISRDSAKNSLYLQMNSLRAEDTAVYYCAR | (SEQ ID NO: 83) |
| 3G9HV3 | (50) | SISS-GGRMYYPDTVKG | RFTISRDNAKNSLYLQMNSLRAEDTAVYYCAR | (SEQ ID NO: 84) |
| VH3-7 | (50) | ----------------- | RFTISRDNAKNSLYLQMNSLRAEDTAVYYCAR | (SEQ ID NO: 85) |

Table 1b - Light Chain Sequences

| | | FR1 | CDR1 | FR2 |
|---|---|---|---|---|
| Murine | (1) | QIVLTQSPAIMSASPGEKVTLTC | SANSSVSSSYLY | WYQQKSGSSPKLWIY |
| 3G9LV1 | (1) | EIVLTQSPATLSLSPGERATLSC | SASSSVSSSYLY | WYQQKPGQAPRLWIY |
| 3G9LV2 | (1) | EIVLTQSPATLSLSPGERATLSC | SASSSVSSSYLY | WYQQKPGQAPRLWIY |
| 3G9LV3 | (1) | EIVLTQSPATLSLSPGERATLSC | SASSSVSSSYLY | WYQQKPGQAPRLWIY |
| 3G9LV4 | (1) | QIVLTQSPATLSLSPGERATLsc | SASSSVSSSYLY | WYQQKPGQAPRLWIY |
| 3G9LV5 | (1) | EIVLTQSPATLSLSPGERATLSC | SASSSVSSSYLY | WYQQKPGQAPRLLIY |
| L6 | (1) | EIVLTQSPATLSLSPGERATLSC | --S--------- | WYQQKPGQAPRLLIY |

| | | CDR2 | FR3 | CDR3 | |
|---|---|---|---|---|---|
| Murine | (51) | STSNLAS | GVPVRFSGSGSGTSFSLTISSMEAEDAASYFC | HQWSTYPPT | (SEQ ID NO: 86) |
| 3G9LV1 | (51) | STSNLAS | GVPVRFSGSGSGTDFTLTISSLEPEDFAVYFC | HQWSTYPPT | (SEQ ID NO: 87) |
| 3G9LV2 | (51) | STSNLAS | GVPARFSGSGSGTDFTLTISSLEPEDFAVYYC | HQWSTYPPT | (SEQ ID NO: 88) |
| 3G9LV3 | (51) | STSNLAS | GIPARFSGSGSGTDFTLTISSLEPEDFAVYYC | HQWSTYPPT | (SEQ ID NO: 89) |
| 3G9LV4 | (51) | STSNLAS | GIPARFSGSGSGTDFTLTISSLEPEDFAVYYC | HQWSTYPPT | (SEQ ID NO: 90) |
| 3G9LV5 | (51) | STSNLAS | GIPARFSGSGSGTDFTLTISSLEPEDFAVYYC | HQWSTYPPT | (SEQ ID NO: 91) |
| L6 | (50) | ------- | GIPARFSGSGSGTDFTLTISSLEPEDFAVYYC | --------- | (SEQ ID NO: 92) |

Versions 1 and 2 of the hu3G9 heavy chain and versions 1, 2, and 3 of the light chain were made synthetically by ligating a combination of phosphorylated top-strand oligonucleotides, held in juxtaposition by short bottom-strand oligonucleotides, with Taq DNA ligase (New England Biolabs). The reactions were incubated through 15 cycles of 1 minute at 94° C., 1 minute at 55° C.-1° C. per cycle and 65° C. for 4 minutes generating single stranded template DNA's including 5' restriction sites (NotI and BamHI), signal sequences, the variable regions, and extending up to (light chain) or into (heavy chain) the constant domains to the first potential unique restriction site (BsiWI for the light chain and AgeI for the heavy chain). The primers for the synthetic genes are described below. The gene templates were amplified by PCR with Pfu DNA polymerase (Stratagene) using oligos:

```
5' GCTGACAGCGGCCGCGGGATCCAC 3',      (SEQ ID NO: 18)
and

5' GCTCACGGTCACCGGTTCGGGG 3'         (SEQ ID NO: 19)
for the heavy chain
and

5' GCTGACAGCGGCCGCGGGATCCAC 3'       (SEQ ID NO: 20)
and
```

-continued

```
5' GGAAGATGAACACACTGGGTGCGG 3'       (SEQ ID NO: 21)
for the light chain
```

to generate double stranded DNA's. The reactions consisted of an initial melt at 95° C. for 2.5 minutes followed by 16 cycles of melting at 94° C. for 30 seconds, annealing at 64° C. for 30 seconds, and elongation at 72° C. for 1 minute. The reaction products were gel purified using the Qiagen Qiaquick get extraction kit following the manufacturer's recommended protocol.

Version 1 of the heavy chain was created synthetically from the following top strand 5' phosphorylated oligonucleotides:

```
                                                (SEQ ID NO: 22)
5'GCTGACAGCGGCCGCGGGATCCACCATGGACTTCGGCCTGAGCTGGGT

GTTCCTGGTGCTGGTGCTGAAGGGCGTGCAGTGCGAGGTGATGCTGGTGG

AGAGCGGCGGC 3',

                                                (SEQ ID NO: 23)
5'GGCCTGGTGCAGCCCGGCGGCAGCCTGAGGCTGAGCTGCGCCGCCAGC

GGCTTCACCTTCAGCCGCTACGTGATGAGCTGGGTGCGCCAGGCCCCCGG

CAAGGGCCTGGAGTGGGTGGCCAG 3',

                                                (SEQ ID NO: 24)
5'CATCAGCAGCGGAGGCCGCATGTACTACCCCGACACCGTGAAGGGCCG

CTTCACCATCAGCCGCGACAGCGCCAAGAACAGCCTGTACCTGCAGATGA

ACAGCCTGCGCGCCGAGGAC 3',
```

-continued (SEQ ID NO: 25)
5'ACCGCCGTGTACTACTGCGCCCGCGGCAGCATCTACGACGGCTACTAC
GTGTTCCCCTACTGGGGCCAGGGCACCCTGGTGACCGTGAGCTCCGCCAG
CACC 3', (SEQ ID NO: 26)
5'AAGGGCCCCAGCGTGTTCCCCCTGGCCCCCAGCAGCAAGAGCACCAGC
GGCGGCACCGCCGCCCTGGGCTGCCTGGTGAAGGACTACTTCCCCGAACC
GGTGACCGTGAGC 3'.

These oligos were held in juxtaposition by the following bottom strand non-phosphorylated oligonucleotides that overlap the juxtaposed top strand oligonucleotides by roughly 15 bp. The bottom strand oligonucleotides are:

(SEQ ID NO: 27)
5'GCTGCACCAGGCCGCCGCCGCTCTCC 3", (SEQ ID NO: 28)
5'CCGCTGCTGATGCTGGCCACCCAC 3", (SEQ ID NO: 29)
5'GCAGTAGTACACGGCGGTGTCCTCGGCGCG 3", (SEQ ID NO: 30)
5'GCTGGGGCCCTTGGTGCTGGCGG 3".

Version 2 of the heavy chain was created synthetically from the following top strand 5' phosphorylated oligonucleotides:

(SEQ ID NO: 31)
5'GCTGACAGCGGCCGCGGGATCCACCATGGACTTCGGCCTGAGCTGGGT
GTTCCTGGTGCTGGTGCTGAAGGGCGTGCAGTGCGAGGTGCAGCTGGTGG
AGAGCGGCGGC 3'

(SEQ ID NO: 32)
5'GGCCTGGTGCAGCCCGGCGGCAGCCTGAGGCTGAGCTGCGCCGCCAGC
GGCTTCACCTTCAGCCGCTACGTGATGAGCTGGGTGCGCCAGGCCCCCGG
CAAGGGCCTGGAGTGGGTGGCCAG 3', (SEQ ID NO: 33)
5'CATCAGCAGCGGAGGCCGCATGTACTACCCCGACACCGTGAAGGGCCG
CTTCACCATCAGCCGCGACAGCGCCAAGAACAGCCTGTACCTGCAGATGA
ACAGCCTGCGCGCCGAGGAC 3', (SEQ ID NO: 34)
5'ACCGCCGTGTACTACTGCGCCCGCGGCAGCATCTACGACGGCTACTAC
GTGTTCCCCTACTGGGGCCAGGGCACCCTGGTGACCGTGAGCTCCGCCAG
CACC 3', (SEQ ID NO: 35)
5'AAGGGCCCCAGCGTGTTCCCCCTGGCCCCCAGCAGCAAGAGCACCAGC
GGCGGCACCGCCGCCCTGGGCTGCCTGGTGAAGGACTACTTCCCCGAACC
GGTGACCGTGAGC 3'.

These oligos were held in juxtaposition by the following bottom strand non-phosphorylated oligonucleotides that overlap the juxtaposed top strand oligonucleotides by roughly 15 bp. The bottom strand oligonucleotides are:

(SEQ ID NO: 36)
5'GCTGCACCAGGCCGCCGCCGCTCTCC 3",

-continued (SEQ ID NO: 37)
5'CCGCTGCTGATGCTGGCCACCCAC 3", (SEQ ID NO: 38)
5"GCAGTAGTACACGGCGGTGTCCTCGGCGCG 3", (SEQ ID NO: 39)
5'GCTGGGGCCCTTGGTGCTGGCGG 3".

Expression vectors for versions 1 and 2 of hu3G9 heavy chains were made by subcloning the 538 bp NotI-AgeI heavy chain variable domain fragments, including the first 105 bp of the human IgG1 constant region, from the synthetically generated humanization variants and the 919 bp AgeI/BamHI fragment from the plasmid pKJS160, containing the remainder of the human IgG1 constant region, into NotI/BamHI digested pKJS160 (identical to pCEP4 (Invitrogen) derived EBV expression vector pCH269) producing heavy chain expression vectors pKJS166 (version 1) and pKJS167 (version 2).

Version 3 of the heavy chain was created by performing a single round of Quickchange site directed mutagenesis on plasmid pKJS167 with oligonucleotides:
5'CCATCAGCCGCGACAACGCCAAGAACAGCCTG 3' (SEQ ID NO: 40), and
5'CAGGCTGTTCTTGGCGTTGTCGCGGCTGATGG 3' (SEQ ID NO: 41).
The resultant version 3 heavy chain plasmid was designated pKJS168. The variable region cDNA sequences in the resultant plasmids were confirmed by DNA sequencing.

Version 1 of the light chain was created synthetically from the following top strand 5' phosphorylated oligonucleotides:

(SEQ ID NO: 42)
5'GCTGACAGCGGCCGCGGGATCCACCATGGACTTCCAGGTGCAGATCTT
CAGCTTCCTGCTGATCAGCGTGAGCGTGATCATGAGCCGCGGCGAGATCG
TGCTGACC 3', (SEQ ID NO: 43)
5'CAGAGCCCCGCCACCCTGAGCCTGAGCCCCGGCGAGAGGGCCACCCTG
AGCTGCAGCGCCAGCAGCAGCGTGAGCAGCAGCTACCTGTACTGGTACCA
GCAGAAGCCCGGCCAGGCC 3', (SEQ ID NO: 44)
5'CCCAGGCTGTGGATCTACAGCACCAGCAACCTGGCCAGCGGCGTGCCC
GTGCGCTTCAGCGGCAGCGGCAGCGGCACCGACTTCACCCTGACCATCAG
CAGCCTGGAGCCCGAGGAC 3', (SEQ ID NO: 45)
5'TTCGCCGTGTACTTCTGCCACCAGTGGAGCACCTACCCCCCCACCTTC
GGCGGCGGCACCAAGGTGGAGATCAAGCGTACGGTGGCCGCACCCAGTGT
GTTCATCTTCC 3'.

These oligos were held in juxtaposition by the following bottom strand non-phosphorylated oligonucleotides that overlap the juxtaposed top strand oligonucleotides by roughly 15 bp. The bottom strand oligonucleotides are:

(SEQ ID NO: 46)
5'GCGGGGCTCTGGGTCAGCACGATC 3", (SEQ ID NO: 47)
5'CCACAGCCTGGGGGCCTGGCCG 3", (SEQ ID NO: 48)
5'GTACACGGCGAAGTCCTCGGGCTC 3".

Version 2 of the light chain was created synthetically from the following top strand 5' phosphorylated oligonucleotides:

(SEQ ID NO: 49)
5'GCTGACAGCGGCCGCGGGATCCACCATGGACTTCCAGGTGCAGATCTT
CAGCTTCCTGCTGATCAGCGTGAGCGTGATCATGAGCCGCGGCGAGATCG
TGCTGACC 3', (SEQ ID NO: 50)
5'CAGAGCCCCGCCACCCTGAGCCTGAGCCCCGGCGAGAGGGCCACCCTG
AGCTGCAGCGCGAGCAGCAGCGTGAGCAGCAGCTACCTGTACTGGTACCA
GCAGAAGCCCGGCCAGGCC 3', (SEQ ID NO: 51)
5'CCCAGGCTGTGGATCTACAGCACCAGCAACCTGGCCAGCGGCGTGCCC
GCCCGCTTCAGCGGCAGCGGCAGCGGCACCGACTTCACCCTGACCATCAG
CAGCGTGGAGCCCGAGGAC 3', (SEQ ID NO: 52)
5'TTCGCCGTGTACTACTGCCACCAGTGGAGCACCTACCCCCCCACCTTC
GGCGGCGGCACCAAGGTGGAGATCAAGCGTACGGTGGCCGCACCCAGTGT
GTTCATCTTCC 3'.

These oligos were held in juxtaposition by the following bottom strand non-phosphorylated oligonucleotides that overlap the juxtaposed top strand oligonucleotides by roughly 15 bp. The bottom strand oligonucleotides are:

5'GCGGGGCTCTGGGTCAGCACGATC 3", (SEQ ID NO: 53)

5'CCACAGCCTGGGGGCCTGGCCG 3", (SEQ ID NO: 54)

5'GTACACGGCGAAGTCCTCGGGCTC 3". (SEQ ID NO: 55)

Version 3 of the light chain was created synthetically from the following top strand 5' phosphorylated oligonucleotides:

(SEQ ID NO: 56)
5'GCTGACAGCGGCCGCGGGATCCACCATGGACTTCCAGGTGCAGATCTT
CAGCTTCCTGCTATCAGCGTGAGCGTGATCATGAGCCGCGGCGAGATCGT
GCTGACC 3'

(SEQ ID NO: 57)
5'CAGAGCCCCGCCACCCTGAGCCTGAGCCCCGGCGAGAGGGCCACCCTG
AGCTGCAGCGCCAGCAGCAGGGTGAGCAGCAGCTACCTGTACTGGTACCA
GCAGAAGCCCGGCCAGGCC 3', (SEQ ID NO: 58)
5'CCCAGGCTGTGGATCTACAGCACCAGCAACCTGGCCAGCGGCATCCCC
GCCCGCTTCAGCGGCAGCGGCAGCGGCACCGACTTCACCCTGACCATCAG
CAGCGTGGAGCCCGAGGAC 3', (SEQ ID NO: 59)
5'TTCGCCGTGTACTACTGCCACGAGTGGAGCACCTACCCCCCCACCTTC
GGCGGCGGCACCAAGGTGGAGATCAAGCGTACGGTGGCCGCACCCAGTGT
GTTCATCTTCC 3'.

These oligos were held in juxtaposition by the following bottom strand non-phosphorylated oligonucleotides that overlap the juxtaposed top strand oligonucleotides by roughly 15 bp. The bottom strand oligonucleotides are:

5'GCGGGGCTCTGGGTCAGCACGATC 3", (SEQ ID NO: 60)

5'CCACAGCCTGGGGGCCTGGCCG 3", (SEQ ID NO: 61)

5'GTACACGGCGAAGTCCTCGGGCTC 3". (SEQ ID NO: 62)

Expression vectors for versions 1, 2 and 3 of hu3G9 light chains were made by subcloning the 400 bp NotI/BsiWI light chain variable domain fragments from the synthetically generated humanization variants and the 324 bp BsiWI/BamHI fragment from pKJS162, containing the human immunoglobulin kappa constant region, into NotI/BamHI digested pKJS161 (also identical to the pCEP4 (Invitrogen) derived EBV expression vector pCH269). The resultant plasmids were designated pKJS172 (version 1), pKJS173 (version 2), and pKJS174 (version 3).

Example 4

Expression of the hu3G9 Versions 1, 2 & 3 and Construction of Versions 4 and 5

All possible combinations of humanized and chimeric heavy and light chain expression vectors were co-transfected into 293-EBNA cells (16 combinations). Transfected cells were tested for antibody secretion and specificity. Western blot analysis (detection with anti-human heavy and light chain antibodies) and Easy Titer (Pierce) analysis of conditioned medium indicated that hu3G9-transfected cells synthesized and efficiently secreted heavy and light chains and that the levels of expression appeared to increase with increasing antibody humanization. As displayed in FIG. 2, variants containing version 1 of the light chain were poorly expressed while variants containing version 2 of the light chain are expressed at higher levels, suggesting that increasing humanization tends to lead to higher expression.

FACS analysis of $\alpha_v\beta_6$ expressing SW480 cells stained with conditioned medium from transfected cells indicated that humanization of the 3G9 heavy chain had no negative impact on the antibody's ability to bind to $\alpha_v\beta_6$ expressing cells, with version 3 of the heavy chain (CDR grafted version) having increasing binding activity as compared to versions 1 and 2 (FIG. 3). FACS analysis also demonstrated that hu3G9 mAb variants containing version 3 of the light chain bound slightly less well than variants containing hu3G9 light chain version 2 although both versions appeared to bind at least as well as chimeric 3G9 (FIG. 3). There are only 2 and 1 amino acid differences between light chains version 2 and 3 respectively, and CDR grafted 3G9. Since these versions of the light chain had similar binding activity to $\alpha_v\beta_6$ as chimeric 3G9, two additional versions were created to determine if binding activity could be improved or if a CDR grafted version would be functional.

Version 4 explored the effects of the glutamine to glutamic acid substitution at position 1 of the light chain and version 5 is a completely CDR grafted 3G9 light chain (Table 1). To examine the individual contributions of each of these changes, new light chain expression vectors were constructed. Plasmid pKJS186, the E1Q variant of version 3 light chain, was made by site directed mutagenesis of plasmid pKJS174 with oligonucleotides:

(SEQ ID NO: 63)
5'GTCAGCACGATCTGGCCGCGGCTCATGATC 3'
and (SEQ ID NO: 64)
5'GATCATGAGCCGCGGCCAGATCGTGCTGAC 3' using Stratagene's Quickchange mutagenesis kit and is designated light chain version 4. Plasmid pKJS188, the CDR grafted 3G9 light chain, was made by site directed mutagenesis of plasmid pKJS174 with oligonucleotides:

```
5'CCCAGGCTGCTGATCTACAGCACC 3'    (SEQ ID NO: 65)
and

5'GGTGCTGTAGATCAGCAGCCTGGG 3'    (SEQ ID NO: 66)
```

and is designated light chain version 5. These versions of the light chain were sequence confirmed and then co-transfected into 293-EBNA cells with heavy chain versions 2 or 3. FACS analysis indicated that heavy chain version 3 and light chain version 5, the completely CDR grafted pair, bound to $\alpha_v\beta_6$ expressing cells equal to or better than any other humanized variant pair (FIG. 4). The pKJS168 and pKJS188 pairing was designated hu3G9 version 5 (H3/L5).

Co-transfections of 293-EBNA cells with ch3G9 and hu3G9 versions 2-5 were scaled up and conditioned medium was harvested. Antibody was purified on Protein A-Sepharose and purified mAbs were assayed for activity. Binding to $\alpha_v\beta_6$ was determined by, FACS analysis on the cell-line FDCP1-β6 (FIG. 5), ELISA (FIG. 6), and blocking of biotinylated $\alpha_v\beta_6$ to LAP (FIG. 7). Rank ordering of binding activity was version 5 (H3/L5)>version 3 (H3/L3) =ch3G9=version 2 (H2/L2). Blocking ($\alpha_v\beta_6$-mediated FDCP1-β6 cell-adhesion to LAP is shown in FIG. 8. Rank ordering of bioactivity was ch3G9=version 5 (H3/L5)=version 2 (H2/L2)>version 3 (H3/L3). Because version 5 was more humanized than version 2, it was selected for the generation of a stable CHO cell line.

The DNA and corresponding protein sequences of the different versions of hu3G9 heavy (versions 1, 2, 3 and 5) and light (versions 1-5) variable domains are shown in Table 2. For the heavy chain variable domains, the sequences comprise:

(a) a human FR1 derived from the FR1 of VH3-7;
(b) the murine 3G9 CDR1 heavy chain sequence;
(c) a human FR2 derived from the FR2 of VH3-7;
(d) the murine 3G9 CDR2 heavy chain sequence;
(e) a human FR3 derived from the FR3 of VH3-7;
(f) the murine 3G9 CDR3 heavy chain sequence; and
(g) a human FR4 derived from a consensus framework sequence present in a large majority of human antibodies with the following sequence: WGQGTLVTVSS. (SEQ ID NO: 151)

For the light chain variable domains, the sequences comprise:

(a) a human FR1 derived from the FR1 of L6;
(b) the murine 3G9 CDR1 light chain sequence with an asparagine (N) to serine (S) amino acid substitution;
(c) a human FR2 derived from the FR2 of L6;
(d) the murine 3G9 CDR2 light chain sequence;
(e) a human FR3 derived from the FR3 of L6;
(f) the murine 3G9 CDR3 light chain sequence; and
(g) a human FR4 derived from a consensus framework sequence present in a large majority of human antibodies with the following sequence: FGGGTKVEIK (SEQ ID NO: 152).

TABLE 2

Heavy and Light Chain Sequences of hu3G9 Variable Domains

```
hu3G9 version 1 light chain (SEQ ID NOS: 67 and 139)
  1 GAGATCGTGCTGACCCAGAGCCCCGCCACCCTGAGCCTGAGCCCCGGCGAGAGGGCCACC
     E  I  V  L  T  Q  S  P  A  T  L  S  L  S  P  G  E  R  A  T
 61 CTGAGCTGCAGCGCCAGCAGCAGCGTGAGCAGCAGCTACCTGTACTGGTACCAGCAGAAG
     L  S  C  S  A  S  S  S  V  S  S  S  Y  L  Y  W  Y  Q  Q  K
121 CCCGGCCAGGCCCCCAGGCTGTGGATCTACAGCACCAGCAACCTGGCCAGCGGCGTGCCC
     P  G  Q  A  P  R  L  W  I  Y  S  T  S  N  L  A  S  G  V  P
181 GTGCGCTTCAGCGGCAGCGGCAGCGGCACCGACTTCACCCTGACCATCAGCAGCCTGGAG
     V  R  F  S  G  S  G  S  G  T  D  F  T  L  T  I  S  S  L  E
241 CCCGAGGACTTCGCCGTGTACTTCTGCCACCAGTGGAGCACCTACCCCCCCACCTTCGGC
     P  E  D  F  A  V  Y  F  C  H  Q  W  S  T  Y  P  P  T  F  G
301 GGCGGCACCAAGGTGGAGATCAAG
     G  G  T  K  V  E  I  K

hu3G9 version 2 light chain (SEQ ID NOS: 68 and 140)
  1 GAGATCGTGCTGACCCAGAGCCCCGCCACCCTGAGCCTGAGCCCCGGCGAGAGGGCCACC
     E  I  V  L  T  Q  S  P  A  T  L  S  L  S  P  G  E  R  A  T
 61 CTGAGCTGCAGCGCCAGCAGCAGCGTGAGCAGCAGCTACCTGTACTGGTACCAGCAGAAG
     L  S  C  S  A  S  S  S  V  S  S  S  Y  L  Y  W  Y  Q  Q  K
121 CCCGGCCAGGCCCCCAGGCTGTGGATCTACAGCACCAGCAACCTGGCCAGCGGCGTGCCC
     P  G  Q  A  P  R  L  W  I  Y  S  T  S  N  L  A  S  G  V  P
181 GCCCGCTTCAGCGGCAGCGGCAGCGGCACCGACTTCACCCTGACCATCAGCAGCCTGGAG
     A  R  F  S  G  S  G  S  G  T  D  F  T  L  T  I  S  S  L  E
241 CCCGAGGACTTCGCCGTGTACTACTGCCACCAGTGGAGCACCTACCCCCCCACCTTCGGC
     P  E  D  F  A  V  Y  Y  C  H  Q  W  S  T  Y  P  P  T  F  G
301 GGCGGCACCAAGGTGGAGATCAAG
     G  G  T  K  V  E  I  K

hu3G9 version 3 light chain (SEQ ID NOS: 69 and 141)
  1 GAGATCGTGCTGACCCAGAGCCCCGCCACCCTGAGCCTGAGCCCCGGCGAGAGGGCCACC
     E  I  V  L  T  Q  S  P  A  T  L  S  L  S  P  G  E  R  A  T
 61 CTGAGCTGCAGCGCCAGCAGCAGCGTGAGCAGCAGCTACCTGTACTGGTACCAGCAGAAG
     L  S  C  S  A  S  S  S  V  S  S  S  Y  L  Y  W  Y  Q  Q  K
121 CCCGGCCAGGCCCCCAGGCTGTGGATCTACAGCACCAGCAACCTGGCCAGCGGCATCCCC
     P  G  Q  A  P  R  L  W  I  Y  S  T  S  N  L  A  S  G  I  P
181 GCCCGCTTCAGCGGCAGCGGCAGCGGCACCGACTTCACCCTGACCATCAGCAGCCTGGAG
     A  R  F  S  G  S  G  S  G  T  D  F  T  L  T  I  S  S  L  E
241 CCCGAGGACTTCGCCGTGTACTACTGCCACCAGTGGAGCACCTACCCCCCCACCTTCGGC
     P  E  D  F  A  V  Y  Y  C  H  Q  W  S  T  Y  P  P  T  F  G
301 GGCGGCACCAAGGTGGAGATCAAG
     G  G  T  K  V  E  I  K
```

TABLE 2-continued

Heavy and Light Chain Sequences of hu3G9 Variable Domains hu3G9 version 4 light chain (SEQ ID NOS: 70 and 142)
1 CAGATCGTGCTGACCCAGAGCCCCGCCACCCTGAGCCTGAGCCCCGGCGAGAGGGCCACC
Q I V L T Q S P A T L S L S P G E R A T
61 CTGAGCTGCAGCGCCAGCAGCAGCGTGAGCAGCAGCTACCTGTACTGGTACCAGCAGAAG
L S C S A S S S V S S S Y L Y W Y Q Q K
121 CCCGGCCAGGCCCCCAGGCTGTGGATCTACAGCACCAGCAACCTGGCCAGCGGCATCCCC
P G Q A P R L W I Y S T S N L A S G I P
181 GCCCGCTTCAGCGGCAGCGGCAGCGGCACCGACTTCACCCTGACCATCAGCAGCCTGGAG
A R F S G S G S G T D F T L T I S S L E
241 CCCGAGGACTTCGCCGTGTACTACTGCCACCAGTGGAGCACCTACCCCCCCACCTTCGGC
P E D F A V Y Y C H Q W S T Y P P T F G
301 GGCGGCACCAAGGTGGAGATCAAG
G G T K V E I K hu3G9 version 5 light chain (SEQ ID NOS: 71 and 143)
1 GAGATCGTGCTGACCCAGAGCCCCGCCACCCTGAGCCTGAGCCCCGGCGAGAGGGCCACC
E I V L T Q S P A T L S L S P G E R A T
61 CTGAGCTGCAGCGCCAGCAGCAGCGTGAGCAGCAGCTACCTGTACTGGTACCAGCAGAAG
L S C S A S S S V S S S Y L Y W Y Q Q K
121 CCCGGCCAGGCCCCCAGGCTGCTGATCTACAGCACCAGCAACCTGGCCAGCGGCATCCCC
P G Q A P R L L I Y S T S N L A S G I P
181 GCCCGCTTCAGCGGCAGCGGCAGCGGCACCGACTTCACCCTGACCATCAGCAGCCTGGAG
A R F S G S G S G T D F T L T I S S L E
241 CCCGAGGACTTCGCCGTGTACTACTGCCACCAGTGGAGCACCTACCCCCCCACCTTCGGC
P E D F A V Y Y C H Q W S T Y P P T F G
301 GGCGGCACCAAGGTGGAGATCAAG
G G T K V E I K hu3G9 version 1 heavy chain (SEQ ID NOS: 72 and 144)
1 GAGGTGATGCTGGTGGAGAGCGGCGGCGGCCTGGTGCAGCCCGGCGGCAGCCTGAGGCTG
E V M L V E S G G G L V Q P G G S L R L
61 AGCTGCGCCGCCAGCGGCTTCACCTTCAGCCGCTACGTGATGAGCTGGGTGCGCCAGGCC
S C A A S G F T F S R Y V M S W V R Q A
121 CCCGGCAAGGGCCTGGAGTGGGTGGCCAGCATCAGCAGCGGAGGCCGCATGTACTACCCC
P G K G L E W V A S I S S G G R M Y Y P
181 GACACCGTGAAGGGCCGCTTCACCATCAGCCGCGACAGCGCCAAGAACAGCCTGTACCTG
D T V K G R F T I S R D S A K N S L Y L
241 CAGATGAACAGCCTGCGCGCCGAGGACACCGCCGTGTACTACTGCGCCCGCGGCAGCATC
Q M N S L R A E D T A V Y Y C A R G S I
301 TACGACGGCTACTACGTGTTCCCCTACTGGGGCCAGGGCACCCTGGTGACCGTGAGCTCC
Y D G Y Y V F P Y W G Q G T L V T V S S hu3G9 version 2 heavy chain (SEQ ID NOS: 73 and 145)
1 GAGGTGCAGCTGGTGGAGAGCGGCGGCGGCCTGGTGCAGCCCGGCGGCAGCCTGAGGCTG
E V Q L V E S G G G L V Q P G G S L R L
61 AGCTGCGCCGCCAGCGGCTTCACCTTCAGCCGCTACGTGATGAGCTGGGTGCGCCAGGCC
S C A A S G F T F S R Y V M S W V R Q A
121 CCCGGCAAGGGCCTGGAGTGGGTGGCCAGCATCAGCAGCGGAGGCCGCATGTACTACCCC
P G K G L E W V A S I S S G G R M Y Y P
181 GACACCGTGAAGGGCCGCTTCACCATCAGCCGCGACAGCGCCAAGAACAGCCTGTACCTG
D T V K G R F T I S R D S A K N S L Y L
241 CAGATGAACAGCCTGCGCGCCGAGGACACCGCCGTGTACTACTGCGCCCGCGGCAGCATC
Q M N S L R A E D T A V Y Y C A R G S I
301 TACGACGGCTACTACGTGTTCCCCTACTGGGGCCAGGGCACCCTGGTGACCGTGAGCTCC
Y D G Y Y V F P Y W G Q G T L V T V S S hu3G9 versions 3 and 5 heavy chain (SEQ ID NOS: 74 and 146)
1 GAGGTGCAGCTGGTGGAGAGCGGCGGCGGCCTGGTGCAGCCCGGCGGCAGCCTGAGGCTG
E V Q L V E S G G G L V Q P G G S L R L
61 AGCTGCGCCGCCAGCGGCTTCACCTTCAGCCGCTACGTGATGAGCTGGGTGCGCCAGGCC
S C A A S G F T F S R Y V M S W V R Q A
121 CCCGGCAAGGGCCTGGAGTGGGTGGCCAGCATCAGCAGCGGAGGCCGCATGTACTACCCC
P G K G L E W V A S I S S G G R M Y Y P
181 GACACCGTGAAGGGCCGCTTCACCATCAGCCGCGACAACGCCAAGAACAGCCTGTACCTG
D T V K G R F T I S R D N A K N S L Y L
241 CAGATGAACAGCCTGCGCGCCGAGGACACCGCCGTGTACTACTGCGCCCGCGGCAGCATC
Q M N S L R A E D T A V Y Y C A R G S I
301 TACGACGGCTACTACGTGTTCCCCTACTGGGGCCAGGGCACCCTGGTGACCGTGAGCTCC
Y D G Y Y V F P Y W G Q G T L V T V S S Example 5

Construction of Stable CHO Expression Vectors for Wild-Type and Aglycosyl-hu3G9 Version 5

The EBV vectors described above contain extraneous 5' and 3' UTRs that are undesirable. Stable CHO expression vectors were created for hu-3G9 heavy chain version 3 and light chain version 5 (H3/L5), collectively termed version 5, in which the extraneous sequences were removed. Additionally, an aglycosyl heavy chain vector was created to remove potential interactions between the expressed 3G9 antibody and Fc gamma receptors.

The light chain stable CHO expression vector was created by ligating the 723 base pair BamH1 fragment of pKJS188 into the 6188 base pair neo-containing BamH1 digested vector fragment of pKJS77 (PDM-64-02-13) generating plasmid pKJS195, as displayed in FIG. 9.

The heavy chain stable CHO expression vector was created by initially ligating the 1449 base pair BamH1 fragment from pKJS168 into the 6051 base pair BamH1 digested vector fragment of pKJS078 (PDM-64-02-13) to remove the NotI restriction sites flanking the heavy chain coding sequence and generating pKJS171. To genetically remove the C-terminal lysine residue from the heavy chain encoded by pKJS171, the 2190 base pair BsrG1 to Xba1 fragment of pKJS171 was replaced with the 2187 base pair BsrG1 to Xba1 fragment of pKJS078 (PDM-64-02-13) generating pKJS189. Plasmid pKJS189 represents the dhfr-containing wild type hu-3G9 stable CHO expression vector, as displayed in FIG. 10. To generate the aglycosyl form of the heavy chain, the 587 base pair Age1/BsrG1 fragment of pKJS189 was replaced with the 587 base pair Age1/BsrG1 fragment from pCR076 generating pKJS196. This vector represents the dhfr-containing aglycosyl hu-3G9 stable CHO expression vector, containing a N319Q substitution that removes a glycosylation signal required for normal Fc receptor binding, as displayed in FIG. 11.

The DNA sequences of the BamHI cDNA inserts in pKJS189, pKJS196, and pKJS195 were confirmed. Expression vectors were co-transfected into CHO cells and transfected cells were tested for antibody secretion. The Easy-Titer (Pierce) human antibody detection assay of conditioned medium indicated that transfected cells synthesized and efficiently secreted heavy and light chains from the CHO expression vectors, as displayed in FIG. 12.

Thus, there are two potential glycosylation sites that can be modified in the hu-3G9 antibody without affecting the binding affinity of the antibody: (1) in the hu-3G9 light chain variable domains within the CDR1 region at amino acid residue 26 of SEQ ID NO:2 where an asparagine (N) to serine (S) substitution removes a glycosylation site which improves protein expression and purification (this site is modified in all five versions of the light chain variable domain sequences); and (2) in the hu-3G9 heavy chain version 3 constant region wherein an asparagine (N) to glutamine (Q) substitution removes a glycosylation site required for Fc receptor binding.

Example 6

CHO Cell Lines Expressing hu3G9 Version 5

Expression plasmids pKJS189, pKJS196 and pKJS195 for hu3G9 version 5 were transfected into CHO cells. Expression of hu3G9 version 5 (H3/L5) and aglycosylated hu3G9 version 5 (a-H3/L5) was observed from transfected cells with antibody secretion displaying binding specificity for $\alpha_v\beta_6$.

Example 7

Humanization Design of the 8G6 Anti-$\alpha_v\beta_6$ Antibody

In the design of humanized antibodies, the complementarity determining regions (CDRs) contain the residues most likely to bind antigen and must be retained in the reshaped antibody. CDRs are defined by sequence according to Kabat et al., Sequences of Proteins of Immunological Interest. 5th Edition, U.S. Dept. Health and Human Services, U.S. Govt. Printing Office (1991). CDRs fall into canonical classes (Chothia et al., *Nature,* 342:877-883 (1989)) where key residues determine to a large extent the structural conformation of the CDR loop. These residues are almost always retained in the reshaped antibody. The CDRs of the heavy and light chain were classified into canonical classes as follows:

| Light Chain: | | Heavy Chain: | |
|---|---|---|---|
| L1: 15 residues | Class 4 | H1: 5 residues | Class 1 |
| L2: 7 residues | Class 1 | H2: 17 residues | Class 2 |
| L3: 9 residues | Class 1 | H3: 17 residues | No canonical class |

The canonical residues important for these classes are indicated in Table 3. All canonical residues are as described by the rules. There are no canonical classes for loop H3.

TABLE 3

| | | |
|---|---|---|
| L1 | Class 4 | 2(I) 25(A) 29(V) 33(M) 71(F) |
| L2 | Class 1 | 48(I) 51(A) 52(S) 64(G) |
| L3 | Class 1 | 90(H) 95(P) |
| H1 | Class 1 | 24(G) 26(S) 27(Y) 29(F) 34(M) 94(R) |
| H2 | Class 2 | 52a(T) 55(G) 71(V) |
| H3 | No Canonical Class | |

The variable light and heavy chains were compared with the consensus sequences for mouse and human subgroups (Kabat et al., 1991) using the program FASTA.

The 8G6 variable light chain is a member of mouse subgroup Kappa 3 with an 81.250% identity in 112 amino acid overlap and the 8G6 variable heavy chain is a member of mouse subgroup 2a with a 71.318% identity in 129 aa overlap. The 8G6 variable light chain corresponds to human subgroup Kappa 4 with a 65.487% identity in 113 aa overlap. The 8G6 variable heavy chain corresponds to human subgroup 1 with a 58.955% identity in 134 aa overlap. The VH/VL packing interface residues are conserved, except for an unusual F at amino acid position 50 in the light chain (of SEQ ID NO: 4) and unusual L at amino acid position 39 in the heavy chain (of SEQ ID NO: 3).

Modeling of the structure of the variable regions was performed as follows. The light and heavy chains were aligned against a local copy of the most recent PDB database to determine structural frames to be used to construct three dimensional models of the light and heavy chains. Using FASTA, the 8G6 light chain was found to have 90.991% sequence identity in 111 aa overlap to murine N10 Fab (1NSN; 2.9 Å resolution). The 8G6 heavy chain was found to have 80.952% sequence identity in 126 amino acid overlap to murine JEL42 Fab (2JEL; 2.5 Å resolution). Full structural template was obtained by combining the heavy chain of 2JEL and light chain of 1NSN. Using the molecular modeling package Modeler 5.0 (Accelrys Inc.), the three dimensional structures of the light and heavy chains were built using the template structure. Ten homology models were created, and the best one in terms of Modeler energy was selected. Procheck analysis showed that no residues were in a disallowed region of the phi/psi map.

In designing the reshaped variable regions, an attempt was made to find the most similar human expressed antibody sequences for use as the antibody frameworks. To find the closest expressed sequences, a search for the most homologous expressed human frameworks in the NCBI NR database, TrEMBL database, and the Kabat database was performed. For heavy and light chain sequences, two searches (with CDR masked and unmasked) were performed. The selection of the most suitable expressed sequence includes checking for sequence identity of the canonical and interface residues, as well as checking for the similarity in CDR loop lengths. The source of the antibody is also a determining factor. Previously humanized antibodies are excluded. For the NCBI NR and TrEMBL database searches, BLAST was used, and for the Kabat database search, FASTA was used.

The most similar expressed light chain was found in the Kabat database (kabat id 026520 AC21B'CL; Ohlin et al., *Mol. Immunol.*, 33:47-56 (1996)). This is a PCR amplified scFv from phage-display but it is 100% identical to the L6 germline in the framework regions. For the heavy chain, the human framework gi|392715 from the NR database at NCBI was selected. It is 100% identical to germline VH1-2 in the framework regions. Both sequences were searched against the database of germline sequences, and this resulted in the following selected germlines: L6 for the light chain, and 1-2 for the heavy chain.

The most important procedure in the humanization of monoclonal antibodies is the identification of backmutations from human framework residues to mouse. Experience has shown that it is especially important to retain canonical residues, interface packing residues, and unusual murine residues, which are close to the binding site. In addition, residues located within 6 Å of any of the CDR residues need to be analyzed closely for potential effects on the conformation of the CDRs.

Three versions of the 8G6 variable light reshaped chain and three versions of the 8G6 variable heavy reshaped chain have been designed. The first version contains the most backmutations and the third version contains the fewest (i.e. the most "humanized"). Table 4 displays the heavy and light chain variable domain sequences for humanized 8G6 (hu8G6) antibodies.

TABLE4

Heavy and Light Chain Sequences for hu8G6

Heavy Chain Sequences

| | | FR1 | CDR1 | FR2 |
|---|---|---|---|---|
| Murine | (1) | QVQLQQSGPELVRPGVSVKISCKGSSYTFT | DYAMH | WVKLSHAKSLEWIG |
| 8G6HV1 | (1) | QVQLVQSGAEVKKPGASVKVSCKGSSYTFT | DYAMH | WVRLAPGQGLEWIG |
| 8G6HV2 | (1) | QVQLVQSGAEVKKPGASVKVSCKASGYTFT | DYAMH | WVRQAPGQGLEWIG |
| 8G6HV3 | (1) | QVQLVQSGAEVKKPGASVKVSCKASGYTFT | DYAMH | WVRQAPGQGLEWMG |
| VH1-2 | (1) | QVQLVQSGAEVKKPGASVKVSCKASGYTFT | ----- | WVRQAPGQGLEWMG |

| | | CDR2 | FR3 | |
|---|---|---|---|---|
| Murine | (50) | VISTYYGNTNYNQKFKG | KATMTVDKSSSTAYMELARLTSEDSAVYYCAR | (SEQ ID NO: 93) |
| 8G6HV1 | (50) | VISTYYGNTNYNQKFKG | R**A**TMT**V**D**K**SISTAYMELSRLRSDDTAVYYCAR | (SEQ ID NO: 94) |
| 8G6HV2 | (50) | VISTYYGNTNYNQKFKG | R**A**TMT**V**D**K**SISTAYMELSRLRSDDTAVYYCAR | (SEQ ID NO: 95)u |
| 8G6HV3 | (50) | VISTYYGNTNYNQKFKG | R**A**TMT**V**D**K**SISTAYMELSRLRSDDTAVYYCAR | (SEQ ID NO: 96) |
| VH1-2 | (50) | ----------------- | RVTMTRDTSISTAYMELSRLRSDDTAVYYCAR | (SEQ ID NO: 97) |

Light Chain Sequences

| | | FR1 | CDR1 | FR2 |
|---|---|---|---|---|
| Murine | (1) | DIVLTQSPASLAVSLGQRAIISC | RASQSVSTSSYSYMY | WYQQKPGQSPKFLIK |
| 8G6LV1 | (1) | DIVLTQSPATLSLSPGERATLSC | RASQSVSTSSYSYMY | WYQQKPGQAPR**F**LI**K** |
| 8G6LV2 | (1) | EIVLTQSPATLSLSPGERATLSC | RASQSVSTSSYSYMY | WYQQKPGQAPR**F**LI**K** |
| 8G6LV3 | (1) | EIVLTQSPATLSLSPGERATLSC | RASQSVSTSSYSYMY | WYQQKPGQAPRLLI**K** |
| L6 | (1) | EIVLTQSPATLSLSPGERATLSC | --------------- | WYQQKPGQAPRLLIY |

| | | CDR2 | FR3 | CDR3 | |
|---|---|---|---|---|---|
| Murine | (54) | YASNLES | GVPARFSGSGSGTDFTLNIHPVEEEDTATYYC | QHNWEIP | (SEQ ID NO: 98) |
| 8G6LV1 | (54) | YASNLES | GIPARFSGSGSGTDFTLTISSLEPEDFAVYYC | QHNWEIP | (SEQ ID NO: 99) |
| 8G6LV2 | (54) | YASNLES | GIPARFSGSGSGTDFTLTISSLEPEDFAVYYC | QHNWEIP | (SEQ ID NO: 100) |
| 8G6LV3 | (54) | YASNLES | GIPARFSGSGSGTDFTLTISSLEPEDFAVYYC | QHNWEIP | (SEQ ID NO: 134) |
| L6 | (50) | ------- | GIPARFSGSGSGTDFTLTISSLEPEDFAVYYC | ------- | (SEQ ID NO: 135) |

The protein sequences of the different versions of hu8G6 heavy (versions 1, 2 and 3) and light (versions 1, 2 and 3) variable domains are shown in Table 5. For the heavy chain variable domains, the sequences comprise:

(a) a human FR1 derived from the FR1 of VH1-2;

(b) the murine 8G6 CDR1 heavy chain sequence;

(c) a human FR2 derived from the FR2 of VH1-2;

(d) the murine 8G6 CDR2 heavy chain sequence;

(e) a human FR3 derived from the FR3 of VH1-2;

(f) the murine 8G6 CDR3 heavy chain sequence; and (g) a human FR4 derived from a consensus framework sequence which is 100% identical to the human framework gi|1392715 from the NR database and is present in a large majority of human antibodies with the following sequence: WGQGTLVTVSS (SEQ ID NO: 151).

For the light chain variable domains, the sequences comprise:

(a) a human FR1 derived from the FR1 of L6;

(b) the murine 8G6 CDR1 light chain sequence;

(c) a human FR2 derived from the FR2 of L6;

(d) the murine 8G6 CDR2 light chain sequence;

(e) a human FR3 derived from the FR3 of L6;

(f) the murine 8G6 CDR3 light chain sequence; and (g) a human FR4 derived from a consensus framework sequence present in a large majority of human antibodies with the following sequence: FGGGTKVEIK. (SEQ ID NO: 152)

TABLE 5

| Heavy and Light Chain Sequences of hu8G6 Variable Domains |
|---|
| hu8G6 version 1 heavy chain (SEQ ID NO: 78) |
| QVQLVQSGAEVKKPGASVKVSCKGSSYTFTDYAMHWVRLAPGQGLEWIGVIST<br>YYGNTNYNQKFKGRATMTVDKSISTAYMELSRLRSDDTAVYYCARGGLRRGD<br>RPSLRYAMDYWGQGTLVTVSS |
| hu8G6 version 2 heavy chain (SEQ ID NO: 79) |
| QVQLVQSGAEVKKPGASVKVSCKASGYTFTDYAMHWVRQAPGQGLEWIGVIS<br>TYYGNTNYNQKFKGRATMTVDKSISTAYMELSRLRSDDTAVYYCARGGLRRG<br>DRPSLRYAMDYWGQGTLVTVSS |
| hu8G6 version 3 heavy chain (SEQ ID NO: 80) |
| QVQLVQSGAEVKKPGASVKVSCKASGYTFTDYAMHWVRQAPGQGLEWMGVI<br>STYYGNTNYNQKFKGRATMTVDKSISTAYMELRLRSDDTAVYYCARGGLRRG<br>DRPSLRYAMDYWGQGTLVTVSS |
| hu8G6 version 1 light chain (SEQ ID NO: 75) |
| DIVLTQSPATLSLSPGERATLSCRASQSVSTSSYSYMYWYQQKPGQAPRFLIKYA<br>SNLESGIPARFSGSGSGTDFTLTISSLEPEDFAVYYCQHNWEIPFTFGGGTKVEIK |
| hu8G6 version 2 light chain (SEQ ID NO: 76) |
| EIVLTQSPATLSLSPGERATLSCRASQSVSTSSYSYMYWYQQKPGQAPRFLIKYA<br>SNLESSGIPARGSGSGSGTDFTLTISSLEPEDFAVYYCQHNWEIPFTFGGGTKVEIK |
| hu8G6 version 3 light chain (SEQ ID NO: 77) |
| EIVLTQSPATLSLSPGERATLSCRASQSVSTSSYSYMYWYQQKPGQAPRLLIKYA<br>SNLESGIPARFSGSGSGTDFTLTISSLEPEDFAVYYCQHNWEIPFTFGGTKVEIK |

The following describes the backmutations in the reshaped variable light chain:

E1D—This has been shown to influence CDR conformation/antigen binding (Kolbinger et al., *Protein Eng.,* 8:971-980 (1993)). In the model, it might interact with the backbone or sidechains of S26, Q27 and/or E93 in CDRs L1 and L3. It is removed in versions 2 and 3 since the substitution is conservative.

L46F—This is a VH/VL packing interface residue. It also appears to be right underneath CDR-L2 residue E55. It is removed in version 3.

Y49K—This is adjacent to CDR-L2 and appears to be interacting with residue E55 in the model. This is likely to be a very important backmutation and, therefore, is not removed.

The following describes the backmutations in the reshaped variable heavy chain:

A24G—This is a canonical residue for CDR-H1. Conservative mutation. Removed in version 2.

G26S—This is canonical residue for CDR-H1. Conservative mutation. Removed in version 2.

Q39L—This is packing interface residue. It has very limited interaction with the light chain and, therefore, is removed in version 2. M48I—This is a common backmutation. In the model it may be interacting with Y59 and F63 in CDR-H2. It is dismissed in version 3. V68A—This residues is located underneath CDR-H2 possibly interacting with Y59 and F63.

R72V—This is a canonical residue for CDR-H2 T74K—This residue is located underneath CDR-H2 possibly interacting with Y53 or contacting antigen directly.

Example 8

$\alpha_v\beta_6$ Antibody Internalization

Antibodies that are internalized by cells offer an advantage for certain clinical indications such as cancer, because the antibodies can then be conjugated with toxins, radioactive compounds or other anti-cancer agents to selectively target and inhibit growth of cancer cells. The ability of anti-$\alpha_v\beta_6$ antibodies to be internalized was previously described in WO 03/100033, herein incorporated in its entirety by reference. WO 03/100033 disclosed that internalization was observed for cation-dependent monoclonal antibodies (RGD-containing ligand mimetics) such as 6.8G6 and 6.1 A8. However, no internalization was observed for cation-independent mAbs such as 6.3G9, 7.1C5, and 6.4B4. The ability of an antibody to be internalized by cells, such as 8G6, affords the advantage of coupling the internalizing antibody with therapeutic moieties/agents to allow delivery of the moieties/agent into the cell. For example drug or toxin moieties may be conjugated to the 8G6 internalizing antibody. However, this same application can also be applied to non-internalizing antibodies, such as 3G9, wherein a chemical moiety may be conjugated to such antibodies to allow delivery to the cell surface of a target (e.g., tumor cell surface).

Example 9

$\alpha_v\beta_6$ is Highly Expressed in Metastases Relative to Primary Tumors

In the present experiments, we set out to study the expression of $\alpha_v\beta_6$ in a variety of cancers of epithelial origin and on metastatic lesions and to determine if function blocking $\alpha_v\beta_6$ mAbs could inhibit the growth of $\alpha_v\beta_6$ expressing tumors in vivo. We evaluated the in vitro and in vivo anti-tumor activity of our anti-human $\alpha_v\beta_6$ mAbs on a human pharyngeal carcinoma, Detroit62, and compared this to the in vivo anti-tumor activity of TβRII:Fc. Our data support a role in human cancer for $\alpha_v\beta_6$ and potential for therapeutic intervention with a function-blocking $\alpha_v\beta_6$ mAb.

A. Materials and Methods:

For immunohistochemistry, tissue sections were deparaffinized in xylene and ethanol, rehydrated in distilled water, and then immersed in methanol containing 0.45% $H_2O$. Tissues were incubated with pepsin (00-3009, Zymed, San Francisco, Calif.) and blocked with avidin and biotin (SP-2001; Vector Laboratories, Burlingame, Calif.). Primary antibody was diluted in phosphate-buffered saline (PBS) containing 0.1% bovine serum albumin (BSA) and tissues were incubated overnight at 4° C. For immunostaining β6 on mouse xenograft tissue, sections were incubated with a human/mouse chimeric form of the anti-$\alpha_v\beta_6$ mAb, 2A1 (Weinreb, P. H. et al., *J. Biol. Chem.* 279(17):17875-17887 (2004)), and an anti-human biotinylated secondary antibody (PK-6103, Vector Laboratories, Burlingame, Calif.). For immunostaining $\beta_6$ on human tissue, sections were incubated with murine 2A1 and an anti-mouse-biotinylated secondary antibody (PK-6102, Vector Laboratories). Avidin-biotin complex-horseradish peroxidase (Vector Kit, PK-6102) was applied to sections, incubated for 30 minutes at room temperature, and 3,3'-diaminobenzidine (DAB) substrate was prepared as directed (SK-4100, Vector Laboratories) and applied to sections for five minutes at room temperature. Tissue sections were stained with Mayer's Hematoxylin for 1 minute and rinsed in water and PBS.

B. Results:

1. $\alpha_v\beta_6$ Expression in Metastases $\alpha_v\beta_6$ immunostaining was evaluated on a variety of tumor metastases. 78% of the metastases (43/55) were positively immunostained showing intense staining over a majority of the metastases (FIGS. 13A-F; FIGS. 14A-I). This result was found to be an increase in percent positive immunostaining in that only head and neck, cervical and pancreatic tumors were found to have an equivalent level of expression (Table 1):

TABLE 1 avb6 Expression in Human Tumors (immunohistochemistry)

| Tissue | $\alpha_v\beta_6^+$/total | % $\alpha_v\beta_6^+$ |
|---|---|---|
| Oral | 4/4 | 100% |
| Cervical | 79/98 | 81% |
| Pancreas | 31/39 | 80% |
| Skin | 41/53 | 77% |
| Larynx & pharynx | 43/64 | 67% |
| Esophageal | 35/56 | 63% |
| Endometrium | 17/32 | 53% |
| Lung | 28/70 | 40% |
| Breast | 41/101 | 41% |
| Colorectal | 181/488 | 37% |

2. $\alpha_v\beta_6$ Expression in Endometrial Tumors and Patient-Matched Metastases As noted above in Table 1, $\alpha_v\beta_6$ immunostaining was positive on 53% of endometrial tumors examined. With a few exceptions, staining was more prominent in more invasive regions of higher grade tumors. Three primary tumor samples had matched lymph node metastases. In two of these cases, immunostaining was significantly higher on the lymph node metastases relative to the matched primary tumor (compare FIG. 15A to FIG. 15B, and FIG. 15C to FIG. 15D). In the third case, immunostaining was high on both the lymph node metastases and matched primary tumor (data not shown). Percent $\alpha_v\beta_6$ positive tumor epithelium staining in the three primary tumors was 10%, 20% and 90%, respectively, while percent $\alpha_v\beta_6$ positive tumor epithelium in the matched metastatic lymph nodes was 80%, 100% and 100%, respectively. In normal endometrium, staining was confined to occasional cells on the surface layer, as well as cysts.

3. $\alpha_v\beta_6$ Expression in Invasive Human Breast Tumor Samples

Figure 16:
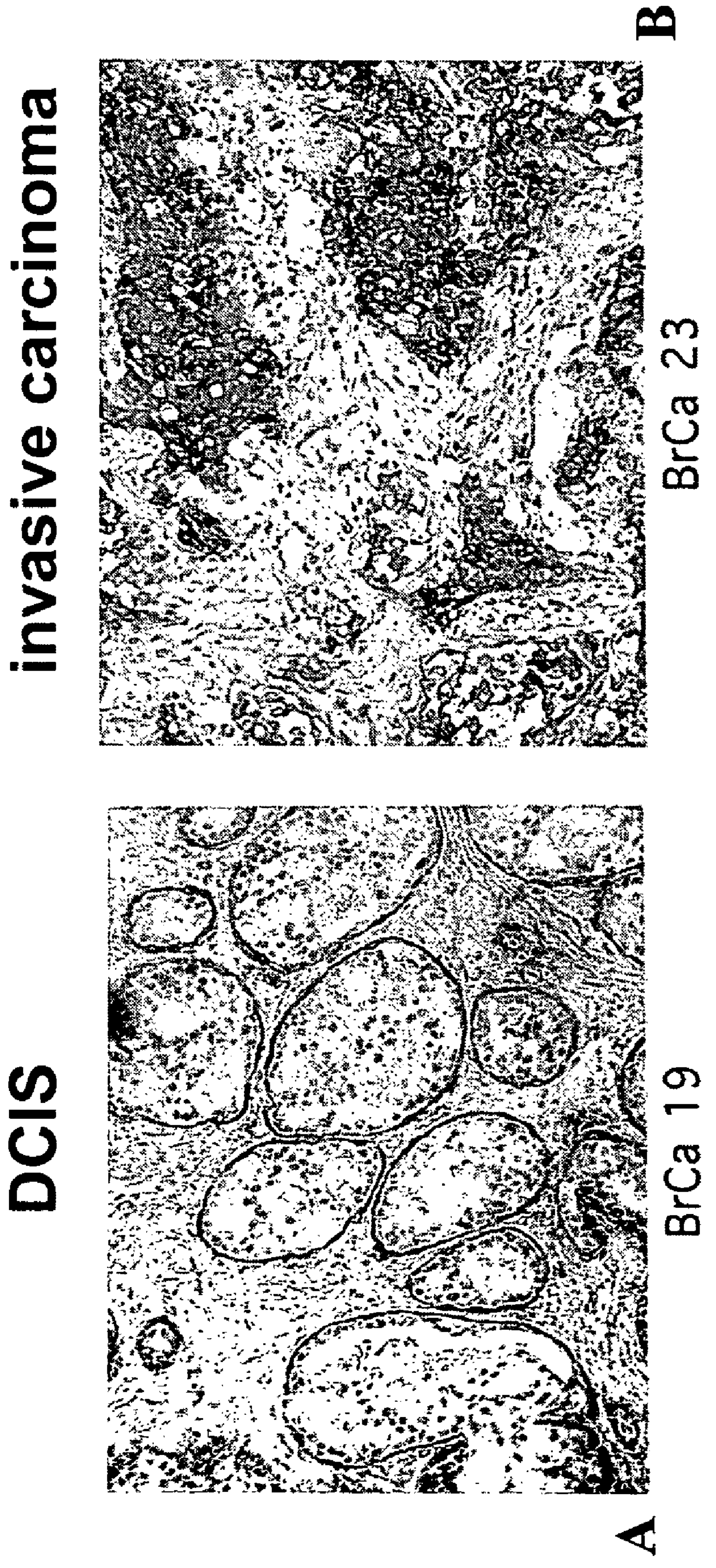
FIG. 16 is a composite of photomicrographs depicting the levels of $\alpha_v\beta_6$ expression (dark areas) observed in human breast tumor samples.

Greater than 100 samples of human breast cancer were evaluated for level of expression of $\alpha_v\beta_6$ using immunohistochemistry, according to procedures described above in Materials and Methods. In several cases of ductal carcinoma in situ (DCIS), $\alpha_v\beta_6$ was expression was limited to the myoepithelium surrounding a tumor and was not observed on the tumor itself (see, e.g., BrCa19; FIG. 16A). However, in several cases of invasive breast carcinoma, $\alpha_v\beta_6$ was expressed on the tumor as well (see, e.g., BrCa23, FIG. 16B).

There is evidence that the expression of specific genes in cells of breast tissue (epithelial cells, myoepithelial cells, and fibroblasts) is altered comparing normal breast tissue, to breast tissue containing a non-invasive tumor such as DCIS, to a breast tissue containing an invasive breast carcinoma (Alinen, M. et al., *Cancer Cell* 6:17-32 (2004); Burstein, H. J. et al., *N. Engl. J. Med.* 350:1430-1441 (2004)). Many of these gene expression changes have been dectected in the myoepithelial cells. It is possible that the expression of the $\alpha_v\beta_6$ integrin on the myoepithelium (both in normal tissue, and in DCIS) lends to a microenvironment, perhaps through localized TGF-β activation, supporting tumor viability, and promoting the progression of an invasive tumor. An in vivo model of DCIS that can progress to an invasive carcinoma, such as MCF10DCIS.com (Miller, F. R. et al., *J. Natl. Canc. Inst.* 92:1185-1186 (2000)), would provide a method to evaluate the expression of $\alpha_v\beta_6$ within the context of a progressing breast tumor. One could evaluate the expression of $\alpha_v\beta_6$ in the myoepithelium in the early non-invasive stage of the tumor and expression of $\alpha_v\beta_6$ as the tumor progresses to an invasive phenotype in vivo. This model would also allow one to test the functional role of $\alpha_v\beta_6$ using blocking $\alpha_v\beta_6$ mAbs and also to test the efficacy of conjugated anti-$\alpha_v\beta_6$ mAbs.

Figure 17:
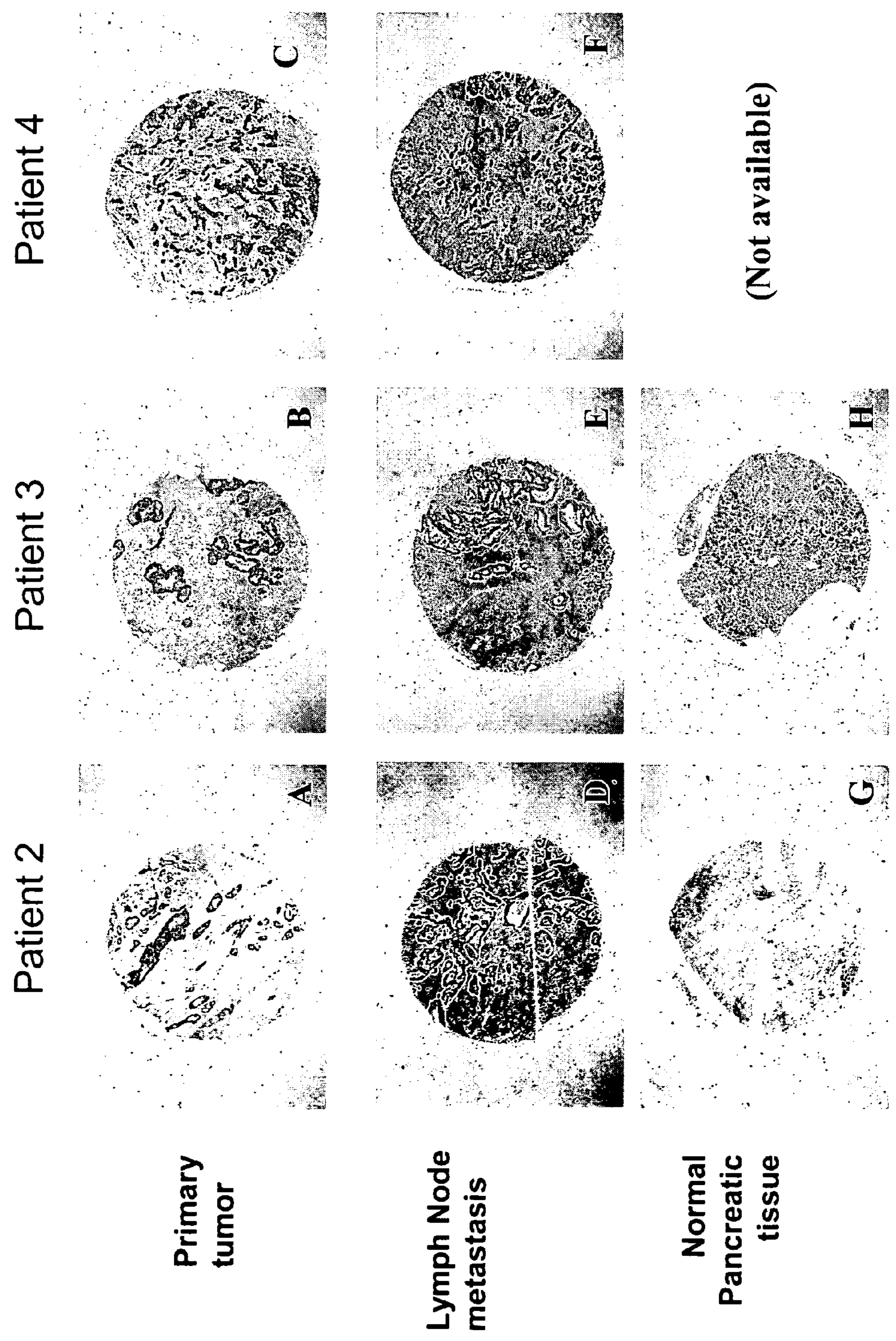
FIG. 17 is a composite of photomicrographs depicting the levels of $\alpha_v\beta_6$ expression (dark areas) observed in matched samples of primary and metatstatic pancreatic ductal adenocarcinoma tumors from three different patients.
Figure 18:
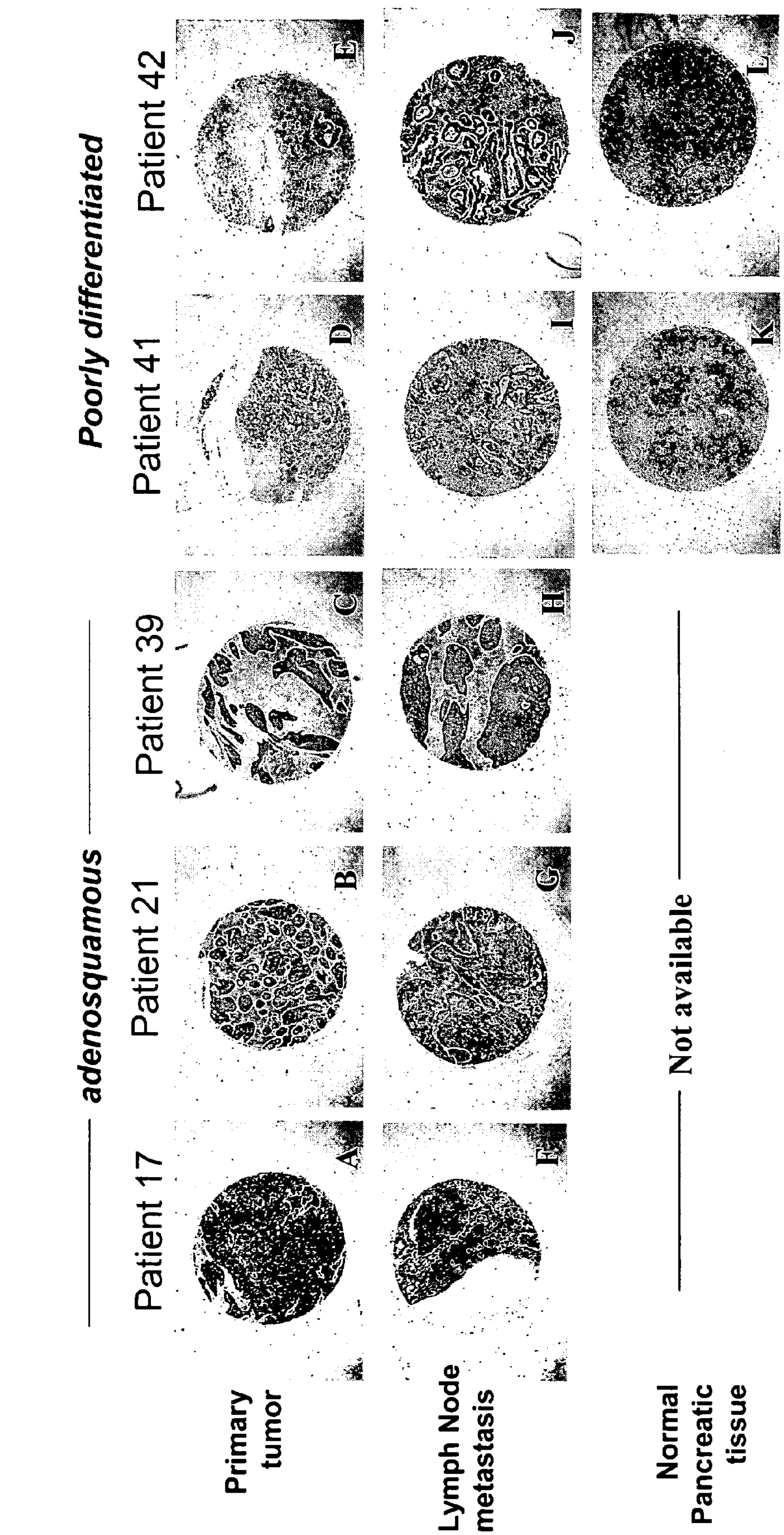
FIG. 18 is a composite of photomicrographs depicting the levels of $\alpha_v\beta_6$ expression (dark areas) observed in matched samples of primary and metatstatic pancreatic adenocarcinoma tumors from five different patients.

4. $\alpha_v\beta_6$ Expression in Human Pancreatic Tumor Samples, Patient-Matched Metastases and Mouse Xenograft Model of Invasive Pancreatic Tumor As noted above in Table 1, $\alpha_v\beta_6$ immunostaining was positive on 80% of pancreatic tumors examined. When samples from primary pancreatic tumors from eight different patients were examined by immunohistochemistry, staining was prominent in invasive regions of high grade tumors (FIGS. 17A-17C; 18A-18E). The primary tumor samples also had matched lymph node metastases (FIGS. 17D-17F; 18F-18J), which also demonstrated strong $\alpha_v\beta_6$ staining, supporting the notion that $\alpha_v\beta_6$-positive cells have disseminated from the primary tumor site. In normal pancreas (FIGS. 17G-17H; 18K-18L), staining was confined to occasional cells on the surface layer.

To further examine the influence of $\alpha_v\beta_6$ expression on tumor cell invasion, we used a BxPC-3 mouse tumor xenograft as a model of invasive human pancreatic adenocarcinoma. Animals were implanted (day 0) subcutaneously on the flank with $5\times10^6$ cells/mouse, suspended in sterile saline, using a injection of 0.1 ml/mouse. At day 30, mice with established tumors (~60-100 $mm^3$) were pair-matched to each of three treatment groups (PBS; mAb 3G9; soluble TGF-β receptor II-Ig fusion protein (solTGFβRII-Fc)) for all studies. Test agents were administered to mice intraperitoneally on a 3 times per week treatment schedule. Mice were injected with 3G9 at 10 mg/kg, solTGFβRII-Fc at 2 mg/kg, or PBS (negative control). Tumor growth was measured twice a week and tumor volume estimated according to the formula: $[(\text{width})^2\times\text{length}]/2$. Tumors from treatment groups were excised, fixed in 10% paraformaldehyde, paraffin-embedded and sectioned for immunohistochemical analysis using the non-blocking v6 chimeric mAb 6.2A1.

Figure 19:
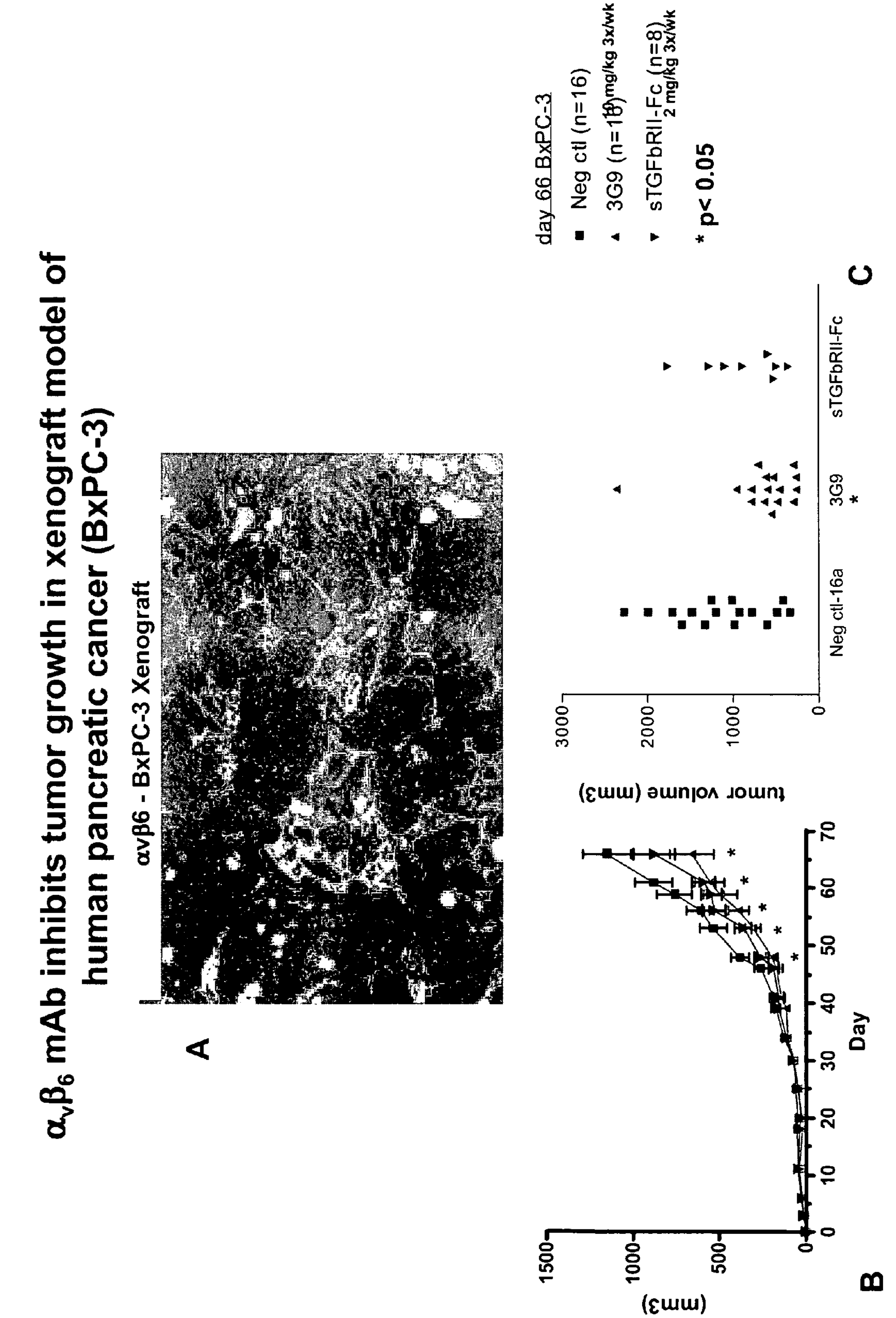
FIG. 19 demonstrates the ability of an anti-$\alpha_v\beta_6$ monoclonal antibody (3G9) to inhibit tumor growth in the BxPC-3 mouse xenograft model of human pancreatic cancer.

Treatment with anti-$\alpha_v\beta_6$ mAb 3G9 had a direct effect on tumor growth (FIGS. 19B, 19C), with significantly reduced tumor growth observed after about 48 days of treatment with the antibody. The level of growth inhibition observed with solTGFβR-Fc was somewhat lower than that observed for 3G9. These results indicate that the anti-$\alpha_v\beta_6$ mAb 3G9 inhibits tumor growth in a xenograft model of human pancreatic cancer, and suggest that such blocking antibodies could be useful in inhibiting tumor growth, and by extension tumor invasion, in primary human pancreatic adenocarcinomas.

Example 10

$\alpha_v\beta_6$ Function-Blocking mAbs Inhibit Tumor Cell Migration, Invasion, and MMP Production of $\alpha_v\beta_6$ Expressing Tumor Cells The $\alpha_v\beta_6$ blocking monoclonal antibody (mAb) 3G9 (Weinreb, P. H. et al., *J. Biol. Chem.* 279(17):17875-17887 (2004)), and soluble recombinant TGF-βRII-Ig (Cosgrove, D. et al., *Am. J. Pathol.* 157(5):1649-1659 (2000)), were evaluated for their ability to block the capacity of $\beta_6$-transfected cells to invade, migrate, and produce matrix metalloproteinase 9 (MMP-9) in vitro. These activities were monitored as each has been associated with tumor cell invasion and migration. The effects of 3G9 and TGF-βRII-Ig were evaluated using untransfected parent cells (C1) and a $\beta_6$-transfected derivative of C1 cells (VB6).

Migration and Invasion Assay. C1 and VB6 human oral squamous carcinoma cells were grown in KGM media as previously described (Thomas, G. J. et al., *J. Invest. Derm.* 117(1):67-73 (2001). To measure migration, we used FLUOROBLOK™ plates and inserts (BD Biosciences; Bedford, Mass.) according to manufacturer's instructions. Briefly, empty wells were filled with KGM media or serum free KGM as a negative control. Cells were harvested and preincubated in serum free media with antibody. 50,000 cells were added to the insert, which was then placed inside the wells and incubated for 24 hours at 37° C. in a tissue culture incubator. After the incubation, cells and media were removed from the top of the insert. The cells that migrated to the filter underside were quantified by labeling with 2 μg/mL Calcein (Invitrogen Corpn., Carlsbad, Calif.) for 1 hour and measuring fluorescence in bottom-read mode. The percent inhibition was calculated as the decrease in the number of cells migrated in the presence of antibody compared to media alone. Invasion was measured in a similar fashion, using MATRIGEL®-coated FLUROBLOK inserts and incubating for 48 hours.

Quantification of MMP Production. Cells in media containing 1% FBS were cultured in MATRIGEL-coated wells (BD Biosciences) for the time indicated. Supernatants were harvested, centrifuged to remove cell debris, and frozen until assayed. MMP levels were quantified by ELISA (R&D Systems, Minneapolis, Minn.).

Figure 20:
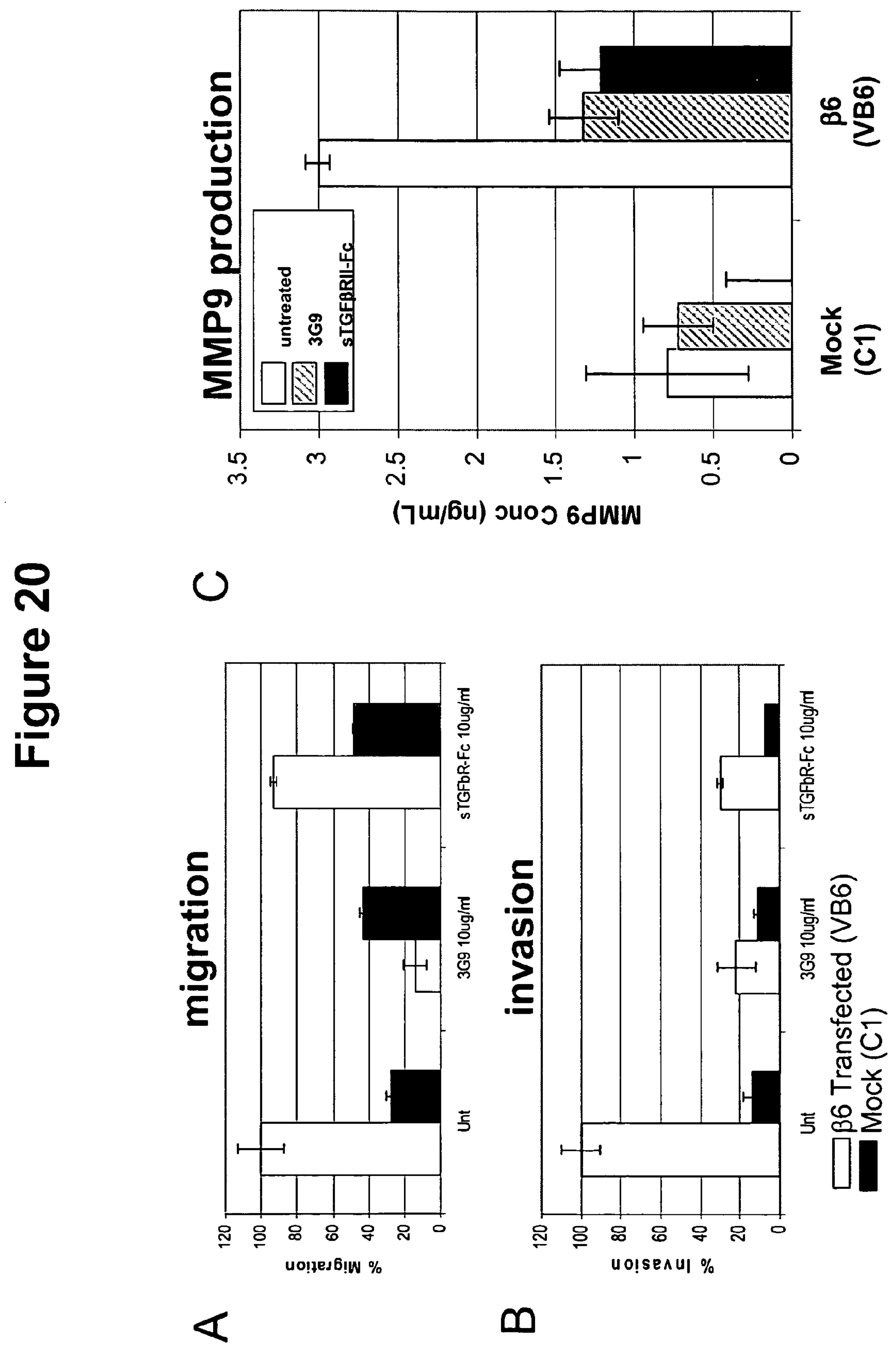
FIG. 20 is a series of bar graphs demonstrating the effects of an anti-$\alpha_v\beta_6$ monoclonal antibody (3G9), and of a soluble TGF-β receptor-antibody fragment conjugate (sTGF-βRII-Fc), on transmatrix migration, invasion and matrix metalloproteinase 9 (MMP9) production by VB6 cells expressing $\beta_6$ (transfected with $\beta_6$) and by mock-transfected cells.
Figure 21:
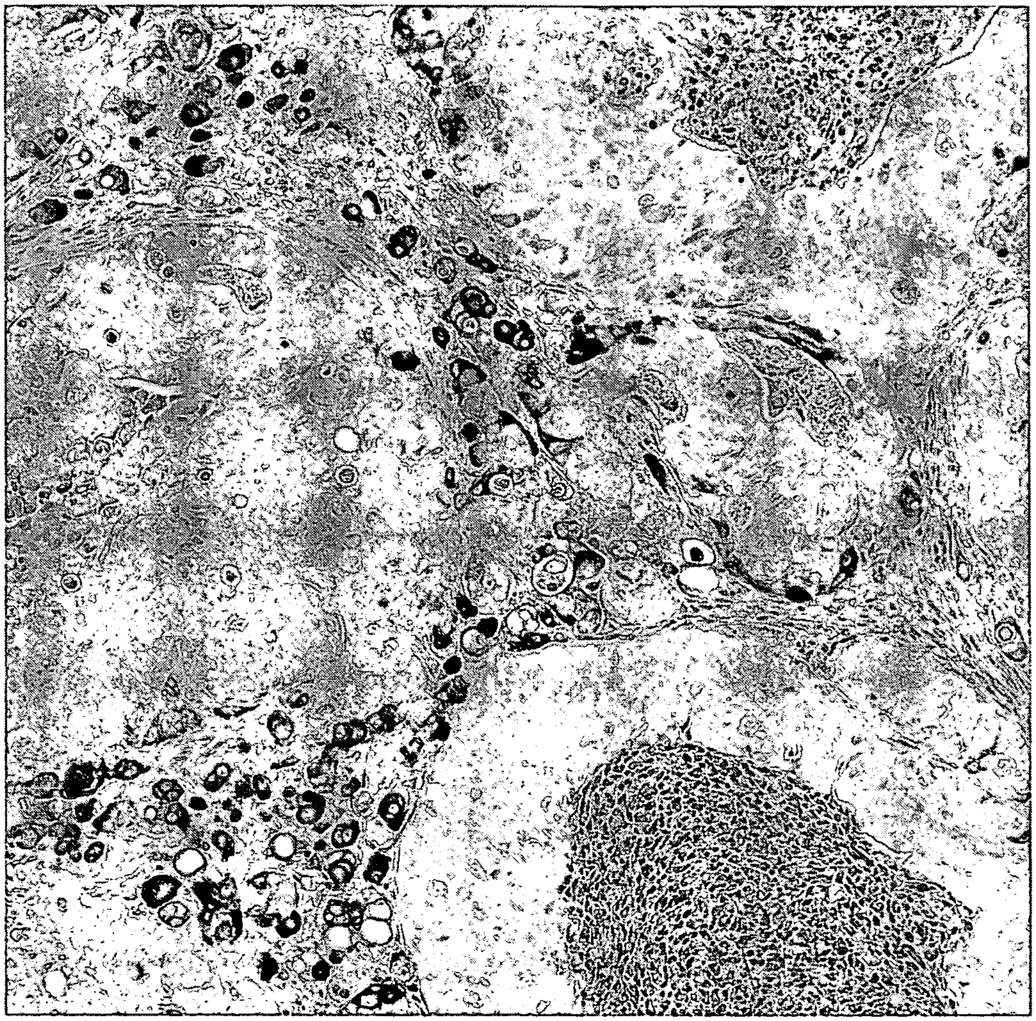
FIG. 21 is a photomicrograph of an immunohistochemistry section, demonstrating $\alpha_v\beta_6$ expression (dark areas) on tumor cells invading into the stroma in a LIM1863 xenograft model. Anti-human keratin staining on consecutive sections (not shown) confirmed that these cells were human epithelial (i.e., LIM1863) tumor-derived.

Results:

As shown in FIG. 20A-20C, the $\alpha_v\beta_6$-blocking mAb 3G9 significantly inhibited migration, invasion, and production of MMP-9 by VB6 cells in vitro. Blocking TGF-β activity with recombinant soluble TGF-βRII-Ig also inhibited invasion and MMP-9 production by VB6 cells (FIGS. 20B and 20C), but did not affect their migration (FIG. 21A). These data show a distinct functional difference comparing blockade of $\alpha_v\beta_6$ function versus blockade of TGF-β activity. This conclusion is consistent with the ability of $\alpha_v\beta_6$ to mediate both cell adhesion and migration through binding to fibronectin, as well the activation of latent precursor TGF-β (Sheppard, D., *Cancer Metast. Rev.* 24:395-402 (2005)).

Example 11

$\alpha_v\beta_6$ mAb Inhibits Stromal Invasion in Xenograft Model of Human Colorectal Cancer (LIM1863)

1. Background

A novel colon carcinoma model, LIM1863, was recently characterized (Bates, R. C. and Mercurio, A. M., *Mol. Biol. Cell* 14:1790-1800 (2003); Bates, R. C. et al., *J. Clin. Invest.* 115(2):339-347 (2005)). In vitro, LIM1863 cells grow in a suspension culture in well-differentiated 3D spheroids (organoids). Following exposure to TGF-β and TNFα, however, this cell line converts to a migratory monolayer phenotype, with morphological changes characteristic of an epithelial-to-mesenchymal transition (EMT), typified by the loss of E-cadherin. This transition is accompanied by a significant increase in $\alpha_v\beta_6$ expression. In vivo, LIM1863 cells are tumorigenic when injected subcutaneously in the flank of nude mice (Bates, R. C. et al., *J. Clin. Invest.* 115(2):339-347 (2005)). As demonstrated in FIG. 6, LIM1863 cells exhibit a striking pattern of $\alpha_v\beta_6$ expression (id.). Specifically, the expression of $\alpha_v\beta_6$ is particularly prominent on cells that appear to have invaded from the primary tumor mass into the tumor stroma. This finding is consistent with the notion that these cells have undergone epithelial-mesenchymal transition (EMT) that has been described previously (see id.).

Therefore, we chose to use LIM1863 cells as a xenograft model of human colorectal cancer, to examine the possible involvement of $\alpha_v\beta_6$ in stromal invasion in this model.

2. Materials And Methods

LIM1863 cells were grown as organoids in RPMI-1640 (GIBCO; Invitrogen Corp., La Jolla, Calif.) supplemented with 5% fetal calf serum (FCS). LIM1863 organoids (approximately $8\times10^6$ cells) were inoculated subcutaneously into the flanks of female nude mice. All animal studies were approved by the Institutional Animal Care and Use Committee (IACUC) of Biogen Idec. Mice were treated by intraperitoneal injection three times a week with 10 mg/kg anti-$\alpha_v\beta_6$ specific murine monoclonal antibody 3G9 (Weinreb, P. H. et al., *J. Biol. Chem.* 279(17):17875-17887 (2004)), 2 mg/kg recombinant soluble TGF-βRII-Ig fusion protein (Cosgrove, D. et al., *Am. J. Pathol.* 157(5):1649-1659 (2000)), or vehicle control (PBS). Tumor volumes were measured at the corresponding timepoints using a caliper, and tumor volume was calculated using the formula $(L\times W^2)/2$. Xenografts were harvested seven weeks later and formalin-fixed, paraffin-embedded sections were used for immunohistochemistry, which was performed as described above in Example 9 (FIG. 21).

Results

Figures 22A, 22B, 22C:
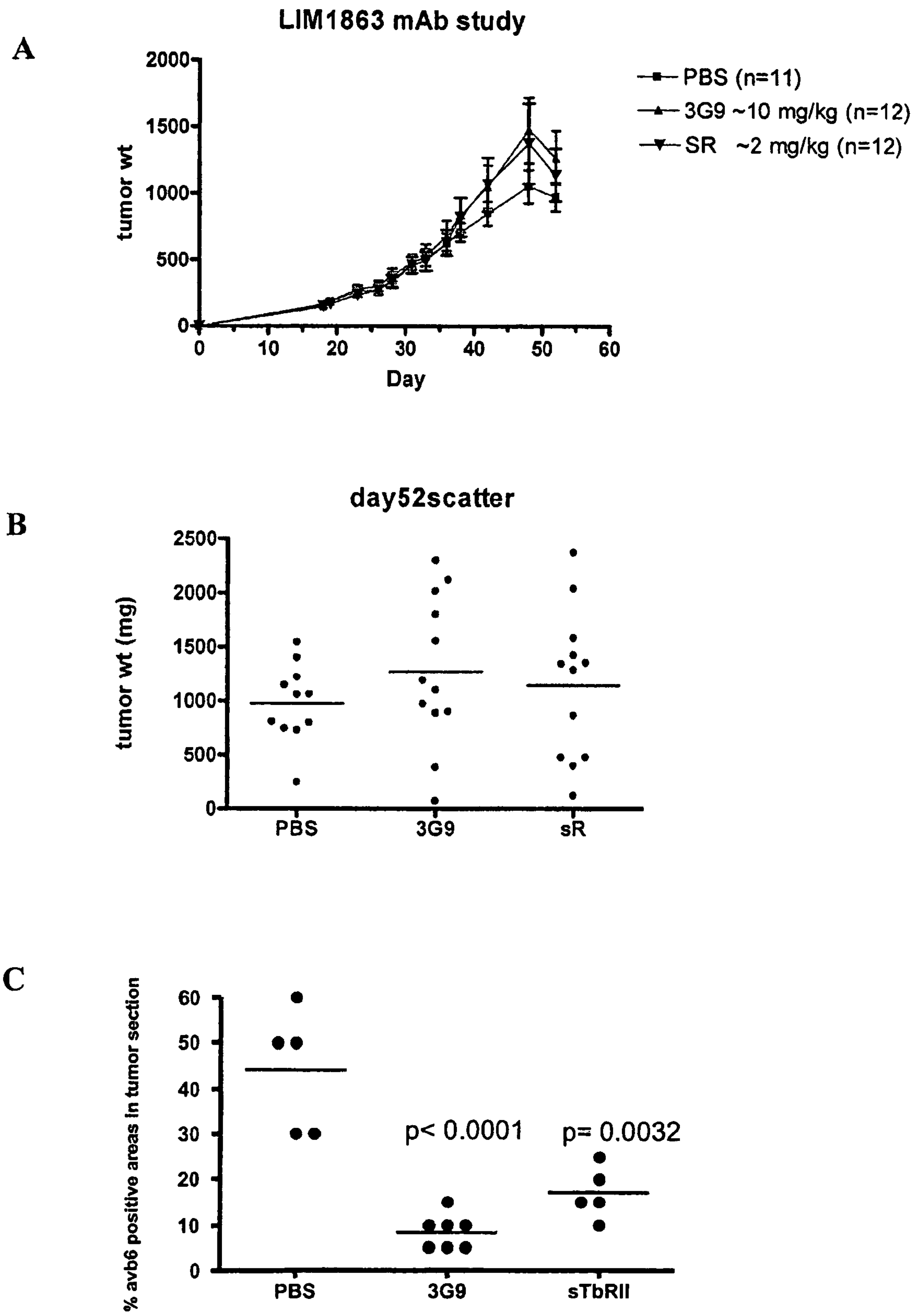
FIGS. 22A-22F depict the effects of $\alpha_v\beta_6$ mAb 3G9 and recombinant soluble TGFbRII-Fc-Ig fusion protein on tumor growth and stromal invasion in the LIM1863 xenograft tumor model.
Figures 22D, 22E, 22F:
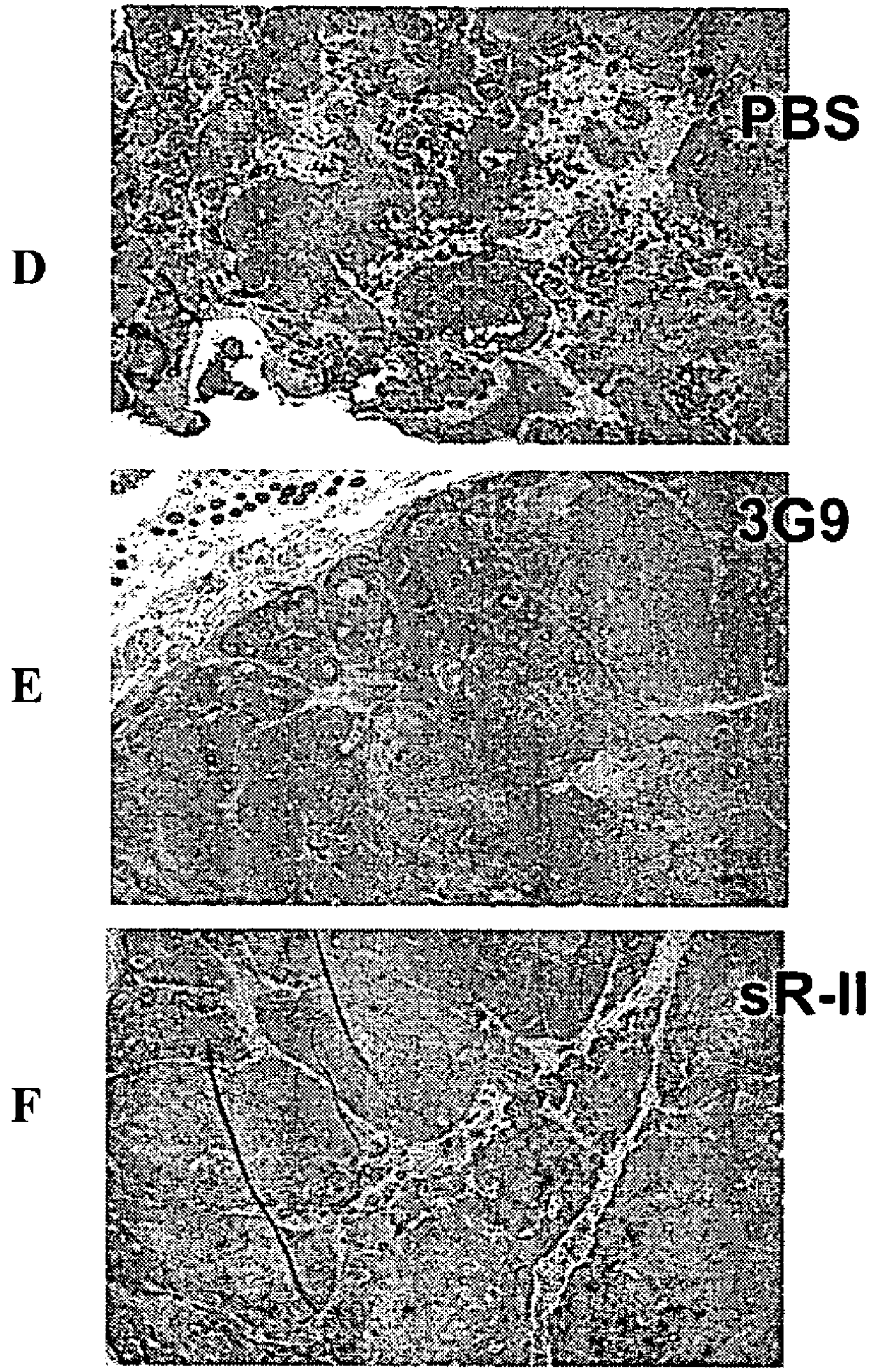

Anti-$\alpha_v\beta_6$ mAb 3G9 and/or recombinant soluble TGF-βRII-Ig had no direct effect on tumor growth (FIG. 22A, 22B). However, these ligands significantly inhibited stromal invasion of LIM1863 cells by approximately 80% (FIG. 22C), as assessed by quantitation of $\alpha_v\beta_6$ positive tumor cell areas within the stroma (FIG. 22D-22F) performed by a pathologist blinded to the treatment.

Example 12

Affinity and Bioactivity of Murine 6.3G9 (m3G9) for $\alpha_v\beta_6$ Integrin Expressed on Non-Human Primate Cells SUMMARY. The affinity and bioactivity of anti-$\alpha_v\beta_6$ blocking monoclonal antibody 6.3G9 (m3G9) on non-human primate (NHP) $\alpha_v\beta_6$ integrin was determined through a variety of in vitro methods. Using fluorescence activated cell sorting (FACS), NHP cell lines expressing high levels of $\alpha_v\beta_6$ were identified from 2 different species (12 MBr6 from African green monkey, and 4 MBr5 from rhesus monkey). m3G9 bound to $\alpha_v\beta_6$ expressed on 12 MBr6 and 4 MBr5 with $ED_{50}$ values of 0.30 μg/mL and 0.38 μg/mL, respectively. m3G9 also inhibited the binding of 12 MBr6 and 4 MBr5 to TGFβ1 latency associated peptide (LAP) with $IC_{50}$ values of 0.22 μg/mL and 0.29 μg/mL, respectively. Finally, m3G9 blocked the ability of the 4 MBr5 cell line to activate latent TGFβ, as determined using a coculture assay with TGFβ responsive mink lung epithelial reporter cells stably expressing a portion of the plasminogen activator inhibitor 1 promoter (TMLC), with an $IC_{50}$ value of 0.31 μg/mL.

INTRODUCTION. The purpose of this study was to determine the affinity and bioactivity of anti-$\alpha_v\beta_6$ monoclonal antibody 6.3G9 (m3G9) for $\alpha_v\beta_6$ integrin expressed on non-human primate (NHP) cells. m3G9 is the murine precursor of humanized monoclonal antibody hu3G9 (BG00011). This murine antibody is a high-affinity, specific $\alpha_v\beta_6$ integrin-targeted reagent.[1] m3G9 binds to its target, the $\alpha_v\beta_6$ integrin, with high affinity ($K_D$=16 pM), inhibits the binding of cell-expressed $\alpha_v\beta_6$ to ligands (TGFβ1 latency associated peptide (LAP) and fibronectin), and blocks the ability of $\alpha_v\beta_6$ to activate latent TGFβ1.[1] The antibody requires the presence of both $\alpha_v$ and β6 subunits for binding, and no cross-reactivity to other related integrins (αvβ3, αvβ3, αvβ5, αvβ3, and αIIbβ3) was observed, indicating that m3G9 is highly specific for αvβ6.[1]

Murine and human β6 integrins have a high degree of sequence similarity (89.5% identity)[2], as do murine and human αv integrins (92.8% identity)[3]. The sequence of αvβ6 from NHP has not been determined, but would also be expected to share a high level of sequence identity.

In order to determine the affinity of m3G9 for NHP αvβ6, binding was measured by FACS. The ability of m3G9 to block cell adhesion to human TGFβ1 LAP was evaluated in a cell adhesion assay. Finally, the ability of m3G9 to block NHP αvβ6-mediated activation of latent TGFβ was determined using a coculture assay.

Materials and Methods:

Reagents. The mouse monoclonal antibodies 6.3G9 (m3G9) and 6.4B4 were generated and purified as described in ref. 1 and hereinabove. Recombinant human LAP (LAP) was purchased from R&D Systems (catalog #246-LP). The human β6-transfected SW480 (human colorectal adenocarcinoma) cell line (SW480β6) was provided by Dean Sheppard (UCSF).

NHP Cell lines. The following cell lines were obtained from the American Type Culture Collection (ATCC):

| Name | Source species | Cell type | Age of source |
|---|---|---|---|
| Vero | African Green Monkey | kidney epithelial | adult |
| 12MBr6 | African Green Monkey | lung epithelial | 2-3 year old male |
| LLC-MK2 | Rhesus Monkey | kidney epithelial | adult |
| 4MBr5 | Rhesus Monkey | lung epithelia | 2-3 year old |

Fluorescence-activated cell sorting (FACS). Cells were harvested by trypsinization, washed once in phosphate buffered saline, and then resuspended in FC buffer (PBS, 2% FBS, 0.1% $NaN_3$, 1 mM $CaCl_2$, and 1 mM $MgCl_2$). $1\times10^6$ cells were then incubated with 10 μg/mL m3G9 on ice for 0.5 h in a total of 50 μL of FC buffer. After incubation cells were washed two times with ice cold FACS buffer (PBS, 2% FBS, 0.1% $NaN_3$) and resuspended in 100 μL FC buffer containing a 1:200 dilution of Alexa488-conjugated goat anti-Mouse IgG (Jackson ImmunoResearch) and incubated on ice for 30 min. Cells were then washed two times with ice cold FC buffer and resuspended in 100 μL FC buffer and 50 μL of 4% paraformaldehyde. Binding of the labeled secondary antibody was monitored by flow cytometry (Biogen Idec Research core facility).

Cell adhesion assay. A 96-well microtiter plate was coated with 50 μL/well of 0.5 μg/mL LAP diluted in 50 mM sodium bicarbonate, pH 9.2 at 4° C. overnight. The plate was washed twice with PBS (100 μL/well), blocked with 1% BSA in PBS (100 μL/well) for 1 h at 25° C., and washed twice with 100 μL/well of assay buffer (50 mM Tris, pH 7.5, 150 mM NaCl, 1 mM $CaCl_2$, 1 mM $MgCl_2$). 12 MBr6 or 4 MBr5 cells ($4\text{-}12\times10^6$ cells/mL) were incubated with 2 μM fluorescent dye (BCECF-AM, Molecular Probes) in assay buffer with gentle shaking in a 37° C. water bath for 15 min, collected by centrifugation, and resuspended in assay buffer to $4\text{-}12\times10^6$ cells/mL. To individual wells of the washed plate were added 25 μL of 2× concentrated m3G9 and 25 μL of labeled cells, and the plate was incubated at 25° C. for 0.5 h. The plate was washed 4-6 times with assay buffer (100 μL/well) and the fluorescence due to captured cells on the plate was recorded on a 96-well fluorescence plate reader (CytoFluor Series 4000, Perseptive Biosystems). Percent binding was determined by comparing the fluorescence prior to the final wash step (i.e. total cells added) to that after washing (i.e. bound cells).

Coculture assay. TMLC (mink lung epithelial cell line Mv 1 Lu stably transfected with a portion of the plasminogen-activator inhibitor 1 protein)[4] were grown in DMEM+10% fetal bovine serum with 2 mM L-glutamine, penicillin-streptomycin and 200 μg/mL G418. Cells were lifted from flasks with PBS+5 mM EDTA, washed in PBS+0.1% BSA, counted by hemocytometer and plated in 96-well plates. αvβ6-expressing cells were stored on ice for 2 h while TMLC were plated in 96-well plates at $10^4$ cells/well in DMEM+0.1% FBS and allowed to adhere at 37° C., after which bound TMLC were washed once with DMEM+0.1% BSA. Monoclonal antibodies were diluted in DMEM+0.1% BSA added to the αvβ6-expressing cells and pre-incubated for 20 min at room temperature. The αvβ6-expressing cells were then added to the TMLC at $4\times10^4$/well in DMEM+0.1% BSA (100 uL/well). Plates were incubated for 20 h at 37° C. in a humidified, $CO_2$-enriched incubator. Supernatant was discarded and replaced with 100 μL PBS+1 mM $Ca^{+2}$ and 1 mM $Mg^{+2}$. Cells were lysed and luciferase was detected with a LucLite kit (Perkin Elmer Life Sciences, Boston, Mass.) using a microplate luminometer (Tropix TR717 microplate luminometer, Perkin Elmer Life Sciences).

Figure 23:
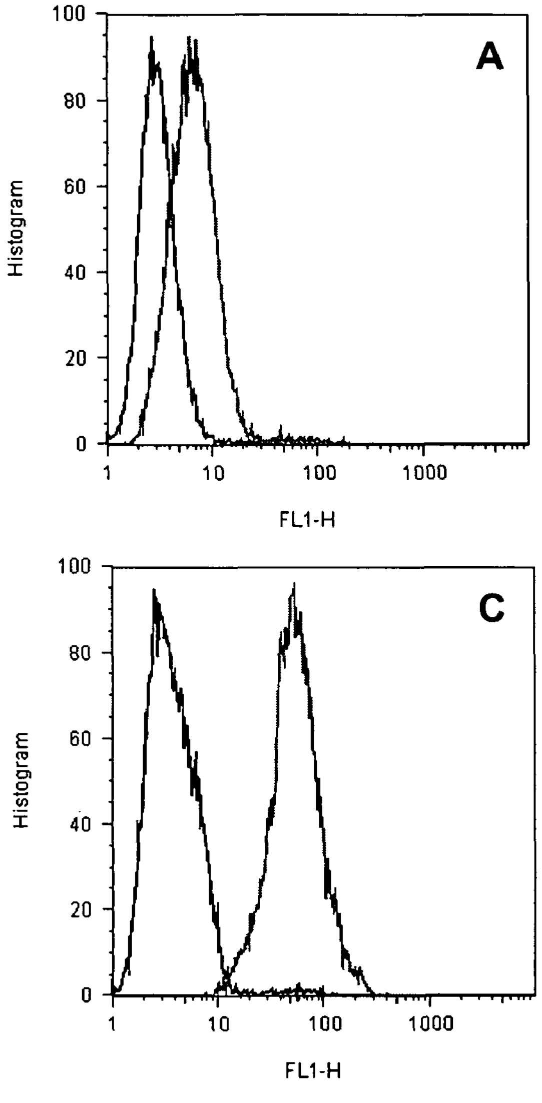
FIGS. 23A-23D are histograms from fluorescence-activated cell sorter (FACS) analysis of various cell lines treated with murine 3G9 mAb or a control mAb, and demonstrating the level of binding of m3G9 to NHP $\alpha_v\beta_6$-expressing cell lines (A, Vero; B, LLC-MK2; C, 12 MBr6; D, 4 MBr5).

Results:

1. Binding affinity and blocking potency of mouse 6.3G9 (m3G9) for primate αvβ6 integrin. In order to study the affinity of m3G9 for non-human primate (NHP) αvβ6 integrin, four NHP cell lines were obtained from ATCC. An initial screen (FIG. 23) indicated that αvβ6 expression was highest on the 12 MBr6 and 4 MBr5 cell lines, so these two lines were used for the characterization of m3G9. An αvβ6 non-blocking antibody, 6.4B4, also bound to 12 MBr6 and 4 MBr5 with a similar mean fluorescence intensity as observed for m3G9.

Figure 24:
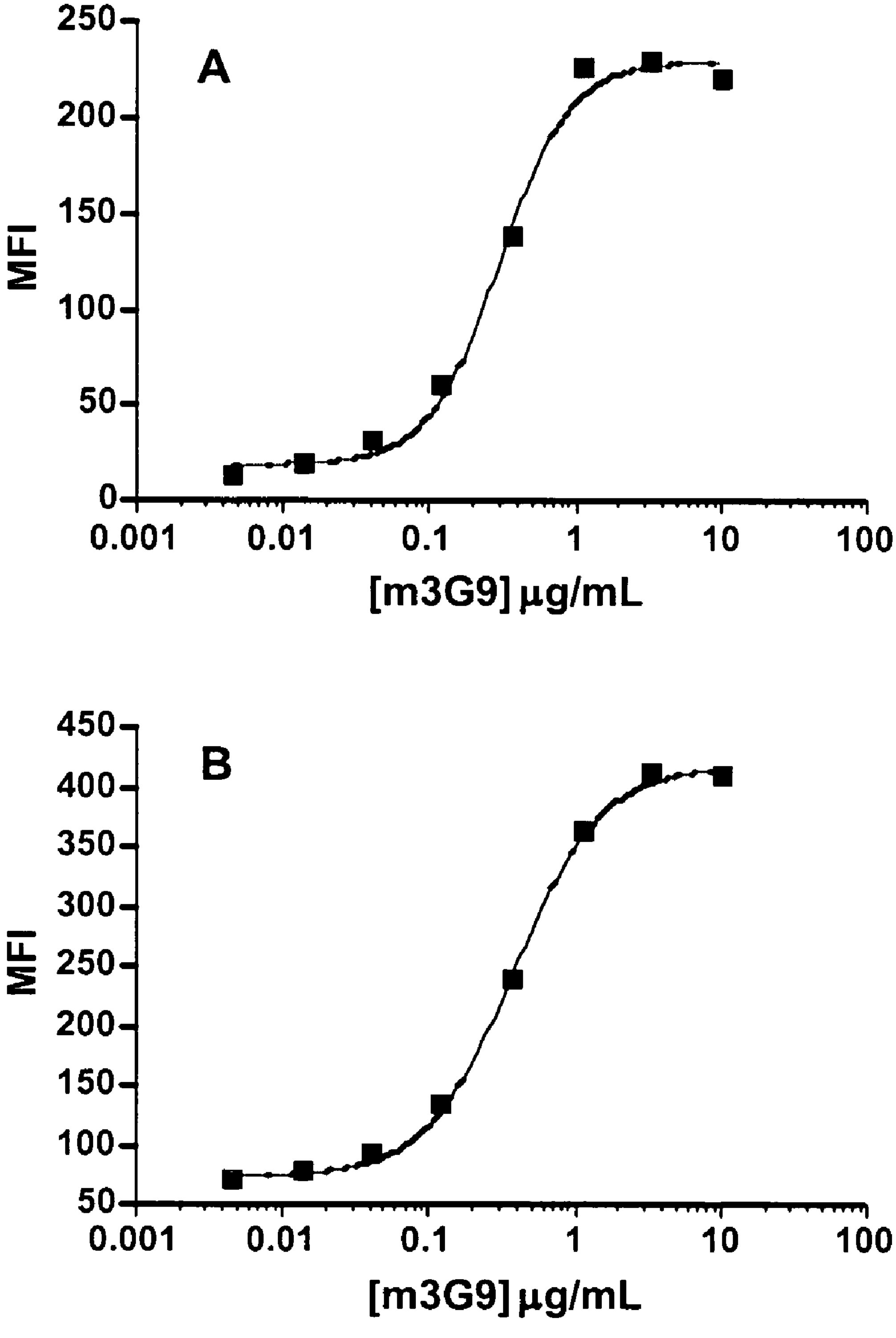
FIGS. 24A-24B are titration curves demonstrating the level of binding of murine 3G9 to NHP $\alpha_v\beta_6$-expressing cell lines (A, 12 MBr6; B, 4 MBr5).

1.1 Binding to cell-expressed integrin (FACS). The binding of m3G9 to 12 MBr6 and 4 MBr5 was measured using fluorescence-activated cell sorting (FACS) as described in Materials and Methods. A full titration of m3G9 was performed on each cell line, and an $ED_{50}$ (concentration of antibody giving a half-maximal signal) was determined using non-linear regression. The $ED_{50}$ values for 12 MBr6 and 4 MBr5 were 0.30 μg/mL (FIG. 24A) and 0.38 μg/mL (FIG. 24B), respectively.

Figure 25:
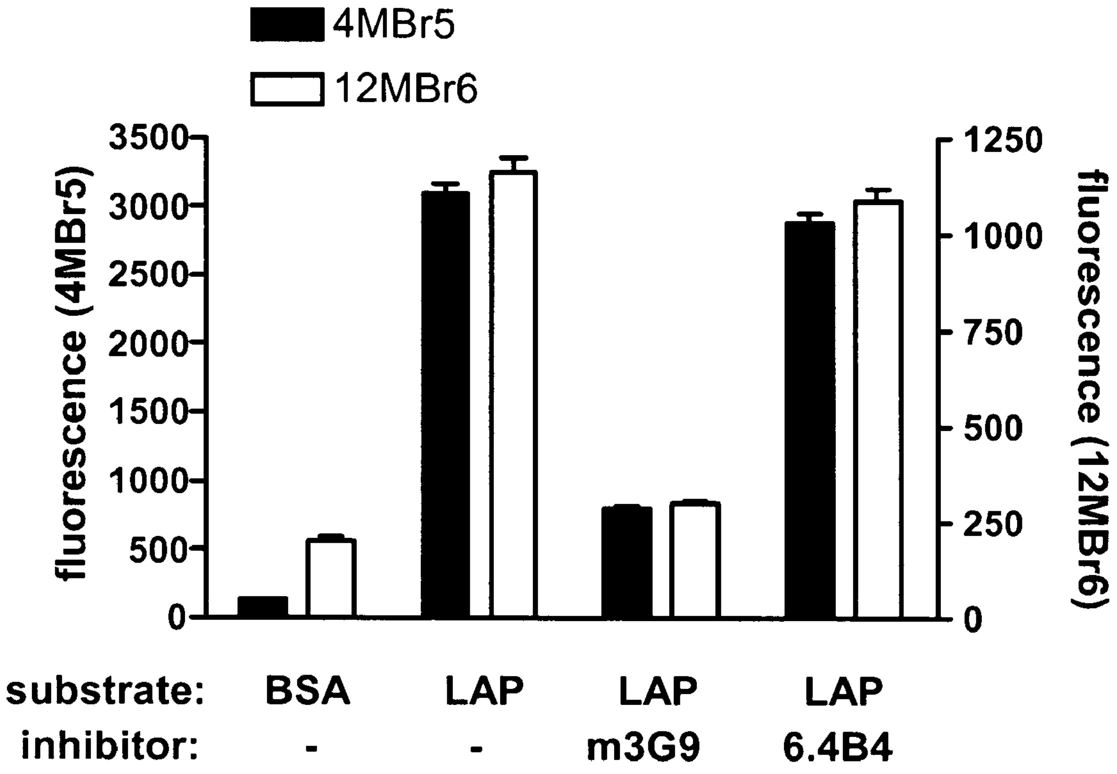
FIG. 25 is a bar graph demonstrating the adhesion of NHP $\alpha_v\beta_6$-expressing cell lines to LAP (A, 12 MBr6; B, 4 MBr5).

1.2 Cell Adhesion to LAP. The abilities of 12 MBr6 and 4 MBr5 to bind to LAP were demonstrated using a cell adhesion assay. This adhesion was blocked by m3G9, but not by a control protein (BSA) or by an αvβ6 non-blocking antibody (6.4B4) (FIG. 25). The potency of m3G9 to block this interaction was evaluated by measuring the concentration dependence of inhibition on each cell line (FIG. 26). From these experiments, an $IC_{50}$ (concentration of antibody giving half-maximal inhibition) was determined. The $IC_{50}$ values for 12 MBr6 and 4 MBr5 were 0.22 μg/mL and 0.29 μg/mL, respectively.

Figure 27:
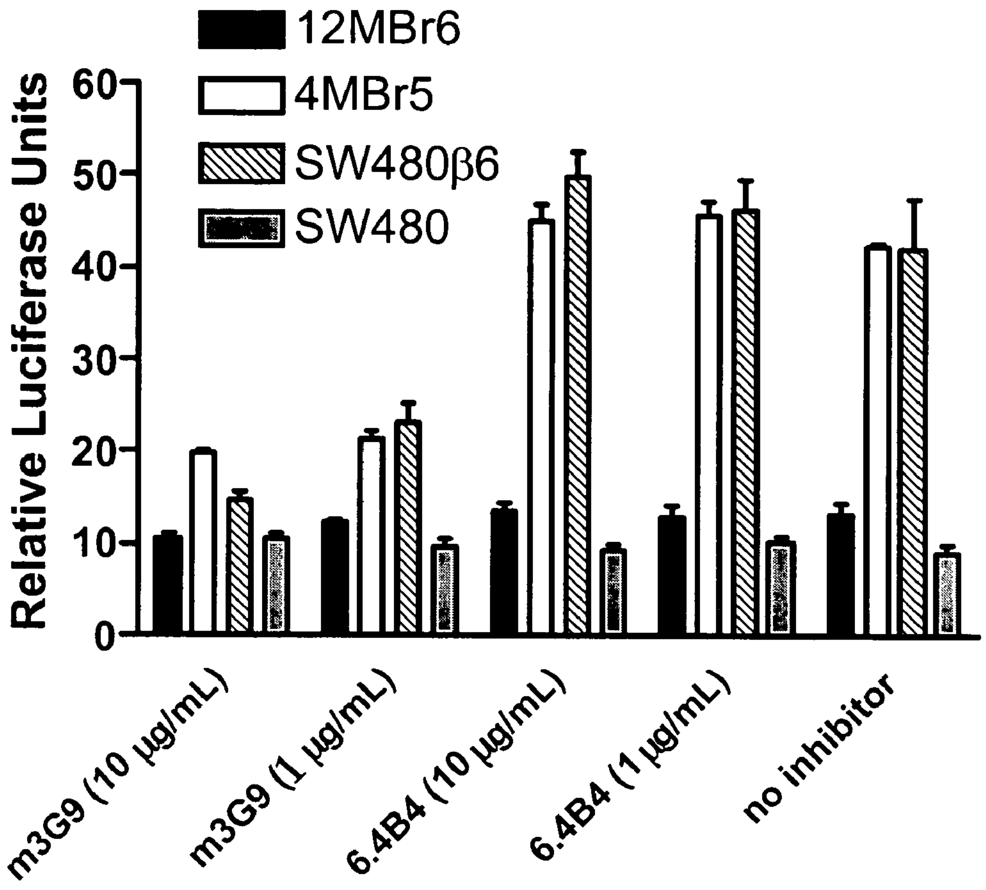
FIG. 27 is a bar graph demonstrating the activation of latent TGFβ by human and primate $\alpha_v\beta_6$-expressing cell lines.

1.3 TGFβ Activation (Coculture Assay). The abilities of 12 MBr6 and 4 MBr5 to activate latent TGFβ were determined using a coculture assay, in which cells are incubated with TGFβ responsive mink lung epithelial reporter cells stably expressing a portion of the plasminogen activator inhibitor 1 promoter (TMLC) (FIG. 27). Expression of αvβ6 is not sufficient to promote TGFβ activation, since differences in intracellular signaling and/or the production of latent TGFβ will also impact activity in this assay. Of these two cell lines, only 4 MBr5 was effective at activating latent TGFβ, while 12 MBr5 showed no effect. Activation was also observed using the positive control cell line SW480β6, a β6-transfected human colon carcinoma cell line stably expressing human αvβ6. The untransfected parental control cell line (SW480) showed no activation, as expected.

Figure 28:
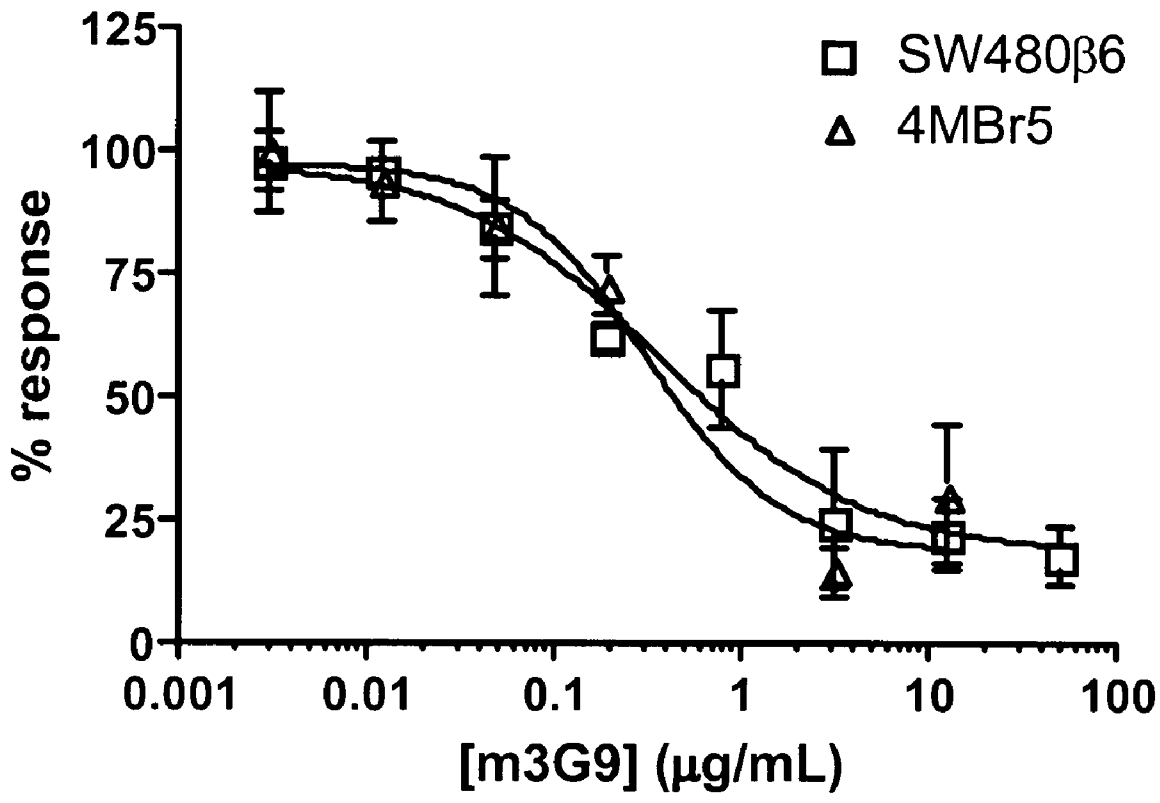
FIG. 28 is a titration curve demonstrating the inhibition of TGFβ activation by m3G9 on SW480β6 and 4 MBr5 cell lines.

The ability of m3G9 to block TGFβ activation by 4 MBr5 was measured in the same experiment. TGFβ activation was blocked by the addition of m3G9 at either 1 μg/mL or 10 μg/mL, but not by addition of the non-blocking anti-αvβ6 antibody 6.4B4. The inhibitory effect on 4 MBr5 cells of m3G9 at these concentrations was similar to that observed using the SW480β6 cell line. In a separate experiment, the dose dependence of m3G9 inhibition of 4 MBr5-mediated TGFβ activation was determined (FIG. 28). The $IC_{50}$ values for 4 MBr5 and SW4806 were 0.31 μg/mL and 0.37 μg/mL, respectively.

2. Comparison of m3G9 Affinity Across Species. The data generated for binding and activity of m3G9 on mouse, NHP, and human αvβ6 are summarized in the following Table. The first column in the Table shows the binding $ED_{50}$s determined by FACS. In each case the measured $ED_{50}$ was ≦0.38 μg/mL (2.5 nM). The second column in the Table shows the $IC_{50}$ for inhibition of cell adhesion by m3G9. In each case m3G9 blocked cell adhesion with an $IC_{50}$ of ≦0.29 μg/mL (1.9 nM). The third column in the Table shows the $IC_{50}$ for inhibition of αvβ6-mediated TGFβ activation, as determined using the coculture assay. NHP cell line 4 MBr5 showed similar activity to the human cell line SW480β6 ($IC_{50}$ values of 0.40 and 0.24 μg/mL, respectively).

Comparison of m3G9 activity using mouse, NHP and human cell lines

| Species | Cell line | Binding (FACS) $ED_{50}$, μg/mL | Cell Adhesion $IC_{50}$, μg/mL | Coculture $IC_{50}$, μg/mL |
|---|---|---|---|---|
| mouse | NIH3T3β6 | 0.30[a] | n.d.[b] | n.d. |
| | FDC-P1β6 | n.d. | 0.02[a] | n.d. |
| NHP | 4MBr5 | 0.30 | 0.22 | 0.31 |
| | 12MBr6 | 0.38 | 0.29 | n.d. |
| human | SW480β6 | 0.05[a] | 0.03 | 0.37 |
| | Detroit562 | n.d. | 0.04 | n.d. |
| | SCC-14 | n.d. | 0.16 | n.d. |

[a]ref. 1
[b]n.d., not determined

3. References

1. Weinreb, P. H. et al., J. Biol. Chem., 2004, 279, 17875-87.

2. Arend, L. J. et al., *J Am. Soc. Nephrol.* 2000, 11, 2297-305.

3. Wada, J. et al., *J. Cell Biol.,* 1996, 132, 1161-76.

4. Abe, M. et al, *Anal. Biochem.,* 1994, 216, 276-84.

Example 13

Effects of Murine Anti-$\alpha_v\beta_6$ mAbs in Alport (Col4A3−/−) Mice

SUMMARY: αvβ6 is a TGF-β-inducible integrin that is preferentially expressed at sites of epithelial remodeling and has been shown to bind and activate latent precursor TGF-β. Herein, we show that αvβ6 is overexpressed in human kidney epithelium in membranous glomerulonephritis, diabetes mellitus, IgA nephropathy, Goodpasture, and Alport renal epithelium. To assess the potential regulatory role of αvβ6 in renal disease, we have studied effects of function blocking αvβ6 mAbs and genetic ablation of the β6 subunit on kidney fibrosis in Col4A3−/− mice, a mouse model of Alport syndrome. Expression of αvβ6 in Alport mouse kidneys was observed primarily in cortical tubular epithelial cells and correlated with the progression of fibrosis. Treatment with αvβ6-blocking mAbs inhibited accumulation of activated fibroblasts and deposition of interstitial collagen matrix. Similar inhibition of renal fibrosis was observed in β6-deficient Alport mice. Transcript profiling of kidney tissues showed that αvβ6 blocking mAbs significantly inhibited disease-associated changes in expression of fibrotic and inflammatory mediators. Similar patterns of transcript modulation were produced with recombinant soluble TGF-β RII treatment suggesting shared regulatory functions of αvβ6 and TGF-β. These findings demonstrate αvβ6 can contribute to the regulation of renal fibrosis and suggest this integrin as a potential therapeutic target.

Introduction:

Progressive fibrosis is a common process leading to the development of end stage renal disease and promoted by epithelial remodeling, fibroblast activation, inflammation, and reorganization of cellular interactions with the extracellular matrix (ECM). Molecular mechanisms contributing to these events are complex and include misregulation of the TGF-β axis, aberrant ECM remodeling, and altered expression and function of cell adhesion receptors of the integrin superfamily[1-5]. Recent studies have revealed important regulatory functions of several integrins and associated molecules in renal epithelial and mesenchymal cells[3,6-8].

Among the integrins whose expression is strongly increased in renal disease is the TGF-β-inducible integrin αvβ6[5,9,10]. αvβ6 expression is generally restricted to epithelial cells where it is expressed at low levels in normal adult tissues and elevated during development, injury, and neoplasia[9,11-13]. Although αvβ6 is expressed at relatively low levels in healthy adult kidney, its expression is prominent in the developing mouse kidney, particularly in the proximal tubules, loop of Henle, and collecting ducts[11,12,14]. Recently, elevated expression of αvβ6 has been reported for various forms of human kidney pathology[10].

Consistent with the increased expression of αvβ6 in vivo during tissue remodeling, expression of the αvβ6 integrin in cultured epithelial cells can be induced by cytokines that regulate epithelial remodeling, including EGF and TGF-β[5,9]. Moreover, overexpression of β6 in the skin of transgenic mice has been shown to provoke formation of spontaneous chronic wounds[15] suggesting that αvβ6 may play an important role in regulating epithelial tissue remodeling.

Known ligands for αvβ6 include fibronectin, tenascin, and the latency associated peptides 1 and 3 (LAP1 and LAP3), the N-terminal fragments of the latent precursor forms of TGF-β1 and β3[16-19]. As a result of binding to these ligands, αvβ6 can mediate cell adhesion, spreading, migration, and activation of latent TGF-β. TGF-β is synthesized as a latent protein that is cleaved and secreted with the N-terminal LAP non-covalently associated with the mature active C-terminal TGF-β cytokine. The latent TGF-β complex cannot bind to its cognate receptor and thus remains biologically inactive until converted to the active form by one of several alternative mechanisms that include cleavage by proteases, exposure to low pH or ionizing radiation, and conformational changes in the latent complex allowing it to bind to its cognate receptors[20-22]. An activating conformational change can be induced by αvβ6 involving direct binding of the integrin to an RGD motif contained within LAP1 and LAP3. This binding converts the TGF-β precursor into a receptor binding-competent state. These findings suggest that upregulation of αvβ6 expression on the surface of epithelial cells can lead to local TGF-β activation followed by paracrine activation of TGF-β-dependent events in bystander cells. This would include the possibility for indirect downstream effects on TGF-β activity that could be mediated by altering inflammation and fibrosis initially at sites of αvβ6 expression.

Since TGF-β has been implicated as a central regulator of renal fibrosis, we hypothesized that its local activation by αvβ6 may be an important process in the onset and progression of renal disease and blockade of αvβ6 function could suppress the development of kidney fibrosis. In the studies described herein we show that αvβ6 is highly upregulated in a mouse model of kidney fibrosis and in human kidney samples with fibrotic pathology. Using Col4A3−/− mice, a model of progressive kidney disease similar to that observed in the human Alport syndrome, we show that mAbs blocking the ligand binding and TGF-β activation functions of αvβ6, as well as genetic ablation of β6, potently inhibit both glomerular and tubulointerstitial fibrosis and delay destruction of kidney tissue architecture. We show that although the αvβ6 integrin has restricted expression in the kidney to tubular epithelial cells it can provide protective effects at distal sites in the tissue. These findings raise the possibility that the anti-fibrotic effects may also be mediated through indirect extrarenal effects in addition to direct effects of blocking αvβ6 on tubular epithelial cells. Delayed treatment studies indicate that therapeutic blockade of αvβ6 not only inhibits the progression of kidney fibrosis but has the potential to allow resolution of existing fibrotic lesions. Our analysis of molecular signatures associated with kidney disease progression and affected by αvβ6 inhibition indicates that the therapeutic impact of the αvβ6 blocking antibodies is similar to that of systemic TGF-β blockade and is mechanistically related to decreased TGF-β activity. These data suggest that αvβ6 is involved in the regulation of renal fibrosis and could provide a novel molecular target for its therapeutic modulation.

Materials and Methods:

1. Reagents. αvβ6 mAbs were generated as described herein and as previously described[23]. Human/mouse chimeric 2A1 and 3G9 cDNAs were generated from the respective parent hybridoma total RNAs with constant region primers CDL-739 for the heavy chain and CDL-738 for the light chain using the First Strand cDNA synthesis kit (Amersham/Pharmacia, Piscataway, N.J.). The heavy and light chain variable region genes were amplified by the polymerase chain reaction using the same 3' primers used for cDNA synthesis and pools of degenerate primers specific for most murine antibody gene signal sequences (sequences available upon request) and Pfu DNA polymerase (Stratagene, La Jolla Calif.). Cloned heavy and light chain variable regions were ligated into mammalian expression vectors with human IgG1 constant regions. Recombinant soluble murine TGF-β receptor type II-Ig fusion protein (rsTGF-βRII-Ig) was generated as previously described 7 and purchased from R&D Systems (532-R2, Minneapolis, Minn.). Antibodies were purchased as indicated. FITC conjugated pan anti-cytokeratin mAb (C-11), Sigma-Aldrich (F3418, St. Louis, Mo.); anti-laminin B1 chain mAb (LT3), Chemicon (MAB1928, Temecula, Calif.); phycoerythrin (PE) conjugated anti-αv mAb (RMV7), Chemicon (CBL1346P); rabbit anti-αv, Chemicon (AB1930); PE-rat IgG1, BD Biosciences (553925, San Jose, Calif.); and anti-smooth muscle actin (SMA)-Cy3, Sigma-Aldrich (C-6198). We identified rabbit polyclonal anti-TGF-β, Santa Cruz Biotechnology (sc-146, Santa Cruz, Calif.) as an antibody that preferentially binds xenograft sections of 293 cells expressing a constitutively active form of TGF-β compared to xenografts sections of 293 cells expressing latent TGF-β[24].

2. Animals. Col4A3+/− mice in a 129Sv/J background were obtained from Dr. Dominique Cosgrove (Boy's Town National Research Hospital, Omaha, Nebr.) and bred to generate Col4A3−/− mice for injection studies. Beta6−/− mice in an 129SV background were obtained from Dr. Dean Sheppard (University of California San Francisco, Calif.) and crossed with Col4A3+/− mice. All animals were housed at Biogen Idec and all animal studies were approved and carried out in accordance with the Institutional Animal Care and Use Committee.

3. Flow Cytometry. Murine β6 stable transfected NIH3T3 cells (NIH3T3b6) were generated as previously described[23]. Cells were harvested by trypsinization, washed in PBS, and resuspended in FC buffer (1×PBS, 2% FBS, 0.1% $NaN_3$, 1 mM $CaCl_2$, and 1 mM $MgCl_2$). $0.2\times10^5$ cells were incubated on ice for 1 h in FC buffer containing purified primary antibodies in a total volume of 100 μl. After incubation, cells were washed two times with ice-cold FC buffer and resuspended in 100 μl FC buffer containing 5 μg/ml PE-conjugated donkey anti-mouse IgG (Jackson ImmunoResearch) and incubated on ice for 30 min. For monitoring αv expression, cells were incubated with a PE-conjugated rat anti-mouse αv mAb (RMV-7) and a PE conjugated rat IgG1 control. Cells were washed two times with ice-cold FC buffer and binding of the labeled secondary antibody was monitored by flow cytomery.

Immunohistochemistry. Tissue sections were deparaffinized in xylene and ethanol, rehydrated in distilled water, and then immersed in methanol containing 0.45% $H_2O$. Tissues were incubated with pepsin (00-3009, Zymed, San Francisco, Calif.) and blocked with avidin and biotin (SP-2001; Vector Laboratories, Burlingame, Calif.). Primary antibody was diluted in PBS containing 0.1% BSA and tissues were incubated overnight at 4° C. For immunostaining β6 on mouse tissue, sections were incubated with a human/mouse chimeric form of the anti-αvβ6 mAb, 2A1[23], and an anti-human biotinylated secondary antibody (PK-6103, Vector Laboratories, Burlingame, Calif.). For immunostaining β6 on human tissue, sections were incubated with murine 2A1[23], and an anti-mouse-biotinylated secondary antibody (PK-6102, Vector Laboratories). Avidin-biotin complex-horseradish peroxidase (Vector Kit, PK-6102) was applied to sections, incubated for 30 minutes at room temperature, and 3,3'-diaminobenzidine (DAB) substrate was prepared as directed (SK-4100, Vector Laboratories) and applied to sections for 5 min at room temperature. Tissue sections were stained with Mayer's Hematoxylin for 1 minute and rinsed in water and PBS.

Frozen tissue sections embedded in O.C.T. Compound (Cat.#4583, Sakura Tokyo, Japan) were fixed in acetone and blocked with 0.5% casein/0.05% thimerosal in PBS. For immunostaining β6 on human tissue, sections were incubated with murine 2A1[23] and an anti-mouse Alexa fluor 594 secondary antibody (A-11032, Molecular Probes Eugene, Oreg.). For immunostaining β6 on mouse tissue, sections were incubated with a human/mouse chimeric form of 2A1 and an anti-human Alexa fluo 594 conjugated secondary antibody (A-11014, Molecular Probes). For laminin and αv immunostaining, an anti-rat Alexa fluor 488 conjugated secondary antibody (A-1006, Molecular Probes) was used. All other antibodies were directly conjugated as indicated previously. All images were taken at 20× with the exception of FIG. 2A which was taken at 40×. All human tissue samples were obtained under approval of local institutional review and patient approval.

5. Quantification of immunohistochemistry. SMA immunostaining was quantitated using MetaMorph v5.0 (Universal Imaging Corporation, Sunnyvale, Calif.) and expressed as percent positive relative to total image size. For each animal, 20× images from at least 5 cortical and 1 to 2 medullary sections were analyzed. Statistical analysis of treatment groups was carried out using ANOVA.

6. Treatment of Col4A3−/− mice with mAbs and rsTGF-βRII-Ig. Col4A3+/− mice in a 129Sv/J background were bred to generate Col4A3−/− mice. Mice were injected intraperitoneally with proteins three times a week from 3 weeks of age to 7 or 8.5 weeks of age, as indicated. MAbs were injected intraperitoneally at 4 mg/kg and rsTGF-βRII-Ig was injected at 2 mg/kg. Mice were euthanized and kidneys collected for RNA and immunostaining. All animal studies were approved and carried out in accordance with the Institutional Animal Care and Use Committee.

7. Total RNA purification and cDNA synthesis. Kidneys were homogenized directly into TRIzol (155-96-018, Invitrogen, Carlsbad, Calif.) and RNA extracted according to manufacturer's protocol with an additional 1 ml acidic phenol:chloroform:isoamyl alcohol 25:24:1 pH 6.6 extraction. Purified total RNA was resuspended in diethylpyrocarbonate (DEPC) treated $H_20$ (Ambion Inc, Austin, Tex.) and 260 and 280 recorded (Spectra max Plus, Molecular devices, Sunnyvale, Calif.). Residual DNA was removed using 5 units DNase I amplification grade (cat#18068-015, Invitrogen) at 20° C. for 15 min. cDNA was generated using a high capacity cDNA archive kit according to manufacture's protocol (cat#4322171, Applied Biosystems Inc, Foster City, Calif.).

8. Design of primers, probes, and oligonucleotide standard templates for Taqman. Oligonucleotide primers and Taqman MGB probes were designed from Affymetrix consensus sequences using Primer Express version 2.0.0 (Applied Biosystems Inc.). Taqman MGB probes were designed with a 5' covalently linked fluorescent reporter dye (FAM) and a minor groove binder/ non-fluorescent quencher (MGBNF) covalently linked to the 3' end. Oligonucleotide standard templates were designed by the addition of 10 by of gene specific sequence to the 5' and 3' ends of the amplicon. Reverse phase HPLC purified primers and oligonucleotide standard templates were purchased from Biosearch technologies Inc., Novato, CA. HPLC purified primers and probe for murine glyceraldehyde-3-phosphate dehydrogenase (GAPDH) were synthesized at Biogen Idec [CATGGCCTTCCGTGTTCCTA (SEQ ID NO: 147), GCGGCACGTCAGATCC (SEQ ID NO: 148), 6FAM-CCCCAATGTGTCCGTC (SEQ ID NO: 149).

9. Taqman thermal cycling. Quadruplicate PCR reactions for samples and standards were cycled in a 7900HT (Applied Biosystems Inc.) thermal cycler under the following conditions: 50° C. for 2 min (uracil N-deglycosylase digest), 95° C. 10 min (activation of Taq thermostable polymerase), and 40 cycles of 95° C. for 15 s and 60° C. for 60 s. The fluorescence emission was collected every 7 s for the length of the run for each reaction well. Relative transcript quantities were determined for each sample by comparison to oligonucleotide standard curve using Sequence Detection Software (Applied Biosystems Inc.)

10. Probe labeling, hybridization and scanning for transcript profiling. Sample labeling, hybridization, and staining were carried out according to the Eukaryotic Target Preparation protocol in the Affymetrix Technical Manual (701021 rev 1) for Genechip® Expression Analysis (Affymetrix, Santa Clara, CA). In summary, 5 μis of purified total RNA was used in a 20 μL first strand reaction with 200 U SuperScript II (cat #, 18064-022, Invitrogen) and 0.5 ug (dT)-T7 primer [5'-GGCCAGTGAATTGTAATACGACTCACTATAGGGAGGCGG$(T)_{24}$] (SEQ ID NO: 150) at 42° C. for 1 h. Second strand synthesis was carried out by the addition of 40 U *E. coli* DNA Polymerase (cat # 18010-025, Invitrogen), 2 U *E. coli* RNase H (cat #18021-071, Invitrogen) and 10 U *E. coli* DNA Ligase (cat # 18052-019, Invitrogen) followed by incubation at 16° C. for 2 h. The second strand synthesis reaction was purified using the Genechip® Sample Cleanup Module according to the manufacturer's protocol (cat #900371, Affymetrix, Santa Clara, CA). Purified cDNA was amplified using BioArray high yield RNA transcription labeling kit (cat #42655-40, Enzo Life Sciences, Inc., Parmingdale, NY) according to manufacturer's protocol to produce 70-120 μg of biotin labeled cRNA (compliment RNA). Mouse MgU74Av2, MgU74Bv2, and MgU74Cv2 GeneChip® probe arrays were pre-hybridized in a GeneChip® Hybridization Oven 640 (Affymetrix, Santa Clara, CA) according to the manufacturer's protocol. Fragmented labeled cRNA was resuspended in 300 μL 1× hybridization buffer containing 100 mM 2-morpholinoethanesulfonic acid, 1 M [Na+], 20 mM EDTA, 0.01% Tween 20, 0.5 mg/mL Acetylated BSA, 0.1 mg/mL herring sperm DNA, control oligo B2, and control transcripts bioB 1.5 pM, bioC 5 pM, bioD 25 pM, and cre 100 pM, and hybridized to Genechip® probe arrays according to manufacturer's protocol (Affymetrix, Santa Clara, CA). The hybridized GeneChip® probe arrays were washed and stained using Streptavidin-Phycoerythrinin (cat # S866, Molecular Probes, Eugene, OR) and amplified with biotinylated anti-streptavidin (BA-0500, Vector Laboratories, Burlingame, CA) using GeneChip® Fluidics Station 400 (Affymetrix, Santa Clara, CA). The GeneChip® probe arrays were scanned using GeneArray Scanner (Hewlett Packard, Corvallis, OR).

11. Transcript profiling data analysis. The array scans were converted into Affymetrix .CEL files and the resulting data set (group of .CEL files representing the complete experiment) was normalized using the Robust Microarray Average (RMA) method. Statistical and clustering analyses were done using the GeneSpring (Agilent) and Spotfire (Spotfire) data mining tools. We used a two-step ANOVA and fold-change filtering to identify probe-sets whose signal intensity was altered by experimental treatment compared to the untreated Col4a3-/- group at $p<0.05$ and at least 2-fold. Similarly, disease-associated transcripts were selected for differential expression between the untreated Col4a3-null and the naive wild type groups using the statistical cutoff of $p<0.01$ and the signal fold-change cutoff of 2. The profiles of the resulting group of genes and the grouping of experimental conditions were analyzed and visualized by hierarchical clustering. Virtual pathway analysis was performed using the Ingenuity Pathway Analysis database (Ingenuity Systems).

Figure 29:
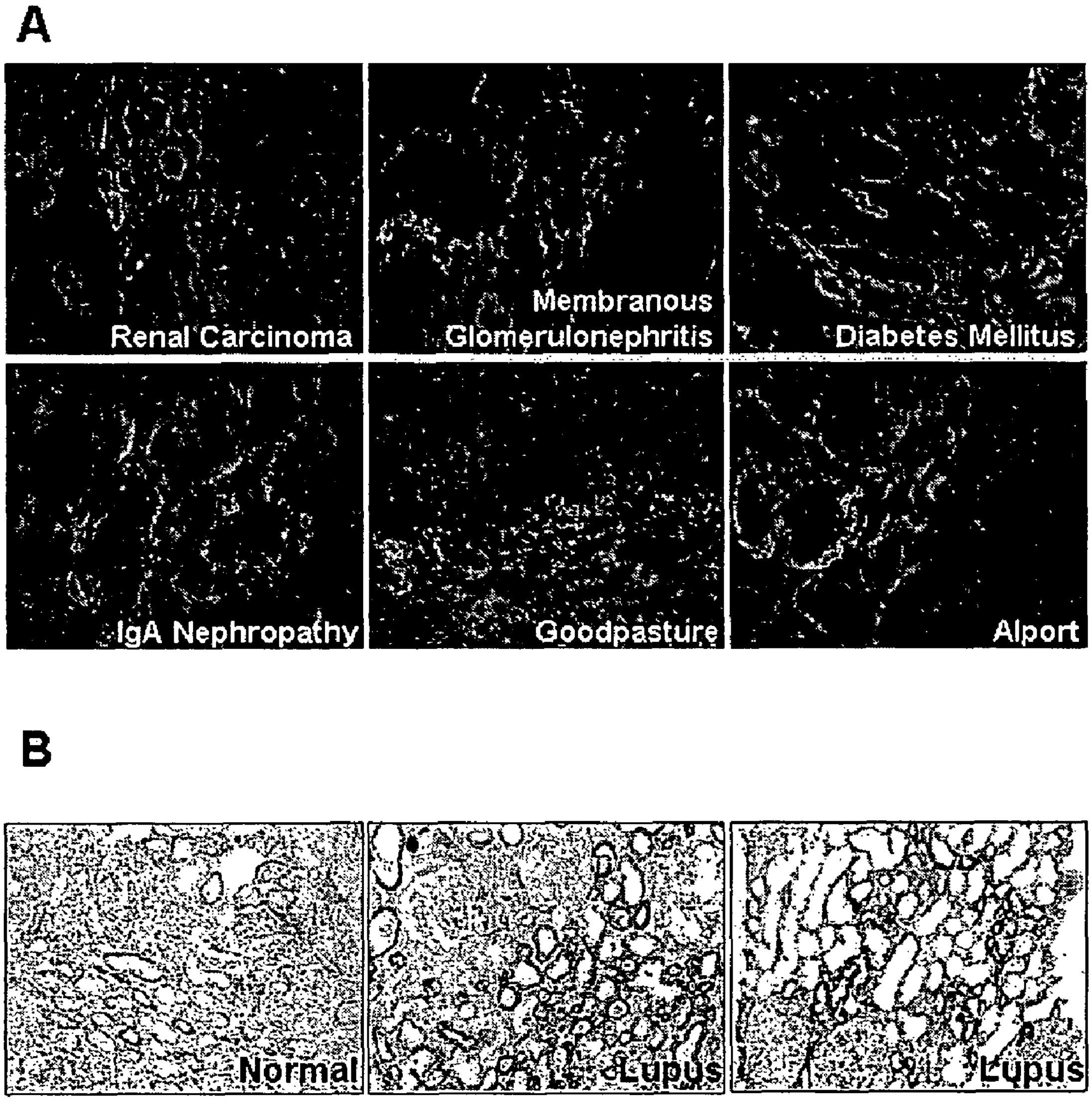
FIG. 29 is a series of photomicrographs demonstrating $\alpha_v\beta_6$ immunostaining in human kidney disease. (A) Frozen human kidney sections immunostained with an $\alpha_v\beta_6$ mAb (red) and a pan-cytokeratin mAb (green). (B) Paraffin embedded human kidney sections immunostained with an $\alpha_v\beta_6$ mAb.

Results:

1. Expression of αvβ6 in human kidney samples with fibrotic pathology. Several different types of human kidney disease, associated with inflammatory/fibrotic pathology, have shown a corresponding increased expression of TGF-β in the kidney tissue[25-27]. Using immunohistochemical analysis we examined the expression of αvβ6 in human kidney biopsy samples associated with chronic inflammation and fibrosis as a potential mechanism leading to increased activation of TGF-β (FIGS. 29A and 29B). Tissue samples from membraneous glomerulonephritis, diabetes mellitus, IgA nephropathy, Goodpasture, Alport, and Lupus all showed prominent αvβ6 staining in the epithelial lining of dilated and damaged tubules. In contrast, samples of morphologically normal kidneys (renal carcinoma and normal tissue), showed minimal occasional immunostaining in tubules. Glomerular staining was absent in all kidney samples analyzed. This finding is consistent with previous reports that αvβ6 is expressed at low levels in healthy adult epithelium but is upregulated during tissue injury and repair[10,11,13,15,17].

Figures 30A, 30B:
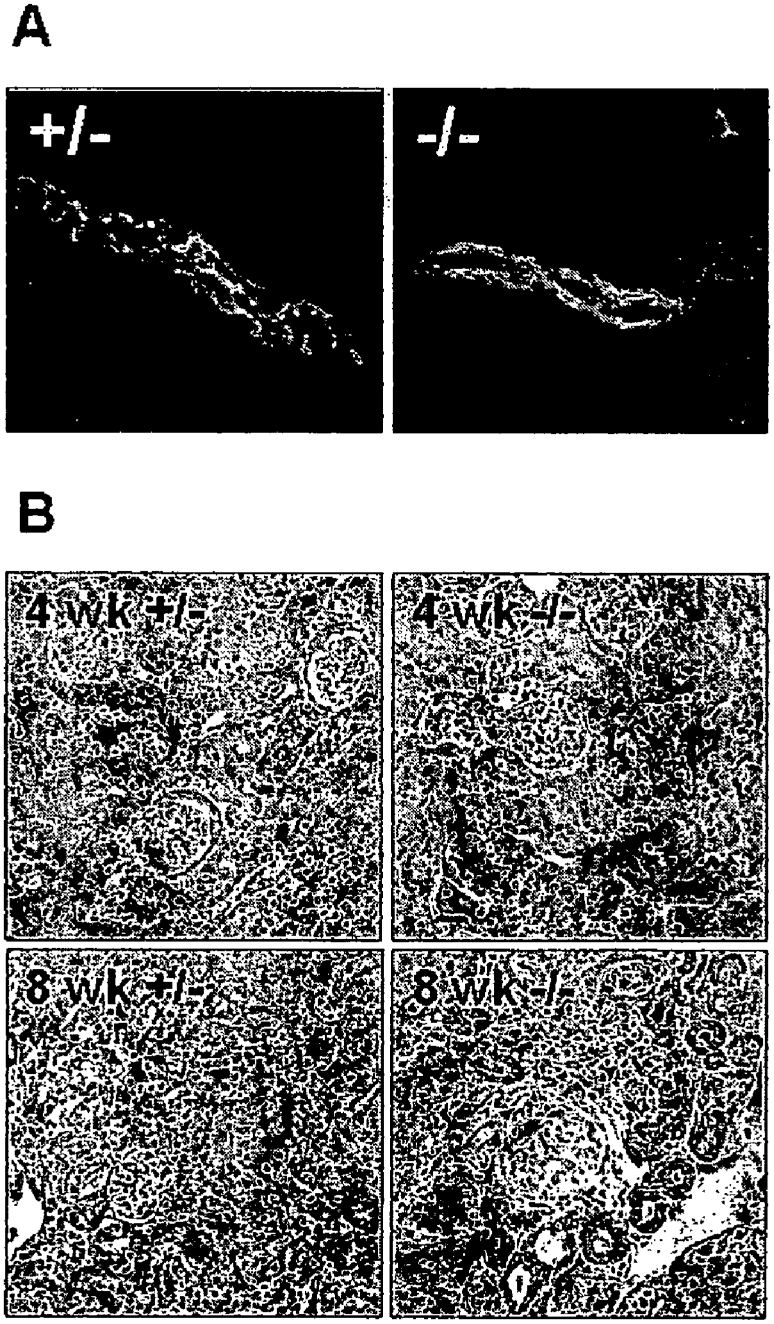
FIG. 30A: photomicrograph of frozen kidney sections from 7 week old Col4A3 +/− mice and Col4A3 −/− mice immunostained with an $\alpha_v\beta_6$ mAb (red) and a pan-cytokeratin mAb (green).
FIG. 30B: Paraffin embedded kidney sections from 4 and 8 week old Col4A3 +/− and Col4A3 −/− mice immunostained with an $\alpha_v\beta_6$ mAb.
Figure 30C:
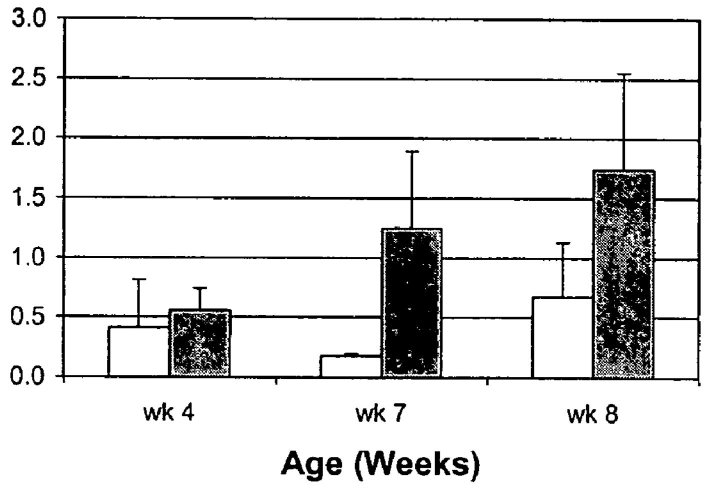
FIG. 30C: bar graph demonstrating quantitation of $\alpha_v\beta_6$ immunostaining in kidneys from 4, 7, and 8 week old Col4A3 +/− and Col4A3 −/− mice (n=3).

2. Expression of αvβ6 in the kidneys of Col4A3-/- mice correlates with progression of kidney fibrosis. Col4A3-/- mice, a mouse model of human Alport disease, develop progressive glomerulonephritis leading to the accumulation of ECM in both the glomerular and interstitial regions of the kidney accompanied by increased expression of a number of standard markers of fibrosis[28,29]. It has been previously reported that treatment of Col4A3-/- mice with rsTGF-βRII-Ig leads to inhibition of kidney fibrosis [7]. Kidneys from Col4A3-/- mice begin to show histological signs of fibrosis at approximately 5 to 6 weeks of age. The disease progresses rapidly with age and the mice die of renal failure at approximately 11 weeks. Heterozygous Col4A3+/- mice do not develop glomerulonephritis and their kidneys are histologically indistinguishable from those of wild-type littermates. To examine the dynamics of αvβ6 expression in kidneys of Col4A3+/-, and Col4A3-/- (Alport) mice of increasing age, we performed immunohistochemical analysis of αvβ6 expression in kidneys isolated from 4-, 7-, and 8-week old mice (FIG. 30A-C). At four weeks of age, there was occasional expression of αvβ6 in kidney tubules of both Col4A3+/- and Col4A3-/- mice. By 7 weeks, expression of αvβ6 was markedly increased in tubular epithelial cells of Col4A3-/- mice but not in the Col4A3+/-kidneys. This increased expression of αvβ6 was persistent in the Col4A3-/- mice beyond 8 weeks of age. We also observed an increase in the intensity of αvβ6 staining in the epithelial cells of dilated and damaged tubules in Col4A3-/- (Alport) mice after 6 weeks of age, which was accompanied by a significant increase in the area of kidney tissue displaying strong αvβ6 expression. The increased expression during the 7-8 weeks of age period coincided with rapid progression of kidney fibrosis in Col4A3-/- mice. In contrast, only minimal αvβ6 expression, and a slight detectable age-dependent increase of its intensity of immunostaining, was detected in the kidneys of Col4A3+/- mice throughout the time course. Since the expression of αvβ6 in kidneys of Col4A3-/- mice correlated with progression of fibrosis, we wished to determine whether blockade of αvβ6 function could inhibit the initiation and progression of fibrotic lesions.

Figure 31A:
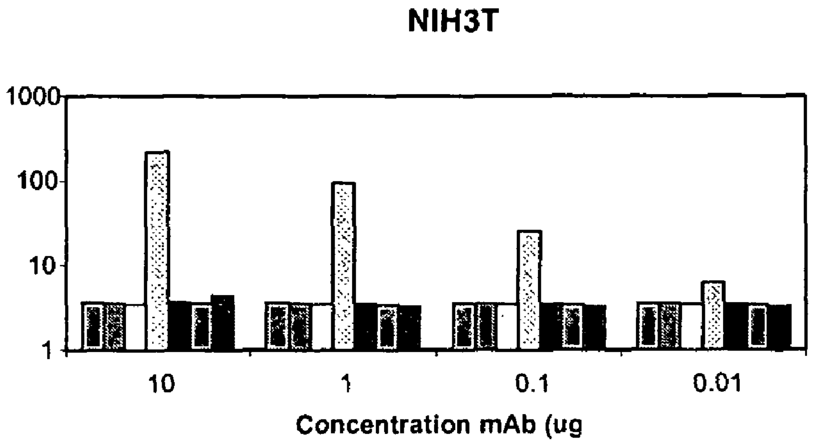
FIG. 31A: Flow cytometry analysis of $\alpha_v\beta_6$ mAbs (3G9, 8G6, 8B3), anti-αv mAb (RMV-7), negative control mAbs (1E6 and MOPC21), and isotype control (rat IgG1) binding to NIH3T3 cells and NIH3T3b6 cells.
Figures 31B, 31C:
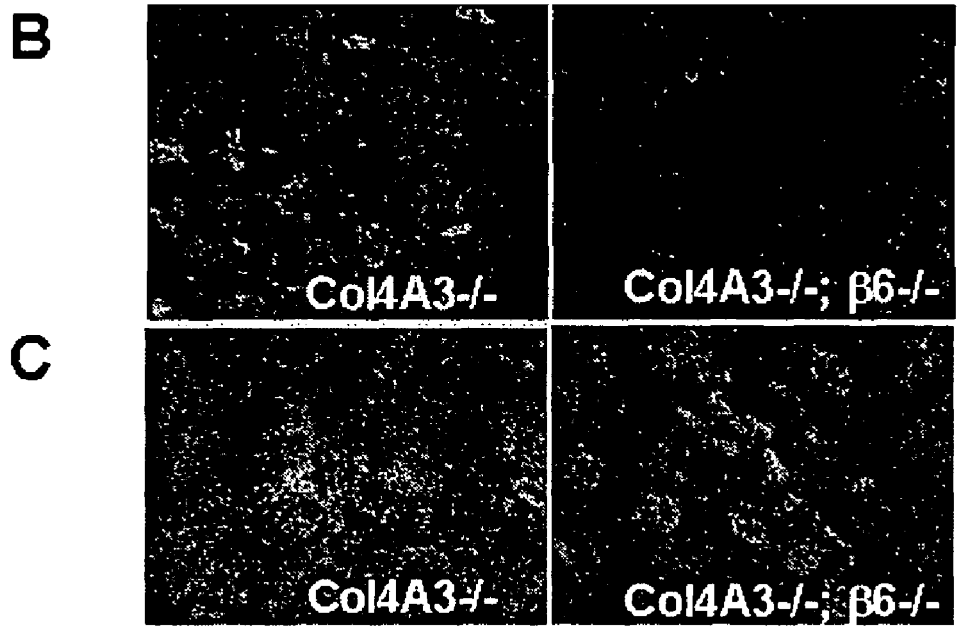
FIG. 31B: immunostaining of Col4A3−/−, and Col4A3−/−; β6−/− kidney sections with anti-$\alpha_v\beta_6$ mAb (human/mouse chimeric 3G9).
FIG. 31C: immunostaining of Col4A3−/−, and Col4A3−/−; β6−/− kidney sections with anti-αv polyclonal antibody.

3. Specificity of mAbs binding to αvβ6 in the kidneys of Col4A3-/- mice. We have previously reported the generation of potent and selective anti-αvβ6 mAbs[23], including mAbs that bind to αvβ6 without affecting its ability to bind ligands (non-blocking mAbs) and mAbs that that block both ligand binding and αvβ6-mediated TGF-β activation (blocking mAbs). To verify that αvβ6 blocking mAbs used for in vivo studies were selective for binding to the αvβ6 integrin we carried out FACs analysis (FIG. 31A) comparing the binding of the αvβ6 mAbs to untransfected parent NIH3T3 cells and to NIH3T3 cells transfected with murine β6 cDNA (NIH3T3b6). While a control anti-αv mAb, RMV7, stained both untransfected and αvβ6-expressing NIH3T3 cells, the anti-αvβ6 mAbs selectively bound only NIH3T3b6 cells. To confirm specificity of binding αvβ6 in kidneys, we generated a human/mouse chimeric form of one of the blocking αvβ6 mAbs, 3G9, and the compared the pattern of immunostaining produced with a rabbit anti-αv polyclonal antibody (FIGS. 31B and 31C). The chimeric and the original murine form of 3G9 had comparable target binding affinities as determined by FACS and ELISA (data not shown). The chimeric form of 3G9 specifically immunostained tubular epithelial cells in kidneys of Col4A3-/- mice and showed no immunostaining of kidney sections from Col4A3-/- crossed with β6-/- mice (Col4A3-/-; β6-/-). Immunostaining of kidneys with the anti-αv antibody revealed no significant differences between the Col4A3-/- mice or Col4A3-/-; β6-/- mice.

Figure 32A:
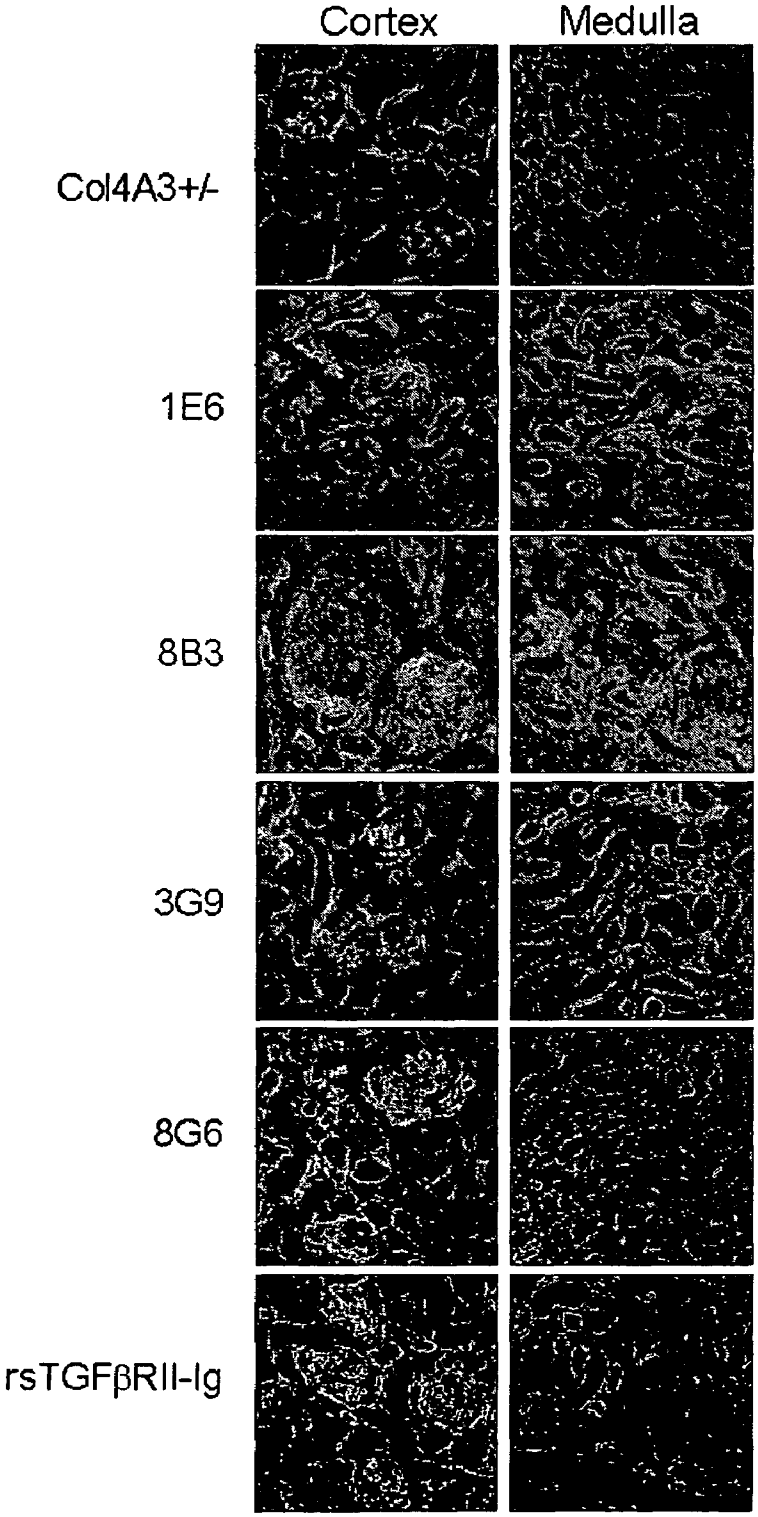
FIG. 32A: immunostaining SMA (red) and laminin (green) in kidneys is shown for Col4A3−/− mice treated from 3 weeks to 8.5 weeks of age and untreated age matched Col4A3+/− mice. Immunostaining (cortex and medulla) of a representative section for each treatment group is shown (n=8 per group).
Figures 32B, 32C:
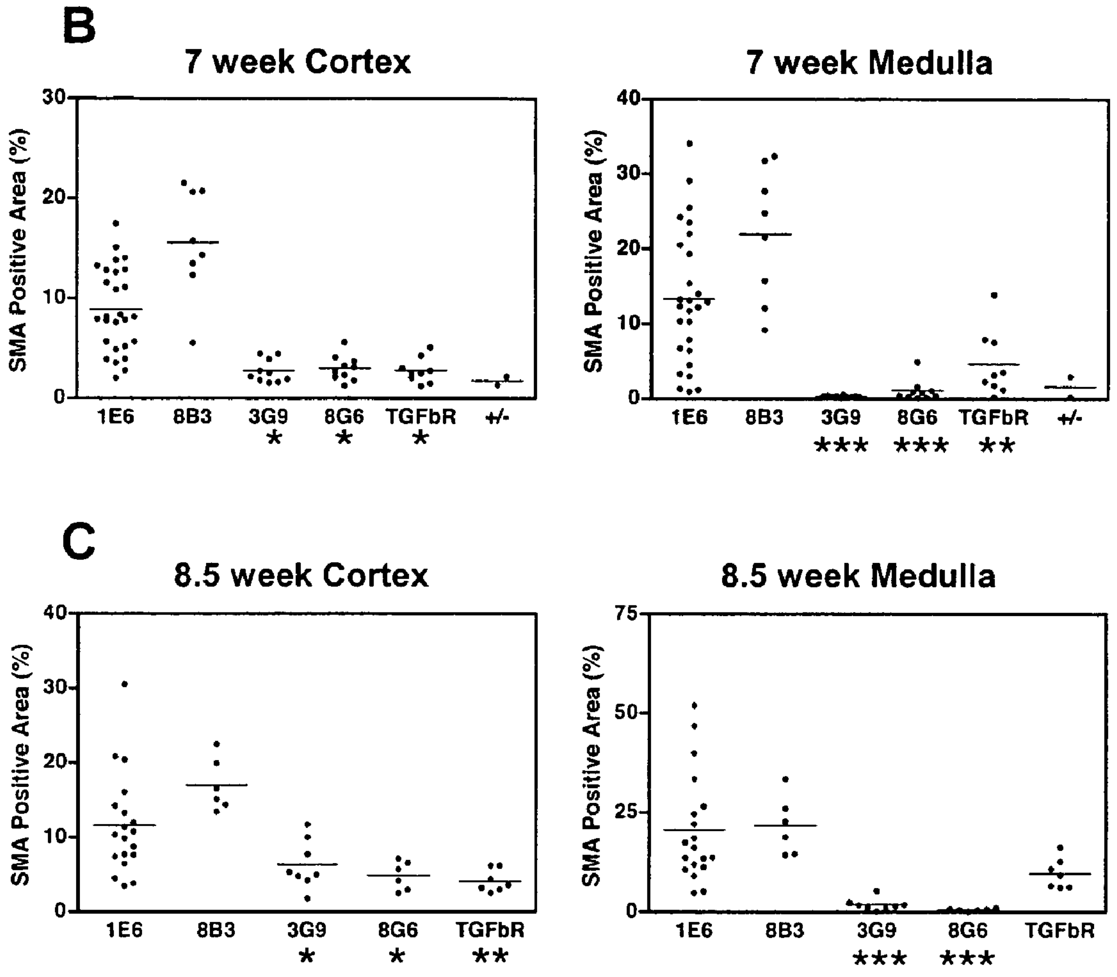
FIGS. 32B and 32C: SMA quantitation in kidneys of untreated Col4A3+/− mice and Col4A3−/− mice treated with various agents from 3 weeks to 7 weeks of age or from 3 weeks to 8.5 week of age. Percent positive immunostaining for cortex (32B) and medulla (32C) relative to total image size is shown. N-value for each treatment group designated in scatter-plot. (*=p<0.01, =p<0.05, *=p<0.001 comparing treatment groups to negative control mAb, 1E6, treated).
Figure 33:
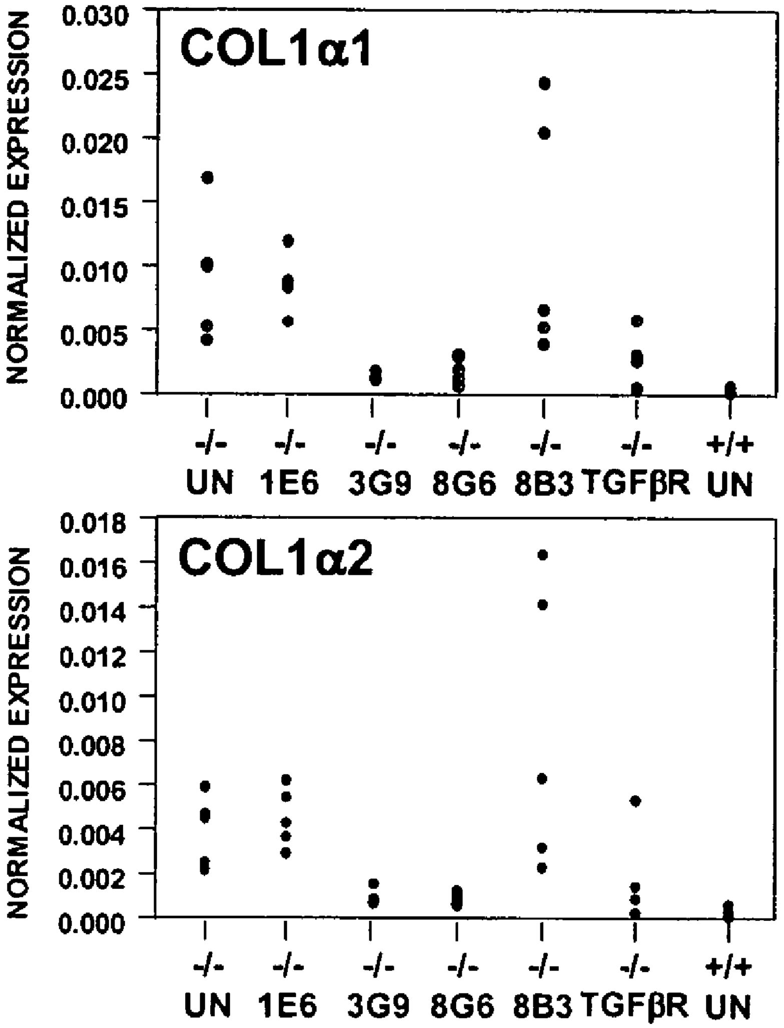
FIGS. 33A and 33B are scatter plots representing Taqman analysis of collagen 1α1 (FIG. 33A), and collagen 1α2 (FIG. 33B), mRNA levels. RNA was isolated from kidneys of 7 week old untreated or treated Col4A3−/− mice and 7 week old untreated Col4A3+/+ mice.

4. Treatment of Col4A3-/- (Alport) mice with anti-αvβ6 mAbs inhibits kidney fibrosis. To determine the potential functional involvement of αvβ6 in the regulation of kidney fibrosis, we have tested the ability of blocking αvβ6 mAbs to affect the initiation and progression of advanced fibrotic lesions. To assess the preventive effects of αvβ6 blockade, Col4A3-/- mice were treated from 3 weeks to 7 weeks of age or from 3 weeks to 8.5 weeks of age with two different blocking αvβ6 mAbs, 3G9 or 8G6; a non-blocking αvβ6 mAb, 6.8B3; or an isotype matched negative control mAb, 1E6. For phenotypic reference and to monitor the effects of systemic TGF-β inhibition, these studies also included Col4A3-/- mice treated with rsTGFβRII-Ig. Kidneys were collected for histological evaluation and for isolation of RNA. Histological hallmarks of fibrosis as well as SMA expression were dramatically increased in the Col4A3-/- kidneys at 7 and 8.5 weeks compared to kidneys from age matched Col4A3+/- mice. Kidneys from negative control mAb treated Col4A3-/- mice presented with an expanded and fibrotic glomerular messangium and a crescent formation in the Bowman's capsule (FIG. 32A, 1E6). These kidneys also showed marked myofibroblast activation and interstitial fibrosis that was associated with tubular epithelial injury and dilation. Treatment of Col4A3−/− mice with blocking αvβ6 mAbs, 6.3G9 or 6.8G6, markedly reduced glomerular and interstitial injury and fibrosis, resulting in considerable gross preservation of kidney architecture (FIG. 32A, 3G9 and 8G6). These effects of the blocking αvβ6 mAbs were accompanied by reduction of SMA expression by >65% in the glomeruli and by >90% in the interstitial regions (FIGS. 32B and 32C). The effect of the blocking mAbs on SMA expression in the glomeruli suggest that while the expression of the αvβ6 integrin is restricted to tubular epithelial cells, blocking its function can have effects at more distal sites in the tissue. Which could be mediated at least in part due to indirect systemic effects of the blocking αvβ6 mAbs. No effect on the progression of fibrosis was seen in kidneys of Col4A3−/− mice injected with the non-blocking αvβ6 mAb, 8B3. Consistent with previously reported inhibition of kidney fibrosis via blockade of TGF-β[7,30-33], treatment of Col4A3−/− mice with rsTGFβRII-Ig produced inhibition of renal fibrosis similar to that produced by the blocking αvβ6 mAbs, as judged by changes in histological appearance and SMA content of the kidney tissues. The effects of αvβ6 blocking mAbs on SMA expression were paralleled by reduction in total kidney tissue levels of collagen1α1 and collagen1α2 mRNA (FIGS. 33A and 33B). Treatment of the Col4A3−/− mice with 3G9, 8G6, or rsTGF-βRII-Ig caused a significant reduction of collagen1α1 and collagen1α2 mRNA abundance, whereas the non-blocking αvβ6 mAb, and isotope control mAb, had no significant effect on the levels of these transcripts.

Figure 34:
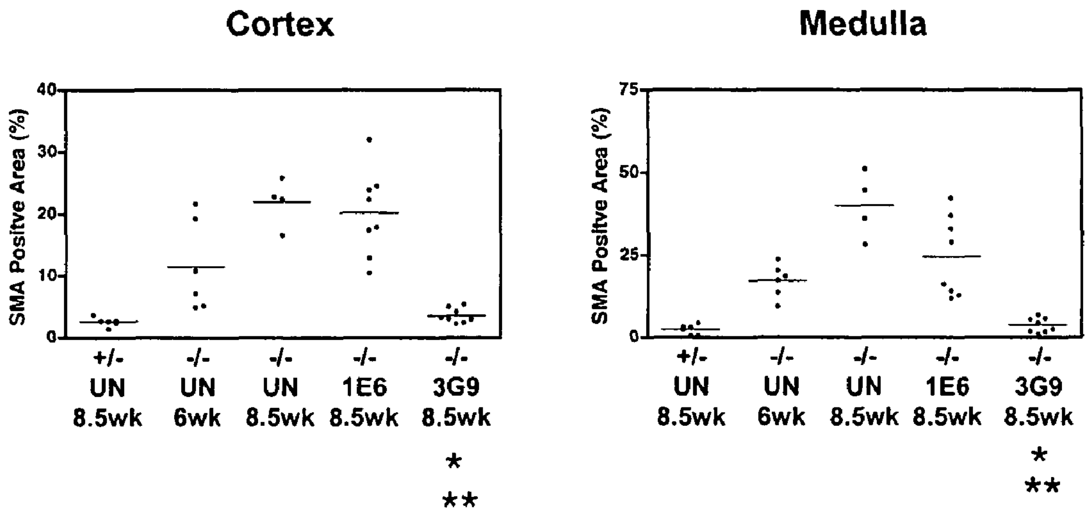
FIG. 34 is a pair of scatter plots demonstrating SMA immunostaining Col4A3−/− kidneys with delayed mAb treatment. Untreated 8.5 week Col4A3+/−; untreated 6 week Col4A3−/−; untreated 8.5 week Col4A3−/−; and 8.5 week Col4A3−/− mice treated with 1E6 and 3G9, 6 weeks to 8.5 weeks. N-values designated in scatter plot. *=p<0.0005, comparing treatment to neg. control 1E6, treated Col4A3−/− mice. **=p<0.02 comparing treatment to untreated 6 week Col4A3−/− mice.

To test the impact of αvβ6 blockade on advanced renal fibrosis, we have studied the effects of αvβ6 blocking mAbs on kidney fibrosis in six week old Col4A3−/− mice, at which time kidney pathology is manifested by measurable injury and accumulation of SMA-positive activated fibroblasts. Mice were treated with the αvβ6 blocking mAb, 3G9, or with an isotype control mAb, 1E6, for 2.5 weeks and then sacrificed at 8.5 weeks of age. Quantitation of SMA immunostaining revealed a decrease in the presence of SMA positive fibroblasts in the kidneys from Col4A3−/− mice treated with 3G9 compared to isotype control mAb treated mice (FIG. 34A). Of equal importance, the intensity and area of SMA immunostaining with delayed 3G9 treatment was diminished compared to the level of SMA observed at the onset of treatment (6 weeks). Delayed treatment of Col4A3−/− mice with 3G9 induced a marked reversion in pathology, including a significant reduction in damaged tubules and fibrosis in the interstitium compared to kidneys isolated from Col4A3−/− mice treated with 1E6.

These results suggest that therapeutic blockade of αvβ6 not only inhibits the progression of kidney fibrosis but can allow resolution of existing fibrotic lesions.

Figure 35:
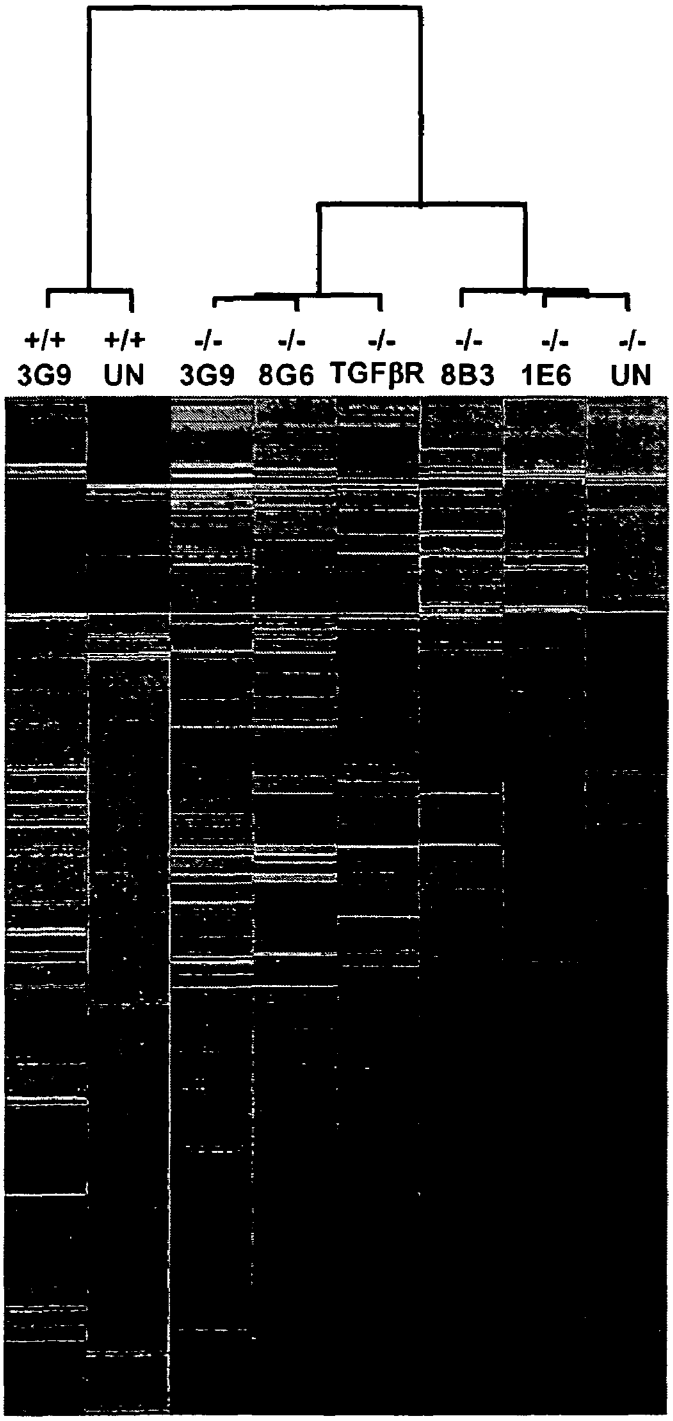
FIG. 35 depicts the Patterns of gene expression and modulation in the kidneys of 7 week-old Col4A3−/− mice. Shown are 395 GeneChip probesets selected for 2-fold or greater variation between the wild type (WT) and untreated Alport (UN) groups at p<0.01. The columns of the heat map display patterns of relative gene expression levels for individual experimental groups. Each column represents 395 normalized mean probeset signal intensity values for a single experimental group of 5 mice. Changes in gene expression across the experimental conditions are reflected in the color variation as shown by the colorbar. Two-dimensional hierarchical clustering was performed to explore relationships (shown by the dendrogram) among the experimental groups.
Figure 36:
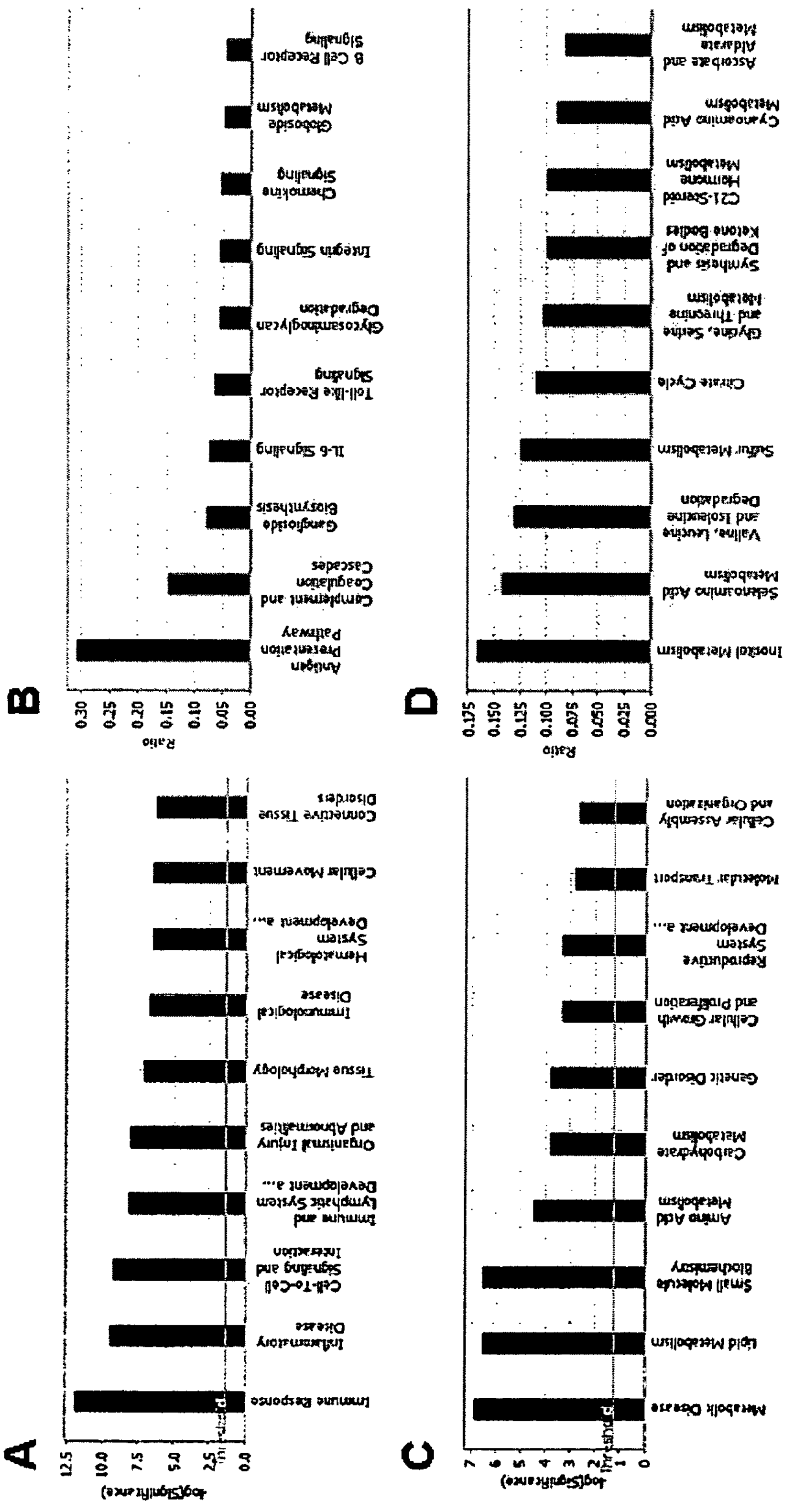
FIG. 36A-36D are bar graphs demonstrating the functional annotation of $\alpha_v\beta_6$-dependent genes associated with renal disease in Col4A3−/− kidneys. Ingenuity Pathways Analysis (IPA) was performed separately on the lists of probesets corresponding to the genes over- or under-expressed in the Alport kidneys compared to wild type. The lists used for IPA were subsets of the 395 probesets originally selected for significant (>2-fold, p<0.01) variation between the Alport and wild type groups. Shown are rank-ordered lists of biological functions (A,C) and canonical pathways (B,D) associated with the genes over-expressed (A, B) and down-modulated (C,D) in the 7 wk old mouse Alport kidneys.

5. Regulation of kidney gene expression by the anti-αvβ6 mAbs. To gain further insight into disease mechanisms associated with αvβ6 function, we have performed an Affymetrix GeneChip analysis of gene expression in kidney tissues from the wild type and Alport mice. A group of genes with altered expression in the Col4a3−/− kidneys was identified as 395 GeneChip probesets showing at least 2-fold mean difference in normalized signal intensity between 7 week-old Col4a3−/− age-matched wild type kidneys at $p<0.01$ (FIG. 35). Functional annotation of the differentially expressed genes was performed using the Ingenuity Pathway Analysis (EPA) tool and has indicated predominant association of genes overexpressed in the Col4a3−/− kidneys with inflammation and regulation of leukocyte functions, whereas genes whose expression was decreased were associated primarily with metabolic regulation (FIG. 36).

Treatment of the animals with αvβ6-blocking mAbs attenuated differential expression of a subset of genes in Col4A3−/− kidneys. We have used analysis of variance (Welch ANOVA) to identify transcripts affected by the experimental treatments at $p<0.05$ and further filtered the resulting probesets to select those showing at least a 2-fold difference in signal intensity in response to a treatment. This procedure yielded 56, 42, and 28 probesets significantly affected by 3G9, 8G6, and TGFβRII-Fc respectively. These groups of probesets showed a considerable overlap and each of the groups represented a fully included subset of the 395 corresponding to the transcripts differentially expressed in Col4a3−/− kidneys (FIG. 37A). We observed similar modulation of gene expression by the αvβ6 blocking mAbs 3G9 and 8G6 (FIG. 35, FIG. 37A) previously shown to belong to two different biochemical classes[23]. Neither the non-blocking anti-αvβ6 mAb 8B3, nor the isotype control mAb 1E6 had a significant effect on gene expression. Therefore, the impact of the αvβ6 mAbs on kidney gene expression was likely due to the blockade of αvβ6 function rather than to activation of integrin signaling or to non-specific events. We found no significant effects of the blocking αvβ6 mAb 3G9 on gene expression in the normal wild type kidney tissue. This observation suggested that the effects of the αvβ6-blocking mAbs observed in our experiments reflected primarily disease-specific regulatory functions of αvβ6.

Figure 37:
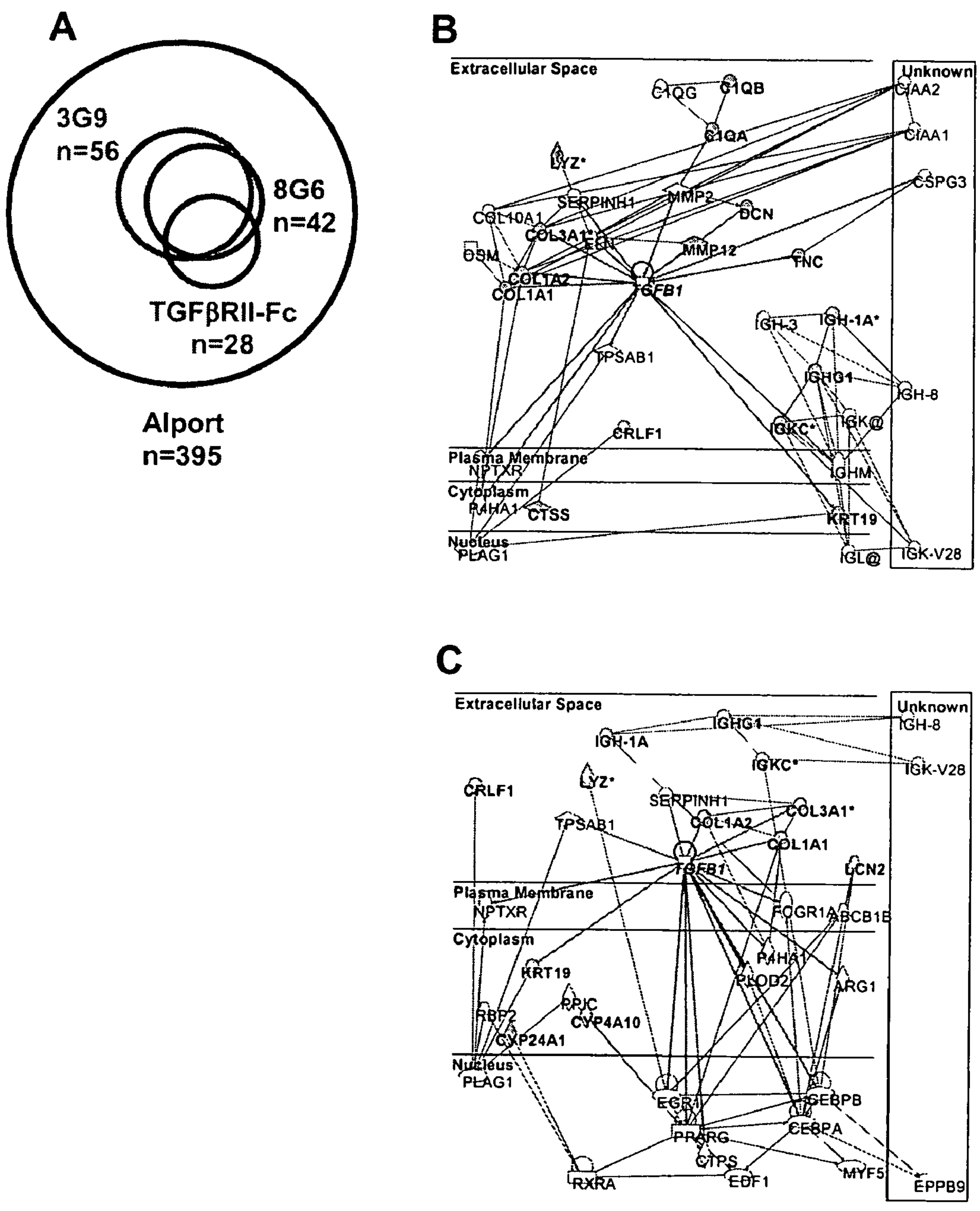
FIGS. 37A-37C are schematic representations of Subset and network analysis of genes differentially expressed in Col4A3−/− kidneys and modulated by blocking $\alpha_v\beta_6$ mAb treatment.

To explore potential relationships of the genes modulated by αvβ6-mAbs with major regulatory pathways, we subjected the respective gene lists to virtual regulatory network analysis using the IPA software (FIG. 37). IPA compares gene lists provided as input to a curated database of known physical and regulatory interactions among genes and proteins. This analysis produces a ranked list and individual configurations of regulatory pathways that are most likely to be reflected by a given list of modulated genes. Although the lists of genes modulated by 3G9 and 8G6 were not completely identical. IPA has revealed TGFβ-dependent networks as the highest-scoring regulatory networks affected by 3G9 (FIG. 37A) as well as by 8G6 (FIG. 37B). Consistent with this finding, hierarchical clustering of the mean gene expression profiles of the experimental groups has demonstrated similarity between patterns of gene modulation by αvβ6 mAbs and by rsTGFβRII-Ig (FIG. 35).

Figure 38:
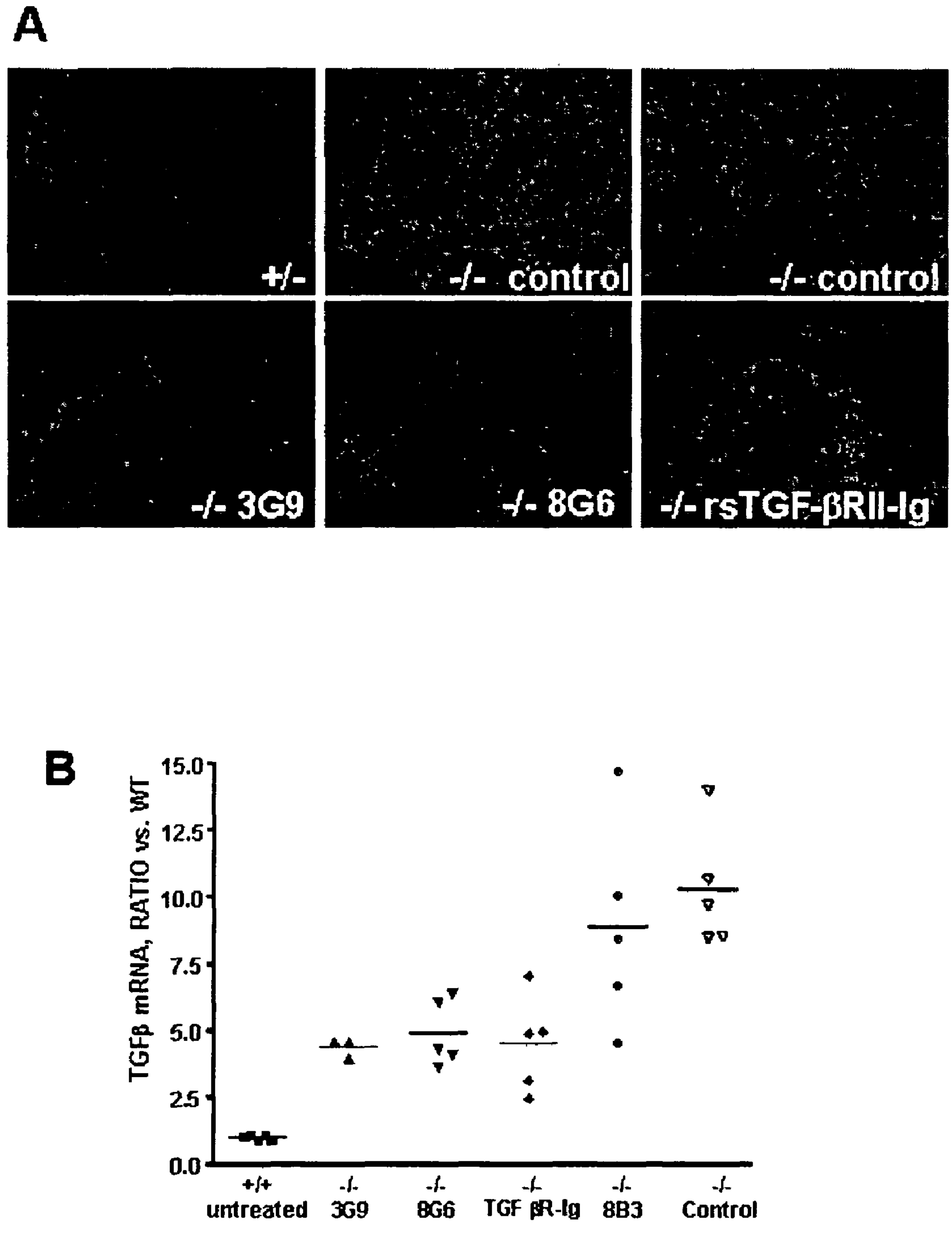
FIG. 38 depicts immunohistochemical and Taqman analysis of TGF-β1 expression.

6. Blockade of αvβ6 reduces expression of TGFβ in the Col4A3−/− kidneys. To determine if decreased kidney fibrosis, detected with 3G9 and 8G6 mAb treatment, was associated with decreased TGF-β expression, kidney sections were immunostained with an anti-TGF-β1 mAb (FIG. 38A). The mAb that was used for immunostaining was one that preferentially binds to tissue sections expressing constitutively active TGF-β versus latent TGF-β (data not shown) 24. Treatment of the mice with 3G9 or with 8G6 caused a significant reduction in TGF-β1 immunostaining in both the interstitial and glomerular regions of the kidneys. These changes in TGF-γ expression were accompanied by analogous changes in the total kidney tissue levels of TGF-β mRNA (FIG. 38B). The pattern of TGF-β1 immunostaining indicated that although the expression of αvβ6 is restricted to the epithelial lining of the kidney tubules, inhibition of αvβ6 function could lead to decreased TGF-β expression at distal sites such as the glomerular regions, which are not immediately adjacent to areas of αvβ6-expression. This may suggest that although αvβ6 could serve as an initial trigger of local TGF-β activation, it could also produce long-range regulatory effects on TGF-β. One possible mechanism of such long-range effects could be based on the ability of TGF-β to activate is own expression in an autocrine or paracrine fashion leading to the expansion of TGF-β expressing tissue areas. It also includes the possibility that an initial local inhibition of TGF-β activation by blockade of αvβ6 interferes with the process of inflammation and fibrosis which could then indirectly further down modulate TGF-β activity.

Figure 39:
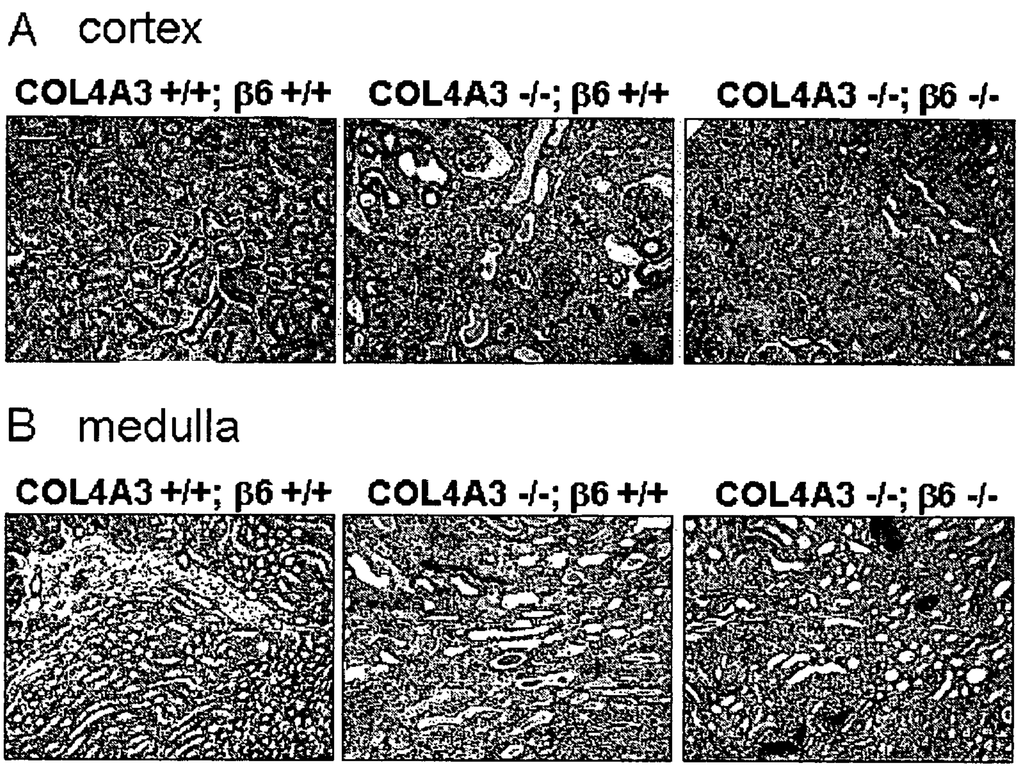
FIG. 39 depicts Trichrome staining for collagen expression in kidneys. Staining for 10 week old Col4A3+/+; β6+/+, Col4A3−/−; β6+/+, and Col4A3−/−; β6−/− mice. Representative tissue sections are shown for cortex (FIG. 39A) and medullary (FIG. 39B) regions of the kidneys.

7. Genetic ablation of the β6 gene in Col4A3−/− mice. To validate findings from mAb experiments, we generated Col4A3 and β6 double knockout mice (Col4A3−/−; β6−/−). Histological examination of kidneys of age matched Col4A3−/−; β6+/−, and Col4A3−/−; β6−/− mice confirmed results obtained in studies with αvβ6-blocking mAbs. There was a significant reduction of SMA immunuostaining in kidneys from 7 to 10 week old Col4A3−/−; β6−/− mice compared to age matched Col4A3−/−; β6+/− mice (data not shown). This was accompanied by a dramatic decrease in fibrosis in the glomerular and interstial regions of the kidneys (FIG. 39). This is demonstrated by a reduction of collagen expression and a well preserved kidney architecture as observed in trichrome-masson stained kidneys from 10 week old Col4A3−/−; β6−/− as compared to age matched kidneys from Col4A3−/−; β6+/− mice. The consistency of the anti-fibrotic effects observed with blocking αvβ6 mAbs treatment compared to genetic ablation of αvβ6 function indicates that mAb treatment is an efficient approach to blocking αvβ6 function in vivo.

Figure 40A:
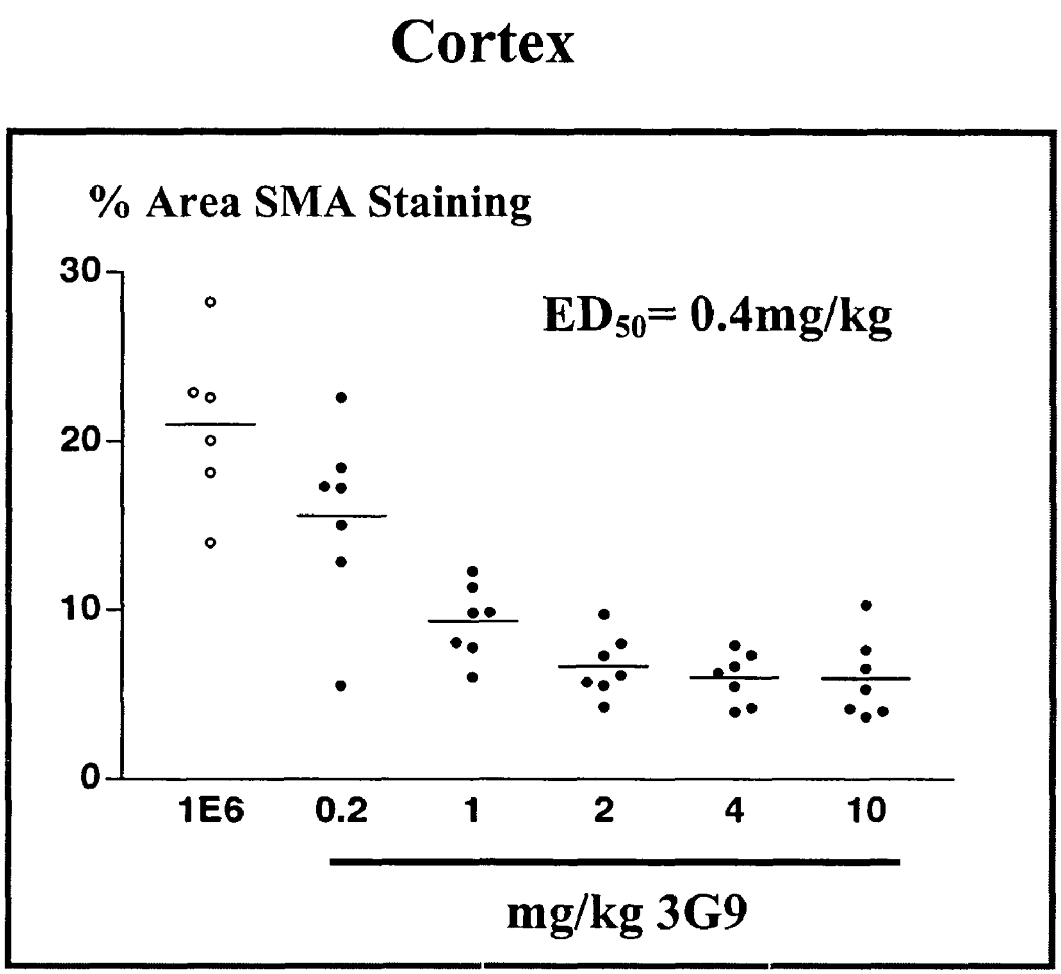
FIGS. 40A and 40B are scatter plots depicting SMA immunostaining with dose titration of 3G9 treatment. Quantitative analysis of SMA immuno-staining is shown for glomerular (cortex) (FIG. 40A), and interstitial (medulla) (FIG. 40B) regions of kidneys after treatment with designated doses of mu3G9, or 10 mg/kg of mu1E6 (IgG control), 3 times per week, from 3 to 7 weeks of age. $ED_{50}$ for cortex=0.4 mg/kg; ED50 for medulla=0.3 mg/kg. Horizontal lines represent mean values.
Figure 40B:
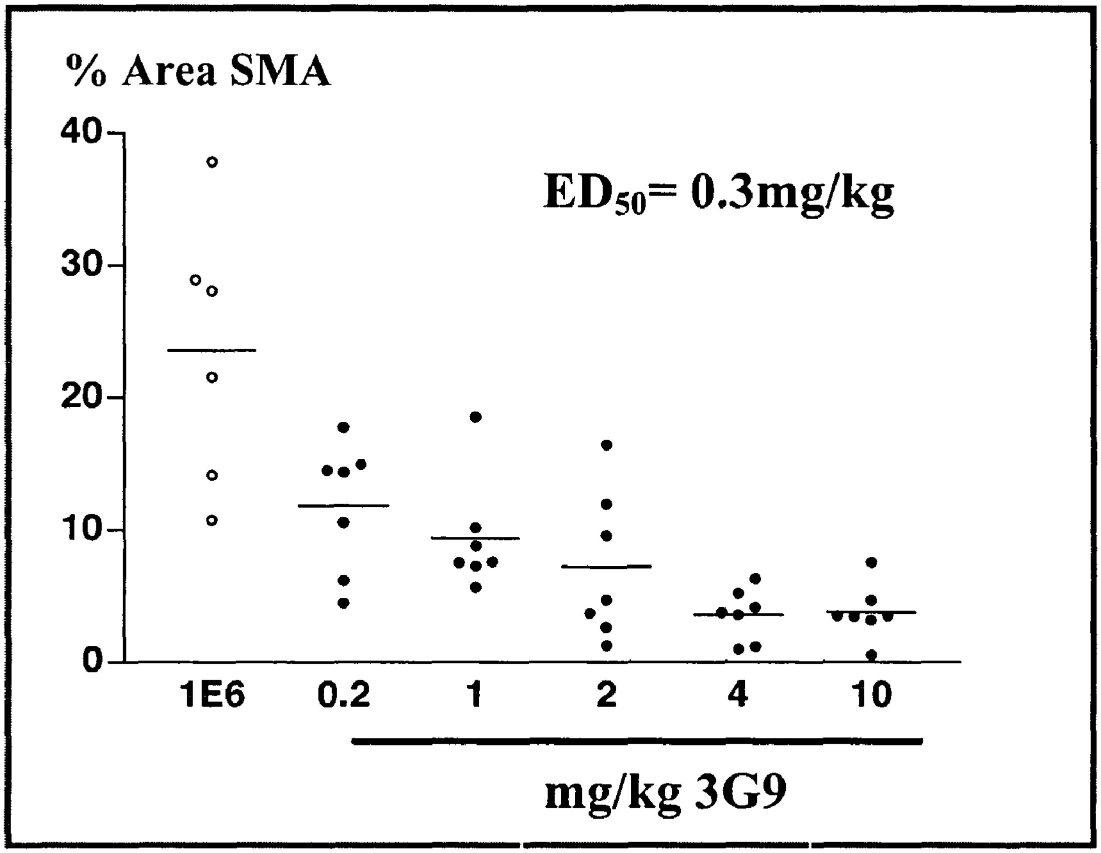

7. Dose response of 3G9 inhibition of kidney fibrosis in Col4A3−/− mice. Col4A3−/− mice were treated 3× per week with increasing concentrations of 3G9. Mice were treated from 3 weeks of age to 7 weeks and then sacrificed. Immunohistochemical analysis of SMA was analyzed in both the cortex and medullary regions of the kidney. A dose-titration demonstrated that 3G9 inhibited SMA expression with an ED50 of 0.3 to 0.4 mg/kg in the Col4A3−/− mice (FIG. 40).

2. Discussion

Progression of renal disease is accompanied by intense tissue remodeling, inflammation, and formation of fibrotic lesions ultimately leading to disruption of the kidney tissue architecture and to loss of renal function. Fibrosis is central to this process and involves activation and expansion of fibroblasts, neovascularization of the diseased tissue, and massive deposition of the extracellular matrix. Molecular mechanisms implicated as major drivers of these events, include misregulation of the TGF-β, axis accompanied by altered expression of ECM proteins and their receptors in the cells populating fibrotic lesions[34-36]. Elevated expression of TGF-β is a hallmark of fibrotic human tissues[25-27], and the functional importance of TGF-β in promoting tissue fibrosis has been documented in vitro and in animal disease models. Overexpression of TGF-β is sufficient to induce fibroblast activation and angiogenesis in vivo and to activate excessive production of ECM in organotypic and cell cultures[34,37,38]. Conversely, genetic or pharmacological disruption of TGF-β signaling provides efficient protection from fibrosis in pulmonary, dermal, and renal fibrosis models[30,32,33,39-41].

Several studies directed at systemic inhibition of TGF-β function (blocking mAbs, rsTGF-βRII-Ig, TGF-β receptor kinase inhibitors) have been shown to attenuate fibrosis in animal disease models. However, all of these approaches have been aimed at blocking the activated form of TGF-β while the therapeutic potential of agents that can block TGF-β activation remains less explored. TGF-β is expressed as a latent precursor and can be converted into a biologically active cytokine by a number of mechanisms that include reactive oxygen species, pH, thrombospondin-1, extracellular proteinases, and integrins[21,42-44]. Of particular interest among the latter is αvβ6, a TGF-β-inducible integrin expressed at sites of epithelial remodeling and shown to function as a receptor and activator of the latent TGF-β[11,17,45]. The β6 subunit is up-regulated in several forms of renal disease[10], and its genetic ablation was shown to provide marked protection from injury-induced renal fibrosis in the mouse model of unilateral ureteral obstruction (UUO)[46]. Similar protection of αvβ6-deficient mice from fibrosis has been observed in the bleomycin lung fibrosis model suggesting that αvβ6 can mediate fibrosis in diverse tissues[17,47]. Interestingly, UUO-induced phosphorylation of SMAD2, a central mediator of TGF-β signaling was markedly attenuated in the β6-deficient kidneys, indicating that αvβ6 may indeed operate in vivo as a part of the TGF-β regulatory circuitry[46].

Previous studies with β6 knockout mice have provided evidence that αvβ6 can play a role in the initiation of fibrosis, suggesting this integrin as a potential novel therapeutic target. We sought to determine whether pharmacological inhibition of αvβ6 function with blocking mAbs could attenuate renal fibrosis in Col4A3−/− mice, an animal model of the autosomal recessive Alport syndrome[28,29]. Alport syndrome is a hereditary disease caused by mutations in Col4A3, Col4A4, or Col4A5 genes[48]. Defects in these genes result in aberrant assembly of the collagen IV networks and abnormal formation of the glomerular and tubular basement membranes. Alport patients develop progressive glomerulonephritis that leads to end stage renal disease. We observed marked upregulation of αvβ6 in human Alport as well as in mouse Col4A3−/− kidney tissues. In Col4A3−/− mouse kidney, the increased expression of αvβ6 was particularly prominent in the tubular epithelium where it preceded and accompanied broad expansion of SMA-positive cells and collagen deposition. Based on this pattern of expression, we hypothesized that αvβ6 becomes up-regulated early in the cycle of epithelial response to injury and may be an important mediator in both the initiation and maintenance of fibrosis in a setting of persistent epithelial damage. The results of our studies show that antibody-mediated blockade of αvβ6 can both inhibit initiation, as well as early progression of renal fibrosis and suppress its maintenance. Consistent with previous findings from the β6-deficient mouse model of UUO[46], the anti-fibrotic effects of the αvβ6-blocking mAbs observed in our experiments correlated with decreased TGF-β activity and expression. Interestingly, the apparent decrease in TGF-β and SMA expression following αvβ6 mAb treatment occurred not only in the immediate vicinity of αvβ6 positive cells but was detectable in relatively distal tissue regions as well. While this finding may suggest that αvβ6 can contribute to the activation of the TGF-β axis both directly and in an indirect fashion, e.g. via paracrine auto-activation of TGF-β expression, it does not rule out the possibility that αvβ6 blockade may provide protection through extrarenal effects, including altering systemic immune function. We have evaluated serum levels of a number of chemokines and cytokines and peripheral blood populations in mice after four weeks of αvβ6 mAb treatment and found no significant changes. Additionally, only minimal changes in monocytes in the kidneys of Col4A3−/− kidneys was detected by immunohistochemistry with αvβ6 mAb treatment or genetic knockout of the β6 gene. Further studies evaluating the functional status of the immune system with αvβ6 mAb treatment or with transplantation studies could address this more completely.

Misregulation and hyperactivity of the TGF-β pathway have been implicated as a prominent mechanism involved in the progression of renal disease in the $Col4A3^{-/-}$ mice[6]. One interesting feature of the TGF-β circuit that could help explain the apparently dominant role of this cytokine in fibrotic disease is the ability of TGF-β to induce its own expression. This raises the possibility that the anti-fibrotic effects of αvβ6 blockade may be mediated at least in part by indirect mechanisms. This could include downstream effects on TGF-β expression by altering inflammation and fibrosis locally and interfering with subsequent increased TGF-β activity. Since αvβ6 can be induced by TGF-β and promote latent TGF-β activation, we explored the functional relationship between TGF-β and αvβ6 in mediating the Col4A3−/− kidney pathology. We compared the impacts of the αvβ6 mAbs and the rsTGF-βRII-Ig on the expression of disease-associated transcripts in the kidneys of Col4A3−/− mice. This comparison has revealed a distinct functional association of the αvβ6-dependent genes with TGF-β as well as a close similarity of the patterns of gene modulation by the αvβ6 mAbs and by the rsTGF-βRII-Ig. Furthermore, treatment of Col4A3−/− mice with αvβ6-blocking mAbs inhibited the kidney expression of TGF-β. These findings show that the disease-modifying effects of the inhibitory αvβ6 mAbs could result from inhibition of TGF-β function, possibly via suppression of αvβ6-mediated activation of the latent TGF-β in the diseased tissue. One intriguing aspect of the above data is the inhibition of pro-inflammatory gene expression through the blockade of αvβ6 or TGF-β. TGF-β has well established anti-inflammatory and immunosuppressive functions, however, the patterns of gene modulation by the rsTGF-βRII-Ig and by the anti-αvβ6 mAbs in our experiments were indicative of a pro-inflammatory function of TGF-β in the Alport disease model. Although the actual mechanism of this apparent pro-inflammatory effect needs further investigation, it could be based on the known ability of TGF-β to induce growth arrest and death of epithelial cells[31,49-51]. Since epithelial damage provides an important mechanism for the activation of early innate immune responses to tissue injury, the apparent pro-inflammatory function of TGF-β suggested by our data could be indirect and mediated by TGF-β-promoted injury to the kidney epithelium. According to this model, αvβ6 may function as an important component of the TGF-β-dependent mechanism of epithelial remodeling, and misregulation of its function in disease could further promote disease-associated tissue damage and inflammation.

The results of our study demonstrate that αvβ6 is highly upregulated in human kidney disease and targeting of αvβ6 with function-blocking antibodies may provide an effective novel approach to therapeutic modulation of renal fibrosis. Since the expression of αvβ6 is largely restricted to epithelial cells in the diseased tissue, this approach allows for selective local suppression of TGFβ-function. As TGFβ is expressed in a variety of cells and tissue types, and plays and important role in regulating a number of different homeostatic processes, blocking αvβ6 function offers a potentially safer alternative to systemic inhibition of TGF-β in those diseases where the αvβ6 integrin is upregulated.

Conclusions

αvβ6 is overexpressed in human kidney disease associated with inflammatory and fibrotic pathology.

αvβ6-blocking mAbs inhibit fibrosis in Col4A3−/− (Alport) model of kidney fibrosis.

Delayed treatment studies indicate that therapeutic blockade of αvβ6 not only inhibits the progression of kidney fibrosis but can allow resolution of existing fibrotic lesions.

Genetic knockout of β6 leads to protection in the Col4A3−/− mice.

Transcript profiling of kidney tissues showed that αvβ6 blocking mAbs significantly inhibited disease-associated changes in expression of fibrotic and inflammatory mediators.

Similar patterns of transcript modulation were produced with recombinant soluble TGF-βRII treatment suggesting shared regulatory functions of αvβ6 and TGF-β.

References

1. Okada H, Kalluri R: Cellular and molecular pathways that lead to progression and regression of renal fibrogenesis. Curr Mol Med 2005, 5:467-474

2. Sheppard D: Functions of pulmonary epithelial integrins: from development to disease. Physiol Rev 2003, 83:673-686

3. Norman J T, Fine L G: Progressive renal disease: fibroblasts, extracellular matrix, and integrins. Exp Nephrol 1999, 7:167-177

4. Border W A, Noble N A: Interactions of transforming growth factor-beta and angiotensin II in renal fibrosis. Hypertension 1998, 31:181-188

5. Wang W, Koka V, Lan H Y: Transforming growth factor-beta and Smad signalling in kidney diseases. Nephrology 2005, 10:48-56

6. Sampson N S, Ryan S T, Enke D A, Cosgrove D, Koteliansky V, Gotwals P: Global Gene Expression Analysis Reveals a Role for the alpha 1 Integrin in Renal Pathogenesis. J Biol Chem 2001, 276:34182-34188

7. Cosgrove D, Rodgers K, Meehan D, Miller C, Bovard K, Gilroy A, Gardner H, Kotelianski V, Gotwals P, Amattucci A, Kalluri R: Integrin α1β1 and transforming growth factor-β1 play distinct roles in alport glomerular pathogenesis and serve as dual targets for metabolic therapy. Amer J of Pathol 2000, 157:1649-1659

8. Hamerski D A, Santoro S A: Integrins and the kidney: biology and pathobiology. Curr Opin Nephrol Hypertens 1999, 8:9-14

9. Zambruno G, Marchisio P C, Marconi A, Vaschieri C, Melchiori A, Giannetti A, De Luca M: Transforming growth factor-β1 modulates β1 and β5 integrin receptors and induces the de novo expression of the αvβ6 heterodimer in normal human keratinocytes: implications for wound healing. J Cell Biol 1995, 129:853-865

10. Trevillian P, Paul H, Millar E, Hibberd A, Agrez M V: alpha(v)beta(6) Integrin expression in diseased and transplanted kidneys. Kidney Int 2004, 66:1423-1433

11. Breuss J M, Gallo J, DeLisser H M, Klimanskaya I V, Folkesson H G, Pittet J F, Nishimura S, Aldape K, Landers D V, Carpenter W, Gillett N, Sheppard D, Matthay M A, Albelda S M, Kramer R H, Pytella R: Expression of the β6 subunit in development, neoplasia and tissue repair suggests a role in epithelial remodeling. J Cell Sci 1995, 108:2241-2251

12. Breuss J M, Gillett N, Lu L, Sheppard D, Pytella R: Restricted distribution of integrin β6 mRNA in primate epithelial tissues. J Histochem and Cytochem 1993, 41:1521-1527

13. Hakkinen L, Hildebrand H C, Berndt A, Kosmehl H, Larjava H: Immunolocalization of tenascin-C, α9 integrin subunit, and αvβ6 integrin during wound healing in human oral mucosa. J of Histochem and Cytochem 2000, 48:985-998

14. Arend L J, Smart A M, Briggs J P: Mouse β6 integrin sequence, pattern of expression, and role in kidney development. J Amer Soc Nephrol 2000, 11:2297-2305

15. Hakkinen L, Koivisto L, Gardner H, Saarialho-Kere U, Carroll J M, Lakso M, Rauvala H, Laato M, Heino J, Larjava H: Increased expression of β6-integrin in skin leads to spontaneous development of chronic wounds. Am J Pathol 2004, 164:229-242

16. Huang X Z, J. W, Spong S, Sheppard D: The integrin αvβ6 is critical for keratinocyte migration on both its known ligand, fibronectin, and on vitronectin. J Cell Sci 1998, 111: 2189-2195

17. Munger J S, Huang X, Kawakatsu H, Griffiths M J D, Dalton S L, Wu J, Pittet J F, Kaminski N, Garat C, Matthay M A, Rifkin D B, Sheppard D: The integrin αvβ6 binds and activates latent TGFβ1: a mechanism for regulating pulmonary inflammation and fibrosis. Cell 1999, 96:319-328

18. Yokosaki Y, Monis H, Chen A, Sheppard D: Differential effects of the integrins alpha9beta1, alphavbeta3, and alphavbeta6 on cell proliferative responses to tenascin. Roles of the beta subunit extracellular and cytoplasmic domains. J Biol Chem 1996, 271:24144-24150

19. Annes J P, Rifkin D B, Munger J S: The integrin αvβ6 binds and activates latent TGFβ3. FEBS lett 2002, 511:65-68

20. Munger J S, Harpel J G, Gleizes P E, Mazzieri R, Nunes I, Rifkin D B: Latent transforming growth factor-β:structural feature and mechanisms of activation. Kid Int 1997, 51:1376-1382

21. Khalil N: TGF-beta: from latent to active. Microbes Infect 1999, 1:1255-1263

22. Barcellos-Hoff M H: Latency and activation in the control of TGF-β. J Mamm Gland Biol 1996, 1:353-363

23. Weinreb P H, Simon K J, Rayhorn P, Yang W J, Leone D R, Dolinski B M, Pearse B R, Yokota Y, Kawakatsu H, Atakilit A, Sheppard D, Violette S M: Function-blocking integrin alphavbeta6 monoclonal antibodies. J Biol Chem 2004, 279:17875-17887

24. Barcellos-Hoff M H, Ehrhart E J, Kalia M, Jirtle r, Flanders K C, Tsang M L-S: Immunohistochemical detection of active transforming growth factor-β in situ using engineered tissue. Amer J of Pathol 1995, 147:1228-1237

25. Yamamoto T, Nakamura T, Noble N A, Ruoslahti E, Border W A: Expression of transforming growth factor beta is elevated in human and experimental diabetic nephropathy. Proc Natl Acad Sci, USA 1993, 90:1814-1818

26. Yamamoto T, Noble N A, Cohen A H, Nast C C, Hishida A, I. G L, Border W A: Expression of transforming growth factor-beta isoforms in human glomerular diseases. Kidney Int 1996, 49:461-469

27. Shihab F S, Yamamoto T, Nast C C, H. C A, Noble N A, Gold L I, Border W A: Transforming growth factor-beta and matrix protein expression in acute and chronic rejection of human renal allografts. J Am Soc Nephrol 1995, 6:286-294

28. Cosgrove D, Meehan D, Grunkemeyer J A, Kornak J M, Sayers R, Hunter W J, Samuelson G C: Collagen COL4A3 knockout: a mouse model for autosomal Alport syndrome. Genes Dev 1996, 10:2981-2992

29. Miner J H, Sanes J R: Molecular and functional defects in kidneys of mice lacking collagen a3(IV): implications for alport syndrome. J Cell Biol 1996, 135:1403-1413

30. Sharma K, Jin Y, Guo J, Ziyadeh F N: Neutralization of TGF-beta by an anti-TGF-beta antibody attenuates kidney hypertrophy and the enhanced extracellular matrix gene expresssion in STZ-induced diabetic mice. Diabetes 1996, 45:522-530

31. Miyajima A, Chen J, Lawrence C, Ledbetter S, Soslow R A, Stern J, Jha S, Pigato J, Lerner M L, Poppas D P, Darracott Vaughan Jr. E, Felson D: Antibody to transforming growth factor-β ameliorates tubular apoptosis in unilateral ureteral obstruction. Kid Int 2000, 58:2310-2313

32. Ziyadeh F N, Hoffman B B, Han D C, Iglesias-de la Cruz M C, Hong S W, Isono M, Chen S, McGowan T A, Sharma K: Long-term prevention of renal insufficiency, excess matrix gene expression, and glomerular mesangial matrix expansion by treatment with monoclonal antitransforming growth factor-γ antibody in db/db diabetic mice. Proc Natl Acad Sci, USA 2000, 97:8015-8020

33. Kasuga H, Ito Y, Sakamoto S, Kawachi H, Shimizu F, Yuzawa Y, S. M: Effects of anti-TGF-γ type II receptor antibody on experimental glomerulonephritis. Kid Int 2001, 60:1745-1755

34. Roberts A B, Sporn M B: Regulation of endothelial cell growth, architecture, and matrix synthesis by TGF-beta. Am Rev Respir Dis 1989, 140:1126-1128

35. Eickelberg O, Kohler E, Reichenberger F, Bertschin S, Woodtli T, Eme P, Perruchoud A P, Roth M: Extracellular matrix deposition by primary human lung fibroblasts in response to TGF-beta1 and TGF-beta3. Am J Physiol 1999, 276:L814-L824

36. Varga J, Rosenbloom J, Jimenez S A: Transforming growth factor beta (TGF beta) causes a persistent increase in steady-state amounts of type I and type III collagen and fibronectin mRNAs in normal human dermal fibroblasts. Biochem J 1987, 247:597-604

37. Konig A, Bruckner-Tuderman L: Transforming growth factor-beta promotes deposition of collagen VII in a modified organotypic skin model. Lab Invest 1994, 70:203-209

38. Sime P J, Xing Z, Graham F L, Csaky K G, Gauldie J: Adenovector-mediated gene transfer of active transforming growth factor-β1 induces prolonged severe fibrosis in rat lung. J clin Invest 1997, 100:768-776

39. Laping N J: ALK5 Inhibition in renal disease. Curr Opin Pharmacol 2003, 3:204-208

40. Bonniaud P, Kolb M, Galt T, Robertson J, Robbins C, Stampfli M, Layery C, Margetts P J, Roberts A B, Gauldie J: Smad3 null mice develop airspace enlargement and are resistant to TGF-beta-mediated pulmonary fibrosis. J Immunol 2004, 173:2099-2108

41. Inazaki K, Kanamaru Y, Kojima Y, Sueyoshi N, Okumura K, Kaneko K, Yamashiro Y, Ogawa H, Nakao A: Smad3 deficiency attenuates renal fibrosis, inflammation, and apoptosis after unilateral ureteral obstruction. Kidney Int 2004, 66:597-604

42. Murphy-Ullrich J E, Poczatek M: Activation of latent TGF-beta by thrombospondin-1 mechanisms and physiology. Cytokine Growth Factor Rev 2000, 11:59-69

43. Annes J P, Munger J S, Rifkin D B: Making sense of latent TGFβ activation. J Cell Sci 2003, 116:217-224

44. Sheppard D: Integrin-mediated activation of latent transforming growth factor beta. Cancer Metastasis Rev 2005, 24:395-402

45. Sheppard D: Integrin-Mediated Activation of Transforming Growth Factor-{beta}1 in Pulmonary Fibrosis. chest 2001, 120:49 S-53

46. Ma L J, Yang H, Gaspert A, Carlesso G, Barty M M, Davidson J M, Sheppard D, Fogo A B: Transforming growth factor-β-dependent and independent pathways of induction of tubulointerstitial fibrosis in β6−/− mice. Am J Pathol 2003, 163:1261-1273

47. Kaminiski N, Allard J D, Pittet J F, Fengrong Z, Griffiths M J D, Morris D, X. H, Sheppard D, Heller R A: Global analysis of gene expression in pulmonary fibrosis reveals distinct programs regulating lung inflammation and fibrosis. Proc Natl Acad Sci, USA 2000, 97:1778-1783

48. Torra R, Tazon-Vega B, Ars E, Ballarin J: Collagen type IV ({alpha}3-{alpha}4) nephropathy: from isolated haematuria to renal failure. Nephrol Dial Transplant 2004, 19:2429-2432

49. Bottinger E P, Bitzer M: TGF-beta signaling in renal disease. J Am Soc Nephrol 2002, 13:2600-2610

50. Goumenos D S, Tsamandas A C, El Nahas A M, Thomas G, Tsakas S, Sotsiou F, Bonikos D S, Vlachojannis J G: Apoptosis and myofibroblast expression in human glomerular disease: a possible link with transforming growth factor-beta-1. Nephron 2002, 92:287-296

51. Dai C, Yang J, Liu Y: Transforming growth factor-beta1 potentiates renal tubular epithelial cell death by a mechanism independent of Smad signaling. J Biol Chem 2003, 278: 12537-12545

Example 14

Efficacy of Murine 3G9 (mu3G9) in Mouse Unilateral Ureteral Obstruction Model of Kidney Fibrosis Summary Unilateral ureteral obstruction (UUO) is a well-established animal model of renal injury leading to accelerated renal tubulointerstitial fibrosis. Urinary tract obstruction produces increased intraluminal pressure in the ureter and renal tubules that causes renal parenchymal damage. UUO is characterized by hydronephrosis, tubular dilatation, renal tubular apoptosis, progressive renal atrophy, interstitial cellular infiltration, an increase in renal TGF-β and renal interstitial fibrosis[1]. Integrin αvβ6 function can participate in both TGF-β activation and in the process of epithelial-to-mesenchymal transformation. Since these processes contribute to the progression of disease, the UUO model was used to evaluate efficacy of the anti-αvβ6 monoclonal antibody mu3G9 and recombinant soluble murine TGF-β receptor type II-Ig fusion protein (rsTGF-βRII-Ig) against rapidly progressive renal fibrosis. Mean percent inhibition of smooth muscle actin staining with mu3G9 at 4 mg/kg, dosed i.p. three times per week for the ten day course of the experiment, was 32%.

Introduction

Progressive fibrosis is a common process leading to the development of end stage renal disease and promoted by epithelial remodeling, fibroblast activation, inflammation, and reorganization of cellular interactions with the extracellular matrix (ECM). Molecular mechanisms contributing to these events are complex and include misregulation of the TGF-βaxis, aberrant ECM remodeling, and altered expression and function of cell adhesion receptors of the integrin superfamily[2-9]. Recent studies have revealed important regulatory functions of several integrins and associated molecules in renal epithelial and mesenchymal cells[8,10-13].

Among the integrins whose expression is strongly increased in renal disease is the TGF-β-inducible integrin αvβ6[3,14,15]. αvβ6 expression is generally restricted to epithelial cells where it is expressed at low levels in normal adult tissues and elevated during development, injury, and neoplasia[14,16-18]. Although αvβ6 is expressed at relatively low levels in healthy adult kidney, its expression is prominent in the developing mouse kidney, particularly in the proximal tubules, loop of Henle, and collecting ducts[16,17,19]. Recently, elevated expression of αvβ6 has been reported for various forms of human kidney pathology[15].

Consistent with the increased expression of αvβ6 in vivo during tissue remodeling, expression of the αvβ6 integrin in cultured epithelial cells can be induced by cytokines that regulate epithelial remodeling, including EGF and TGF-β[3,14]. Moreover, overexpression of β6 in the skin of transgenic mice has been shown to provoke formation of spontaneous chronic wounds[20] suggesting that αvβ6 may play an important role in regulating epithelial tissue remodeling.

Known ligands for αvβ6 include fibronectin, tenascin, and the latency associated peptides 1 and 3 (LAP1 and LAP3), the N-terminal fragments of the latent precursor forms of TGF-β1 and -β3[21-25]. As a result of binding to these ligands, αvβ6 can mediate cell adhesion, spreading, migration, and activation of latent TGF-β. TGF-β is synthesized as a latent protein that is cleaved and secreted with the N-terminal LAP non-covalently associated with the mature active C-terminal TGF-β cytokine. The latent TGF-β complex cannot bind to its cognate receptor and thus remains biologically inactive until converted to the active form by one of several alternative mechanisms that include cleavage by proteases, exposure to low pH or ionizing radiation, and conformational changes in the latent complex allowing it to bind to its cognate receptors[26-29]. An activating conformational change can be induced by αvβ6 involving direct binding of the integrin to an RGD motif contained within LAP1 and LAP3. This binding converts the TGF-β precursor into a receptor binding-competent state[22,25]. These findings suggest that upregulation of αvβ6 expression on the surface of epithelial cells can lead to local TGF-β activation followed by paracrine activation of TGF-β-dependent events in bystander cells.

Since TGF-β has been implicated as a central regulator of renal fibrosis, we hypothesized that its local activation by αvβ6 may be an important process in the onset and progression of renal disease and blockade of αvβ6 function could suppress the development of kidney fibrosis. In the studies described herein we show that αvβ6 is significantly upregulated in the mouse unilateral ureteral obstruction model of kidney fibrosis. We show that mAbs blocking the ligand binding and TGF-β activation functions of αvβ6[30] inhibit fibrosis in this model.

Materials and Methods

1. Animals. Male 8-12 week old 25.5±0.2 g viral antigen-free C57BL mice (Jackson Laboratories, Bar Harbor, Me.) were used in the studies. Animals were housed in the Biogen Idec virus-free laboratory animal facility in ventilated isolator cage racks and allowed to accommodate for seven days prior to beginning the study. Mice had ad libitum access to irradiated standard mouse chow (LabDiet Prolab® 5P75 Isopro® RMH 3000) and sterile water throughout the accommodation and experimental period. Body weight was measured at intervals as part of animal health monitoring.

2. Antibodies and reagents. αvβ6 mAbs were generated as described herein and as previously described 30. Human/mouse chimeric 2A1 and 3G9 cDNAs were generated from the respective parent hybridoma total RNAs with constant region primers CDL-739 for the heavy chain and CDL-738 for the light chain using the First Strand cDNA synthesis kit (Amersham/Pharmacia, Piscataway, N.J.). The heavy and light chain variable region genes were amplified by the polymerase chain reaction using the same 3' primers used for cDNA synthesis and pools of degenerate primers specific for most murine antibody gene signal sequences (sequences available upon request) and Pfu DNA polymerase (Stratagene, La Jolla Calif.). Cloned heavy and light chain variable regions were ligated into mammalian expression vectors with human IgG1 constant regions. Recombinant soluble murine TGF-β receptor type II-Ig fusion protein (rsTGF-βRII-Ig) was generated as previously described[11] and purchased from R&D Systems (532-R2, Minneapolis, Minn.).

3. Immunohistochemistry. Tissue sections were deparaffinized in xylene and ethanol, rehydrated in distilled water, and then immersed in methanol containing 0.45% $H_2O$. Tissues were incubated with pepsin (00-3009, Zymed, San Francisco, Calif.) and blocked with avidin and biotin (SP-2001; Vector Laboratories, Burlingame, Calif.). Primary antibody was diluted in PBS containing 0.1% BSA and tissues were incubated overnight at 4° C. For immunostaining β6 on mouse tissue, sections were incubated with a human/mouse chimeric form of the anti-αvβ6 mAb, 2A1[30], and an anti-human biotinylated secondary antibody (PK-6103, Vector Laboratories, Burlingame, Calif.). For immunostaining β6 on murine tissue 2A1[30], and an anti-mouse-biotinylated secondary antibody (PK-6102, Vector Laboratories). Avidin-biotin complex-horseradish peroxidase (Vector Kit, PK-6102) was applied to sections, incubated for 30 minutes at room temperature, and 3,3'-diaminobenzidine (DAB) substrate was prepared as directed (SK-4100, Vector Laboratories) and applied to sections for 5 min at room temperature. Tissue sections were stained with Mayer's Hematoxylin for 1 minute and rinsed in water and PBS.

4. Unilateral ureteral obstruction induction of kidney fibrosis. Surgery for the studies was performed over a two-day period and dosing schedules for the mice were timed in relation to the day of ureter ligation. The left ureter was aseptically isolated via a left-of-midline laparotomy under ketamine:xylazine (1000:10 mg/kg s.c.) anesthesia. Two tight, occlusive 6-0 silk ligatures were placed on the ureter at the level of the lower pole of the kidney, and the ureter cut between the ligatures. The abdominal wall was closed with 4-0 Vicryl suture and the skin closed with 4-0 nylon. Animals were allowed to recover on a heating pad and given 0.05 mg/kg s.c. buprenorphine twice daily on Days 0 and 1. Animals were dosed three times weekly with mu3G9 or two times weekly with sTGF-βRII-Ig beginning on the day before surgery. The procedure was adapted from the previously described report.[31]

5. Tissue sample collection and histological analysis for indicators of disease. Animals were euthanized with carbon dioxide on Day 10 after ligation. Both kidneys (left ligated, right unligated) were removed and halved transversely through the center of the renal pelvis. One half of each kidney was laced in 10% neutral buffered formalin for fixed-tissue staining. The other half of each kidney was placed in 15% sucrose, followed by 30% sucrose for immunohistochemical staining of smooth muscle actin.

Formalin-fixed kidney sections were stained for collagen content with Masson's trichrome stain, and for structural anatomy with H & E. Trichrome-stained sections were morphometrically qunatitated in images captured by brightfield microscopy using a leica Qwin image analysis system. Images were captured using standardized lighting conditions and digital cameral exposure settings, corrected for background, and calibrated to distance standards.

Thresholds were set to detect dark blue for collagen staining in Masson's trichrome-stained slides. Collagen area was analyzed in images taken at 200×. Images of contiguous fields covering the entire left kidney section were taken from each animal for quantitation.

6. Statistical analysis. Collagen content in each measured field was expressed as a percent of total tissue area within the 200× field (excluding any white space), i.e. blue area %. Sixteen to thirty five individual fields were measured from each kidney. These included all cortical and medullary tissue from the section and excluded the renal papilla. The average blue area % taken from all fields in the left ligated kidney was calculated for each animal and acted as the animal's fibrosis score for statistical testing. The statistical significance of treatment-related differences in blue area % among the several treatment groups was determined by one-way analysis of variance, followed by the Student-Newman-Keuls procedure for pairwise multiple comparisons. Differences were taken to be statistically significant when $p<0.05$.

Results

Figure 41:
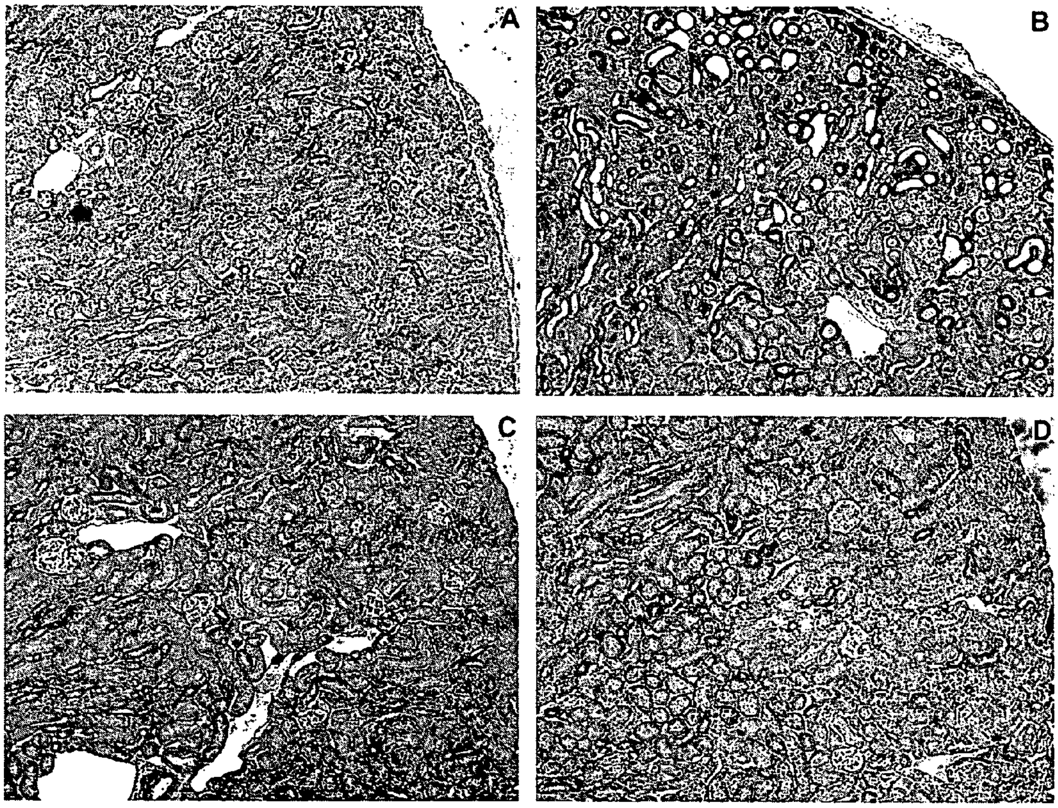
FIG. 41 is a series of photomicrographs demonstrating immunohistochemistry analysis $\alpha_v\beta_6$ expression in normal kidney and kidney after UUO.

1. Expression of αvβ6 in kidneys after UUO. The expression of αvβ6 integrin in kidneys after UUO was examined by immunohistochemical analysis. Minimal αvβ6 expression was detected in uninjured (normal) kidneys while significant upregulated expression was demonstrated at 7, 10, and 14 days after UUO (FIG. 41). Detectable expression was measured as early as 3 days after UUO.

2. Inhibition of smooth muscle actin immunostaining in UUO kidneys with mu3G9 treatment. Extent of fibrosis in the murine UUO model was measured by histomorphometric analysis of immunohistochemical α-smooth muscle actin staining (brown stain) or Masson's trichrome collagen matrix staining (blue stain). In each study, the proportion of tissue area occupied by fibrosis was determined in UUO mice receiving vehicle or isotype control mAb (negative control groups), in groups receiving test therapeutic treatment, and in unligated normal mice. Therapeutic effects are expressed as percent inhibition of Masson's trichrome collagen matrix (blue) staining or smooth muscle actin (brown) staining by calculating the ratio of the difference in stained area between negative control and test therapeutic over the difference between negative control and unligated normal mice.

For the purpose of relating results over multiple studies, therapeutic effects are expressed as percent inhibition of α-smooth muscle actin staining. Mean percent inhibition of smooth muscle actin staining at 4 mg/kg mu3G9, dosed i.p. three times per week for the ten day course of the experiment, was 32.8%. While rsTGF-βRII-Ig showed a mean % inhibition of 13.2 at 2 mg/kg (Table 14.1).

TABLE 14.1

Mean percent inhibition of α-smooth muscle actin staining for mu3G9 and rsTGF-βRII-Ig combining data from multiple studies.

| Molecule | Dose mg/kg | Mean % Inhibition | S.D | n | UUO Study #'s |
|---|---|---|---|---|---|
| 3G9 | 0.02 | 14.5 | 3.8 | 8 | 2 |
| 3G9 | 0.2 | 6.7 | 3.2 | 8 | 2 |
| 3G9 | 1 | 14.7 | 9.4 | 7 | 2 |
| 3G9 | 2 | 12.9 | 4.8 | 14 | 4, 9 |
| 3G9 | 4 | 32.8 | 5.0 | 30 | 4, 6, 7, 14 |
| 3G9 | 10 | 17.7 | 2.4 | 7 | 4 |
| rsTGF-βRII-Ig | 2 | 13.2 | 5.7 | 31 | 4, 6, 8, 9 |

Intraperitoneal dosing 3×/week, for 10 days
See Table 14.8 for individual mice at each dose

TABLE 14.2

UUO-4 Mean percent inhibition of smooth muscle actin staining.

| UUO-4 ASMA Brown Area % of Tissue | | | | | | |
|---|---|---|---|---|---|---|
| Veh | 3G9 (1) | 3G9 (2) | 3G9 (4) | 3G9 (10) | rsTGFβR (2) | Norm |
| 54 | 45 | 51 | 52 | 43 | 48 | 2 |
| 55 | 36 | 47 | 47 | 45 | 45 | 3 |
| 41 | 54 | 56 | 42 | 42 | 55 | 2 |
| 59 | 63 | 46 | 22 | 41 | 70 | 2 |
| 50 | 33 | 46 | 53 | 45 | 53 | 2 |
| 46 | 43 | 43 | 42 | 36 | 55 | 1 |
| 48 | 29 | 38 | 41 | 41 | 52 | 2 |
| 50.4 | 43.3 | 46.7 | 42.7 | 41.9 | 54.0 | 2.0 |
| 2.3 | 4.5 | 2.2 | 3.9 | 1.2 | 3.0 | 0.2 |
| 7 | 7 | 7 | 7 | 7 | 7 | 7 |

TABLE 14.2-continued

UUO-4 Mean percent inhibition of smooth muscle actin staining.

| | UUO-4 ASMA Brown Area % of Tissue | | | | | | |
|---|---|---|---|---|---|---|---|
| | Veh | 3G9 (1) | 3G9 (2) | 3G9 (4) | 3G9 (10) | rsTGFβR (2) | Norm |
| Control: | 50.4 | | | | | | |
| Signal: | 48.4 | | | | | | |
| % Inh: | | 11.2 | −1.2 | −3.2 | 15.3 | 5.0 | |
| | | 29.8 | 7.1 | 7.1 | 11.2 | 11.2 | |
| | | −7.4 | −11.5 | 17.4 | 17.4 | −9.4 | |
| | | −26.0 | 9.1 | 58.7 | 19.5 | −40.4 | |
| | | 36.0 | 9.1 | −5.3 | 11.2 | −5.3 | |
| | | 15.3 | 15.3 | 17.4 | 29.8 | −9.4 | |
| | | 44.2 | 25.7 | 19.5 | 19.5 | −3.2 | |
| Mean: | | 14.7 | 7.7 | 15.9 | 17.7 | −7.4 | |
| sem: | | 9.4 | 4.5 | 8.1 | 2.4 | 6.2 | |

TABLE 14.3

UUO-6 Mean percent inhibition of smooth muscle actin staining

| | UUO-6 ASMA Brown Area % of Tissue | | | | | |
|---|---|---|---|---|---|---|
| | Veh | 3G9 (4) | 8G6 (4) | 4B4 (4) | rsTGFβR (2) | Norm |
| | 38 | 66 | 33 | 45 | 40 | 1 |
| | 34 | 32 | 31 | 51 | 51 | 2 |
| | 30 | 29 | 42 | 48 | 52 | |
| | 49 | 40 | 31 | 37 | 55 | |
| | 57 | 42 | 48 | 44 | 45 | |
| | 46 | 45 | 28 | 43 | 44 | |
| | 60 | 26 | 57 | 39 | 41 | |
| | 51 | 28 | 40 | 36 | 47 | |
| | 45.6 | 38.5 | 38.8 | 42.9 | 46.9 | 1.5 |
| | 3.8 | 4.7 | 3.5 | 1.9 | 1.9 | 0.5 |
| | 8 | 8 | 8 | 8 | 8 | 2 |
| Control: | 45.6 | | | | | |
| Signal: | 44.1 | | | | | |
| % Inh: | | −46.2 | 28.6 | 1.4 | 12.7 | |
| | | 30.9 | 33.1 | −12.2 | −12.2 | |
| | | 37.7 | 8.2 | −5.4 | −14.4 | |
| | | 12.7 | 33.1 | 19.5 | −21.2 | |
| | | 8.2 | −5.4 | 3.7 | 1.4 | |
| | | 1.4 | 39.9 | 5.9 | 3.7 | |
| | | 44.5 | −25.8 | 15.0 | 10.5 | |
| | | 39.9 | 12.7 | 21.8 | −3.1 | |
| Mean: | | 16.1 | 15.6 | 6.2 | −2.8 | |
| sem: | | 10.5 | 8.0 | 4.2 | 4.3 | |

TABLE 14.4A

UUO-7 Mean percent inhibition of smooth muscle actin staining

| | UUO-7 ASMA Brown Area % of Tissue | | | | | |
|---|---|---|---|---|---|---|
| | Veh | LAPIg (1) | LAPIg (5) | LAPIg (10) | 3G9 (4) | Norm |
| | 31 | 30 | 33 | 26 | 18 | 1 |
| | 39 | 35 | 35 | 45 | 21 | 1 |
| | 49 | 45 | 33 | 20 | 13 | 1 |
| | 45 | 46 | 14 | 20 | 24 | 1 |
| | 39 | 43 | 17 | 23 | 18 | 1 |
| | 40 | 58 | 56 | 33 | 13 | |
| | 41 | 55 | 40 | 23 | 16 | |
| | 52 | 33 | 35 | 23 | 21 | |
| | 42.0 | 43.1 | 32.9 | 26.6 | 18.0 | 1.0 |
| | 2.3 | 3.6 | 4.6 | 3.0 | 1.4 | 0.0 |
| | 8 | 8 | 8 | 8 | 8 | 5 |
| Control: | 42.0 | | | | | |
| Signal: | 41.0 | | | | | |
| % Inh: | | 29.3 | 22.0 | 39.0 | 58.5 | |
| | | 17.1 | 17.1 | −7.3 | 51.2 | |
| | | −7.3 | 22.0 | 53.7 | 70.7 | |

TABLE 14.4A-continued

UUO-7 Mean percent inhibition of smooth muscle actin staining

| | UUO-7 ASMA Brown Area % of Tissue | | | | | |
|---|---|---|---|---|---|---|
| | Veh | LAPIg (1) | LAPIg (5) | LAPIg (10) | 3G9 (4) | Norm |
| | | −9.8 | 68.3 | 53.7 | 43.9 | |
| | | −2.4 | 61.0 | 46.3 | 58.5 | |
| | | −39.0 | −34.1 | 22.0 | 70.7 | |
| | | −31.7 | 4.9 | 46.3 | 63.4 | |
| | | 22.0 | 17.1 | 46.3 | 51.2 | |
| Mean: | | −2.7 | 22.3 | 37.5 | 58.5 | |
| sem: | | 8.7 | 11.3 | 7.3 | 3.4 | |

TABLE 14.4B

UUO-7 Mean percent inhibition of Masson trichrome staining

| | UUO-7 Blue Area % of Tissue | | | | | |
|---|---|---|---|---|---|---|
| | PBS | LAPIg 1 | LAPIg 5 | LAPIg 10 | 3G9 4 | Norm |
| | 5.6 | 5.9 | 4.2 | 4.9 | 4.0 | 3.5 |
| | 7.8 | 5.1 | 6.6 | 4.2 | 7.0 | 2.4 |
| | 6.8 | 5.1 | 12.6 | 4.1 | 4.6 | 2.1 |
| | 6.5 | 5.4 | 3.8 | 5.1 | 4.8 | 2.7 |
| | 4.8 | 5.5 | 4.9 | 4.5 | 5.4 | 2.3 |
| | 8.2 | 4.7 | 4.7 | 5.7 | 4.0 | |
| | 5.1 | 9.2 | 5.1 | 3.9 | 4.3 | |
| | 10.9 | 5.8 | 6.5 | 6.3 | 6.2 | |
| | 7.0 | 5.8 | 6.1 | 4.8 | 5.0 | 2.6 |
| | 0.7 | 0.5 | 1.0 | 0.3 | 0.4 | 0.2 |
| | 8 | 8 | 8 | 8 | 8 | 5 |
| Control: | 7.0 | | | | | |
| Signal: | 4.4 | | | | | |
| % Inh: | % inh. | 24.4 | 63.3 | 47.3 | 67.9 | |
| | | 42.7 | 8.3 | 63.3 | −0.9 | |
| | | 42.7 | −129.2 | 65.6 | 54.2 | |
| | | 35.8 | 72.5 | 42.7 | 49.6 | |
| | | 33.5 | 47.3 | 56.4 | 35.8 | |
| | | 51.9 | 51.9 | 28.9 | 67.9 | |
| | | −51.3 | 42.7 | 70.2 | 61.0 | |
| | | 26.6 | 10.6 | 15.2 | 17.5 | |
| Mean: | Mean | 25.8 | 20.9 | 48.7 | 44.1 | |
| sem: | sem | 11.5 | 22.9 | 6.8 | 8.8 | |

TABLE 14.5

UUO-8 Mean percent inhibition of smooth muscle actin staining

| | UUO-8 ASMA Brown Area % of Tissue | | | | |
|---|---|---|---|---|---|
| | Veh | sTGFbR (0.5) | sTGFbR (2) | rsTGFβR (5) | Norm |
| | 38 | 42 | 13 | 29 | 2 |
| | 35 | 42 | 10 | 31 | 2 |
| | 36 | 35 | 32 | 35 | 1 |
| | 42 | 23 | 51 | 39 | 2 |
| | 47 | 30 | 30 | 39 | 1 |
| | 28 | 35 | 29 | 27 | |
| | 51 | 31 | 27 | 32 | |
| | 48 | 30 | 42 | 41 | |
| | 40.6 | 33.5 | 29.3 | 34.1 | 1.6 |
| | 2.8 | 2.3 | 4.8 | 1.8 | 0.2 |
| | 8 | 8 | 8 | 8 | 5 |
| Control: | 40.6 | | | | |
| Signal: | 39.0 | | | | |
| % Inh: | | −3.5 | 70.8 | 29.8 | |
| | | −3.5 | 78.5 | 24.7 | |
| | | 14.4 | 22.1 | 14.4 | |
| | | 45.2 | −26.6 | 4.2 | |
| | | 27.2 | 27.2 | 4.2 | |
| | | 14.4 | 29.8 | 34.9 | |
| | | 24.7 | 34.9 | 22.1 | |
| | | 27.2 | −3.5 | −1.0 | |

TABLE 14.5-continued

UUO-8 Mean percent inhibition of smooth muscle actin staining

| | UUO-8 ASMA Brown Area % of Tissue | | | | |
|---|---|---|---|---|---|
| | Veh | sTGFbR (0.5) | sTGFbR (2) | rsTGFβR (5) | Norm |
| Mean: | | 18.3 | 29.1 | 16.7 | |
| sem: | | 5.8 | 12.3 | 4.7 | |

TABLE 14.6

UUO-9 Mean percent inhibition of smooth muscle actin staining

| | UUO-9 ASMA Brown Area % of Tissue | | | | | | |
|---|---|---|---|---|---|---|---|
| | Veh | 3G9 (0.02) | 3G9 (0.2) | 3G9 (2) | 8B3 (4) | rsTGFβR (2) | Norm |
| | 65.0 | 56.0 | 68.0 | 65.0 | 60.0 | 37.0 | 1.0 |
| | 69.0 | 59.0 | 63.0 | 60.0 | 64.0 | 56.0 | 2.0 |
| | 80.0 | 63.0 | 57.0 | 24.0 | 63.0 | 34.0 | 1.0 |
| | 76.0 | 58.0 | 63.0 | 64.0 | 61.0 | 42.0 | 1.0 |
| | 62.0 | 51.0 | 54.0 | 52.0 | 57.0 | 52.0 | 2.0 |
| | 58.0 | 44.0 | 62.0 | 64.0 | 53.0 | 56.0 | |
| | 61.0 | 62.0 | 60.0 | 56.0 | 71.0 | 56.0 | |
| | 64.0 | 66.0 | 73.0 | | 67.0 | 38.0 | |
| | 66.9 | 57.4 | 62.5 | 55.0 | 62.0 | 46.4 | 1.4 |
| | 2.7 | 2.5 | 2.1 | 5.5 | 2.0 | 3.4 | 0.2 |
| | 8 | 8 | 8 | 7 | 8 | 8 | 5 |
| Control: | 66.9 | | | | | | |
| Signal: | 65.5 | | | | | | |
| % Inh: | | 16.6 | −1.7 | 2.9 | 10.5 | 45.6 | |
| | | 12.0 | 5.9 | 10.5 | 4.4 | 16.6 | |
| | | 5.9 | 15.1 | 65.5 | 5.9 | 50.2 | |
| | | 13.6 | 5.9 | 4.4 | 9.0 | 38.0 | |
| | | 24.2 | 19.7 | 22.7 | 15.1 | 22.7 | |
| | | 34.9 | 7.4 | 4.4 | 21.2 | 16.6 | |
| | | 7.4 | 10.5 | 16.6 | −6.3 | 16.6 | |
| | | 1.3 | −9.4 | | −0.2 | 44.1 | |
| Mean: | | 14.5 | 6.7 | 18.1 | 7.4 | 31.3 | |
| sem: | | 3.8 | 3.2 | 8.4 | 3.0 | 5.2 | |

TABLE 14.8

Percent inhibiton of smooth muscle actin immunostaining in individual animals with mu3G9 or rsTGF-βRII-Ig treatment

| mu3G9 0.02 mg/kg | % Inhibition | mu3G9 0.2 mg/kg | % Inhibition | mu3G9 1 mg/kg | % Inhibition |
|---|---|---|---|---|---|
| UUO-9 | 16.6 | UUO-9 | −1.7 | UUO-4 | 11.2 |
| UUO-9 | 12.0 | UUO-9 | 5.9 | UUO-4 | 29.8 |
| UUO-9 | 5.9 | UUO-9 | 15.1 | UUO-4 | −7.4 |
| UUO-9 | 13.6 | UUO-9 | 5.9 | UUO-4 | −26 |
| UUO-9 | 24.2 | UUO-9 | 19.7 | UUO-4 | 36 |
| UUO-9 | 34.9 | UUO-9 | 7.4 | UUO-4 | 15.3 |
| UUO-9 | 7.4 | UUO-9 | 10.5 | UUO-4 | 44.2 |
| UUO-9 | 1.3 | UUO-9 | −9.4 | | −3.5 |
| mean | 14.5 | mean | 6.7 | mean | 14.7 |
| SD | 3.8 | SD | 3.2 | SD | 9.4 |
| n | 8.0 | n | 8 | n | 7 |
| mu3G9 2 mg/kg | mu3G9 % Inhibition | mu3G9 4 mg/kg | mu3G9 % Inhibition | mu3G9 10 mg/kg | mu3G9 % Inhibition |
| UUO-4 | −1.2 | UUO-4 | −3.2 | UUO-4 | 15.3 |
| UUO-4 | 7.1 | UUO-4 | 7.1 | UUO-4 | 11.2 |
| UUO-4 | −11.5 | UUO-4 | 17.4 | UUO-4 | 17.4 |
| UUO-4 | 9.1 | UUO-4 | 58.7 | UUO-4 | 19.5 |
| UUO-4 | 9.1 | UUO-4 | −5.3 | UUO-4 | 11.2 |
| UUO-4 | 15.3 | UUO-4 | 17.4 | UUO-4 | 29.8 |
| UUO-4 | 25.7 | UUO-4 | 19.5 | UUO-4 | 19.5 |
| UUO-9 | 2.9 | UUO-6 | −46.2 | | |
| UUO-9 | 10.5 | UUO-6 | 30.9 | | |
| UUO-9 | 65.5 | UUO-6 | 37.7 | | |
| UUO-9 | 4.4 | UUO-6 | 12.7 | | |
| UUO-9 | 22.7 | UUO-6 | 8.2 | | |
| UUO-9 | 4.4 | UUO-6 | 1.4 | | |
| UUO-9 | 16.6 | UUO-6 | 44.5 | | |
| | | UUO-6 | 39.9 | | |
| | | UUO-7 | 58.5 | | |
| | | UUO-7 | 51.2 | | |
| | | UUO-7 | 70.7 | | |
| | | UUO-7 | 43.9 | | |
| | | UUO-7 | 58.5 | | |
| | | UUO-7 | 70.7 | | |

TABLE 14.7

UUO-14 Mean percent inhibition of smooth muscle actin staining
UUO-14 ASMA Brown Area % of Tissue

| | Veh | wt3G9G1 (4) | wt3G9G2a (4) | agly3G9G2a (4) | Norm | |
|---|---|---|---|---|---|---|
| | 54 | 34 | 18 | 33 | 3 | |
| | 62 | 24 | 32 | 23 | 4 | |
| | 63 | 19 | 42 | 21 | 1 | |
| | 51 | 40 | 35 | 24 | 3 | |
| | 61 | 42 | 28 | 20 | 1 | |
| | 58 | 45 | 26 | 35 | | |
| | 47 | 43 | | 18 | | |
| | 56.5714286 | 35.2857143 | 30.1666667 | 24.8571429 | 2.4 | Mean |
| | 6.07884701 | 10.1277554 | 8.20771994 | 6.56832225 | 1.34164079 | s.d. |
| Control: | 56.6 | | | | | |
| Signal: | 54.2 | | | | | |
| % Inh: | | 41.7 | | | | |
| | | 60.1 | | | | |
| | | 69.4 | | | | |
| | | 30.6 | | | | |
| | | 26.9 | | | | |
| | | 21.4 | | | | |
| | | 25.1 | | | | |
| Mean % inhib | | 39.3 | | | | |
| s.d. | | 18.6900534 | | | | |

TABLE 14.8-continued

| Percent inhibiton of smooth muscle actin immunostaining in individual animals with mu3G9 or rsTGF-βRII-Ig treatment | | | | | |
|---|---|---|---|---|---|
| | | UUO-7 | 63.4 | | |
| | | UUO-7 | 51.2 | | |
| | | UU0-14 | 41.7 | | |
| | | UU0-14 | 60.1 | | |
| | | UU0-14 | 69.4 | | |
| | | UU0-14 | 30.6 | | |
| | | UU0-14 | 26.9 | | |
| | | UU0-14 | 21.4 | | |
| | | UU0-14 | 25.1 | | |
| mean | 12.9 | mean | 32.8 | mean | 17.7 |
| SD | 4.8 | s.d. | 5.0 | SD | 2.4 |
| n | 14 | # | 30 | n | 7 |

| rsTGFβRII-Ig | % Inhibition |
|---|---|
| UUO-8 | 70.8 |
| | 78.5 |
| | 22.1 |
| | −26.6 |
| | 27.2 |
| | 29.8 |
| | 34.9 |
| UUO-9 | 45.6 |
| | 16.6 |
| | 50.2 |
| | 38.0 |
| | 22.7 |
| | 16.6 |
| | 16.6 |
| | 44.1 |
| UUO-6 | 12.7 |
| | −12.2 |
| | −14.4 |
| | −21.2 |
| | 1.4 |
| | 3.7 |
| | 10.5 |
| | −3.1 |
| UUO-4 | 5.0 |
| | 11.2 |
| | −9.4 |
| | −40.4 |
| | −5.3 |
| | −9.4 |
| | −3.2 |
| mean | 13.2 |
| s.d. | 5.678 |
| # | 31 |

References

1. Miyajima A, Chen J, Lawrence C, Ledbetter S, Soslow R A, Stern J, Jha S, Pigato J, Lerner M L, Poppas D P, Darracott Vaughan Jr. E, Felson D: Antibody to transforming growth factor-β ameliorates tubular apoptosis in unilateral ureteral obstruction. Kid Int 2000, 58:2310-2313.

2. Okada H, Kalluri R: Cellular and molecular pathways that lead to progression and regression of renal fibrogenesis. Curr Mol Med 2005, 5:467-474.

3. Wang W, Koka V, Lan H Y: Transforming growth factor-beta and Smad signalling in kidney diseases. Nephrology 2005, 10:48-56.

4. Leask A, Abraham D J: TGF-beta signaling and the fibrotic response. FASEB J 2004, 18:816-827.

5. Chapman H A: Disorders of lung matrix remodeling. J Clin Invest 2004, 113:148-157.

6. Sheppard D: Functions of pulmonary epithelial integrins: from development to disease. Physiol Rev 2003, 83:673-686.

7. Ihn H: Pathogenesis of fibrosis: role of TGF-beta and CTGF. Curr Opin Rheumatol 2002, 14:681-685.

8. Norman J T, Fine L G: Progressive renal disease: fibroblasts, extracellular matrix, and integrins. Exp Nephrol 1999, 7:167-177.

9. Border W A, Noble N A: Interactions of transforming growth factor-beta and angiotensin II in renal fibrosis. Hypertension 1998, 31:181-188.

10. Sampson N S, Ryan S T, Enke D A, Cosgrove D, Koteliansky V, Gotwals P: Global Gene Expression Analysis Reveals a Role for the alpha 1 Integrin in Renal Pathogenesis. J Biol Chem 2001, 276:34182-34188.

11. Cosgrove D, Rodgers K, Meehan D, Miller C, Bovard K, Gilroy A, Gardner H, Kotelianski V, Gotwals P, Amattucci A, Kalluri R: Integrin α1β1 and transforming growth factor-β1 play distinct roles in alport glomerular pathogenesis and serve as dual targets for metabolic therapy. Amer J of Pathol 2000, 157:1649-1659.

12. Prols F, Hartner A, Schocklmann H O, Sterzel R B: Mesangial cells and their adhesive properties. Exp Nephrol 1999, 7:137-146.

13. Hamerski D A, Santoro S A: Integrins and the kidney: biology and pathobiology. Curr Opin Nephrol Hypertens 1999, 8:9-14.

14. Zambruno G, Marchisio P C, Marconi A, Vaschieri C, Melchiori A, Giannetti A, De Luca M: Transforming growth factor-β1 modulates β1 and β5 integrin receptors and induces the de novo expression of the αvβ6 heterodimer in normal human keratinocytes: implications for wound healing. J Cell Biol 1995, 129:853-865.

15. Trevillian P, Paul H, Millar E, Hibberd A, Agrez M V: alpha(v)beta(6) Integrin expression in diseased and transplanted kidneys. Kidney Int 2004, 66:1423-1433.

16. Breuss J M, Gallo J, DeLisser H M, Klimanskaya I V, Folkesson H G, Pittet J F, Nishimura S, Aldape K, Landers D V, Carpenter W, Gillett N, Sheppard D, Matthay M A, Albelda S M, Kramer R H, Pytella R: Expression of the β6 subunit in development, neoplasia and tissue repair suggests a role in epithelial remodeling. J Cell Sci 1995, 108:2241-2251.

17. Breuss J M, Gillett N, Lu L, Sheppard D, Pytella R: Restricted distribution of integrin β6 mRNA in primate epithelial tissues. J Histochem and Cytochem 1993, 41:1521-1527.

18. Hakkinen L, Hildebrand H C, Berndt A, Kosmehl H, Larjava H: Immunolocalization of tenascin-C, α9 integrin subunit, and αvβ6 integrin during wound healing in human oral mucosa. J of Histochem and Cytochem 2000, 48:985-998.

19. Arend L J, Smart A M, Briggs J P: Mouse β6 integrin sequence, pattern of expression, and role in kidney development. J Amer Soc Nephrol 2000, 11:2297-2305.

20. Hakkinen L, Koivisto L, Gardner H, Saarialho-Kere U, Carroll J M, Lakso M, Rauvala H, Laato M, Heino J, Larjava H: Increased expression of β6-integrin in skin leads to spontaneous development of chronic wounds. Am J Pathol 2004, 164:229-242.

21. Huang X Z, J. W, Spong S, Sheppard D: The integrin αvβ6 is critical for keratinocyte migration on both its known ligand, fibronectin, and on vitronectin. J Cell Sci 1998, 111: 2189-2195.

22. Munger J S, Huang X, Kawakatsu H, Griffiths M J D, Dalton S L, Wu J, Pittet J F, Kaminski N, Garat C, Matthay M A, Rifkin D B, Sheppard D: The integrin αvβ6 binds and activates latent TGFβ1: a mechanism for regulating pulmonary inflammation and fibrosis. Cell 1999, 96:319-328.

23. Busk M, Pytella R, Sheppard D: Characterization of the integrin alpha v beta 6 as a fibronectin-binding protein. Biol Chem 1992, 267:5790-5796.

24. Yokosaki Y, Monis H, Chen A, Sheppard D: Differential effects of the integrins alpha9beta1, alphavbeta3, and alphavbeta6 on cell proliferative responses to tenascin. Roles of the beta subunit extracellular and cytoplasmic domains. J Biol Chem 1996, 271:24144-24150.

25. Annes J P, Rifkin D B, Munger J S: The integrin αvβ6 binds and activates latent TGFβ3. FEBS lett 2002, 511:65-68.

26. Munger J S, Harpel J G, Gleizes P E, Mazzieri R, Nunes I, Rifkin D B: Latent transforming growth factor-β:structural feature and mechanisms of activation. Kid Int 1997, 51:1376-1382.

27. Gleizes P E, Munger J S, Nunes I, Harpel J G, Mazzieri R, Noguera I, Rifkin D B: TGF-beta latency: biological significance and mechanisms of activation. Stem Cells 1997, 15:190-197.

28. Khalil N: TGF-beta: from latent to active. Microbes Infect 1999, 1:1255-1263.

29. Barcellos-Hoff M H: Latency and activation in the control of TGF-γ. J Mamm Gland Biol 1996, 1:353-363.

30. Weinreb P H, Simon K J, Rayhorn P, Yang W J, Leone D R, Dolinski B M, Pearse B R, Yokota Y, Kawakatsu H, Atakilit A, Sheppard D, Violette S M: Function-blocking integrin alphavbeta6 monoclonal antibodies. J Biol Chem 2004, 279:17875-17887.

31. Ma J, Nichimura H, Fogo A, Kon V, Inagami T, Ichikawa I: Accelerated fibrosis and collagen deposition develop in the renal interstitium of angiotensin type 2 receptor null mutant mice during ureteral obstruction. Kid Int 1998, 53:937-944.

Example 15

Use of Inhibitory Anti-αvβ6 in a Murine Model of Radiation-Induced Lung Fibrosis Introduction Lung fibrosis occurs when disordered matrix remodeling follows lung injury (Chapman 2004). Among many signaling factors that are dysregulated in lung fibrosis, the cytokine TGFβ plays a particularly important role. In animal models, inhibition of TGFβ signaling prevents fibrosis in lung, kidney, liver and skin.

After intracellular processing, TGFβ and its prodomain are secreted as a noncovalently associated complex (Annes, Munger et al. 2003). TGFβ bound to its prodomain is latent, i.e. it cannot bind to TGFβ receptors; hence the prodomain is referred to as the latency-associated peptide (LAP). In addition to acting as a TGFβ inhibitor, LAP interacts via disulfide linkage with proteins of the Latent TGFβ Binding Protein (LTBP) family. LTBPs are matrix proteins and anchor latent TGFβ in the ECM. Release of TGFβ from LAP, a process called latent TGFβ activation, is a necessary step in the TGFβ signaling pathway. The activation step is a potential target for strategies to reduce TGFβ signaling.

The integrins αvβ6 and αvβ8 activate latent TGFβ1 and TGFβ3 by interacting with an RGD amino acid sequence located near the C-termini of the respective LAPs (Munger, Huang et al. 1999; Annes, Rifkin et al. 2002; Mu, Cambier et al. 2002). (TGFβ2, the final TGFβ isoform, does not have an RGD sequence and cannot be activated by these integrins). Within the lung, TGFβ activation by the integrin αvβ6 plays a nonredundant role in homeostasis and response to injury. αvβ6 is expressed in small amounts in normal lung epithelium but is rapidly upregulated following injury. Mice lacking the β6 gene (Itgb6−/−) develop lung inflammation and emphysema as a result of reduced TGFβ signaling. Exposure of mouse lungs to bleomycin causes acute lung injury accompanied by a large increase in αvβ6 expression, followed by TGFβ-dependent lung fibrosis; Itgb6−/− mice do not develop lung fibrosis after bleomycin treatment.

Ionizing radiation causes lung fibrosis (Franko and Sharplin 1994; Movsas, Raffin et al. 1997; Martin, Lefaix et al. 2000; Abratt, Morgan et al. 2004). In contrast to the bleomycin lung fibrosis model, in which fibrosis begins within days after lung injury, radiation-induced lung fibrosis (RILF) starts months after injury. Murine RILF is strain-dependent; the C57BL/6 strain used in these experiments is susceptible. In the murine RILF model there is also substantial late mortality occurring around the time of fibrosis development; this mortality is likely due to loss of lung perfusion (Franko, Nguyen et al. 1996; Haston, Zhou et al. 2002). An inhibitory anti-αvβ6 mAb (3G9) has been developed (Weinreb, Simon et al. 2004). The goals of these studies were to: (1) establish the αvβ6-dependence of RILF in a susceptible mouse strain by comparing the responses of Itgb6+/+ and Itgb6−/− to thoracic radiation, (2) confirm the TGFβ-dependence of the murine RILF model by treating irradiated mice with a TGFβ antagonist (soluble TGFβ receptor) and (3) assess the effects of various doses of 3G9 given to radiated mice.

Materials and Methods

1. Animals. All mice used were female. Itgb6−/− mice were a gift from Dean Sheppard, UCSF, and were bred in our facility on a C57BL/6 background. Wild type mice were C57BL/6 purchased from Jackson Laboratory (Bar Harbor, Me.), 7-9 weeks of age on arrival and allowed one week for acclimatization in our animal facility prior to radiation. All animal handling procedures and experiments were approved by the New York University School of Medicine animal care committee and conformed to NIH guidelines for the care and use of laboratory animals. Cages were restricted to a maximum of 5 mice per cage per animal facility protocol. Mice were monitored daily for morbidity and mortality. Moribund mice were sacrificed.

2. Antibodies. Two antibodies were obtained from Biogen Idec (Cambridge, Mass.), and were prepared as described elsewhere herein. The primary antibody tested, 3G9, is an anti-αvβ6 mAb that blocks αvβ6-mediated TGFβ activation. It is IgG1 subtype and binds αvβ6 in a cation-independent manner. The control Ab (1E6) was a mouse anti-human LFA-3 IgG1 monoclonal Ab that does not interact with mouse LFA-3. Doses of this control Ab up to 200 mg/kg/week for 4 weeks in normal mice have shown no toxicity (data from Biogen Idec). Antibody aliquots were prepared as dilutions in sterile PBS to achieve doses of 0.3, 1, 3, 6, and 10 mg/kg in a total volume of 200 microliters. Subcutaneous injections in the right flank or intraperitoneal injections, depending on the experiment, began on week 15 post-irradiation.

3. Radiation Protocol. Mice were irradiated at age 8-10 weeks. Prior to irradiation, anesthesia was achieved using Avertin (2,2,2-tribromoethanol; Acros Organics, NJ) with 15 μl/g of a 2.5% solution delivered intraperitoneally. Mice were then positioned supine with tape on a plexiglass surface. Appropriate positioning of lead shielding restricted radiation to the thorax. The field from lung apex level to xiphoid process was 1.8 cm. A $^{60}$Co source was used to deliver 14-Gy radiation. Source-to-skin distance was 65 cm. Exposure time with this source was ~11 minutes. After radiation exposure, mice were returned to their cages and positioned face up and monitored during recovery.

4. Sample collections from sacrificed mice. Mice that survived to predetermined time points post-radiation (26, 28 or 32 weeks for the antibody studies) were sacrificed and processed in the following manner. After deep anesthesia was obtained with Avertin, 70% ethanol was sprayed over the thoracic and abdominal skin. The thoracic cavity was opened through the diaphragm. 400-500 μl of blood was aspirated directly from the ventricles. The trachea was exposed and cannulated with a 22-gauge angiocatheter. The lungs were lavaged twice with 700-μl aliquots of PBS. The right mainstem bronchus was ligated at the hilum and each lobe was removed and placed in a separate tube, frozen rapidly in liquid nitrogen, and stored at −80 C. The left lung was inflated with 400 μl 10% formalin, placed in 10% formalin overnight, and embedded in paraffin. The broncho-alveolar lavage (BAL) fluid obtained at time of sacrifice was divided into two aliquots: 200 μl and the remainder. Both tubes were centrifuged at 2000 RPM for 3 minutes. The supernatant from both tubes was combined, frozen in liquid nitrogen and stored at −80 C. The cell pellet from the larger tube was snap-frozen and stored in the same manner. The 200-μl aliquot cell pellet was resuspended with 200 μl RBC lysis buffer and mixed thoroughly. 50 μl were used for cell counting in a hemacytometer. The remaining 150 μl were used for cytospin preparations. Blood obtained by cardiac puncture was used to make serum or plasma as follows. After initial mixing in Capiject tubes or heparinized 1.5 cc micro-centrifuge tubes, samples were centrifuged at 14,000 RPM for 20 minutes. Supernatants were removed and frozen to −80 C immediately.

5. Sample collections from mice found dead or moribund. Mice that were found dead or moribund prior to reaching the sacrifice date were dissected to obtain lung specimens. Moribund mice were euthanized with Avertin prior to dissection. The thoracic cavity was opened through the diaphragm. Dissection up to the trachea was performed with complete exposure. The trachea was cannulated with a 22-gauge angiocatheter. The lungs were inflated with 800-1000 μl of 10% formalin. The contents of the thoracic cavity were removed en bloc and placed in 10% formalin for at least 24 hours prior to lung separation and paraffin embedding.

6. Cell differentials. Cytospin preparations were stained by the DiffQuik method (15-second immersions sequentially in Fixative, 1% Eosin-Y, 1% Azure A, and deionized water). Slides were then dehydrated and mounted. Numbers of neutrophils, lymphocytes, and macrophages were manually counted in two separate high power (400×) fields.

7. Immunohistochemistry. Some formalin-fixed samples were used for immunohistochemical detection of β6. Endogenous peroxidase activity was quenched with 3% hydrogen peroxide in methanol for 15 minutes, and antigen retrieval was accomplished by applying Digest-All 3 Pepsin (Zymed, South San Francisco) for 5-7 minutes. Avidin/Biotin block solution (Vector Laboratories, Burlingame, Calif.) was used according to the manufacturer's instructions. Blocking was with 0.5% casein solution for 15 minutes. The anti-β6 monoclonal antibody ch2A1 (Biogen Idec), which consists of the variable region of a mouse anti-β6 mAb cloned into a human IgG, was used at a dilution of 1:500 in 0.1% BSA for 1 hr at room temperature. Detection was accomplished using a Vectastain ABC kit (Vector Laboratories) with an anti-human secondary antibody according to the manufacturer's directions. Chromogen generation was done with a DAB kit (Sigma, St. Louis, Mo.), followed by hematoxylin counterstaining. The specificity of the procedure was confirmed by omitting the primary antibody in sections treated in parallel, which was done routinely, and by preliminary tests on lung sections from Itgb6−/− mice, which gave negative results.

8. Lung sections, trichrome staining, and percent fibrosis determination. Formalin-fixed, paraffin-embedded lungs were sectioned transversely to 5-micron thickness. Sections of lung were obtained at or near the hilum by visual estimation. Slides were deparaffinized to deionized water (Xylene bath×2 for 3 minutes each, 100% ethanol×2 for 3 minutes each, 95% ethanol×2 for 3 minutes each, 70% ethanol×3 minutes, deionized water×3 minutes). Sections were stained with Masson's trichrome stain (Bouin's solution overnight to mordant, Weigert's iron hematoxylin for 5 minutes, Biebrich's Scarlet-Acid Fucshin for 5 minutes, Phosphotungstic/Phospho-molybdic Acid solution for 5 minutes, Aniline Blue solution for 5 minutes, deionized water rinses in between, and Acetic acid 1% for 2 minutes). Slides were then dehydrated (70% ethanol, 95% ethanol, 100% ethanol, and xylene), and mounted using Permount.

The percent fibrosis technique described by Haston et al. (Cancer Res 2002, 62:372-8) was used. Low power (2-3×) images of trichrome-stained lung sections were obtained and saved in digital format. High power (100-200×) manual inspection of lung sections was performed by light microscopy to identify regions of fibrosis (defined by increased collagen deposition and loss of architecture). Cross-sectional areas of fibrosis along with total cross-sectional area of the lung section were outlined on the digital image using NIH Image 1.62 software. The sum of the areas of fibrosis was divided by total area of lung to establish percent fibrosis. One random transverse section of the lung has been shown to reflect percent fibrosis in the entire lung when compared to 10 random sections (Haston, Amos et al. 1996).

9. Hydroxyproline assay. The measurement of hydroxyproline content was adapted from the method of Reddy and Enwememka. The right lung was removed and weighed. Lung tissue (about 20 mg wet weight) was incubated in 400 μl 2N NaOH solution for 12 hours (room temperature), then homogenized. The homogenates and standard hydroxyproline solutions were hydrolyzed by heating to 120° C. for 30 min. Chloramine-T solution (0.056M, 450 μl) was added to 50 μl of hydrolyzate and oxidation allowed to proceed for 25 min. Ehrlich's reagent (1 M, 500 μl) was added and color allowed to develop for 20 min at 65° C. Absorbance at 550 nm was then measured. The final concentrations are expressed as μg hyproxyproline/mg wet lung tissue.

10. RV/LV Mass Ratio Measurements. Mice used for this experiment were in a cohort that was sacrificed at 32 weeks post irradiation; seven additional unirradiated C57BL/6 mice were used as controls. Hearts from irradiated mice were from mice that died between 28 and 32 weeks or from mice that survived to sacrifice at 32 weeks. Hearts were fixed in formalin. Under the dissecting microscope, the atria were removed, and the right ventricular free wall (RV) was dissected free of the left ventricle and septum (LV). Each piece of ventricular tissue was weighed, and the ratio was calculated. Seven unirradiated C57BL/6 mice were used as controls.

11. Statistics. Statistical significance of percent fibrosis differences between groups was performed using the Mann-Whitney test for nonparametric data. Dates of death were recorded and used to create Kaplan-Meier curves. Individual group comparisons as well as total comparisons of Kaplan-Meier curves were made with Log-rank (Mantel-Cox) testing. Mean values of measurements are reported with the corresponding standard error of the mean or standard deviation. For comparison of the means of RV/LV mass ratio measurements, Student's t-test (non-paired, 2-tailed) was used. Fisher's exact test was used to compare presence or absence of fibrosis among Itgb6−/− and Itgb6+/+ mice. Statistical significance was defined as $p<0.05$.

Results

1. Murine RILF requires αvβ6 expression: comparison of Itgb6+/+ and Itgb6−/− mice after thoracic radiation. This experiment was designed to compare αvβ6 expression at baseline and post irradiation, and to determine if the absence of αvβ6 prevented fibrosis. We irradiated Itgb6−/− and Itgb6+/+ mice and sacrificed them at various time points prior to and at 28 weeks.

Figure 42:
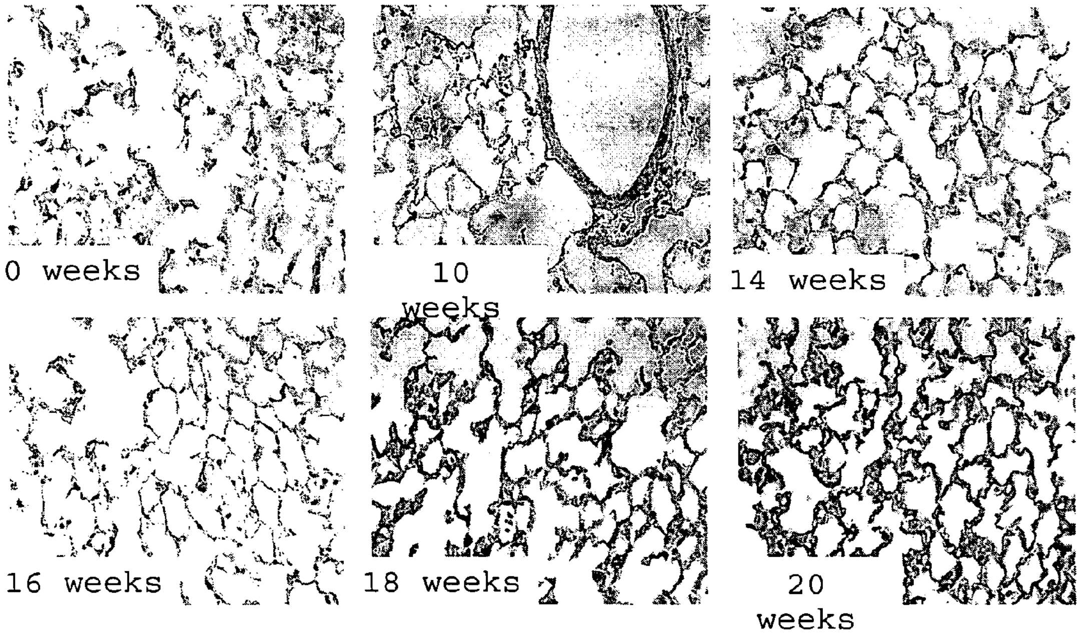
FIG. 42 is a series of photomicrographs demonstrating that $\alpha_v\beta_6$ upregulation occurs at 18 weeks post irradiation. C57BL/6 mice irradiated with 14 Gy were sacrificed at indicated time points and lung sections stained with anti-β6 antibody.

(a) β6 is upregulated at 18-20 weeks post irradiation. Mice sacrificed before 18 weeks post irradiation have normal, low αvβ6 expression, as measured by immunohistochemistry. At 18 weeks, however, diffusely increased expression of β6 throughout the alveolar epithelium is seen (FIG. 42).

Figure 43:
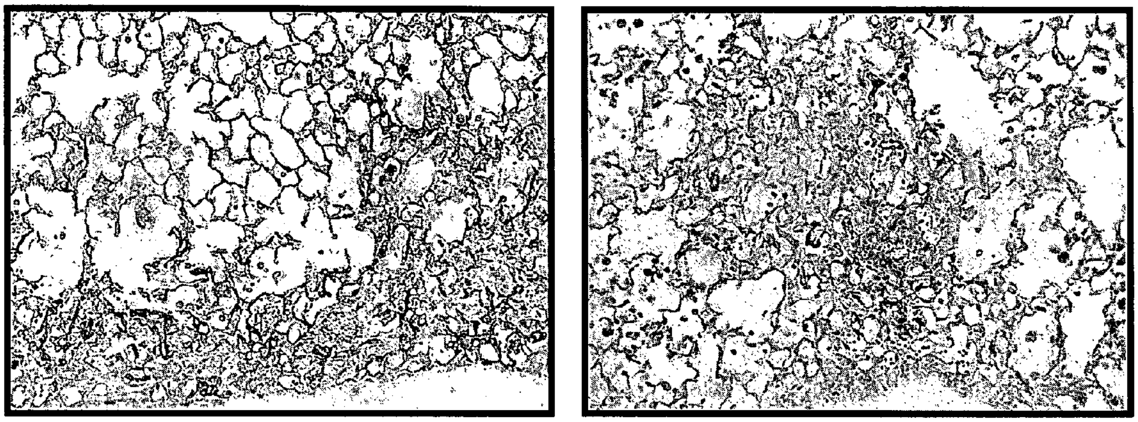
FIG. 43 is a pair of photomicrographs demonstrating that upregulated $\alpha_v\beta_6$ expression persists in areas of fibrosis. Lung sections were stained for β6 expression as in FIG. 1. Sections were from mice sacrificed at 24 weeks (left) or 27 weeks (right) after 14-Gy irradiation. Both sections show fibrotic lesions with numerous epithelial cells expressing high levels of $\alpha_v\beta_6$. In adjacent non-fibrotic epithelium, $\alpha_v\beta_6$ expression remains high at 24 weeks but is much less evident by 27 weeks.

(b) High αvβ6 expression persists in fibrotic regions. We consistently observed high levels of αvβ6 expression in epithelial cells within fibrotic lesions, regardless of time since irradiation (FIG. 43). However, the diffuse increased expression of αvβ6 noted at 18 weeks is often less evident at late time points (FIG. 43, compare 24 weeks and 27 weeks).

Figure 44:
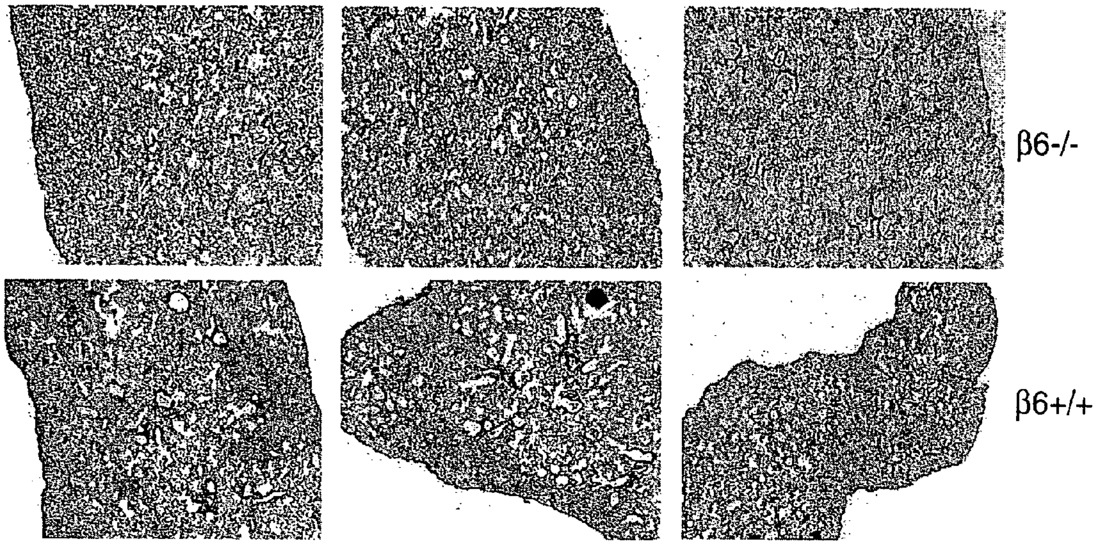
FIG. 44 is a series of photomicrographs demonstrating that Itgb6−/− mice are protected from radiation-induced lung fibrosis. Itgb6+/+ and Itgb6−/− mice (C57BL/6 background) were exposed to 14-Gy thoracic radiation. After 27 weeks, mice were sacrificed and left lungs were stained with Masson's trichrome. Representative lungs are shown; overall, $^{21}/_{23}$ Itgb6+/+ mice had evident fibrosis, whereas none of 17 Itgb6−/− mice had fibrosis.
Figure 45:
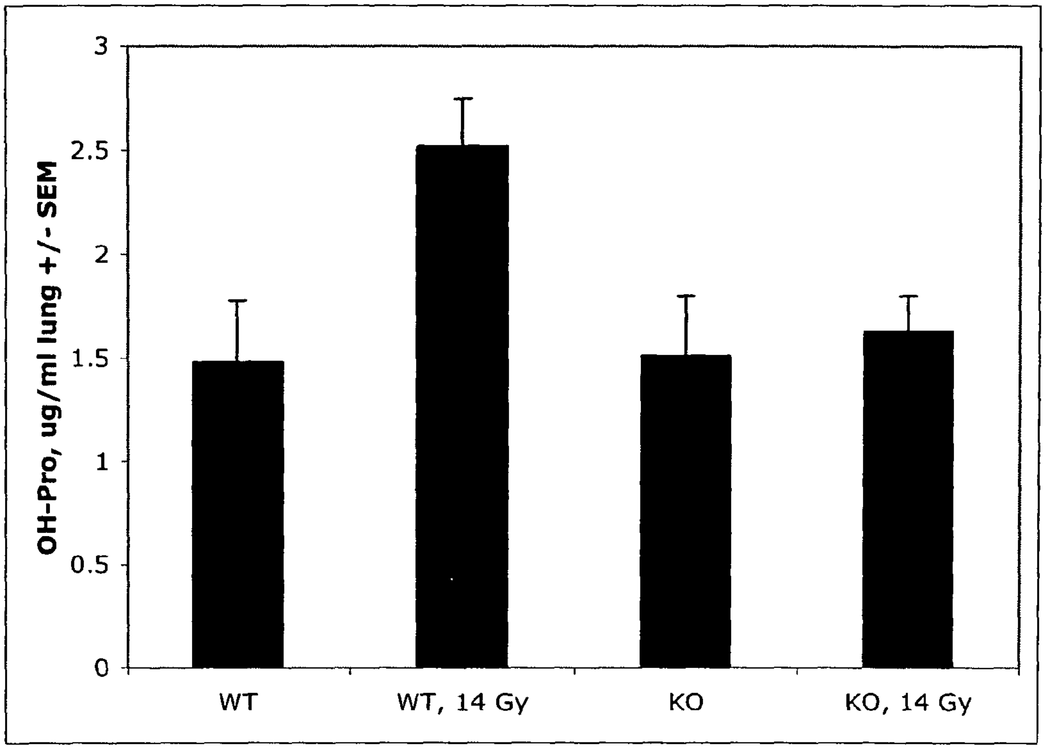
FIG. 45 is a bar graph demonstrating that Itgb6−/− mice are protected from radiation-induced lung fibrosis, as measured by hydroxyproline. Collagen content of irradiated Itgb6+/+ lungs is significantly greater than that of unirradiated Itgb6+/+ lungs and of irradiated and unirradiated Itgb6−/− lungs (p<0.03 versus irradiated Itgb6+/+, N=5-6 for each group).

(c) Mice lacking αvβ6 do not develop RILF. In control mice, the earliest time point at which areas of fibrosis could be discerned was 20-22 weeks post irradiation (not shown). Fibrotic areas typically are well-demarcated and subpleural. We did not find any areas of fibrosis in sections of lung from Itgb6−/− mice sacrificed 27 weeks post irradiation (N=17). In contrast, we found fibrotic areas in sections from 21/23 Itgb6+/+ mice, a difference that is statistically significant ($p<0.001$, two-tailed Fisher's exact test) (FIG. 44). The mean % fibrosis area of sections from Itgb6+/+ mice (27 weeks after irradiation) was 17%+/−3%. We confirmed the histologic findings by measuring the hydroxyproline content of lungs from Itgb6+/+ and Itgb6−/− mice 27 weeks post irradiation (FIG. 45).

Figure 46:
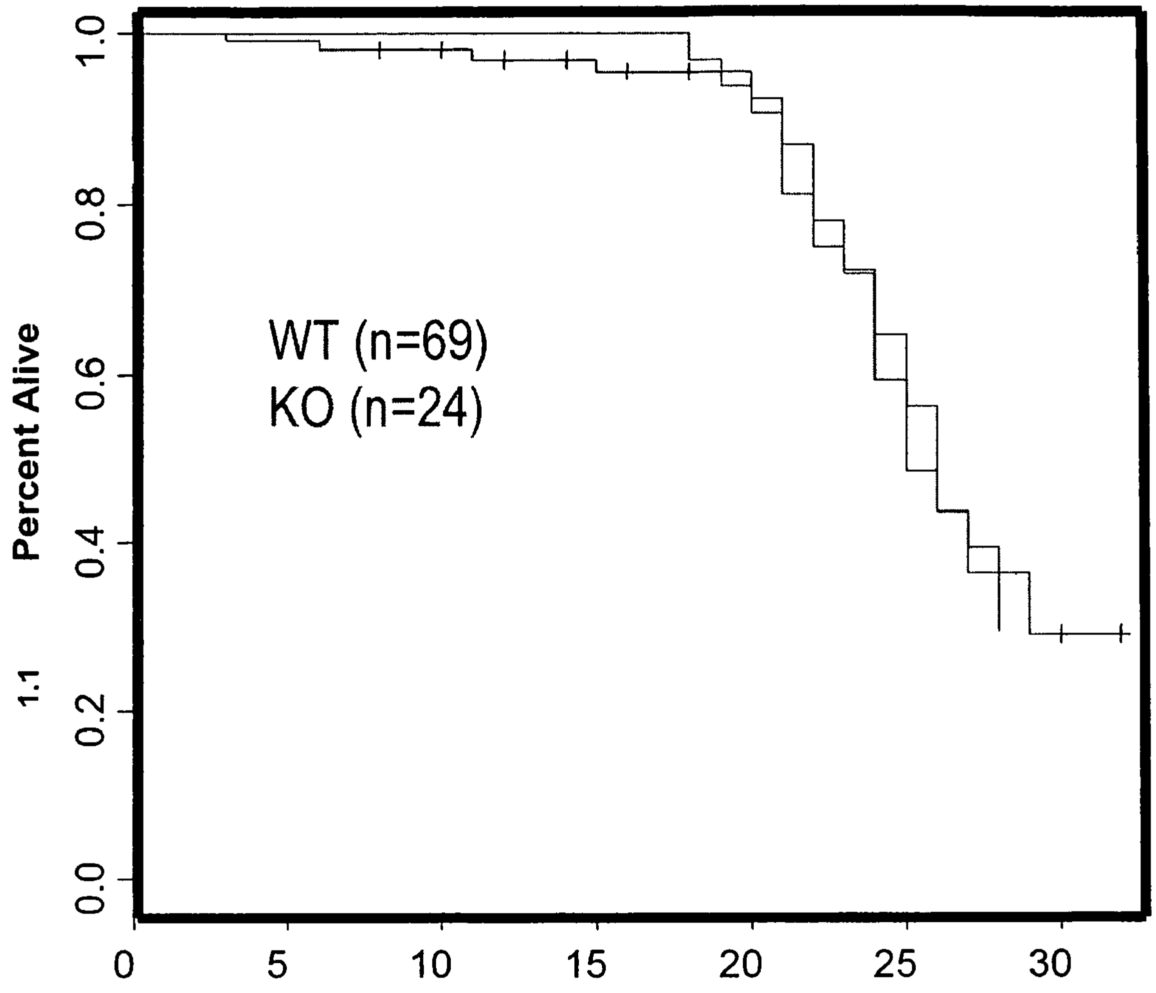
FIG. 46 is a line graph demonstrating that the absence of $\alpha_v\beta_6$ integrin does not affect survival after lung irradiation. Groups of Itgb6+/+ and Itgb6−/− mice were irradiated with 14 Gy. Survival curves for the two groups do not differ significantly (WT=Itgb6+/+, KO=Itgb6−/−).

(d) Absence of αvβ6 does not affect survival after lung irradiation. Following 14 Gy thoracic radiation, mortality was negligible until 18 weeks post irradiation, and reached 50% at approximately 25 weeks post irradiation. There was no significant difference between survival curves of Itgb6+/+ and Itgb6−/− mice (FIG. 46).

2. Effect of 3G9 (0.3, 1 and 1 mg/kg/wk IP dosing) and soluble TGFβR in murine RILF model The previous results indicate that RILF is dependent upon expression of αvβ6 integrin, and that lack of αvβ6 does not worsen post-radiation mortality. The requirement for αvβ6 is consistent with its known function as an activator of latent TGFβ1. These results also suggest the feasibility of αvβ6 inhibition as an antifibrosis strategy. To test this idea, and to confirm that the murine model of RILF is TGFβ-dependent, we treated irradiated mice with either a control Ab, soluble TGFβ receptor, or one of three doses of 3G9 (N=27 per group). A smaller number of mice (N=15) were treated with PBS injections (200 μl) alone. 3G9 was used at doses of 0.3, 1 and 10 mg/kg, the control Ab was used at 10 mg/kg and the soluble TGFβ receptor was used at 5 mg/kg. Treatments were started at 15 weeks post irradiation (approximately three weeks prior to αvβ6 upregulation) and continued weekly until sacrifice at 26 weeks post irradiation (see methods for details).

Figure 47:
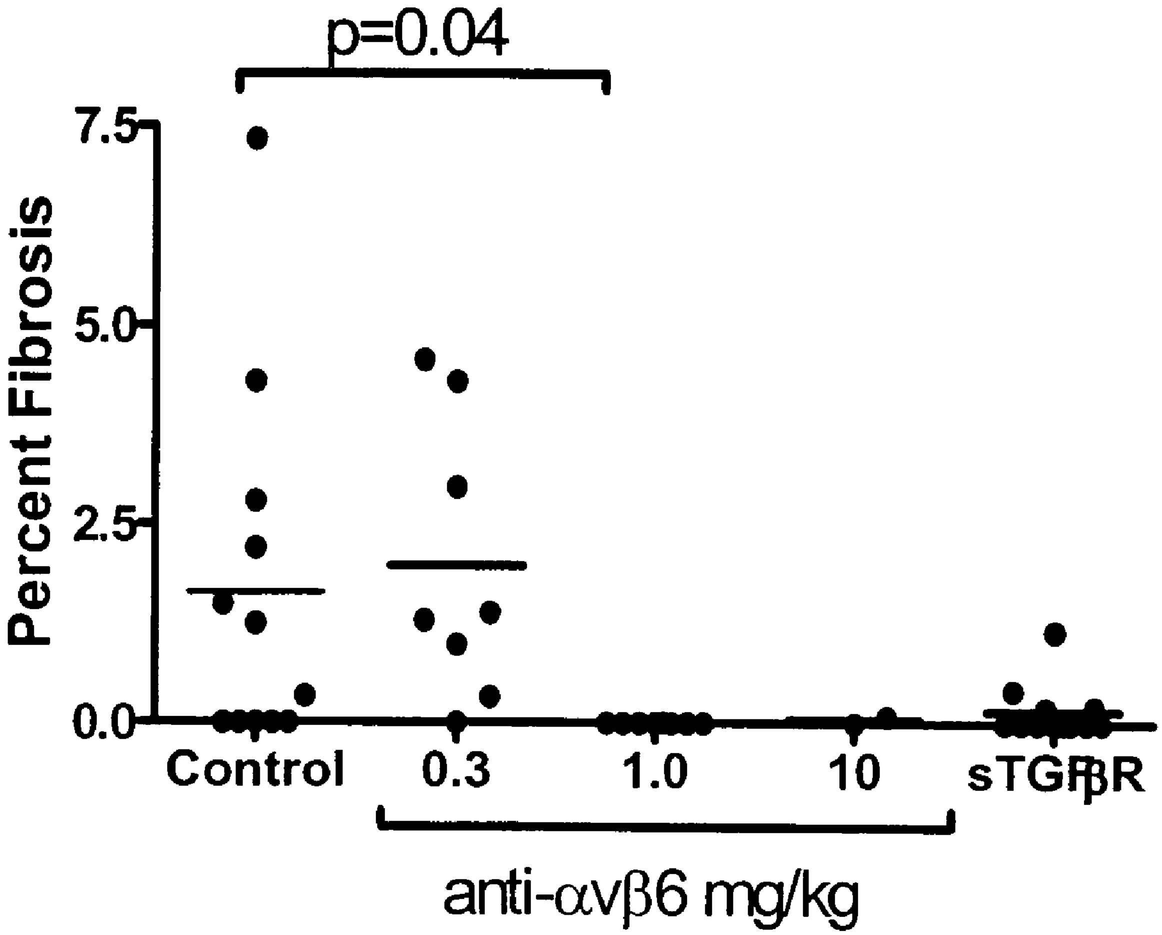
FIG. 47 is a scatter plot depicting lung fibrosis measurements in mice receiving 3G9, soluble TGFβR or control Ab IP sacrificed at 26 weeks post irradiation. Lung fibrosis is prevented in mice receiving 1 mg/kg/week 3G9. Each dot represents an individual mouse, bars represent means. There was no difference in fibrosis between the 0.3-mg/kg group and control group. The 1-mg/kg group had significantly less fibrosis than controls. The 10-mg/kg and soluble TGFβ receptor groups had less fibrosis but the differences from control did not reach significance.
Figure 48:
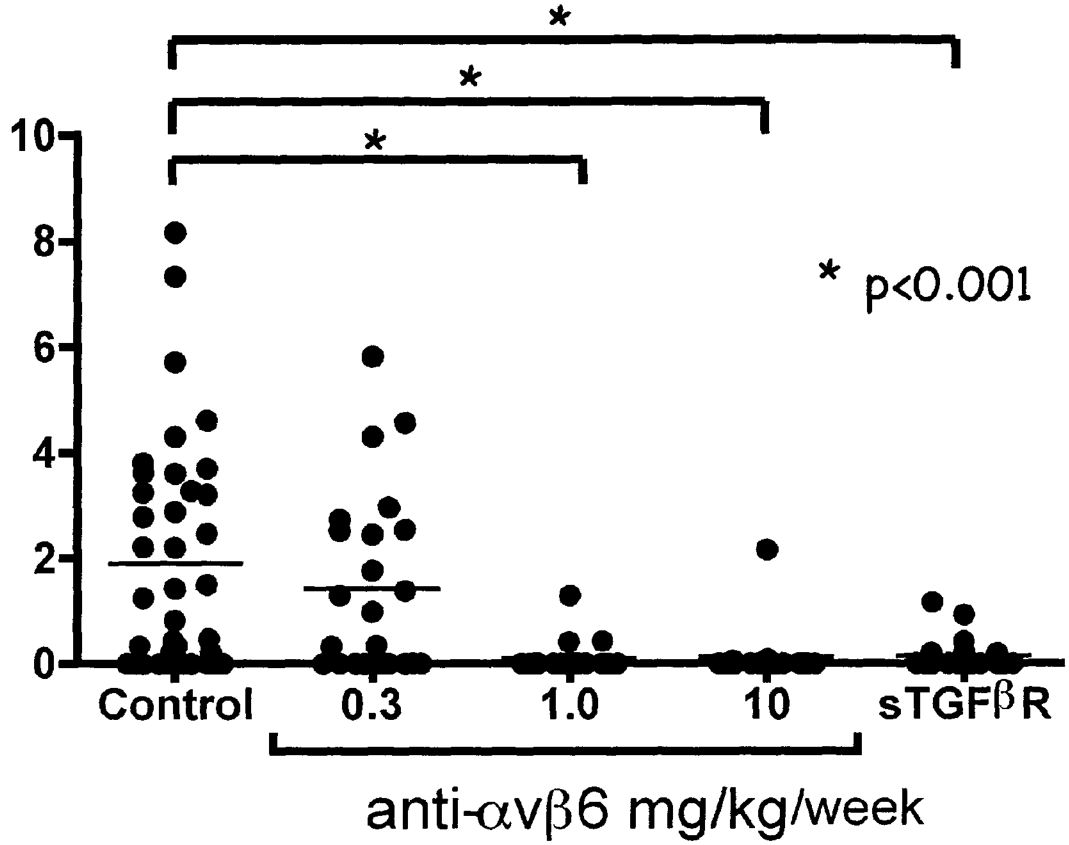
FIG. 48 is a scatter plot depicting lung fibrosis measurements in all mice (sacrificed mice, moribund mice, and mice found dead, from 20 to 26 weeks post irradiation) receiving 3G9, soluble TGFβR or control Ab IP. Data are presented as in FIG. 47. There was no difference in fibrosis between the 0.3-mg/kg group and control group. The 1-mg/kg, 10-mg/kg, and soluble TGFβ receptor groups had significantly less fibrosis than controls.

(a) 3G9 and soluble TGFβ receptor decrease fibrosis. All surviving mice were sacrificed at 26 weeks post irradiation. While the 0.3-mg/kg group showed no reduction in % fibrosis as compared to controls, the 1-mg/kg group had a significant reduction in fibrosis. Although the soluble TGFβ receptor and 10-mg/kg groups also showed less fibrosis than controls, the result did not reach statistical significance in the analysis of sacrificed mice only (FIG. 47). It is possible that the mice that died prior to the planned sacrifice time point differed biologically from the surviving mice. Therefore we performed a similar analysis on all mice that died or were sacrificed during the study period. When considering all mice (sacrificed and mice dying prior to sacrifice), significantly less fibrosis was present in the 1-mg/kg, 10-mg/kg, and soluble TGFβ receptor groups compared to controls. The 0.3-mg/kg group again did not have a significant difference as compared to controls (FIG. 48).

Figure 49:
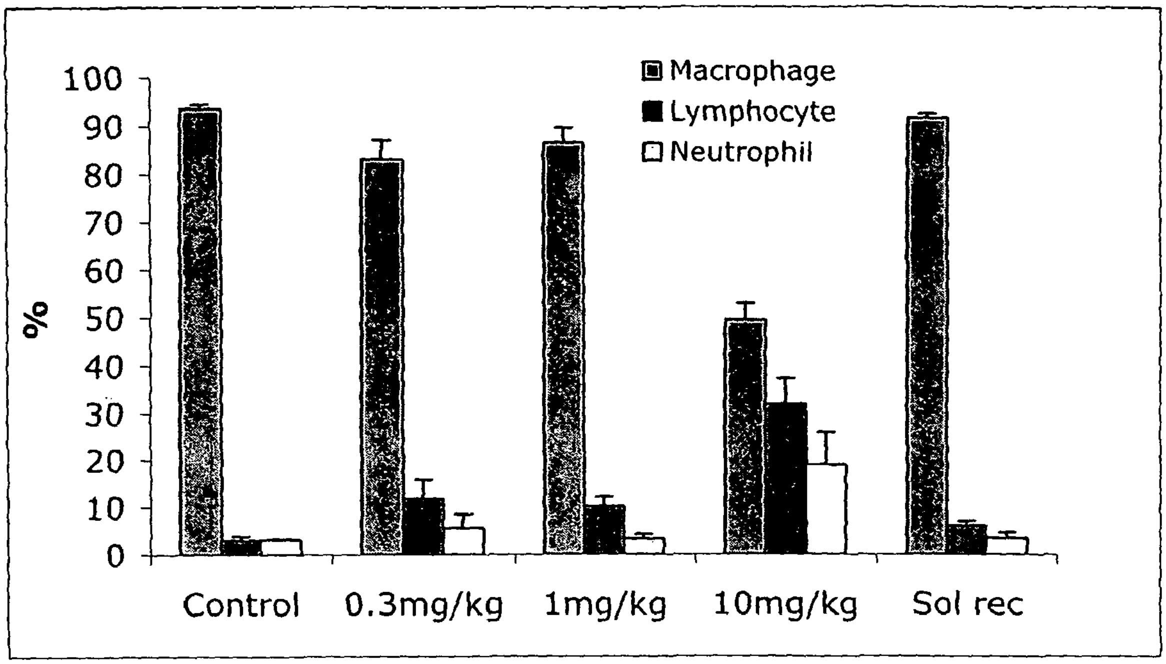
FIG. 49 is a bar graph depicting BAL cell differential counts from mice receiving 3G9, soluble TGFβR or control Ab IP sacrificed at 26 weeks post irradiation.

(b) 3G9 at the 10-mg/kg dose causes a neutrophilic and lymphocytic alveolitis. BAL performed on all sacrificed mice revealed increased percentages of neutrophils and lymphocytes in the 10-mg/kg group as compared to controls (FIG. 49). Other groups showed no similar increases.

Figure 50:
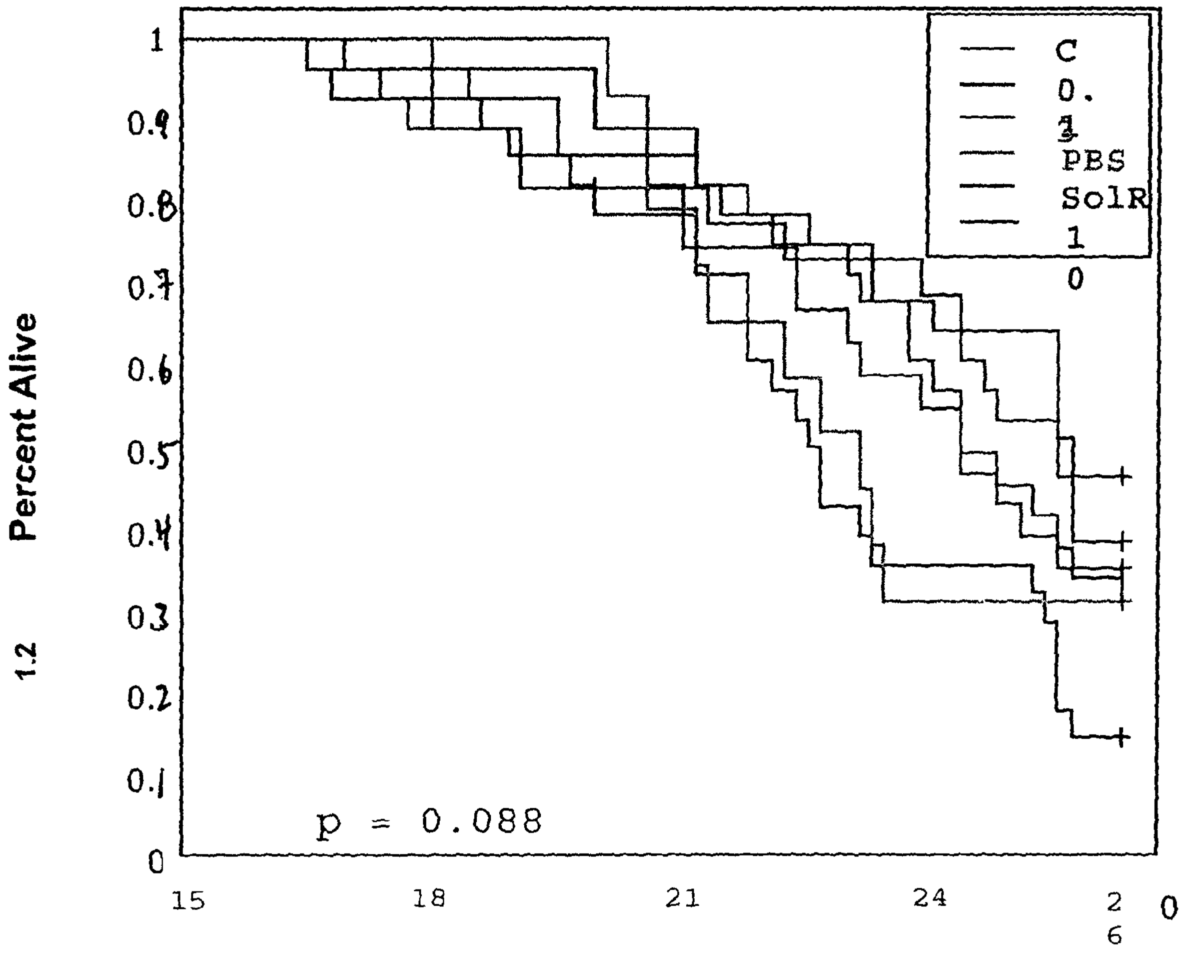
FIG. 50 is a line graph demonstrating that 14-Gy irradiated mice receiving IP 3G9 antibody injections had similar survival to controls. Survival analysis was performed on all groups as a composite analysis (p=0.088, C=control, 0.3=0.3 mg/kg, 1=1 mg/kg, SolR=soluble TGFβ receptor, 10=10 mg/kg).

(c) αvβ6 blockade via antibodies at lower doses does not affect survival after lung irradiation. There was no significant difference in survival when all groups were compared ($p=0.088$; comparison of all groups by log-rank Mantel-Cox test). However, a trend towards increased mortality in the 10-mg/kg group was apparent (FIG. 50). If only the 10-mg/kg/wk and control groups are compared (i.e., no correction for multiple comparisons), the difference between survival curves is statistically significant.

3. Effect of 3G9 (1, 3, 6 and 10 mg/kg/wk SC dosing) in murine RILF model. The previous results indicate that RILF in the murine model is TGFβ-mediated, and is significantly decreased by 3G9 at the 1 mg/kg and 10 mg/kg dose. However, increased alveolar inflammation and a trend towards increased mortality are present at the 10-mg/kg dose. In this experiment, we assessed fibrosis at later time points (up to 32 weeks post irradiation) to test the possibility that 3G9 treatment simply delayed onset of RILF for several weeks rather than preventing it. Also, to better define the differences in alveolar inflammation and possibly in survival between the 1- and 10-mg/kg doses, we tested additional doses between 1 and 10 mg/kg. We irradiated 270 mice and divided them into equal groups to receive one of four doses of 3G9 (1, 3, 6 and 10 mg/kg) or the control Ab (10 mg/kg). Treatments were started at 15 weeks post irradiation and continued weekly to a later sacrifice date. The experiment was done with 2 groups of mice irradiated about a month apart. In one group, the mice starting treatment were sacrificed if they survived to 28 weeks post irradiation (Group 1), and in the other group if they survived to 32 weeks (Group 2). Antibodies were given subcutaneously (not IP as in the previous experiment).

Figure 51:
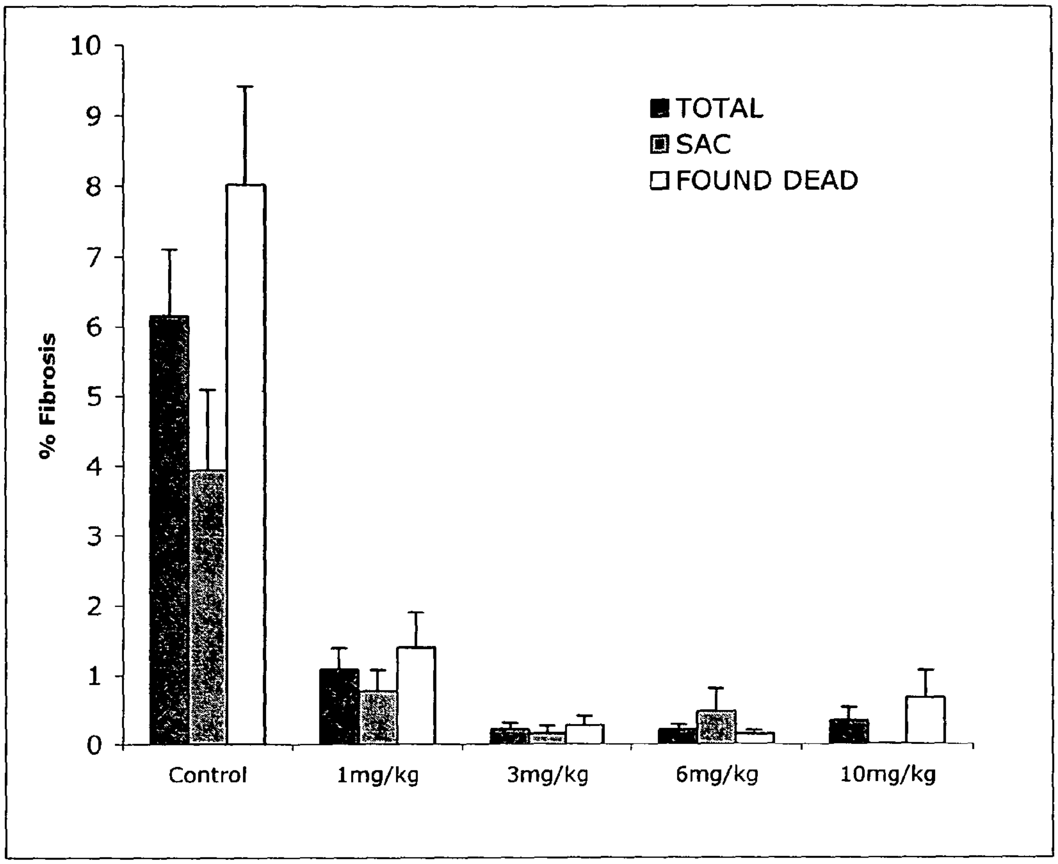
FIG. 51 is a bar graph depicting lung fibrosis measurements in mice treated with 3G9 (1, 3, 6, or 10 mg/kg) weekly SC. Separate results for all mice (mice found dead/moribund and sacrificed mice), mice sacrificed at 28 or 32 weeks, and mice found dead/moribund are shown. Significantly increased fibrosis is present in controls as compared to all antibody groups ($p<0.05$ for all doses versus controls).

(a) 3G9, at doses of 1, 3, 6 and 10 mg/kg, decreases fibrosis. Significantly decreased levels of fibrosis were observed in all groups receiving 3G9 as compared to controls ($p<0.01$). These differences were significant for mice found dead or moribund, mice sacrificed at the final time points, and all mice combined (FIG. 51).

Figure 52:
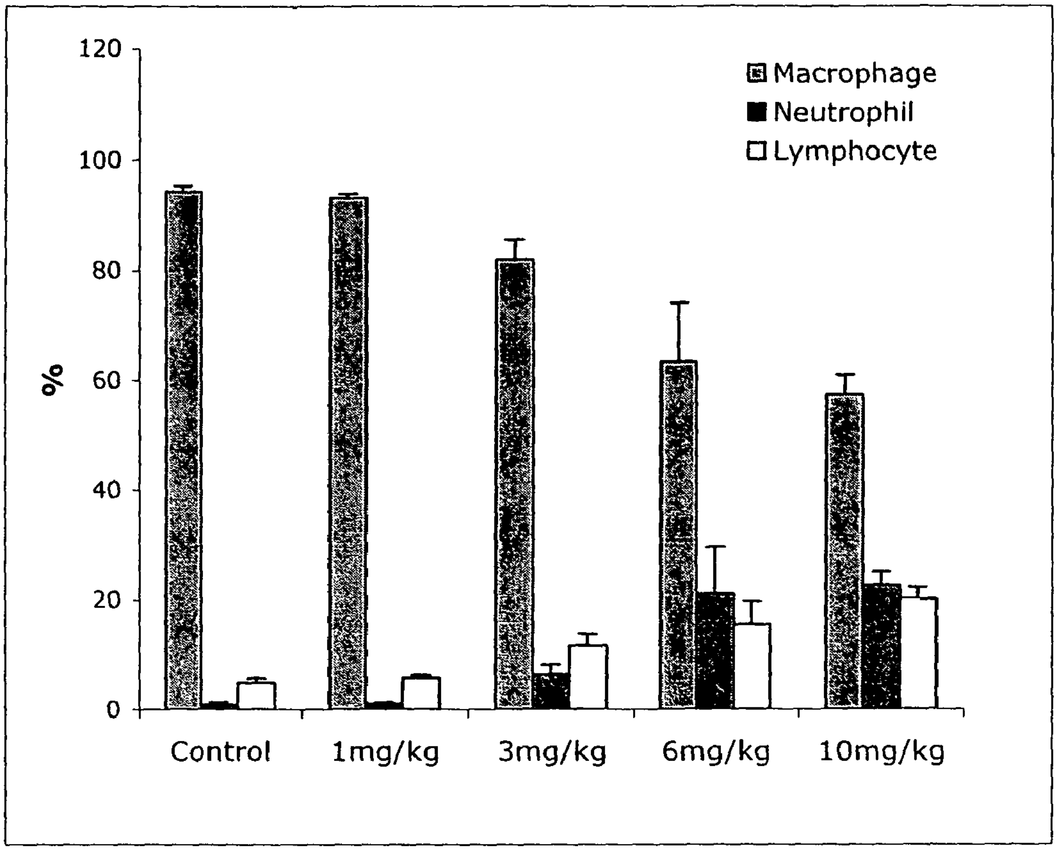
FIG. 52 is a bar graph depicting BAL cell differential counts from mice receiving 3G9 or control Ab SC sacrificed at 28 or 32 weeks post irradiation. 3G9 doses of 3, 6 and 10 mg/kg result in significantly increased percentages of both neutrophils and lymphocytes ($p<0.05$ for all comparisons).
Figure 53:
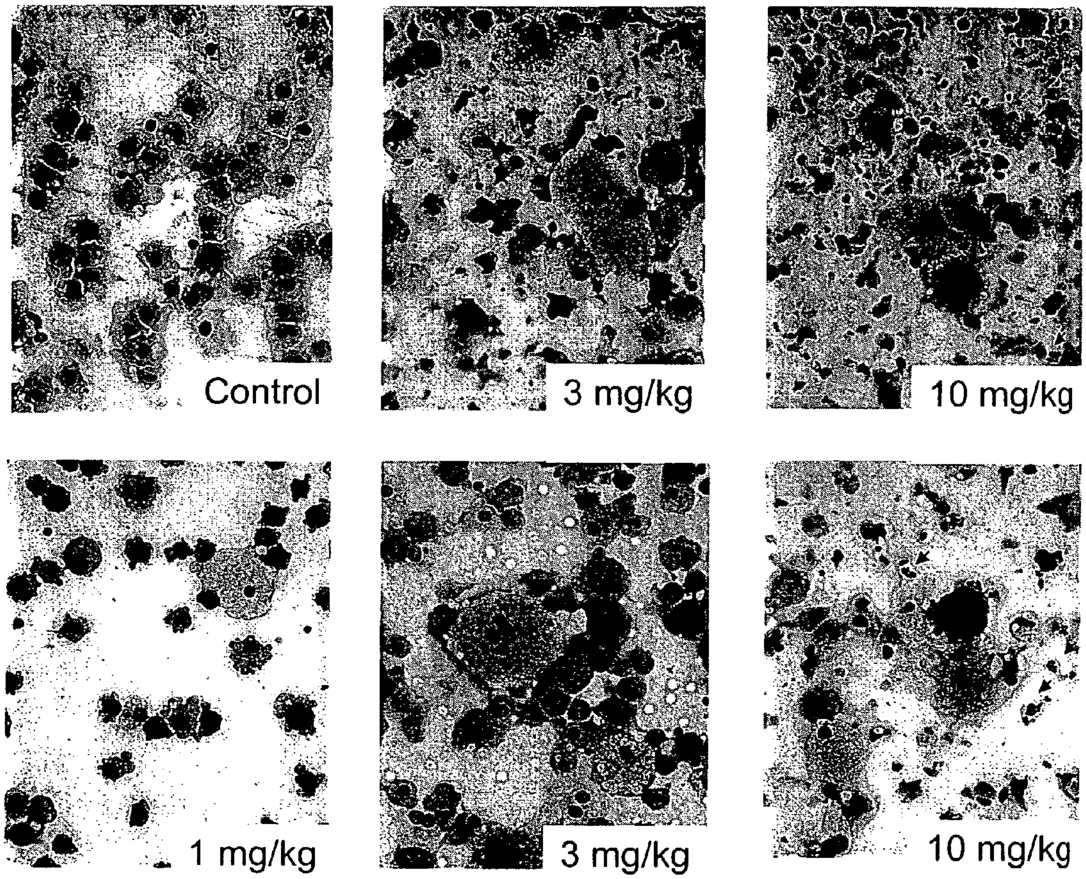
FIG. 53 is a series of photomicrographs depicting the Appearance of BAL cells in control versus 3G9 treated mice. Normal alveolar macrophages are seen in control cytospin. BAL cells from mice treated with 1 mg/kg 3G9 are similar to controls. At a dose of 3 mg/kg, numerous large foamy macrophages become evident. (Similar macrophages are seen in Itgb6−/− mice.) At higher doses (6 mg/kg and, shown here, 10 mg/kg), increased numbers of neutrophils (arrowheads) and lymphocytes are evident, as well as some cellular debris.

(b) 3G9 at higher doses causes a neutrophilic and lymphocytic alveolitis. BALs performed on all sacrificed mice (N=101) revealed higher percentages of neutrophils and lymphocytes (FIG. 52) in the 3-mg/kg, 6-mg/kg, and 10-mg/kg groups as compared to controls ($p<0.02$). Also, significantly higher percentages were present in the 10-mg/kg group as compared to the 1-mg/kg group ($p<0.001$). Qualitatively, increased numbers of "foamy" macrophages (identical to those seen in Itgb6−/− mice) and cellular debris are seen at higher doses (FIG. 53).

Figure 54:
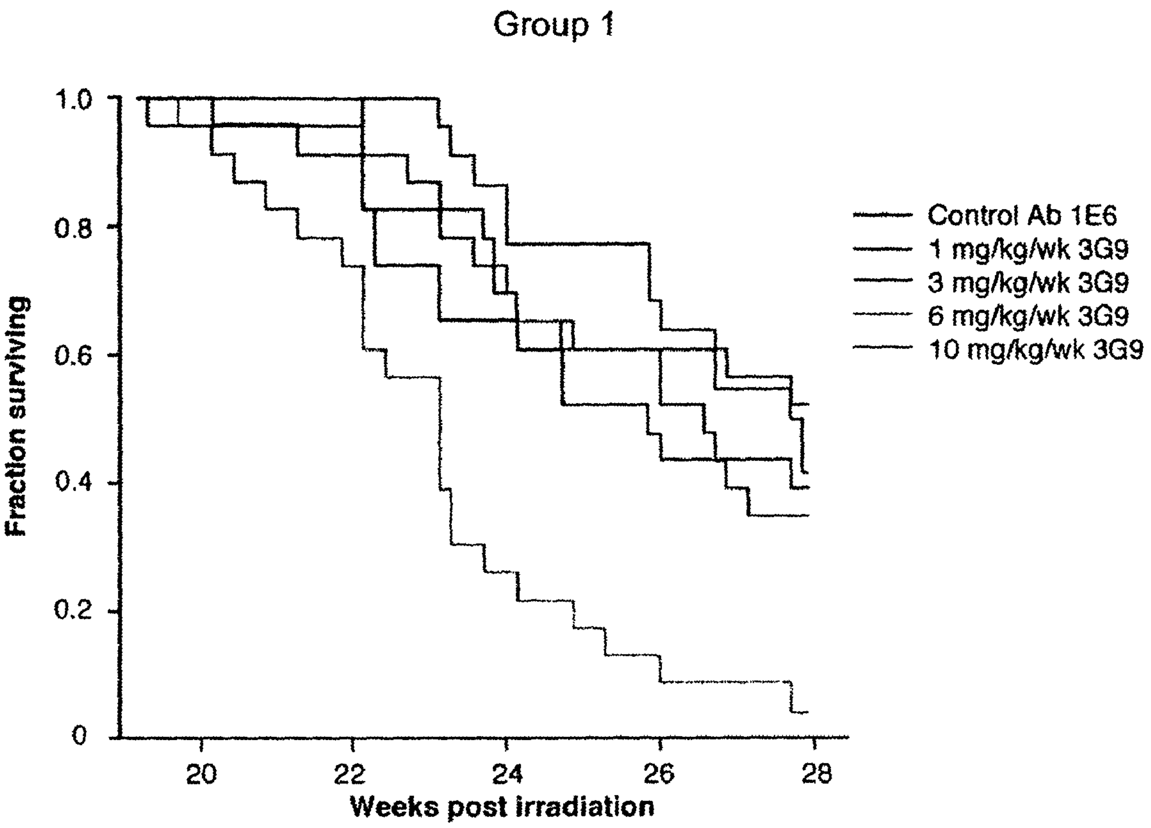
FIG. 54 is a line graph depicting Kaplan-Meier survival curves for cohort of mice sacrificed at 28 weeks post irradiation.
Figure 55:
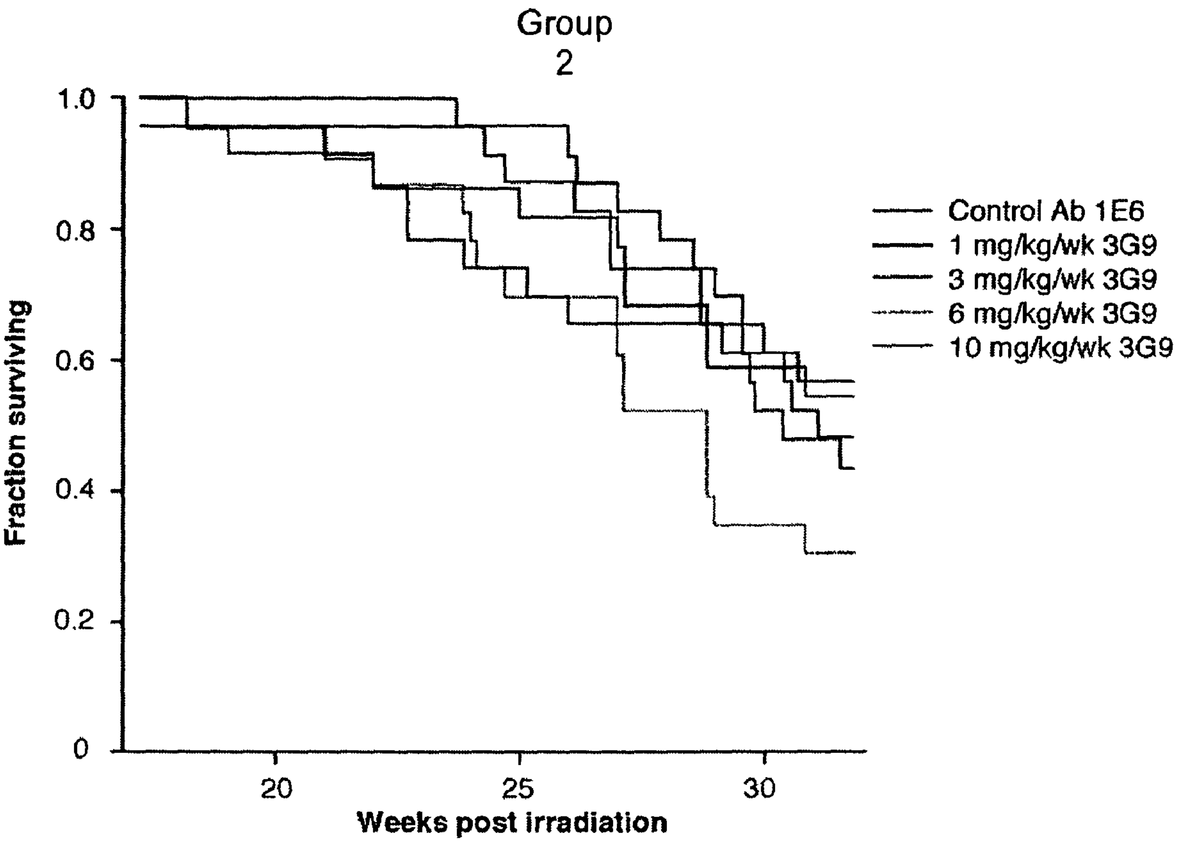
FIG. 55 is a line graph depicting Kaplan-Meier survival curves for cohort of mice sacrificed at 32 weeks post irradiation.

(c) 3G9 at a dose of 6 mg/kg is associated with reduced survival. There was no difference in mortality between the control group as compared to the 1-mg/kg and 3-mg/kg groups (FIGS. 54 and 55). There was, however, a significantly higher mortality in the 6-mg/kg group as compared to controls ($p<0.05$). The 10-mg/kg group did not have a reduction in survival as compared to control mice. The 6-mg/kg/wk 3G9 group had poorer survival in both the 28-week sacrifice (Group 1) and the 32-week sacrifice (Group 2) cohorts, although the difference was more prominent in the 28-week group (FIGS. 54 and 55).

Figure 56:
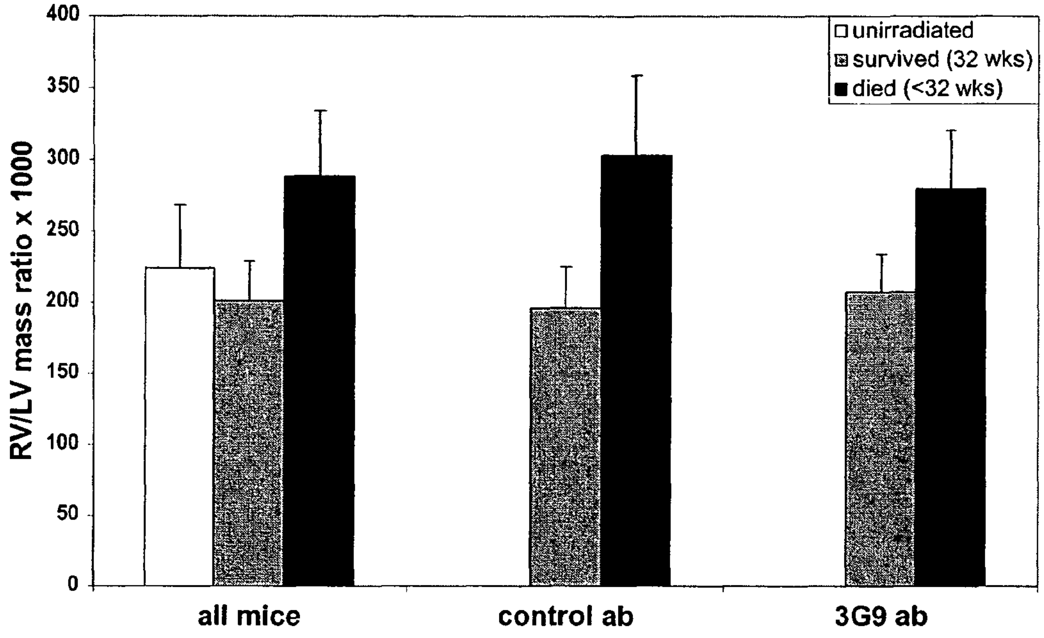
FIG. 56 is a bar graph demonstrating that the RV/LV mass ratio is increased in mice that died between 29-32 weeks post irradiation compared to mice that survived to 32 weeks post irradiation. Hearts of mice were fixed in formalin. The right ventricle (RV) was dissected free of the left ventricle plus septum (LV), and the tissues were weighed. Seven unirradiated mice of the same strain were used as controls. Bars represent means +/−SD. Data for irradiated mice are shown for all mice (treated with 1E6 control antibody or any dose of 3G9), mice treated with control antibody 1E6, and mice treated with any dose of 3G9. Numbers of mice were as follows: unirradiated mice, N=7; 1E6-treated mice: survived N=10, died N=5; 3G9-treated mice: survived, N=8, died N=9. The RV/LV ratio was not significantly different from unirradiated controls in mice that survived. In contrast, the RV/LV ratio was significantly increased in mice that died (all mice and the 1E6 and 3G9 subsets) compared to unirradiated mice ($P<0.02$). Also, the RV/LV ratio was significantly increased in mice that died (all mice and the 1E6 and 3G9 subsets) compared to the equivalent groups of mice that survived ($P<0.0007$).
Figure 57:
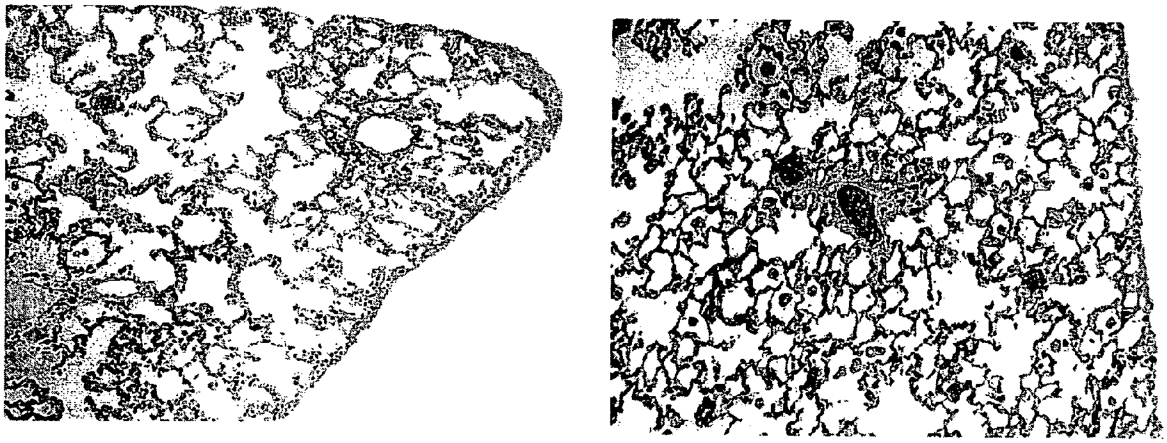
FIG. 57 is a pair of photomicrographs depicting lungs from mice found dead that had been treated with control antibody (1E6), left, or with anti-$\alpha_v\beta_6$ antibody (3G9, 1 mg/kg/wk), right. Note peripheral areas with absence of erythrocytes in alveolar walls. This appearance is consistent with loss of perfusion.

(d) Effect of lung irradiation on R V/L V mass ratio and lung perfusion. Prior studies suggested that deaths during the fibrosis phase after lung irradiation are due to respiratory distress resulting from a combination of airspace obstruction (mainly due to fibrosis) and loss of alveolar perfusion (Sharplin and Franko 1989). Loss of perfusion should lead to pulmonary arterial hypertension and right ventricular hypertrophy, and increased RV mass has been reported in this model. We measured the RV/LV mass ratio of mice that survived to 32 weeks and of mice in the same cohort that died between 28 and 32 weeks. Mice that died had a significantly increased RV/LV ratio compared to mice that survived and compared to unirradiated mice (FIG. 56). In addition, in some mice that died, distinct areas with complete absence of erythrocytes in alveolar walls were noted, a finding that is indicative of complete loss of alveolar perfusion (FIG. 57).

Discussion

TGFβ is known to be a pro-fibrotic mediator. Previous work showed that the integrin αvβ6 activates latent TGFβ1 and TGFβ3 and that Itgb6−/− mice are protected from bleomycin-induced lung fibrosis. The results presented here indicate that Itgb6−/− mice are also protected from radiation-induced lung fibrosis. These results provide a rationale for anti-fibrosis therapy targeting the αvβ6 integrin.

In these studies we found that 3G9 administered at doses of 1 mg/kg/week and higher consistently and effectively reduced RILF. Higher doses, particularly doses of 6-10 mg/kg/wk, were associated with increased percentages of neutrophils and lymphocytes in BAL fluid. These changes are consistent with the phenotype of Itgb6−/− mice and suggest that these doses of 3G9 are inhibiting αvβ6-mediated TGFβ activation to such an extent that the animals phenocopy the knockouts.

In addition, higher doses of 3G9 are associated, variably, with decreased survival in the murine RILF model. In the first trial, there was a strong trend to increased mortality with the 10-mg/kg/wk dose, but not in the mice treated with 1 or 0.3 mg/kg/wk. In the second trial, there was increased mortality in the 6-mg/kg/wk group, but not in the other groups (including 10 mg/kg/wk). Although the reasons for the discrepancies in dose/response are not clear, the general result is a tendency to decreased survival at the highest doses tested.

The deaths that occur in the RILF model appear to be due to respiratory distress. Mortality is strain-dependent and sex-dependent (Haston, Zhou et al. 2002). The causes of lung dysfunction and mortality in the murine RILF model have been extensively studied (Sharplin and Franko 1989). The authors of this study concluded that lung perfusion is reduced after radiation, and this deficit likely contributes to mortality. Mice that are resistant to radiation induced lung fibrosis also have decreased survival in the radiation induced lung fibrosis model. Decreased lung perfusion in these mice has been found to be a major factor contributing to their death in this model. The pattern of perfusion deficit depends upon the strain. In fibrosis-prone mice, complete loss of perfusion (as judged by presence or absence of colloidal carbon injected intravenously 30 sec prior to sacrifice) is restricted to areas of fibrosis and occasional small areas adjacent to fibrotic lesions. In addition, there was greater region-to-region variability in the amount of carbon in perfused areas in irradiated mice than in unirradiated controls, suggesting that there were substantial areas with reduced but not absent perfusion. Other evidence for loss of lung perfusion, seen in multiple mouse strains, was a reduced number of small blood vessels in lesion-free lung, and RV hypertrophy as assessed by RV/LV thickness ratio. The numbers of erythrocytes in alveolar walls (a different method of assessing perfusion) were also reduced in irradiated mice (A/J strain). Most C57BL/6 mice did not have pleural effusions. Except for the C57BL/10J strain, myocardial damage did not occur as a consequence of irradiation.

Our observations on mortality are consistent with the more extensive observations of Sharplin and Franko. In control mice, the amount of fibrosis is greater in mice that died than in those that survive to sacrifice (FIG. 51), suggesting that greater lung dysfunction is associated with death. Mice that die have right ventricular hypertrophy (defined as an increase in the RV/LV mass index), whereas mice surviving to sacrifice do not (FIG. 56), an observation that suggests loss of lung perfusion is associated with death. In some mice that were found dead, areas of lung lacking erythrocytes in alveolar walls were evident on histologic sections (FIG. 57), consistent with complete loss of perfusion in those areas and consistent with prior descriptions (Sharplin and Franko 1989). We have not noted evidence of esophageal dysfunction (scarring, perforation) that would account for death nor have we noted myocardial necrosis. Thus our evidence, interpreted in light of prior work, suggests that loss of lung perfusion occurs in C57BL/6 mice even when fibrosis is prevented and that loss of lung perfusion, not fibrosis, is responsible for death. We also noted that mice were more likely to die during the 2 days after injections (with either control Ab or 3G9), suggesting that the stress of handling, and perhaps extra fluid volume from the injection, hastened death in marginal mice.

Although loss of αvβ6 by gene ablation does not affect mortality in this model, high doses of 3G9 (6-10 mg/kg/wk) were associated with earlier death compared to mice treated with lower dose 3G9 or control Ab. The most obvious interpretation is that higher dose 3G9 worsens mortality. However, we cannot exclude the possibility that the control Ab and lower doses of 3G9 actually improve survival. Comparison of the time to 50% survival for the three experiments appears to reveal two groups. The wild type and Itgb6−/− mice (FIG. 46), the PBS-treated and 10-mg/kg/wk 3G9-treated mice in the IP experiment (FIG. 50) and the 6-mg/kg/wk 3G9-treated mice in the SC experiment (FIG. 54) have median survival times of ~22.5-25 weeks, whereas all other treatment groups have median survival times of ~24.5-30 weeks (FIGS. 50 and 54). Definitive conclusions on this point are not possible because experimental conditions varied and other conditions may have changed between the experiments, causing changes in baseline mortality. In mice treated with 3G9 at 6-10 mg/kg/wk, we did not note novel abnormalities (other than lung inflammation) that would account for changes in survival on gross inspection of the mice at dissection or on lung histology. The reasons for differences in survival between lower and higher doses of 3G9 in the RILF model are not known.

These studies support the conclusion that lower doses of 3G9, which presumably do not maximally reduce αvβ6-mediated TGFβ activation, safely prevent lung fibrosis in the murine RILF model.

References

Abratt, R. P., G. W. Morgan, et al. (2004). "Pulmonary complications of radiation therapy." *Clin Chest Med* 25(1): 167-77.

Armes, J. P., J. S. Munger, et al. (2003). "Making sense of latent TGFβ activation." *J Cell Sci* 116(Pt 2): 217-24.

Annes, J. P., D. B. Rifkin, et al. (2002). "The integrin αvβ6 binds and activates latent TGFβ3." *FEBS Lett* 511(1-3): 65-8.

Chapman, H. A. (2004). "Disorders of lung matrix remodeling." *J Clin Invest* 113(2): 148-57.

Franko, A. J., G. K. Nguyen, et al. (1996). "A comparison of the ultrastructure of perfusion-deficient and functional lung parenchyma in CBA mice during the late phase after irradiation." *Radiat Res* 146(5): 586-9.

Franko, A. J. and J. Sharplin (1994). "Development of fibrosis after lung irradiation in relation to inflammation and lung function in a mouse strain prone to fibrosis." *Radiat Res* 140(3): 347-55.

Haston, C. K., C. I. Amos, et al. (1996) "Inheritance of susceptibility to bleomycin-induced pulmonary fibrosis in the lung." *Cancer Res* 56(11): 2596-601.

Haston, C. K., X. Zhou, et al. (2002). "Universal and radiation-specific loci influence murine susceptibility to radiation-induced pulmonary fibrosis." *Cancer Res* 62(13): 3782-8.

Martin, M., J. Lefaix, et al. (2000). "TGF-β1 and radiation fibrosis: a master switch and a specific therapeutic target?" *Int J Radiat Oncol Biol Phys* 47(2): 277-90.

Movsas, B., T. A. Raffin, et al. (1997). "Pulmonary radiation injury." *Chest* 111(4): 1061-76.

Mu, D., S. Cambier, et al. (2002). "The integrin αvβ6 mediates epithelial homeostasis through MT1-MMP-dependent activation of TGF-beta1." *J Cell Biol* 157(3): 493-507.

Munger, J. S., X. Huang, et al. (1999). "The integrin αvβ6 binds and activates latent TGFβ1: a mechanism for regulating pulmonary inflammation and fibrosis." *Cell* 96(3): 319-28.

Sharplin, J. and A. J. Franko (1989). "A quantitative histological study of strain-dependent differences in the effects of irradiation on mouse lung during the intermediate and late phases." *Radiat Res* 119(1): 15-31.

Weinreb, P. H., K. J. Simon, et al. (2004). "Function-blocking integrin αvβ6 monoclonal antibodies: distinct ligand-mimetic and nonligand-mimetic classes." *J Biol Chem* 279 (17): 17875-87.

Example 16

Efficacy of an Anti-αvβ6 Integrin Monoclonal Antibody in the Bleomycin Model of Pulmonary Fibrosis Summary Current treatments for pulmonary fibrosis are largely ineffective and there is a profound need to develop novel therapeutics. Agents that block the TGF-β pathway are of particular interest due to the central role of TGF-β in driving many of the pathological processes that characterize pulmonary fibrosis, including fibroblast activation and proliferation, and expression of extracellular matrix molecules. In addition to its pro-fibrotic activities, TGF-β is an important anti-inflammatory cytokine, and thus therapeutic inhibition of TGF-β should ideally block fibrosis without promoting excessive inflammation. Previous work has demonstrated that the integrin αvβ6 is a key mediator of TGF-β activation in vivo, particularly in the lung. αvβ6 directly binds to latent TGF-β complexes in the extracellular space and this binding is, in many cases, required for liberation of the active form. Mice deficient for αvβ6 have mild pulmonary inflammation due to impaired TGF-β signaling in the lung and are resistant to bleomycin-induced pulmonary fibrosis. We have developed monoclonal antibodies that block binding of αvβ6 to latent TGF-β and inhibit TGF-β activation and subsequent signaling. Here we demonstrate that these antibodies are effective in attenuating bleomycin-induced fibrosis in mice. We further show that near-maximal efficacy in attenuating lung collagen expression can be achieved at doses which produce no additional inflammation, as measured by numbers of inflammatory cells in bronchoalveolar lavage. While higher doses of the antibody, which also attenuate fibrosis, can induce inflammation consistent with what is seen in αvβ6-deficient mice. These findings demonstrate that the pro-inflammatory and anti-fibrotic effects of blocking αvβ6-mediated TGF-β are separable in this model, and that inhibition of fibrosis occurs at lower doses than the pro-inflammatory effects.

Introduction

The TGF-β1 cytokine is central to both the initiation and maintenance of fibrosis, a pathological process marked by the replacement of diseased tissue with excess extracellular matrix (ECM) and ultimately leading to organ scarring and failure. TGF-β1 promotes fibroblast proliferation and the activation of myofibroblasts which are responsible for secreting ECM and maintaining the progression of the fibrotic process [1-6]. TGF-β1 plays a well regulated role in the tissue remodeling events that take place during wound healing; however, in many diseases this process of tissue remodeling becomes aberrant and is characterized by prolonged upregulated TGF-β signaling, excess fibroblast accumulation, ECM deposition, and scarring. The importance of TGF-β1 in the progression of fibrosis in vivo has been shown by both gain-of-function studies as well as through blockade [1, 7-12]. Adenoviral and transgenic overexpression of various cytokines in lung have shown that TGF-β1 is unique in its ability to promote fibrosis in the absence of significant inflammation. Other cytokines that promote fibrosis frequently do so by upregulating TGF-β1 expression in the tissue. In addition, studies have shown that knockout mice deficient for SMAD3, a mediator of TGF-β signaling, are resistant to the development of lung fibrosis [13]. Numerous studies with anti-TGF-β agents show profound protection from fibrosis in disease models [8, 9, 11, 14-17]. Consequently, TGF-β1 has been identified as a potential therapeutic target for treatment of diseases associated with the pathology of fibrosis.

The αvβ6 integrin has been identified as a critical regulator of TGF-β1 activation. TGF-β1 is synthesized as a latent protein that is cleaved and secreted with the N-terminal LAP non-covalently associated with the mature active C-terminal TGF-β cytokine. The latent TGF-β1 complex cannot bind to its cognate receptor and thus remains biologically inactive until converted to the active form by one of several alternative mechanisms that include cleavage by proteases, exposure to low pH or ionizing radiation, and conformational changes in the latent complex allowing it to bind to its cognate receptors [18-21]. The αvβ6 integrin binds to an RGD motif in the latent TGF-β1 complex and converts it to an active form. [18, 22-25]. Although several other mechanisms for TGF-γ activation have been identified, studies in beta6 integrin deficient mice (β6 null mice) suggest that αvβ6-mediated activation of TGF-γ is necessary for development of fibrosis in lung and kidney [18, 26]. αvβ6 is expressed at low or undetectable levels in normal adult tissues, but is strongly upregulated in inflammatory/fibrotic disease and is generally restricted to epithelial cells [27-30]. Thus, the upregulated expression of αvβ6 in epithelial cells during tissue injury provides a mechanism for increased local activation of TGF-β and subsequent TGF-β-dependent events in bystander cells. Blocking αvβ6 [31] ligand binding provides a method for localized inhibition of TGF-β activation specifically in tissues where there is upregulated expression of αvβ6. This approach offers the potential to decrease clinical safety risks associated with global inhibition of the TGF-β pathway.

In the studies described herein we show that αvβ6 is significantly upregulated in human lung diseases associated with inflammatory and fibrotic pathology, including idiopathic pulmonary fibrosis (IPF). Previous studies have demonstrated that β6 null mice, which lack αvβ6 function are protected from bleomycin-induced pulmonary fibrosis [18]. Here we show that monoclonal antibodies that block the ligand binding and TGF-β activation functions of αvβ6 potently inhibit bleomycin-induced fibrosis, in a variety of mouse strains and by a number of different measures of fibrosis. We further demonstrate that alveolar cell populations are not altered at low efficacious doses in the bleomycin-injured lung and thus the mechanism of anti-fibrotic action is, as expected, not mediated by inhibiting inflammation. Only with high, frequent dosing has additional inflammation been seen in this model, consistent with the finding of additional inflammation in β6 null mice.

Materials and Methods

1. Reagents. αvβ6 mAbs were generated as described elsewhere herein and as previously described [31]. Human/mouse chimeric 2 μl and 3G9 cDNAs were generated from the respective parent hybridoma total RNAs with constant region primers CDL-739 for the heavy chain and CDL-738 for the light chain using the First Strand cDNA synthesis kit (Amersham/Pharmacia, Piscataway, N.J.). The heavy and light chain variable region genes were amplified by the polymerase chain reaction using the same 3' primers used for cDNA synthesis and pools of degenerate primers specific for most murine antibody gene signal sequences (sequences available upon request) and Pfu DNA polymerase (Stratagene, La Jolla Calif.). Cloned heavy and light chain variable regions were ligated into mammalian expression vectors with human IgG1 constant regions. Recombinant soluble murine TGF-β receptor type I-Ig fusion protein (sTGF-bRII-Ig) was generated as previously described [32] Research-grade mu3G9, 1E6 and sTGF-bRII-Ig (purified protein in phosphate buffered saline) were used in all experiments.

2. Animals.

Mice. SV129 mice were used for experiments with lung hydroxyproline as an endpoint (Sheppard Laboratory, UCSF). C57B16 mice were used for experiments with histomorphometry or BAL collection and analysis as endpoints (Biogen Idec). For quantitative analysis of collagen gene expression as an endpoint, transgenic reporter mice were used (Biogen Idec). Transgenic mice carrying a luciferase reporter gene under the control of a 17 kb region of the collα2 gene promoter have been previously described [33]. These mice are maintained by breeding transgenic males to C57B1/6 X DBA/2 F1 hybrid females (Jackson Laboratories). Progeny positive for the transgene (as assessed by tail luciferase expression) were selected for the bleomycin challenge experiments outlined below.

Hamsters (Giri Laboratory). Male Golden Syrian hamsters weighing 90 to 110 g were purchased from Simonsens, Inc. (Gilroy, Calif.). Hamsters were housed in groups of four, in facilities with filtered air and constant temperature and humidity. All care was in accordance with the National Institutes of Health Guide for Animal Welfare Act. The hamsters were allowed to acclimate in facilities for 1 week before any treatments. A 12-h light/dark cycle was maintained.

3. Immunohistochemistry. Mouse lungs were collected in 10% buffered formalin and processed for paraffin histology in accordance with common practices. Paraffin tissue sections from lungs of patients with lung disease with fibrotic pathology were obtained from G. Davis (U. Vermont), R. Lafyatis (Boston University), Ardais Corp. (Lexington, Mass.) and Asterand Inc. (Detroit, Mich.). Tissue sections were deparaffinized in xylene and ethanol, rehydrated in distilled water, and then immersed in methanol containing 0.45% $H_2O$. Tissues were incubated with pepsin (00-3009, Zymed, San Francisco, Calif.) and blocked with avidin and biotin (SP-2001; Vector Laboratories, Burlingame, Calif.). Primary antibody was diluted in PBS containing 0.1% BSA and tissues were incubated overnight at 4° C. Sections were incubated with a human/mouse chimeric form of the anti-αvβ6 mAb, 2A1 [31], and an anti-human biotinylated secondary antibody (PK-6103, Vector Laboratories, Burlingame, Calif.) for mouse tissues.

Sections were incubated with murine 2A1 [31], and an anti-mouse-biotinylated secondary antibody (PK-6102, Vector Laboratories) for human tissues. Avidin-biotin complex-horseradish peroxidase (Vector Kit, PK-6102) was applied to sections, incubated for 30 minutes at room temperature, and 3,3'-diaminobenzidine (DAB) substrate was prepared as directed (SK-4100, Vector Laboratories) and applied to sections for 5 min at room temperature. Tissue sections were stained with Mayer's Hematoxylin for 1 minute and rinsed in water and PBS. All human tissue samples were obtained under approval of local institutional review and patient approval.

3.1 Bleomycin Instillation in Mice.

SV129 Strain (D. Sheppard, UCSF). Mice were instilled with bleomycin or saline into the trachea as previously described [18]. Briefly, age- and sex-matched 8- to 12-week-old mice of strain 129/terSVEMS were maintained in a specific pathogen-free environment. Bleomycin (Mead Johnson, Princeton, N.J.) was dissolved in sterile saline (0.03 or 0.05 units in 60 ml). Bleomycin or saline was administered transtracheally under methoxyflurane anesthesia by direct cut down.

C57Bl/6 Strain and Collagen Reporter Mice (Biogen IDEC). Mice were anesthetized by injecting IP with 100 mg/kg ketamine and 10 mg/kg xylazine. A 0.5-1.0 cm midline incision was made in the neck using a sterile #15 scalpel to expose the trachea for visualization. Bleomycin was instilled with a Penn Century microspraying device after exposing the trachea and placing the spray tip in the trachea through the oral cavity. Saline was instilled in control animals. Following instillation the surgical site was closed with sterile wound clips. Buprenorphine 0.05 mg/kg was administered subcutaneously for postoperative pain.

Multiple treatment protocols were utilized to evaluate the test article in these mouse bleomycin studies and will therefore be described in the results section.

3.2 Bleomycin Instillation in Hamster. Under pentobarbital anesthesia, hamsters were IT instilled with saline (SA; 4 ml/kg) or bleomycin (BL; 6.5 U/4 ml/kg) on days 0, 7 and 14. Animals were randomly divided into six experimental groups: SA-instilled, treated with PBS (SA+PBS); BL-instilled, treated with the PBS (BL+PBS); BL-instilled, treated with mu3G9 beginning at day 0 (BL+Ab1); BL-instilled, treated with mu3G9 beginning at day 7 (BL+Ab2); BL-instilled, treated with mu3G9 beginning at day 14 (BL+Ab3); and BL-instilled, treated with 1E6 beginning at day 0 (BL+1E6). The animals were sacrificed at day 28 and their lungs were removed and processed for hydroxyproline and lipid peroxidation assays.

4. Hydroxyproline Assay for Collagen Content. Lungs were homogenized in 1 ml $dH_2O$ in glass tubes (Fisher #14961). 125 μl of 50% trichloroacetic acid (TCA) was added to the homogenate and incubated on ice for 20 minutes. Samples were centrifuged at 1000 rpm, 5 min, and 4° C. Supernatant was discarded and 1 ml 12N HCL was added to the pellet in glass tube. Samples were then baked at 110° C. for 24 h (in a glass beaker). The dried pellet was reconstituted with 2 ml $dH_2O$, Six hydroxyproline standards (Sigma-H6002) were made starting from 0.25 mg/ml. In a 1.5 ml Eppendorf tube containing 500 μl chloramine T (1.4% chloramine T in 0.5 M Na Acetate and 10% isopropanol), 200 μl of the sample was added and incubated 20 min at room temperature. Then, 500 μl of Ehrlich's/pDMBA (1 M p-DMBA (p-dimethylaminobenzaldehyde) in 70% isopropanol and 30% perchloric acid) was added and incubated at 65° C. for 15 min. 100 μl of the final reaction solution was transferred to a 96-well plate, triplicate measurement was performed for each sample, and samples were read at 550 nm 2 hours later.

5. Histology Index. For experiments with histomorphometry as an endpoint, at the time of sacrifice the whole lung of each mouse was evaluated histologically. Transverse sections were cut and stained with Masson's Trichrome by standard routine. Transverse sections were chosen to include multiple lobes of the lungs from each mouse. High-powered (100×) fields were photographed to cover the entire trichrome-stained section (an average of about thirty per mouse). Each photo was evaluated for collagen content (which appears blue in trichrome-stained histologic sections) by Metamorph 6.0.5 software. Blue areas were selected by color threshold, and expressed as a percentage of total tissue area.

6. Luciferase Assay. Lungs were collected and homogenized in 1 ml of lysis buffer (0.1M $KH_2PO_4$-ph7.8 and 1 mM DL-dithiothreitol). Samples were then placed on ice for 10 minutes, centrifuged at 12,000 rpm for 10 minutes at 4° C., and then 100 μl of each sample was transferred to a Wallac Isoplatter. Samples were placed on ice again for 15 minutes before adding 100 μl of Luclite substrate (Perkin Elmer #601911). Luciferase activity was then read on a luminometer.

7. Bronchoalveolar (BAL) Collection and Differential Staining of BAL Cells. Mice were euthanised with an overdose of Inactin (Sigma) intraperitoneal injection (IP). The trachea was exposed using mostly blunt dissection. The trachea was then opened with scissors between two cartilage rings and a 23-gauge blunt end needle was inserted into the trachea. The needle was held in place by clamping lightly with a Schwartz temporary clip (Roboz). BAL was performed by injecting 0.8 ml of phosphate buffered saline without $Ca^{2+}$ or $Mg^{2+}$ (PBS) into the lungs. Fluid was then retracted into the syringe, without applying much pressure, and transferred into a 15 ml polypropylene Falcon tube on ice. The procedure was then repeated, BAL fluid was sucked back into the syringe without exerting excessive negative pressure. Samples were stored on ice and are processed for cell counts, differentials, and both BAL pellet and fluid were collected and stored at −80° C.

1. The BAL was then spun at 180 g, 1000 rpm (Beckman GPR) for 10 minutes on a tabletop centrifuge at 4° C. Supernatant (BAL fluid) was then removed and frozen at −80° C. 1.0 ml of RBC lysing solution (Sigma) was added to the pellet and vortexed for 20 seconds. Cell counts and cytospins were then done.

2. Samples were stored on ice and counted using a hemocytometer, allowing one minute after applying the cells to the hemocytometer and before reading to allow the cells to settle.

3. 100 μl of cell suspensions were cytospun (ThermoShandon) at 500 RPM for 5 minutes at room temperature. Cytospin preparations were prepared by placing the cell solution into the cytospin apparatus and spinning at 500 rpm for 5 minutes. Cell concentrations were checked to make sure concentrations were not too high on the slide. Slides were allowed to dry overnight and then stained with DiffQuik (Fisher). Staining was done according to the manufacturer's (DiffQuik) protocol. Once the slides were dried and cover slipped with Permount (Fisher), cells were categorized by type, counting 100 randomly selected cells using a laboratory cell counter (Fisher).

8. Statistical Analysis. Statistical comparisons were made between vehicle control and/or isotype control, and test article using analysis of variance (ANOVA). When statistically significant differences were established at a probability of $p<0.05$ using ANOVA, significant differences between groups were evaluated by Dunnet's multiple comparison test.

Results

Figure 58:
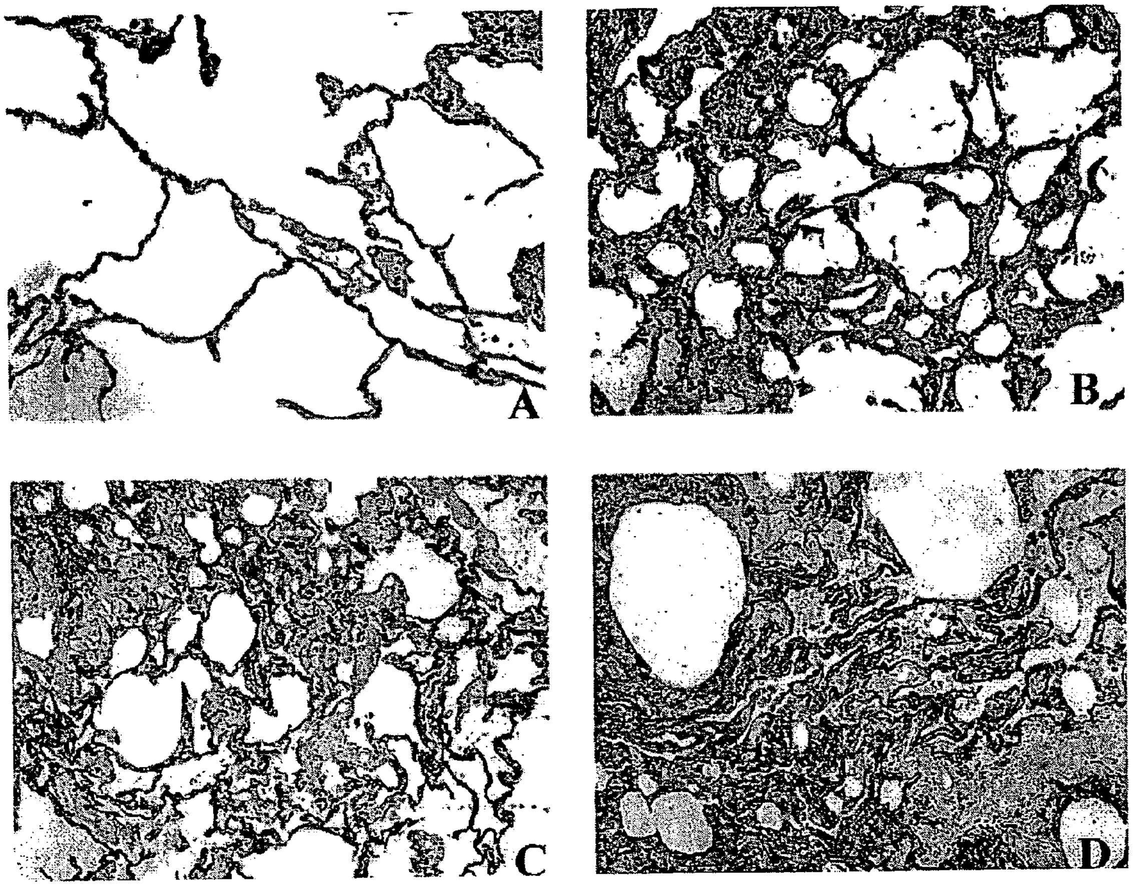
FIG. 58 is a series of photomicrographs depicting the expression of $\alpha_v\beta_6$ in human lung disease, demonstrating that $\alpha_v\beta_6$ expression is strongly upregulated in human lung disease. Paraffin tissue sections of human and mouse lung were immunostained with an $\alpha_v\beta_6$ specific antibody to visualize relative levels of expression in normal (FIG. 58A) and diseased lung: Idiopathic pulmomonary fibrosis (FIG. 58B), diffuse interstitial lung disease (FIG. 58C) and diffuse interstitial lung disease (FIG. 58D). Staining is representative of the level of upregulation seen in the forty-one different patient samples outlined below in Table 16-1 (Example 16).

1. Expression of αvβ6 in human lung disease and in the bleomycin model. Upregulated TGF-β expression and signaling has been described in a variety of human lung diseases involving fibrotic or inflammatory pathology[20, 34]. However, αvβ6 expression has only been described in a small sample of fibro-inflammatory lung disease [28]. We have evaluated the expression of αvβ6 in forty-one lung tissue samples from patients with lung disease characterized as having fibrotic and/or inflammatory changes (Table 16-1). In addition, we stained a lung tissue array from ostensibly normal regions of lung biopsies from cancer patients (Imgenex). Expression of αvβ6 in normal lung was nearly undetectable by immunohistochemistry. Some tissue sections on the "normal" lung tissue array showed positive αvβ6 staining, but each of those sections also had nearby inflammatory pathology. In all 41 diseased lung samples, regions of lung with fibrosis and/or inflammatory changes showed strong upregulation of αvβ6 expression (FIG. 58). αvβ6 was localized to epithelial cells overlying regions of overt fibrosis, or in regions adjacent to inflammatory infiltrates. The presence of upregulated αvβ6 was seen across a spectrum of fibro-inflammatory disease, including idiopathic pulmonary fibrosis, scleroderma lung disease, and chronic obstructive pulmonary disease.

To better correlate expression with specific pathologic changes, we sent the stained tissue samples to an external, trained pulmonary pathologist. Although he was unable to verify the pathological diagnosis of many of the commercially obtained samples (Ardais and Asterand), he consistently noted that "much higher intensity of αvβ6 staining was seen with usual interstitial pneumonitis", a pathology associated with fibrosis and progressive disease, as compared with non-specific interstitial pneumonitis (NSIP), a pathology associated with less fibrosis and a better prognosis. In all of the biopsies from patients with UIP, intense staining is seen within the pneumocytes lining the alveolar ducts and alveoli, both Type II and Type I, while large airways are largely negative and intraalveolar macrophages are negative. In summary, "high level staining was associated with fibrotic areas and UIP," and similar patterns of less intense staining were seen in the other cases of fibrosis, including NSIP. Since UIP is the dominant pathology in patients with idiopathic pulmonary fibrosis (IPF), the intense overexpression of αvβ6, an activator of the pro-fibrotic cytokine TGF-β, in patients with this pathology suggests that it may have a functional role in driving progression of fibrosis.

Figure 59:
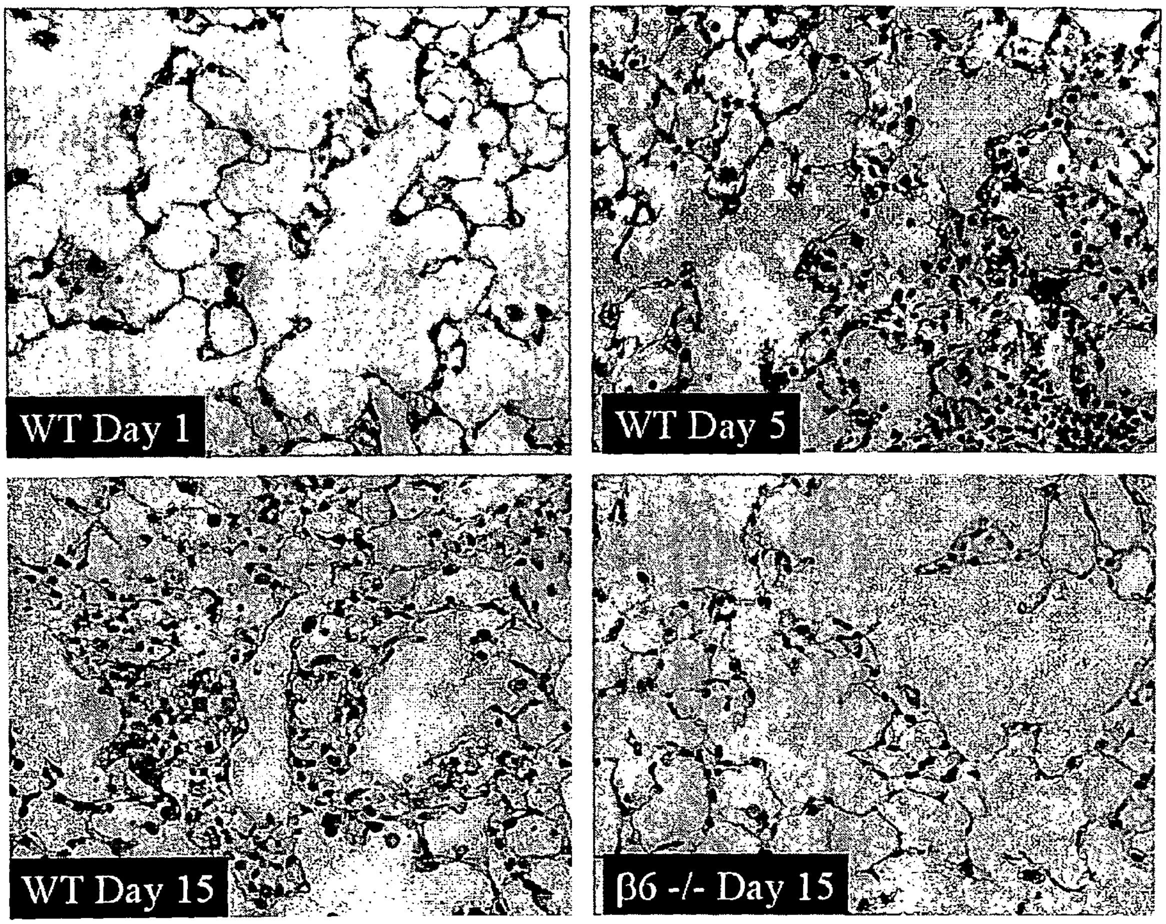
FIG. 59 is a series of photomicrographs depicting the expression of $\alpha_v\beta_6$ is the bleomycin lung fibrosis model, demonstrating that $\alpha_v\beta_6$ expression is strongly upregulated in the mouse model of bleomycin-induced lung fibrosis. Paraffin tissue sections of mouse lung were immunostained with an $\alpha_v\beta_6$ specific antibody to visualize relative levels of expression in bleomycin-instilled lung.

2. Expression of αvβ6 in the mouse bleomycin model. To verify that αvβ6 was also upregulated in the bleomycin mouse model of pulmonary fibrosis, we immunostained for the presence of αvβ6 protein on tissue sections taken 1, 5 and 15 days after bleomycin instillation. At day 5, αvβ6 expression is upregulated on the alveolar epithelium throughout regions of the lung injured by bleomycin challenge (FIG. 59). At day 15, when regions of prominent fibrosis are evident, αvβ6 is more strongly upregulated in alveolar epithelium in these fibrotic areas.

Figure 60:
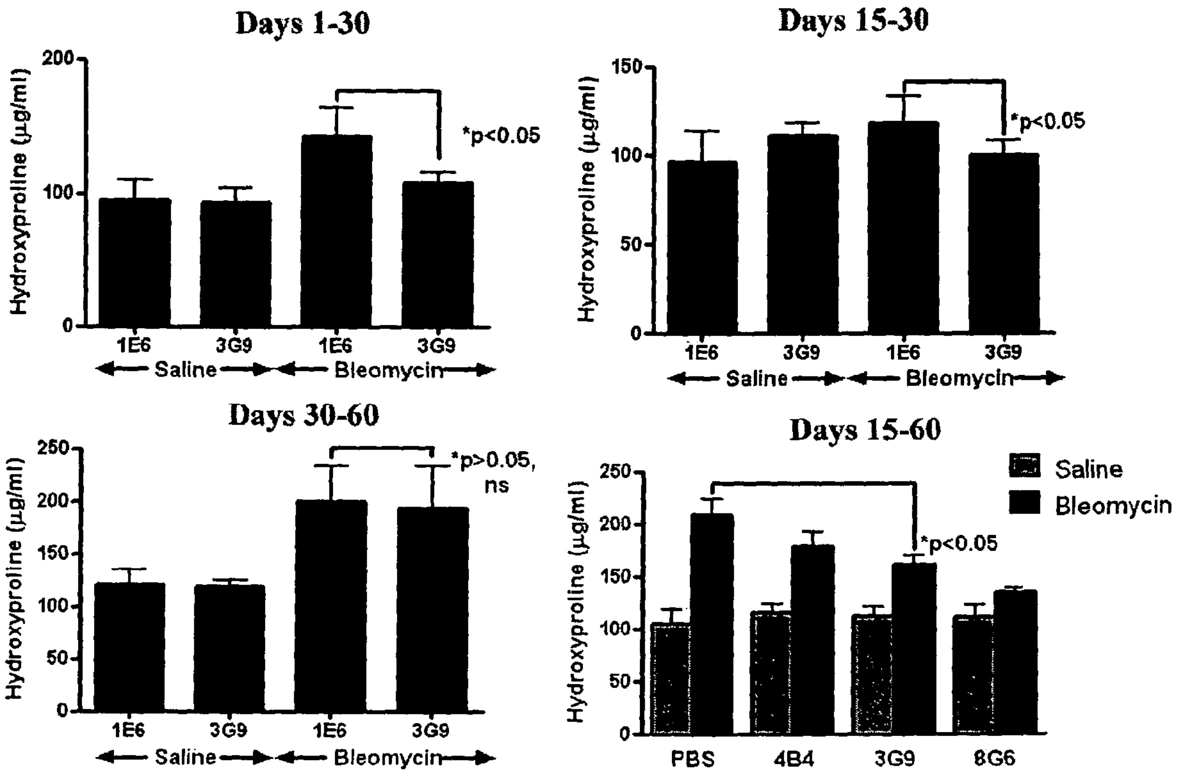
FIG. 60 is a series of bar graphs depicting the effect of mu3G9 treatment on lung hydroxyproline content in bleomycin-treated SV129 mice. Mice each received 4 mg/kg of mu3G9 (blocking $\alpha_v\beta_6$ mAb), 1E6 (control IgG1) in first three experiments shown for the various treatment periods listed. In the fourth experiment, mice each received PBS, 4 mg/kg of mu3G9 (blocking $\alpha_v\beta_6$ mAb), 4B4 (non-blocking $\alpha_v\beta_6$ mAb), or 8G6 (a second blocking $\alpha_v\beta_6$ mAb) three times per week for days 15 to 60 following bleomycin treatment. Error bars represent standard errors. Group means and standard deviations are provided in Appendix A of Example 16.

3. Evaluation of fibrosis by hydroxyproline in SV129 mice. Mice genetically deficient for αvβ6 (β6 null) have previously demonstrated protection from bleomycin-induced pulmonary fibrosis in the SV129 mouse strain [18]. We sought to evaluate the efficacy of the anti-αvβ6 monoclonal antibody, mu3G9, in attenuating bleomycin-induced fibrosis in this same strain. A series of four experiments were conducted in the laboratories of our collaborator, Dean Sheppard at UCSF (Table 16-2). SV129 mice were instilled with bleomycin into the trachea at day 0, and mu3G9 was injected IP at 4 mg/kg, three times per week, beginning at 0, 15 or 30 days after bleomycin instillation. Control mice were injected with PBS, or with a negative control antibody 1E6. 1E6 is a murine IgG1 antibody against human LFA-3, and does not bind to any mouse antigen. Mice were sacrificed at day 30 or 60, and fibrosis was evaluated by hydroxyproline content, a measure of total tissue collagen. In three of the four experiments there was a statistically significant decrease in hydroxyproline in mu3G9-treated mice, indicative of efficacy in attenuating bleomycin-induced fibrosis (FIG. 60). Only when treatment was delayed until 30 days after bleomycin instillation (FIG. 60C) was the hydroxyproline content in lungs of mu3G9-treated mice not significantly decreased compared to PBS-treated or isotype-control treated mice.

4. Evaluation of survival in bleomycin-challenged mice treated 46 days. Anti-fibrotic efficacy in the bleomycin model does not generally correlate with improved survival, and we therefore did not expect survival to be improved in mu3G9-treated mice. However, since these mice treated with mu3G9 at 4 mg/kg, 3 times per week from day 15 to 60 (FIG. 60D) represented the longest treatment period (46 days) we had tested up to that point, we analyzed to see if there was any difference in survival in the groups tested in that experiment. There was no significant difference in overall survival when comparing the mice treated with mu3G9 to those treated with PBS and with the 4B4 non-blocking control antibody (Table 16-2).

Figure 61:
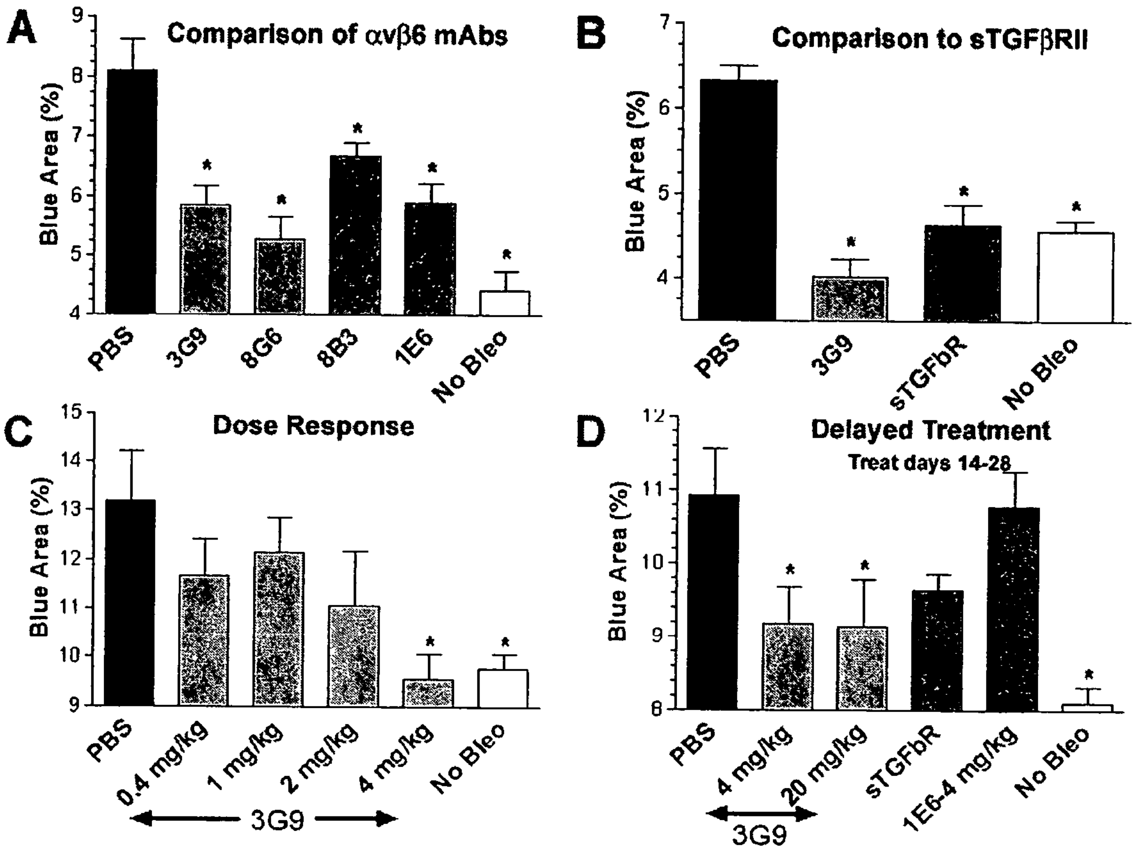
FIG. 61 is a series of bar graphs depicting the effect of mu3G9 treatment on collagen content (histomorphometry) in bleomycin-treated C57B16 mice. Mice received 3 doses per week of mu3G9 (blocking ($\alpha_v\beta_6$ mAb), 8G6 (a second blocking $\alpha_v\beta_6$ mAb), 8B3 (non-blocking $\alpha_v\beta_6$ mAb), 1E6 (control IgG1 mAb), or sTGFbR (soluble TGF-β receptor—positive control for TGF-β inhibition). In the first three experiments shown (FIGS. 61A, 61B and 61C), mice were treated beginning 1 day before bleomycin challenge and were euthanised on day 14. In the first two experiments (FIGS. 61A and 61B), doses of each agent were 4 mg/kg, while in the third experiment (FIG. 61C) the dose of mu3G9 was varied as shown. In the final experiment (FIG. 61D), mice were treated beginning 14 days after bleomycin challenge and were euthanised on day 28. Histologic sections were trichrome stained, imaged, and the area of blue-stained (collagen-containing) tissue was calculated as a percentage of total tissue area using Metamorph software. Error bars represent standard errors. Group means and standard deviations are provided in Appendix B of Example 16. *=significantly different from the PBS-treated group by ANOVA FIG. 62 is a bar graph depicting mu3G9 in bleomycin lung fibrosis using collagen reporter mice. Bleomycin was instilled intratracheally into collagen-luciferase reporter mice. Mice were treated, beginning the day before bleomycin injury, once weekly for two weeks with PBS, 5 mg/kg soluble TGF-bRII-Ig, or mu3G9 at doses of 0.1, 0.3, 1.0, 3 and 10 mg/kg. An additional group of mice treated 3 times weekly with 4 mg/kg of mu3G9 was also included (3×4 mg/kg).

5. Histomorphometric analysis of fibrosis in C57B16 mice. To validate the anti-fibrotic efficacy of mu3G9 in a different mouse strain and in a different lab, mu3G9 was evaluated in a series of experiments at Biogen Idec using the C57B16 mouse strain. This strain is frequently used in the bleomycin model and gives a rapid fibrosis that can be measured 14 days after instillation. In the first three experiments, mice were instilled with bleomycin into the trachea on day 0, treated with mu3G9 three times per week beginning one day before bleomycin challenge (day −1), and euthanised on day 14 for lung collection. In the fourth experiment, treatment was delayed until day 14, and lungs were collected on day 28. In each of these experiments (FIG. 61), mu3G9 consistently decreased the percentage of fibrotic lung tissue relative to PBS-treated controls, measured histomorphometrically as blue staining regions in Masson's trichrome-stained tissue sections. In one of two experiments in which the 1E6 mAb was used as a negative IgG control, the 1E6 mAb also significantly decreased the percent of fibrotic tissue (FIG. 61A). This effect of the 1E6 mAb was not seen in earlier experiments using hydroxyproline as the endpoint (FIG. 60), nor in the delayed treatment (days 14 to 28) experiment (FIG. 61D). In summary, multiple experiments demonstrated efficacy of the mu3G9 mAb in decreasing the percentage of fibrotic tissue induced by bleomycin in C57B16 mice. However, due to the labor-intensive nature of the histomorphometry endpoint, we sought a more rapid and quantitative method for measuring fibrosis.

6. Use of collagen-luciferase reporter transgene as a quantitative endpoint. Transgenic mice carrying a transgene in which a luciferase reporter gene is expressed under the control of the collagen Iα2 promoter have previously been used to provide a quantitative readout of collagen expression in fibrosis models [33]; [35]. At 14 days, the increase in lung luciferase levels in bleomycin-challenged mice relative to saline controls was approximately 10 fold, making it a much more sensitive endpoint than hydroxyproline measurement. Using this system, we performed a dose-titration of the 3G9 antibody using once a week dosing, but including a group of mice that was treated with the 4 mg/kg—3 times per week dosing regimen used in the experiments with hydroxyproline and trichrome histomorphometry as the endpoint. The dose titration was evaluated in three experiments, in which each experiment had a PBS-treated control group (n=6, 5 and 6 for a total n=17). To correct for experiment-to-experiment variation in luciferase measurements, luciferase values for all groups in each experiment were normalized to the average of the PBS controls. mu3G9 treatment of bleomycin-challenged reporter mice produced a dose-dependent decrease in the collagen luciferase reporter (FIG. 62), with significant efficacy seen at a weekly dose of 0.3 mg/kg and maximal efficacy seen at 1 to 3 mg/kg.

Figure 62:
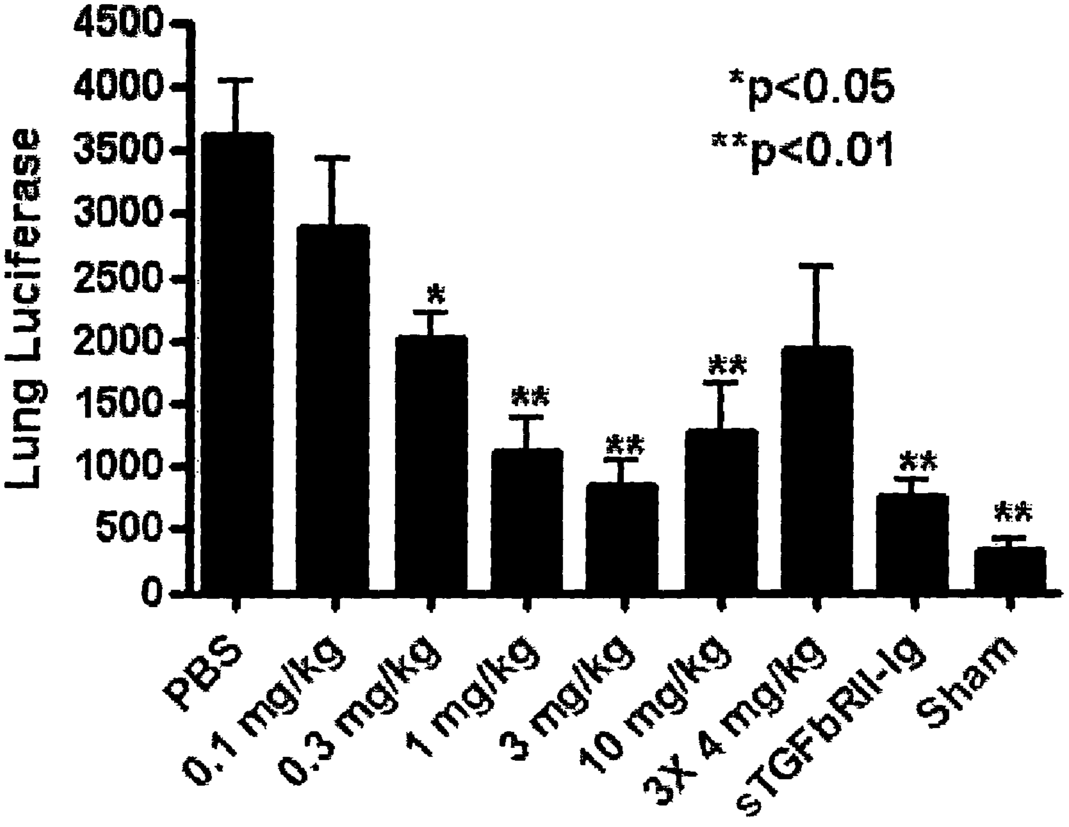
Figure 63:
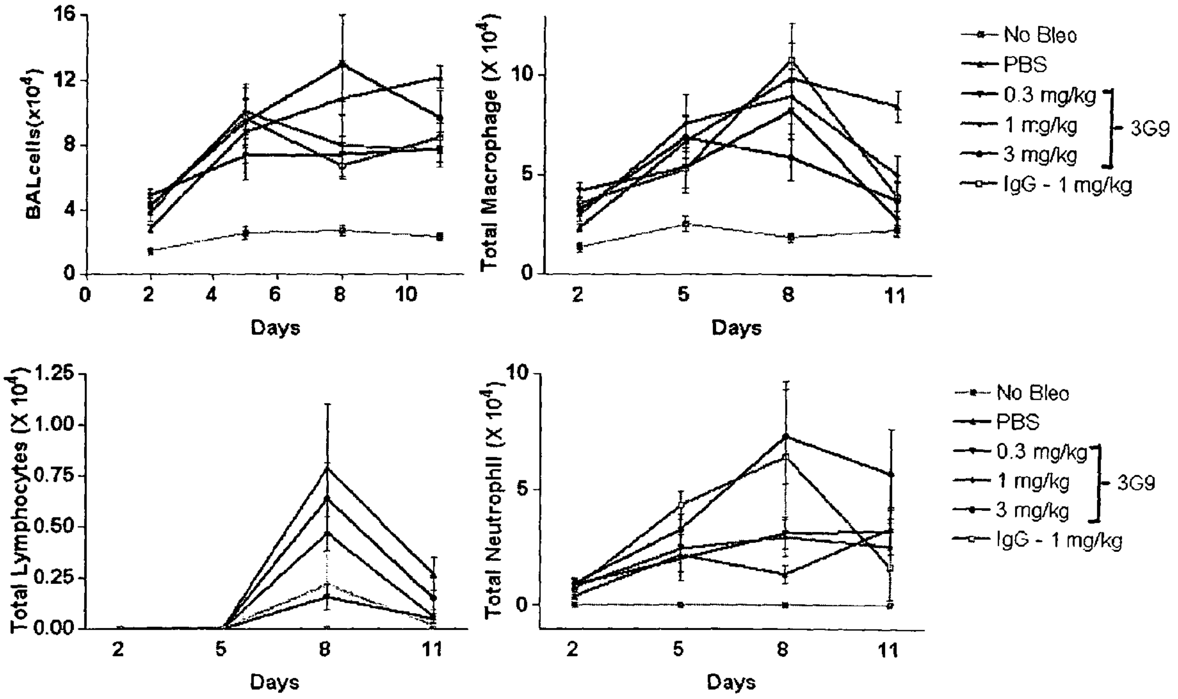
FIG. 63 is a series of line graphs depicting the timecourse to evaluate the effect of low efficacious doses of mu3G9 on major BAL cell populations in bleomycin-challenged mice. Mice were instilled with bleomycin into the lungs on day 0. Mice were treated with PBS, mu3G9 at doses of 0.3, 1.0 and 3.0 mg/kg or control IgG1 (1E6) at a dose of 1.0 mg/kg at days −1 and +6. Mice were sacrificed at days 2, 5, 8 and 11 and lungs were collected and evaluated for total BAL cell counts. Macrophage, neutrophil and lymphocyte populations were analyzed by differential staining of cytospins. Group means and standard deviations are provided in Appendix C of Example 16.
Figure 64:
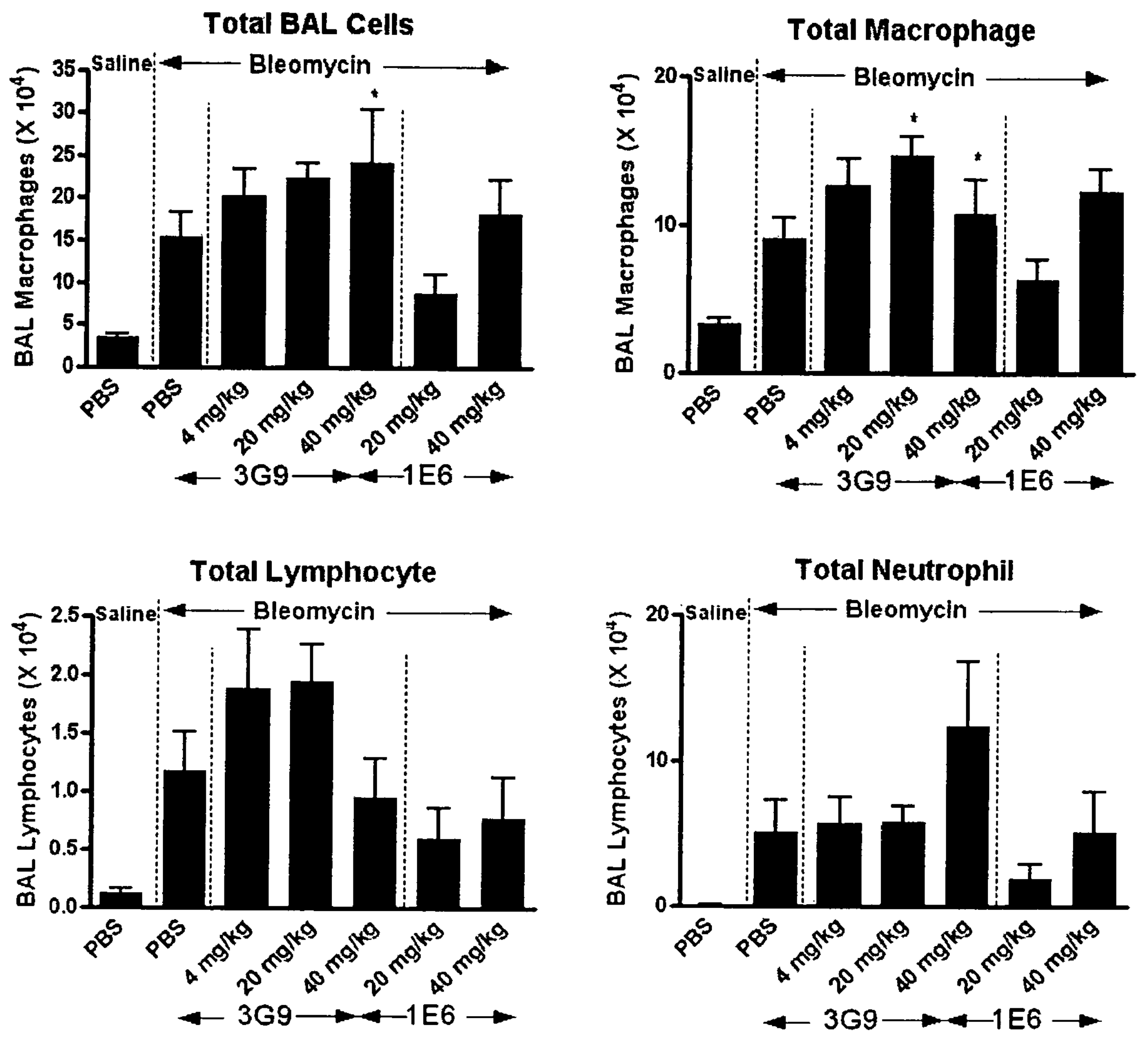
FIG. 64 is a series of bar graphs depicting the effect of high doses of mu3G9 on major BAL cell populations at day 5 in bleomycin-challenged mice. Mice were instilled with bleomycin into the lungs on day 0. Mice were treated with PBS, mu3G9 at doses of 4, 20 and 40 mg/kg or control IgG1 mAb (1E6) at a doses of 20 and 40 mg/kg on days −1, +1 and +3. Mice were sacrificed at day 5, and lungs were collected and evaluated for total BAL cell counts. Macrophage, neutrophil and lymphocyte populations were analyzed by differential staining of cytospins. Group means and standard deviations are provided in Appendix D of Example 16. *=$p<0.05$ relative to Bleomycin-challenged controls treated with PBS but not relative to controls treated with the 1E6 IgG1 mAb.

7. Analysis of bronchoalveolar lavage cell composition. We analyzed the bronchoalveolar lavage (BAL) cell populations at days 2, 5, 8 and 11 of the bleomycin model to determine if the inhibition of fibrosis was due to decreased inflammation or alterations in the major subpopulations of inflammatory cells in the lung. As expected, there were elevations in BAL cell counts due to the intratracheal administration of bleomycin when compared with saline-instilled mice. Throughout the time course however, there was no significant difference in the total number of BAL cells, nor in the numbers or percentages of macrophages, neutrophils or lymphocytes, seen in mice treated with the efficacious doses of 0.3, 1.0, and 3 mg/kg of 3G9 compared with mice treated with an isotype control antibody 1E6. We then tested much higher doses, using the 3 times per week treatment that had initially been used to demonstrate efficacy with the hydroxyproline and histomorphometry endpoints. Mice were given three doses of 4, 20 and 40 mg/kg of m3G9 on days −1, +1 and +3 relative to the bleomycin challenge. Mice were euthanised on day 5 and BAL cell content was analyzed. At a dose of 4 mg/kg (12 mg/kg total dose), there was again no significant change in the total number of BAL cells, nor in the numbers or percentages of macrophages, neutrophils or lymphocytes. At the 20 and 40 mg/kg dose (60 and 120 mg/kg total) there was a significant increase in the number of macrophages relative to the PBS controls, but not relative to the IgG1 control (FIG. 62). At the 40 mg/kg dose there was a significant increase in the percentage of neutrophils in the BAL when compared to both the PBS and IgG controls, although changes in total numbers of neutrophils did not reach significance. This increase in neutrophils that occurs at very high dose (120 mg/kg total) is similar to what was seen with high dose, longer-term treatment (6 and 10 mg/kg treatment, 3-4 months) in the radiation fibrosis model (see Example 15). In summary, anti-αvβ6 antibodies are able to attenuate bleomycin-induced collagen expression at weekly doses as low as 0.3 mg/kg, while doses up to 12 mg/kg total do not produce significant alterations in BAL cell populations in this model. Higher doses can produce increases in total macrophage number and in percentage of neutrophils.

Figure 65A:
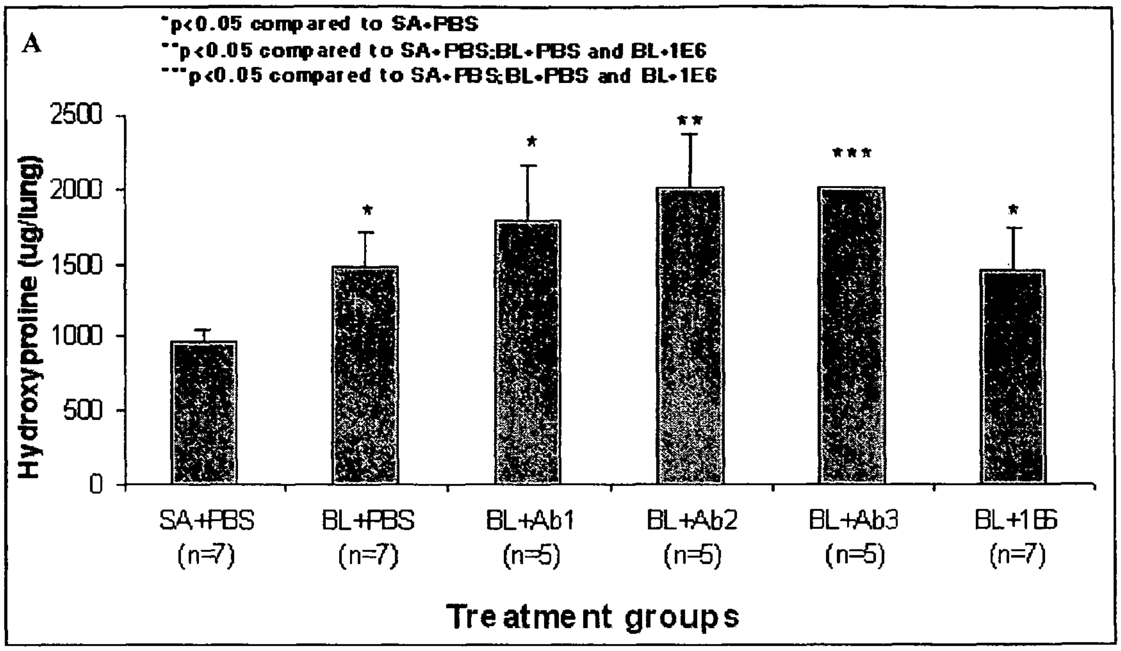
FIG. 65 depicts the lack of efficacy of mu3G9 in a multiple dose bleomycin model in hamsters. Hamsters were instilled with bleomycin (BL) or saline (SA) into the lungs on days 0, 7 and 14. Hamsters were treated with PBS, mu3G9 (Ab1), or control IgG1 (1E6) beginning at day 0. Additional groups were treated with mu3G9 at day 7 (Ab2) or day 14 (Ab3). All antibodies were administered three times per week at a dose of 5 mg/kg. Hamsters that survived were sacrificed at day 28 and lungs were collected and evaluated for hydroxyproline content (FIG. 65AA) and lipid peroxidation (FIG. 65B). Error bars represent standard errors. Survival of hamsters throughout the multi-dose bleomycin study (FIG. 65C). No significant difference was seen in the survival of hamsters treated with mu3G9 when compared with PBS or IgG-treated control groups. Group means and standard deviations are provided in Appendix C of Example 16.
Figure 65B:
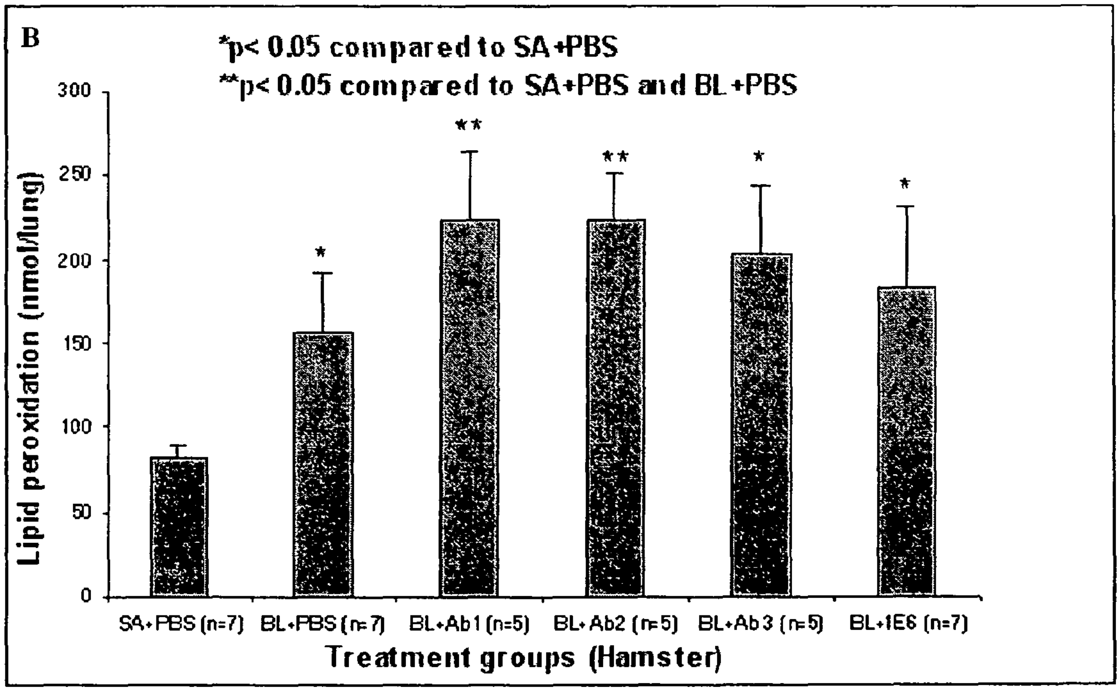
Figure 65C:
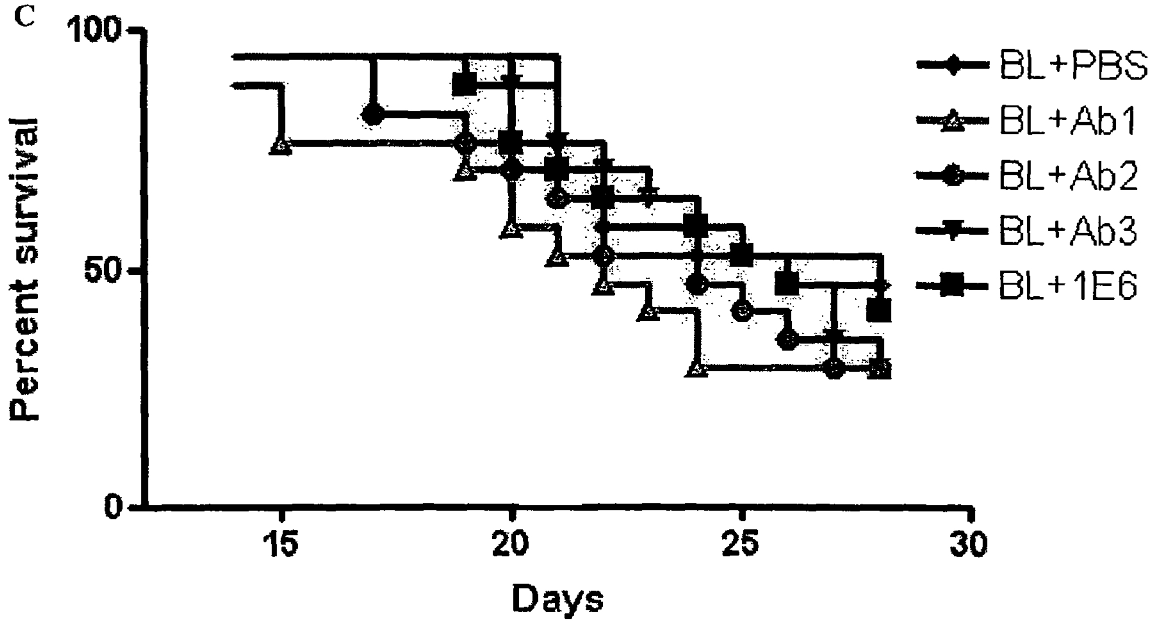

8. Evaluation in a multiple bleomycin dose hamster model. We examined the efficacy of mu3G9 in a hamster pulmonary fibrosis model in which three consecutive bleomycin doses are given intratracheally on days 0, 7 and 14. Three groups of hamsters were treated with mu3G9 at 5 mg/kg for three times per week (15 mg/kg total per week), beginning at days 0, 7 or 14. Animals were sacrificed and evaluated for fibrosis at day 28 by hydroxyproline (FIG. 65A) and lipid peroxidation assays (FIG. 65B) (performed at U. California-Davis, Davis, Calif.). Unexpectedly, efficacy was not seen in attenuating fibrosis in this model. In one of the groups, hamsters treated with mu3G9 beginning at day 7 and 14, the mice showed a statistically significant increase in lung hydroxyproline relative to both the PBS and the IgG control groups. Lipid peroxidation values were not significantly elevated compared to the IgG control group. We analyzed the survival curves of the various treatment groups to see if this apparent exacerbation was having an effect on the survival of the hamsters. The mu3G9 mice treated beginning at day 0 (BL+AB1 group in FIG. 65C) began dying slightly earlier than the PBS and IgG controls; however, when comparing the B1+Ab1 survival curve individually against the PBS and IgG controls, the difference was not significant (log rank test: p=0.15 vs. PBS and p=0.25 vs. IgG control mAb). It is unknown whether the mu3G9 monoclonal antibody cross-reacts with hamster, and it is possible that the hamsters may have generated an antibody response against the murine antibodies used in this model. Due to the difficulties in interpreting outcomes in this model, evaluation of different doses for efficacy were not pursued, since consistent efficacy was seen in two different murine pulmonary fibrosis models (bleomycin- and radiation-induced).

TABLE 16-1

Human Lung Disease Samples Immunostained for αvβ6 Expression

| Pathology/Diagnosis (where available) | Number of Cases | Source |
|---|---|---|
| Diffuse interstitial lung disease | 1 | Dr. Gerald Davis, |
| Inflammatory mass | 1 | University of |
| Sarcoidosis | 1 | Vermont |
| Chronic inflammation and fibrosis (IPF) | 1 | |
| Focal inflammation | 2 | |
| Respiratory bronchiolitis interstitial lung disease | 1 | |
| Bronchiectasis | 1 | |
| Emphysema, focal pneumonia | 1 | |
| Diffuse interstitial fibrosis with emphysema | 1 | |
| Radiation effect fibrosis | 3 | Ardais Corp. |
| Fibrosis | 4 | |
| Cystic Fibrosis | 1 | |
| Chronic obstructive pulmonary disease | 1 | |
| Chronic bronchitis | 2 | |
| Bronchiectasis | 1 | |
| Pneumonia, interstitial, nonspecific, fibrosing (NSIP-F) | 1 | |
| Fibrosis | 2 | Asterand Inc. |
| Pneumonia | 2 | |
| Scleroderma lung disease | 14 | Dr. Robert Lafyatis, Boston University |
| Total Samples: | 41 | |

TABLE 16-2

Survival of Bleomycin-challenged mice treated 46 days with mu3G9

| | PBS | 4B4 | 3G9 | 8G6 |
|---|---|---|---|---|
| Number of Mice Died/ Number of Mice Treated | 4/11 | 3/13 | 2/13 | 5/13 |
| Percent Survival | 64% | 77% | 79% | 62% |

Conclusions mu3G9 is a potent inhibitor of disease severity in the bleomycin model of fibrosis. This series of experiments demonstrated:

(a) αvβ6 expression is upregulated on epithelial cells in a wide spectrum of human lung diseases with fibrotic and/or inflammatory pathology. It is similarly upregulated in the mouse bleomycin fibrosis model.

(b) mu3G9 significantly reduced bleomycin-induced fibrosis in multiple experiments, using multiple endpoints for analysis. Efficacy was seen in all strains of mice tested, SV129, C57B16, and C57B16 X DBA hybrids. Efficacy in suppressing collagen expression was seen at doses as low as 0.3 mg/kg weekly.

(c) The mechanism of action of mu3G9 is via inhibition of TGF-β, a pro-fibrotic cytokine with anti-inflammatory properties. As expected, inhibition of fibrosis occurs without attenuating inflammation. High, frequent doses of mu3G9 (20 and 40 mg/kg given every other day) can induce modest increases relative to PBS but not IgG controls in total BAL cells, macrophages and neutrophils in the bronchoalveolar lavage of the bleomycin-challenged mice at day 5.

(d) mu3G9 was not effective in a multiple dose bleomycin model in hamster. It is unclear if apparent exacerbation of fibrosis in one mu3G9-treated group was test-article related.

(e) mu3G9 treatment at a dose of 4 mg/kg, 3 times per week for 46-days did not affect survival in the bleomycin model.

References

1. Roberts, A. B., et al., Transforming growth factor type B: Rapid induction of fibrosis and angiogenesis in vivo and stimulation of collagen formation in vitro. Proc. Natl. Acad. Sci, USA, 1986. 83: p. 4167-4171.

2. Roberts, A. B. and M. B. Sporn, Regulation of endothelial cell growth, architecture, and matrix synthesis by TGF-beta. Am. Rev. Respir. Dis., 1989. 140: p. 1126-1128.

3. Varga, J., J. Rosenbloom, and S. A. Jimenez, Transforming growth factor beta (TGF beta) causes a persistent increase in steady-state amounts of type I and type III collagen and fibronectin mRNAs in normal human dermal fibroblasts. Biochem. J., 1987. 247(3): p. 597-604.

4. Grande, J. P., D. C. Melder, and A. R. Zinsmeister, Modulation of collagen gene expression by cytokines: stimulatory effect of transforming growth factor-beta1, with divergent effects of epidermal growth factor and tumor necrosis factor-alpha on collagen type I and collagen type IV. J. Lab Clin. Med., 1997. 130(5): p. 476-486.

5. Walker, G. A., et al., Valvular myofibroblasts activation by transforming growth factor-beta: implications for pathological extracellular matrix remodeling in heart valve disease. Circ. Res., 2004. 95(3): p. 253-260.

6. Eickelberg, O., et al., Extracellular matrix deposition by primary human lung fibroblasts in response to TGF-beta1 and TGF-beta3. Am. J. Physiol., 1999. 276(5): p. L814-L824.

7. Sime, P. J., et al., Adenovector-mediated gene transfer of active transforming growth factor-β1 induces prolonged severe fibrosis in rat lung. J. clin. Invest., 1997. 100: p. 768-776.

8. Bonniaud, P., et al., Progressive TGF-(beta)1-induced lung fibrosis is blocked by an orally active ALK5 kinase inhibitor. Am. J. Respir. Crit. Care Med., 2004.171: p. 889-898.

9. Laping, N. J., *ALK5 Inhibition in renal disease*. Curr. Opin. Pharmacol., 2003. 3(2): p. 204-208.

10. Miyajima, A., et al., Antibody to transforming growth factor-β ameliorates tubular apoptosis in unilateral ureteral obstruction. Kid. Int., 2000. 58: p. 2310-2313.

11. Sharma, K., et al., Neutralization of TGF-beta by an anti-TGF-beta antibody attenuates kidney hypertrophy and the enhanced extracellular matrix gene expression in STZ-induced diabetic mice. Diabetes, 1996. 45(4): p. 522-530.

12. Wang, Q., et al., Reduction of bleomycin induced lung fibrosis by transforming growth factor β soluble receptor in hamsters. Thorax, 1999.54: p. 805-812.

13. Bonniaud, P., et al., Smad3 null mice develop airspace enlargement and are resistant to TGF-beta-mediated pulmonary fibrosis. J. Immunol., 2004. 173(3): p. 2099-2108.

14. George, J., et al., In vivo inhibition of rat stellate cell activation by soluble transforming growth factor type II receptor: A potential new therapy for hepatic fibrosis. Proc. Natl. Acad. Sci, USA, 1999. 96(22): p. 12719-12724.

15. Zheng, H., et al., Recombinant soluble transforming growth factor β type II receptor ameliorates radiation enterophay in mice. Gastroenterology, 2000. 119: p. 1286-1296.

16. Kasuga, H., et al., Effects of anti-TGF-β type II receptor antibody on experimental glomerulonephritis. Kid. Int., 2001. 60: p. 1745-1755.

17. Ziyadeh, F. N., et al., Long-term prevention of renal insufficiency, excess matrix gene expression, and glomerular mesangial matrix expansion by treatment with monoclonal antitransforming growth factor-β antibody in db/db diabetic mice. Proc. Natl. Acad. Sci, USA, 2000. 97(14): p. 8015-8020.

18. Munger, J. S., et al., The integrin αvβ6 binds and activates latent TGFβ1: a mechanism for regulating pulmonary inflammation and fibrosis. Cell, 1999.96: p. 319-328.

19. Gleizes, P. E., et al., TGF-beta latency: biological significance and mechanisms of activation. Stem Cells, 1997. 15(3): p. 190-197.

20. Khalil, N., *TGF-beta: from latent to active*. Microbes Infect., 1999. 1(15): p. 1255-1263.

21. Barcellos-Hoff, M. H., *Latency and activation in the control of TGF-*β. J. Mamm. Gland Biol., 1996. 1(4): p. 353-363.

22. Huang, X. Z., et al., The integrin αvβ6 is critical for keratinocyte migration on both its known ligand, fibronectin, and on vitronectin. J. Cell Sci., 1998. 111: p. 2189-2195.

23. Busk, M., R. Pytella, and D. Sheppard, *Characterization of the integrin alpha v beta 6 as a fibronectin-binding protein*. J. Biol. Chem., 1992. 267(9): p. 5790-5796.

24. Yokosaki, Y., et al., Differential effects of the integrins alpha9beta1, alphavbeta3, and alphavbeta6 on cell proliferative responses to tenascin. Roles of the beta subunit extracellular and cytoplasmic domains. J. Biol. Chem., 1996. 271 (39): p. 24144-24150.

25. Annes, J. P., D. B. Rifkin, and J. S. Munger, *The integrin* α*v*β6 *binds and activates latent TGF*β3. FEBS lett., 2002. 511: p. 65-68.

26. Ma, L. J., et al., Transforming growth factor-β-dependent and independent pathways of induction of tubulointerstitial fibrosis in β6−/− mice. Am. J. Pathol., 2003. 163: p. 1261-1273.

27. Breuss, J. M., et al., *Restricted distribution of integrin* β6 *mRNA in primate epithelial tissues*. J. Histochem. and Cytochem., 1993. 41(10): p. 1521-1527.

28. Breuss, J. M., et al., Expression of the β6 subunit in development, neoplasia and tissue repair suggests a role in epithelial remodeling. J. Cell Sci., 1995. 108: p. 2241-2251.

29. Zambruno, G., et al., Transforming growth factor-β1 modulates β1 and β5 integrin receptors and induces the de novo expression of the αvβ6 heterodimer in normal human keratinocytes: implications for wound healing. J. Cell Biol., 1995. 129(3): p. 853-865.

30. Hakkinen, L., et al., Increased expression of β6-integrin in skin leads to spontaneous development of chronic wounds. Am. J. Pathol., 2004. 164: p. 229-242.

31. Weinreb, P. H., et al., *Function-blocking integrin alphavbeta6 monoclonal antibodies*. J. Biol. Chem., 2004. 279(17): p. 17875-17887.

32. Cosgrove, D., et al., Integrin α1β1 and transforming growth factor-β1 play distinct roles in alport glomerular pathogenesis and serve as dual targets for metabolic therapy. Amer. J. of Pathol., 2000. 157(5): p. 1649-1659.

33. Inagaki, Y., et al., Activation of Proalpha2(I) collagen promoter during hepatic fibrogenesis in transgenic mice. Biochem Biophys Res Commun, 1998. 250(3): p. 606-11.

34. Broekelmann, T. J., et al., Transforming growth factor β1 is present at sites of extracellular matrix gene expression in human pulmonary fibrosis. Proc. Natl. Acad. Sci, USA, 1991. 88: p. 6642-6646.

35. Denton, C. P., et al., Activation of a fibroblast-specific enhancer of the proalpha2(I) collagen gene in tight-skin mice. Arthritis Rheum, 2001. 44(3): p. 712-22.

GLOSSARY

| | |
|---|---|
| 1E6 | Murine IgG1 monoclonal antibody against the human LFA-3. Does not bind to mouse antigen. This is used as an IgG1 control mAb. |
| ANOVA | analysis of variance |
| β6 null | mice deficient for the beta6 integrin subunit These mice are deficient for only the αvβ6 integrin |
| BAL | Bronchoalveolar lavage |
| BALF | Bronchoalveolar lavage fluid |
| Ig | Immunoglobulin |
| IP | Intraperitoneal |
| mAb | Monoclonal antibody |
| mu3G9 or 3G9 | Murine IgG1 monoclonal antibody against the avb6 integrin This is the parent form of BG00011, prior to humanization. |
| sTGF-bR or sTGFbRII-Ig | Soluble TGF-β receptor Type I fused to Ig domain |
| TGF-β | Transforming growth factor beta |

APPENDIX A

Variation of Dosing of mu3G9 (hydroxyproline)

| | | 1E6 | 3G9 |
|---|---|---|---|
| Days 1-30 | | | |
| Bleomycin | Mean | 142.49 | 107.86 |
| | Std. Dev. | 21.31 | 8.24 |
| | n | 7 | 3 |
| Saline | Mean | 95.01 | 92.64 |
| | Std. Dev. | 14.66 | 10.78 |
| | n | 6 | 6 |
| Days 15-30 | | | |
| Bleomycin | Mean | 118.33 | 100.2 |
| | Std. Dev. | 15.05 | 8.42 |
| | n | 6 | 7 |
| Saline | Mean | 96.70 | 111.19 |
| | Std. Dev. | 16.82 | 7.26 |
| | n | 6 | 6 |
| Days 30-60 | | | |
| Bleomycin | Mean | 200.07 | 193.68 |
| | Std. Dev. | 33.14 | 39.38 |
| | n | 6 | 7 |
| Saline | Mean | 120.49 | 118.58 |
| | Std. Dev. | 13.57 | 6.26 |
| | n | 6 | 6 |

| Days 15-60 | | PBS | 4B4 | 3G9 | 8G6 |
|---|---|---|---|---|---|
| Bleomycin | Mean | 208.45 | 178.17 | 160.3 | 134.49 |
| | Std. Dev. | 19.36 | 22.4 | 15.25 | 6.29 |
| | n | 7 | 10 | 11 | 8 |
| Saline | Mean | 104.54 | 115.98 | 111.98 | 110.9 |
| | Std. Dev. | 15.13 | 7.26 | 9.5 | 12.44 |
| | n | 5 | 5 | 5 | 5 |

APPENDIX B

Variation of Dossing of mu3G9 (histomorphometry)

| FIG. 61A | PBS | 3G9 | 8G6 | 8B3 | 1E6 | No Bleo |
|---|---|---|---|---|---|---|
| Mean | 8.09 | 5.84 | 5.26 | 6.66 | 5.89 | 4.41 |
| Std Dev | 1.80 | 0.83 | 0.98 | 0.73 | 0.87 | 0.90 |
| n | 12 | 7 | 7 | 9 | 7 | 8 |

| FIG. 61B | PBS | 3G9 | sTGFbR | No Bleo |
|---|---|---|---|---|
| Mean | 6.32 | 4.01 | 4.69 | 4.56 |
| Std Dev | 0.53 | 0.64 | 0.77 | 0.35 |
| n | 9 | 9 | 9 | 8 |

| FIG. 61C | PBS | 0.4 mg/kg | 1 mg/kg | 2 mg/kg | 4 mg/kg | No Bleo |
|---|---|---|---|---|---|---|
| Mean | 13.19 | 11.67 | 12.14 | 11.07 | 9.56 | 9.76 |
| Std Dev | 3.67 | 2.56 | 2.45 | 3.28 | 1.82 | 0.99 |
| n | 13 | 12 | 11 | 9 | 13 | 11 |

| FIG. 61D | PBS | 4 mg/kg | 20 mg/kg | sTGFbR | 1E6-4 mg/kg | No Bleo |
|---|---|---|---|---|---|---|
| Mean | 10.92 | 9.18 | 9.13 | 9.63 | 10.78 | 8.10 |
| Std Dev | 1.88 | 1.41 | 1.85 | 0.66 | 1.45 | 0.80 |
| n | 9 | 8 | 8 | 8 | 9 | 15 |

APPENDIX C

Variation of Dossing of mu3G9 (collagen reporter mice)

| | PBS | 0.1 mg/kg | 0.3 mg/kg | 1 mg/kg | 3 mg/kg | 10 mg/kg | 3 × 4 mg/kg | sTGFbRII-Ig | Sham |
|---|---|---|---|---|---|---|---|---|---|
| Mean | 3617 | 2887 | 2021 | 1121 | 837 | 1274 | 1927 | 768 | 331 |
| Std Dev | 1768 | 1819 | 723 | 1023 | 500 | 872 | 1459 | 286 | 166 |
| n | 17 | 11 | 12 | 15 | 6 | 5 | 5 | 5 | 3 |

APPENDIX D

BAL Composition in Bleo: weekly dosing

| | | No Bleo | | | PBS | | | 0.3 mg/kg | | | 1 mg/kg | | | 3 mg/kg | | | 1E6 | | |
|---|---|---|---|---|---|---|---|---|---|---|---|---|---|---|---|---|---|---|---|
| | | Mean | Std Dev | n | Mean | Std Dev | n | Mean | Std Dev | n | Mean | Std Dev | n | Mean | Std Dev | n | Mean | Std Dev | n |
| Total BAL | Day 2 | 1.40 | 0.45 | 5 | 2.80 | 0.75 | 10 | 4.83 | 1.32 | 10 | 3.78 | 1.67 | 10 | 4.18 | 1.61 | 10 | 4.25 | 0.63 | 10 |
| | Day 5 | 2.51 | 0.87 | 5 | 8.80 | 6.17 | 10 | 7.35 | 4.97 | 10 | 10.03 | 5.35 | 10 | 9.43 | 4.56 | 10 | 9.66 | 5.76 | 10 |
| | Day 8 | 2.70 | 0.69 | 5 | 10.83 | 6.59 | 8 | 7.39 | 2.21 | 9 | 7.95 | 5.69 | 9 | 12.95 | 9.14 | 9 | 6.68 | 2.60 | 10 |
| | Day 11 | 2.26 | 0.55 | 5 | 12.17 | 2.13 | 9 | 7.73 | 2.33 | 8 | 7.67 | 2.62 | 6 | 9.63 | 3.48 | 4 | 8.44 | 2.42 | 7 |
| Macrophage | Day 2 | 1.33 | 0.39 | 3 | 2.33 | 0.54 | 9 | 4.22 | 1.20 | 9 | 2.99 | 1.00 | 10 | 3.24 | 1.09 | 10 | 3.54 | 1.09 | 10 |
| | Day 5 | 2.51 | 0.87 | 5 | 6.65 | 4.26 | 10 | 5.34 | 3.98 | 10 | 7.60 | 4.52 | 10 | 6.86 | 3.14 | 9 | 5.33 | 3.14 | 10 |
| | Day 8 | 1.85 | 0.49 | 5 | 9.86 | 5.57 | 10 | 8.23 | 4.22 | 9 | 8.94 | 4.34 | 10 | 5.90 | 3.63 | 10 | 10.74 | 3.63 | 4 |
| | Day 11 | 2.26 | 0.55 | 5 | 8.50 | 2.15 | 8 | 2.83 | 2.40 | 7 | 5.06 | 2.39 | 6 | 3.78 | 1.93 | 4 | 3.95 | 1.93 | 7 |
| Lymphocyte | Day 2 | 0 | 0 | 3 | 0 | 0 | 9 | 0 | 0 | 9 | 0 | 0 | 10 | 0 | 0 | 10 | 0 | 0 | 10 |
| | Day 5 | 0 | 0 | 5 | 0 | 0 | 10 | 0 | 0 | 10 | 0 | 0 | 10 | 0 | 0 | 9 | 0 | 0 | 10 |
| | Day 8 | 0 | 0 | 5 | 0.78 | 0.98 | 10 | 0.16 | 0.19 | 9 | 0.47 | 0.27 | 10 | 0.63 | 0.56 | 10 | 0.22 | 0.30 | 4 |
| | Day 11 | 0 | 0 | 5 | 0.27 | 0.23 | 8 | 0.05 | 0.07 | 7 | 0.06 | 0.08 | 6 | 0.15 | 0.21 | 4 | 0.02 | 0.04 | 7 |
| Neutrophil | Day 2 | 0.005 | 0.008 | 3 | 0.42 | 0.47 | 9 | 0.92 | 0.56 | 9 | 0.79 | 0.75 | 10 | 0.94 | 0.74 | 10 | 0.71 | 0.74 | 10 |
| | Day 5 | 0 | 0 | 5 | 2.15 | 3.43 | 10 | 2.01 | 1.77 | 10 | 2.43 | 1.91 | 10 | 3.27 | 1.96 | 9 | 4.33 | 1.96 | 10 |
| | Day 8 | 0 | 0 | 5 | 1.33 | 1.21 | 10 | 3.13 | 2.12 | 9 | 2.92 | 2.58 | 10 | 7.29 | 6.44 | 10 | 6.42 | 6.44 | 4 |
| | Day 11 | 0 | 0 | 4 | 3.31 | 2.44 | 8 | 3.22 | 2.50 | 6 | 2.55 | 2.60 | 6 | 5.70 | 3.83 | 4 | 1.70 | 3.83 | 7 |

APPENDIX E

BAL Cell Composition: Three Times per Week Dosing

| | | No Bleo | PBS | mu3G9 | | | 1E6 | |
|---|---|---|---|---|---|---|---|---|
| | | | | 4 mg/kg | 20 mg/kg | 40 mg/kg | 20 mg/kg | 40 mg/kg |
| Total BAL | Mean | 3.38 | 15.37 | 20.26 | 22.36 | 24.03 | 8.69 | 18.10 |
| | Std Dev | 1.68 | 9.27 | 12.17 | 7.10 | 17.06 | 5.42 | 9.12 |
| | n | 12 | 10 | 15 | 16 | 7 | 6 | 5 |

APPENDIX E-continued

BAL Cell Composition: Three Times per Week Dosing

| | | | | mu3G9 | | | 1E6 | |
|---|---|---|---|---|---|---|---|---|
| | | No Bleo | PBS | 4 mg/kg | 20 mg/kg | 40 mg/kg | 20 mg/kg | 40 mg/kg |
| Macrophage | Mean | 3.24 | 9.10 | 12.70 | 14.69 | 10.76 | 6.26 | 12.25 |
| | Std Dev | 1.56 | 4.43 | 6.93 | 5.10 | 6.16 | 3.54 | 3.35 |
| | n | 12 | 10 | 15 | 16 | 7 | 6 | 5 |
| Lymphocyte | Mean | 0.12 | 1.17 | 1.89 | 1.95 | 0.95 | 0.59 | 0.77 |
| | Std Dev | 0.14 | 1.05 | 1.93 | 1.25 | 0.89 | 0.67 | 0.77 |
| | n | 12 | 10 | 15 | 16 | 7 | 6 | 5 |
| Neutrophil | Mean | 0.01 | 5.10 | 5.67 | 5.73 | 12.32 | 1.84 | 5.08 |
| | Std Dev | 0.02 | 6.74 | 7.00 | 4.72 | 11.64 | 2.51 | 6.35 |
| | n | 12 | 10 | 15 | 16 | 7 | 6 | 5 |

Example 17

Molecular Analysis of Effects of an Anti-αvβ6 Integrin Monoclonal Antibody in Normal and Diseased Mouse Lung Summary Animal models for pulmonary fibrosis are effective in modeling some aspects of the fibrotic pathology of human idiopathic pulmonary fibrosis (IPF); however, no animal model accurately mimics the precise pathology of IPF. In addition, since the mechanisms of disease initiation and progression in IPF are incompletely understood, it is important to test potential therapeutic agents in multiple disease models and to assess their efficacy not just in terms of ameliorating the fibrotic pathology, but also in terms of intervening in molecular pathways thought to be relevant in the human disease. The TGF-β pathway has been implicated as a key pathway in IPF. Global transcript profiling of human IPF lung has shown that the dominant signature in this disease is one of an activated TGF-β pathway, which is consistent with the known roles of TGF-β in driving many of the pathological processes that characterize pulmonary fibrosis, including fibroblast activation and proliferation and expression of extracellular matrix molecules. In addition to its pro-fibrotic activities, TGF-β is an important anti-inflammatory cytokine, and thus therapeutic inhibition of TGF-β should ideally block fibrosis without promoting excessive inflammation. The integrin αvβ6 directly binds to latent TGF-β complexes and is required for conversion of TGF-β to an active state. However, since αvβ6-mediated TGF-β activation is critical in only some tissues, mice completely deficient for αvβ6 function show pathology only in the lung, while TGF-β deficient mice show inflammation in multiple organ systems. Thus the therapeutic strategy outlined here is to block αvβ6 function to avoid global inhibition of the TGF-β pathway, and to demonstrate that efficacy in blocking the fibrotic pathology associated with increased TGF-β signaling can be achieved at doses that do not induce the inflammation associated with complete loss of TGF-β. Here, we characterize molecular changes at the mRNA and protein level associated with fibrotic and inflammatory pathology. We demonstrate that high doses of the anti-αvβ6 monoclonal antibody mu3G9, the murine parent of the clinical candidate BG00011, produce mRNA and protein changes in inflammatory markers in the lung that are consistent with the αvβ6-deficient mice. We further demonstrate that low doses of mu3G9 that are effective in attenuating fibrosis do not produce these inflammatory changes in mice.

Introduction

The TGF-β1 cytokine is a profibrotic cytokine known to stimulate fibroblasts to produce excess extracellular matrix (ECM), ultimately leading to organ scarring and failure (Roberts 1986). Adenoviral and transgenic overexpression of various cytokines in lung have shown that TGF-β1 is unique in its ability to promote fibrosis in the absence of significant inflammation. Knockout mouse models of genes in the TGF-β pathway (Bonniaud 2004, Munger 1999) and numerous studies with anti-TGF-β agents have demonstrated the efficacy of inhibiting TGF-β as a means of attenuating fibrosis (George, J. 1999; Sharma, K. 1996; Bonnidaud, P. 2004; Zheng, H. 2000; Kasuga, H. 2001; Ziyadeh, F. N. 2000; Laping, N.J. 2003). The αvβ6 integrin, composed of two subunits: the αv and β6 integrins, is a critical regulator of TGF-β1 activation, particularly in the lung. It is upregulated on epithelial cells during injury, inflammation and fibrosis, and binds to the latent TGF-β1 complex, converting it to an active form. [Huang 1998; Munger 1999; Busk 1992; Yokoaski 1996; Annes 2002]. Blocking αvβ6 binding to latent TGF-β1 provides a method for localized inhibition of TGF-β activation at sites of upregulated expression of αvβ6, thereby avoiding potential clinical safety risks of global inhibition of the TGF-β pathway in all tissues.

In the Examples above, we characterized the efficacy of the murine anti-αvβ6 monoclonal antibody, mu3G9, in two murine pulmonary fibrosis models: bleomycin-induced fibrosis (Example 16), radiation-induced fibrosis (Example 15). In addition, the effects of mu3G9 treatment in normal mice are described in detail in the toxicology reports. In this Example, we characterize the effects of mu3G9 treatment in normal mice and in disease models of pulmonary fibrosis on mRNA and protein levels in the lung.

Transcript profiling of lung tissue demonstrates that αvβ6 blockade attenuates the alters the TGF-β target genes that are associated with bleomycin-induced pulmonary fibrosis. These data suggest that αvβ6 is involved in the regulation of pulmonary fibrosis and could provide a novel molecular target for its therapeutic modulation.

Materials and Methods

1. Reagents. αvβ6 mAbs were generated as described elsewhere herein, and as previously described (29). Human/mouse chimeric 2A1 and 3G9 cDNAs were generated from the respective parent hybridoma total RNAs with constant region primers CDL-739 for the heavy chain and CDL-738 for the light chain using the First Strand cDNA synthesis kit (Amersham/Pharmacia, Piscataway, N.J.). The heavy and light chain variable region genes were amplified by the polymerase chain reaction using the same 3' primers used for cDNA synthesis and pools of degenerate primers specific for most murine antibody gene signal sequences (sequences available upon request) and Pfu DNA polymerase (Stratagene, La Jolla Calif.). Cloned heavy and light chain variable regions were ligated into mammalian expression vectors with human IgG1 constant regions. Recombinant soluble murine TGF-β receptor type II-Ig fusion protein (sTGF-βRII-Ig) was generated as previously described (10) Research-grade mu3G9, 1E6 and sTGF-bRII-Ig (purified protein in phosphate buffered saline) were used in all experiments.

2. Animals.

(a) Mu3G9 treatment in Normal Mice for RNA Analysis: Normal C57B16 mice were treated once per week for 4 weeks (on days 1, 8, 15 and 22) with 5 mg/kg of soluble TGFbRII-Ig, PBS, or the following doses of mu3G9: 0.3, 1, 3, 10 and 30 mg/kg. One cohort of treated mice was collected on day 29 (one week after the last dose=No recovery), while the other cohort was collected on day 78 (8 weeks after the last dose=7-week recovery). These experiments were performed independently of the work described in the mu3G9 mouse toxicology reports, in which the CD-1 strain of mice was tested and an 8 week recovery was used.

(b) Mu3G9 treatment in Normal Mice for Multiple-Analyte Profiling of BAL Proteins: Normal C57B16 mice were treated once per week for 4 weeks (on days 1, 8, 15 and 22) with PBS or the following doses of mu3G9: 0.1, 0.3, 1, 3, and 10 mg/kg. Mice were collected on day 29 (one week after the last dose) for bronchoalveolar lavage (BAL) collection. These experiments were again performed independently of the work described in the mu3G9 mouse toxicology reports, in which the CD-1 strain of mice was tested.

(c) Mu3G9 treatment in the radiation fibrosis model: Details of the treatment groups and endpoints used in assessing the efficacy of attenuating radiation-induced fibrosis are contained in BIIB Report #Rsch-2006-007. Briefly, three studies were carried out in the laboratory of John Munger at New York School of Medicine in which mice received thoracic irradiation and were treated with different doses of mu3G9 between 0.3 and 10 mg/kg weekly, beginning 15 weeks after irradiation. Mouse lungs were collected for histology/fibrosis measurement if found dead during the study. Surviving mice were collected at weeks 26, 28 and 32 postirradiation. BAL fluid was collected from one lung lobe and sent to Biogen IDEC, while other lobes were processed for histology/fibrosis measurement. Analysis of BAL fluid proteins is covered in this report to allow for comparisons with analysis of BAL fluid from normal mice treated with mu3G9 at Biogen IDEC.

3. Broncaoalveolar Lavage Collection. Mice were euthanised with an overdose of Inactin (Sigma) intraperitoneal injection (IP). The trachea was exposed using mostly blunt dissection. The trachea was then opened with scissors between two cartilage rings and a 23 gauge blunt end needle was inserted into the trachea. The needle was held in place by clamping lightly with a Schwartz temporary clip (Roboz). BAL was performed by injecting 0.8 mls of phosphate buffered saline without $Ca^{2+}$ or $Mg^{2+}$ (PBS) into the lungs. Fluid was then retracted into the syringe, without applying much pressure, and transferred into a 15 ml polypropylene Falcon tube on ice. The procedure is then repeated, BAL fluid is sucked back into the syringe without exerting excessive negative pressure. Samples are stored on ice and are processed for cell counts, differentials, and both BAL pellet and fluid are collected and stored at −80° C.

1. The BAL is then spun at 180 g (1000 rpm) (Beckman GPR) for 10 minutes on a tabletop centrifuge at 4° C. Supernatant (BAL fluid) is then removed and frozen at −80° C. Adding 1.0 ml of RBC lysing solution (Sigma) to the pellet and vortexing for 20 seconds. Cell counts and cytospins are then done.

2. Samples are stored on ice and counted using a hemacytometer. Allow one minute after applying the cells to the hemacytometer and before reading to allow the cells to settle.

3. 100 μl of cell suspensions are cytospun (ThermoShandon) at 500 RPM for 5 minutes at room temperature. Cytospin preparations are prepared by placing the cell solution into the cytospin apparatus and spinning at 500 rpm for 5 minutes. Check that cell concentrations are not too high on the slide; if it is, respin the samples. Allow slides to dry for overnight and then stain with DiffQuik (Fisher). Staining is done according to the manufacturer's (DiffQuik) protocol. Once the slides are dried and coverslipped with Permount (Fisher), cells are categorized by type, counting 100 randomly selected cells using a laboratory cell counter (Fisher).

4. Lung Collection for RNA. Mice were euthanised with an overdose of Inactin (Sigma) intraperitoneal injection (IP). The animal is sprayed down with 70% ETOH, using a pair of sterile scissors the skin is cut away starting from the sternum and working towards the head. Once the skin is cleared the sternum and ribs are cut away to expose the heart and lungs. The lungs are removed and placed on a sterile piece of gauze to remove any blood products and quickly put into a 14 ml polypropylene round bottom tube 17×100 mm (Fisher). Liquid nitrogen is added to the polypropylene tube containing the lungs and placed on dry ice. The lungs are then stored at −80° C.

5. RNA preparation. Total RNA was purified from snap-frozen lung tissue samples using the Qiazol reagent (Qiagen) according to the manufacturer's protocol. The RNA quality was verified by capillary electrophoresis on Bioanalyzer 2000 (Agilent).

6. Probe labeling, hybridization and scanning for transcript profiling. Sample labeling, hybridization, and staining were carried out according to the Eukaryotic Target Preparation protocol in the Affymetrix Technical Manual (701021 rev 1) for Genechip® Expression Analysis (Affymetrix, Santa Clara, Calif.). In summary, 5 μg of purified total RNA was used in a 20 μL first strand reaction with 200 U SuperScript II (cat #, 18064-022, Invitrogen) and 0.5 ug (dT)-T7 primer [5'-GGCCAGTGAATTGTAATACGACTCAC-TATAGGGAGGCGG$(T)_{24}$] at 42° C. for 1 h. Second strand synthesis was carried out by the addition of 40 U *E. coli* DNA Polymerase (cat #18010-025, Invitrogen), 2 U *E. coli* RNase H (cat #18021-071, Invitrogen) and 10 U *E. coli* DNA Ligase (cat #18052-019, Invitrogen) followed by incubation at 16° C. for 2 h. The second strand synthesis reaction was purified using the Genechip® Sample Cleanup Module according to the manufacturer's protocol (cat #900371, Affymetrix, Santa Clara, Calif.). Purified cDNA was amplified using BioArray high yield RNA transcription labeling kit (cat #42655-40, Enzo Life Sciences, Inc., Parmingdale, N.Y.) according to manufacturer's protocol to produce 70-120 μg of biotin labeled cRNA (compliment RNA). Mouse MgU74Av2, MgU74Bv2, and MgU74Cv2 GeneChip® probe arrays were pre-hybridized in a GeneChip® Hybridization Oven 640 (Affymetrix, Santa Clara, Calif.) according to the manufacturer's protocol. Fragmented labeled cRNA was resuspended in 300 μL 1× hybridization buffer containing 100 mM 2-morpholinoethanesulfonic acid, 1 M [Na+], 20 mM EDTA, 0.01% Tween 20, 0.5 mg/mL Aceylated BSA, 0.1 mg/mL herring sperm DNA, control oligo B2, and control transcripts bioB 1.5 pM, bioC 5 pM, bioD 25 pM, and cre 100 pM, and hybridized to Genechip® probe arrays according to manufacturer's protocol (Affymetrix, Santa Clara, Calif.). The hybridized GeneChip® probe arrays were washed and stained using Streptavidin-Phycoerythrinin (cat #S866, Molecular Probes, Eugene, Oreg.) and amplified with biotinylated anti-streptavidin (BA-0500, Vector Laboratories, Burlingame, Calif.) using GeneChip® Fluidics Station 400 (Affymetrix, Santa Clara, Calif.). The GeneChip® probe arrays were scanned using GeneArray Scanner (Hewlett Packard, Corvallis, Oreg.).

7. Transcript Profiling Data Analysis. The array scans were converted into Affymetrix CEL files and the resulting data set (group of .CEL files representing the complete experiment) was normalized using the Robust Microarray Average (RMA) method. Statistical and clustering analyses were done using the BRB Array Tools v. 3.4.0-Beta 2 (NCI), GeneSpring (Agilent) and Spotfire (Spotfire) data mining tools. Significance Analysis of Microarrays (SAM) was used to identify probesets whose signal intensities were altered by any of the experimental treatments compared to the PBS-treated group with the False Discovery Rate (FDR) threshold set not to exceed 0.01 at the 0.95 confidence limit (CL). Further filtering was done when necessary by selecting the significantly affected (FDR<0.01, CL 0.95) probesets showing an at least 2-fold change in signal intensity. The profiles of the resulting group of genes and the grouping of experimental conditions were analyzed and visualized by hierarchical clustering. Virtual pathway analysis was performed using the Ingenuity Pathway Analysis database (Ingenuity Systems).

8. Multiplex Analysis of BAL Fluid Protein Levels. Aliquots measuring 200 ul were taken directly from the BAL fluid collected as described above. These aliquots were sent to Rules Based Medicine, Inc. (Austin, Tex.) where they were analyzed for a standard panel of mouse proteins using their Luminex-based technology.

9. Statistical Analysis. Statistical analysis for transcript profiling analysis is described above. Statistical comparisons in analyzing protein levels in the BAL fluid were made between vehicle control and/or isotype control, and various doses of test article using one-way analysis of variance (ANOVA). When statistically significant differences were established at a probability of $p<0.05$ using ANOVA, significant differences between groups were evaluated by Dunnet's multiple comparison test.

Results

1. Effects of treating normal mice with mu3G9: lung transcript analysis. The results of toxicology studies in CD-1 mice identified the lung as a target organ of toxicity for mu3G9. As described in detail in those studies, pulmonary inflammation consistent with findings in the integrin β6 null mice (which are deficient for αvβ6 integrin) is seen in mice treated with mu3G9. This inflammation, as assessed by histopathology, is seen infrequently at doses of 1 mg/kg, but consistently at doses of 10 mg/kg weekly. To assess this inflammation in the C57B16 strain (the strain used in the efficacy studies described above in Examples 15 and 16), mice were treated with mu3G9 at doses between 0.3 and 30 mg/kg weekly, and lungs were processed for RNA and microarray analysis.

Figure 66:
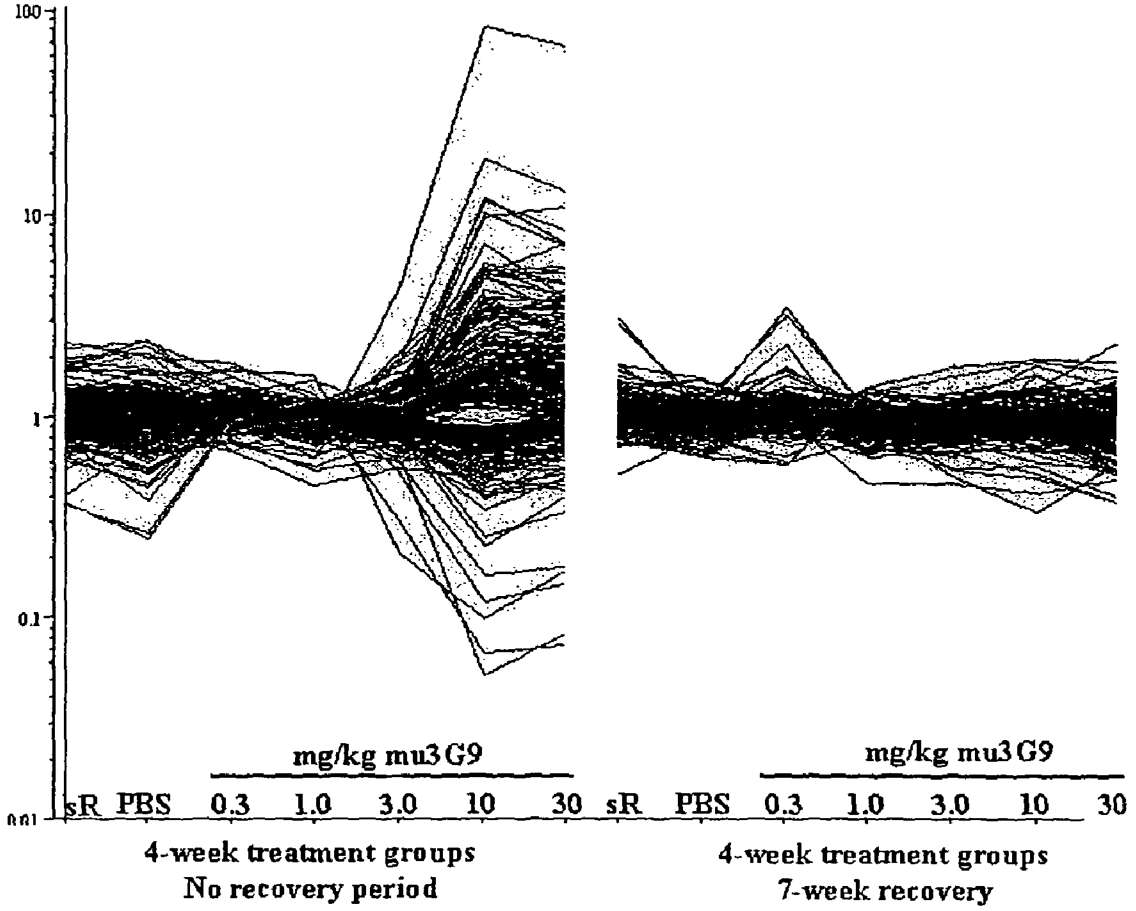
FIG. 66 depicts the profiles of normalized signal intensities for the genes identified as significantly affected by experimental treatments. Mice were treated with 5 mg/kg sTGFbRII-Ig (sR) or with PBS or with mu3G9 at the doses specified between 0.3 and 30 mg/kg on days 1, 8, 15 and 22 and were euthanised on day 29 (No recovery period) or on day 78 (7 week recovery period). RNA was prepared from lungs of treated mice and transcripts analyzed.

Significance Analysis of Microarrays (SAM) with the FDR threshold of 0.01 and CL 0.95 was used to search for differentially expressed genes in a series of pair-wise comparisons between the PBS-treated control group and each of the experimental treatment groups, including the groups treated with 3G9 and the sTGFbRII-Ig group. Such pair-wise SAM analyses were performed separately for the treatment and recovery groups using their respective PBS controls. The resulting gene lists were subjected to an additional filtering step to identify those of the significantly affected probe sets whose signal intensities varied between the PBS control and any of the treatment groups more than 2-fold. The results are summarized in the Tables 17-1 through 17-6. Significant changes in gene expression satisfying the above selection criteria were observed in the 10 mg/kg and 30 mg/kg subgroups of the treatment group (Tables 17-1 and 17-2). The profiles of gene expression for the selected probe sets have shown strong bidirectional shifts in expression levels of the corresponding genes in the 10 mg/kg and 30 mg/kg 3G9 treatment groups (FIG. 66).

Figure 67:
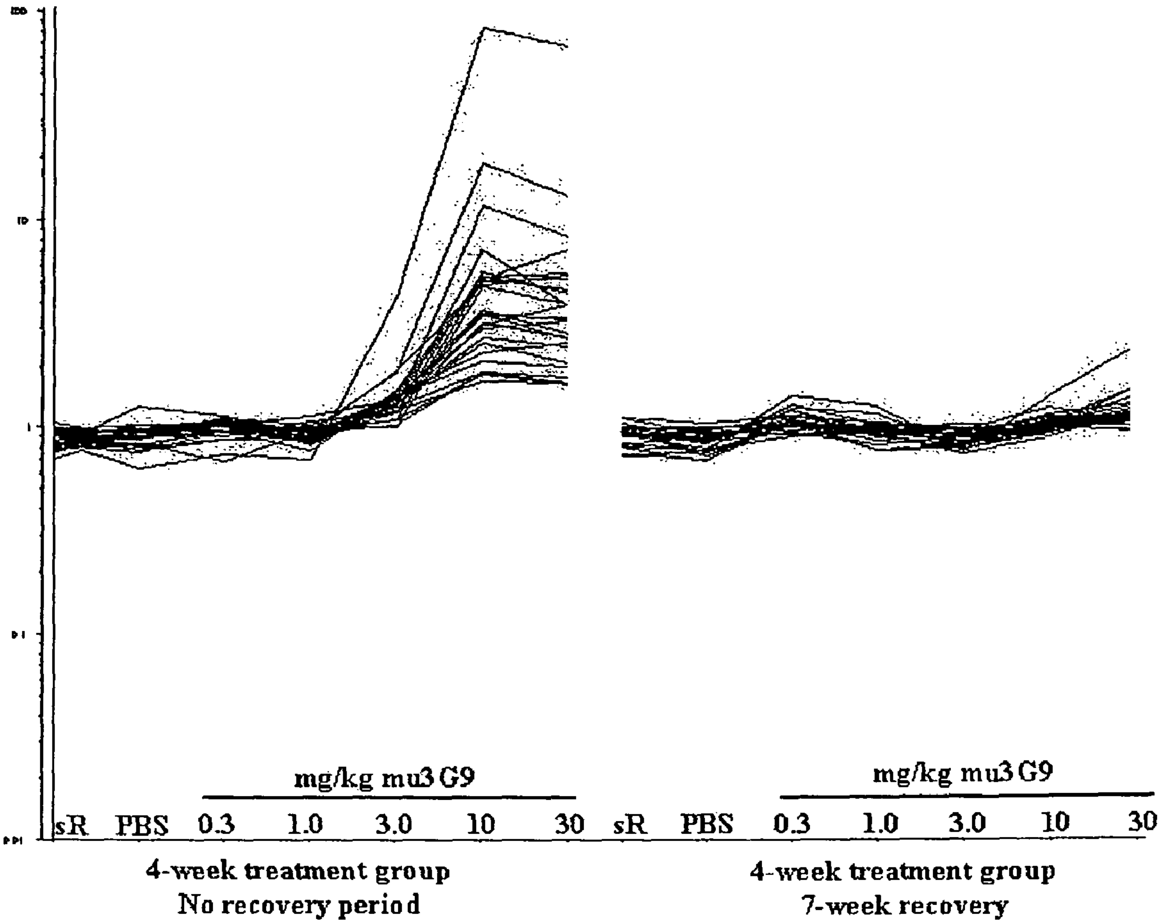
FIG. 67 depicts profiles of gene expression for the genes showing an upward trend at 3 mg/kg 3G9 in the treatment group. Mice were treated with 5 mg/kg sTGFbRII-Ig (sR) or with PBS or with mu3G9 at the doses specified between 0.3 and 30 mg/kg on days 1, 8, 15 and 22 and were euthanised on day 29 (No recovery period) or on day 78 (7 week recovery period). RNA was prepared from lungs of treated mice and transcripts analyzed.

No statistically significant changes of gene expression were detected in any other treatment subgroup or in the recovery group (Tables 17-1 and 17-2). However, MMP12 and 25 other genes selected for greater than 0.95 Pearson correlation of their expression profiles with that of MMP12, have shown a detectable upward trend in the 3 mg/kg 3G9 treatment group (FIG. 67; Table 17-7).

Figure 69A:
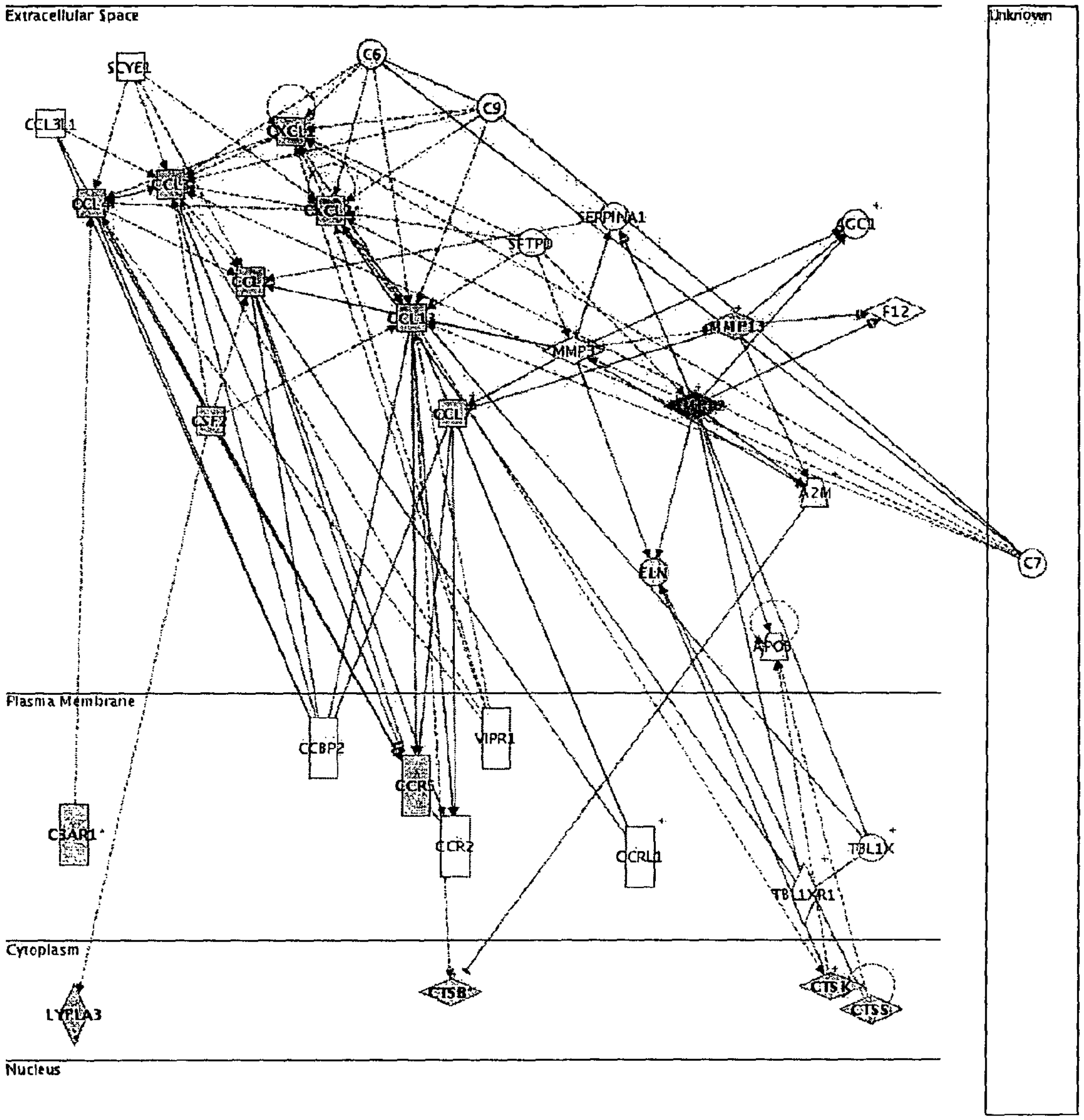
FIGS. 69A and 69B are network maps schematically depicting the regulatory networks that are affected by mu3G9 in mouse lung.
Figure 69B:
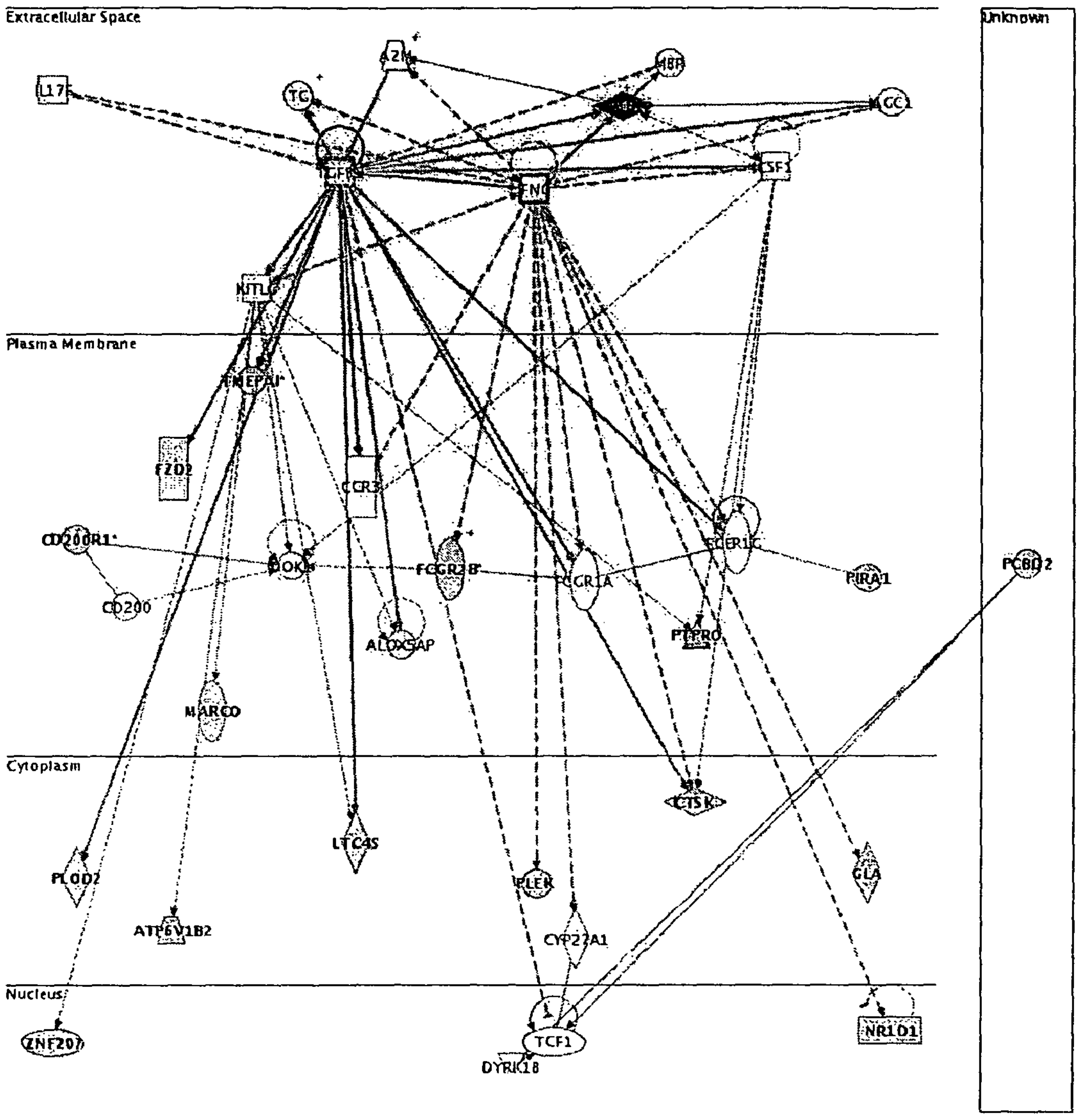

Functional annotation of the gene significantly affected by 3G9 was performed using the Ingenuity Pathway Analysis (IPA) database and has shown strong association of these genes with immune response and immunoregulatory cytokine signaling (FIG. 68). Similarly, virtual regulatory pathway analysis has suggested association of the 3G9-induced changes in gene expression with alterations in chemokine, TGF-β, and interferon signaling. These associations follow from the configurations of the two highest-scoring network (FIGS. 69A, 69B).

2. Quantitative PCR Analysis of MMP-12 Transcripts. MMP-12 shows the greatest fold-upregulation of any transcript in the lungs from mu3G9-treated mice (Table 17-3). MMP-12 had previously been reported as the most highly upregulated transcript in lungs from β6 null mice. To further elucidate the relationship between MMP-12 expression and mu3G9 treatment, we analyzed relative levels of MMP-12 transcript by quantitative PCR, including RNA prepared from the lungs of β6 null mice. Mu3G9 treatment produced a dose-dependent increase in MMP-12 transcript that was significant at 10 and 30 mg/kg. The fold-change in MMP-12 expression was comparable at those doses to that seen in the β6 null mice. Similar to the results described above for the microarray analysis, MMP-12 levels by qPCR trended up at the 3 mg/kg dose, but were unchanged at the 0.3 and 1 mg/kg doses.

3. Protein Analysis of BAL from Lungs of Normal Mice treated with mu3G9. To further characterize molecular changes in the lung attributable to mu3G9 treatment, we analyzed levels of 60 proteins (Table 17-8) in BAL fluid from another cohort of mice treated for 4 weeks with doses of mu3G9 between 0.1 and 10 mg/kg. Protein analysis was carried out by luminex (multiplex protein analysis) assay at Rules Based Medicine, Inc. (Austin, Tex.). Consistent with findings at the transcript level, multiple proteins associated with pulmonary inflammation were elevated in the BAL fluid of mice treated with the 10 mg/kg dose (Table 17-9). In addition, some of these changes were significant by ANOVA at the 3 mg/kg dose as well; however, no proteins on the panel were elevated by the 1 mg/kg dose.

Figure 70:
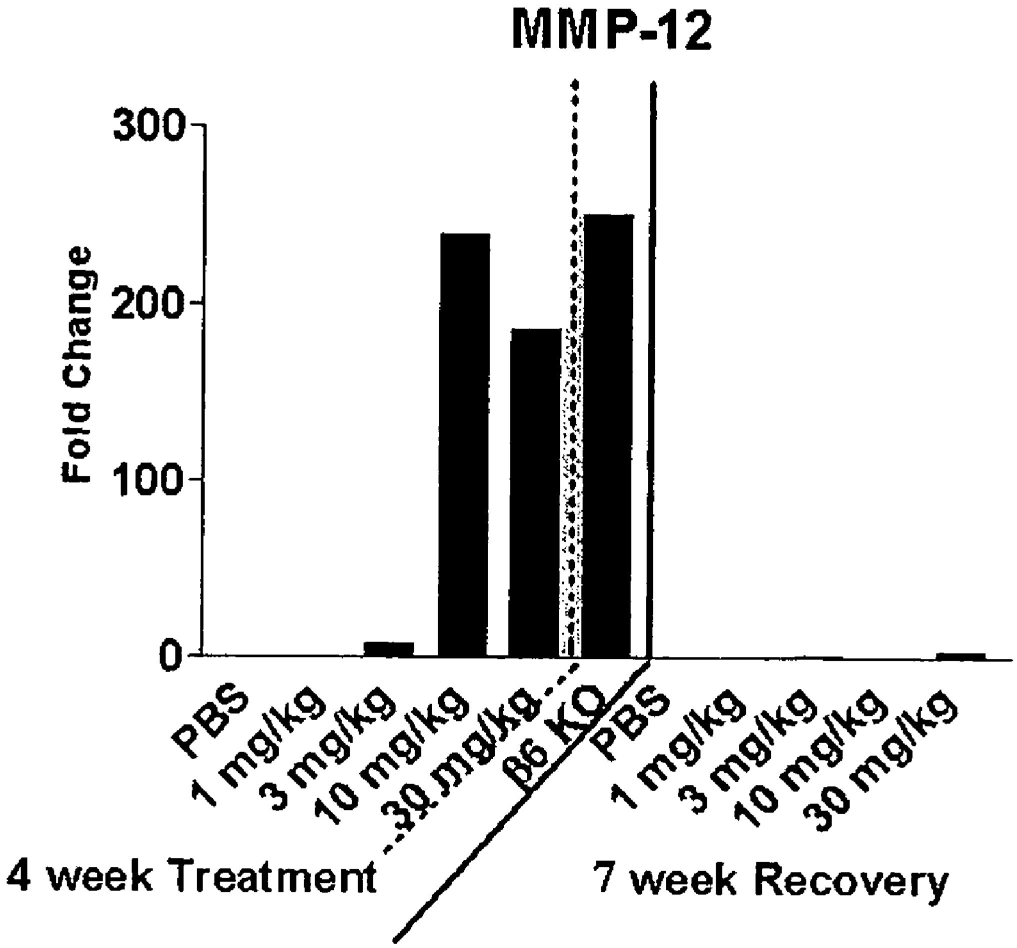
FIG. 70 is a bar graph depicting the dose response of MMP-12 transcript to mu3G9 treatment.

4. Analysis of BAL Fluid Proteins from the Radiation-induced Fibrosis Model. The efficacy of mu3G9 in attenuating radiation induced pulmonary fibrosis is described above in Example 15. BAL fluid (BALF) samples collected in those studies were analyzed by multi-analyte protein profiling, using the same mouse panel as was used in the BALF from normal mice treated with mu3G9. BALF analysis of the week 28 (13 week treatment) and week 32 (17 week treatment) timepoints are analyzed here. Proteins that were significantly changed as determined by ANOVA are summarized in Table 17-11. As with transcript profiling and protein results in normal mice, the majority of proteins that are altered in the radiation fibrosis model reach significance only at the 10 mg/kg dose, although some are significant and all show trends at 3 mg/kg. The majority of these proteins are cytokines or chemokines known to be associated with pulmonary fibrosis. Fourteen of the 20 proteins upregulated by 2-fold or more in normal mice treated with 10 mg/kg mu3G9 (Table 17-10) are also consistently upregulated in the radiation model. Despite the differences in mu3G9 treatment period and in injury/inflammation state, the concordance between findings in the normal and irradiated mice is striking. Many of the proteins show modestly higher-fold upregulation consistent with the longer treatment period in the radiation model (Table 17-12), but overall the findings are consistent in these two very different settings. In addition, despite different baseline levels in normal and irradiated mice (radiation injury upregulates most of these proteins), the dose range over which these inflammatory markers are upregulated is the same in the normal and irradiated mice. Specifically, they are upregulated at the 3 and 10 mg/kg doses but not at the 1 mg/kg dose in both the normal and diseased mice (illustrated with the four most highly upregulated proteins at week 28 in FIG. 70). Thus, despite the much higher expression of the drug target in the radiation model (see Example 15 above), the doses that produce BAL protein changes specific to mu3G9 treatment are the same in both settings. It is important to note that not all of the proteins induced by mu3G9 are thought to have pro-inflammatory and/or profibrotic effects. For instance, the CXCL chemokine IP-10/CXCL10 has demonstrated potent anti-fibrotic efficacy in mouse models, and mice deficient for IP-10 or its receptor CXCR3 show an exaggerated fibrotic response to bleomycin. However, consistent changes are not seen in this or other cytokines at the near maximal efficacious dose of 1 mg/kg dose, so it is unlikely that any of these changes in the cytokine milieu of the lung are required for efficacy of mu3G9 treatment.

Figure 71:
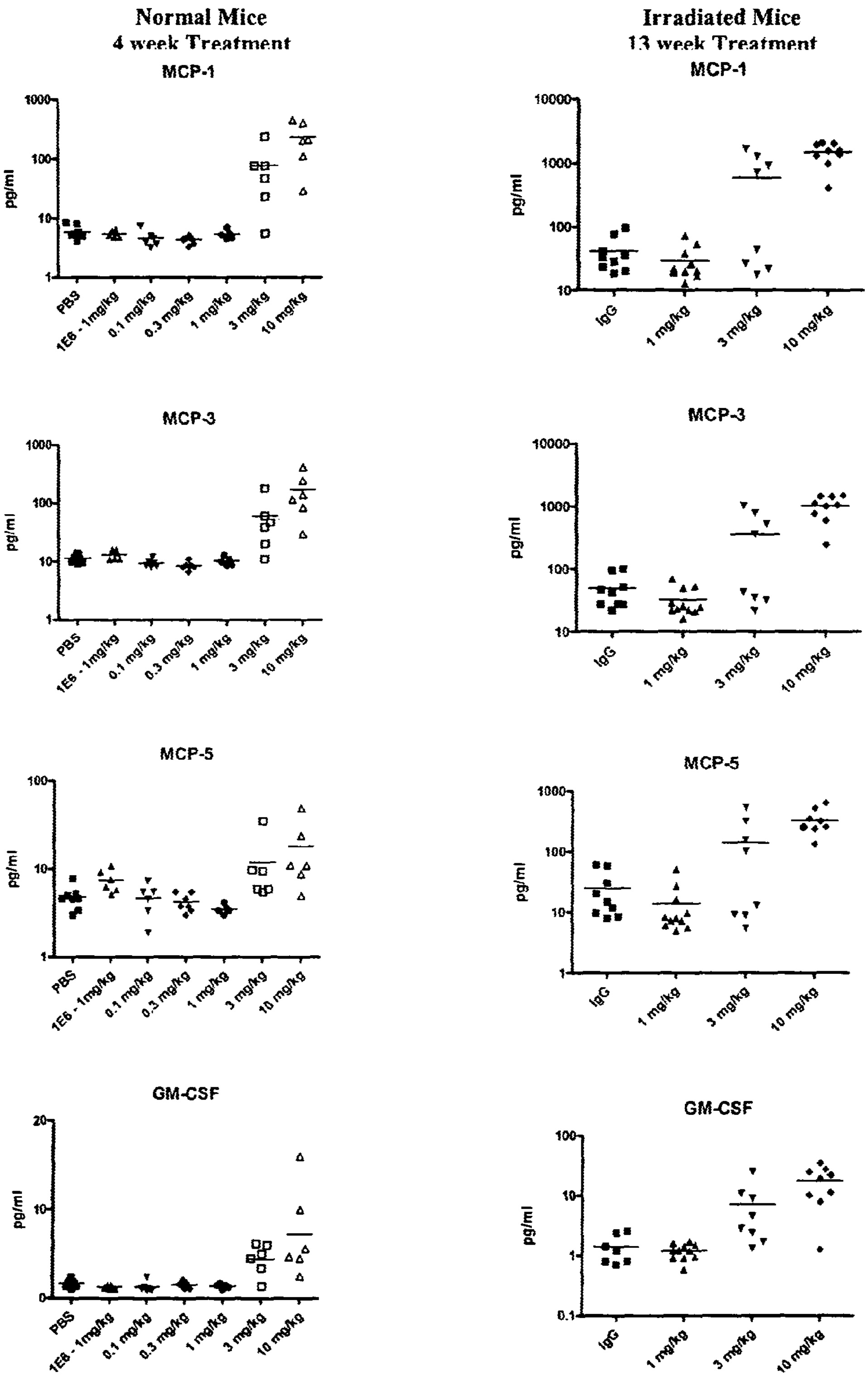
FIG. 71 is a series of scatter plots of BAL fluid protein levels in normal and irradiated mice.
Figure 72:
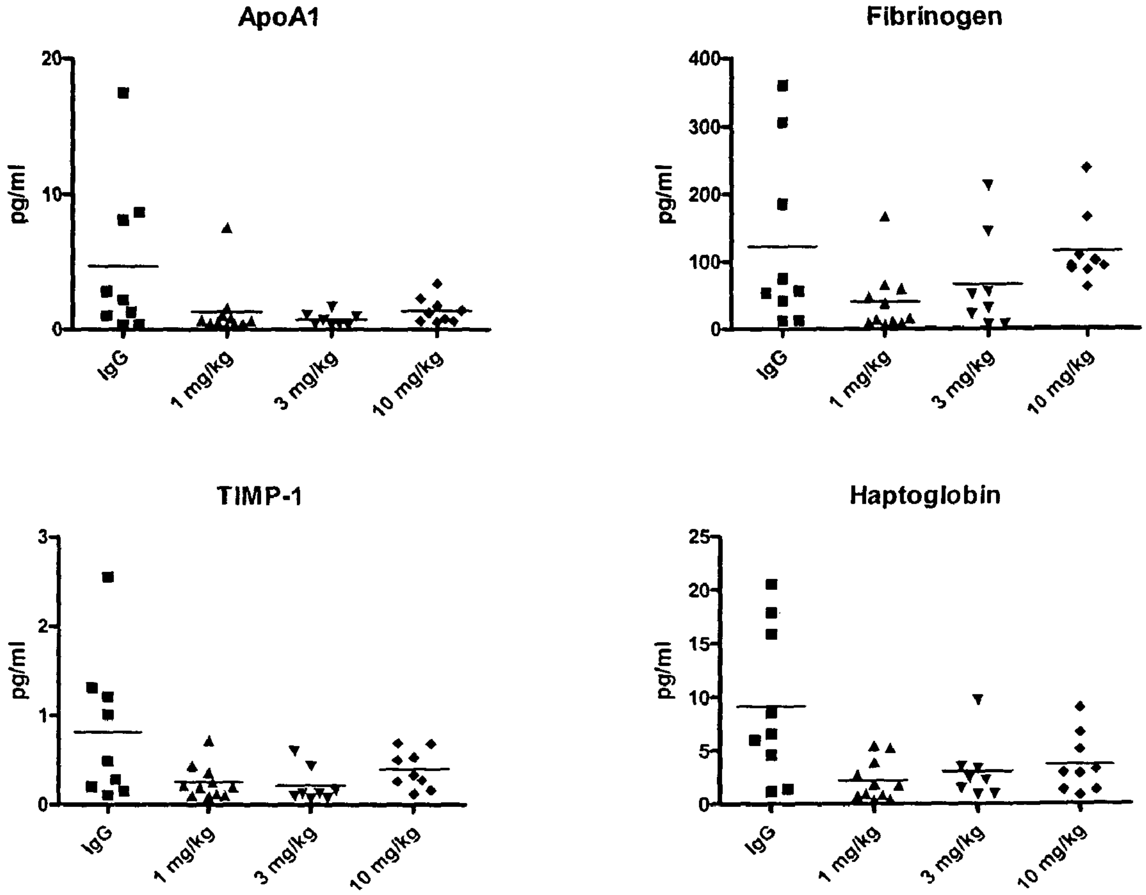
FIG. 72 is a series of scatter plots depicting proteins that are upregulated by radiation-induced fibrosis and that are down-regulated by mu3G9 treatment at 28 weeks.

Among the proteins that were upregulated in normal mice but not in the radiation model were ApoA1, Fibrinogen, and TIMP-1. Levels of these proteins and a fourth protein, haptoglobin, are increased in the BAL fluid of irradiated mice as compared to normal mice, but are decreased by mu3G9 treatment (FIG. 71). Thus the normalization of levels for these proteins at efficacious doses suggests that they may be acting as surrogate markers of efficacy at the 28 week timepoint (FIG. 72). The only proteins on the panel that changed significantly at the lower doses were ones that were decreased by treatment: TIMP-1 and haptoglobin. TIMP-1 is a known TGF-β target and is frequently elevated in fibrotic disease. Its downmodulation is consistent with the mechanism of action of mu3G9, i.e. inhibiting αvβ6-mediated TGF-β activation.

Tables

TABLE 17-1

Analyis of lung transcript changes to mu3G9 in vivo dose escalation. Number of probe sets significantly (FDR < 0.01, CL 0.95) affected by experimental treatments.

| | | 3G9, mg/kg | | | | |
|---|---|---|---|---|---|---|
| | rsTGFbR_Fc | 0.3 | 1 | 3 | 10 | 30 |
| Treatment | 0 | 0 | 0 | 0 | 226 | 91 |
| Recovery | 0 | 0 | 0 | 0 | 0 | 0 |

TABLE 17-2

Analysis of lung transcripts with greater than 2-fold change. Number of probe sets showing significant changes greater than two-fold in signal intensity in response to experimental treatments.

| | | 3G9, mg/kg | | | | |
|---|---|---|---|---|---|---|
| | rsTGFbR_Fc | 0.3 | 1 | 3 | 10 | 30 |
| Treatment | 0 | 0 | 0 | 0 | 69 | 43 |
| Recovery | 0 | 0 | 0 | 0 | 0 | 0 |

TABLE 17-3

List of Transcripts

| | Geom mean of intensities in class 1: 3G9_10 | Geom mean of intensities in class 2: PBS | Fold difference of geom means | Probe set | Gene symbol |
|---|---|---|---|---|---|
| 1 | 1826.8 | 37.7 | 48.456 | 1449153_at | Mmp12 |
| 52 | 1750.3 | 158.3 | 11.057 | 1450826_a_at | Saa3 |
| 17 | 1500 | 277.5 | 5.405 | 1438211_s_at | Dbp |
| 4 | 5169 | 980.2 | 5.273 | 1427747_a_at | Lcn2 |
| 38 | 736.9 | 145.9 | 5.051 | 1425890_at | Ly6i |
| 2 | 379.4 | 75.7 | 5.012 | 1425951_a_at | Clec4n |
| 6 | 706.3 | 150.6 | 4.69 | 1419725_at | Slc26a4 |
| 23 | 181.6 | 38.8 | 4.68 | 1419209_at | Cxcl1 |
| 9 | 911.9 | 200.8 | 4.541 | 1418174_at | Dbp |
| 19 | 234.6 | 52.9 | 4.435 | 1420380_at | Ccl2 |
| 3 | 803.5 | 183.4 | 4.381 | 1448898_at | Ccl9 |
| 7 | 727.7 | 175.6 | 4.144 | 1448303_at | Gpnmb |
| 115 | 2018.4 | 538.6 | 3.747 | 1449025_at | Ifit3 |
| 85 | 126.4 | 34.5 | 3.664 | 1419282_at | Ccl12 |
| 5 | 2667.2 | 736.8 | 3.62 | 1417936_at | Ccl9 |
| 18 | 86.5 | 26.9 | 3.216 | 1419561_at | Ccl3 |
| 73 | 586.9 | 186.8 | 3.142 | 1450291_s_at | Ms4a4c |
| 70 | 88.6 | 28.9 | 3.066 | 1419598_at | Ms4a6d |
| 92 | 105.8 | 34.9 | 3.032 | 1421228_at | Ccl7 |
| 13 | 193.4 | 63.9 | 3.027 | 1435313_at | Cd200r4 |
| 14 | 1999.8 | 669 | 2.989 | 1420394_s_at | Gp49a /// Lilrb4 |
| 8 | 1653.7 | 568.8 | 2.907 | 1420249_s_at | Ccl6 |
| 12 | 996.2 | 347.3 | 2.868 | 1419627_s_at | Clec4n |
| 28 | 342.5 | 123.2 | 2.78 | 1424727_at | Ccr5 |
| 60 | 942.2 | 355.5 | 2.65 | 1436530_at | |
| 49 | 72.5 | 27.4 | 2.646 | 1449984_at | Cxcl2 |
| 50 | 139.3 | 52.9 | 2.633 | 1442082_at | C3ar1 |
| 42 | 444.6 | 170.7 | 2.605 | 1449227_at | Ch25h |
| 126 | 285.5 | 109.9 | 2.598 | 1419599_s_at | Ms4a11 |
| 10 | 1185.1 | 464.1 | 2.554 | 1450652_at | Ctsk |
| 47 | 841.8 | 343.7 | 2.449 | 1418486_at | Vnn1 |
| 41 | 288.4 | 118.4 | 2.436 | 1420464_s_at | Pira1 /// Pira2 /// Pira3 /// Pira4 /// Pira6 /// Lilrb3 /// LOC546027 |
| 35 | 663.4 | 275.7 | 2.406 | 1426464_at | Nr1d1 |
| 16 | 555.3 | 236 | 2.353 | 1451941_a_at | Fcgr2b |
| 51 | 191.9 | 82.4 | 2.329 | 1427221_at | MGI: 2143217 |
| 86 | 384 | 168.9 | 2.274 | 1437939_s_at | Ctsc |
| 112 | 305.2 | 134.7 | 2.266 | 1450403_at | Stat2 |
| 15 | 4853.1 | 2214.3 | 2.192 | 1417266_at | Ccl6 |
| 32 | 266.1 | 122.7 | 2.169 | 1425151_a_at | Noxo1 |
| 20 | 904 | 417 | 2.168 | 1449164_at | Cd68 |
| 123 | 232 | 107.6 | 2.156 | 1419482_at | C3ar1 |
| 25 | 425.2 | 200.1 | 2.125 | 1458176_at | Per3 |
| 96 | 35.8 | 17.1 | 2.094 | 1420768_a_at | D11Lgp2e |
| 21 | 184.8 | 88.8 | 2.081 | 1427313_at | Ptgir |
| 34 | 83.2 | 40.6 | 2.049 | 1416959_at | Nr1d2 |
| 46 | 430.5 | 210.9 | 2.041 | 1422978_at | Cybb |
| 69 | 25.3 | 12.4 | 2.04 | 1417256_at | Mmp13 |
| 89 | 95.1 | 47.3 | 2.011 | 1419754_at | Myo5a |
| 57 | 219.4 | 109.6 | 2.002 | 1419483_at | C3ar1 |
| 22 | 138.2 | 69.1 | 2 | 1418809_at | Pira1 |
| 26 | 269.6 | 137.4 | 1.962 | 1450184_s_at | Tef |

TABLE 17-3-continued

List of Transcripts

| | Geom mean of intensities in class 1: 3G9_10 | Geom mean of intensities in class 2: PBS | Fold difference of geom means | Probe set | Gene symbol |
|---|---|---|---|---|---|
| 124 | 313 | 159.7 | 1.96 | 1421578_at | Ccl4 |
| 106 | 243.8 | 125.8 | 1.938 | 1446834_at | Ctsc |
| 125 | 1336.8 | 707.1 | 1.891 | 1426774_at | Parp12 |
| 31 | 199.1 | 106.7 | 1.866 | 1441445_at | Per3 |
| 11 | 130.8 | 70.3 | 1.861 | 1422191_at | Cd200r1 |
| 30 | 366.9 | 198.3 | 1.85 | 1418797_at | Ms4a8a |
| 27 | 207.1 | 112.5 | 1.841 | 1442243_at | Per3 |
| 36 | 1654.9 | 898.9 | 1.841 | 1416958_at | Nr1d2 |
| 104 | 6572.7 | 3665.8 | 1.793 | 1451537_at | Chi3l1 |
| 103 | 316.2 | 177.9 | 1.777 | 1420998_at | Etv5 |
| 77 | 86.2 | 48.6 | 1.774 | 1418248_at | Gla |
| 88 | 118 | 66.7 | 1.769 | 1421977_at | Mmp19 |
| 120 | 384.5 | 217.6 | 1.767 | 1450241_a_at | Evi2a |
| 66 | 1162.4 | 663.8 | 1.751 | 1448276_at | Tspan4 |
| 87 | 393.3 | 225.3 | 1.746 | 1422875_at | Cd84 |
| 68 | 265.8 | 152.7 | 1.741 | 1444176_at | Atp6v0d2 |
| 83 | 1063.7 | 611 | 1.741 | 1418025_at | Bhlhb2 |
| 29 | 164.1 | 94.7 | 1.733 | 1416986_a_at | Ptpns1 |
| 76 | 304 | 178.3 | 1.705 | 1437729_at | |
| 108 | 1652.4 | 971.4 | 1.701 | 1448883_at | Lgmn |
| 91 | 38.3 | 22.7 | 1.687 | 1419729_at | Tex11 |
| 121 | 35.1 | 20.9 | 1.679 | 1447564_x_at | 9230101H05Rik |
| 97 | 371.8 | 222.8 | 1.669 | 1435263_at | 0610008L10Rik |
| 33 | 103.8 | 62.4 | 1.663 | 1460662_at | Per3 |
| 110 | 138.5 | 83.6 | 1.657 | 1419676_at | Mx2 |
| 43 | 236.3 | 143.4 | 1.648 | 1452367_at | Coro2a |
| 64 | 4218.6 | 2564.1 | 1.645 | 1448732_at | Ctsb |
| 24 | 392.8 | 238.9 | 1.644 | 1417492_at | Ctsb |
| 67 | 54.1 | 33.3 | 1.625 | 1420250_at | |
| 48 | 126.7 | 78.1 | 1.622 | 1433864_at | Lrp12 |
| 79 | 275.8 | 170.1 | 1.621 | 1425407_s_at | Clec4a2 /// Clec4b |
| 62 | 395.4 | 244.1 | 1.62 | 1424356_a_at | Metrnl |
| 93 | 1066 | 657.9 | 1.62 | 1435477_s_at | Fcgr2b |
| 90 | 59.1 | 36.8 | 1.606 | 1425863_a_at | Ptpro |
| 118 | 542.2 | 338 | 1.604 | 1419975_at | |
| 75 | 387.1 | 241.8 | 1.601 | 1441855_x_at | Cxcl1 |
| 80 | 280.7 | 175.6 | 1.599 | 1427429_at | Csf2 |
| 61 | 434.2 | 272.2 | 1.595 | 1425444_a_at | Tgfbr2 |
| 37 | 2066.2 | 1298.3 | 1.591 | 1424175_at | Tef |
| 59 | 5030.6 | 3168.8 | 1.588 | 1448591_at | Ctss |
| 113 | 197.5 | 125 | 1.58 | 1430332_a_at | Gusb |
| 72 | 425.2 | 269.4 | 1.578 | 1423308_at | Tgoln1 |
| 78 | 135.9 | 86.2 | 1.577 | 1450454_at | Tor3a |
| 40 | 3920.1 | 2486.7 | 1.576 | 1421813_a_at | Psap |
| 54 | 960.5 | 609.8 | 1.575 | 1450355_a_at | Capg |
| 39 | 153.2 | 98.1 | 1.562 | 1421792_s_at | Trem2 |
| 45 | 413.1 | 267.1 | 1.547 | 1455332_x_at | Fcgr2b |
| 63 | 327.1 | 212 | 1.543 | 1419883_s_at | Atp6v1b2 |
| 65 | 2946.6 | 1910.8 | 1.542 | 1417868_a_at | Ctsz |
| 82 | 108 | 70.3 | 1.536 | 1436482_a_at | Sdc3 |
| 58 | 441.1 | 287.5 | 1.534 | 1448534_at | Ptpns1 |
| 94 | 168.9 | 110.2 | 1.533 | 1422341_s_at | Lypla3 |
| 95 | 71.2 | 46.8 | 1.521 | 1436397_at | BC027057 |
| 71 | 79.2 | 52.2 | 1.517 | 1425227_a_at | Atp6v0a1 |
| 81 | 342.4 | 226.2 | 1.514 | 1448749_at | Plek |
| 109 | 213.8 | 141.4 | 1.512 | 1424083_at | Rod1 |
| 84 | 1951.7 | 1295.4 | 1.507 | 1417870_x_at | Ctsz |
| 105 | 159 | 106.2 | 1.497 | 1431382_a_at | Rsnl2 |
| 119 | 872.6 | 586.6 | 1.488 | 1435476_a_at | Fcgr2b |
| 55 | 65.3 | 43.9 | 1.487 | 1421851_at | Mtap1b |
| 74 | 990.6 | 675.5 | 1.466 | 1450027_at | Sdc3 |
| 98 | 62.5 | 42.7 | 1.464 | 1421789_s_at | Arf3 |
| 44 | 17.7 | 12.1 | 1.463 | 1439703_at | Cd200r1 |
| 111 | 131.1 | 89.6 | 1.463 | 1425461_at | Fbxw11 |
| 56 | 148.2 | 101.4 | 1.462 | 1456043_at | Usp22 |
| 99 | 407.7 | 282.2 | 1.445 | 1417088_at | Zfp346 |
| 102 | 268.4 | 185.7 | 1.445 | 1425834_a_at | Gpam |
| 100 | 117.8 | 81.6 | 1.444 | 1460650_at | Atp6v0a1 |
| 114 | 105.7 | 73.4 | 1.44 | 1422966_a_at | Tfrc |
| 116 | 197.5 | 139.4 | 1.417 | 1421167_at | Atp11a |

TABLE 17-3-continued

List of Transcripts

| | Geom mean of intensities in class 1: 3G9_10 | Geom mean of intensities in class 2: PBS | Fold difference of geom means | Probe set | Gene symbol |
|---|---|---|---|---|---|
| 53 | 80.3 | 57.3 | 1.401 | 1429562_at | 5031415C07Rik |
| 122 | 587.5 | 429.3 | 1.369 | 1437317_at | Ub3l1 |
| 101 | 5469.4 | 4011.4 | 1.363 | 1415687_a_at | Psap |
| 107 | 253.8 | 193.1 | 1.314 | 1456620_at | MGC79224 |
| 117 | 49.9 | 38 | 1.313 | AFFX-TransRecMur/X57349_3_at | Tfrc |
| 191 | 1557.4 | 1944.4 | 0.801 | 1424368_s_at | Ubgln1 |
| 186 | 489.3 | 626.4 | 0.781 | 1440817_x_at | G630024C07Rik |
| 194 | 385.9 | 496.6 | 0.777 | 1420493_a_at | Pcyt2 |
| 212 | 600.7 | 776.1 | 0.774 | 1452621_at | Pcbd2 |
| 195 | 135.3 | 176.2 | 0.768 | 1443880_at | Zbtb39 |
| 205 | 630.8 | 821.7 | 0.768 | 1419640_at | Purb |
| 214 | 128.9 | 168.5 | 0.765 | 1443104_at | 4933431N12Rik |
| 167 | 1368 | 1802.4 | 0.759 | 1455286_at | Btbd1 |
| 217 | 263.2 | 348.3 | 0.756 | 1419359_at | Hexim1 |
| 184 | 809 | 1075.7 | 0.752 | 1448685_at | 2900010M23Rik |
| 206 | 321.8 | 428.3 | 0.751 | 1435874_at | Prkab2 |
| 224 | 84 | 112.5 | 0.747 | 1458404_at | Ndufb8 |
| 196 | 2304.4 | 3103.5 | 0.743 | 1416183_a_at | Ldh2 |
| 199 | 164.9 | 222.8 | 0.74 | 1451634_at | |
| 220 | 420.3 | 569.4 | 0.738 | 1420631_a_at | Blcap |
| 207 | 283.8 | 386.1 | 0.735 | 1433986_at | BC024659 |
| 215 | 360 | 489.8 | 0.735 | 1451381_at | 1810020D17Rik |
| 177 | 126.6 | 173.3 | 0.731 | 1438422_at | Lrrc20 |
| 155 | 811.3 | 1113.5 | 0.729 | 1452020_a_at | MGI: 1353606 |
| 170 | 56.4 | 77.8 | 0.725 | 1432431_s_at | 1110033L15Rik |
| 190 | 1524 | 2111.1 | 0.722 | 1448237_x_at | Ldh2 |
| 226 | 899.3 | 1250.5 | 0.719 | 1426690_a_at | Srebf1 |
| 148 | 285.6 | 397.6 | 0.718 | 1452411_at | Lrrc1 |
| 204 | 545.9 | 761.5 | 0.717 | 1424455_at | Gprasp1 |
| 182 | 152.2 | 213.4 | 0.713 | 1430375_a_at | Ccl27 |
| 174 | 255.6 | 360.2 | 0.71 | 1456399_at | |
| 216 | 647.4 | 911.6 | 0.71 | 1424746_at | |
| 188 | 421.9 | 594.7 | 0.709 | 1429115_at | 2010003O02Rik |
| 189 | 522.2 | 741.7 | 0.704 | 1447585_s_at | Mrps6 |
| 187 | 129.8 | 185.3 | 0.7 | 1438916_x_at | |
| 197 | 177.1 | 253.9 | 0.698 | 1441880_x_at | MGC30332 |
| 201 | 251.6 | 360.5 | 0.698 | 1435339_at | Kctd15 |
| 209 | 72.9 | 106 | 0.688 | 1447739_x_at | Klhdc4 |
| 153 | 116.8 | 170.5 | 0.685 | 1456904_at | |
| 202 | 44.4 | 65 | 0.683 | 1454877_at | Sertad4 |
| 163 | 116.4 | 170.9 | 0.681 | 1438915_at | 6720401G13Rik |
| 154 | 99.5 | 146.4 | 0.68 | 1455293_at | Leo1 |
| 211 | 223 | 327.8 | 0.68 | 1418469_at | Nrip1 |
| 198 | 232.8 | 344.2 | 0.676 | 1429197_s_at | Rabgap1l |
| 140 | 295.9 | 439 | 0.674 | 1424970_at | Purg |
| 158 | 180.7 | 268.3 | 0.673 | 1440971_x_at | G630024C07Rik |
| 183 | 725.2 | 1077 | 0.673 | 1424313_a_at | Ndufs7 |
| 180 | 206.6 | 307.6 | 0.672 | 1417220_at | Fah |
| 171 | 399.2 | 602.2 | 0.663 | 1456603_at | 1500005K14Rik |
| 159 | 79.3 | 120 | 0.661 | 1452295_at | Tmepai |
| 152 | 208.7 | 317.7 | 0.657 | 1422561_at | Adamts5 |
| 149 | 295.2 | 449.9 | 0.656 | 1418172_at | Hebp1 |
| 162 | 58.9 | 90.3 | 0.652 | 1457021_x_at | Amhr2 |
| 193 | 36.6 | 56.7 | 0.646 | 1433855_at | Abat |
| 200 | 62.7 | 97.3 | 0.644 | 1438515_at | Zfp207 |
| 156 | 151 | 235.2 | 0.642 | 1427410_at | Dleu2 |
| 218 | 226.1 | 357.8 | 0.632 | 1417430_at | Cdr2 |
| 165 | 470.8 | 748.4 | 0.629 | 1430612_at | 1810033B17Rik |
| 166 | 40.5 | 64.4 | 0.629 | 1435939_s_at | AI987662 |
| 161 | 83.5 | 133 | 0.628 | 1456980_at | 9830134C10Rik |
| 150 | 107.3 | 171.2 | 0.627 | 1417355_at | Peg3 |
| 168 | 196.1 | 316.3 | 0.62 | 1428749_at | Dmxl2 |
| 223 | 54.6 | 88 | 0.62 | 1440227_at | BF642829 |
| 142 | 140 | 226.4 | 0.618 | 1439777_at | B230218O03 |
| 181 | 78.9 | 127.6 | 0.618 | 1457740_at | Arntl |
| 210 | 147.4 | 238.4 | 0.618 | 1418534_at | Fzd2 |
| 213 | 126.1 | 205 | 0.615 | 1456722_at | Chrdl1 |
| 169 | 54.8 | 89.3 | 0.614 | 1424945_at | Chrdl1 |
| 172 | 304.3 | 504.4 | 0.603 | 1448269_a_at | Klhl13 |

TABLE 17-3-continued

List of Transcripts

| | Geom mean of intensities in class 1: 3G9_10 | Geom mean of intensities in class 2: PBS | Fold difference of geom means | Probe set | Gene symbol |
|---|---|---|---|---|---|
| 175 | 450.9 | 747.6 | 0.603 | 1429214_at | Adamtsl2 |
| 135 | 542.3 | 900.3 | 0.602 | 1434245_a_at | Cybasc3 |
| 151 | 249.7 | 428.4 | 0.583 | 1435484_at | BF642829 |
| 179 | 470.3 | 808.4 | 0.582 | 1416687_at | Plod2 |
| 203 | 204.1 | 357.8 | 0.57 | 1422953_at | Fpr-rs2 |
| 225 | 42.8 | 76.8 | 0.557 | 1445032_at | Dapk1 |
| 147 | 118.3 | 213.1 | 0.555 | 1436528_at | Kazald1 |
| 176 | 110.8 | 201 | 0.551 | 1422155_at | Hist2h3c2 |
| 208 | 95.4 | 173.3 | 0.55 | 1438069_a_at | Rbm5 |
| 164 | 636.8 | 1161.2 | 0.548 | 1420855_at | Eln |
| 143 | 374 | 689 | 0.543 | 1429764_at | 1500005K14Rik |
| 160 | 39.2 | 72.3 | 0.542 | 1441353_at | |
| 192 | 127.1 | 250.1 | 0.508 | 1455299_at | 1700110N18Rik |
| 136 | 210.1 | 415 | 0.506 | 1422705_at | Tmepai |
| 178 | 91.2 | 180.4 | 0.506 | 1418932_at | Nfil3 |
| 137 | 182.6 | 362.8 | 0.503 | 1433924_at | Peg3 |
| 141 | 129.5 | 264.2 | 0.49 | 1446471_at | |
| 222 | 133.7 | 273.6 | 0.489 | 1459984_at | Mia3 |
| 185 | 163.5 | 336.4 | 0.486 | 1419692_a_at | Ltc4s |
| 219 | 1684.9 | 3504.9 | 0.481 | 1449846_at | Ear2 |
| 173 | 270.4 | 581.1 | 0.465 | 1417388_at | Bex2 |
| 145 | 93.1 | 203.4 | 0.458 | 1438862_at | A630005l04Rik |
| 139 | 63.3 | 139.3 | 0.454 | 1450808_at | Fpr1 |
| 221 | 56.4 | 125.9 | 0.448 | 1449498_at | Marco |
| 157 | 192.6 | 440.6 | 0.437 | 1423566_a_at | Hsp110 |
| 134 | 152.9 | 363.5 | 0.421 | 1460061_at | |
| 146 | 745.2 | 1784.8 | 0.418 | 1425993_a_at | Hsp110 |
| 133 | 51.8 | 138.1 | 0.375 | 1424975_at | Siglec5 |
| 144 | 169.7 | 457.5 | 0.371 | 1417860_a_at | Spon2 |
| 138 | 69.5 | 196.3 | 0.354 | 1421037_at | Npas2 |
| 131 | 122.3 | 378.8 | 0.323 | 1425099_a_at | Arntl |
| 132 | 31.3 | 109.2 | 0.287 | 1417556_at | Fabp1 |
| 130 | 18.5 | 71.4 | 0.259 | 1448764_a_at | Fabp1 |
| 128 | 80.2 | 355.3 | 0.226 | 1427352_at | BC031593 |
| 129 | 34 | 194.7 | 0.175 | 1424451_at | MGC29978 |
| 127 | 18.6 | 282.8 | 0.066 | 1421802_at | Ear1 |

TABLE 17-4

Genes significantly affected by 30 mg/kg 3G9 in the treatment group.

| | Geom mean of intensities in class 1: 3G9_30_T | Geom mean of intensities in class 2: PBS | Fold difference of geom means | Probe set | Description | Gene Symbol |
|---|---|---|---|---|---|---|
| 1 | 1546.4 | 37.7 | 41.019 | 1449153_at | | Mmp12 |
| 2 | 1737.4 | 568.8 | 3.055 | 1420249_s_at | | Ccl6 |
| 3 | 2719.8 | 736.8 | 3.691 | 1417936_at | | Ccl9 |
| 4 | 4556.8 | 980.2 | 4.649 | 1427747_a_at | | Lcn2 |
| 5 | 862.7 | 183.4 | 4.704 | 1448898_at | | Ccl9 |
| 6 | 1335.4 | 464.1 | 2.877 | 1450652_at | | Ctsk |
| 7 | 889.6 | 175.6 | 5.066 | 1448303_at | | Gpnmb |
| 8 | 346.7 | 75.7 | 4.58 | 1425951_a_at | | Clec4n |
| 9 | 5373.9 | 2214.3 | 2.427 | 1417266_at | | Ccl6 |
| 10 | 979.1 | 347.3 | 2.819 | 1419627_s_at | | Clec4n |
| 11 | 1998.2 | 669 | 2.987 | 1420394_s_at | | Gp49a /// Lilrb4 |
| 12 | 691.5 | 150.6 | 4.592 | 1419725_at | | Slc26a4 |
| 13 | 66 | 33.3 | 1.982 | 1420250_at | | |
| 14 | 134.1 | 70.3 | 1.908 | 1422191_at | | Cd200r1 |
| 15 | 1006.7 | 417 | 2.414 | 1449164_at | | Cd68 |
| 16 | 185.8 | 88.8 | 2.092 | 1427313_at | | Ptgir |
| 17 | 71 | 43.9 | 1.617 | 1421851_at | | Mtap1b |
| 18 | 53.1 | 38 | 1.397 | AFFX-TransRecMur/X57349_3_at | | Tfrc |
| 19 | 400.4 | 198.3 | 2.019 | 1418797_at | | Ms4a8a |
| 20 | 640.8 | 200.8 | 3.191 | 1418174_at | | Dbp |
| 21 | 291.8 | 122.7 | 2.378 | 1425151_a_at | | Noxo1 |
| 22 | 1064.8 | 277.5 | 3.837 | 1438211_s_at | | Dbp |
| 23 | 419.2 | 170.7 | 2.456 | 1449227_at | | Ch25h |
| 24 | 166.5 | 63.9 | 2.606 | 1435313_at | | Cd200r4 |
| 25 | 77.3 | 26.9 | 2.874 | 1419561_at | | Ccl3 |
| 26 | 459 | 269.4 | 1.704 | 1423308_at | | Tgoln1 |
| 27 | 144.4 | 66.7 | 2.165 | 1421977_at | | Mmp19 |
| 28 | 1093.4 | 355.5 | 3.076 | 1436530_at | | |
| 29 | 5068.1 | 3168.8 | 1.599 | 1448591_at | | Ctss |
| 30 | 267.3 | 193.1 | 1.384 | 1456620_at | | MGC79224 |
| 31 | 80.8 | 40.6 | 1.99 | 1416959_at | | Nr1d2 |
| 32 | 118.4 | 38.8 | 3.052 | 1419209_at | | Cxcl1 |
| 33 | 172.5 | 100.4 | 1.718 | 1417263_at | | Ptgs2 |
| 34 | 332.9 | 152.7 | 2.18 | 1444176_at | | Atp6v0d2 |

TABLE 17-4-continued

Genes significantly affected by 30 mg/kg 3G9 in the treatment group.

| Geom mean of intensities in class 1: 3G9_30_T | Geom mean of intensities in class 2: PBS | Fold difference of geom means | Probe set | Description | Gene Symbol |
|---|---|---|---|---|---|
| 35 | 454 | 225.3 | 2.015 | 1422875_at | Cd84 |
| 36 | 390.7 | 168.9 | 2.313 | 1437939_s_at | Ctsc |
| 37 | 1228.1 | 158.3 | 7.758 | 1450826_a_at | Saa3 |
| 38 | 17.7 | 12.1 | 1.463 | 1439703_at | Cd200r1 |
| 39 | 461.9 | 210.9 | 2.19 | 1422978_at | Cybb |
| 40 | 136 | 78.1 | 1.741 | 1433864_at | Lrp12 |
| 41 | 133.3 | 69.1 | 1.929 | 1418809_at | Pira1 |
| 42 | 390.9 | 244.1 | 1.601 | 1424356_a_at | Metrnl |
| 43 | 573.3 | 145.9 | 3.929 | 1425890_at | Ly6i |
| 44 | 268.5 | 170.1 | 1.578 | 1425407_s_at | Clec4a2 /// Clec4b |
| 45 | 328.6 | 198.9 | 1.652 | 1418318_at | Rnf128 |
| 46 | 1000.5 | 609.8 | 1.641 | 1450355_a_at | Capg |
| 47 | 195.6 | 82.4 | 2.374 | 1427221_at | MGI: 2143217 |
| 48 | 374.3 | 226.2 | 1.655 | 1448749_at | Plek |
| 49 | 585.1 | 338 | 1.731 | 1419975_at | |
| 50 | 209.7 | 132.8 | 1.579 | 1449949_a_at | Cxadr |
| 51 | 168.9 | 110.2 | 1.533 | 1422341_s_at | Lypla3 |
| 52 | 178.5 | 98.1 | 1.82 | 1421792_s_at | Trem2 |
| 53 | 396.6 | 238.9 | 1.66 | 1417492_at | Ctsb |
| 54 | 157.1 | 52.9 | 2.97 | 1420380_at | Ccl2 |
| 55 | 124.6 | 95.6 | 1.303 | 1452461_a_at | MGC79224 |
| 56 | 218.4 | 109.6 | 1.993 | 1419483_at | C3ar1 |
| 57 | 109.3 | 73.4 | 1.489 | 1422966_a_at | Tfrc |
| 58 | 141.6 | 90.6 | 1.563 | 1442019_at | |
| 59 | 283.6 | 175.6 | 1.615 | 1427429_at | Csf2 |
| 60 | 6424.8 | 3665.8 | 1.753 | 1451537_at | Chi3l1 |
| 61 | 147.2 | 94.7 | 1.554 | 1416986_a_at | Ptpns1 |
| 62 | 206.7 | 143.4 | 1.441 | 1452367_at | Coro2a |
| 63 | 135.9 | 52.9 | 2.569 | 1442082_at | C3ar1 |
| 64 | 202.5 | 150.4 | 1.346 | 1418623_at | Rab2 |
| 65 | 97.8 | 47.3 | 2.068 | 1419754_at | Myo5a |
| 66 | 432.4 | 259.4 | 1.667 | 1419321_at | F7 |
| 67 | 325.6 | 241.8 | 1.347 | 1416827_at | Tbxas1 |
| 68 | 74.8 | 355.3 | 0.211 | 1427352_at | BC031593 |
| 69 | 44.3 | 194.7 | 0.228 | 1424451_at | MGC29978 |
| 70 | 21.2 | 71.4 | 0.297 | 1448764_a_at | Fabp1 |
| 71 | 34.9 | 109.2 | 0.32 | 1417556_at | Fabp1 |
| 72 | 33.2 | 282.8 | 0.117 | 1421802_at | Ear1 |
| 73 | 546.6 | 900.3 | 0.607 | 1434245_a_at | Cybasc3 |
| 74 | 178.8 | 378.8 | 0.472 | 1425099_a_at | Arntl |
| 75 | 70.7 | 139.3 | 0.508 | 1450808_at | Fpr1 |
| 76 | 87.6 | 133 | 0.659 | 1456980_at | 9830134C10Rik |
| 77 | 228.9 | 415 | 0.552 | 1422705_at | Tmepai |
| 78 | 172.9 | 363.5 | 0.476 | 1460061_at | |
| 79 | 172.8 | 440.6 | 0.392 | 1423566_a_at | Hsp110 |
| 80 | 762.6 | 1784.8 | 0.427 | 1425993_a_at | Hsp110 |
| 81 | 266.2 | 400 | 0.665 | 1435247_at | Ube1dc1 |
| 82 | 464.7 | 689 | 0.674 | 1429764_at | 1500005K14Rik |
| 83 | 632.4 | 821.7 | 0.77 | 1419640_at | Purb |
| 84 | 388.1 | 577.7 | 0.672 | 1453313_at | Sesn3 |
| 85 | 489.7 | 626.4 | 0.782 | 1440817_x_at | G630024C07Rik |
| 86 | 539 | 741.7 | 0.727 | 1447585_s_at | Mrps6 |
| 87 | 152.2 | 233.5 | 0.652 | 1442051_at | Hist2h3c1 |
| 88 | 990.3 | 1438.3 | 0.689 | 1438058_s_at | Ptov1 |
| 89 | 80 | 127.6 | 0.627 | 1457740_at | Arntl |
| 90 | 270.4 | 428.4 | 0.631 | 1435484_at | BF642829 |
| 91 | 193.2 | 268.3 | 0.72 | 1440971_x_at | G630024C07Rik |

TABLE 17-5

Genes significantly affected by 10 mg/kg 3G9 and showing >2-fold change in the corresponding probeset signal intensity in the treatment group.

| Gene Row (Double-click) | Probe set | Description | Gene symbol |
|---|---|---|---|
| 1720 | 1417388_at | brain expressed X-linked 2 | Bex2 |
| 1888 | 1417556_at | fatty acid binding protein 1, liver | Fabp1 |
| 2192 | 1417860_a_at | spondin 2, extracellular matrix protein | Spon2 |
| 4024 | 1419692_a_at | leukotriene C4 synthase | Ltc4s |
| 5334 | 1421037_at | neuronal PAS domain protein 2 | Npas2 |
| 6109 | 1421802_at | eosinophil-associated, ribonuclease A family, member 1 | Ear1 |
| 7873 | 1423566_a_at | heat shock protein 110 | Hsp110 |
| 8758 | 1424451_at | 3-ketoacyl-CoA thiolase B | MGC29978 |
| 9282 | 1424975_at | sialic acid binding Ig-like lectin 5 | Siglec5 |
| 9406 | 1425099_a_at | aryl hydrocarbon receptor nuclear translocator-like | Arntl |
| 10300 | 1425993_a_at | heat shock protein 110 | Hsp110 |
| 11659 | 1427352_at | cDNA sequence BC031593 | BC031593 |
| 23169 | 1438862_at | RIKEN cDNA A630005I04 gene | A630005I04Rik |
| 30778 | 1446471_at | | |
| 33065 | 1448764_a_at | fatty acid binding protein 1, liver | Fabp1 |
| 33799 | 1449498_at | macrophage receptor with collagenous structure | Marco |
| 34142 | 1449846_at | eosinophil-associated, ribonuclease A family, member 2 | Ear2 |
| 35104 | 1450808_at | formyl peptide receptor 1 | Fpr1 |
| 44278 | 1459984_at | melanoma inhibitory activity 3 | Mia3 |
| 44355 | 1460061_at | Adult male olfactory brain cDNA, RIKEN full-length enriched library | |
| 1291 | 1416959_at | nuclear receptor subfamily 1, group D, member 2 | Nr1d2 |
| 1588 | 1417256_at | matrix metallopeptidase 13 | Mmp13 |
| 1598 | 1417266_at | chemokine (C-C motif) ligand 6 | Ccl6 |
| 2268 | 1417936_at | chemokine (C-C motif) ligand 9 | Ccl9 |
| 2506 | 1418174_at | D site albumin promoter binding protein | Dbp |
| 2818 | 1418486_at | vanin 1 | Vnn1 |
| 3541 | 1419209_at | chemokine (C-X-C motif) ligand 1 | Cxcl1 |
| 3614 | 1419282_at | chemokine (C-C motif) ligand 12 | Ccl12 |
| 3814 | 1419482_at | complement component 3a receptor 1 | C3ar1 |
| 3815 | 1419483_at | complement component 3a receptor 1 | C3ar1 |
| 3893 | 1419561_at | chemokine (C-C motif) ligand 3 | Ccl3 |
| 3930 | 1419598_at | membrane-spanning 4-domains, subfamily A, member 6D | Ms4a6d |
| 3931 | 1419599_s_at | membrane-spanning 4-domains, subfamily A, member 11 | Ms4a11 |
| 3959 | 1419627_s_at | C-type lectin domain family 4, member n | Clec4n |
| 4057 | 1419725_at | solute carrier family 26, member 4 | Slc26a4 |
| 4086 | 1419754_at | myosin Va | Myo5a |
| 4569 | 1420249_s_at | chemokine (C-C motif) ligand 6 | Ccl6 |
| 4687 | 1420380_at | chemokine (C-C motif) ligand 2 | Ccl2 |
| 4701 | 1420394_s _at | glycoprotein 49 A /// leukocyte immunoglobulin-like receptor, subfamily B, member 4 | Gp49a /// Lilrb4 |
| 4771 | 1420464_s_at | | Pira1 /// Pira2 /// Pira3 /// Pira4 /// Pira6 /// Lilrb3 /// LOC546027 |
| 5075 | 1420768_a_at | DNA segment, Chr 11, Lothar Hennighausen 2, expressed | D11Lgp2e |
| 5535 | 1421228_at | chemokine (C-C motif) ligand 7 | Ccl7 |
| 7285 | 1422978_at | cytochrome b-245, beta polypeptide | Cybb |
| 9034 | 1424727_at | chemokine (C-C motif) receptor 5 | Ccr5 |
| 9458 | 1425151_a_at | NADPH oxidase organizer 1 | Noxo1 |
| 10197 | 1425890_at | lymphocyte antigen 6 complex, locus I | Ly6i |
| 10258 | 1425951_a_at | C-type lectin domain family 4, member n | Clec4n |
| 10771 | 1426464_at | nuclear receptor subfamily 1, group D, member 1 | Nr1d1 |
| 11528 | 1427221_at | X transporter protein 3 similar 1 gene | MGI: 2143217 |
| 11620 | 1427313_at | prostaglandin I receptor (IP) | Ptgir |
| 12054 | 1427747_a_at | lipocalin 2 | Lcn2 |
| 19620 | 1435313_at | Cd200 receptor 4 | Cd200r4 |
| 20837 | 1436530_at | CDNA clone MGC: 107680 IMAGE: 6766535 | |
| 22246 | 1437939_s_at | Cathepsin C (Ctsc), mRNA | Ctsc |
| 22518 | 1438211_s_at | D site albumin promoter binding protein | Dbp |
| 26389 | 1442082_at | complement component 3a receptor 1 | C3ar1 |
| 32604 | 1448303_at | glycoprotein (transmembrane) nmb | Gpnmb |
| 33199 | 1448898_at | chemokine (C-C motif) ligand 9 | Ccl9 |
| 33326 | 1449025_at | interferon-induced protein with tetratricopeptide repeats 3 | Ifit3 |
| 33454 | 1449153_at | matrix metallopeptidase 12 | Mmp12 |
| 33465 | 1449164_at | CD68 antigen | Cd68 |
| 33528 | 1449227_at | cholesterol 25-hydroxylase | Ch25h |
| 34280 | 1449984_at | chemokine (C-X-C motif) ligand 2 | Cxcl2 |
| 34587 | 1450291_s_at | membrane-spanning 4-domains, subfamily A, member 4C | Ms4a4c |
| 34699 | 1450403_at | signal transducer and activator of transcription 2 | Stat2 |
| 34948 | 1450652_at | cathepsin K | Ctsk |
| 35122 | 1450826_a_at | serum amyloid A 3 | Saa3 |
| 36237 | 1451941_a_at | Fc receptor, IgG, low affinity IIb | Fcgr2b |
| 42472 | 1458176_at | Period homolog 3 (*Drosophila*) (Per3), mRNA | Per3 |

TABLE 17-6

Transcripts changed >2-fold in the 30 mg/kg group. Genes significantly affected by 30 mg/kg 3G9 and showing >2-fold change in the corresponding probeset signal intensity in the treatment group.

| Gene Row (Double-click) | Probe set | Description | Gene symbol |
|---|---|---|---|
| 1888 | 1417556_at | fatty acid binding protein 1, liver | Fabp1 |
| 6109 | 1421802_at | eosinophil-associated, ribonuclease A family, member 1 | Ear1 |
| 7873 | 1423566_a_at | heat shock protein 110 | Hsp110 |
| 8758 | 1424451_at | 3-ketoacyl-CoA thiolase B | MGC29978 |
| 9406 | 1425099_a_at | aryl hydrocarbon receptor nuclear translocator-like | Arntl |
| 10300 | 1425993_a_at | heat shock protein 110 | Hsp110 |
| 11659 | 1427352_at | cDNA sequence BC031593 | BC031593 |
| 33065 | 1448764_a_at | fatty acid binding protein 1, liver | Fabp1 |
| 44355 | 1460061_at | Adult male olfactory brain cDNA, RIKEN full-length enriched library | |
| 1598 | 1417266_at | chemokine (C-C motif) ligand 6 | Ccl6 |
| 2268 | 1417936_at | chemokine (C-C motif) ligand 9 | Ccl9 |
| 2506 | 1418174_at | D site albumin promoter binding protein | Dbp |
| 3129 | 1418797_at | membrane-spanning 4-domains, subfamily A, member 8A | Ms4a8a |
| 3541 | 1419209_at | chemokine (C-X-C motif) ligand 1 | Cxcl1 |
| 3893 | 1419561_at | chemokine (C-C motif) ligand 3 | Ccl3 |
| 3959 | 1419627_s_at | C-type lectin domain family 4, member n | Clec4n |
| 4057 | 1419725_at | solute carrier family 26, member 4 | Slc26a4 |
| 4086 | 1419754_at | myosin Va | Myo5a |
| 4569 | 1420249_s_at | chemokine (C-C motif) ligand 6 | Ccl6 |
| 4687 | 1420380_at | chemokine (C-C motif) ligand 2 | Ccl2 |
| 4701 | 1420394_s_at | glycoprotein 49 A /// leukocyte immunoglobulin-like receptor, subfamily B, member 4 | Gp49a /// Lilrb4 |
| 6284 | 1421977_at | matrix metallopeptidase 19 | Mmp19 |
| 7182 | 1422875_at | CD84 antigen | Cd84 |
| 7285 | 1422978_at | cytochrome b-245, beta polypeptide | Cybb |
| 9458 | 1425151_a_at | NADPH oxidase organizer 1 | Noxo1 |
| 10197 | 1425890_at | lymphocyte antigen 6 complex, locus l | Ly6i |
| 10258 | 1425951_a_at | C-type lectin domain family 4, member n | Clec4n |
| 11528 | 1427221_at | X transporter protein 3 similar 1 gene | MGI: 2143217 |
| 11620 | 1427313_at | prostaglandin I receptor (IP) | Ptgir |
| 12054 | 1427747_a_at | lipocalin 2 | Lcn2 |
| 19620 | 1435313_at | Cd200 receptor 4 | Cd200r4 |
| 20837 | 1436530_at | CDNA clone MGC: 107680 IMAGE: 6766535 | |
| 22246 | 1437939_s_at | Cathepsin C (Ctsc), mRNA | Ctsc |
| 22518 | 1438211_s_at | D site albumin promoter binding protein | Dbp |
| 26389 | 1442082_at | complement component 3a receptor 1 | C3ar1 |
| 28483 | 1444176_at | AtPase, H+ transporting, V0 subunit D, isoform 2 | Atp6v0d2 |
| 32604 | 1448303_at | glycoprotein (transmembrane) nmb | Gpnmb |
| 33199 | 1448898_at | chemokine (C-C motif) ligand 9 | Ccl9 |
| 33454 | 1449153_at | matrix metallopeptidase 12 | Mmp12 |
| 33465 | 1449164_at | CD68 antigen | Cd68 |
| 33528 | 1449227_at | cholesterol 25-hydroxylase | Ch25h |
| 34948 | 1450652_at | cathepsin K | Ctsk |
| 35122 | 1450826_a_at | serum amyloid A 3 | Saa3 |

TABLE 17-7

Transcripts showing an upward trend in the 3 mg/kg group

| Probe Set ID | Gene Title | Gene Symbol |
|---|---|---|
| 1417266_at | chemokine (C-C motif) ligand 6 | Ccl6 |
| 1417936_at | chemokine (C-C motif) ligand 9 | Ccl9 |
| 1418486_at | vanin 1 | Vnn1 |
| 1419209_at | chemokine (C-X-C motif) ligand 1 | Cxcl1 |
| 1419598_at | membrane-spanning 4-domains, subfamily A, member 6D | Ms4a6d |
| 1419599_s_at | membrane-spanning 4-domains, subfamily A, member 11 | Ms4a11 |
| 1419627_s_at | C-type lectin domain family 4, member n | Clec4n |
| 1420394_s_at | glycoprotein 49 A /// leukocyte immunoglobulin-like receptor, subfam B, member 4 | Gp49a /// Lilrb4 |
| 1421228_at | chemokine (C-C motif) ligand 7 | Ccl7 |
| 1422191_at | CD200 receptor 1 | Cd200r1 |
| 1424727_at | chemokine (C-C motif) receptor 5 | Ccr5 |
| 1425407_s_at | C-type lectin domain family 4, member a2 ///member b | Clec4a2 /// Clec4b |
| 1425890_at | lymphocyte antigen 6 complex, locus I | Ly6i |
| 1427747_a_at | lipocalin 2 | Lcn2 |
| 1435477_s_at | Fc receptor, IgG, low affinity IIb | Fcgr2b |
| 1436530_at | CDNA clone MGC: 107680 IMAGE: 6766535 | — |

TABLE 17-7-continued

| Transcripts showing an upward trend in the 3 mg/kg group | | |
|---|---|---|
| Probe Set ID | Gene Title | Gene Symbol |
| 1437939_s_at | cathepsin C | Ctsc |
| 1448303_at | glycoprotein (transmembrane) nmb | Gpnmb |
| 1448591_at | cathepsin S | Ctss |
| 1448898_at | chemokine (C-C motif) ligand 9 | Ccl9 |
| 1449153_at | matrix metallopeptidase 12 | Mmp12 |
| 1449984_at | chemokine (C-X-C motif) ligand 2 | Cxcl2 |
| 1450652_at | cathepsin K | Ctsk |
| 1450826_a_at | serum amyloid A 3 | Saa3 |
| 1451941_a_at | Fc receptor, IgG, low affinity IIb | Fcgr2b |
| 1455332_x_at | Fc receptor, IgG, low affinity IIb | Fcgr2b |

TABLE 17-8

| Total Proteins Analyzed by Multi-Analyte Protein Profiling | | |
|---|---|---|
| Apo A1 (Apolipoprotein A1) | IL-12p70 (Interleukin-12p70) | M-CSF (Macrophage-Colony Stimulating Factor) |
| CD40 | IL-17 (Interleukin-17) | MDC (Macrophage-Derived Chemokine/CCL22) |
| CD40 Ligand | IL-18 (Interleukin-18) | MIP-1α (Macrophage Inflammatory Protein-1α/CCL3) |
| CRP (C Reactive Protein) | IL-1alpha (Interleukin-1alpha) | MIP-1β (Macrophage Inflammatory Protein-1β/CCL4) |
| EGF (Epidermal Growth Factor) | IL-1beta (Interleukin-1beta) | MIP-1γ (Macrophage Inflammatory Protein-1γ/CCL9) |
| Endothelin-1 | IL-2 (Interleukin-2) | MIP-2 (Macrophage Inflammatory Protein-2/CXCL2) |
| Eotaxin (CCL11) | IL-3 (Interleukin-3) | MIP-3β (Macrophage Inflammatory Protein-3β/CCL19) |
| Factor VII | IL-4 (Interleukin-4) | MMP-9 (Matrix Metalloproteinase-9) |
| FGF-9 (Fibroblast Growth Factor-9) | IL-5 (Interleukin-5) | Myoglobin |
| FGF-basic (Fibroblast Growth Factor-basic) | IL-6 (Interleukin-6) | OSM (Oncostatin M) |
| Fibrinogen | IL-7 (Interleukin-7) | RANTES (CCL5) |
| GCP-2 (Granulocyte Chemotactic Protein-2/CXCL6) | Insulin | SCF (Stem Cell Factor) |
| GM-CSF (Gran/Mac-Colony Stimulating Factor) | IP-10 (Inducible Protein-10/CXCL10) | SGOT (Serum Glutamic-Oxaloacetic Transaminase) |
| Growth Hormone | KC/GROalpha (CXCL1) | TIMP-1 (Tissue Inhibitor of Metalloproteinase Type-1) |
| GST-alpha (Glutathione S-Transferase alpha) | Leptin | Tissue Factor |
| Haptoglobin | LIF (Leukemia Inhibitory Factor) | TNF-alpha (Tumor Necrosis Factor-alpha) |
| IFN-gamma (Interferon-gamma) | Lymphotactin | TPO (Thrombopoietin) |
| IgA (Immunoglobulin A) | MCP-1 (Monocyte Chemoattractant Protein-1/CCL2) | VCAM-1 (Vascular Cell Adhesion Molecule-1) |
| IL-10 (Interleukin-10) | MCP-3 (Monocyte Chemoattractant Protein-3/CCL7) | VEGF (Vascular Endothelial Cell Growth Factor) |
| IL-11 (Interleukin-11) | MCP-5 (Monocyte Chemoattractant Protein-5/CCL12) | vWF (von Willebrand Factor) |

TABLE 17-9

| Proteins changed at different doses of mu3G9 treatment | | |
|---|---|---|
| | Number of BALF proteins significantly changed by treatment | Number of BALF proteins with greater than 2-fold change |
| PBS vs 1E6 - 1 mg/kg | 1 | 0 |
| PBS vs 0.1 mg/kg | 1 | 0 |
| PBS vs 0.3 mg/kg | 2 | 0 |
| PBS vs 1 mg/kg | 4 | 0 |
| PBS vs 3 mg/kg | 15 | 11 |
| PBS vs 10 mg/kg | 27 | 20 |

TABLE 17-10

| BALF proteins with greater than 2-fold change in normal mice | |
|---|---|
| 3 mg/kg | 10 mg/kg |
| Apo A1 | Apo A1 |
| CD40 | CD40 |
| Factor VII | Factor VII |
| Fibrinogen | Fibrinogen |
| GCP-2 | GCP-2 |
| MDC | GM-CSF |
| MIP-1gamma | IL-18 |

TABLE 17-10-continued

| BALF proteins with greater than 2-fold change in normal mice | |
|---|---|
| 3 mg/kg | 10 mg/kg |
| MIP-2 | IP-10 |
| Tissue Factor | MCP-1 |
| VCAM-1 | MCP-3 |
| VEGF | MCP-5 |
| | MDC |
| | MIP-1gamma |
| | MIP-2 |
| | MMP-9 |
| | TIMP-1 |
| | Tissue Factor |
| | TPO |
| | VCAM-1 |
| | VEGF |

TABLE 17-11

BAL Fluid proteins significantly changed in radiation model

| | Radiation Model Week 28 | | | | Radiation Model Week 32 | | |
|---|---|---|---|---|---|---|---|
| | 1 mg/kg | 3 mg/kg | 10 mg/kg | | 1 and 3 mg/kg | 6 mg/kg | 10 mg/kg |
| p < 0.05 | TIMP-1 | Haptoglobin<br>IL-10<br>IL-7<br>MIP-3beta<br>Myoglobin<br>TIMP-1<br>TNF-alpha<br>vWF | Haptoglobin<br>IL-1beta<br>IL-5 | p < 0.05 | NONE | GCP-2<br>GM-CSF<br>IL-10<br>IP-10<br>MIP-1alpha<br>SCF<br>TNF-alpha | IL-18<br>MIP-3beta<br>MMP-9<br>VCAM |
| p < 0.01 | Haptoglobin | ApoA1<br>EGF<br>IL-1alpha<br>MIP-1alpha<br>OSM<br>VEGF | CD40<br>GCP-2<br>GM-CSF<br>IP-10<br>MCP-1<br>MCP-3<br>MCP-5<br>M-CSF<br>MIP-1alpha<br>MIP-1beta<br>MIP-2<br>MMP-9<br>Myoglobin<br>Oncostatin M<br>SCF<br>TNF-alpha<br>TPO<br>VEGF<br>vWF | p < 0.01 | NONE | MCP-1<br>MCP-3<br>MIP-1beta<br>MMP-9<br>Oncostatin M<br>VEGF | CD40<br>GCP-2<br>GM-CSF<br>IgA<br>IL-10<br>IP-10<br>MCP-1<br>MCP-3<br>MCP-5<br>M-CSF<br>MIP-1alpha<br>MIP-1beta<br>MIP-1gamma<br>MIP-2<br>Myoglobin<br>Oncostatin M<br>SCF<br>TNF-alpha<br>TPO<br>VEGF |

TABLE 17-12

Comparison of fold-change in BAL proteins in normal and irradiated mice

| | Fold-Change at 10 mg/kg/week | |
|---|---|---|
| | Normal Mice 4 week treatment | Radiation Model 3-4 month treatment |
| MCP-1 | 39 | 46-85 |
| MCP-3 | 11 | 25-50 |
| MCP-5 | 2.4 | 18-32 |
| GM-CSF | 2.9 | 16 |
| CD40 | 3 | 6-10 |
| MMP-9 | 3 | 5-6 |
| MIP-1beta | 1.3 | 6 |
| VEGF | 3 | 5-7 |
| MIP-2 | 7.6 | 5-6 |
| MIP-1gamma | 65 | 2-4 |
| GCP-2 | 3.6 | 4 |
| IgA | 5.7 | 5.5 |
| M-CSF | 4.5 | 2.5-3 |

Conclusions

The effects of mu3G9-treatment have been characterized in normal mice by transcript profiling and by multiple analyte protein profiling:

(a) Transcript profiling analysis of lungs from high-dose mu3G9-treated mice induces significant changes in a number of transcripts associated with pulmonary inflammation. These changes are consistent with transcript profiling results from integrin β6 null mice αvβ6-deficient). The specific targets that are misregulated are consistent with decreased TGF-β signaling in the lung due to mu3G9's mechanism of action.

(b) Protein profiling results likewise demonstrate consistent increases in some cytokines and chemokines associated with the mu3G9 mechanism of action.

(c) Changes in transcripts reach significance only at the mg/kg dose, although a number of transcripts trend upwards at the 3 mg/kg dose. Some protein changes are significant at the 3 mg/kg dose, but most reach significance at the 10 mg/kg dose. No changes in protein or transcript are significant at the 1 mg/kg dose.

The effects of mu3G9-treatment have been characterized in the radiation fibrosis model by multiple analyte protein profiling:

(a) Many of the same cytokines and chemokines induced by high-dose mu3G9 in normal are also elevated by high dose mu3G9 in the radiation fibrosis model.

(b) Despite the much higher expression of mu3G9's target, integrin αvβ6, elevations in these inflammatory markers are seen at the same doses in the radiation model and in normal mice, i.e. elevation at 3 and 10 mg/kg, but not at 1 mg/kg, which is a near maximal efficacious dose in this model (see Example 15).

Some proteins associated with fibrosis, especially TIMP-1 and haptoglobin, were normalized by mu3G9 treatment at efficacious doses at the 28 week timepoint.

References

Annes J P, Rifkin D B, Munger J S. The integrin αvβ6 binds and activates latent TGFβ3. FEBS lett 2002; 511:65-68.

Bonniaud P, Kolb M, Galt T, Robertson J, Robbins C, Stampfli M, Layery C, Margetts P J, Roberts A B, Gauldie J. Smad3 null mice develop airspace enlargement and are resistant to TGF-beta-mediated pulmonary fibrosis. J. Immunol. 2004; 173(3):2099-108.

Bonniaud P, Margetts P J, Schroeder J A, Kapoun A M, Damm D, Murphy A, Chakravarty S, Dugar S, Higgins L, Protter A A and others. Progressive TGF-(beta)1-induced lung fibrosis is blocked by an orally active ALK5 kinase inhibitor. Am J Respir Crit. Care Med. 2004.

Breuss J M, Gallo J, DeLisser H M, Klimanskaya I V, Folkesson H G, Pittet J F, Nishimura S, Aldape K, Landers D V, Carpenter W et al. Expression of the β6 subunit in development, neoplasia and tissue repair suggests a role in epithelial remodeling. J Cell Sci 1995; 108:2241-2251.

Chevalier R L, Goyal S, Kim A, Landau D, LeRoith D. Renal tubulointerstitial injury from ureteral obstruction in the neonatal rat is attenuated by IGF-1. Kidney Int 2000; 57:882-890.

Collard H R, Ryu J H, Douglas W W, Schwarz M I, Curran-Everett D, King T E, Brown K K. Combined Corticosteroid and Cyclophosphamide Therapy does not alter survival in Idiopathic Pulmonary Fibrosis. Chest 2004; 125:2169-2174.

Coultas D B, Zumwalt R E, Black W C Sobonya R E. The Epidemiology of Interstitial Lung Disease. Am J Respir Crit. Care Med 1994; 150:967-972.

Cosgrove D, Meehan D, Grunkemeyer J A, Komak J M, Sayers R, Hunter W J, Samuelson G C. Collagen COL4A3 knockout: a mouse model for autosomal Alport syndrome. Genes Dev 1996; 10:2981-2992.

Douglas W W, Ryu J H, Swensen S J, Offord K P, Schroeder D R, Caron G M, Remee R A. Colchicine versus Prednisone in the Treatment of Idiopathic Pulmonary Fibrosis: a randomized prospective study. Am J Respir Crit. Care Med 1998; 158:220-225.

Eickelberg O, Kohler E, Reichenberger F, Bertschin S, Woodtli T, Erne P, Perruchoud A P, Roth M. Extracellular matrix deposition by primary human lung fibroblasts in response to TGF-beta1 and TGF-beta3. Am J Physiol 1999 276(5):L814-L824.

Flaherty K R, Toesw G B, Lynch J P, Kazerooni E A, Gross B H, Strawderman R L, Hariharan K, Flint A, Martinez F J. Steroids in Idiopathic Pulmonary Fibrosis: A prospective assessment of adverse reactions, response to therapy, and survival. Am J Med 2001; 110:278-282.

George J, Roulot D, Koteliansky V E, Bissell D M. In vivo inhibition of rat stellate cell activation by soluble transforming growth factor type II receptor: A potential new therapy for hepatic fibrosis. Proc Natl Acad Sci, USA 1999; 96(22): 12719-12724.

Gleizes P E, Munger J S, Nunes I, Harpel J G, Mazzieri R, Noguera I, Rifkin D B. TGF-beta latency: biological significance and mechanisms of activation. Stem Cells 1997; 15:190-197.

Hakkinen L, Hildebrand H C, Berndt A, Kosmehl H, Larjava H. Immunolocalization of tenascin-C, alpha9 integrin subunit, and alphavbeta6 integrin during wound healing in human oral mucosa. J Histochem Cytochem. 2000 48(7):985-98.

Hakkinen L, Koivisto L, Gardner H, Saarialho-Kre U, Carroll J M, Lakso M, Rauvala H, Laato M, Heino J, Larjava H. Increased expression of beta6-integrin in skin leads to spontaneous development of chronic wounds. Am J Pathol 2004 164(1):229-42.

Huang X Z, Wu J F, Cass D, Erle D J, Corry D, Young S G, Farese R V Jr, Sheppard D. Inactivation of the integrins in regulating inflammation in the lung and skin. J. Cell Biol. 1996 May; 133(4): 921-8.

Huang X, Wu J, Spong S, Sheppard D. The integrin alphavbeta6 is critical for keratinocyte migration on both its known ligand, fibronectin, and on vitronectin. J Cell Sci 1998; 111: 2189-95.

Kaminski N, Belperio J A, Bitterman P B, Chen L, Chensue S W, and others. Idiopathic Pulmonary Fibrosis. Proceedings of the 1st Annual Pittsburgh International Lung Conference. October 2002. Am J Respir Cell Mol. Biol. 2003 September; 29(3 Suppl):S1-105.

Kasuga H, Ito Y, Sakamoto S, Kawachi H, Shimizu F, Yuzawa Y, S. M. Effects of anti-TGF-β type II receptor antibody on experimental glomerulonephritis. Kid Int 2001; 60:1745-1755.

Laping N J. ALK5 Inhibition in renal disease. Curr Opin Pharmacol 2003; 3(2):204-208.

Ma L J, Yang H, Gaspert A, Carlesso G, Barty M M, Davidson J M, Sheppard D, Fogo A B. Transforming growth factor-β-dependent and independent pathways of induction of tubulointerstitial fibrosis in β6−/− mice. Am J Pathol 2003; 163:1261-1273.

Miner J H, Sanes J R. Molecular and functional defects in kidneys of mice lacking collagen α3(IV): implications for alport syndrome. Cell Biol 1996; 135:1403-1413.

Miyajima A, Chen J, Lawrence C, Ledbetter S, Soslow R A, Stern J, Jha S, Pigato J, Lerner M L, Poppas D P, Vaughan E D, Felsen D. Antibody to transforming growth factor-beta ameliorates tubular apoptosis in unilateral ureteral obstruction. Kidney Int 2000; 58(6):2301-13.

Morris D G, Huang X, Kaminski N, Wang Y, Shapiro S D, Dolganov G, Glick A, Sheppard D. Loss of integrin alpha(v) beta6-mediated TGF-beta activation causes Mmp12-dependent emphysema. Nature. 2003 Mar. 13; 422(6928):130-1.

Munger J S, Harpel J G, Gleizes P E, Mazzieri R, Nunes I, Rifkin D B. Latent transforming growth factor-beta: structural features and mechanisms of activation. Kidney Int 1997; 51:1376-1382.

Munger J S, Huang X, Kawakatsu H, Griffiths M J D, Dalton S L, Wu J, Pittet J F, Kaminski N, Garat C, Matthay M A and others. The integrin αvβ6 binds and activates latent TGFβ1: a mechanism for regulating pulmonary inflammation and fibrosis. Cell 1999; 96:319-328.

Pittet J. F., Griffiths M. J., Geiser T., Kaminski N., Dalton S. L., Huang X., Brown L. A., Gotwals P. J., Koteliansky V. E., Matthay M. A. and others. TGF-beta is a critical mediator of acute lung injury. Clin Invest 2001; 107(12):1537-1544.

Roberts A B, Sporn M B. Regulation of endothelial cell growth, architecture, and matrix synthesis by TGF-beta. Am Rev Respir Dis 1989; 140:1126-1128.

Roberts A B, Sporn M B, Assoian R K, Smith J M, Roche N S, Wakefiled L M, Heine U I, Liotta L A, Falanga V, Kehrl J H and others. Transforming growth factor type B: Rapid induction of fibrosis and angiogenesis in vivo and stimulation of collagen formation in vitro. Proc Natl Acad Sci, USA 1986; 83:4167-4171.

Selman M. Idiopathic pulmonary fibrosis challenges for the future. Chest 2001; 120(1): 8-10.

Sleijfer-S. Bleomycin-induced pneumonitis. Chest 2001; 120(2): 617-24.

Sharma K, Jin Y, Guo J, Ziyadeh F N. Neutralization of TGF-β antibody attenuates kidney hypertrophy and the enhanced extracellular matrix gene expression in STZ-induced diabetic mice. Diabetes 1996; 45:522-530.

Sime P J, Xing Z, Graham F L, Csaky K G, Gauldie J. Adenovector-mediated gene transfer of active transforming growth factor-β1 induces prolonged severe fibrosis in rat lung. J Clin Invest 1997; 100:768-776.

Turner-Warwick M, Burrows B, Johnson A. Cryptogenic fibrosin alveolitis: response to corticosteroid treatment and its effect on survival. Thorax 1980; 35:593-599.

Varga J, Rosenbloom J, Jimenez S A. Transforming growth factor beta (TGF beta) causes a persistent increase in steady-state amounts of type I and type III collagen and fibronectin mRNAs in normal human dermal fibroblasts. Biochem J 1987; 247(3):597-604.

Wang Q, Hyde D M, Gotwals P J, Giri S N. Effects of delayed treatment with soluble transforming growth factor-beta receptor in a three-dose bleomycin model of lung fibrosis in hamsters. Exp Lung Res 2002; 28(6):405-17.

Weinreb P H, Simon K J, Rayhorn P, Yang W J, Leone D R, Dolinski B M, Pearse B R, Yokota Y, Kawakatsu H, Atakilit A and others. Function-blocking integrin αvβ6 monoclonal antibodies. J Biol Chem 2004; 279(17):17875-17887.

Zheng H, Wang J, Koteliansky V, J. GP, Hauer-Jensen M. Recombinant soluble transforming growth factor β type II receptor ameliorates radiation enterophay in mice. Gastroenterology 2000; 119:1286-1296.

Zisman D A, Lynch J P, Toews G B, Kazerooni E A, Flint A, Martinez F J. Cyclophosphamide in the Treatment of Idiopathic Pulmonary Fibrosis. Chest 2000; 117:1619-1626.

Ziyadeh F N, Hoffman B B, Han D C, Iglesias-de la Cruz M C, Hong S W, Isono M, Chen S, McGowan T A, Sharma K. Long-term prevention of renal insufficiency, excess matrix gene expression, and glomerular mesangial matrix expansion by treatment with monoclonal antitransforming growth factor-γ antibody in db/db diabetic mice. Proc Natl Acad Sci, USA 2000; 97(14):8015-8020.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

The Sequence Listing written in the file named "sequence listing ascii.txt", 107,345 created on Apr. 27, 2007, on a compact disc for U.S. application Ser. No. 11/483,190, Violette et al., Anti-$\alpha_v\beta_6$ Antibodies and Uses Thereof, is herein incorporated by reference.

What is claimed is:

1. A humanized antibody that specifically binds to $\alpha_v\beta_6$ comprising a heavy chain variable domain sequence of SEQ ID NO: 1 and a light chain variable domain of SEQ ID NO: 2.

2. A humanized antibody that specifically binds $\alpha_v\beta_6$ wherein said humanized antibody comprises a heavy chain variable domain selected from the group consisting of SEQ ID NO:144, SEQ ID NO:145, or SEQ ID NO:146 and a light chain variable domain sequence selected from the group consisting of SEQ ID NO: 139, SEQ ID NO:140, SEQ ID NO:141, SEQ ID N:142 and SEQ ID NO:143.

3. A humanized antibody that specifically binds $\alpha_v\beta_6$ wherein said humanized antibody comprises a heavy chain variable domain sequence of SEQ ID NO:146 and a light chain variable domain sequence of SEQ ID NO:141 or SEQ ID NO:143.

4. A humanized antibody that specifically binds $\alpha_v\beta_6$, wherein said antibody comprises a heavy chain variable domain (HV2) sequence of SEQ ID NO:145 and a light chain variable domain of SEQ ID NO:140.

5. A humanized antibody that specifically binds to $\alpha_v\beta_6$ and comprises a heavy chain variable domain sequence of SEQ ID NO: 146 (HV3) and a light chain variable domain of SEQ ID NO: 143 (LV5).

6. A humanized antibody that specifically binds to $\alpha_v\beta_6$ comprising a heavy chain variable domain sequence of SEQ ID NO: 3 and a light chain variable domain of SEQ ID NO: 4.

7. The humanized antibody of claim 2, wherein said antibody comprises a heavy chain variable domain (HV1) sequence of SEQ ID NO:144 and a light chain variable domain sequence of SEQ ID NO:139.

8. A humanized antibody that specifically binds to $\alpha_v\beta_6$ comprising a variant of a heavy chain variable domain sequence of SEQ ID NO: 1 and/or a variant of a light chain variable domain of SEQ ID NO: 2, wherein said variant of SEQ ID NO: 1 comprises one or both of Q3M and N73S and said variant of SEQ ID NO:2 comprises one or more of the variations selected from the group consisting of L48W, I59V, A61V and Y88F as compared to SEQ ID NO:2.

9. A humanized antibody that specifically binds $\alpha_v\beta_6$ wherein said humanized antibody comprises a heavy chain variable domain sequence selected from the group consisting of SEQ ID NO:78, SEQ ID NO:79, and SEQ ID NO:80 and the light chain variable domain sequence selected from the group consisting of SEQ ID NO:75, SEQ ID NO:76, and SEQ ID NO:77.

10. A humanized antibody that specifically binds $\alpha_v\beta_6$ wherein said humanized antibody comprises a light chain variable domain sequence of SEQ ID NO:75 and a heavy chain variable domain sequence of SEQ ID NO:78.

11. A humanized antibody that specifically binds $\alpha_v\beta_6$ wherein said humanized antibody comprises a light chain variable domain sequence of SEQ ID NO:76 and a heavy chain variable domain sequence of SEQ ID NO:79.

12. A humanized antibody that specifically binds $\alpha_v\beta_6$ wherein said humanized antibody comprises a light chain variable domain sequence of SEQ ID NO:77 and a heavy chain variable domain sequence of SEQ ID NO:80.

13. A composition comprising the antibody of any one of claims 1, 2, 3, 7, 4, 5, 8, 9, 10, 11, and 12, and a pharmaceutically acceptable carrier.

14. A composition comprising the antibody of claim 6 and a pharmaceutically acceptable carrier.

* * * * *

UNITED STATES PATENT AND TRADEMARK OFFICE

CERTIFICATE OF CORRECTION

PATENT NO. : 7,943,742 B2
APPLICATION NO. : 11/483190
DATED : May 17, 2011
INVENTOR(S) : Violette et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 406 days.

Signed and Sealed this
Thirtieth Day of October, 2012

David J. Kappos
*Director of the United States Patent and Trademark Office*

UNITED STATES PATENT AND TRADEMARK OFFICE

CERTIFICATE OF CORRECTION

PATENT NO. : 7,943,742 B2
APPLICATION NO. : 11/483190
DATED : May 17, 2011
INVENTOR(S) : Shelia M. Violette et al.

It is certified that error appears in the above-identified patent and that said Letters Patent is hereby corrected as shown below:

In the Specification

Column 30
Line 37, delete "SASSSCSSSYLY" and insert --SASSSVSSSYLY--.

Signed and Sealed this
Seventeenth Day of December, 2013

Margaret A. Focarino
*Commissioner for Patents of the United States Patent and Trademark Office*